US008664249B2

(12) United States Patent
Shapiro et al.

(10) Patent No.: US 8,664,249 B2
(45) Date of Patent: *Mar. 4, 2014

(54) TETRASUBSTITUTED BENZENES

(71) Applicant: EnVivo Pharmaceuticals, Inc., Watertown, MA (US)

(72) Inventors: Gideon Shapiro, Gainesville, FL (US); Richard Chesworth, Boston, MA (US)

(73) Assignee: EnVivo Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/756,871

(22) Filed: Feb. 1, 2013

(65) Prior Publication Data

US 2013/0165486 A1 Jun. 27, 2013

Related U.S. Application Data

(63) Continuation of application No. 13/486,201, filed on Jun. 1, 2012, now Pat. No. 8,367,863, which is a continuation of application No. 12/341,201, filed on Dec. 22, 2008, now Pat. No. 8,217,064.

(60) Provisional application No. 61/015,605, filed on Dec. 20, 2007, provisional application No. 61/109,665, filed on Oct. 30, 2008.

(51) Int. Cl.
*A61K 31/4245* (2006.01)
*A61K 31/433* (2006.01)
*A61K 31/192* (2006.01)
*C07D 498/00* (2006.01)
*C07C 59/48* (2006.01)

(52) U.S. Cl.
USPC ........... 514/362; 514/364; 514/567; 514/570; 548/126; 562/435; 562/452; 562/469

(58) Field of Classification Search
None
See application file for complete search history.

(56) References Cited

U.S. PATENT DOCUMENTS

| | | | |
|---|---|---|---|
| 3,860,640 A | 1/1975 | Tamura et al. |
| 4,443,631 A | 4/1984 | Padilla |
| 4,518,799 A | 5/1985 | Hylton |
| 4,827,845 A | 5/1989 | Grote et al. |
| 4,898,874 A | 2/1990 | Walsh et al. |
| 5,089,501 A | 2/1992 | Molleyres |
| 5,281,617 A | 1/1994 | Kirschenheuter et al. |
| 5,444,050 A | 8/1995 | Kogan et al. |
| 5,550,237 A | 8/1996 | Vermehren |
| 5,691,337 A | 11/1997 | Muller et al. |
| 5,698,046 A | 12/1997 | St. Laurent et al. |
| 5,750,783 A | 5/1998 | Goldmann et al. |
| 5,962,743 A | 10/1999 | Gruber et al. |
| 6,072,073 A | 6/2000 | Kawatsura et al. |
| 6,140,353 A | 10/2000 | Ackermann et al. |
| 6,262,832 B1 | 7/2001 | Lomprey et al. |
| 6,348,627 B1 | 2/2002 | Ross, Jr. et al. |
| 6,710,906 B2 | 3/2004 | Guarr et al. |
| 6,861,448 B2 | 3/2005 | Brouillette et al. |
| 7,005,538 B1 | 2/2006 | Malm et al. |
| 7,141,596 B2 | 11/2006 | Combs et al. |
| 7,176,199 B2 | 2/2007 | Morie et al. |
| 7,244,739 B2 | 7/2007 | Cheng et al. |
| 7,244,763 B2 | 7/2007 | Bratton et al. |
| 7,244,861 B2 | 7/2007 | Matsuura et al. |
| 7,319,163 B2 | 1/2008 | Malm et al. |
| 7,485,752 B2 | 2/2009 | Michoud |
| 7,897,631 B2 | 3/2011 | Melander et al. |
| 8,217,064 B2 | 7/2012 | Shapiro et al. |
| 8,367,863 B2 | 2/2013 | Shapiro et al. |
| 2003/0092774 A1 | 5/2003 | Parkinson et al. |
| 2003/0105078 A1 | 6/2003 | Haning et al. |
| 2004/0106622 A1 | 6/2004 | Morie et al. |
| 2004/0167165 A1 | 8/2004 | Shankar et al. |
| 2004/0209936 A1 | 10/2004 | Bratton et al. |
| 2004/0220259 A1 | 11/2004 | Yu et al. |
| 2005/0085388 A1 | 4/2005 | Fursch et al. |
| 2006/0004013 A1 | 1/2006 | Kimura et al. |
| 2006/0063937 A1 | 3/2006 | Munoz et al. |
| 2006/0081819 A1 | 4/2006 | Li et al. |
| 2006/0211645 A1 | 9/2006 | Scott et al. |
| 2007/0054902 A1 | 3/2007 | Fukui et al. |
| 2007/0117839 A1 | 5/2007 | Kimura et al. |
| 2007/0135437 A1 | 6/2007 | Benjamin et al. |
| 2007/0185152 A1 | 8/2007 | Yamashita et al. |
| 2007/0249686 A1 | 10/2007 | Bonnert et al. |
| 2007/0249833 A1 | 10/2007 | Cheng et al. |
| 2007/0260058 A1 | 11/2007 | Cheng et al. |

(Continued)

FOREIGN PATENT DOCUMENTS

| | | |
|---|---|---|
| CN | 1562926 A | 1/2005 |
| DE | 2351217 A1 | 6/1974 |

(Continued)

OTHER PUBLICATIONS

Zhang, Weijiang et al. "Synthesis of Benzo-Fused Benzodiazepines Employed as Probes of the Agonist Pharmacophore of Benzodiazepine Receptors." J. Med. Chem. Mar. 18, 1994. vol. 37, No. 6. American Chemical Society. pp. 745-757. 14 pages.

Patani, George A. et al. "Bioisosterism: A Rational Approach in Drug Design." Chemical Reviews. Dec. 19, 1996. vol. 96, No. 8. pp. 3147-3176. 30 pages.

Asberom et al., "Discovery of .gamma.-secretase inhibitors efficacious in a transgenic animal model of Alzheimer's disease," Bioorganic and Medicinal Chem. Letters, 2007, pp. 511-516.

Burton et al., "A remarkably Simple Preparation of (Trifluoromethyl)cadmium and-zinc Reagents Directly from Difluorodihalomethanes," J. Am. Chem. Soc., Aug. 21, 1985, vol. 107, No. 17, 3 pages.

(Continued)

*Primary Examiner* — Alicia L Otton
(74) *Attorney, Agent, or Firm* — Wilmer Cutler Pickering Hale and Dorr LLP

(57) ABSTRACT

Tetrasubstituted benzenes that act as modulators of gamma secretase and their use in the treatment of one or more symptoms of treating neurodegenerative disorders, e.g., Alzheimer's disease, are described.

33 Claims, 1 Drawing Sheet

(56) References Cited

U.S. PATENT DOCUMENTS

| | | |
|---|---|---|
| 2007/0265345 A1 | 11/2007 | Chaudhari et al. |
| 2008/0194836 A1 | 8/2008 | Gharbaoui et al. |
| 2008/0207900 A1 | 8/2008 | Kimura et al. |
| 2009/0004508 A1 | 1/2009 | Funaki et al. |
| 2009/0131384 A1 | 5/2009 | Uysal et al. |
| 2010/0069360 A1 | 3/2010 | Revesz et al. |
| 2010/0190766 A1 | 7/2010 | Moser et al. |
| 2010/0331381 A1 | 12/2010 | Frank et al. |
| 2011/0003795 A1 | 1/2011 | Frank et al. |
| 2011/0008259 A1 | 1/2011 | Binch et al. |
| 2011/0092554 A1 | 4/2011 | Chesworth et al. |
| 2011/0152315 A1 | 6/2011 | Ulven et al. |
| 2012/0010201 A1 | 1/2012 | Gobbi et al. |
| 2012/0046307 A1 | 2/2012 | Engel et al. |

FOREIGN PATENT DOCUMENTS

| | | |
|---|---|---|
| DE | 4239150 A1 | 5/1994 |
| DE | 19530204 A1 | 2/1997 |
| DE | 19530205 A1 | 2/1997 |
| EP | 184752 A2 | 6/1986 |
| EP | 254971 A1 | 2/1988 |
| EP | 260924 A1 | 3/1988 |
| EP | 275354 A1 | 7/1988 |
| EP | 382375 A2 | 8/1990 |
| EP | 405602 A1 | 1/1991 |
| EP | 405782 A1 | 1/1991 |
| EP | 415889 A2 | 3/1991 |
| EP | 434517 A2 | 6/1991 |
| EP | 582154 A1 | 2/1994 |
| EP | 716082 A1 | 6/1996 |
| EP | 757669 A1 | 2/1997 |
| EP | 759425 A2 | 2/1997 |
| EP | 802186 A1 | 10/1997 |
| EP | 1255726 A2 | 11/2002 |
| EP | 1484304 A1 | 12/2004 |
| EP | 01604970 A1 | 12/2005 |
| EP | 01650183 A1 | 4/2006 |
| EP | 1764075 A1 | 3/2007 |
| EP | 01808432 A1 | 7/2007 |
| EP | 1847524 A1 | 10/2007 |
| EP | 01849762 A1 | 10/2007 |
| EP | 1882475 A1 | 1/2008 |
| FR | 6978 M | 5/1969 |
| FR | 2473507 A1 | 7/1981 |
| FR | 2736053 A1 | 1/1997 |
| FR | 2830861 A1 | 4/2003 |
| GB | 2051043 A | 1/1981 |
| GB | 2065654 A | 7/1981 |
| GB | 2253624 A | 9/1992 |
| GB | 2255092 A | 10/1992 |
| JP | 06287578 A | 10/1994 |
| JP | 7247235 A | 9/1995 |
| JP | 08003173 A | 1/1996 |
| JP | 3598327 | 9/2004 |
| WO | WO-95/01326 A1 | 1/1995 |
| WO | WO-95/29682 A1 | 11/1995 |
| WO | WO-9616656 A1 | 6/1996 |
| WO | WO-96/22770 A1 | 8/1996 |
| WO | WO-97/01335 A1 | 1/1997 |
| WO | WO-97/01536 A1 | 1/1997 |
| WO | WO-97/27847 A1 | 8/1997 |
| WO | WO-97/27857 A1 | 8/1997 |
| WO | WO-97/28115 A1 | 8/1997 |
| WO | WO-97/28137 A1 | 8/1997 |
| WO | WO-97/28149 A1 | 8/1997 |
| WO | WO-98/00134 A1 | 1/1998 |
| WO | WO-9827061 A1 | 6/1998 |
| WO | WO-98/31697 A1 | 7/1998 |
| WO | WO-99/63983 A1 | 12/1999 |
| WO | WO-00/05221 A1 | 2/2000 |
| WO | WO-0018725 A1 | 4/2000 |
| WO | WO-00/31053 A1 | 6/2000 |
| WO | WO-01/36365 A2 | 5/2001 |
| WO | WO-01/58852 A2 | 8/2001 |
| WO | WO-01/87826 A1 | 11/2001 |
| WO | WO-02/13824 A1 | 2/2002 |
| WO | WO-02051805 A1 | 7/2002 |
| WO | WO-02/074743 | 9/2002 |
| WO | WO-02/081428 | 10/2002 |
| WO | WO-03/042153 A1 | 5/2003 |
| WO | WO-03/074050 A1 | 9/2003 |
| WO | WO-2004048335 A2 | 6/2004 |
| WO | WO-2004/064771 A2 | 8/2004 |
| WO | WO-2004/065354 A1 | 8/2004 |
| WO | WO-2004074232 A1 | 9/2004 |
| WO | WO-2004/087159 A1 | 10/2004 |
| WO | WO-2004/096747 A1 | 11/2004 |
| WO | WO-2004/096781 A1 | 11/2004 |
| WO | WO-2004/110350 A2 | 12/2004 |
| WO | WO-2005/000309 A2 | 1/2005 |
| WO | WO-2005/037763 A1 | 4/2005 |
| WO | WO-2005/054213 A1 | 6/2005 |
| WO | WO-2005054193 A1 | 6/2005 |
| WO | WO-2005058881 A1 | 6/2005 |
| WO | WO-2005/065683 A1 | 7/2005 |
| WO | WO-2005/094810 A2 | 10/2005 |
| WO | WO-2005/097759 A1 | 10/2005 |
| WO | WO-2005/097775 A1 | 10/2005 |
| WO | WO-2005/108362 A1 | 11/2005 |
| WO | WO-2005/110963 A1 | 11/2005 |
| WO | WO-2005/115990 A1 | 12/2005 |
| WO | WO-2006/004030 A1 | 1/2006 |
| WO | WO-2006/008558 A1 | 1/2006 |
| WO | WO-2006/021441 A1 | 3/2006 |
| WO | WO-2006/025783 A1 | 3/2006 |
| WO | WO-2006/044732 A2 | 4/2006 |
| WO | WO-2006041874 A2 | 4/2006 |
| WO | WO-2006043064 A1 | 4/2006 |
| WO | WO-2006/045554 A1 | 5/2006 |
| WO | WO-2006/046575 A1 | 5/2006 |
| WO | WO-2006/048219 A1 | 5/2006 |
| WO | WO-2006/123165 A2 | 11/2006 |
| WO | WO-2007/039736 A1 | 4/2007 |
| WO | WO-2007/056366 A2 | 5/2007 |
| WO | WO-2007/056497 A1 | 5/2007 |
| WO | WO-2007/058304 A1 | 5/2007 |
| WO | WO-2007/058305 A1 | 5/2007 |
| WO | WO-2007/075895 A2 | 7/2007 |
| WO | WO-2007/102580 A1 | 9/2007 |
| WO | WO-2007/110667 A1 | 10/2007 |
| WO | WO-2007/116228 A1 | 10/2007 |
| WO | WO-2007/124394 A1 | 11/2007 |
| WO | WO-2007/125364 A1 | 11/2007 |
| WO | WO-2007/140174 A2 | 12/2007 |
| WO | WO-2007/140183 A1 | 12/2007 |
| WO | WO-2008/013213 A1 | 1/2008 |
| WO | WO-2008/039882 A1 | 4/2008 |
| WO | WO-2008/108378 A2 | 9/2008 |
| WO | WO-2008/137102 A2 | 11/2008 |
| WO | WO-2010070076 A1 | 6/2010 |
| WO | WO-2010086613 A1 | 8/2010 |
| WO | WO-2010/112211 A1 | 10/2010 |
| WO | WO-2010/138901 A1 | 12/2010 |
| WO | WO-2010/148422 A1 | 12/2010 |
| WO | WO-2011/041686 A1 | 4/2011 |
| WO | WO-2011079315 A1 | 6/2011 |
| WO | WO-2011/146855 A1 | 11/2011 |
| WO | WO-2012019093 A1 | 2/2012 |

OTHER PUBLICATIONS

Citron et al., "Mutant presenilins of Alzheimer's disease increase production of 42-residue amyloid .beta.-protein in both transfected cells and transgenic mice," Nature, vol. 2, No. 1, Jan. 1997, 8 pages.

Couch et al., "Studies on the reactivity of CDDO, a promising new chemopreventive and chemotherapeutic agent: implications for a molecular mechanism of action," Bioorganic and Medicinal Chem. Letters, 2005, 5 pages.

Damasio, Antonio R., Alzheimer's Disease and Related Dementias, Cecil Textbook of Medicine, 20th edition (1996), vol. 2, pp. 1992-1996.

(56) References Cited

OTHER PUBLICATIONS

Ebner et al., "Disposition and chemical stability of telmisartan 1-0-Acylglucuronide," Drug Metabolism and Disposition, vol. 27, No. 10, 1999, pp. 1143-1149.
FDA mulls drug to slow late-stage Alzheimer's [online], [retrieved on Sep. 23, 2003]. Retrieved from the internet, URL: http://www.cnn.com/2003/HEALTH/conditions/09/24/alzheimers.drug.ap/indez.-html, pp. 1 and 2.
Kolesnikov et al. "Factor VIIa inhibitors: Improved pharmacokinetic parameters," Bioorg. Med. Chem. 16 (2006) pp. 2243-2246.
Lanz et al., "Demonstration of a common artifact in immunosorbent assays of brain extracts: Development of a solid-phase extraction protocol to enable measurement of amyloid-.beta. from wild-type rodent brain," J. Neuro. Methods., 2006, 11 pages.
Lanz et al., "Solid-phase extraction enhances detection of beta-amyloid peptides in plasma and enables A.beta. quantification following passive immunization with A.beta. antibodies,", J. Neuro. Methods, 2008, 7 pages.
Lazorthes et al., "Advances in Drug Delivery Systems and Applications in Neurosurgery," Advances and Technical Standards in Neurosurgery, vol. 18, 1991, 52 pages.
Miller et al., "Synthesis of 2,6-Bis (trifluoromethyl) phenol and Its Elaboration Into "Metabolism-Resistant". Analogs of Tebufelone," J. Org. Chem 1993, vol. 53, No. 9, 4 pages.
Minto et al., "Pharmacokinetics and Pharmacodynamics of Nandrolone Esters in Oil Vehicle: Effects of Ester, Injection Site and Injection Volume," J. Pharmacology, vol. 281, No. 1, Apr. 1997, pp. 93-102.
Ogino, Akio et al. "Structure-Activity Study of Antiulcerous and Antiinflammatory Drugs by Discriminant Analysis." Journal of Medicinal Chemistry. Published 1980, vol. 23, No. 4, pp. 437-444.
Ommaya et al., "Implantable Devices for Chronic Access and Drug Delivery to the Central Nervous System," Cancer Drug Deliver, vol. 1, No. 2, 1984, pp. 169-179.
Peretto et al., "Synthesis and Biological Activity of Flurbiprofen Analogues as Selective Inhibitors of .beta.-Amyloid1-42 Secretion," J. Med. Chem., 2005, 48, pp. 5705-2720.
Pulley, Shon R. et al. "Synthesis of arylglycines via the Doetz benzannulation reaction" Tetrahedron Letters, 46(52), 9039-9042 (2005).
Seubert et al., "Isolation and quantification of soluble Alzheimer's B-peptide from biological fluids," Nature, vol. 359, No. 6393, Sep. 24, 1992, 5 pages.
Stahl et al., "Handbook of Pharmaceutical Salts: Properties, Selection, and Use," 2d Ed., International Union of Pure and Applied Chemistry, Published jointly by VHCA and WILEY-VCH, 2011.
Stock et al., "The geminal dimethyl analogue of Flourbiprofen as a novel A.beta.42 inhibitor and potential Alzheimer's disease modifying agent," Bioorganic and Medicinal Chem. Letters, 2006, 5 pages.
Sugiyama, Makoto. "Correlation Between Anti-Inflammatory Activity and Peropheral Drug in Rat After Administration of Bi-Phenylylacetic Acid Derivatives." Journal of Pharmacobio-Dynamics. Mar. 1979, vol. 2, No. 2. pp. 67-73.
Tamura. Yasumitsu et al. "Nonsteriodal Antiiflammatory Agents. 1. 5-Alkoxy-3-biphenylyacetic Aceids and Related Compounds as a NEw Potential Antiiflammatory Agents." Journal of Medicinal Chemistry. Published 1977, vol. 20, No. 5 pp. 709-713.
Thompson et al., "Synthesis and evaluation of succinoyl-caprolactam .gamma.-secretase inhibitors," Bioorganic and Medicinal Chem. Letters, 2006, pp. 2357-2363.
Vasiliou, S. 12th International Conference on Alzheimer's Disease (ICAD) 2009: Emerging Therapeutic Strategies, Diagnostic Techniques and Imaging Technologies for AD. Drugs of the Future. Jul. 2009. vol. 34, No. 7 pp. 587-597.
Vassar et al., ".beta.-Secretase Cleavage of Alzheimer's Amyloid Precursor Protein by the Transmembrane Aspartic Protease BACE," Science, Oct. 22, 1999, No. 5440 vol. 286, 9 pages.
Wang et al., "The Profile of Soluble Amyloid .beta. Protein in Cultured Cell Media," J. Bio. Chem., vol. 271, No. 50, Dec. 13, 1996, 9 pages.
Wiemers et al., "Pregeneration, Spectroscopic Detection, and Chemical Reacitivity of (Trifluoromethyl)copper, an Elusive and Comples Species," J. Am. Chem. Soc., Feb. 19, 1986, vol. 108, No. 4, 4 pages.
Wright et al., "Polymers Containing Ring-Strain Energy. 1. New Monomers and Polymers Based on Cyclopropane, Norbornadiene, and Quadricyclane," J. Org. Chem. 1993, vol. 58, No. 15, 6 pages.
Ishii, et al., "Basic Intramolecular Acylation. Synthesis of 2-Aryl-1-tetralones Bearing Isopropoxy or Benzylozy Groups, Synthetic Key Intermediates for Phenolic Antileukaemic Benzo[c]phenanthridine Alkaloids, from 2,4-Diarylbutyric Acid Derivatives", *J. Chem. Society, Perkin Transactions*1, p. 2415-2420, No Month Given 1987, 6 pages.
Zbinden, et al., "Dose-dependent Antithrombotic Activity of an Orally Active Tissue Factor/Factor VIIa Inhibitor without Concomitant Enhancement of Bleeding Propensity", Bioorganic & Medicinal Chemistry, 14:5357-5369, Apr. 18, 2006, 13 pages.
Boger, et al., "Synthesis of (R)-(4-Methoxy-3,5-dihydroxyphenyl)glycine Derivatives: The Central Amino Acid of Vancomycin and Related Agents", J. Organic Chemistry, 61:3561-3565, May 17, 1996, 5 pages.
Pearson, et al., "Synthetic Studies on the BCDF Ring System of Ristocetin A via Ruthenium-promoted $S_NAr$ Reaction", Tetrahedron Letters, 42:8765-8768, Dec. 10, 2001, 4 pages.
Nie, et al., "Synthesis of Metabolites of 6-fluoro-DOPA", Journal of Fluorine Chemistry, 55(3):259-269, Feb. 1991, 11 pages.
Ishii, et al., Studies on the Chemical Constituents of Rutaceous Plants. L.1 Development of a Versatile Method for the Synthesis of Antitumor-Active Benzo[c]phenanthridine Alkaloids. (2).1) Preparation of 2-Aryl-1-tetralone Derivatives, Chem. Pharm. Bull., 31(9):3039-3055, No Month Given 1983, 17 pages.

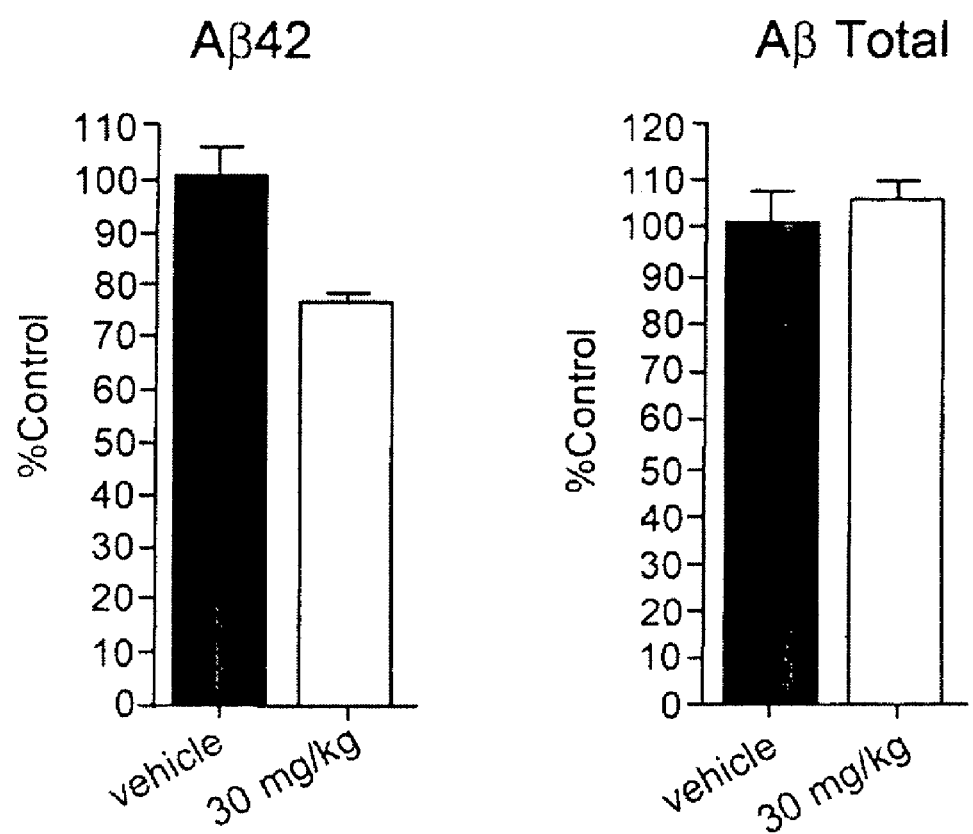

TETRASUBSTITUTED BENZENES

RELATED APPLICATION INFORMATION

This application is a continuation of U.S. patent application Ser. No. 13/486,201, filed Jun. 1, 2012, now U.S. Pat. No. 8,367,863, which is a continuation of U.S. patent application Ser. No. 12/341,201, filed Dec. 22, 2008, now U.S. Pat. No. 8,217,064, which claims priority to U.S. provisional application Ser. No. 61/015,605, filed Dec. 20, 2007, and to U.S. provisional application Ser. No. 61/109,665, filed Oct. 30, 2008, all of which are herein incorporated by reference.

BACKGROUND

Alzheimer's disease (AD) is the most prevalent form of dementia. It is a neurodegenerative disorder that is associated (though not exclusively) with aging. The disorder is clinically characterized by a progressive loss of memory, cognition, reasoning and judgment that leads to an extreme mental deterioration and ultimately death. The disorder is pathologically characterized by the deposition of extracellular plaques and the presence of neurofibrillary tangles. These plaques are considered to play an important role in the pathogenesis of the disease.

These plaques mainly comprise of fibrillar aggregates of β-amyloid peptide (Aβ), which are products of the amyloid precursor protein (APP), a 695 amino-acid protein. APP is initially processed by β-secretase forming a secreted peptide and a membrane bound C99 fragment. The C99 fragment is subsequently processed by the proteolytic activity of γ-secretase. Multiple sites of proteolysis on the C99 fragment lead to the production of a range of smaller peptides (Aβ 37-42 amino acids). N-terminal truncations can also be found e.g. Aβ (4-42, 11-42) for convenience Aβ40 and Aβ42 as used herein incorporates these N-terminal truncated peptides. Upon secretion, the Aβ peptides initially form soluble aggregates which ultimately lead to the formation of insoluble deposits and plaques. Aβ42 is believed to be the most neurotoxic, the shorter peptides have less propensity to aggregate and form plaques. The Aβ plaques in the brain are also associated with cerebral amyloid angiopathy, hereditary cerebral hemorrhage with amyloidosis, multi infarct dementia, dementia pugilistisca, inclusion body myositis and Down's Syndrome.

γ-secretase is an association of four proteins: Aph1, Nicastrin, Presenillin and Pen-2 (review De Strooper 2003, Neuron 38, 9). Aβ42 is selectively increased in patients carrying particular mutations in one of these components, presenilin. These mutations are correlated with early onset a familial AD. Inhibition of γ-secretase resulting in the lowering of Aβ42 is a desirable activity for the pharmaceutical community and numerous inhibitors have been found, e.g., Thompson et al (Bio. Org. and Med. Chem. Letters 2006, 16, 2357-63), Shaw et al (Bio. Org. and Med. Chem. Letters 2006, 17, 511-16) and Asberom et al (Bio. Org. and Med. Chem. Letters 2007, 15, 2219-2223). Inhibition of γ-secretase though is not without side-effects, some of which are due to the γ-secretase complex processing substrates other than C99, for e.g. Notch. A more desirable approach is to modulate the proteolytic activity of the γ-secretase complex in a manner that lowers Aβ42 in favor of shorter peptides without significantly affecting the activity of γ-secretase on substrates such as Notch.

Compounds that have shown modulation of γ-secretase include certain non-steroidal, anti-inflammatory drugs (NSAIDs), for example Flurbiprofen, (Stock et al Bio. Org. and Med. Chem. Letters 2006, 16, 2219-2223). Other publications that disclose agents said to reduce Aβ42 through the modulation of γ-secretase include: WO 04/074232, WO 05/054193, Perreto et al Journal of Medicinal Chemistry 2005, 48 5705-20, WO05/108362, WO 06/008558, WO 06/021441, WO 06/041874, WO 06/045554, WO04110350, WO 06/043964, WO 05/115990, EP1847524, WO 07/116, 228, WO 07/110,667, WO 07/124,394, EP184752, EP 01849762, WO 07/125,364.

SUMMARY

Described herein are tetrasubstituted benzene compounds of formulas (I) and (II) and pharmaceutically acceptable salts thereof

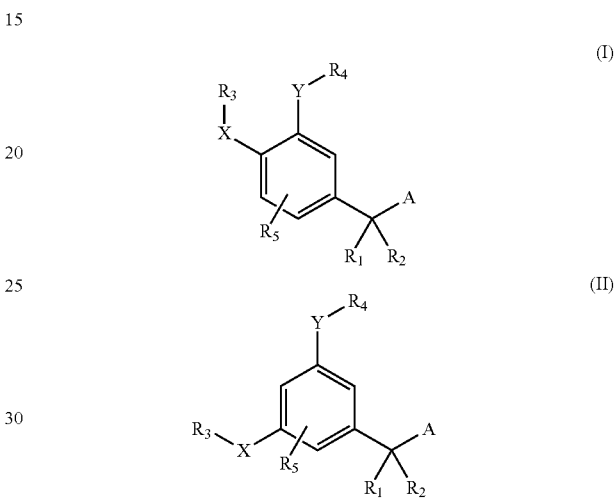

Wherein:
A is $CO_2H$ or tetrazole;
$R_1$ and $R_2$ are independently selected from: (a) H, (b) F, (c) OH, (d) $OR_6$, (e) $SR_6$, (f) $NHR_7$, (g) $N(R_7)_2$ (h) $NHC(O)R_6$, (i) $NHCO_2R_6$, (j) ($C_2$-$C_6$)alkyl, (k) ($C_0$-$C_3$)alkyl-($C_3$-$C_7$)cycloalkyl, (l) $C_1$-$C_6$ alkyl that is independently interrupted by one or more —O—, —S—, —S(O)—, or —S(O)$_2$— groups, (m) ($C_3$-$C_7$)cycloalkyl, (n) ($C_0$-$C_3$)alkyl-($C_3$-$C_7$)cycloalkyl, (o) heterocycloalkylalky and (p) $(CH_2)_nQ$ wherein n=0-2 and wherein Q is a mono- or bicyclic aromatic or heteroaromatic ring system having 5 to 10 ring atoms independently selected from C, N, O and S, provided that not more than 3 ring atoms in any single ring are other than C, and wherein Q is optionally independently substituted with up to 3 groups selected from alkyl, halogen, $CF_3$, OH, $OCF_3$, alkoxy, $OCH_2CH_2OCH_3$, $NH_2$, alkylamino, dialkylamino, morpholino, CN, $NO_2$, alkylthio and alkylsulfonyl,
and wherein each alkyl or cycloalkyl of $R_1$ and $R_2$ is optionally independently substituted with one or more halo, hydroxy, oxo, cyano, $CF_3$, $C_1$-$C_4$ alkyl,
provided that both $R_1$ and $R_2$ are not H,
or
$R_1$ and $R_2$ are taken together to form a 3-7 membered cycloalkyl or heterocycloalkyl ring which is optionally independently singly or multiply substituted with halo, hydroxy, oxo, cyano, $CF_3$, $C_1$-$C_4$ alkyl,
or
$R_1$ and $R_2$ are taken together to form a 3-7 membered cycloalkyl ring substituted with $R_{20}$ and $R_{21}$ where $R_{20}$ and $R_{21}$ are taken together to form a 3-7 membered cycloalkyl ring wherein each cycloalkyl is optionally independently singly or multiply substituted with halo, hydroxy, oxo, cyano, $CF_3$, $C_1$-$C_4$ alkyl $R_6$ is selected from:
  (a) $C_1$-$C_6$ alkyl optionally and independently interrupted by one or more —O—, —S—, —S(O), or —S(O)$_2$— groups,
  (b) ($C_3$-$C_7$)cycloalkyl,
  (c) ($C_0$-$C_3$)alkyl-($C_3$-$C_7$)cycloalkyl, (d) heterocycloalkylalky and
  (e) $(CH_2)_nQ$ wherein n=0-2 and wherein Q is a mono- or bicyclic aromatic or heteroaromatic ring system having 5 to 10 ring atoms independently selected from C, N, O and S, provided that not more than 3 ring atoms in any single ring are other than C, and wherein Q is optionally independently substituted with up to 3 groups selected from alkyl, halogen, $CF_3$, OH, $OCF_3$, alkoxy, $OCH_2CH_2OCH_3$, $NH_2$, alkylamino, dialkylamino, morpholino, CN, $NO_2$, alkylthio and alkylsulfonyl;

$R_7$ is independently chosen from alkyl, alkoxyethyl, cycloalkyl, cycloalkylalkyl, heterocycloalkylalkyl or $(CH_2)_nQ$, wherein n=0-2 and wherein Q is a mono or bicyclic aromatic or heteroaromatic ring system having 5 to 10 ring atoms independently selected from C, N, O and S, provided that not more than 3 ring atoms in any single ring are other than C and wherein Q is optionally substituted with up to 3 groups independently selected from alkyl, halogen, $CF_3$, OH, $OCF_3$, alkoxy, $OCH_2CH_2OCH_3$, $NH_2$, alkylamino, dialkylamino, morpholino, CN, $NO_2$, alkylthio, alkylsulfonyl; or in the case when two $R_7$ are attached to the same N and are both alkyl, they can be taken together to form a 5-membered or 6-membered ring optionally containing O, S, N(H) or N-alkyl;

X is a bond or a divalent linking group selected from —O—, —OCH$_2$—, —OCH(R$_7$)—, —OCH$_2$CH$_2$—, —CH$_2$—, —C(O)—, —CH═CH—, —CH$_2$CH$_2$—, —CH$_2$O—, —CH$_2$OCH$_2$—, —CH$_2$CH$_2$O—, —S—, —SCH$_2$—, CH$_2$S—, —CH$_2$SCH$_2$—, —C(O)NH—, —C(O)N(R$_7$)—, —NHC(O)—, —N(R$_7$)C(O)—, —S(O)—, —S(O)$_2$—, —S(O)$_2$N(H)—, —S(O)$_2$N(R$_7$)—, —N(H)S(O)$_2$—, —N(R$_7$)S(O)$_2$— wherein the point of attachment of divalent linking groups, X, to $R_3$ in the Formulas I and II is to the right;

Y is a bond or a divalent linking group selected from —O—, —OCH$_2$—, —OCH(R$_7$), —OCH$_2$CH$_2$—, —CH$_2$—, —C(O)—, —CH═CH—, —CH$_2$CH$_2$—, —CH$_2$O—, —CH$_2$OCH$_2$—, —CH$_2$CH$_2$O—, —S—, —SCH$_2$—, CH$_2$S—, —CH$_2$SCH$_2$—, —C(O)NH—, —C(O)N(R$_7$)—, —NHC(O)—, —N(R$_7$)C(O)—, —S(O)—, —S(O)$_2$—, —S(O)$_2$N(H)—, —S(O)$_2$N(R$_7$)—, —N(H)S(O)$_2$—, —N(R$_7$)S(O)$_2$— wherein the point of attachment of divalent linking groups, Y, to $R_4$ in the Formulas I and II is to the right;

$R_3$ is (a) $C_1$-$C_7$ alkyl optionally and independently interrupted by one or more —O—, —S—, —S(O)—, and —S(O)$_2$— groups,
  (b) ($C_0$-$C_3$)alkyl-($C_3$-$C_7$)cycloalkyl,
  (c) heterocycloalkylalkyl, or
  (d) a group Z, wherein Z is a mono- or bi-cyclic ring system having 3 to 10 ring atoms independently selected from C, N, O and S, provided that not more than 3 ring atoms in any single ring are other than C, said ring system optionally bearing up to 3 substituents independently selected from halogen, $R_6$, $CF_3$, CN, $NO_2$, OH, C1-C4 alkoxy, aryloxy, heteroaryloxy, $OCH_2CH_2OCH_3$, $OC(O)R_6$, $OC(O)OR_6$, $OC(O)NHR_7$, $OC(O)N(R_7)_2$, $SR_6$, $S(O)R_6$, $S(O)_2R_6$, $S(O)_2NHR_7$, $S(O)_2N(R_7)_2$, $NHR_7$, $N(R_7)_2$, $NHC(O)R_6$, $N(R_7)C(O)R_6$, $NHC(O)OR_6$, $N(R_7)C(O)OR_6$, $N(R_7)C(O)NH(R_7)$, $N(R_7)C(O)NH(R_7)_2$, $C(O)NH_2$, $C(O)NHR_7$, $C(O)N(R_7)_2$, $CO_2H$, $CO_2R_6$, $COR_6$. In the case where $R_3$ is a mono- or bi-cyclic ring system having 5 to 10 ring atoms, the attachment site may be either at a carbon atom or a nitrogen atom of the mono- or bi-cyclic ring system provided that only three bonds are made to nitrogen;

$R_4$ is a (a) $C_1$-$C_7$ alkyl group optionally and independently interrupted by one or more —O—, —S—, —S(O)—, or —S(O)$_2$— groups,
  (b) ($C_0$-$C_3$)alkyl-($C_3$-$C_7$)cycloalkyl,
  (c) heterocycloalkylalkyl or
  (d) a group Z, wherein Z is a mono- or bi-cyclic ring system having 5 to 10 ring atoms independently selected from C, N, O and S, provided that not more than 3 ring atoms in any single ring are other than C, said ring system optionally bearing up to 3 substituents independently selected from halogen, $R_6$, $CF_3$, CN, $NO_2$, OH, C1-C4 alkoxy, aryloxy, heteroaryloxy, $OCH_2CH_2OCH_3$, $OC(O)R_6$, $OC(O)OR_6$, $OC(O)NHR_7$, $OC(O)N(R_7)_2$, $SR_6$, $S(O)R_6$, $S(O)_2R_6$, $S(O)_2NHR_7$, $S(O)_2N(R_7)_2$, $NHR_7$, $N(R_7)_2$, $NHC(O)R_6$, $N(R_7)C(O)R_6$, $NHC(O)OR_6$, $N(R_7)C(O)OR_6$, $N(R_7)C(O)NH(R_7)$, $N(R_7)C(O)NH(R_7)_2$, $C(O)NH_2$, $C(O)NHR_7$, $C(O)N(R_7)_2$, $CO_2H$, $CO_2R_6$, $COR_6$. In the case where $R_4$ is a mono- or bi-cyclic ring system having 5 to 10 ring atoms, the attachment site may be either at a carbon atom or a nitrogen atom of the mono- or bi-cyclic ring system provided that only three bonds are made to nitrogen; and $R_5$ is selected from: $NO_2$, $NH_2$, aryl, heteroaryl, F, Cl, Br, CN, OH, $C_1$-$C_4$ alkoxy, $SR_6$, $S(O)_2R_6$, $S(O)_2N(R_7)_2$, ($C_1$-$C_4$) alkyl, ($C_0$-$C_3$)alkyl-($C_3$-$C_7$) cycloalkyl, —O—($C_0$-$C_3$)alkyl-($C_3$-$C_7$)cycloalkyl, and ($C_2$-$C_4$) alkynyl, wherein each alkyl or cycloalkyl is optionally independently substituted with one or more halo, hydroxy, oxo, cyano, $CF_3$, $C_1$-$C_4$ alkyl provided that one or both of $R_3$ and $R_4$ is Z.

In one embodiment $R_1$ and $R_2$ are taken together form a 3-7 membered cycloalkyl or heterocycloalkyl ring. In another embodiment $R_1$ is hydrogen and $R_2$ is F, $R_6$, OH, $OR_6$, $SR_6$, $NHR_7$, $N(R_7)_2$ $NHC(O)R_6$, $NHCO_2R_6$ wherein $R_6$ and $R_7$ are as defined previously. In a further embodiment $R_1$ is hydrogen and $R_2$ is $R_6$, $OR_6$ or $SR_6$. In an additional embodiment $R_1$ is hydrogen and $R_2$ is alkyl, alkoxy or thioalkyl. In another embodiment $R_1$ is hydrogen and $R_2$ is $R_6$. In a further embodiment $R_1$ is hydrogen and $R_2$ is C1-C4 alkyl.

In one embodiment X is a bond. In another embodiment X is a divalent linking group selected from —O—, —OCH$_2$—, —OCH(R$_7$)—, —OCH$_2$CH$_2$—, —CH$_2$—, —C(O)—, —CH═CH—, —CH$_2$CH$_2$—, —CH$_2$O—, —CH$_2$OCH$_2$—, —CH$_2$CH$_2$O—, —S—, —SCH$_2$—, CH$_2$S—, —CH$_2$SCH$_2$—, —C(O)NH—, —C(O)N(R$_7$)—, —NHC(O)—, —N(R$_7$)C(O)—, —S(O)—, —S(O)$_2$—, S(O)$_2$N(H)—, —S(O)$_2$N(R$_7$)—, —N(H)S(O)$_2$—, —N(R$_7$)S(O)$_2$— wherein the point of attachment of divalent linking groups, X, to $R_3$ in the Formulas I and II is to the right. In another embodiment X is —O—, —OCH$_2$—, —OCH(R$_7$)—, CH$_2$O—, —S—, —S(O)$_2$—, —S(O)$_2$N(H)—, —S(O)$_2$N(R$_7$)—, —C(O)NH— or —C(O)N(R$_7$)—. In a further embodiment X is —O—, —S(O)$_2$—, —S(O)$_2$N(H)— or —S(O)$_2$N(R$_7$)—. In another embodiment X is —O— or —S(O)$_2$—.

In one embodiment Y is a bond. In another embodiment Y is a divalent linking group selected from —O—, —OCH$_2$—, —OCH(R$_7$)—, —OCH$_2$CH$_2$—, —CH$_2$—, —C(O)—, —CH═CH—, —CH$_2$CH$_2$—, —CH$_2$O—, —CH$_2$OCH$_2$—, —CH$_2$CH$_2$O—, —S—, —SCH$_2$—, CH$_2$S—, —CH$_2$SCH$_2$—, —C(O)NH—, —C(O)N(R$_7$)—, —NHC(O)—, —N(R$_7$)C(O)—, —S(O)—, —S(O)$_2$—, —S(O)$_2$N(H)—, —S(O)$_2$N(R$_7$)—, —N(H)S(O)$_2$—, —N(R$_7$)S(O)$_2$— wherein the point of attachment of divalent linking groups, X, to $R_3$ in the Formulas I and II is to the right. In another embodiment Y is —O—, —OCH$_2$—, —OCH(R$_7$)—

$CH_2O$—, —S—, —$S(O)_2$—, —$S(O)_2N(H)$—, —$S(O)_2N(R_7)$—, —C(O)NH— or —$C(O)N(R_7)$—. In a further embodiment Y is —O—, —$S(O)_2$—, —$S(O)_2N(H)$— or —$S(O)_2N(R_7)$—. In another embodiment Y is —O— or —$S(O)_2$—.

In one embodiment $R_3$ is a C1-C7 alkyl group optionally interrupted by —O—, —S—, —S(O)—, or —$S(O)_2$— groups. In another embodiment $R_3$ is a C1-C7 alkyl group. In a further embodiment $R_3$ is a C1-C4 alkyl group examples include but are not limited to methyl, ethyl, cyclopropylmethyl, trifluoroethyl. In another embodiment $R_3$ is a cycloalkylalkyl group with examples including but not limited to cyclopropylmethyl, cyclobutylmethyl, cyclopentylmethyl and cyclohexylmethyl. In another embodiment $R_3$ is heterocycloalkylalkyl. In another embodiment $R_3$ is a group Z as defined above wherein Z is a mono- or bi-cyclic ring system having 5 to 10 ring atoms independently selected from C, N, O and S, provided that not more than 3 ring atoms in any single ring are other than C, said ring system optionally bearing up to 3 substituents independently selected from halogen, $R_6$, $CF_3$, CN, $NO_2$, OH, $C_1$-$C_4$ alkoxy, aryloxy, heteroaryloxy, $OCH_2CH_2OCH_3$, $OC(O)R_6$, $OC(O)OR_6$, $OC(O)NHR_7$, $OC(O)N(R_7)_2$, $SR_6$, $S(O)R_6$, $S(O)_2R_6$, $S(O)_2NHR_7$, $S(O)_2N(R_7)_2$, $NHR_7$, $N(R_7)_2$, $NHC(O)R_6$, $N(R_7)C(O)R_6$, $NHC(O)OR_6$, $N(R_7)C(O)OR_6$, $N(R_7)C(O)NH(R_7)$, $N(R_7)C(O)NH(R_7)_2$, $C(O)NH_2$, $C(O)NHR_7$, $C(O)N(R_7)_2$, $CO_2H$, $CO_2R_6$, $COR_6$. In the latter embodiment Z comprises mono- or bi-cyclic ring system ring systems that furthermore may be fully saturated, partially saturated or aromatic. Examples of monocyclic ring systems that are fully saturated include but are not limited to 5-6 membered ring systems such as cyclohexyl, cyclopentanyl, piperazinyl, tetrahydrofuranyl and piperidinyl. Examples of monocyclic ring systems that are partially saturated include but are not limited to 5-6 membered ring systems such as cyclohexenyl, cyclopentenyl, dihydrofuranyl and tetrahydropyridinyl. piperidinyl. Examples of monocyclic ring systems that are aromatic include but are not limited to 5-6 membered ring systems such as phenyl, pyridyl, pyrimidyl, pyrrazolyl, thiophene-yl, furanyl, oxadiazolyl, thiadizolyl, triazolyl, oxazolyl and thiazolyl. Examples of bicyclic ring systems that are fully saturated include but are not limited to 9-10 membered bicyclic ring systems such as decalinyl, decahydroquinolinyl and decahydroisoquinolinyl. Examples of bicyclic ring systems that are partially saturated include but are not limited to 9-10 membered bicyclic ring systems such as tetrahydronapthyl, tetrahydroquinolinyl and tetrahydroisoquinolinyl. Examples of bicyclic ring systems that are aromatic include but are not limited to 9-10 membered bicyclic ring systems such as napthyl, indolyl, indazolyl, benzimidazolyl, benzthiadiazolyl and imidazopyridinyl. In one further embodiment the mono- or bi-cyclic ring system ring system comprises up to 2 nitrogen atoms and up to 1 sulfur or oxygen atoms.

In one embodiment $R_4$ is a C1-C7 alkyl group optionally interrupted by —O—, —S—, —S(O)—, or —$S(O)_2$— groups. In another embodiment $R_4$ is a C1-C7 alkyl group. In a further embodiment $R_4$ is a C1-C4 alkyl group examples include but are not limited to methyl, ethyl, cyclopropylmethyl, trifluoroethyl. In another embodiment $R_4$ is a cycloalkylalkyl group with examples including but not limited to cyclopropylmethyl, cyclobutylmethyl, cyclopentylmethyl and cyclohexylmethyl. In another embodiment $R_4$ is heterocycloalkylalkyl. In another embodiment $R_4$ is a group Z as defined above wherein Z is a mono- or bi-cyclic ring system having 5 to 10 ring atoms independently selected from C, N, O and S, provided that not more than 3 ring atoms in any single ring are other than C, said ring system optionally bearing up to 3 substituents independently selected from halogen, $R_6$, $CF_3$, CN, $NO_2$, OH, $C_1$-$C_4$ alkoxy, aryloxy, heteroaryloxy, $OCH_2CH_2OCH_3$, $OC(O)R_6$, $OC(O)OR_6$, $OC(O)NHR_7$, $OC(O)N(R_7)_2$, $SR_6$, $S(O)R_6$, $S(O)_2R_6$, $S(O)_2NHR_7$, $S(O)_2N(R_7)_2$, $NHR_7$, $N(R_7)_2$, $NHC(O)R_6$, $N(R_7)C(O)R_6$, $NHC(O)OR_6$, $N(R_7)C(O)OR_6$, $N(R_7)C(O)NH(R_7)$, $N(R_7)C(O)NH(R_7)_2$, $C(O)NH_2$, $C(O)NHR_7$, $C(O)N(R_7)_2$, $CO_2H$, $CO_2R_6$, $COR_6$. In the latter embodiment Z comprises mono- or bi-cyclic ring system ring systems that furthermore may be fully saturated, partially saturated or aromatic. Examples of monocyclic ring systems that are fully saturated include but are not limited to 5-6 membered ring systems such as cyclohexyl, cyclopentanyl, piperazinyl, tetrahydrofuranyl and piperidinyl. Examples of monocyclic ring systems that are partially saturated include but are not limited to 5-6 membered ring systems such as cyclohexenyl, cyclopentenyl, dihydrofuranyl and tetrahydropyridinyl. piperidinyl. Examples of monocyclic ring systems that are aromatic include but are not limited to 5-6 membered ring systems such as phenyl, pyridyl, pyrimidyl, pyrrazolyl, thiophene-yl, furanyl, oxadiazolyl, thiadizolyl, triazolyl, oxazolyl and thiazolyl. Examples of bicyclic ring systems that are fully saturated include but are not limited to 9-10 membered bicyclic ring systems such as decalinyl, decahydroquinolinyl and decahydroisoquinolinyl. Examples of bicyclic ring systems that are partially saturated include but are not limited to 9-10 membered bicyclic ring systems such as tetrahydronapthyl, tetrahydroquinolinyl and tetrahydroisoquinolinyl. Examples of bicyclic ring systems that are aromatic include but are not limited to 9-10 membered bicyclic ring systems such as napthyl, indolyl, indazolyl, benzimidazolyl, benzthiadiazolyl and imidazopyridinyl. In one further embodiment the mono- or bi-cyclic ring system ring system comprises up to 2 nitrogen atoms and up to 1 sulfur or oxygen atoms.

Other embodiments include compounds of Formulas III, IV, V, and VI and pharmaceutically acceptable salts thereof wherein $R_1$, $R_2$, $R_3$, $R_4$, $R_5$, X, Y and Z are as defined above.

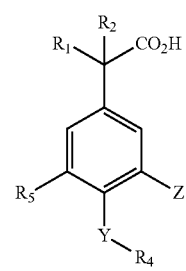

III

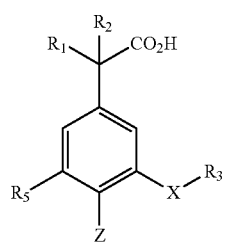

IV

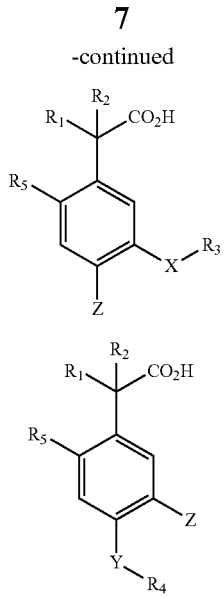

V

VI

Other embodiments include compounds of Formulas VII, VIII, IX, and X and pharmaceutically acceptable salts thereof wherein $R_1$, $R_2$, $R_3$, $R_4$ $R_5$, X, Y and Z are as defined above.

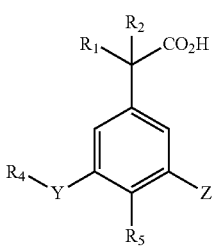

VII

VIII

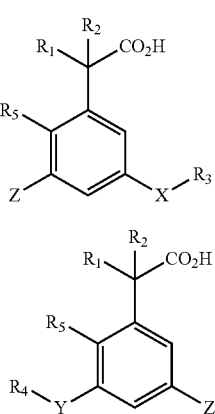

IX

Other embodiments include compounds of Formulas III, IV, V, and VI wherein $R_2$, $R_3$, $R_4$, $R_5$, X, Y and Z are as defined above and $R_1$ is hydrogen. Other embodiments include compounds of Formulas III, IV, V, and VI wherein $R_3$, $R_4$, $R_5$ and Z are as defined above; $R_1$ is hydrogen and $R_2$ is C1-C4 alkyl.

Other embodiments include compounds of Formulas III, IV, V, and VI wherein $R_1$, $R_2$, $R_3$, $R_4$ and $R_5$, and Z are as defined above and X and Y are independently chosen from a bond, —O—, —OCH$_2$—, —C(O)—, —S—, —S(O)$_2$—, —S(O)$_2$N(R$_7$)— and —N(R$_7$)S(O)$_2$—. Other embodiments include compounds of Formulas III, IV, V, and VI wherein $R_1$, $R_2$, $R_3$, $R_4$ and $R_5$, and Z are as defined above and X and Y are independently chosen from a bond, —O—, —S(O)$_2$— and —S(O)$_2$N(R$_7$). Another embodiment comprises compounds of Formulas III, IV, V, and VI wherein $R_1$, $R_2$, $R_3$, $R_4$ and $R_5$, and Z are as defined above and X and Y are independently chosen from a bond, —O— and S(O)$_2$N(R$_7$). A further embodiment comprises compounds of Formulas III, IV, V, and VI wherein $R_1$, $R_2$, $R_3$, $R_4$, $R_5$, and Z are as defined above and X and Y are independently chosen from a bond and —O—.

Other embodiments include compounds of Formulas III, IV, V, and VI wherein $R_1$, $R_2$, $R_5$, X, Y and Z are as defined above and $R_3$ and $R_4$ and are independently chosen from a C1-C7 alkyl optionally and independently interrupted by one or more —O—, —S—, —S(O)—, and —S(O)$_2$— groups, cycloalkylalkyl and heterocycloalkylalkyl. Other embodiments include compounds of Formulas III, IV, V, and VI wherein $R_1$, $R_2$, $R_5$, X, Y and Z are as defined above and $R_3$ and $R_4$ and are independently chosen from $C_1$-$C_4$ alkyl and cyclopropylmethyl. Other embodiments include compounds of Formulas III, IV, V, and VI wherein $R_1$, $R_2$, $R_5$, Z are as defined above and X, Y and are independently chosen from a bond, —S—, —SO2- and —O— and $R_3$ and $R_4$ and are independently chosen from C1-C4 alkyl and cyclopropylmethyl. Other embodiments include compounds of Formulas III, IV, V, and VI wherein $R_1$, $R_2$, $R_5$, X, Y and Z are as defined above and $R_3$ and $R_4$ and are independently chosen from a group Z wherein Z is as defined above.

Other embodiments include compounds of Formulas III, IV, V, and VI wherein $R_1$, $R_2$, $R_3$, $R_4$ and $R_5$, X and Y are as defined above and Z is a phenyl ring bearing up to 3 substituents independently selected from halogen, $R_6$, CF$_3$, CN, NO$_2$, OH, $C_1$-$C_4$ alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH2, C(O)NHR$_7$, C(O)N(R$_7$)$_2$, CO$_2$H, CO$_2$R$_6$, COR$_6$. Other embodiments include compounds of Formulas III, IV, V, and VI wherein $R_1$, $R_2$, $R_3$, $R_4$ and $R_5$, X and Y are as defined above, and Z is a mono- or bi-cyclic ring system having 5 to 10 ring atoms independently selected from C, N, O and S, provided that not more than 3 ring atoms in any single ring are other than C, said ring system optionally bearing up to 3 substituents independently selected from halogen, $R_6$, CF$_3$, CN, NO$_2$, OH, $C_1$-$C_4$ alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH$_2$, C(O)NHR$_7$, C(O)N(R$_7$)$_2$, CO$_2$H, CO$_2$R$_6$, COR$_6$.

Other embodiments include compounds of Formulas III, IV, V, and VI wherein $R_1$, $R_2$, $R_3$, $R_4$ X, Y and Z are as defined above and $R_5$ is NO$_2$, NH$_2$, F, Cl, Br, CN, OH, C1-C4 alkoxy, SR$_6$, S(O)$_2$R$_6$ or S(O)$_2$N(R$_7$)$_2$. Other embodiments include compounds of Formulas III, IV, V, and VI wherein $R_1$, $R_2$, $R_3$, $R_4$ X, Y and Z are as defined above and $R_5$ is aryl or heteroaryl. Other embodiments include compounds of Formulas III, IV, V, and VI wherein $R_1$, $R_2$, $R_3$, $R_4$ X, Y and Z are as defined above and $R_5$ is chlorine or fluorine.

Other embodiments include compounds of Formulas VII, VIII, IX, and X wherein $R_2$, $R_3$, $R_4$, $R_5$, X, Y and Z are as defined above and $R_1$ is hydrogen. Other embodiments include compounds of Formulas VII, VIII, IX, and X wherein $R_3$, $R_4$, $R_5$ and Z are as defined above; $R_1$ is hydrogen and $R_2$ is C1-C4 alkyl.

Other embodiments include compounds of Formulas VII, VIII, IX, and X wherein $R_1$, $R_2$, $R_3$, $R_4$ and $R_5$, and Z are as defined above and X and Y are independently chosen from a bond, —O—, —OCH$_2$—, —C(O)—, —S—, —S(O)$_2$—, —S(O)$_2$N(R$_7$)— and —N(R$_7$)S(O)$_2$—. Other embodiments include compounds of Formulas VII, VIII, IX, and X wherein R$_1$, R$_2$, R$_3$, R$_4$ and R$_5$, and Z are as defined above and X and Y are independently chosen from a bond, —O—, —S(O)$_2$— and —S(O)$_2$N(R$_7$). Other embodiments include compounds of Formulas VII, VIII, IX, and X wherein R$_1$, R$_2$, R$_3$, R$_4$ and R$_5$, and Z are as defined above and X and Y are independently chosen from a bond, —O— and S(O)$_2$N(R$_7$). Other embodiments include compounds of Formulas VII, VIII, IX, and X wherein R$_1$, R$_2$, R$_3$, R$_4$ and R$_5$, and Z are as defined above and X and Y are independently chosen from a bond and —O—.

Other embodiments include compounds of Formulas VII, VIII, IX, and X wherein R$_1$, R$_2$, R$_5$, X, Y and Z are as defined above and R$_3$ and R$_4$ and are independently chosen from a C1-C7 alkyl optionally and independently interrupted by one or more —O—, —S—, —S(O)—, and —S(O)$_2$— groups, cycloalkylalkyl and heterocycloalkylalkyl. Other embodiments include compounds of Formulas III, IV, V, and VI wherein R$_1$, R$_2$, R$_5$, X, Y and Z are as defined above and R$_3$ and R$_4$ and are independently chosen from C$_1$-C$_4$ alkyl and cyclopropylmethyl. Other embodiments include compounds of Formulas VII, VIII, IX, and X wherein R$_1$, R$_2$, R$_5$, Z are as defined above and X, Y and are independently chosen from a bond, —S—, —SO$_2$— and —O— and R$_3$ and R$_4$ and are independently chosen from C1-C4 alkyl and cyclopropylmethyl. Other embodiments include compounds of Formulas VII, VIII, IX, and X wherein R$_1$, R$_2$, R$_5$, X, Y and Z are as defined above and R$_3$ and R$_4$ and are independently chosen from a group Z wherein Z is as defined above.

Other embodiments include compounds of Formulas VII, VIII, IX, and X wherein R$_1$, R$_2$, R$_3$, R$_4$ and R$_5$, X and Y are as defined above and Z is a phenyl ring bearing up to 3 substituents independently selected from halogen, R$_6$, CF$_3$, CN, NO$_2$, OH, C$_1$-C$_4$ alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH2, C(O)NHR$_7$, C(O)N(R$_7$)$_2$, CO$_2$H, CO$_2$R$_6$, COR$_6$. Other embodiments include compounds of Formulas VII, VIII, IX, and X wherein R$_1$, R$_2$, R$_3$, R$_4$ and R$_5$, X and Y are as defined above, and Z is a mono- or bi-cyclic ring system having 5 to 10 ring atoms independently selected from C, N, O and S, provided that not more than 3 ring atoms in any single ring are other than C, said ring system optionally bearing ring bearing up to 3 substituents independently selected from halogen, R$_6$, CF$_3$, CN, NO$_2$, OH, C$_1$-C$_4$ alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH$_2$, C(O)NHR$_7$, C(O)N(R$_7$)$_2$, CO$_2$H, CO$_2$R$_6$, COR$_6$.

Other embodiments include compounds of Formulas VII, VIII, IX, and X wherein R$_1$, R$_2$, R$_4$ X, Y and Z are as defined above and R$_5$ is NO$_2$, NH$_2$, F, Cl, Br, CN, OH, C1-C4 alkoxy, SR$_6$, S(O)$_2$R$_6$ or S(O)$_2$N(R$_7$)$_2$. Other embodiments include compounds of Formulas VII, VIII, IX, and X wherein R$_1$, R$_2$, R$_4$ X, Y and Z are as defined above and R$_5$ is aryl or heteroaryl. Other embodiments include compounds of Formulas VII, VIII, IX, and X wherein R$_1$, R$_2$, R$_4$ X, Y and Z are as defined above and R$_5$ is chlorine or fluorine.

The compounds of formulas I-IX are expected to alter the activity of γ-secretase and are expected to be useful for the treatment of Alzheimer's disease and other neurodegenerative disorders.

In another embodiment A is CO$_2$H.

In another embodiment a compound of formula (I) is selected.

In another embodiment a compound of formula (II) is selected.

In another embodiment a compound of formula (III) is selected.

In another embodiment a compound of formula (IV) is selected.

In another embodiment a compound of formula (V) is selected.

In another embodiment a compound of formula (VI) is selected.

In another embodiment a compound of formula (VII) is selected.

In another embodiment a compound of formula (VIII) is selected.

In another embodiment a compound of formula (IX) is selected.

In another embodiment R$_1$ and R$_2$ are independently selected from: H, (C$_1$-C$_6$)alkyl, (C$_0$-C$_3$)alkyl-(C$_3$-C$_7$)cycloalkyl, C$_1$-C$_6$ alkyl that is independently interrupted by one or more —O—, —S—, —S(O)—, or —S(O)$_2$— groups or heterocycloalkylalkyl wherein each alkyl or cycloalkyl is optionally independently singly or multiply substituted with halo, hydroxy, cyano, oxo, CF$_3$, C$_1$-C$_4$ alkyl provided that R$_1$ and R$_2$ are not H simultaneously or R$_1$ and R$_2$ are taken together to form a 3-7 membered cycloalkyl or heterocycloalkyl ring which are; optionally independently singly or multiply substituted with halo, hydroxy, cyano, CF$_3$, C$_1$-C$_4$ alkyl or R$_1$ and R$_2$ are taken together to form a 3-7 membered cycloalkyl ring substituted with R$_{20}$ and R$_{21}$ where R$_{20}$ and R$_{21}$ are taken together to form a 3-7 membered cycloalkyl ring wherein each cycloalkyl is optionally independently singly or multiply substituted with halo, hydroxy, oxo, cyano, CF$_3$, C$_1$-C$_4$ alkyl.

In another embodiment R$_1$ and R$_2$ are independently selected from: H, (C$_1$-C$_6$)alkyl, (C$_0$-C$_3$)alkyl-(C$_3$-C$_7$)cycloalkyl wherein each alkyl or cycloalkyl is optionally independently singly or multiply substituted with halo, hydroxy, cyano, CF$_3$, C$_1$-C$_4$ alkyl provided that R$_1$ and R$_2$ are not H simultaneously.

In another embodiment R$_1$ and R$_2$ are independently selected from: H, (C$_1$-C$_6$)alkyl, wherein alkyl is optionally independently singly or multiply substituted with halo, hydroxy, oxo, cyano, CF$_3$, C$_1$-C$_4$ alkyl provided that R$_1$ and R$_2$ are not H simultaneously.

In another embodiment R$_1$ and R$_2$ are independently selected from: H, (C$_3$-C$_6$)alkyl, wherein alkyl is optionally independently singly or multiply substituted with halo, hydroxy, oxo, cyano, CF$_3$, C$_1$-C$_4$ alkyl provided that R$_1$ and R$_2$ are not H simultaneously.

In another embodiment R$_1$ and R$_2$ are independently selected from: H, n-propyl, iso-propyl, iso-butyl, n-butyl, iso-pentyl, and n-pentyl wherein alkyl is optionally independently singly or multiply substituted with halo, hydroxy, oxo, cyano, CF$_3$, C$_1$-C$_4$ alkyl provided that R$_1$ and R$_2$ are not H simultaneously.

In another embodiment R$_1$ is H.

In another embodiment R$_1$ is H and R$_2$ is n-propyl.

In another embodiment $R_1$ is H and $R_2$ is iso-butyl.
In another embodiment $R_1$ is H and $R_2$ is n-butyl.
In another embodiment $R_1$ is H and $R_2$ is iso-pentyl.
In another embodiment $R_1$ is H and $R_2$ is n-pentyl.
In another embodiment $R_1$ and $R_2$ are independently selected from: H, $(C_0\text{-}C_3)$alkyl-$(C_3\text{-}C_7)$cycloalkyl wherein cycloalkyl is optionally independently singly or multiply substituted with halo, hydroxy, oxo, cyano, $CF_3$, $C_1\text{-}C_4$ alkyl provided that $R_1$ and $R_2$ are not H simultaneously.

In another embodiment $R_1$ and $R_2$ are independently selected from: H, $(C_0\text{-}C_1)$alkyl-$(C_3\text{-}C_7)$cycloalkyl wherein cycloalkyl is optionally independently singly or multiply substituted with halo, hydroxy, oxo, cyano, $CF_3$, $C_1\text{-}C_4$ alkyl provided that $R_1$ and $R_2$ are not H simultaneously.

In another embodiment $R_1$ and $R_2$ are independently selected from: H, $(C_0\text{-}C_1)$alkyl-$(C_3\text{-}C_5)$cycloalkyl wherein cycloalkyl is optionally independently singly or multiply substituted with halo, hydroxy, oxo, cyano, $CF_3$, $C_1\text{-}C_4$ alkyl provided that $R_1$ and $R_2$ are not H simultaneously.

In another embodiment $R_1$ is H and $R_2$ is selected from cyclopentyl, cyclopropylmethyl and cyclobutylmethyl.

In another embodiment $R_1$ is H and $R_2$ is cyclopentyl.

In another embodiment $R_1$ is H and $R_2$ is cyclopropylmethyl.

In another embodiment $R_1$ is H and $R_2$ is cyclobutylmethyl.

In another embodiment $R_1$ and $R_2$ are taken together to form a 3-7 membered cycloalkyl or heterocycloalkyl ring which are; optionally independently singly or multiply substituted with halo, hydroxy, oxo, cyano, $CF_3$, $C_1\text{-}C_4$ alkyl or
$R_1$ and $R_2$ are taken together to form a 3-7 membered cycloalkyl ring substituted with $R_{20}$ and $R_{21}$ where $R_{20}$ and $R_{21}$ are taken together to form a 3-7 membered cycloalkyl ring wherein each cycloalkyl is optionally independently singly or multiply substituted with halo, hydroxy, oxo, cyano, $CF_3$, $C_1\text{-}C_4$ alkyl.

In another embodiment $R_1$ and $R_2$ are taken together to form a 3-7 membered cycloalkyl or heterocycloalkyl ring which are; optionally independently singly or multiply substituted with halo, hydroxy, oxo, cyano, $CF_3$, $C_1\text{-}C_4$ alkyl.

In another embodiment $R_1$ and $R_2$ are taken together to form a 3-7 membered cycloalkyl ring which are; optionally independently singly or multiply substituted with halo, hydroxy, oxo, cyano, $CF_3$, $C_1\text{-}C_4$ alkyl.

In another embodiment $R_1$ and $R_2$ are taken together to form a cyclopropyl ring.

In another embodiment $R_1$ and $R_2$ are taken together to form a cyclobutyl ring.

In another embodiment $R_1$ and $R_2$ are taken together to form a cyclopentyl ring.

In another embodiment $R_1$ and $R_2$ are taken together to form a cyclohexyl ring.

In another embodiment $R_1$ and $R_2$ are taken together to form a 3-7 membered cycloalkyl ring substituted with $R_{20}$ and $R_{21}$ where $R_{20}$ and $R_{21}$ are taken together to form a 3-7 membered cycloalkyl ring wherein each cycloalkyl is optionally independently singly or multiply substituted with halo, hydroxy, oxo, cyano, $CF_3$, $C_1\text{-}C_4$ alkyl.

In another embodiment $R_1$ and $R_2$ are taken together to form a 3-7 membered cycloalkyl ring substituted on the same carbon atom with $R_{20}$ and $R_{21}$ where $R_{20}$ and $R_{21}$ are taken together to form a 3-7 membered cycloalkyl ring wherein each cycloalkyl is optionally independently singly or multiply substituted with halo, hydroxy, oxo, cyano, $CF_3$, $C_1\text{-}C_4$ alkyl.

In another embodiment $R_1$ and $R_2$ are taken together to form a spiro[2.3]hexane, a spiro[3.3]heptane or a spiro[3.4]octane ring system.

In another embodiment $R_1$ and $R_2$ are taken together to form a spiro[2.3]hexane ring system.

In another embodiment $R_1$ and $R_2$ are taken together to form a spiro[3.3]heptane ring system.

In another embodiment $R_1$ and $R_2$ are taken together to form a spiro[3.4]octane ring system.

In another embodiment $R_1$ and $R_2$ are taken together to form a 5,5-disubstituted spiro[2.3]hexane ring system.

In another embodiment $R_1$ and $R_2$ are taken together to form a 2,2-disubstituted spiro[3.3]heptane ring system.

In another embodiment $R_1$ and $R_2$ are taken together to form a 2,2-disubstituted spiro[3.4]octane ring system.

In another embodiment $R_1$ and $R_2$ are independently selected from: H, F, OH, $OR_6$, $SR_6$, $NHR_7$, $N(R_7)_2$ $NHC(O)R_6$ or $NHCO_2R_6$ provided that $R_1$ and $R_2$ are not H simultaneously.

In another embodiment $R_1$ and $R_2$ if not H are unsubstituted, except that when $R_1$ and $R_2$ are taken with the carbon to which they are attached form $C_3\text{-}C_7$ ring, the ring may be substituted with $R_{20}$ and $R_{21}$, which themselves are unsubstituted.

In another embodiment $R_1$ and $R_2$ if not H are optionally singly or multiply independently substituted with halo, hydroxy, oxo, cyano, $CF_3$, $C_1\text{-}C_4$ alkyl In another embodiment $R_1$ and $R_2$ if not H are singly or multiply independently substituted with halo, hydroxy, oxo, cyano, $CF_3$, $C_1\text{-}C_4$ alkyl In another embodiment $R_6$ is $C_1\text{-}C_6$ alkyl optionally and independently interrupted by one or more —O—, —S—, —S(O)—, or —S(O)$_2$— groups, $(C_3\text{-}C_7)$cycloalkyl, $(C_4\text{-}C_8)$ cycloalkylalkyl, heterocycloalkylalkyl.

In another embodiment $R_6$ is $C_1\text{-}C_6$ alkyl optionally and independently interrupted by one or more —O—, —S—, —S(O)—, or —S(O)$_2$— groups.

In another embodiment $R_6$ $(C_3\text{-}C_7)$cycloalkyl.

In another embodiment $R_6$ is a $(C_0\text{-}C_3)$alkyl-$(C_3\text{-}C_7)$cycloalkyl In another embodiment $R_6$ heterocycloalkylalkyl.

In another embodiment $R_6$ is $(CH_2)_nQ$.

In another embodiment $R_6$ is —$CH_2$-Q.

In another embodiment Q is aryl.

In another embodiment Q is heteroaryl.

In another embodiment Q is monocyclic heteroaryl.

In another embodiment Q is bicyclic heteroaryl.

In another embodiment X is a bond or a divalent linking group selected from —O—, —OCH$_2$—, —OCH(R$_7$)—, —OCH$_2$CH$_2$—, —CH$_2$—, —C(O)—, —CH=CH—, —CH$_2$CH$_2$—, —CH$_2$O—, —CH$_2$OCH$_2$—, —CH$_2$CH$_2$O—, —S—, —SCH$_2$—, CH$_2$S— or —CH$_2$SCH$_2$—.

In another embodiment X is a bond or a divalent linking group selected from —O—, —OCH$_2$—, —OCH(R$_7$)—, —OCH$_2$CH$_2$—, —CH$_2$O—, —CH$_2$OCH$_2$—, or —CH$_2$CH$_2$O.

In another embodiment X is a bond or a divalent linking group selected from —CH$_2$—, —C(O)—, —CH=CH— or —CH$_2$CH$_2$—

In another embodiment X is a bond or a divalent linking group selected from —S—, —SCH$_2$—, CH$_2$S— or —CH$_2$SCH$_2$—.

In another embodiment X is a bond or a divalent linking group selected from —O— or —S—.

In another embodiment X is a bond.

In another embodiment X is the divalent linking group —O—.

In another embodiment X is the divalent linking group —S—.

In another embodiment Y is a bond or a divalent linking group selected from —O—, —OCH$_2$—, —OCH(R$_7$)—, —OCH$_2$CH$_2$—, —CH$_2$—, —C(O)—, —CH=CH—, —CH$_2$CH$_2$—, —CH$_2$O—, —CH$_2$OCH$_2$—, —CH$_2$CH$_2$O—, —S—, —SCH$_2$—, CH$_2$S— or —CH$_2$SCH$_2$—.

In another embodiment Y is a bond or a divalent linking group selected from —O—, —OCH$_2$—, —OCH(R$_7$)—, —OCH$_2$CH$_2$—, —CH$_2$O—, —CH$_2$OCH$_2$—, or —CH$_2$CH$_2$O In another embodiment Y is a bond or a divalent linking group selected from —CH$_2$—, —C(O)—, —CH=CH— or —CH$_2$CH$_2$—.

In another embodiment Y is a bond or a divalent linking group selected from —S—, —SCH$_2$—, CH$_2$S— or —CH$_2$SCH$_2$—.

In another embodiment Y is a bond or a divalent linking group selected from —O— or —S—.

In another embodiment Y is a bond.

In another embodiment Y is the divalent linking group —O—.

In another embodiment Y is the divalent linking group —S—.

In another embodiment R$_3$ is a C$_1$-C$_4$ alkyl group.
In another embodiment R$_3$ is a C$_1$-C$_3$ alkyl group.
In another embodiment R$_3$ is a C$_2$-C$_3$ alkyl group.
In another embodiment R$_3$ is selected from ethyl, n-propyl, iso-propyl, trifluoroethyl, or trifluoropropyl.
In another embodiment R$_3$ is ethyl.
In another embodiment R$_3$ is n-propyl.
In another embodiment R$_3$ is iso-propyl.
In another embodiment R$_3$ is trifluoroethyl.
In another embodiment R$_3$ is trifluoropropyl.
In another embodiment R$_3$ is a (C$_4$-C$_{10}$) cycloalkylalkyl group.
In another embodiment R$_3$ is a (C$_0$-C$_3$)alkyl-(C$_3$-C$_7$) cycloalkyl group.
In another embodiment R$_3$ is a (C$_3$-C$_7$) cycloalkyl group.
In another embodiment R$_3$ is a (C$_1$-C$_3$)alkyl-(C$_3$-C$_7$) cycloalkyl group.
In another embodiment R$_3$ is a (C$_1$)alkyl-(C$_3$-C$_7$) cycloalkyl group.
In another embodiment R$_3$ is a (C$_1$)alkyl-(C$_3$-C$_4$) cycloalkyl group.
In another embodiment R$_3$ is a cyclopropylmethyl group.
In another embodiment R$_3$ is a cyclobutylmethyl group.
In another embodiment R$_3$ is heterocycloalkylalkyl group.
In another embodiment R$_3$ is represented by the group Z.
In another embodiment R$_3$ is not cyclopropylmethyl
In another embodiment Z is monocyclic.
In another embodiment Z is bicyclic
In another embodiment Z is heteroaryl
In another embodiment Z is unsubstituted heteroaryl
In another embodiment Z is benzo[b]thiophenyl, benzo[c][1,2,5]oxadiazoyl, benzo[c][1,2,5]thiadiazolyl or benzo[d]thiazolyl
In another embodiment Z is benzo[b]thiophenyl or benzo[d]thiazolyl
In another embodiment Z is benzo[c][1,2,5]oxadiazoyl or benzo[c][1,2,5]thiadiazolyl
In another embodiment Z is benzo[b]thiophenyl
In another embodiment Z is benzo[c][1,2,5]oxadiazoyl
In another embodiment Z is benzo[c][1,2,5]thiadiazolyl
In another embodiment Z is benzo[d]thiazolyl
In another embodiment Z is aryl In another embodiment Z is substituted phenyl
In another embodiment Z is 4-substituted phenyl
In another embodiment Z is optionally substituted with up to 3 substituents independently selected from halogen, R$_6$, CF$_3$, CN, NO$_2$, OH, C$_1$-C$_4$ alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH$_2$, C(O)NHR$_7$, C(O)N(R$_7$)$_2$, CO$_2$H, CO$_2$R$_6$ or COR$_6$ In another embodiment Z is optionally substituted with up to 3 substituents independently selected from halogen, R$_6$, CF$_3$, CN, NO$_2$, C$_1$-C$_4$ alkoxy, aryloxy, heteroaryloxy, OCH$_2$CH$_2$OCH$_3$, OC(O)R$_6$, OC(O)OR$_6$, SR$_6$, NHR$_7$, N(R$_7$)$_2$CO$_2$H, CO$_2$R$_6$ or COR$_6$ In another embodiment Z is optionally substituted with up to 3 substituents independently selected from halogen, R$_6$, CF$_3$, CN, NO$_2$, C$_1$-C$_4$ alkoxy, aryloxy, OCH$_2$CH$_2$OCH$_3$, OC(O)R$_6$, OC(O)OR$_6$ or SR$_6$ In another embodiment Z is optionally substituted with up to 3 substituents independently selected from halogen, R$_6$, CF$_3$, CN, NO$_2$, C$_1$-C$_4$ alkoxy, OCH$_2$CH$_2$OCH$_3$, OC(O)R$_6$, OC(O)OR$_6$ or SR$_6$ In another embodiment Z is optionally substituted with up to 3 substituents independently selected from halogen, C$_1$-C$_6$ alkyl, (C$_0$-C$_3$)alkyl-(C$_3$-C$_7$)cycloalkyl, CF$_3$, C$_1$-C$_4$ alkoxy, or SR$_6$ In another embodiment Z is optionally substituted with up to 3 substituents independently selected from F, Cl, C$_1$-C$_3$ alkyl, (C$_3$-C$_6$)cycloalkyl, CF$_3$, C$_1$-C$_4$ alkoxy, S—(C$_1$-C$_4$)alkyl or S—(C$_0$-C$_3$)alkyl-(C$_3$-C$_7$)cycloalkyl In another embodiment Z is optionally substituted with up to 3 substituents independently selected from F, Cl, C$_1$-C$_3$ alkyl, (C$_3$-C$_6$)cycloalkyl, CF$_3$, C$_1$-C$_4$ alkoxy, or S—(C$_1$-C$_3$) alkyl In another embodiment Z is substituted CF$_3$, OCF$_3$, OCH$_2$CF$_3$, F, Cl, SMe, Me, Et, iPr
In another embodiment Z is substituted with F
In another embodiment Z is substituted with Cl
In another embodiment Z is substituted with C$_1$-C$_3$ alkyl
In another embodiment Z is substituted with (C$_3$-C$_6$)cycloalkyl
In another embodiment Z is substituted with CF$_3$,
In another embodiment Z is substituted with C$_1$-C$_4$ alkoxy
In another embodiment Z is substituted with S—(C$_1$-C$_3$) alkyl In another embodiment R$_4$ is a C$_1$-C$_7$ alkyl group.
In another embodiment R$_4$ is a C$_1$-C$_4$ alkyl group.
In another embodiment R$_4$ is a C$_1$-C$_3$ alkyl group.
In another embodiment R$_4$ is a C$_2$-C$_3$ alkyl group.
In another embodiment R$_4$ is selected from ethyl, n-propyl, iso-propyl, trifluoroethyl, or trifluoropropyl.
In another embodiment R$_4$ is ethyl.
In another embodiment R$_4$ is n-propyl.
In another embodiment R$_4$ is iso-propyl.
In another embodiment R$_4$ is trifluoroethyl.
In another embodiment R$_4$ is trifluoropropyl.
In another embodiment R$_4$ is a (C$_4$-C$_{10}$) cycloalkylalkyl group.
In another embodiment R$_4$ is a (C$_0$-C$_3$)alkyl-(C$_3$-C$_7$) cycloalkyl group.
In another embodiment R$_4$ is a (C$_3$-C$_7$) cycloalkyl group.
In another embodiment R$_4$ is a (C$_1$-C$_3$)alkyl-(C$_3$-C$_7$) cycloalkyl group.
In another embodiment R$_4$ is a (C$_1$)alkyl-(C$_3$-C$_7$) cycloalkyl group.

In another embodiment R$_4$ is a (C$_1$)alkyl-(C$_3$-C$_4$) cycloalkyl group.

In another embodiment R$_4$ is a cyclopropylmethyl group.

In another embodiment R$_4$ is a cyclobutylmethyl group.

In another embodiment R$_4$ is heterocycloalkylalkyl group.

In another embodiment R$_4$ is represented by the group Z.

In another embodiment R$_4$ is not cyclopropylmethyl

In another embodiment R$_5$ is, F, Cl, Br, CN, C$_1$-C$_4$ alkoxy, SR$_6$, (C$_1$-C$_4$) alkyl, (C$_0$-C$_3$)alkyl-(C$_3$-C$_7$) cycloalkyl, —(C$_3$-C$_7$) cycloalkly or (C$_2$-C$_4$) alkynyl, where each alkyl or cycloalkly is optionally independently singly or multiply substituted with halo, hydroxy, cyano, CF$_3$, C$_1$-C$_4$ alkyl.

In another embodiment R$_5$ is, F, Cl, Br, CN, C$_1$-C$_4$ alkoxy, SR$_6$, (C$_1$-C$_4$) alkyl, (C$_0$-C$_3$)alkyl-(C$_3$-C$_7$) cycloalkyl, —(C$_3$-C$_7$) cycloalkly or (C$_2$-C$_4$) alkynyl, where each alkyl or cycloalkly is optionally independently singly or multiply substituted with halo, hydroxy, cyano, CF$_3$, C$_1$-C$_4$ alkyl.

In another embodiment R$_5$ is F, Cl, Br, CN, C$_1$-C$_4$ alkoxy, —S—(C$_1$-C$_4$)alkyl or (C$_1$-C$_4$) alkyl, where each alkyl is optionally independently singly or multiply substituted with halo, hydroxy, cyano, CF$_3$, C$_1$-C$_4$ alkyl.

In another embodiment R$_5$ is F, Cl, Br, CN, C$_1$-C$_3$ alkoxy —S—(C$_1$-C$_3$)alkyl or (C$_1$-C$_3$) alkyl, where each alkyl is optionally independently singly or multiply substituted with halo, hydroxy, cyano, CF$_3$, C$_1$-C$_4$ alkyl.

In another embodiment R$_5$ is F, Cl, Br or CN.

In another embodiment R$_5$ is F or Cl.

In another embodiment R$_5$ is F.

In another embodiment R$_5$ is Cl.

In another embodiment R$_5$ is Br.

In another embodiment R$_5$ is CN.

In another embodiment R$_5$ is C$_1$-C$_3$ alkoxy —S—(C$_1$-C$_3$) alkyl or (C$_1$-C$_3$) alkyl.

In another embodiment R$_5$ is C$_1$-C$_3$ alkoxy.

In another embodiment R$_5$ is tri-fluoroethoxy or tri-fluoropropoxy.

In another embodiment R$_5$ is (C$_1$-C$_3$) alkyl.

In another embodiment R$_5$ is CF$_3$.

In another embodiment R$_5$ is —S—(C$_1$-C$_3$)alkyl.

In another embodiment R$_5$ is —S-Me, —S-Et or —S—CH$_2$CF$_3$.

In another embodiment R$_5$ is SR$_6$.

In another embodiment R$_5$ is (C$_0$-C$_3$)alkyl-(C$_3$-C$_7$) cycloalkyl, (C$_2$-C$_4$) alkynyl, or —(C$_3$-C$_7$) cycloalkyl.

In another embodiment R$_5$ is (C$_0$-C$_3$)alkyl-(C$_3$-C$_7$) cycloalkyl.

In another embodiment R$_5$ is (C$_2$-C$_4$) alkynyl.

In another embodiment R$_5$ is trifluoroethynyl.

In another embodiment R$_5$ is (C$_3$-C$_7$) cycloalkyl.

In another embodiment R$_5$ is cyclopropyl.

In another embodiment R$_5$ is NO$_2$ or NH$_2$.

In another embodiment R$_5$ is aryl or heteroaryl.

In another embodiment the compound is a compound selected from examples 100-3217.

In another embodiment a racemic compound described in the disclosure is selected.

In another embodiment a single enantiomer of the previous embodiments is selected.

In another embodiment a single enantiomer of configuration (R) of the previous embodiments is selected.

In another embodiment a single enantiomer of configuration (S) of the previous embodiments is selected.

In another embodiment a solvate of a compound of formula (I-IX) is selected.

In another embodiment a polymorph of compound of formula (I-IX) is selected.

In a separate embodiment, a pharmaceutical composition comprising of the compound of the previous embodiments and a pharmaceutically acceptable carrier.

In a separate embodiment, a method for treating a neurodegenerative disorder comprising administering to a patient an effective amount of the pharmaceutical composition of the previous embodiments.

In another embodiment a method for treating Alzheimer's Disease comprising administering to a patient an effective amount of the pharmaceutical composition of the previous embodiments.

In the case compounds of Formula (I-IX) may contain asymmetric centers and exist as different enantiomers or diastereomers. All enantiomers or diastereomeric forms are embodied herein.

Compounds in the disclosure, e.g., compounds of Formulas I-IX, may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary (e.g. Tromethamine), secondary and tertiary amines, and amino acids (e.g. Lysine). Salts derived from inorganic acids include sulfuric, hydrochloric, phosphoric, methanesulphonic, hydrobromic. Salts derived from organic acids include C$_{1-6}$ alkyl carboxylic acids, di-carboxylic acids and tricarboxylic acids such as acetic acid, propionic acid, fumaric acid, maleic acid, succinic acid, tartaric acid, adipic acid and citric acid, and alkylsulfonic acids such as methanesulphonic, and aryl sulfonic acids such as para-tolouene sulfonic acid and benzene sulfonic acid. For detailed list of slats see P. H. Stahl and C. G. Wermuth (eds.) "Handbook of Pharmaceutical Salts, Properties, Selection and Use" Wiley-VCH (ISBN 3-906390-26-8)

Compounds and pharmaceutically acceptable salts thereof may be in the form of a solvates. This occurs when a compound of formula (I-IX)) crystallizes in a manner that it incorporates solvent molecules into the crystal lattice. Examples of solvents forming solvates are water (hydrates), MeOH, EtOH, iPrOH, and acetone. Formulas I-IX cover all solvates of the depicted compounds.

Compounds in the disclosure may exist in different crystal forms known as polymorphs.

Practitioners of the art will recognize that certain chemical groups may exist in multiple tautomeric forms. The scope of this disclosure is meant to include all such tautomeric forms. For example, a tetrazole may exist in two tautomeric forms, 1-H tetrazole and a 2-H tetrazole. This is depicted in FIGURE below. This example is not meant to be limiting in the scope of tautomeric forms.

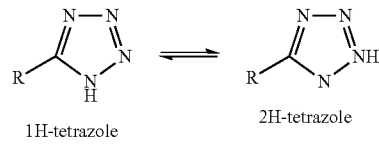

1H-tetrazole    2H-tetrazole

Practitioners of the art will recognize that certain electrophilic ketones, may exist in a hydrated form. The scope of this disclosure is to include all such hydrated forms. For example, a trifluoromethyl ketone may exist in a hydrated form via addition of water to the carbonyl group. This is depicted in FIGURE below. This example is not meant to be limiting in the scope of hydrated forms.

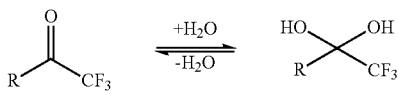

Abbreviations used in the following examples and preparations include:
- Aβ Amyloid-beta
- ABL Aβ lowering
- Ac acyl (Me-C(O)—)
- AD Alzheimer's Disease
- APP Amyloid Precursor Protein
- Bn Benzyl
- b/p brain/plasma
- BSA Bovine serum Albumin
- c Cyclo
- calcd. Calculated
- cBu Cylcobutyl
- c-Bu Cylcobutyl
- $c_{max}$ Maximal concentration
- cPr Cyclopropyl
- c-Pr Cyclopropyl
- CHAPS 3-[3-cholamidopropyl)-dimethyl-ammonio]-1-propane sulfonate
- CTF Carboxy Terminal Fragment
- CSF Cerebrospinal fluid
- DAPT N-[(3,5-Difluorophenyl)acetyl]-L-alanyl-2-phenyl]glycine-1,1-dimethylethyl ester
- DCC N,N', Dicyclohexylcarbodiimide
- DEA Di-ethylamine
- DIEA Di-isopropylethyl amine
- DMAP 4-Dimethylamino Pyridine
- DMF Dimethylformamide
- DMSO Dimethyl sulfoxide
- Dppf 1,4-Bis(diphenylphosphino) ferrocene
- EDC 1-(3-Dimethylaminopropyl)-3-ethylcarbodiimide Hydrochloride
- EDTA Ethylene Diamine Tetra-acetic Acid
- ELISA Enzyme-Linked Immuno Sorbent Assay
- Et$_3$N Triethylamine
- Eq. Equivalent
- g gram(s)
- HOBt 1-Hydroxybenzotriazole
- HPLC High Pressure Liquid Chromatography
- h Hour(s)
- hr Hour(s)
- i.v or IV. Intravenous
- KHMDS Potassium Hexamethydisilazide
- LC-MS Liquid Chromatography-Mass Spectrometry
- LDA Lithium Di-isopropylamide
- m Multiplet
- MeOH Methyl Alcohol or Methanol
- m meta
- mcpba meta-chloro perbenzoic acid
- min Minute(s)
- mmol millimoles
- mmole millimoles
- ul Microliter
- μl microliter
- Ms Mesylate
- MS Mass Spectrometry
- MW Molecular Weight (all values are ±0.05)
- n normal
- NBS N-Bromosuccinimide
- NCS N-Chlorosuccinimide
- NIS N-Iodosuccinimide
- NMR Nuclear Magnetic Resonance
- NMM N-Methyl Morpholine
- NSAIDS Non-Steroidal Anti-Inflammatory Drugs
- o ortho
- o/n overnight
- p para
- PBS Phosphate Buffered Saline
- PEPPSI 1,3-Bis(2,6-diisopropylphenyl)imidazolidene)(3-chloropyridyl) palladium(II) dichloride
- PhNTf$_2$ 1,1,1-trifluoro-N-phenyl-N-(trifluoromethylsulfonyl)methanesulfonamide
- POPd Dihydrogen dichlorobis(di-tert-butylphosphinito-kp) palladate (2-)
- p.s.i. Pounds per square inch
- PPAA 1-Propanephosphonic Acid Cyclic Anhydride
- PyBOP® Benzotriazol-1-yl-oxytripyrrolidinophosphonium hexafluorophosphate
- PK Pharmacokinetics
- RT (or rt) room temperature (about 20-25° C.)
- s Singlet
- sat. Saturated
- sec secondary
- t Triplet
- tert tertiary
- TBAF Tetra-butyl ammonium fluoride
- TFA Trifluoroacetic Acid
- THF Tetrahydrofuran
- TMB 3,3'5,5' Tetramethylbenzidine
- TMS Trimethylsilyl
- Tf Triflate
- Ts Tosylate
- v/v volume/volume
- wt/v weight/volume

DESCRIPTION OF THE FIGURE

FIG. 1 demonstrates the desirable effect on Aβ after the administration of example 1301 (2-(5-chloro-4'-isopropyl-6-(2,2,2-trifluoroethoxy)biphenyl-3-yl)-3-cyclopropylpropanoic acid) to in C57BL/6 mice when give one dose at 30 mg/kg in a Solutol HS 15:Ethanol:Water (15:10:75) formulation (measuring Aβ at 3 hours).

DETAILED DESCRIPTION

Described below are compounds within Formulas I and II as well as methods for preparing the compounds and using the compounds to treat one or more symptoms of Alzheimer's disease. The compounds of the disclosure are gamma secretase modulators (GSMs), i.e., compounds that act to shift the relative levels of Aβ peptides produced by γ-secretase. In some cases the compounds alter the relative levels of Aβ peptides produced by γ-secretase without significantly changing the total level of Aβ peptides produced.

General Reaction Schemes

The tetrasubstituted benzene compounds of Formulas I and II may be prepared by multistep organic synthetic routes from known fluoronitrobenzene and chloronitrobenzene starting materials e.g. 2,4-difluoronitrobenzene, 4-fluoro-2-cyano-nitrobenzene, 3-nitro-4-chlorobenzene, 2,4,5-trifluoronitrobenzene, 2,4,5-trichloronitrobenzene or alternatively from 4-hydroxyphenyl and 4-aminophenyl acetic acid starting materials by one skilled in the art of organic synthesis using established organic synthesis procedures.

The 1-position acetic acid moiety common to compounds of Formulas I and II, as the free acid itself or as an ester derivative thereof, is already present in the case of a 4-hydroxyphenyl acetic acid or 4-hydroxyphenyl acetic acid ester starting material. In the case of a 4-fluoronitrobenzene starting materials or intermediates, the acetic acid moiety can be introduced by standard nucleophilic aromatic substitution of the 4-fluoro group with an unsubstituted malonic ester (eg diethyl malonate) or a malonic ester derivative already bearing an $R_1$ group (eg. diethyl 2-isobutylmalonate). Introduction of the X—$R_3$ and Y—$R_4$ groups or intermediate groups that are further elaborated to X—$R_3$ and Y—$R_4$ can be carried out by substitution or manipulation of suitable 3 or 4-position functional groups in appropriate starting materials or intermediates en route to Formulas I and II respectively. In cases where X or Y is a bond, a 3 or 4-position halogen or triflate group is replaced with an aryl or heteroaryl group by carbon-carbon bond forming reaction typically a Suzuki coupling reaction. In cases where X or Y is O, S or N, a 3 or 4-position halogen (eg the corresponding 2-fluoro group of a 2,4-difluoronitrobenzene starting material) substitution reaction is performed using HO—$R_3$ or HS—$R_3$ or $H_2$N—$R_3$ and a base (eg NaH, $K_2CO_3$) in a suitable solvent (eg DMF). Compounds where X or Y is —S(O)— or —S($O_2$)— are prepared by oxidation of compounds where X or Y is S. Compounds where X or Y is —S(O)$_2$N(H)—, —S(O)$_2$N($R_5$)— can be prepared by conversion of a 3 or 4-position nitro group (eg the nitro group of the nitrobenzene starting material) to a sulfonyl chloride via Sandmeyer reaction followed by addition of the corresponding amine. Compounds where X or Y is N(H)S(O)$_2$— or —N($R_5$)S(O)$_2$— can be prepared by reduction of a 3 or 4-position nitro group to the corresponding aniline followed by reaction with the corresponding sulfonylchloride. Compounds where X or Y is NHC(O)— or —N($R_5$)C(O)— can be prepared by reduction of a 3 or 4-position nitro group to the corresponding aniline followed by reaction with the corresponding carboxylic acid chloride. Compounds where X or Y is a —C(O)— can be prepared by addition of an organometallic reagent (e.g., a Grignard reagent or organolithium) to a 3 or 4-position cyano group directly or in a 2-step sequence by addition of an organometallic reagent to a 3 or 4-position carboxaldehyde group followed by oxidation. Compounds where X or Y is —C(O)NH— or C(O)N($R_5$)—)— can be prepared by addition of a corresponding amine to a 3 or 4-position carboxylic acid which in turn may be prepared by hydrolysis of a 3 or 4-position cyano group. Either aromatic nucleophilic substitution of a 2-fluoro-1-nitrobenzene intermediate or alkylation of a 3 or 4-hydroxybenzene intermediate with the corresponding alkyl bromide or triflate may be used to prepare compounds of Formulas I and II where the $R_4$ group is $OCH_2CF_3$, $C_2$-$C_4$ alkoxy, or cyclopropyloxymethyl. Compounds wherein the $R_4$ group is an alkyl, aryl or heteroaryl group attached by a carbon-carbon bond may be prepared by a Suzuki coupling reaction. In this process an aryl or heteroaryl boronic acid or borate ester is reacted with an intermediate compound having a 3 or 4-position halogen or triflate group. This method results in replacement of the halogen or triflate group with an aryl or heteroaryl group which is then bonded to the intermediate at the carbon atom previously bearing the boronic acid or ester group. Compounds wherein the $R_4$ group is a heteroaryl group attached by a carbon-nitrogen bond may be prepared by reacting a 3 or 4-iodo intermediate with a heteroaromatic heterocycle having an acidic N—H group under Ulman reaction or copper catalyzed reaction conditions.

Compounds of Formulas I and II wherein A=tetrazole may be prepared from their corresponding nitriles A=CN which are available via dehydration of the corresponding primary amides A=$CONH_2$ whose preparation is described above. Thus, treatment of the nitrile with an azide, such as sodium azide or tributylstanyl azide ($Bu_3SnN_3$) at a temperature of 20-100° C., optionally with a solvent such as DMF, THF or DMSO.

Compounds of the disclosure of Formula III in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl, or an arylalkyl group, Y is O, X is a bond, $R_3$ is Z, $R_4$ and $R_5$ are as described previously and thus having general Formula XXIV may be prepared generally as depicted in Scheme 1.

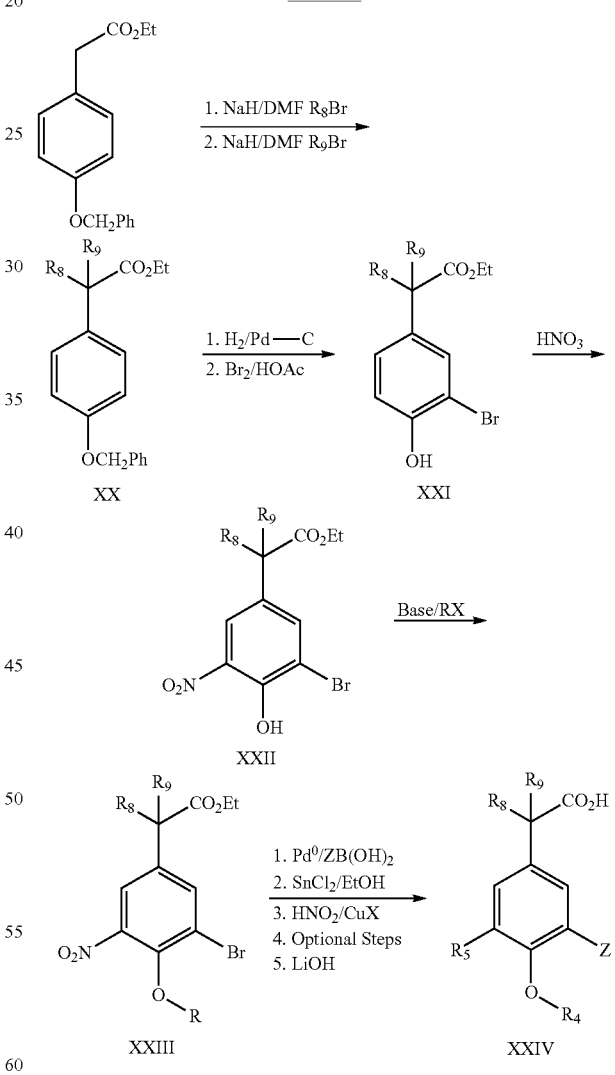

Thus, as depicted in Scheme 1 an alkyl, cycloalkylalkyl, heterocycloalkylalkyl, alkoxyalkyl, heteroarylalkyl or arylalkyl $R_8$ group is introduced in the first step by treating ethyl 4-benzyloxyphenylacetate one equivalent of a suitable deprotonating base such as sodium hydride in an appropriate organic solvent followed by the addition of the corresponding reactive alkyl bromide $R_8Br$ such as isobutylbromide to yield XX where $R_9$ is hydrogen. In cases where a second alkyl or aralkyl group is present this alkylation step is repeated using $R_9Br$ as an alkylating agent. In cases where a spirocyclic ring is formed by $R_8$ and $R_9$ (e.g. cyclopropyl) then the appropriate dibromide is used (e.g. dibromoethane in the case of cyclopropyl). The benzyl group is then removed under standard catalytic hydrogenation conditions and the resulting phenol is treated with bromine in acetic acid to give the bromophenol intermediate XXI. Nitration of XXI then yields nitrophenol intermediate XXII which then us subjected to a standard base mediated aliphatic or aromatic nucleophilic substitution reaction with an alkyl or aryl halide $R_4$—X to give intermediate XXIII where $R_4$ is alkyl, cycloalkylalkyl, heterocycloalkylalkyl, alkoxyalkyl, arylalkyl, heteroarylalkyl, aryl or heteroaryl. This is then followed by introduction of the Z group by standard reactions. Such reactions are exemplified by the well established Suzuki coupling of a substituted aryl or heteroaryl boronic acid derivative Z—$B(OH)_2$ using a suitable palladium(0) catalyst typically bearing with phosphine ligands (e.g. $Pd(PPh_3)_4$ or tetrakistriphenylphosphine) in the case where Z is linked by a carbon-carbon bond and by copper (eg CuI) mediated Ulman type coupling of a heteroaryl ring bearing an active N—H group where Z is a heteroaryl ring linked by a nitrogen-carbon bond.

reduction conditions (eg $SnCl_2$ reduction). This is followed by conversion of the resulting aniline to the diazonium salt which is then converted "in situ" either directly to $R_5$ either directly in the case where $R_5$ is F, Cl, Br, CN, OH, C1-C4 alkoxy or $SR_6$, by using the appropriate copper salt ie CuCl, CuBr, CuCN or nucleophile ie water, alcohol or thiol or in a subsequent step e.g. oxidation (eg with MCPBA) of the product of thiol coupling when $R_5$ is $S(O)_2R_6$; e.g. Suzuki coupling of the bromide product when $R_5$ is heteroaryl e.g. treatment of an intermediate sulfonylchloride obtained via CuCl/$SO_2$ conditions with an amine $HN(R_7)_2$, when $R_5$ is $S(O)_2N(R_7)_2$, e.g. Burton trifluoromethylation reaction of the iodide product (Burton, D. J.; Wiemers, D. M. J. Am. Chem. Soc. 1985, 107, 5014 and 1986, 108, 832; Miller, J. A., Coleman, M. C.; Matthews, R. S. J. Org. Chem. 1993, 58, 2637) when $R_5$ is $CF_3$ Standard ester hydrolysis yields compounds of Formula XXIV.

Compounds of the disclosure of Formula III in which $R_1$ is OH, $OR_6$, $SR_6$, $NHR_7$, $N(R_7)_2$ $NHC(O)R_6$ or $NHCO_2R_6$; $R_2$ is H; Y is O, X is a bond, $R_3$ is Z, $R_4$ and $R_5$ are as described previously and thus having general Formula XXVII may be prepared generally as depicted in Scheme 2. Thus, as depicted in Scheme 2 bromination of intermediates of general Formula XXV, prepared according to Scheme 1, e.g. with N-bromosuccinimide (NBS) yields intermediate XXVI. In a subsequent step the Br atom is replaced by a suitable alkoxide, thiolate or masked amine nucleophile (eg azide or $N_3$). The product of the latter reaction is either directly subjected to ester hydrolysis or further processed in optional steps (eg by conversion the masked amine to an amino group followed by reductive amination to give mono or dialkylamine derivatives, and optionally acylation or carbamoylation of such amine derivatives) and then subjected to final ester hydrolysis to give compounds of Formula XXVII in which $R_{10}$ is OH, $OR_6$, $SR_6$, $NHR_7$, $N(R_7)_2$ $NHC(O)R_6$ or $NHCO_2R_6$

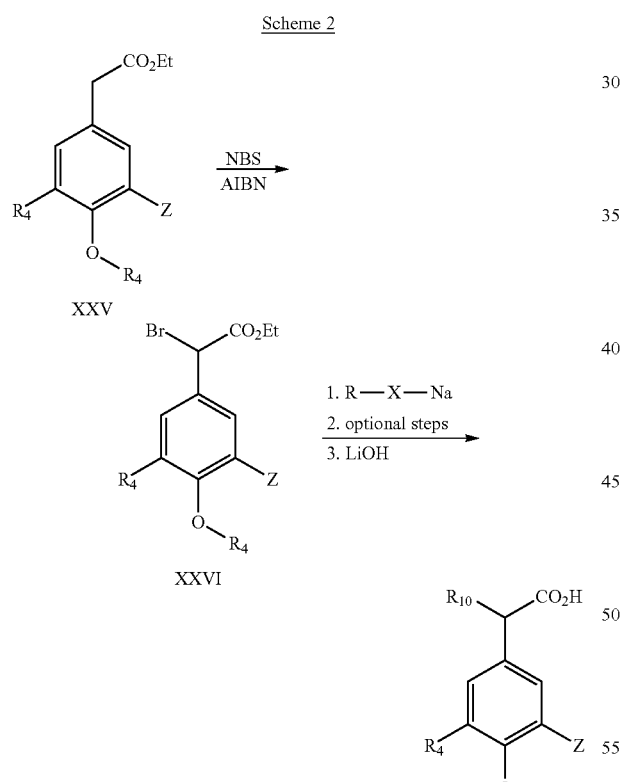

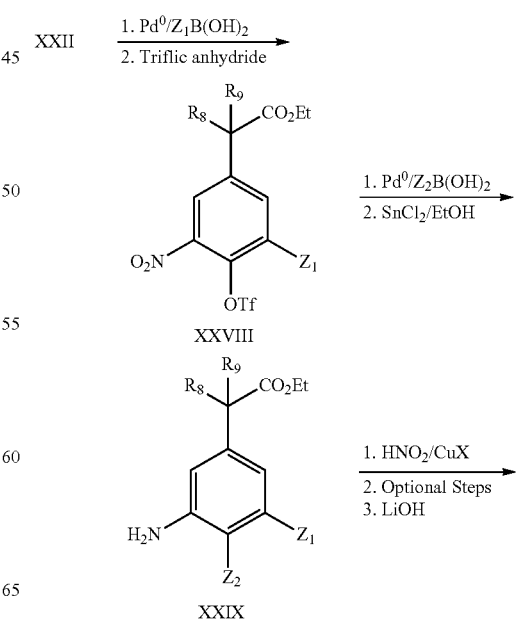

After introduction of the Z group, the nitro group is converted to the corresponding aniline by any number of standard -continued

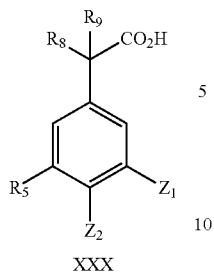

XXX

Compounds of the disclosure of Formula III and IV in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl, X and Y are a bond, $R_3$ and $R_4$ are respectively $Z_1$ and $Z_2$ representing independently chosen Z groups as defined above and $R_5$ is as described previously and thus having general Formula XXX may be prepared generally as depicted in Scheme 3 starting from compounds of general Formula XXII which can be prepared as described in Scheme 1.

Compounds of Formula V in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl; X is Q=O, S, or $SO_2$; $R_5$ is F or Cl; $R_3$ and Z are as described previously and thus having general Formula XXXIV may be prepared generally as depicted in Scheme 4. Accordingly, the 4-halo group of 2,4,5-trifluoronitrobenzene or 2,4,5-trichloronitrobenzene is selectively displaced by reaction with a 2-substituted diethylmalonate $R_8YCH(CO_2Et)_2$ under basic conditions (eg NaH/DMF) followed by hydrolysis and esterification to give intermediate XXXI. Subsequently the 2-halo group undergoes nucleophilic aromatic substitution reaction by treatment with a $R_3$-J-H compound (wherein J is O, S) under basic conditions (eg NaH/DMF) followed by reduction and Sandmeyer reaction to give iodide XXXII.

Scheme 4

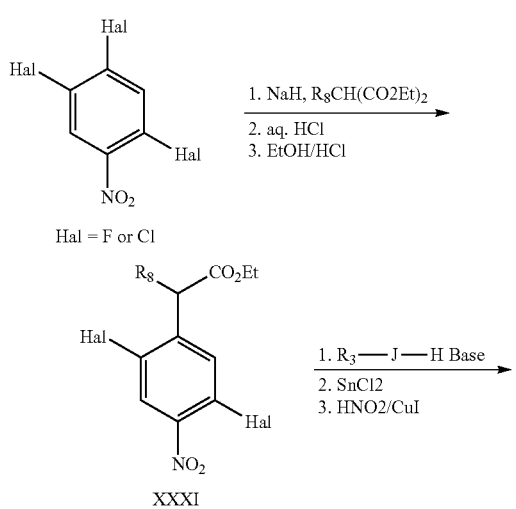

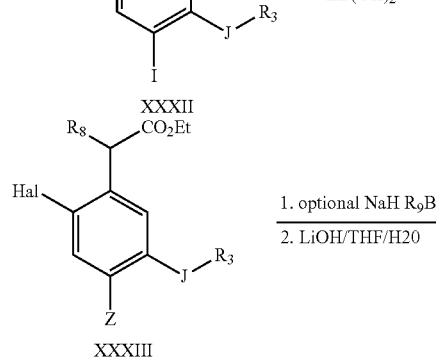

Suzuki coupling then gives intermediates of general formula XXXIII. Introduction of an $R_9$ group may be conducted using alkylation conditions described above. Compounds wherein J is $SO_2$ may be prepared by standard oxidation of intermediates XXXIII wherein J is S. Final products having general Formula XXXIV are then prepared by standard ester hydrolysis.

Compounds of Formula IV in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl; X is O; $R_5$ is Cl; $R_3$ and Z are as described previously and thus having general Formula XXXVIII may be prepared generally as depicted in Scheme 5. Accordingly, the 4-fluoro group of 2,4-difluoronitrobenzene is selectively displaced by reaction with a 2-substituted diethylmalonate $R_8CH_2(CO_2Et)_2$ under basic conditions (eg NaH/DMF) followed by hydrolysis and esterification to give intermediate XXXV. Subsequently the 2-halo group undergoes nucleophilic aromatic substitution reaction by treatment with a $R_3$—O—H compound under basic conditions (eg NaH/DMF) followed by reduction and chlorination reaction (eg with N-chlorosuccinimide) to give chloroaniline intermediates of general formula XXXVI. Sandmeyer iodination reaction to followed by Suzuki coupling then gives intermediates of general formula XXXVII. Introduction of an $R_9$ group may be conducted using alkylation conditions described above. Final products having general Formula XXXVIII are then prepared by standard ester hydrolysis.

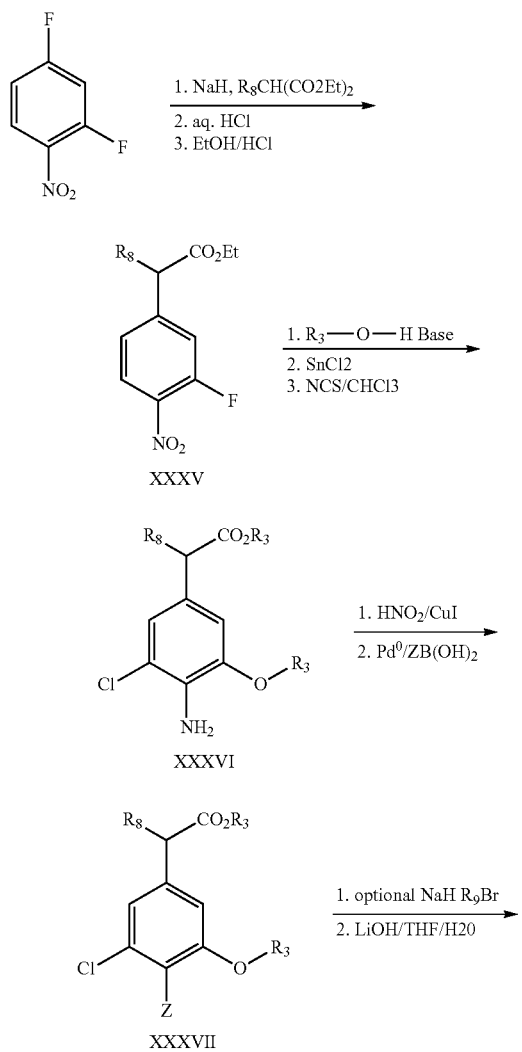

Scheme 5

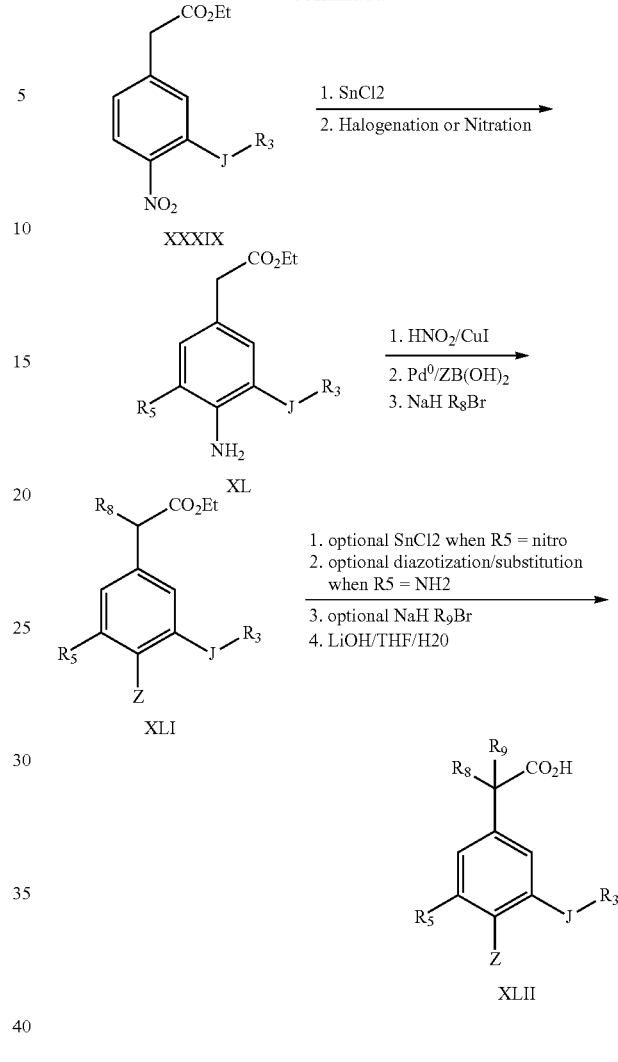

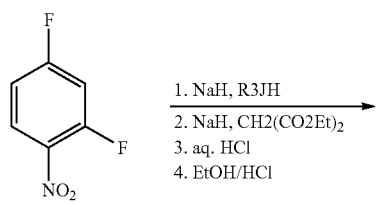

Scheme 6

Compounds of Formula IV in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl; X is J=O, S; $R_5$ is $NO_2$, $NH_2$, CN, $SR_6$, $SO_2R_6$, $SO_2N(R_7)_2$ F, Cl, Br; $R_3$ and Z are as described previously and thus having general Formula XLII may be prepared generally as depicted in Scheme 6. Accordingly, the 2-fluoro group of 2,4-difluoronitrobenzene is selectively displaced by reaction with a an alcohol or thiol of formula $R_3$-J-H under basic conditions (eg NaH/DMF). The 4-fluoro group of the resulting product is substituted with diethylmalonate under basic conditions (eg NaH/DMF) followed by hydrolysis and esterification to give intermediates of Formula XXXIX. Reduction of the nitro group of XXXIX followed by nitration of the resulting aniline give nitroaniline intermediates of Formula XL. Sandmeyer iodination reaction, followed by Suzuki coupling and finally alkylation reaction to introduce $R_8$ then gives intermediates of general Formula XLI. The nitro group of XLI may be optionally reduced via any number of standard reduction conditions (eg $SnCl_2$) to an aniline which may in turn optionally be converted to diverse other $R_5$ groups either directly or in multistep procedures. Thus, in the case where $R_5$ is F, Cl, Br, CN, OH, C1-C4 alkoxy or $SR_6$, diazotization of the aniline is followed by direct "in situ" conversion to $R_5$ using the appropriate copper salt ie CuCl, CuBr, CuCN or nucleophile ie water, alcohol or thiol. Intermediates where $R_5$ is $S(O)_2R_6$ may be prepared by subsequent step oxidation (eg with MCPBA) of the above products of thiol coupling wherein $R_5$ is $SR_6$. Intermediates where $R_5$ is eg heteroaryl, $C_2$-$C_4$ alkynyl or cyclopropyl may be prepared by subsequent Suzuki coupling of the above products wherein $R_5$ is Br or I. Intermediates where $R_5$ is $CF_3$ may be prepared by Burton reaction of the above products wherein $R_5$ is I. Intermediates where $R_5$ is $S(O)_2N(R_7)_2$, may be prepared by subsequent reaction of above direct sulfonylchloride products (obtained via $CuCl/SO_2$ conditions) with an amine $HN(R_7)_2$, Final products having general Formula XLII are then prepared by optional alkylation reaction to introduce $R_9$ followed by standard ester hydrolysis.

ll

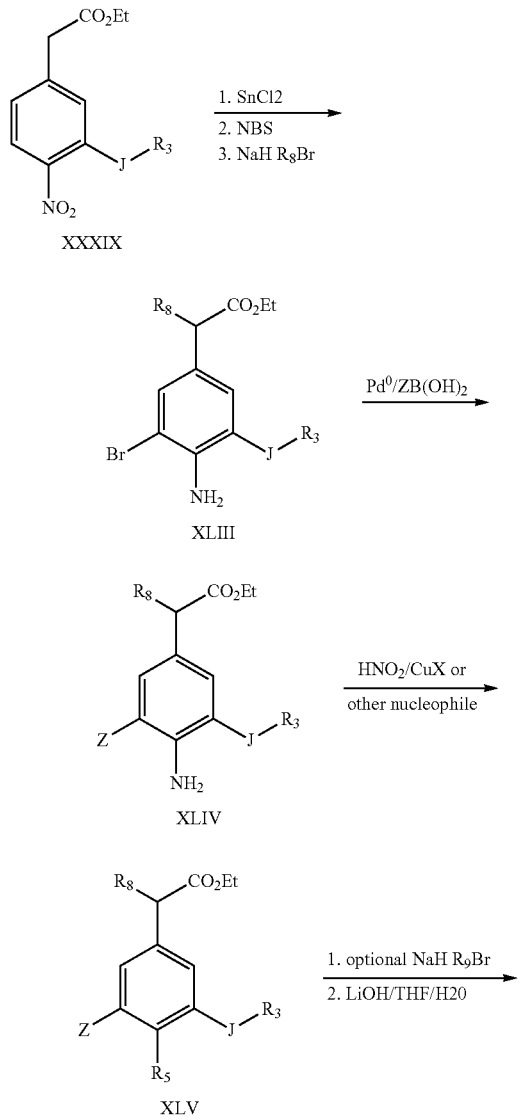

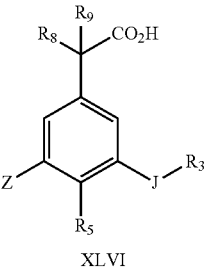

Compounds of Formula VII in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl; X is J=O, S; $R_5$ is $NO_2$, $NH_2$, CN, $SR_6$, $SO_2R_6$, $SO_2N(R_7)_2$ F, Cl, Br; $R_3$ and Z are as described previously and thus having general Formula XLV may be prepared generally as depicted in Scheme 7. Reduction of the nitro group of XXXIX followed by bromination (eg with NBS) of the resulting aniline and prepared by 1 alkylation reaction to introduce $R_9$ gives bromoaniline intermediates of Formula XLIII Suzuki coupling reaction substitutes Z groups for the Br group to give intermediates of general Formula XLIV. The aniline group in intermediates of Formula XLIV may in turn optionally be converted to diverse other $R_5$ groups either directly or in multistep procedures. Thus, in the case where $R_5$ is F, Cl, Br, CN, OH, C1-C4 alkoxy or $SR_6$, diazotization of the aniline is followed by direct "in situ" conversion to $R_5$ using the appropriate copper salt ie CuCl, CuBr, CuCN or nucleophile ie water, alcohol or thiol. Intermediates where $R_5$ is $S(O)_2R_6$ may be prepared by subsequent step oxidation (eg with MCPBA) of the above products of thiol coupling wherein $R_5$ is $SR_6$. Intermediates where $R_5$ is eg heteroaryl, C2-C4 alkynyl or cyclopropyl may be prepared by subsequent Suzuki coupling of the above products wherein $R_5$ is Br or I. Intermediates where $R_5$ is $CF_3$ may be prepared by Burton reaction of the above products wherein $R_5$ is I. Intermediates where $R_5$ is $S(O)_2N(R_7)_2$, may be prepared by subsequent reaction of above direct sulfonylchloride products (obtained via $CuCl/SO_2$ conditions) with an amine $HN(R_7)_2$, Final products having general Formula XLII are then prepared by optional alkylation reaction to introduce $R_9$ followed by standard ester hydrolysis.

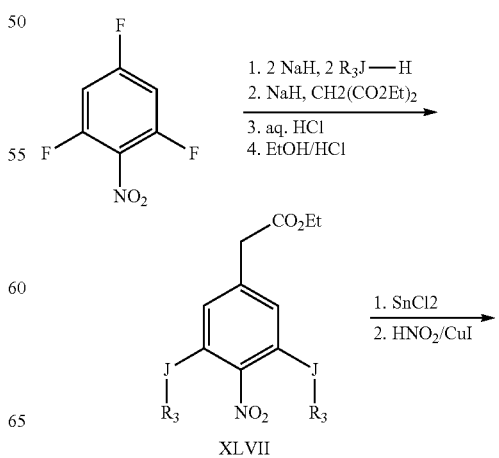

Enantioselective Methods

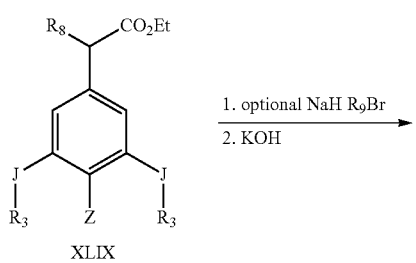

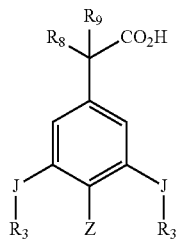

Scheme 9

Compounds of Formula IV in which $R_1$ is $R_8$ an alkyl, cycloalkylalkyl, heterocycloalkylalkyl, alkoxyalkyl, heteroarylalkyl, or an arylalkyl group, $R_2$ is $R_9$ a hydrogen, alkyl, cycloalkylalkyl, heterocycloalkylalkyl, alkoxyalkyl, heteroarylalkyl; $X$—$R_3$ and $R_5$ are identical (J-R3 in Scheme 8) and are either C1-C4 alkoxy or $SR_6$ groups; and Z is as described previously and thus having general Formula L may be prepared generally as depicted in Scheme 8. Accordingly, the 2 and 6-fluoro groups of 2,4,6-trifluoronitrobenzene are selectively displaced by reaction with a an alcohol or thiol of formula $R_3$-J-H under basic conditions (eg NaH/DMF). The 4-fluoro group of the resulting product is substituted with diethylmalonate under basic conditions (eg NaH/DMF) followed by hydrolysis and esterification to give intermediates of Formula XLVIII. Reduction of the nitro group of followed by Sandmeyer iodination reaction of the resulting aniline gives intermediates of Formula XLVIII. Suzuki coupling and followed by alkylation reaction to introduce $R_8$ then gives intermediates of general Formula XLIX. Final products having general Formula L are then prepared by optional alkylation reaction to introduce $R_9$ followed by standard ester hydrolysis.

Compounds of formulas I-IX may be prepared in an enantioselectively, this can be accomplished via resolution via chiral HPLC (CHIRALPAK-AD H (250×4.6 mm, 5 μm). Mobile phase: Hexane (0.1% TFA):IPA (93:7), Flow rate 0.8 mL/min., Diluent Hexane:IPA (90:10); Column temperature 40° C.) or via asymmetric synthesis. The phenyl acetic acids of formula (XXXV) are converted into the corresponding acid chlorides, via treatment with $SOCl_2$ or oxalyl chloride with a catalytic amount of DMF. The reaction is performed in an inert solvent such as $CH_2Cl_2$, $CHCl_3$, THF, or toluene at a temperature of 0-80° C. The acid chloride is treated with either (R)- or (S)-4-benzyloxazolidin-2-one to (R isomer depicted-XXXXVI) give the oxazolidinone (XXXVII). The oxazolidinone ( ) is then subjected to a base such as NaHMDs, LiHMDS, KHMDS, BuLi or KO$^t$Bu in an inert solvent such as THF, Me-THF or $Et_2O$ at a temperature of –78 to 0° C. The subsequent enolate is then treated with the appropriate electrophile to give the alkylated oxazolidinone (XXXVIII). The chiral auxillary is removed under conditions such as LiOH/$H_2O_2$ followed by a reductive work up with a reagent such as sodium bi-sulfite to give the desired products of formulas (I-IX).

Alternatively the racemic compound of formula (1-IX) may be coupled to the Evans chiral oxazolidinone via an intermediate such as the corresponding acid chloride. Upon completion of the coupling, the reaction produces a mixture of diastereoisomers which may be separated by methods such as flash chromatography or crystallization to give single diastereoisomers or enriched mixtures favouring one diastereoisomer over the other (see scheme 10). The auxillary may be removed as described previously.

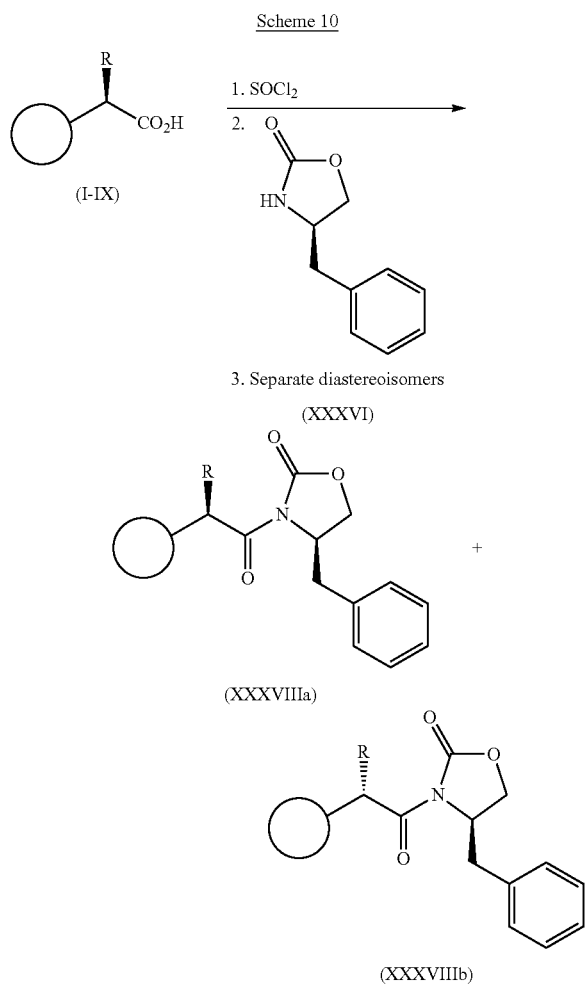

Examples of enantiomers include but are not limited to;
(R)-2-(3-(benzo[c][1,2,5]oxadiazol-5-yl)-4-(2,2,2-trifluoroethoxy)-5-(trifluoromethyl)phenyl)-3-cyclopropylpropanoic acid
(S)-2-(3-(benzo[c][1,2,5]oxadiazol-5-yl)-4-(2,2,2-trifluoroethoxy)-5-(trifluoromethyl)phenyl)-3-cyclopropylpropanoic acid
(R)-2-(5-chloro-6-(2,2,2-trifluoroethoxy)-4'-(trifluoromethyl)biphenyl-3-yl)-2-cyclopentylacetic acid compound
(R)-2-(5-chloro-6-(2,2,2-trifluoroethoxy)-4'-(trifluoromethyl)biphenyl-3-yl)-3-cyclobutylpropanoic acid
(R)-2-(6-chloro-5-(2,2,2-trifluoroethoxy)-4'-(trifluoromethyl)biphenyl-3-yl)-3-cyclopropylpropanoic acid
(S)-2-(6-chloro-5-(2,2,2-trifluoroethoxy)-4'-(trifluoromethyl)biphenyl-3-yl)-3-cyclopropylpropanoic acid
(R)-4-methyl-2-(5-(2,2,2-trifluoroethoxy)-4',6-bis(trifluoromethyl)biphenyl-3-yl)pentanoic acid
(S)-4-methyl-2-(5-(2,2,2-trifluoroethoxy)-4',6-bis(trifluoromethyl)biphenyl-3-yl)pentanoic acid
(R)-2-(3-(benzo[c][1,2,5]oxadiazol-5-yl)-4-(2,2,2-trifluoroethoxy)-5-(trifluoromethyl)phenyl)-4-methylpentanoic acid
(S)-2-(3-(benzo[c][1,2,5]oxadiazol-5-yl)-4-(2,2,2-trifluoroethoxy)-5-(trifluoromethyl)phenyl)-4-methylpentanoic acid
(R)-4-methyl-2-(6-(2,2,2-trifluoroethoxy)-4',5-bis(trifluoromethyl)biphenyl-3-yl)pentanoic acid
(S)-4-methyl-2-(6-(2,2,2-trifluoroethoxy)-4',5-bis(trifluoromethyl)biphenyl-3-yl)pentanoic acid
(R)-3-cyclopropyl-2-(6-(2,2,2-trifluoroethoxy)-4',5-bis(trifluoromethyl)biphenyl-3-yl)propanoic acid
(S)-3-cyclopropyl-2-(6-(2,2,2-trifluoroethoxy)-4',5-bis(trifluoromethyl)biphenyl-3-yl)propanoic acid
(R)-3-cyclopropyl-2-(5-(2,2,2-trifluoroethoxy)-4',6-bis(trifluoromethyl)biphenyl-3-yl)propanoic acid
(S)-3-cyclopropyl-2-(5-(2,2,2-trifluoroethoxy)-4',6-bis(trifluoromethyl)biphenyl-3-yl)propanoic acid
(R)-2-(3-(benzo[c][1,2,5]oxadiazol-5-yl)-5-(2,2,2-trifluoroethoxy)-4-(trifluoromethyl)phenyl)-3-cyclopropylpropanoic acid
(S)-2-(3-(benzo[c][1,2,5]oxadiazol-5-yl)-5-(2,2,2-trifluoroethoxy)-4-(trifluoromethyl)phenyl)-3-cyclopropylpropanoic acid
(R)-2-(5-chloro-6-(2,2,2-trifluoroethoxy)-4'-(trifluoromethyl)biphenyl-3-yl)-3-cyclopropylpropanoic acid
(S)-2-(5-chloro-6-(2,2,2-trifluoroethoxy)-4'-(trifluoromethyl)biphenyl-3-yl)-3-cyclopropylpropanoic acid
(R)-2-(3-(benzo[c][1,2,5]oxadiazol-5-yl)-5-(2,2,2-trifluoroethoxy)-4-(trifluoromethyl)phenyl)-4-methylpentanoic acid
(S)-2-(3-(benzo[c][1,2,5]oxadiazol-5-yl)-5-(2,2,2-trifluoroethoxy)-4-(trifluoromethyl)phenyl)-4-methylpentanoic acid
(R)-2-(2-chloro-6-(2,2,2-trifluoroethoxy)-4'-(trifluoromethyl)biphenyl-4-yl)-3-cyclopropylpropanoic acid
(S)-2-(2-chloro-6-(2,2,2-trifluoroethoxy)-4'-(trifluoromethyl)biphenyl-4-yl)-3-cyclopropylpropanoic acid
(R)-3-cyclopropyl-2-(2-(2,2,2-trifluoroethoxy)-4',6-bis(trifluoromethyl)biphenyl-4-yl)propanoic acid compound
(S)-3-cyclopropyl-2-(2-(2,2,2-trifluoroethoxy)-4',6-bis(trifluoromethyl)biphenyl-4-yl)propanoic acid compound
(R)-2-(4-(benzo[c][1,2,5]oxadiazol-5-yl)-3-(2,2,2-trifluoroethoxy)-5-(trifluoromethyl)phenyl)-3-cyclopropylpropanoic acid
(S)-2-(4-(benzo[c][1,2,5]oxadiazol-5-yl)-3-(2,2,2-trifluoroethoxy)-5-(trifluoromethyl)phenyl)-3-cyclopropylpropanoic acid
(R)-2-(5-chloro-6-(2,2,2-trifluoroethoxy)-4'-(trifluoromethyl)biphenyl-3-yl)-4-methylpentanoic acid
(S)-2-(5-chloro-6-(2,2,2-trifluoroethoxy)-4'-(trifluoromethyl)biphenyl-3-yl)-4-methylpentanoic acid
(R)-2-(4-(benzo[c][1,2,5]oxadiazol-5-yl)-3-(2,2,2-trifluoroethoxy)-5-(trifluoromethyl)phenyl)-4-methylpentanoic acid
(S)-2-(4-(benzo[c][1,2,5]oxadiazol-5-yl)-3-(2,2,2-trifluoroethoxy)-5-(trifluoromethyl)phenyl)-4-methylpentanoic acid
(S)-2-(5-chloro-6-(2,2,2-trifluoroethoxy)-4'-(trifluoromethyl)biphenyl-3-yl)-2-cyclopentylacetic acid
(S)-2-(5-chloro-6-(2,2,2-trifluoroethoxy)-4'-(trifluoromethyl)biphenyl-3-yl)-3-cyclobutylpropanoic acid
(R)-2-(5-chloro-4'-(methylthio)-6-(2,2,2-trifluoroethoxy)biphenyl-3-yl)-2-cyclopentylacetic acid (S)-2-(5-chloro-4'-(methylthio)-6-(2,2,2-trifluoroethoxy)biphenyl-3-yl)-2-cyclopentylacetic acid
(R)-2-(5-chloro-4'-(methylthio)-6-(2,2,2-trifluoroethoxy)biphenyl-3-yl)-3-cyclobutylpropanoic acid
(S)-2-(5-chloro-4'-(methylthio)-6-(2,2,2-trifluoroethoxy)biphenyl-3-yl)-3-cyclobutylpropanoic acid
(R)-2-(5-chloro-4'-(methylthio)-6-(2,2,2-trifluoroethoxy)biphenyl-3-yl)-3-cyclopropylpropanoic acid
(S)-2-(5-chloro-4'-(methylthio)-6-(2,2,2-trifluoroethoxy)biphenyl-3-yl)-3-cyclopropylpropanoic acid
(R)-2-(5-chloro-4'-(methylthio)-6-(2,2,2-trifluoroethoxy)biphenyl-3-yl)-4-methylpentanoic acid
(S)-2-(5-chloro-4'-(methylthio)-6-(2,2,2-trifluoroethoxy)biphenyl-3-yl)-4-methylpentanoic acid
(R)-2-(5-chloro-4'-isopropyl-6-(2,2,2-trifluoroethoxy)biphenyl-3-yl)-2-cyclopentylacetic acid
(S)-2-(5-chloro-4'-isopropyl-6-(2,2,2-trifluoroethoxy)biphenyl-3-yl)-2-cyclopentylacetic acid
(R)-2-(2-chloro-6-(2,2,2-trifluoroethoxy)-4'-(trifluoromethyl)biphenyl-4-yl)-4-methylpentanoic acid
(S)-2-(2-chloro-6-(2,2,2-trifluoroethoxy)-4'-(trifluoromethyl)biphenyl-4-yl)-4-methylpentanoic acid
(R)-2-(5-chloro-4'-isopropyl-6-(2,2,2-trifluoroethoxy)biphenyl-3-yl)-3-cyclobutylpropanoic acid
(S)-2-(5-chloro-4'-isopropyl-6-(2,2,2-trifluoroethoxy)biphenyl-3-yl)-3-cyclobutylpropanoic acid
(R)-2-(5-chloro-4'-isopropyl-6-(2,2,2-trifluoroethoxy)biphenyl-3-yl)-3-cyclopropylpropanoic acid
(S)-2-(5-chloro-4'-isopropyl-6-(2,2,2-trifluoroethoxy)biphenyl-3-yl)-3-cyclopropylpropanoic acid
(R)-2-(5-chloro-4'-isopropyl-6-(2,2,2-trifluoroethoxy)biphenyl-3-yl)-4-methylpentanoic acid
(S)-2-(5-chloro-4'-isopropyl-6-(2,2,2-trifluoroethoxy)biphenyl-3-yl)-4-methylpentanoic acid
(R)-2-(3-(benzo[c][1,2,5]thiadiazol-5-yl)-4-(2,2,2-trifluoroethoxy)-5-(trifluoromethyl)phenyl)-3-cyclopropylpropanoic acid
(S)-2-(3-(benzo[c][1,2,5]thiadiazol-5-yl)-4-(2,2,2-trifluoroethoxy)-5-(trifluoromethyl)phenyl)-3-cyclopropylpropanoic acid
(R)-2-(3-(benzo[c][1,2,5]thiadiazol-5-yl)-4-(2,2,2-trifluoroethoxy)-5-(trifluoromethyl)phenyl)-4-methylpentanoic acid
(S)-2-(3-(benzo[c][1,2,5]thiadiazol-5-yl)-4-(2,2,2-trifluoroethoxy)-5-(trifluoromethyl)phenyl)-4-methylpentanoic acid
(R)-2-(6-chloro-5-(2,2,2-trifluoroethoxy)-4'-(trifluoromethyl)biphenyl-3-yl)-4-methylpentanoic acid
(S)-2-(6-chloro-5-(2,2,2-trifluoroethoxy)-4'-(trifluoromethyl)biphenyl-3-yl)-4-methylpentanoic acid
(R)-2-(3-(benzo[c][1,2,5]thiadiazol-5-yl)-5-(2,2,2-trifluoroethoxy)-4-(trifluoromethyl)phenyl)-3-cyclopropylpropanoic acid
(S)-2-(3-(benzo[c][1,2,5]thiadiazol-5-yl)-5-(2,2,2-trifluoroethoxy)-4-(trifluoromethyl)phenyl)-3-cyclopropylpropanoic acid
(R)-2-(3-(benzo[c][1,2,5]thiadiazol-5-yl)-5-(2,2,2-trifluoroethoxy)-4-(trifluoromethyl)phenyl)-4-methylpentanoic acid
(S)-2-(3-(benzo[c][1,2,5]thiadiazol-5-yl)-5-(2,2,2-trifluoroethoxy)-4-(trifluoromethyl)phenyl)-4-methylpentanoic acid
(R)-2-(4-(benzo[c][1,2,5]thiadiazol-5-yl)-3-(2,2,2-trifluoroethoxy)-5-(trifluoromethyl)phenyl)-3-cyclopropylpropanoic acid
(S)-2-(4-(benzo[c][1,2,5]thiadiazol-5-yl)-3-(2,2,2-trifluoroethoxy)-5-(trifluoromethyl)phenyl)-3-cyclopropylpropanoic acid
(R)-2-(4-(benzo[c][1,2,5]thiadiazol-5-yl)-3-(2,2,2-trifluoroethoxy)-5-(trifluoromethyl)phenyl)-4-methylpentanoic acid
(S)-2-(4-(benzo[c][1,2,5]thiadiazol-5-yl)-3-(2,2,2-trifluoroethoxy)-5-(trifluoromethyl)phenyl)-4-methylpentanoic acid
(R)-4-methyl-2-(2-(2,2,2-trifluoroethoxy)-4',6-bis(trifluoromethyl)biphenyl-4-yl)pentanoic acid
(S)-4-methyl-2-(2-(2,2,2-trifluoroethoxy)-4',6-bis(trifluoromethyl)biphenyl-4-yl)pentanoic acid In a further aspect the compounds of the disclosure are embodied in with distinct examples listed in Tables below.

TABLE 1

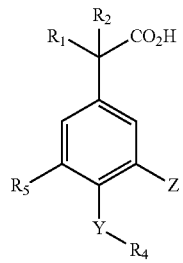

Formula III

| Ex | R1 | R2 | Y | R4 | R5 | Z |
|---|---|---|---|---|---|---|
| 100 | CH3 | H | O | CH2CH3 | F | 4-fluorophenyl |
| 101 | CH2CH3 | H | O | CH2CH3 | F | 4-fluorophenyl |
| 102 | CH2CF3 | H | O | CH2CH3 | F | 4-fluorophenyl |
| 103 | CH2CH2CH3 | H | O | CH2CH3 | F | 4-fluorophenyl |
| 104 | CH2CH(CH3)2 | H | O | CH2CH3 | F | 4-fluorophenyl |
| 105 | cyclopropylmethyl | H | O | CH2CH3 | F | 4-fluorophenyl |
| 106 | SCH(CH3)2 | H | O | CH2CH3 | F | 4-fluorophenyl |
| 107 | OCH2CH3 | H | O | CH2CH3 | F | 4-fluorophenyl |
| 108 | (CH2)2 | | O | CH2CH3 | F | 4-fluorophenyl |
| 109 | (CH2)4 | | O | CH2CH3 | F | 4-fluorophenyl |
| 110 | CH3 | H | O | CH2CH3 | F | 4-chlorophenyl |
| 111 | CH2CH3 | H | O | CH2CH3 | F | 4-chlorophenyl |
| 112 | CH2CF3 | H | O | CH2CH3 | F | 4-chlorophenyl |
| 113 | CH2CH2CH3 | H | O | CH2CH3 | F | 4-chlorophenyl |

TABLE 1-continued

Formula III $$\text{Structure: benzene ring with } R_1R_2C(CO_2H) \text{ at top, } R_5 \text{ and } Z \text{ at meta positions, } Y-R_4 \text{ at para position}$$

| Ex | R1 | R2 | Y | R4 | R5 | Z |
|---|---|---|---|---|---|---|
| 114 | CH2CH(CH3)2 | H | O | CH2CH3 | F | 4-chlorophenyl |
| 115 | cyclopropylmethyl | H | O | CH2CH3 | F | 4-chlorophenyl |
| 116 | SCH(CH3)2 | H | O | CH2CH3 | F | 4-chlorophenyl |
| 117 | OCH2CH3 | H | O | CH2CH3 | F | 4-chlorophenyl |
| 118 | (CH2)2 | | O | CH2CH3 | F | 4-chlorophenyl |
| 119 | (CH2)4 | | O | CH2CH3 | F | 4-chlorophenyl |
| 120 | CH3 | H | O | CH2CH3 | F | 4-trifluoromethylphenyl |
| 121 | CH2CH3 | H | O | CH2CH3 | F | 4-trifluoromethylphenyl |
| 122 | CH2CF3 | H | O | CH2CH3 | F | 4-trifluoromethylphenyl |
| 123 | CH2CH2CH3 | H | O | CH2CH3 | F | 4-trifluoromethylphenyl |
| 124 | CH2CH(CH3)2 | H | O | CH2CH3 | F | 4-trifluoromethylphenyl |
| 125 | cyclopropylmethyl | H | O | CH2CH3 | F | 4-trifluoromethylphenyl |
| 126 | SCH(CH3)2 | H | O | CH2CH3 | F | 4-trifluoromethylphenyl |
| 127 | OCH2CH3 | H | O | CH2CH3 | F | 4-trifluoromethylphenyl |
| 128 | (CH2)2 | | O | CH2CH3 | F | 4-trifluoromethylphenyl |
| 129 | (CH2)4 | | O | CH2CH3 | F | 4-trifluoromethylphenyl |
| 130 | CH3 | H | O | CH2CH3 | F | 4-methoxyphenyl |
| 131 | CH2CH3 | H | O | CH2CH3 | F | 4-methoxyphenyl |
| 132 | CH2CF3 | H | O | CH2CH3 | F | 4-methoxyphenyl |
| 133 | CH2CH2CH3 | H | O | CH2CH3 | F | 4-methoxyphenyl |
| 134 | CH2CH(CH3)2 | H | O | CH2CH3 | F | 4-methoxyphenyl |
| 135 | cyclopropylmethyl | H | O | CH2CH3 | F | 4-methoxyphenyl |
| 136 | SCH(CH3)2 | H | O | CH2CH3 | F | 4-methoxyphenyl |
| 137 | OCH2CH3 | H | O | CH2CH3 | F | 4-methoxyphenyl |
| 138 | (CH2)2 | | O | CH2CH3 | F | 4-methoxyphenyl |
| 139 | (CH2)4 | | O | CH2CH3 | F | 4-methoxyphenyl |
| 140 | $CH_3$ | H | O | $CH_2CH_3$ | F | 3,4 dichloro phenyl |
| 141 | $CH_2CH_3$ | H | O | $CH_2CH_3$ | F | 3,4 dichloro phenyl |
| 142 | $CH_2CF_3$ | H | O | $CH_2CH_3$ | F | 3,4 dichloro phenyl |
| 143 | $CH_2CH_2CH_3$ | H | O | $CH_2CH_3$ | F | 3,4 dichloro phenyl |
| 144 | $CH_2CH(CH_3)_2$ | H | O | $CH_2CH_3$ | F | 3,4 dichloro phenyl |
| 145 | cyclopropylmethyl | H | O | $CH_2CH_3$ | F | 3,4 dichloro phenyl |
| 146 | $SCH(CH_3)_2$ | H | O | $CH_2CH_3$ | F | 3,4 dichloro phenyl |
| 147 | $OCH_2CH_3$ | H | O | $CH_2CH_3$ | F | 3,4 dichloro phenyl |
| 148 | $(CH_2)_2$ | | O | $CH_2CH_3$ | F | 3,4 dichloro phenyl |
| 149 | $(CH_2)_4$ | | O | $CH_2CH_3$ | F | 3,4 dichloro phenyl |
| 150 | $CH_3$ | H | O | $CH_2CH_3$ | F | 5-benzo[c][1,2,5]oxadiazolyl |
| 151 | $CH_2CH_3$ | H | O | $CH_2CH_3$ | F | 5-benzo[c][1,2,5]oxadiazolyl |
| 152 | $CH_2CF_3$ | H | O | $CH_2CH_3$ | F | 5-benzo[c][1,2,5]oxadiazolyl |
| 153 | $CH_2CH_2CH_3$ | H | O | $CH_2CH_3$ | F | 5-benzo[c][1,2,5]oxadiazolyl |
| 154 | $CH_2CH(CH_3)_2$ | H | O | $CH_2CH_3$ | F | 5-benzo[c][1,2,5]oxadiazolyl |
| 155 | cyclopropylmethyl | H | O | $CH_2CH_3$ | F | 5-benzo[c][1,2,5]oxadiazolyl |
| 156 | $SCH(CH_3)_2$ | H | O | $CH_2CH_3$ | F | 5-benzo[c][1,2,5]oxadiazolyl |
| 157 | $OCH_2CH_3$ | H | O | $CH_2CH_3$ | F | 5-benzo[c][1,2,5]oxadiazolyl |
| 158 | $(CH_2)_2$ | | O | $CH_2CH_3$ | F | 5-benzo[c][1,2,5]oxadiazolyl |
| 159 | $(CH_2)_4$ | | O | $CH_2CH_3$ | F | 5-benzo[c][1,2,5]oxadiazolyl |
| 160 | $CH_3$ | H | O | $CH_2CH_3$ | F | 5-benzo[c][1,2,5]thiadiazolyl |
| 161 | $CH_2CH_3$ | H | O | $CH_2CH_3$ | F | 5-benzo[c][1,2,5]thiadiazolyl |
| 162 | $CH_2CF_3$ | H | O | $CH_2CH_3$ | F | 5-benzo[c][1,2,5]thiadiazolyl |
| 163 | $CH_2CH_2CH_3$ | H | O | $CH_2CH_3$ | F | 5-benzo[c][1,2,5]thiadiazolyl |
| 164 | $CH_2CH(CH_3)_2$ | H | O | $CH_2CH_3$ | F | 5-benzo[c][1,2,5]thiadiazolyl |
| 165 | cyclopropylmethyl | H | O | $CH_2CH_3$ | F | 5-benzo[c][1,2,5]thiadiazolyl |
| 166 | $SCH(CH_3)_2$ | H | O | $CH_2CH_3$ | F | 5-benzo[c][1,2,5]thiadiazolyl |
| 167 | $OCH_2CH_3$ | H | O | $CH_2CH_3$ | F | 5-benzo[c][1,2,5]thiadiazolyl |
| 168 | $(CH_2)_2$ | | O | $CH_2CH_3$ | F | 5-benzo[c][1,2,5]thiadiazolyl |
| 169 | $(CH_2)_4$ | | O | $CH_2CH_3$ | F | 5-benzo[c][1,2,5]thiadiazolyl |
| 170 | $CH_3$ | H | O | $CH_2CF_3$ | F | 4-fluorophenyl |
| 171 | $CH_2CH_3$ | H | O | $CH_2CF_3$ | F | 4-fluorophenyl |
| 172 | $CH_2CF_3$ | H | O | $CH_2CF_3$ | F | 4-fluorophenyl |
| 173 | $CH_2CH_2CH_3$ | H | O | $CH_2CF_3$ | F | 4-fluorophenyl |
| 174 | $CH_2CH(CH_3)_2$ | H | O | $CH_2CF_3$ | F | 4-fluorophenyl |
| 175 | cyclopropylmethyl | H | O | $CH_2CF_3$ | F | 4-fluorophenyl |
| 176 | $SCH(CH_3)_2$ | H | O | $CH_2CF_3$ | F | 4-fluorophenyl |
| 177 | $OCH_2CH_3$ | H | O | $CH_2CF_3$ | F | 4-fluorophenyl |
| 178 | $(CH_2)_2$ | | O | $CH_2CF_3$ | F | 4-fluorophenyl |

TABLE 1-continued

Formula III

| Ex | R1 | R2 | Y | R4 | R5 | Z |
|---|---|---|---|---|---|---|
| 179 | (CH₂)₄ | | O | CH₂CF₃ | F | 4-fluorophenyl |
| 180 | CH₃ | H | O | CH₂CF₃ | F | 4-chlorophenyl |
| 181 | CH₂CH₃ | H | O | CH₂CF₃ | F | 4-chlorophenyl |
| 182 | CH₂CF₃ | H | O | CH₂CF₃ | F | 4-chlorophenyl |
| 183 | CH₂CH₂CH₃ | H | O | CH₂CF₃ | F | 4-chlorophenyl |
| 184 | CH₂CH(CH₃)₂ | H | O | CH₂CF₃ | F | 4-chlorophenyl |
| 185 | cyclopropylmethyl | H | O | CH₂CF₃ | F | 4-chlorophenyl |
| 186 | SCH(CH₃)₂ | H | O | CH₂CF₃ | F | 4-chlorophenyl |
| 187 | OCH₂CH₃ | H | O | CH₂CF₃ | F | 4-chlorophenyl |
| 188 | (CH₂)₂ | | O | CH₂CF₃ | F | 4-chlorophenyl |
| 189 | (CH₂)₄ | | O | CH₂CF₃ | F | 4-chlorophenyl |
| 190 | CH₃ | H | O | CH₂CF₃ | F | 4-trifluoromethylphenyl |
| 191 | CH₂CH₃ | H | O | CH₂CF₃ | F | 4-trifluoromethylphenyl |
| 192 | CH₂CF₃ | H | O | CH₂CF₃ | F | 4-trifluoromethylphenyl |
| 193 | CH₂CH₂CH₃ | H | O | CH₂CF₃ | F | 4-trifluoromethylphenyl |
| 194 | CH₂CH(CH₃)₂ | H | O | CH₂CF₃ | F | 4-trifluoromethylphenyl |
| 195 | cyclopropylmethyl | H | O | CH₂CF₃ | F | 4-trifluoromethylphenyl |
| 196 | SCH(CH₃)₂ | H | O | CH₂CF₃ | F | 4-trifluoromethylphenyl |
| 197 | OCH₂CH₃ | H | O | CH₂CF₃ | F | 4-trifluoromethylphenyl |
| 198 | (CH₂)₂ | | O | CH₂CF₃ | F | 4-trifluoromethylphenyl |
| 199 | (CH₂)₄ | | O | CH₂CF₃ | F | 4-trifluoromethylphenyl |
| 200 | CH₃ | H | O | CH₂CF₃ | F | 4-methoxyphenyl |
| 201 | CH₂CH₃ | H | O | CH₂CF₃ | F | 4-methoxyphenyl |
| 202 | CH₂CF₃ | H | O | CH₂CF₃ | F | 4-methoxyphenyl |
| 203 | CH₂CH₂CH₃ | H | O | CH₂CF₃ | F | 4-methoxyphenyl |
| 204 | CH₂CH(CH₃)₂ | H | O | CH₂CF₃ | F | 4-methoxyphenyl |
| 205 | cyclopropylmethyl | H | O | CH₂CF₃ | F | 4-methoxyphenyl |
| 206 | SCH(CH₃)₂ | H | O | CH₂CF₃ | F | 4-methoxyphenyl |
| 207 | OCH₂CH₃ | H | O | CH₂CF₃ | F | 4-methoxyphenyl |
| 208 | (CH₂)₂ | | O | CH₂CF₃ | F | 4-methoxyphenyl |
| 209 | (CH₂)₄ | | O | CH₂CF₃ | F | 4-methoxyphenyl |
| 210 | CH₃ | H | O | CH₂CF₃ | F | 3,4 dichloro phenyl |
| 211 | CH₂CH₃ | H | O | CH₂CF₃ | F | 3,4 dichloro phenyl |
| 212 | CH₂CF₃ | H | O | CH₂CF₃ | F | 3,4 dichloro phenyl |
| 213 | CH₂CH₂CH₃ | H | O | CH₂CF₃ | F | 3,4 dichloro phenyl |
| 214 | CH₂CH(CH₃)₂ | H | O | CH₂CF₃ | F | 3,4 dichloro phenyl |
| 215 | cyclopropylmethyl | H | O | CH₂CF₃ | F | 3,4 dichloro phenyl |
| 216 | SCH(CH₃)₂ | H | O | CH₂CF₃ | F | 3,4 dichloro phenyl |
| 217 | OCH₂CH₃ | H | O | CH₂CF₃ | F | 3,4 dichloro phenyl |
| 218 | (CH₂)₂ | | O | CH₂CF₃ | F | 3,4 dichloro phenyl |
| 219 | (CH₂)₄ | | O | CH₂CF₃ | F | 3,4 dichloro phenyl |
| 220 | CH₃ | H | O | CH₂CF₃ | F | 5-benzo[c][1,2,5]oxadiazolyl |
| 221 | CH₂CH₃ | H | O | CH₂CF₃ | F | 5-benzo[c][1,2,5]oxadiazolyl |
| 222 | CH₂CF₃ | H | O | CH₂CF₃ | F | 5-benzo[c][1,2,5]oxadiazolyl |
| 223 | CH₂CH₂CH₃ | H | O | CH₂CF₃ | F | 5-benzo[c][1,2,5]oxadiazolyl |
| 224 | CH₂CH(CH₃)₂ | H | O | CH₂CF₃ | F | 5-benzo[c][1,2,5]oxadiazolyl |
| 225 | cyclopropylmethyl | H | O | CH₂CF₃ | F | 5-benzo[c][1,2,5]oxadiazolyl |
| 226 | SCH(CH₃)₂ | H | O | CH₂CF₃ | F | 5-benzo[c][1,2,5]oxadiazolyl |
| 227 | OCH₂CH₃ | H | O | CH₂CF₃ | F | 5-benzo[c][1,2,5]oxadiazolyl |
| 228 | (CH₂)₂ | | O | CH₂CF₃ | F | 5-benzo[c][1,2,5]oxadiazolyl |
| 229 | (CH₂)₄ | | O | CH₂CF₃ | F | 5-benzo[c][1,2,5]oxadiazolyl |
| 230 | CH₃ | H | O | CH₂CF₃ | F | 5-benzo[c][1,2,5]thiadiazolyl |
| 231 | CH₂CH₃ | H | O | CH₂CF₃ | F | 5-benzo[c][1,2,5]thiadiazolyl |
| 232 | CH₂CF₃ | H | O | CH₂CF₃ | F | 5-benzo[c][1,2,5]thiadiazolyl |
| 233 | CH₂CH₂CH₃ | H | O | CH₂CF₃ | F | 5-benzo[c][1,2,5]thiadiazolyl |
| 234 | CH₂CH(CH₃)₂ | H | O | CH₂CF₃ | F | 5-benzo[c][1,2,5]thiadiazolyl |
| 235 | cyclopropylmethyl | H | O | CH₂CF₃ | F | 5-benzo[c][1,2,5]thiadiazolyl |
| 236 | SCH(CH₃)₂ | H | O | CH₂CF₃ | F | 5-benzo[c][1,2,5]thiadiazolyl |
| 237 | OCH₂CH₃ | H | O | CH₂CF₃ | F | 5-benzo[c][1,2,5]thiadiazolyl |
| 238 | (CH₂)₂ | | O | CH₂CF₃ | F | 5-benzo[c][1,2,5]thiadiazolyl |
| 239 | (CH₂)₄ | | O | CH₂CF₃ | F | 5-benzo[c][1,2,5]thiadiazolyl |
| 240 | CH₃ | H | O | CH₂—c-Pr | F | 4-fluorophenyl |
| 241 | CH₂CH₃ | H | O | CH₂—c-Pr | F | 4-fluorophenyl |
| 242 | CH₂CF₃ | H | O | CH₂—c-Pr | F | 4-fluorophenyl |
| 243 | CH₂CH₂CH₃ | H | O | CH₂—c-Pr | F | 4-fluorophenyl |

TABLE 1-continued

Formula III $$\text{Structure: central CH(R_1)(R_2)CO_2H attached to a phenyl ring with R_5 and Z at meta positions and Y-R_4 at para position}$$

| Ex | R1 | R2 | Y | R4 | R5 | Z |
|---|---|---|---|---|---|---|
| 244 | CH$_2$CH(CH$_3$)$_2$ | H | O | CH$_2$—c-Pr | F | 4-fluorophenyl |
| 245 | cyclopropylmethyl | H | O | CH$_2$—c-Pr | F | 4-fluorophenyl |
| 246 | SCH(CH$_3$)$_2$ | H | O | CH$_2$—c-Pr | F | 4-fluorophenyl |
| 247 | OCH$_2$CH$_3$ | H | O | CH$_2$—c-Pr | F | 4-fluorophenyl |
| 248 | (CH$_2$)$_2$ | | O | CH$_2$—c-Pr | F | 4-fluorophenyl |
| 249 | (CH$_2$)$_4$ | | O | CH$_2$—c-Pr | F | 4-fluorophenyl |
| 250 | CH$_3$ | H | O | CH$_2$—c-Pr | F | 4-chlorophenyl |
| 251 | CH$_2$CH$_3$ | H | O | CH$_2$—c-Pr | F | 4-chlorophenyl |
| 252 | CH$_2$CF$_3$ | H | O | CH$_2$—c-Pr | F | 4-chlorophenyl |
| 253 | CH$_2$CH$_2$CH$_3$ | H | O | CH$_2$—c-Pr | F | 4-chlorophenyl |
| 254 | CH$_2$CH(CH$_3$)$_2$ | H | O | CH$_2$—c-Pr | F | 4-chlorophenyl |
| 255 | cyclopropylmethyl | H | O | CH$_2$—c-Pr | F | 4-chlorophenyl |
| 256 | SCH(CH$_3$)$_2$ | H | O | CH$_2$—c-Pr | F | 4-chlorophenyl |
| 257 | OCH$_2$CH$_3$ | H | O | CH$_2$—c-Pr | F | 4-chlorophenyl |
| 258 | (CH$_2$)$_2$ | | O | CH$_2$—c-Pr | F | 4-chlorophenyl |
| 259 | (CH$_2$)$_4$ | | O | CH$_2$—c-Pr | F | 4-chlorophenyl |
| 260 | CH$_3$ | H | O | CH$_2$—c-Pr | F | 4-trifluoromethylphenyl |
| 261 | CH$_2$CH$_3$ | H | O | CH$_2$—c-Pr | F | 4-trifluoromethylphenyl |
| 262 | CH$_2$CF$_3$ | H | O | CH$_2$—c-Pr | F | 4-trifluoromethylphenyl |
| 263 | CH$_2$CH$_2$CH$_3$ | H | O | CH$_2$—c-Pr | F | 4-trifluoromethylphenyl |
| 264 | CH$_2$CH(CH$_3$)$_2$ | H | O | CH$_2$—c-Pr | F | 4-trifluoromethylphenyl |
| 265 | cyclopropylmethyl | H | O | CH$_2$—c-Pr | F | 4-trifluoromethylphenyl |
| 266 | SCH(CH$_3$)$_2$ | H | O | CH$_2$—c-Pr | F | 4-trifluoromethylphenyl |
| 267 | OCH$_2$CH$_3$ | H | O | CH$_2$—c-Pr | F | 4-trifluoromethylphenyl |
| 268 | (CH$_2$)$_2$ | | O | CH$_2$—c-Pr | F | 4-trifluoromethylphenyl |
| 269 | (CH$_2$)$_4$ | | O | CH$_2$—c-Pr | F | 4-trifluoromethylphenyl |
| 270 | CH$_3$ | H | O | CH$_2$—c-Pr | F | 4-methoxyphenyl |
| 271 | CH$_2$CH$_3$ | H | O | CH$_2$—c-Pr | F | 4-methoxyphenyl |
| 272 | CH$_2$CF$_3$ | H | O | CH$_2$—c-Pr | F | 4-methoxyphenyl |
| 273 | CH$_2$CH$_2$CH$_3$ | H | O | CH$_2$—c-Pr | F | 4-methoxyphenyl |
| 274 | CH$_2$CH(CH$_3$)$_2$ | H | O | CH$_2$—c-Pr | F | 4-methoxyphenyl |
| 275 | cyclopropylmethyl | H | O | CH$_2$—c-Pr | F | 4-methoxyphenyl |
| 276 | SCH(CH$_3$)$_2$ | H | O | CH$_2$—c-Pr | F | 4-methoxyphenyl |
| 277 | OCH$_2$CH$_3$ | H | O | CH$_2$—c-Pr | F | 4-methoxyphenyl |
| 278 | (CH$_2$)$_2$ | | O | CH$_2$—c-Pr | F | 4-methoxyphenyl |
| 279 | (CH$_2$)$_4$ | | O | CH$_2$—c-Pr | F | 4-methoxyphenyl |
| 280 | CH$_3$ | H | O | CH$_2$—c-Pr | F | 3,4 dichloro phenyl |
| 281 | CH$_2$CH$_3$ | H | O | CH$_2$—c-Pr | F | 3,4 dichloro phenyl |
| 282 | CH$_2$CF$_3$ | H | O | CH$_2$—c-Pr | F | 3,4 dichloro phenyl |
| 283 | CH$_2$CH$_2$CH$_3$ | H | O | CH$_2$—c-Pr | F | 3,4 dichloro phenyl |
| 284 | CH$_2$CH(CH$_3$)$_2$ | H | O | CH$_2$—c-Pr | F | 3,4 dichloro phenyl |
| 285 | cyclopropylmethyl | H | O | CH$_2$—c-Pr | F | 3,4 dichloro phenyl |
| 286 | SCH(CH$_3$)$_2$ | H | O | CH$_2$—c-Pr | F | 3,4 dichloro phenyl |
| 287 | OCH$_2$CH$_3$ | H | O | CH$_2$—c-Pr | F | 3,4 dichloro phenyl |
| 288 | (CH$_2$)$_2$ | | O | CH$_2$—c-Pr | F | 3,4 dichloro phenyl |
| 289 | (CH$_2$)$_4$ | | O | CH$_2$—c-Pr | F | 3,4 dichloro phenyl |
| 290 | CH$_3$ | H | O | CH$_2$—c-Pr | F | 5-benzo[c][1,2,5]oxadiazolyl |
| 291 | CH$_2$CH$_3$ | H | O | CH$_2$—c-Pr | F | 5-benzo[c][1,2,5]oxadiazolyl |
| 292 | CH$_2$CF$_3$ | H | O | CH$_2$—c-Pr | F | 5-benzo[c][1,2,5]oxadiazolyl |
| 293 | CH$_2$CH$_2$CH$_3$ | H | O | CH$_2$—c-Pr | F | 5-benzo[c][1,2,5]oxadiazolyl |
| 294 | CH$_2$CH(CH$_3$)$_2$ | H | O | CH$_2$—c-Pr | F | 5-benzo[c][1,2,5]oxadiazolyl |
| 295 | cyclopropylmethyl | H | O | CH$_2$—c-Pr | F | 5-benzo[c][1,2,5]oxadiazolyl |
| 296 | SCH(CH$_3$)$_2$ | H | O | CH$_2$—c-Pr | F | 5-benzo[c][1,2,5]oxadiazolyl |
| 297 | OCH$_2$CH$_3$ | H | O | CH$_2$—c-Pr | F | 5-benzo[c][1,2,5]oxadiazolyl |
| 298 | (CH$_2$)$_2$ | | O | CH$_2$—c-Pr | F | 5-benzo[c][1,2,5]oxadiazolyl |
| 299 | (CH$_2$)$_4$ | | O | CH$_2$—c-Pr | F | 5-benzo[c][1,2,5]oxadiazolyl |
| 300 | CH$_3$ | H | O | CH$_2$—c-Pr | F | 5-benzo[c][1,2,5]thiadiazolyl |
| 301 | CH$_2$CH$_3$ | H | O | CH$_2$—c-Pr | F | 5-benzo[c][1,2,5]thiadiazolyl |
| 302 | CH$_2$CF$_3$ | H | O | CH$_2$—c-Pr | F | 5-benzo[c][1,2,5]thiadiazolyl |
| 303 | CH$_2$CH$_2$CH$_3$ | H | O | CH$_2$—c-Pr | F | 5-benzo[c][1,2,5]thiadiazolyl |
| 304 | CH$_2$CH(CH$_3$)$_2$ | H | O | CH$_2$—c-Pr | F | 5-benzo[c][1,2,5]thiadiazolyl |
| 305 | cyclopropylmethyl | H | O | CH$_2$—c-Pr | F | 5-benzo[c][1,2,5]thiadiazolyl |
| 306 | SCH(CH$_3$)$_2$ | H | O | CH$_2$—c-Pr | F | 5-benzo[c][1,2,5]thiadiazolyl |
| 307 | OCH$_2$CH$_3$ | H | O | CH$_2$—c-Pr | F | 5-benzo[c][1,2,5]thiadiazolyl |
| 308 | (CH$_2$)$_2$ | | O | CH$_2$—c-Pr | F | 5-benzo[c][1,2,5]thiadiazolyl |

TABLE 1-continued

Formula III $$\text{Structure: benzene ring with R1, R2, CO2H group at top; R5 and Z at meta positions; Y-R4 at para position}$$

| Ex | R1 | R2 | Y | R4 | R5 | Z |
|---|---|---|---|---|---|---|
| 309 | (CH$_2$)$_4$ | | O | CH$_2$—c-Pr | F | 5-benzo[c][1,2,5]thiadiazolyl |
| 310 | CH$_3$ | H | O | CH$_2$CH$_3$ | Cl | 4-fluorophenyl |
| 311 | CH$_2$CH$_3$ | H | O | CH$_2$CH$_3$ | Cl | 4-fluorophenyl |
| 312 | CH$_2$CF$_3$ | H | O | CH$_2$CH$_3$ | Cl | 4-fluorophenyl |
| 313 | CH$_2$CH$_2$CH$_3$ | H | O | CH$_2$CH$_3$ | Cl | 4-fluorophenyl |
| 314 | CH$_2$CH(CH$_3$)$_2$ | H | O | CH$_2$CH$_3$ | Cl | 4-fluorophenyl |
| 315 | cyclopropylmethyl | H | O | CH$_2$CH$_3$ | Cl | 4-fluorophenyl |
| 316 | SCH(CH$_3$)$_2$ | H | O | CH$_2$CH$_3$ | Cl | 4-fluorophenyl |
| 317 | OCH$_2$CH$_3$ | H | O | CH$_2$CH$_3$ | Cl | 4-fluorophenyl |
| 318 | (CH$_2$)$_2$ | | O | CH$_2$CH$_3$ | Cl | 4-fluorophenyl |
| 319 | (CH$_2$)$_4$ | | O | CH$_2$CH$_3$ | Cl | 4-fluorophenyl |
| 320 | CH$_3$ | H | O | CH$_2$CH$_3$ | Cl | 4-chlorophenyl |
| 321 | CH$_2$CH$_3$ | H | O | CH$_2$CH$_3$ | Cl | 4-chlorophenyl |
| 322 | CH$_2$CF$_3$ | H | O | CH$_2$CH$_3$ | Cl | 4-chlorophenyl |
| 323 | CH$_2$CH$_2$CH$_3$ | H | O | CH$_2$CH$_3$ | Cl | 4-chlorophenyl |
| 324 | CH$_2$CH(CH$_3$)$_2$ | H | O | CH$_2$CH$_3$ | Cl | 4-chlorophenyl |
| 325 | cyclopropylmethyl | H | O | CH$_2$CH$_3$ | Cl | 4-chlorophenyl |
| 326 | SCH(CH$_3$)$_2$ | H | O | CH$_2$CH$_3$ | Cl | 4-chlorophenyl |
| 327 | OCH$_2$CH$_3$ | H | O | CH$_2$CH$_3$ | Cl | 4-chlorophenyl |
| 328 | (CH$_2$)$_2$ | | O | CH$_2$CH$_3$ | Cl | 4-chlorophenyl |
| 329 | (CH$_2$)$_4$ | | O | CH$_2$CH$_3$ | Cl | 4-chlorophenyl |
| 330 | CH$_3$ | H | O | CH$_2$CH$_3$ | Cl | 4-trifluoromethylphenyl |
| 331 | CH$_2$CH$_3$ | H | O | CH$_2$CH$_3$ | Cl | 4-trifluoromethylphenyl |
| 332 | CH$_2$CF$_3$ | H | O | CH$_2$CH$_3$ | Cl | 4-trifluoromethylphenyl |
| 333 | CH$_2$CH$_2$CH$_3$ | H | O | CH$_2$CH$_3$ | Cl | 4-trifluoromethylphenyl |
| 334 | CH$_2$CH(CH$_3$)$_2$ | H | O | CH$_2$CH$_3$ | Cl | 4-trifluoromethylphenyl |
| 335 | cyclopropylmethyl | H | O | CH$_2$CH$_3$ | Cl | 4-trifluoromethylphenyl |
| 336 | SCH(CH$_3$)$_2$ | H | O | CH$_2$CH$_3$ | Cl | 4-trifluoromethylphenyl |
| 337 | OCH$_2$CH$_3$ | H | O | CH$_2$CH$_3$ | Cl | 4-trifluoromethylphenyl |
| 338 | (CH$_2$)$_2$ | | O | CH$_2$CH$_3$ | Cl | 4-trifluoromethylphenyl |
| 339 | (CH$_2$)$_4$ | | O | CH$_2$CH$_3$ | Cl | 4-trifluoromethylphenyl |
| 340 | CH$_3$ | H | O | CH$_2$CH$_3$ | Cl | 4-methoxyphenyl |
| 341 | CH$_2$CH$_3$ | H | O | CH$_2$CH$_3$ | Cl | 4-methoxyphenyl |
| 342 | CH$_2$CF$_3$ | H | O | CH$_2$CH$_3$ | Cl | 4-methoxyphenyl |
| 343 | CH$_2$CH$_2$CH$_3$ | H | O | CH$_2$CH$_3$ | Cl | 4-methoxyphenyl |
| 344 | CH$_2$CH(CH$_3$)$_2$ | H | O | CH$_2$CH$_3$ | Cl | 4-methoxyphenyl |
| 345 | cyclopropylmethyl | H | O | CH$_2$CH$_3$ | Cl | 4-methoxyphenyl |
| 346 | SCH(CH$_3$)$_2$ | H | O | CH$_2$CH$_3$ | Cl | 4-methoxyphenyl |
| 347 | OCH$_2$CH$_3$ | H | O | CH$_2$CH$_3$ | Cl | 4-methoxyphenyl |
| 348 | (CH$_2$)$_2$ | | O | CH$_2$CH$_3$ | Cl | 4-methoxyphenyl |
| 349 | (CH$_2$)$_4$ | | O | CH$_2$CH$_3$ | Cl | 4-methoxyphenyl |
| 350 | CH$_3$ | H | O | CH$_2$CH$_3$ | Cl | 3,4 dichloro phenyl |
| 351 | CH$_2$CH$_3$ | H | O | CH$_2$CH$_3$ | Cl | 3,4 dichloro phenyl |
| 352 | CH$_2$CF$_3$ | H | O | CH$_2$CH$_3$ | Cl | 3,4 dichloro phenyl |
| 353 | CH$_2$CH$_2$CH$_3$ | H | O | CH$_2$CH$_3$ | Cl | 3,4 dichloro phenyl |
| 354 | CH$_2$CH(CH$_3$)$_2$ | H | O | CH$_2$CH$_3$ | Cl | 3,4 dichloro phenyl |
| 355 | cyclopropylmethyl | H | O | CH$_2$CH$_3$ | Cl | 3,4 dichloro phenyl |
| 356 | SCH(CH$_3$)$_2$ | H | O | CH$_2$CH$_3$ | Cl | 3,4 dichloro phenyl |
| 357 | OCH$_2$CH$_3$ | H | O | CH$_2$CH$_3$ | Cl | 3,4 dichloro phenyl |
| 358 | (CH$_2$)$_2$ | | O | CH$_2$CH$_3$ | Cl | 3,4 dichloro phenyl |
| 359 | (CH$_2$)$_4$ | | O | CH$_2$CH$_3$ | Cl | 3,4 dichloro phenyl |
| 360 | CH$_3$ | H | O | CH$_2$CH$_3$ | Cl | 5-benzo[c][1,2,5]oxadiazolyl |
| 361 | CH$_2$CH$_3$ | H | O | CH$_2$CH$_3$ | Cl | 5-benzo[c][1,2,5]oxadiazolyl |
| 362 | CH$_2$CF$_3$ | H | O | CH$_2$CH$_3$ | Cl | 5-benzo[c][1,2,5]oxadiazolyl |
| 363 | CH$_2$CH$_2$CH$_3$ | H | O | CH$_2$CH$_3$ | Cl | 5-benzo[c][1,2,5]oxadiazolyl |
| 364 | CH$_2$CH(CH$_3$)$_2$ | H | O | CH$_2$CH$_3$ | Cl | 5-benzo[c][1,2,5]oxadiazolyl |
| 365 | cyclopropylmethyl | H | O | CH$_2$CH$_3$ | Cl | 5-benzo[c][1,2,5]oxadiazolyl |
| 366 | SCH(CH$_3$)$_2$ | H | O | CH$_2$CH$_3$ | Cl | 5-benzo[c][1,2,5]oxadiazolyl |
| 367 | OCH$_2$CH$_3$ | H | O | CH$_2$CH$_3$ | Cl | 5-benzo[c][1,2,5]oxadiazolyl |
| 368 | (CH$_2$)$_2$ | | O | CH$_2$CH$_3$ | Cl | 5-benzo[c][1,2,5]oxadiazolyl |
| 369 | (CH$_2$)$_4$ | | O | CH$_2$CH$_3$ | Cl | 5-benzo[c][1,2,5]oxadiazolyl |
| 370 | CH$_3$ | H | O | CH$_2$CH$_3$ | Cl | 5-benzo[c][1,2,5]thiadiazolyl |
| 371 | CH$_2$CH$_3$ | H | O | CH$_2$CH$_3$ | Cl | 5-benzo[c][1,2,5]thiadiazolyl |
| 372 | CH$_2$CF$_3$ | H | O | CH$_2$CH$_3$ | Cl | 5-benzo[c][1,2,5]thiadiazolyl |
| 373 | CH$_2$CH$_2$CH$_3$ | H | O | CH$_2$CH$_3$ | Cl | 5-benzo[c][1,2,5]thiadiazolyl |

TABLE 1-continued

Formula III

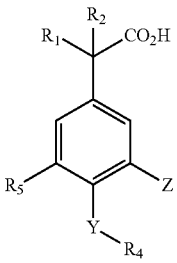

| Ex | R1 | R2 | Y | R4 | R5 | Z |
|---|---|---|---|---|---|---|
| 374 | $CH_2CH(CH_3)_2$ | H | O | $CH_2CH_3$ | Cl | 5-benzo[c][1,2,5]thiadiazolyl |
| 375 | cyclopropylmethyl | H | O | $CH_2CH_3$ | Cl | 5-benzo[c][1,2,5]thiadiazolyl |
| 376 | $SCH(CH_3)_2$ | H | O | $CH_2CH_3$ | Cl | 5-benzo[c][1,2,5]thiadiazolyl |
| 377 | $OCH_2CH_3$ | H | O | $CH_2CH_3$ | Cl | 5-benzo[c][1,2,5]thiadiazolyl |
| 378 | $(CH_2)_2$ | | O | $CH_2CH_3$ | Cl | 5-benzo[c][1,2,5]thiadiazolyl |
| 379 | $(CH_2)_4$ | | O | $CH_2CH_3$ | Cl | 5-benzo[c][1,2,5]thiadiazolyl |
| 380 | $CH_3$ | H | O | $CH_2CF_3$ | Cl | 4-fluorophenyl |
| 381 | $CH_2CH_3$ | H | O | $CH_2CF_3$ | Cl | 4-fluorophenyl |
| 382 | $CH_2CF_3$ | H | O | $CH_2CF_3$ | Cl | 4-fluorophenyl |
| 383 | $CH_2CH_2CH_3$ | H | O | $CH_2CF_3$ | Cl | 4-fluorophenyl |
| 384 | $CH_2CH(CH_3)_2$ | H | O | $CH_2CF_3$ | Cl | 4-fluorophenyl |
| 385 | cyclopropylmethyl | H | O | $CH_2CF_3$ | Cl | 4-fluorophenyl |
| 386 | $SCH(CH_3)_2$ | H | O | $CH_2CF_3$ | Cl | 4-fluorophenyl |
| 387 | $OCH_2CH_3$ | H | O | $CH_2CF_3$ | Cl | 4-fluorophenyl |
| 388 | $(CH_2)_2$ | O | O | $CH_2CF_3$ | Cl | 4-fluorophenyl |
| 389 | $(CH_2)_4$ | O | O | $CH_2CF_3$ | Cl | 4-fluorophenyl |
| 400 | $CH_3$ | H | O | $CH_2CF_3$ | Cl | 4-chlorophenyl |
| 401 | $CH_2CH_3$ | H | O | $CH_2CF_3$ | Cl | 4-chlorophenyl |
| 402 | $CH_2CF_3$ | H | O | $CH_2CF_3$ | Cl | 4-chlorophenyl |
| 403 | $CH_2CH_2CH_3$ | H | O | $CH_2CF_3$ | Cl | 4-chlorophenyl |
| 404 | $CH_2CH(CH_3)_2$ | H | O | $CH_2CF_3$ | Cl | 4-chlorophenyl |
| 405 | cyclopropylmethyl | H | O | $CH_2CF_3$ | Cl | 4-chlorophenyl |
| 406 | $SCH(CH_3)_2$ | H | O | $CH_2CF_3$ | Cl | 4-chlorophenyl |
| 407 | $OCH_2CH_3$ | H | O | $CH_2CF_3$ | Cl | 4-chlorophenyl |
| 408 | $(CH_2)_2$ | | O | $CH_2CF_3$ | Cl | 4-chlorophenyl |
| 409 | $(CH_2)_4$ | | O | $CH_2CF_3$ | Cl | 4-chlorophenyl |
| 410 | $CH_3$ | H | O | $CH_2CF_3$ | Cl | 4-trifluoromethylphenyl |
| 411 | $CH_2CH_3$ | H | O | $CH_2CF_3$ | Cl | 4-trifluoromethylphenyl |
| 412 | $CH_2CF_3$ | H | O | $CH_2CF_3$ | Cl | 4-trifluoromethylphenyl |
| 413 | $CH_2CH_2CH_3$ | H | O | $CH_2CF_3$ | Cl | 4-trifluoromethylphenyl |
| 414 | $CH_2CH(CH_3)_2$ | H | O | $CH_2CF_3$ | Cl | 4-trifluoromethylphenyl |
| 415 | cyclopropylmethyl | H | O | $CH_2CF_3$ | Cl | 4-trifluoromethylphenyl |
| 416 | $SCH(CH_3)_2$ | H | O | $CH_2CF_3$ | Cl | 4-trifluoromethylphenyl |
| 417 | $OCH_2CH_3$ | H | O | $CH_2CF_3$ | Cl | 4-trifluoromethylphenyl |
| 418 | $(CH_2)_2$ | | O | $CH_2CF_3$ | Cl | 4-trifluoromethylphenyl |
| 419 | $(CH_2)_4$ | | O | $CH_2CF_3$ | Cl | 4-trifluoromethylphenyl |
| 420 | $CH_3$ | H | O | $CH_2CF_3$ | Cl | 4-methoxyphenyl |
| 421 | $CH_2CH_3$ | H | O | $CH_2CF_3$ | Cl | 4-methoxyphenyl |
| 422 | $CH_2CF_3$ | H | O | $CH_2CF_3$ | Cl | 4-methoxyphenyl |
| 423 | $CH_2CH_2CH_3$ | H | O | $CH_2CF_3$ | Cl | 4-methoxyphenyl |
| 424 | $CH_2CH(CH_3)_2$ | H | O | $CH_2CF_3$ | Cl | 4-methoxyphenyl |
| 425 | cyclopropylmethyl | H | O | $CH_2CF_3$ | Cl | 4-methoxyphenyl |
| 426 | $SCH(CH_3)_2$ | H | O | $CH_2CF_3$ | Cl | 4-methoxyphenyl |
| 427 | $OCH_2CH_3$ | H | O | $CH_2CF_3$ | Cl | 4-methoxyphenyl |
| 428 | $(CH_2)_2$ | | O | $CH_2CF_3$ | Cl | 4-methoxyphenyl |
| 429 | $(CH_2)_4$ | | O | $CH_2CF_3$ | Cl | 4-methoxyphenyl |
| 430 | $CH_3$ | H | O | $CH_2CF_3$ | Cl | 3,4 dichloro phenyl |
| 431 | $CH_2CH_3$ | H | O | $CH_2CF_3$ | Cl | 3,4 dichloro phenyl |
| 432 | $CH_2CF_3$ | H | O | $CH_2CF_3$ | Cl | 3,4 dichloro phenyl |
| 433 | $CH_2CH_2CH_3$ | H | O | $CH_2CF_3$ | Cl | 3,4 dichloro phenyl |
| 434 | $CH_2CH(CH_3)_2$ | H | O | $CH_2CF_3$ | Cl | 3,4 dichloro phenyl |
| 435 | cyclopropylmethyl | H | O | $CH_2CF_3$ | Cl | 3,4 dichloro phenyl |
| 436 | $SCH(CH_3)_2$ | H | O | $CH_2CF_3$ | Cl | 3,4 dichloro phenyl |
| 437 | $OCH_2CH_3$ | H | O | $CH_2CF_3$ | Cl | 3,4 dichloro phenyl |
| 438 | $(CH_2)_2$ | | O | $CH_2CF_3$ | Cl | 3,4 dichloro phenyl |
| 439 | $(CH_2)_4$ | | O | $CH_2CF_3$ | Cl | 3,4 dichloro phenyl |
| 440 | $CH_3$ | H | O | $CH_2CF_3$ | Cl | 5-benzo[c][1,2,5]oxadiazolyl |
| 441 | $CH_2CH_3$ | H | O | $CH_2CF_3$ | Cl | 5-benzo[c][1,2,5]oxadiazolyl |
| 442 | $CH_2CF_3$ | H | O | $CH_2CF_3$ | Cl | 5-benzo[c][1,2,5]oxadiazolyl |
| 443 | $CH_2CH_2CH_3$ | H | O | $CH_2CF_3$ | Cl | 5-benzo[c][1,2,5]oxadiazolyl |
| 444 | $CH_2CH(CH_3)_2$ | H | O | $CH_2CF_3$ | Cl | 5-benzo[c][1,2,5]oxadiazolyl |
| 445 | cyclopropylmethyl | H | O | $CH_2CF_3$ | Cl | 5-benzo[c][1,2,5]oxadiazolyl |
| 446 | $SCH(CH_3)_2$ | H | O | $CH_2CF_3$ | Cl | 5-benzo[c][1,2,5]oxadiazolyl |
| 447 | $OCH_2CH_3$ | H | O | $CH_2CF_3$ | Cl | 5-benzo[c][1,2,5]oxadiazolyl |
| 448 | $(CH_2)_2$ | | O | $CH_2CF_3$ | Cl | 5-benzo[c][1,2,5]oxadiazolyl |

TABLE 1-continued

Formula III

| Ex | R1 | R2 | Y | R4 | R5 | Z |
|---|---|---|---|---|---|---|
| 449 | (CH$_2$)$_4$ | | O | CH$_2$CF$_3$ | Cl | 5-benzo[c][1,2,5]oxadiazolyl |
| 450 | CH$_3$ | H | O | CH$_2$CF$_3$ | Cl | 5-benzo[c][1,2,5]thiadiazolyl |
| 451 | CH$_2$CH$_3$ | H | O | CH$_2$CF$_3$ | Cl | 5-benzo[c][1,2,5]thiadiazolyl |
| 452 | CH$_2$CF$_3$ | H | O | CH$_2$CF$_3$ | Cl | 5-benzo[c][1,2,5]thiadiazolyl |
| 453 | CH$_2$CH$_2$CH$_3$ | H | O | CH$_2$CF$_3$ | Cl | 5-benzo[c][1,2,5]thiadiazolyl |
| 454 | CH$_2$CH(CH$_3$)$_2$ | H | O | CH$_2$CF$_3$ | Cl | 5-benzo[c][1,2,5]thiadiazolyl |
| 455 | cyclopropylmethyl | H | O | CH$_2$CF$_3$ | Cl | 5-benzo[c][1,2,5]thiadiazolyl |
| 456 | SCH(CH$_3$)$_2$ | H | O | CH$_2$CF$_3$ | Cl | 5-benzo[c][1,2,5]thiadiazolyl |
| 457 | OCH$_2$CH$_3$ | H | O | CH$_2$CF$_3$ | Cl | 5-benzo[c][1,2,5]thiadiazolyl |
| 458 | (CH$_2$)$_2$ | | O | CH$_2$CF$_3$ | Cl | 5-benzo[c][1,2,5]thiadiazolyl |
| 459 | (CH$_2$)$_4$ | | O | CH$_2$CF$_3$ | Cl | 5-benzo[c][1,2,5]thiadiazolyl |
| 460 | CH$_3$ | H | O | CH$_2$—c-Pr | Cl | 4-fluorophenyl |
| 461 | CH$_2$CH$_3$ | H | O | CH$_2$—c-Pr | Cl | 4-fluorophenyl |
| 462 | CH$_2$CF$_3$ | H | O | CH$_2$—c-Pr | Cl | 4-fluorophenyl |
| 463 | CH$_2$CH$_2$CH$_3$ | H | O | CH$_2$—c-Pr | Cl | 4-fluorophenyl |
| 464 | CH$_2$CH(CH$_3$)$_2$ | H | O | CH$_2$—c-Pr | Cl | 4-fluorophenyl |
| 465 | cyclopropylmethyl | H | O | CH$_2$—c-Pr | Cl | 4-fluorophenyl |
| 466 | SCH(CH$_3$)$_2$ | H | O | CH$_2$—c-Pr | Cl | 4-fluorophenyl |
| 467 | OCH$_2$CH$_3$ | H | O | CH$_2$—c-Pr | Cl | 4-fluorophenyl |
| 468 | (CH$_2$)$_2$ | | O | CH$_2$—c-Pr | Cl | 4-fluorophenyl |
| 469 | (CH$_2$)$_4$ | | O | CH$_2$—c-Pr | Cl | 4-fluorophenyl |
| 470 | CH$_3$ | H | O | CH$_2$—c-Pr | Cl | 4-chlorophenyl |
| 471 | CH$_2$CH$_3$ | H | O | CH$_2$—c-Pr | Cl | 4-chlorophenyl |
| 472 | CH$_2$CF$_3$ | H | O | CH$_2$—c-Pr | Cl | 4-chlorophenyl |
| 473 | CH$_2$CH$_2$CH$_3$ | H | O | CH$_2$—c-Pr | Cl | 4-chlorophenyl |
| 474 | CH$_2$CH(CH$_3$)$_2$ | H | O | CH$_2$—c-Pr | Cl | 4-chlorophenyl |
| 475 | cyclopropylmethyl | H | O | CH$_2$—c-Pr | Cl | 4-chlorophenyl |
| 476 | SCH(CH$_3$)$_2$ | H | O | CH$_2$—c-Pr | Cl | 4-chlorophenyl |
| 477 | OCH$_2$CH$_3$ | H | O | CH$_2$—c-Pr | Cl | 4-chlorophenyl |
| 478 | (CH$_2$)$_2$ | | O | CH$_2$—c-Pr | Cl | 4-chlorophenyl |
| 479 | (CH$_2$)$_4$ | | O | CH$_2$—c-Pr | Cl | 4-chlorophenyl |
| 480 | CH$_3$ | H | O | CH$_2$—c-Pr | Cl | 4-trifluoromethylphenyl |
| 481 | CH$_2$CH$_3$ | H | O | CH$_2$—c-Pr | Cl | 4-trifluoromethylphenyl |
| 482 | CH$_2$CF$_3$ | H | O | CH$_2$—c-Pr | Cl | 4-trifluoromethylphenyl |
| 483 | CH$_2$CH$_2$CH$_3$ | H | O | CH$_2$—c-Pr | Cl | 4-trifluoromethylphenyl |
| 484 | CH$_2$CH(CH$_3$)$_2$ | H | O | CH$_2$—c-Pr | Cl | 4-trifluoromethylphenyl |
| 485 | cyclopropylmethyl | H | O | CH$_2$—c-Pr | Cl | 4-trifluoromethylphenyl |
| 486 | SCH(CH$_3$)$_2$ | H | O | CH$_2$—c-Pr | Cl | 4-trifluoromethylphenyl |
| 487 | OCH$_2$CH$_3$ | H | O | CH$_2$—c-Pr | Cl | 4-trifluoromethylphenyl |
| 488 | (CH$_2$)$_2$ | | O | CH$_2$—c-Pr | Cl | 4-trifluoromethylphenyl |
| 489 | (CH$_2$)$_4$ | | O | CH$_2$—c-Pr | Cl | 4-trifluoromethylphenyl |
| 490 | CH$_3$ | H | O | CH$_2$—c-Pr | Cl | 4-methoxyphenyl |
| 491 | CH$_2$CH$_3$ | H | O | CH$_2$—c-Pr | Cl | 4-methoxyphenyl |
| 492 | CH$_2$CF$_3$ | H | O | CH$_2$—c-Pr | Cl | 4-methoxyphenyl |
| 493 | CH$_2$CH$_2$CH$_3$ | H | O | CH$_2$—c-Pr | Cl | 4-methoxyphenyl |
| 494 | CH$_2$CH(CH$_3$)$_2$ | H | O | CH$_2$—c-Pr | Cl | 4-methoxyphenyl |
| 495 | cyclopropylmethyl | H | O | CH$_2$—c-Pr | Cl | 4-methoxyphenyl |
| 496 | SCH(CH$_3$)$_2$ | H | O | CH$_2$—c-Pr | Cl | 4-methoxyphenyl |
| 497 | OCH$_2$CH$_3$ | H | O | CH$_2$—c-Pr | Cl | 4-methoxyphenyl |
| 498 | (CH$_2$)$_2$ | | O | CH$_2$—c-Pr | Cl | 4-methoxyphenyl |
| 499 | (CH$_2$)$_4$ | | O | CH$_2$—c-Pr | Cl | 4-methoxyphenyl |
| 500 | CH$_3$ | H | O | CH$_2$—c-Pr | Cl | 3,4 dichloro phenyl |
| 501 | CH$_2$CH$_3$ | H | O | CH$_2$—c-Pr | Cl | 3,4 dichloro phenyl |
| 502 | CH$_2$CF$_3$ | H | O | CH$_2$—c-Pr | Cl | 3,4 dichloro phenyl |
| 503 | CH$_2$CH$_2$CH$_3$ | H | O | CH$_2$—c-Pr | Cl | 3,4 dichloro phenyl |
| 504 | CH$_2$CH(CH$_3$)$_2$ | H | O | CH$_2$—c-Pr | Cl | 3,4 dichloro phenyl |
| 505 | cyclopropylmethyl | H | O | CH$_2$—c-Pr | Cl | 3,4 dichloro phenyl |
| 506 | SCH(CH$_3$)$_2$ | H | O | CH$_2$—c-Pr | Cl | 3,4 dichloro phenyl |
| 507 | OCH$_2$CH$_3$ | H | O | CH$_2$—c-Pr | Cl | 3,4 dichloro phenyl |
| 508 | (CH$_2$)$_2$ | | O | CH$_2$—c-Pr | Cl | 3,4 dichloro phenyl |
| 509 | (CH$_2$)$_4$ | | O | CH$_2$—c-Pr | Cl | 3,4 dichloro phenyl |
| 510 | CH$_3$ | H | O | CH$_2$—c-Pr | Cl | 5-benzo[c][1,2,5]oxadiazolyl |
| 511 | CH$_2$CH$_3$ | H | O | CH$_2$—c-Pr | Cl | 5-benzo[c][1,2,5]oxadiazolyl |
| 512 | CH$_2$CF$_3$ | H | O | CH$_2$—c-Pr | Cl | 5-benzo[c][1,2,5]oxadiazolyl |
| 513 | CH$_2$CH$_2$CH$_3$ | H | O | CH$_2$—c-Pr | Cl | 5-benzo[c][1,2,5]oxadiazolyl |

TABLE 1-continued

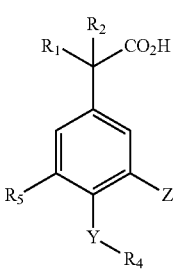

Formula III

| Ex | R1 | R2 | Y | R4 | R5 | Z |
|---|---|---|---|---|---|---|
| 514 | $CH_2CH(CH_3)_2$ | H | O | $CH_2$—c-Pr | Cl | 5-benzo[c][1,2,5]oxadiazolyl |
| 515 | cyclopropylmethyl | H | O | $CH_2$—c-Pr | Cl | 5-benzo[c][1,2,5]oxadiazolyl |
| 516 | $SCH(CH_3)_2$ | H | O | $CH_2$—c-Pr | Cl | 5-benzo[c][1,2,5]oxadiazolyl |
| 517 | $OCH_2CH_3$ | H | O | $CH_2$—c-Pr | Cl | 5-benzo[c][1,2,5]oxadiazolyl |
| 518 | $(CH_2)_2$ | | O | $CH_2$—c-Pr | Cl | 5-benzo[c][1,2,5]oxadiazolyl |
| 519 | $(CH_2)_4$ | | O | $CH_2$—c-Pr | Cl | 5-benzo[c][1,2,5]oxadiazolyl |
| 520 | $CH_3$ | H | O | $CH_2$—c-Pr | Cl | 5-benzo[c][1,2,5]thiadiazolyl |
| 521 | $CH_2CH_3$ | H | O | $CH_2$—c-Pr | Cl | 5-benzo[c][1,2,5]thiadiazolyl |
| 522 | $CH_2CF_3$ | H | O | $CH_2$—c-Pr | Cl | 5-benzo[c][1,2,5]thiadiazolyl |
| 523 | $CH_2CH_2CH_3$ | H | O | $CH_2$—c-Pr | Cl | 5-benzo[c][1,2,5]thiadiazolyl |
| 524 | $CH_2CH(CH_3)_2$ | H | O | $CH_2$—c-Pr | Cl | 5-benzo[c][1,2,5]thiadiazolyl |
| 525 | cyclopropylmethyl | H | O | $CH_2$—c-Pr | Cl | 5-benzo[c][1,2,5]thiadiazolyl |
| 526 | $SCH(CH_3)_2$ | H | O | $CH_2$—c-Pr | Cl | 5-benzo[c][1,2,5]thiadiazolyl |
| 527 | $OCH_2CH_3$ | H | O | $CH_2$—c-Pr | Cl | 5-benzo[c][1,2,5]thiadiazolyl |
| 528 | $(CH_2)_2$ | | O | $CH_2$—c-Pr | Cl | 5-benzo[c][1,2,5]thiadiazolyl |
| 529 | $(CH_2)_4$ | | O | $CH_2$—c-Pr | Cl | 5-benzo[c][1,2,5]thiadiazolyl |
| 530 | $CH_3$ | H | O | $CH_2$—c-Pr | NO2 | 4-trifluoromethylphenyl |
| 531 | $CH_2CH_3$ | H | O | $CH_2$—c-Pr | NO2 | 4-trifluoromethylphenyl |
| 532 | $CH_2CF_3$ | H | O | $CH_2$—c-Pr | NO2 | 4-trifluoromethylphenyl |
| 533 | $CH_2CH_2CH_3$ | H | O | $CH_2$—c-Pr | NO2 | 4-trifluoromethylphenyl |
| 534 | $CH_2CH(CH_3)_2$ | H | O | $CH_2$—c-Pr | NO2 | 4-trifluoromethylphenyl |
| 535 | cyclopropylmethyl | H | O | $CH_2$—c-Pr | NO2 | 4-trifluoromethylphenyl |
| 536 | $SCH(CH_3)_2$ | H | O | $CH_2$—c-Pr | NO2 | 4-trifluoromethylphenyl |
| 537 | $OCH_2CH_3$ | H | O | $CH_2$—c-Pr | NO2 | 4-trifluoromethylphenyl |
| 538 | $(CH_2)_2$ | | O | $CH_2$—c-Pr | NO2 | 4-trifluoromethylphenyl |
| 539 | $(CH_2)_4$ | | O | $CH_2$—c-Pr | NO2 | 4-trifluoromethylphenyl |
| 540 | $CH_3$ | H | O | $CH_2$—c-Pr | NO2 | 5-benzo[c][1,2,5]oxadiazolyl |
| 541 | $CH_2CH_3$ | H | O | $CH_2$—c-Pr | NO2 | 5-benzo[c][1,2,5]oxadiazolyl |
| 542 | $CH_2CF_3$ | H | O | $CH_2$—c-Pr | NO2 | 5-benzo[c][1,2,5]oxadiazolyl |
| 543 | $CH_2CH_2CH_3$ | H | O | $CH_2$—c-Pr | NO2 | 5-benzo[c][1,2,5]oxadiazolyl |
| 544 | $CH_2CH(CH_3)_2$ | H | O | $CH_2$—c-Pr | NO2 | 5-benzo[c][1,2,5]oxadiazolyl |
| 545 | cyclopropylmethyl | H | O | $CH_2$—c-Pr | NO2 | 5-benzo[c][1,2,5]oxadiazolyl |
| 546 | $SCH(CH_3)_2$ | H | O | $CH_2$—c-Pr | NO2 | 5-benzo[c][1,2,5]oxadiazolyl |
| 547 | $OCH_2CH_3$ | H | O | $CH_2$—c-Pr | NO2 | 5-benzo[c][1,2,5]oxadiazolyl |
| 548 | $(CH_2)_2$ | | O | $CH_2$—c-Pr | NO2 | 5-benzo[c][1,2,5]oxadiazolyl |
| 549 | $(CH_2)_4$ | | O | $CH_2$—c-Pr | NO2 | 5-benzo[c][1,2,5]oxadiazolyl |
| 550 | $CH_3$ | H | O | $CH_2$—c-Pr | NH2 | 4-trifluoromethylphenyl |
| 551 | $CH_2CH_3$ | H | O | $CH_2$—c-Pr | NH2 | 4-trifluoromethylphenyl |
| 552 | $CH_2CF_3$ | H | O | $CH_2$—c-Pr | NH2 | 4-trifluoromethylphenyl |
| 553 | $CH_2CH_2CH_3$ | H | O | $CH_2$—c-Pr | NH2 | 4-trifluoromethylphenyl |
| 554 | $CH_2CH(CH_3)_2$ | H | O | $CH_2$—c-Pr | NH2 | 4-trifluoromethylphenyl |
| 555 | cyclopropylmethyl | H | O | $CH_2$—c-Pr | NH2 | 4-trifluoromethylphenyl |
| 556 | $SCH(CH_3)_2$ | H | O | $CH_2$—c-Pr | NH2 | 4-trifluoromethylphenyl |
| 557 | $OCH_2CH_3$ | H | O | $CH_2$—c-Pr | NH2 | 4-trifluoromethylphenyl |
| 558 | $(CH_2)_2$ | | O | $CH_2$—c-Pr | NH2 | 4-trifluoromethylphenyl |
| 559 | $(CH_2)_4$ | | O | $CH_2$—c-Pr | NH2 | 4-trifluoromethylphenyl |

TABLE 2

Formula V

| EX | R1 | R2 | X | R3 | R5 | Z |
|---|---|---|---|---|---|---|
| 560 | CH$_3$ | H | O | CH$_2$CH$_3$ | F | 4-fluorophenyl |
| 561 | CH$_2$CH$_3$ | H | O | CH$_2$CH$_3$ | F | 4-fluorophenyl |
| 562 | CH$_2$CF$_3$ | H | O | CH$_2$CH$_3$ | F | 4-fluorophenyl |
| 563 | CH$_2$CH$_2$CH$_3$ | H | O | CH$_2$CH$_3$ | F | 4-fluorophenyl |
| 564 | CH$_2$CH(CH$_3$)$_2$ | H | O | CH$_2$CH$_3$ | F | 4-fluorophenyl |
| 565 | cyclopropylmethyl | H | O | CH$_2$CH$_3$ | F | 4-fluorophenyl |
| 566 | SCH(CH$_3$)$_2$ | H | O | CH$_2$CH$_3$ | F | 4-fluorophenyl |
| 567 | OCH$_2$CH$_3$ | H | O | CH$_2$CH$_3$ | F | 4-fluorophenyl |
| 568 | (CH$_2$)$_2$ | | O | CH$_2$CH$_3$ | F | 4-fluorophenyl |
| 569 | (CH$_2$)$_4$ | | O | CH$_2$CH$_3$ | F | 4-fluorophenyl |
| 570 | CH$_3$ | H | O | CH$_2$CH$_3$ | F | 4-chlorophenyl |
| 571 | CH$_2$CH$_3$ | H | O | CH$_2$CH$_3$ | F | 4-chlorophenyl |
| 572 | CH$_2$CF$_3$ | H | O | CH$_2$CH$_3$ | F | 4-chlorophenyl |
| 573 | CH$_2$CH$_2$CH$_3$ | H | O | CH$_2$CH$_3$ | F | 4-chlorophenyl |
| 574 | CH$_2$CH(CH$_3$)$_2$ | H | O | CH$_2$CH$_3$ | F | 4-chlorophenyl |
| 575 | cyclopropylmethyl | H | O | CH$_2$CH$_3$ | F | 4-chlorophenyl |
| 576 | SCH(CH$_3$)$_2$ | H | O | CH$_2$CH$_3$ | F | 4-chlorophenyl |
| 577 | OCH$_2$CH$_3$ | H | O | CH$_2$CH$_3$ | F | 4-chlorophenyl |
| 578 | (CH$_2$)$_2$ | | O | CH$_2$CH$_3$ | F | 4-chlorophenyl |
| 579 | (CH$_2$)$_4$ | | O | CH$_2$CH$_3$ | F | 4-chlorophenyl |
| 580 | CH$_3$ | H | O | CH$_2$CH$_3$ | F | 4-trifluoromethylphenyl |
| 581 | CH$_2$CH$_3$ | H | O | CH$_2$CH$_3$ | F | 4-trifluoromethylphenyl |
| 582 | CH$_2$CF$_3$ | H | O | CH$_2$CH$_3$ | F | 4-trifluoromethylphenyl |
| 583 | CH$_2$CH$_2$CH$_3$ | H | O | CH$_2$CH$_3$ | F | 4-trifluoromethylphenyl |
| 584 | CH$_2$CH(CH$_3$)$_2$ | H | O | CH$_2$CH$_3$ | F | 4-trifluoromethylphenyl |
| 585 | cyclopropylmethyl | H | O | CH$_2$CH$_3$ | F | 4-trifluoromethylphenyl |
| 586 | SCH(CH$_3$)$_2$ | H | O | CH$_2$CH$_3$ | F | 4-trifluoromethylphenyl |
| 587 | OCH$_2$CH$_3$ | H | O | CH$_2$CH$_3$ | F | 4-trifluoromethylphenyl |
| 588 | (CH$_2$)$_2$ | | O | CH$_2$CH$_3$ | F | 4-trifluoromethylphenyl |
| 589 | (CH$_2$)$_4$ | | O | CH$_2$CH$_3$ | F | 4-trifluoromethylphenyl |
| 590 | CH$_3$ | H | O | CH$_2$CH$_3$ | F | 4-methoxyphenyl |
| 591 | CH$_2$CH$_3$ | H | O | CH$_2$CH$_3$ | F | 4-methoxyphenyl |
| 592 | CH$_2$CF$_3$ | H | O | CH$_2$CH$_3$ | F | 4-methoxyphenyl |
| 593 | CH$_2$CH$_2$CH$_3$ | H | O | CH$_2$CH$_3$ | F | 4-methoxyphenyl |
| 594 | CH$_2$CH(CH$_3$)$_2$ | H | O | CH$_2$CH$_3$ | F | 4-methoxyphenyl |
| 595 | cyclopropylmethyl | H | O | CH$_2$CH$_3$ | F | 4-methoxyphenyl |
| 596 | SCH(CH$_3$)$_2$ | H | O | CH$_2$CH$_3$ | F | 4-methoxyphenyl |
| 597 | OCH$_2$CH$_3$ | H | O | CH$_2$CH$_3$ | F | 4-methoxyphenyl |
| 598 | (CH$_2$)$_2$ | | O | CH$_2$CH$_3$ | F | 4-methoxyphenyl |
| 599 | (CH$_2$)$_4$ | | O | CH$_2$CH$_3$ | F | 4-methoxyphenyl |
| 600 | CH$_3$ | H | O | CH$_2$CH$_3$ | F | 3,4 dichloro phenyl |
| 601 | CH$_2$CH$_3$ | H | O | CH$_2$CH$_3$ | F | 3,4 dichloro phenyl |
| 602 | CH$_2$CF$_3$ | H | O | CH$_2$CH$_3$ | F | 3,4 dichloro phenyl |
| 603 | CH$_2$CH$_2$CH$_3$ | H | O | CH$_2$CH$_3$ | F | 3,4 dichloro phenyl |
| 604 | CH$_2$CH(CH$_3$)$_2$ | H | O | CH$_2$CH$_3$ | F | 3,4 dichloro phenyl |
| 605 | cyclopropylmethyl | H | O | CH$_2$CH$_3$ | F | 3,4 dichloro phenyl |
| 606 | SCH(CH$_3$)$_2$ | H | O | CH$_2$CH$_3$ | F | 3,4 dichloro phenyl |
| 607 | OCH$_2$CH$_3$ | H | O | CH$_2$CH$_3$ | F | 3,4 dichloro phenyl |
| 608 | (CH$_2$)$_2$ | | O | CH$_2$CH$_3$ | F | 3,4 dichloro phenyl |
| 609 | (CH$_2$)$_4$ | | O | CH$_2$CH$_3$ | F | 3,4 dichloro phenyl |
| 610 | CH$_3$ | H | O | CH$_2$CH$_3$ | F | 5-benzo[c][1,2,5]oxadiazolyl |
| 611 | CH$_2$CH$_3$ | H | O | CH$_2$CH$_3$ | F | 5-benzo[c][1,2,5]oxadiazolyl |
| 612 | CH$_2$CF$_3$ | H | O | CH$_2$CH$_3$ | F | 5-benzo[c][1,2,5]oxadiazolyl |
| 613 | CH$_2$CH$_2$CH$_3$ | H | O | CH$_2$CH$_3$ | F | 5-benzo[c][1,2,5]oxadiazolyl |
| 614 | CH$_2$CH(CH$_3$)$_2$ | H | O | CH$_2$CH$_3$ | F | 5-benzo[c][1,2,5]oxadiazolyl |
| 615 | cyclopropylmethyl | H | O | CH$_2$CH$_3$ | F | 5-benzo[c][1,2,5]oxadiazolyl |
| 616 | SCH(CH$_3$)$_2$ | H | O | CH$_2$CH$_3$ | F | 5-benzo[c][1,2,5]oxadiazolyl |
| 617 | OCH$_2$CH$_3$ | H | O | CH$_2$CH$_3$ | F | 5-benzo[c][1,2,5]oxadiazolyl |
| 618 | (CH$_2$)$_2$ | | O | CH$_2$CH$_3$ | F | 5-benzo[c][1,2,5]oxadiazolyl |
| 619 | (CH$_2$)$_4$ | | O | CH$_2$CH$_3$ | F | 5-benzo[c][1,2,5]oxadiazolyl |
| 620 | CH$_3$ | H | O | CH$_2$CH$_3$ | F | 5-benzo[c][1,2,5]thiadiazolyl |
| 621 | CH$_2$CH$_3$ | H | O | CH$_2$CH$_3$ | F | 5-benzo[c][1,2,5]thiadiazolyl |
| 622 | CH$_2$CF$_3$ | H | O | CH$_2$CH$_3$ | F | 5-benzo[c][1,2,5]thiadiazolyl |
| 623 | CH$_2$CH$_2$CH$_3$ | H | O | CH$_2$CH$_3$ | F | 5-benzo[c][1,2,5]thiadiazolyl |
| 624 | CH$_2$CH(CH$_3$)$_2$ | H | O | CH$_2$CH$_3$ | F | 5-benzo[c][1,2,5]thiadiazolyl |
| 625 | cyclopropylmethyl | H | O | CH$_2$CH$_3$ | F | 5-benzo[c][1,2,5]thiadiazolyl |

TABLE 2-continued

Formula V

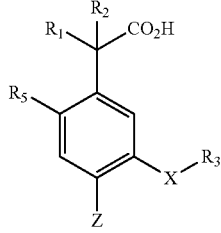

| EX | R1 | R2 | X | R3 | R5 | Z |
|---|---|---|---|---|---|---|
| 626 | SCH(CH$_3$)$_2$ | H | O | CH$_2$CH$_3$ | F | 5-benzo[c][1,2,5]thiadiazolyl |
| 627 | OCH$_2$CH$_3$ | H | O | CH$_2$CH$_3$ | F | 5-benzo[c][1,2,5]thiadiazolyl |
| 628 | (CH$_2$)$_2$ | | O | CH$_2$CH$_3$ | F | 5-benzo[c][1,2,5]thiadiazolyl |
| 629 | (CH$_2$)$_4$ | | O | CH$_2$CH$_3$ | F | 5-benzo[c][1,2,5]thiadiazolyl |
| 630 | CH$_3$ | H | O | CH$_2$CF$_3$ | F | 4-fluorophenyl |
| 631 | CH$_2$CH$_3$ | H | O | CH$_2$CF$_3$ | F | 4-fluorophenyl |
| 632 | CH$_2$CF$_3$ | H | O | CH$_2$CF$_3$ | F | 4-fluorophenyl |
| 633 | CH$_2$CH$_2$CH$_3$ | H | O | CH$_2$CF$_3$ | F | 4-fluorophenyl |
| 634 | CH$_2$CH(CH$_3$)$_2$ | H | O | CH$_2$CF$_3$ | F | 4-fluorophenyl |
| 635 | cyclopropylmethyl | H | O | CH$_2$CF$_3$ | F | 4-fluorophenyl |
| 636 | SCH(CH$_3$)$_2$ | H | O | CH$_2$CF$_3$ | F | 4-fluorophenyl |
| 637 | OCH$_2$CH$_3$ | H | O | CH$_2$CF$_3$ | F | 4-fluorophenyl |
| 638 | (CH$_2$)$_2$ | | O | CH$_2$CF$_3$ | F | 4-fluorophenyl |
| 639 | (CH$_2$)$_4$ | | O | CH$_2$CF$_3$ | F | 4-fluorophenyl |
| 640 | CH$_3$ | H | O | CH$_2$CF$_3$ | F | 4-chlorophenyl |
| 641 | CH$_2$CH$_3$ | H | O | CH$_2$CF$_3$ | F | 4-chlorophenyl |
| 642 | CH$_2$CF$_3$ | H | O | CH$_2$CF$_3$ | F | 4-chlorophenyl |
| 643 | CH$_2$CH$_2$CH$_3$ | H | O | CH$_2$CF$_3$ | F | 4-chlorophenyl |
| 644 | CH$_2$CH(CH$_3$)$_2$ | H | O | CH$_2$CF$_3$ | F | 4-chlorophenyl |
| 645 | cyclopropylmethyl | H | O | CH$_2$CF$_3$ | F | 4-chlorophenyl |
| 646 | SCH(CH$_3$)$_2$ | H | O | CH$_2$CF$_3$ | F | 4-chlorophenyl |
| 647 | OCH$_2$CH$_3$ | H | O | CH$_2$CF$_3$ | F | 4-chlorophenyl |
| 648 | (CH$_2$)$_2$ | | O | CH$_2$CF$_3$ | F | 4-chlorophenyl |
| 649 | (CH$_2$)$_4$ | | O | CH$_2$CF$_3$ | F | 4-chlorophenyl |
| 650 | CH$_3$ | H | O | CH$_2$CF$_3$ | F | 4-trifluoromethylphenyl |
| 651 | CH$_2$CH$_3$ | H | O | CH$_2$CF$_3$ | F | 4-trifluoromethylphenyl |
| 652 | CH$_2$CF$_3$ | H | O | CH$_2$CF$_3$ | F | 4-trifluoromethylphenyl |
| 653 | CH$_2$CH$_2$CH$_3$ | H | O | CH$_2$CF$_3$ | F | 4-trifluoromethylphenyl |
| 654 | CH$_2$CH(CH$_3$)$_2$ | H | O | CH$_2$CF$_3$ | F | 4-trifluoromethylphenyl |
| 655 | cyclopropylmethyl | H | O | CH$_2$CF$_3$ | F | 4-trifluoromethylphenyl |
| 656 | SCH(CH$_3$)$_2$ | H | O | CH$_2$CF$_3$ | F | 4-trifluoromethylphenyl |
| 657 | OCH$_2$CH$_3$ | H | O | CH$_2$CF$_3$ | F | 4-trifluoromethylphenyl |
| 658 | (CH$_2$)$_2$ | | O | CH$_2$CF$_3$ | F | 4-trifluoromethylphenyl |
| 659 | (CH$_2$)$_4$ | | O | CH$_2$CF$_3$ | F | 4-trifluoromethylphenyl |
| 660 | CH$_3$ | H | O | CH$_2$CF$_3$ | F | 4-methoxyphenyl |
| 661 | CH$_2$CH$_3$ | H | O | CH$_2$CF$_3$ | F | 4-methoxyphenyl |
| 662 | CH$_2$CF$_3$ | H | O | CH$_2$CF$_3$ | F | 4-methoxyphenyl |
| 663 | CH$_2$CH$_2$CH$_3$ | H | O | CH$_2$CF$_3$ | F | 4-methoxyphenyl |
| 664 | CH$_2$CH(CH$_3$)$_2$ | H | O | CH$_2$CF$_3$ | F | 4-methoxyphenyl |
| 665 | cyclopropylmethyl | H | O | CH$_2$CF$_3$ | F | 4-methoxyphenyl |
| 666 | SCH(CH$_3$)$_2$ | H | O | CH$_2$CF$_3$ | F | 4-methoxyphenyl |
| 667 | OCH$_2$CH$_3$ | H | O | CH$_2$CF$_3$ | F | 4-methoxyphenyl |
| 668 | (CH$_2$)$_2$ | | O | CH$_2$CF$_3$ | F | 4-methoxyphenyl |
| 669 | (CH$_2$)$_4$ | | O | CH$_2$CF$_3$ | F | 4-methoxyphenyl |
| 670 | CH$_3$ | H | O | CH$_2$CF$_3$ | F | 3,4 dichloro phenyl |
| 671 | CH$_2$CH$_3$ | H | O | CH$_2$CF$_3$ | F | 3,4 dichloro phenyl |
| 672 | CH$_2$CF$_3$ | H | O | CH$_2$CF$_3$ | F | 3,4 dichloro phenyl |
| 673 | CH$_2$CH$_2$CH$_3$ | H | O | CH$_2$CF$_3$ | F | 3,4 dichloro phenyl |
| 674 | CH$_2$CH(CH$_3$)$_2$ | H | O | CH$_2$CF$_3$ | F | 3,4 dichloro phenyl |
| 675 | cyclopropylmethyl | H | O | CH$_2$CF$_3$ | F | 3,4 dichloro phenyl |
| 676 | SCH(CH$_3$)$_2$ | H | O | CH$_2$CF$_3$ | F | 3,4 dichloro phenyl |
| 677 | OCH$_2$CH$_3$ | H | O | CH$_2$CF$_3$ | F | 3,4 dichloro phenyl |
| 678 | (CH$_2$)$_2$ | | O | CH$_2$CF$_3$ | F | 3,4 dichloro phenyl |
| 679 | (CH$_2$)$_4$ | | O | CH$_2$CF$_3$ | F | 3,4 dichloro phenyl |
| 680 | CH$_3$ | H | O | CH$_2$CF$_3$ | F | 5-benzo[c][1,2,5]oxadiazolyl |
| 681 | CH$_2$CH$_3$ | H | O | CH$_2$CF$_3$ | F | 5-benzo[c][1,2,5]oxadiazolyl |
| 682 | CH$_2$CF$_3$ | H | O | CH$_2$CF$_3$ | F | 5-benzo[c][1,2,5]oxadiazolyl |
| 683 | CH$_2$CH$_2$CH$_3$ | H | O | CH$_2$CF$_3$ | F | 5-benzo[c][1,2,5]oxadiazolyl |
| 684 | CH$_2$CH(CH$_3$)$_2$ | H | O | CH$_2$CF$_3$ | F | 5-benzo[c][1,2,5]oxadiazolyl |
| 685 | cyclopropylmethyl | H | O | CH$_2$CF$_3$ | F | 5-benzo[c][1,2,5]oxadiazolyl |
| 686 | SCH(CH$_3$)$_2$ | H | O | CH$_2$CF$_3$ | F | 5-benzo[c][1,2,5]oxadiazolyl |
| 687 | OCH$_2$CH$_3$ | H | O | CH$_2$CF$_3$ | F | 5-benzo[c][1,2,5]oxadiazolyl |
| 688 | (CH$_2$)$_2$ | | O | CH$_2$CF$_3$ | F | 5-benzo[c][1,2,5]oxadiazolyl |
| 689 | (CH$_2$)$_4$ | | O | CH$_2$CF$_3$ | F | 5-benzo[c][1,2,5]oxadiazolyl |
| 690 | CH$_3$ | H | O | CH$_2$CF$_3$ | F | 5-benzo[c][1,2,5]thiadiazolyl |
| 691 | CH$_2$CH$_3$ | H | O | CH$_2$CF$_3$ | F | 5-benzo[c][1,2,5]thiadiazolyl |

TABLE 2-continued

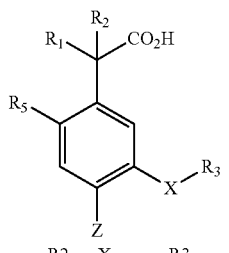

Formula V

| EX | R1 | R2 | X | R3 | R5 | Z |
|---|---|---|---|---|---|---|
| 692 | CH$_2$CF$_3$ | H | O | CH$_2$CF$_3$ | F | 5-benzo[c][1,2,5]thiadiazolyl |
| 693 | CH$_2$CH$_2$CH$_3$ | H | O | CH$_2$CF$_3$ | F | 5-benzo[c][1,2,5]thiadiazolyl |
| 694 | CH$_2$CH(CH$_3$)$_2$ | H | O | CH$_2$CF$_3$ | F | 5-benzo[c][1,2,5]thiadiazolyl |
| 695 | cyclopropylmethyl | H | O | CH$_2$CF$_3$ | F | 5-benzo[c][1,2,5]thiadiazolyl |
| 696 | SCH(CH$_3$)$_2$ | H | O | CH$_2$CF$_3$ | F | 5-benzo[c][1,2,5]thiadiazolyl |
| 697 | OCH$_2$CH$_3$ | H | O | CH$_2$CF$_3$ | F | 5-benzo[c][1,2,5]thiadiazolyl |
| 698 | (CH$_2$)$_2$ | | O | CH$_2$CF$_3$ | F | 5-benzo[c][1,2,5]thiadiazolyl |
| 699 | (CH$_2$)$_4$ | | O | CH$_2$CF$_3$ | F | 5-benzo[c][1,2,5]thiadiazolyl |
| 700 | CH$_3$ | H | O | CH$_2$—c-Pr | F | 4-fluorophenyl |
| 701 | CH$_2$CH$_3$ | H | O | CH$_2$—c-Pr | F | 4-fluorophenyl |
| 702 | CH$_2$CF$_3$ | H | O | CH$_2$—c-Pr | F | 4-fluorophenyl |
| 703 | CH$_2$CH$_2$CH$_3$ | H | O | CH$_2$—c-Pr | F | 4-fluorophenyl |
| 704 | CH$_2$CH(CH$_3$)$_2$ | H | O | CH$_2$—c-Pr | F | 4-fluorophenyl |
| 705 | cyclopropylmethyl | H | O | CH$_2$—c-Pr | F | 4-fluorophenyl |
| 706 | SCH(CH$_3$)$_2$ | H | O | CH$_2$—c-Pr | F | 4-fluorophenyl |
| 707 | OCH$_2$CH$_3$ | H | O | CH$_2$—c-Pr | F | 4-fluorophenyl |
| 708 | (CH$_2$)$_2$ | | O | CH$_2$—c-Pr | F | 4-fluorophenyl |
| 709 | (CH$_2$)$_4$ | | O | CH$_2$—c-Pr | F | 4-fluorophenyl |
| 710 | CH$_3$ | H | O | CH$_2$—c-Pr | F | 4-chlorophenyl |
| 711 | CH$_2$CH$_3$ | H | O | CH$_2$—c-Pr | F | 4-chlorophenyl |
| 712 | CH$_2$CF$_3$ | H | O | CH$_2$—c-Pr | F | 4-chlorophenyl |
| 713 | CH$_2$CH$_2$CH$_3$ | H | O | CH$_2$—c-Pr | F | 4-chlorophenyl |
| 714 | CH$_2$CH(CH$_3$)$_2$ | H | O | CH$_2$—c-Pr | F | 4-chlorophenyl |
| 715 | cyclopropylmethyl | H | O | CH$_2$—c-Pr | F | 4-chlorophenyl |
| 716 | SCH(CH$_3$)$_2$ | H | O | CH$_2$—c-Pr | F | 4-chlorophenyl |
| 717 | OCH$_2$CH$_3$ | H | O | CH$_2$—c-Pr | F | 4-chlorophenyl |
| 718 | (CH$_2$)$_2$ | | O | CH$_2$—c-Pr | F | 4-chlorophenyl |
| 719 | (CH$_2$)$_4$ | | O | CH$_2$—c-Pr | F | 4-chlorophenyl |
| 720 | CH$_3$ | H | O | CH$_2$—c-Pr | F | 4-trifluoromethylphenyl |
| 721 | CH$_2$CH$_3$ | H | O | CH$_2$—c-Pr | F | 4-trifluoromethylphenyl |
| 722 | CH$_2$CF$_3$ | H | O | CH$_2$—c-Pr | F | 4-trifluoromethylphenyl |
| 723 | CH$_2$CH$_2$CH$_3$ | H | O | CH$_2$—c-Pr | F | 4-trifluoromethylphenyl |
| 724 | CH$_2$CH(CH$_3$)$_2$ | H | O | CH$_2$—c-Pr | F | 4-trifluoromethylphenyl |
| 725 | cyclopropylmethyl | H | O | CH$_2$—c-Pr | F | 4-trifluoromethylphenyl |
| 726 | SCH(CH$_3$)$_2$ | H | O | CH$_2$—c-Pr | F | 4-trifluoromethylphenyl |
| 727 | OCH$_2$CH$_3$ | H | O | CH$_2$—c-Pr | F | 4-trifluoromethylphenyl |
| 728 | (CH$_2$)$_2$ | | O | CH$_2$—c-Pr | F | 4-trifluoromethylphenyl |
| 729 | (CH$_2$)$_4$ | | O | CH$_2$—c-Pr | F | 4-trifluoromethylphenyl |
| 730 | CH$_3$ | H | O | CH$_2$—c-Pr | F | 4-methoxyphenyl |
| 731 | CH$_2$CH$_3$ | H | O | CH$_2$—c-Pr | F | 4-methoxyphenyl |
| 732 | CH$_2$CF$_3$ | H | O | CH$_2$—c-Pr | F | 4-methoxyphenyl |
| 733 | CH$_2$CH$_2$CH$_3$ | H | O | CH$_2$—c-Pr | F | 4-methoxyphenyl |
| 734 | CH$_2$CH(CH$_3$)$_2$ | H | O | CH$_2$—c-Pr | F | 4-methoxyphenyl |
| 735 | cyclopropylmethyl | H | O | CH$_2$—c-Pr | F | 4-methoxyphenyl |
| 736 | SCH(CH$_3$)$_2$ | H | O | CH$_2$—c-Pr | F | 4-methoxyphenyl |
| 737 | OCH$_2$CH$_3$ | H | O | CH$_2$—c-Pr | F | 4-methoxyphenyl |
| 738 | (CH$_2$)$_2$ | | O | CH$_2$—c-Pr | F | 4-methoxyphenyl |
| 739 | (CH$_2$)$_4$ | | O | CH$_2$—c-Pr | F | 4-methoxyphenyl |
| 740 | CH$_3$ | H | O | CH$_2$—c-Pr | F | 3,4 dichloro phenyl |
| 741 | CH$_2$CH$_3$ | H | O | CH$_2$—c-Pr | F | 3,4 dichloro phenyl |
| 742 | CH$_2$CF$_3$ | H | O | CH$_2$—c-Pr | F | 3,4 dichloro phenyl |
| 743 | CH$_2$CH$_2$CH$_3$ | H | O | CH$_2$—c-Pr | F | 3,4 dichloro phenyl |
| 744 | CH$_2$CH(CH$_3$)$_2$ | H | O | CH$_2$—c-Pr | F | 3,4 dichloro phenyl |
| 745 | cyclopropylmethyl | H | O | CH$_2$—c-Pr | F | 3,4 dichloro phenyl |
| 746 | SCH(CH$_3$)$_2$ | H | O | CH$_2$—c-Pr | F | 3,4 dichloro phenyl |
| 747 | OCH$_2$CH$_3$ | H | O | CH$_2$—c-Pr | F | 3,4 dichloro phenyl |
| 748 | (CH$_2$)$_2$ | | O | CH$_2$—c-Pr | F | 3,4 dichloro phenyl |
| 749 | (CH$_2$)$_4$ | | O | CH$_2$—c-Pr | F | 3,4 dichloro phenyl |
| 750 | CH$_3$ | H | O | CH$_2$—c-Pr | F | 5-benzo[c][1,2,5]oxadiazolyl |
| 751 | CH$_2$CH$_3$ | H | O | CH$_2$—c-Pr | F | 5-benzo[c][1,2,5]oxadiazolyl |
| 752 | CH$_2$CF$_3$ | H | O | CH$_2$—c-Pr | F | 5-benzo[c][1,2,5]oxadiazolyl |
| 753 | CH$_2$CH$_2$CH$_3$ | H | O | CH$_2$—c-Pr | F | 5-benzo[c][1,2,5]oxadiazolyl |
| 754 | CH$_2$CH(CH$_3$)$_2$ | H | O | CH$_2$—c-Pr | F | 5-benzo[c][1,2,5]oxadiazolyl |
| 755 | cyclopropylmethyl | H | O | CH$_2$—c-Pr | F | 5-benzo[c][1,2,5]oxadiazolyl |
| 756 | SCH(CH$_3$)$_2$ | H | O | CH$_2$—c-Pr | F | 5-benzo[c][1,2,5]oxadiazolyl |
| 757 | OCH$_2$CH$_3$ | H | O | CH$_2$—c-Pr | F | 5-benzo[c][1,2,5]oxadiazolyl |

TABLE 2-continued

Formula V

| EX | R1 | R2 | X | R3 | R5 | Z |
|---|---|---|---|---|---|---|
| 758 | (CH$_2$)$_2$ | | O | CH$_2$—c-Pr | F | 5-benzo[c][1,2,5]oxadiazolyl |
| 759 | (CH$_2$)$_4$ | | O | CH$_2$—c-Pr | F | 5-benzo[c][1,2,5]oxadiazolyl |
| 760 | CH$_3$ | H | O | CH$_2$—c-Pr | F | 5-benzo[c][1,2,5]thiadiazolyl |
| 761 | CH$_2$CH$_3$ | H | O | CH$_2$—c-Pr | F | 5-benzo[c][1,2,5]thiadiazolyl |
| 762 | CH$_2$CF$_3$ | H | O | CH$_2$—c-Pr | F | 5-benzo[c][1,2,5]thiadiazolyl |
| 763 | CH$_2$CH$_2$CH$_3$ | H | O | CH$_2$—c-Pr | F | 5-benzo[c][1,2,5]thiadiazolyl |
| 764 | CH$_2$CH(CH$_3$)$_2$ | H | O | CH$_2$—c-Pr | F | 5-benzo[c][1,2,5]thiadiazolyl |
| 765 | cyclopropylmethyl | H | O | CH$_2$—c-Pr | F | 5-benzo[c][1,2,5]thiadiazolyl |
| 766 | SCH(CH$_3$)$_2$ | H | O | CH$_2$—c-Pr | F | 5-benzo[c][1,2,5]thiadiazolyl |
| 767 | OCH$_2$CH$_3$ | H | O | CH$_2$—c-Pr | F | 5-benzo[c][1,2,5]thiadiazolyl |
| 768 | (CH$_2$)$_2$ | | O | CH$_2$—c-Pr | F | 5-benzo[c][1,2,5]thiadiazolyl |
| 769 | (CH$_2$)$_4$ | | O | CH$_2$—c-Pr | F | 5-benzo[c][1,2,5]thiadiazolyl |
| 770 | CH$_3$ | H | O | CH$_2$CH$_3$ | Cl | 4-fluorophenyl |
| 771 | CH$_2$CH$_3$ | H | O | CH$_2$CH$_3$ | Cl | 4-fluorophenyl |
| 772 | CH$_2$CF$_3$ | H | O | CH$_2$CH$_3$ | Cl | 4-fluorophenyl |
| 773 | CH$_2$CH$_2$CH$_3$ | H | O | CH$_2$CH$_3$ | Cl | 4-fluorophenyl |
| 774 | CH$_2$CH(CH$_3$)$_2$ | H | O | CH$_2$CH$_3$ | Cl | 4-fluorophenyl |
| 775 | cyclopropylmethyl | H | O | CH$_2$CH$_3$ | Cl | 4-fluorophenyl |
| 776 | SCH(CH$_3$)$_2$ | H | O | CH$_2$CH$_3$ | Cl | 4-fluorophenyl |
| 777 | OCH$_2$CH$_3$ | H | O | CH$_2$CH$_3$ | Cl | 4-fluorophenyl |
| 778 | (CH$_2$)$_2$ | | O | CH$_2$CH$_3$ | Cl | 4-fluorophenyl |
| 779 | (CH$_2$)$_4$ | | O | CH$_2$CH$_3$ | Cl | 4-fluorophenyl |
| 780 | CH$_3$ | H | O | CH$_2$CH$_3$ | Cl | 4-chlorophenyl |
| 781 | CH$_2$CH$_3$ | H | O | CH$_2$CH$_3$ | Cl | 4-chlorophenyl |
| 782 | CH$_2$CF$_3$ | H | O | CH$_2$CH$_3$ | Cl | 4-chlorophenyl |
| 783 | CH$_2$CH$_2$CH$_3$ | H | O | CH$_2$CH$_3$ | Cl | 4-chlorophenyl |
| 784 | CH$_2$CH(CH$_3$)$_2$ | H | O | CH$_2$CH$_3$ | Cl | 4-chlorophenyl |
| 785 | cyclopropylmethyl | H | O | CH$_2$CH$_3$ | Cl | 4-chlorophenyl |
| 786 | SCH(CH$_3$)$_2$ | H | O | CH$_2$CH$_3$ | Cl | 4-chlorophenyl |
| 787 | OCH$_2$CH$_3$ | H | O | CH$_2$CH$_3$ | Cl | 4-chlorophenyl |
| 788 | (CH$_2$)$_2$ | | O | CH$_2$CH$_3$ | Cl | 4-chlorophenyl |
| 789 | (CH$_2$)$_4$ | | O | CH$_2$CH$_3$ | Cl | 4-chlorophenyl |
| 790 | CH$_3$ | H | O | CH$_2$CH$_3$ | Cl | 4-trifluoromethylphenyl |
| 791 | CH$_2$CH$_3$ | H | O | CH$_2$CH$_3$ | Cl | 4-trifluoromethylphenyl |
| 792 | CH$_2$CF$_3$ | H | O | CH$_2$CH$_3$ | Cl | 4-trifluoromethylphenyl |
| 793 | CH$_2$CH$_2$CH$_3$ | H | O | CH$_2$CH$_3$ | Cl | 4-trifluoromethylphenyl |
| 794 | CH$_2$CH(CH$_3$)$_2$ | H | O | CH$_2$CH$_3$ | Cl | 4-trifluoromethylphenyl |
| 795 | cyclopropylmethyl | H | O | CH$_2$CH$_3$ | Cl | 4-trifluoromethylphenyl |
| 796 | SCH(CH$_3$)$_2$ | H | O | CH$_2$CH$_3$ | Cl | 4-trifluoromethylphenyl |
| 797 | OCH$_2$CH$_3$ | H | O | CH$_2$CH$_3$ | Cl | 4-trifluoromethylphenyl |
| 798 | (CH$_2$)$_2$ | | O | CH$_2$CH$_3$ | Cl | 4-trifluoromethylphenyl |
| 799 | (CH$_2$)$_4$ | | O | CH$_2$CH$_3$ | Cl | 4-trifluoromethylphenyl |
| 800 | CH$_3$ | H | O | CH$_2$CH$_3$ | Cl | 4-methoxyphenyl |
| 801 | CH$_2$CH$_3$ | H | O | CH$_2$CH$_3$ | Cl | 4-methoxyphenyl |
| 802 | CH$_2$CF$_3$ | H | O | CH$_2$CH$_3$ | Cl | 4-methoxyphenyl |
| 803 | CH$_2$CH$_2$CH$_3$ | H | O | CH$_2$CH$_3$ | Cl | 4-methoxyphenyl |
| 804 | CH$_2$CH(CH$_3$)$_2$ | H | O | CH$_2$CH$_3$ | Cl | 4-methoxyphenyl |
| 805 | cyclopropylmethyl | H | O | CH$_2$CH$_3$ | Cl | 4-methoxyphenyl |
| 806 | SCH(CH$_3$)$_2$ | H | O | CH$_2$CH$_3$ | Cl | 4-methoxyphenyl |
| 807 | OCH$_2$CH$_3$ | H | O | CH$_2$CH$_3$ | Cl | 4-methoxyphenyl |
| 808 | (CH$_2$)$_2$ | | O | CH$_2$CH$_3$ | Cl | 4-methoxyphenyl |
| 809 | (CH$_2$)$_4$ | | O | CH$_2$CH$_3$ | Cl | 4-methoxyphenyl |
| 810 | CH$_3$ | H | O | CH$_2$CH$_3$ | Cl | 3,4 dichloro phenyl |
| 811 | CH$_2$CH$_3$ | H | O | CH$_2$CH$_3$ | Cl | 3,4 dichloro phenyl |
| 812 | CH$_2$CF$_3$ | H | O | CH$_2$CH$_3$ | Cl | 3,4 dichloro phenyl |
| 813 | CH$_2$CH$_2$CH$_3$ | H | O | CH$_2$CH$_3$ | Cl | 3,4 dichloro phenyl |
| 814 | CH$_2$CH(CH$_3$)$_2$ | H | O | CH$_2$CH$_3$ | Cl | 3,4 dichloro phenyl |
| 815 | cyclopropylmethyl | H | O | CH$_2$CH$_3$ | Cl | 3,4 dichloro phenyl |
| 816 | SCH(CH$_3$)$_2$ | H | O | CH$_2$CH$_3$ | Cl | 3,4 dichloro phenyl |
| 817 | OCH$_2$CH$_3$ | H | O | CH$_2$CH$_3$ | Cl | 3,4 dichloro phenyl |
| 818 | (CH$_2$)$_2$ | | O | CH$_2$CH$_3$ | Cl | 3,4 dichloro phenyl |
| 819 | (CH$_2$)$_4$ | | O | CH$_2$CH$_3$ | Cl | 3,4 dichloro phenyl |
| 820 | CH$_3$ | H | O | CH$_2$CH$_3$ | Cl | 5-benzo[c][1,2,5]oxadiazolyl |
| 821 | CH$_2$CH$_3$ | H | O | CH$_2$CH$_3$ | Cl | 5-benzo[c][1,2,5]oxadiazolyl |
| 822 | CH$_2$CF$_3$ | H | O | CH$_2$CH$_3$ | Cl | 5-benzo[c][1,2,5]oxadiazolyl |
| 823 | CH$_2$CH$_2$CH$_3$ | H | O | CH$_2$CH$_3$ | Cl | 5-benzo[c][1,2,5]oxadiazolyl |

TABLE 2-continued

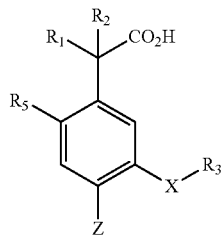

Formula V

| EX | R1 | R2 | X | R3 | R5 | Z |
|---|---|---|---|---|---|---|
| 824 | $CH_2CH(CH_3)_2$ | H | O | $CH_2CH_3$ | Cl | 5-benzo[c][1,2,5]oxadiazolyl |
| 825 | cyclopropylmethyl | H | O | $CH_2CH_3$ | Cl | 5-benzo[c][1,2,5]oxadiazolyl |
| 826 | $SCH(CH_3)_2$ | H | O | $CH_2CH_3$ | Cl | 5-benzo[c][1,2,5]oxadiazolyl |
| 827 | $OCH_2CH_3$ | H | O | $CH_2CH_3$ | Cl | 5-benzo[c][1,2,5]oxadiazolyl |
| 828 | $(CH_2)_2$ | | O | $CH_2CH_3$ | Cl | 5-benzo[c][1,2,5]oxadiazolyl |
| 829 | $(CH_2)_4$ | | O | $CH_2CH_3$ | Cl | 5-benzo[c][1,2,5]oxadiazolyl |
| 830 | $CH_3$ | H | O | $CH_2CH_3$ | Cl | 5-benzo[c][1,2,5]thiadiazolyl |
| 831 | $CH_2CH_3$ | H | O | $CH_2CH_3$ | Cl | 5-benzo[c][1,2,5]thiadiazolyl |
| 832 | $CH_2CF_3$ | H | O | $CH_2CH_3$ | Cl | 5-benzo[c][1,2,5]thiadiazolyl |
| 833 | $CH_2CH_2CH_3$ | H | O | $CH_2CH_3$ | Cl | 5-benzo[c][1,2,5]thiadiazolyl |
| 834 | $CH_2CH(CH_3)_2$ | H | O | $CH_2CH_3$ | Cl | 5-benzo[c][1,2,5]thiadiazolyl |
| 835 | cyclopropylmethyl | H | O | $CH_2CH_3$ | Cl | 5-benzo[c][1,2,5]thiadiazolyl |
| 836 | $SCH(CH_3)_2$ | H | O | $CH_2CH_3$ | Cl | 5-benzo[c][1,2,5]thiadiazolyl |
| 837 | $OCH_2CH_3$ | H | O | $CH_2CH_3$ | Cl | 5-benzo[c][1,2,5]thiadiazolyl |
| 838 | $(CH_2)_2$ | | O | $CH_2CH_3$ | Cl | 5-benzo[c][1,2,5]thiadiazolyl |
| 839 | $(CH_2)_4$ | | O | $CH_2CH_3$ | Cl | 5-benzo[c][1,2,5]thiadiazolyl |
| 840 | $CH_3$ | H | O | $CH_2CF_3$ | Cl | 4-fluorophenyl |
| 841 | $CH_2CH_3$ | H | O | $CH_2CF_3$ | Cl | 4-fluorophenyl |
| 842 | $CH_2CF_3$ | H | O | $CH_2CF_3$ | Cl | 4-fluorophenyl |
| 843 | $CH_2CH_2CH_3$ | H | O | $CH_2CF_3$ | Cl | 4-fluorophenyl |
| 844 | $CH_2CH(CH_3)_2$ | H | O | $CH_2CF_3$ | Cl | 4-fluorophenyl |
| 845 | cyclopropylmethyl | H | O | $CH_2CF_3$ | Cl | 4-fluorophenyl |
| 846 | $SCH(CH_3)_2$ | H | O | $CH_2CF_3$ | Cl | 4-fluorophenyl |
| 847 | $OCH_2CH_3$ | H | O | $CH_2CF_3$ | Cl | 4-fluorophenyl |
| 848 | $(CH_2)_2$ | O | O | $CH_2CF_3$ | Cl | 4-fluorophenyl |
| 849 | $(CH_2)_4$ | O | O | $CH_2CF_3$ | Cl | 4-fluorophenyl |
| 850 | $CH_3$ | H | O | $CH_2CF_3$ | Cl | 4-chlorophenyl |
| 851 | $CH_2CH_3$ | H | O | $CH_2CF_3$ | Cl | 4-chlorophenyl |
| 852 | $CH_2CF_3$ | H | O | $CH_2CF_3$ | Cl | 4-chlorophenyl |
| 853 | $CH_2CH_2CH_3$ | H | O | $CH_2CF_3$ | Cl | 4-chlorophenyl |
| 854 | $CH_2CH(CH_3)_2$ | H | O | $CH_2CF_3$ | Cl | 4-chlorophenyl |
| 855 | cyclopropylmethyl | H | O | $CH_2CF_3$ | Cl | 4-chlorophenyl |
| 856 | $SCH(CH_3)_2$ | H | O | $CH_2CF_3$ | Cl | 4-chlorophenyl |
| 857 | $OCH_2CH_3$ | H | O | $CH_2CF_3$ | Cl | 4-chlorophenyl |
| 858 | $(CH_2)_2$ | | O | $CH_2CF_3$ | Cl | 4-chlorophenyl |
| 859 | $(CH_2)_4$ | | O | $CH_2CF_3$ | Cl | 4-chlorophenyl |
| 860 | $CH_3$ | H | O | $CH_2CF_3$ | Cl | 4-trifluoromethylphenyl |
| 861 | $CH_2CH_3$ | H | O | $CH_2CF_3$ | Cl | 4-trifluoromethylphenyl |
| 862 | $CH_2CF_3$ | H | O | $CH_2CF_3$ | Cl | 4-trifluoromethylphenyl |
| 863 | $CH_2CH_2CH_3$ | H | O | $CH_2CF_3$ | Cl | 4-trifluoromethylphenyl |
| 864 | $CH_2CH(CH_3)_2$ | H | O | $CH_2CF_3$ | Cl | 4-trifluoromethylphenyl |
| 865 | cyclopropylmethyl | H | O | $CH_2CF_3$ | Cl | 4-trifluoromethylphenyl |
| 866 | $SCH(CH_3)_2$ | H | O | $CH_2CF_3$ | Cl | 4-trifluoromethylphenyl |
| 867 | $OCH_2CH_3$ | H | O | $CH_2CF_3$ | Cl | 4-trifluoromethylphenyl |
| 868 | $(CH_2)_2$ | | O | $CH_2CF_3$ | Cl | 4-trifluoromethylphenyl |
| 869 | $(CH_2)_4$ | | O | $CH_2CF_3$ | Cl | 4-trifluoromethylphenyl |
| 870 | $CH_3$ | H | O | $CH_2CF_3$ | Cl | 4-methoxyphenyl |
| 871 | $CH_2CH_3$ | H | O | $CH_2CF_3$ | Cl | 4-methoxyphenyl |
| 872 | $CH_2CF_3$ | H | O | $CH_2CF_3$ | Cl | 4-methoxyphenyl |
| 873 | $CH_2CH_2CH_3$ | H | O | $CH_2CF_3$ | Cl | 4-methoxyphenyl |
| 874 | $CH_2CH(CH_3)_2$ | H | O | $CH_2CF_3$ | Cl | 4-methoxyphenyl |
| 875 | cyclopropylmethyl | H | O | $CH_2CF_3$ | Cl | 4-methoxyphenyl |
| 876 | $SCH(CH_3)_2$ | H | O | $CH_2CF_3$ | Cl | 4-methoxyphenyl |
| 877 | $OCH_2CH_3$ | H | O | $CH_2CF_3$ | Cl | 4-methoxyphenyl |
| 878 | $(CH_2)_2$ | | O | $CH_2CF_3$ | Cl | 4-methoxyphenyl |
| 879 | $(CH_2)_4$ | | O | $CH_2CF_3$ | Cl | 4-methoxyphenyl |
| 880 | $CH_3$ | H | O | $CH_2CF_3$ | Cl | 3,4 dichloro phenyl |
| 881 | $CH_2CH_3$ | H | O | $CH_2CF_3$ | Cl | 3,4 dichloro phenyl |
| 882 | $CH_2CF_3$ | H | O | $CH_2CF_3$ | Cl | 3,4 dichloro phenyl |
| 883 | $CH_2CH_2CH_3$ | H | O | $CH_2CF_3$ | Cl | 3,4 dichloro phenyl |
| 884 | $CH_2CH(CH_3)_2$ | H | O | $CH_2CF_3$ | Cl | 3,4 dichloro phenyl |
| 885 | cyclopropylmethyl | H | O | $CH_2CF_3$ | Cl | 3,4 dichloro phenyl |
| 886 | $SCH(CH_3)_2$ | H | O | $CH_2CF_3$ | Cl | 3,4 dichloro phenyl |
| 887 | $OCH_2CH_3$ | H | O | $CH_2CF_3$ | Cl | 3,4 dichloro phenyl |
| 888 | $(CH_2)_2$ | | O | $CH_2CF_3$ | Cl | 3,4 dichloro phenyl |
| 889 | $(CH_2)_4$ | | O | $CH_2CF_3$ | Cl | 3,4 dichloro phenyl |

TABLE 2-continued

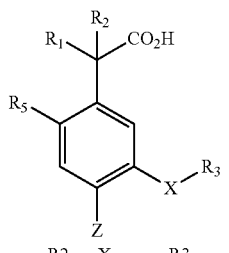

Formula V

| EX | R1 | R2 | X | R3 | R5 | Z |
|---|---|---|---|---|---|---|
| 890 | CH$_3$ | H | O | CH$_2$CF$_3$ | Cl | 5-benzo[c][1,2,5]oxadiazolyl |
| 891 | CH$_2$CH$_3$ | H | O | CH$_2$CF$_3$ | Cl | 5-benzo[c][1,2,5]oxadiazolyl |
| 892 | CH$_2$CF$_3$ | H | O | CH$_2$CF$_3$ | Cl | 5-benzo[c][1,2,5]oxadiazolyl |
| 893 | CH$_2$CH$_2$CH$_3$ | H | O | CH$_2$CF$_3$ | Cl | 5-benzo[c][1,2,5]oxadiazolyl |
| 894 | CH$_2$CH(CH$_3$)$_2$ | H | O | CH$_2$CF$_3$ | Cl | 5-benzo[c][1,2,5]oxadiazolyl |
| 895 | cyclopropylmethyl | H | O | CH$_2$CF$_3$ | Cl | 5-benzo[c][1,2,5]oxadiazolyl |
| 896 | SCH(CH$_3$)$_2$ | H | O | CH$_2$CF$_3$ | Cl | 5-benzo[c][1,2,5]oxadiazolyl |
| 897 | OCH$_2$CH$_3$ | H | O | CH$_2$CF$_3$ | Cl | 5-benzo[c][1,2,5]oxadiazolyl |
| 898 | (CH$_2$)$_2$ | | O | CH$_2$CF$_3$ | Cl | 5-benzo[c][1,2,5]oxadiazolyl |
| 899 | (CH$_2$)$_4$ | | O | CH$_2$CF$_3$ | Cl | 5-benzo[c][1,2,5]oxadiazolyl |
| 900 | CH$_3$ | H | O | CH$_2$CF$_3$ | Cl | 5-benzo[c][1,2,5]thiadiazolyl |
| 901 | CH$_2$CH$_3$ | H | O | CH$_2$CF$_3$ | Cl | 5-benzo[c][1,2,5]thiadiazolyl |
| 902 | CH$_2$CF$_3$ | H | O | CH$_2$CF$_3$ | Cl | 5-benzo[c][1,2,5]thiadiazolyl |
| 903 | CH$_2$CH$_2$CH$_3$ | H | O | CH$_2$CF$_3$ | Cl | 5-benzo[c][1,2,5]thiadiazolyl |
| 904 | CH$_2$CH(CH$_3$)$_2$ | H | O | CH$_2$CF$_3$ | Cl | 5-benzo[c][1,2,5]thiadiazolyl |
| 905 | cyclopropylmethyl | H | O | CH$_2$CF$_3$ | Cl | 5-benzo[c][1,2,5]thiadiazolyl |
| 906 | SCH(CH$_3$)$_2$ | H | O | CH$_2$CF$_3$ | Cl | 5-benzo[c][1,2,5]thiadiazolyl |
| 907 | OCH$_2$CH$_3$ | H | O | CH$_2$CF$_3$ | Cl | 5-benzo[c][1,2,5]thiadiazolyl |
| 908 | (CH$_2$)$_2$ | | O | CH$_2$CF$_3$ | Cl | 5-benzo[c][1,2,5]thiadiazolyl |
| 909 | (CH$_2$)$_4$ | | O | CH$_2$CF$_3$ | Cl | 5-benzo[c][1,2,5]thiadiazolyl |
| 910 | CH$_3$ | H | O | CH$_2$—c-Pr | Cl | 4-fluorophenyl |
| 911 | CH$_2$CH$_3$ | H | O | CH$_2$—c-Pr | Cl | 4-fluorophenyl |
| 912 | CH$_2$CF$_3$ | H | O | CH$_2$—c-Pr | Cl | 4-fluorophenyl |
| 913 | CH$_2$CH$_2$CH$_3$ | H | O | CH$_2$—c-Pr | Cl | 4-fluorophenyl |
| 914 | CH$_2$CH(CH$_3$)$_2$ | H | O | CH$_2$—c-Pr | Cl | 4-fluorophenyl |
| 915 | cyclopropylmethyl | H | O | CH$_2$—c-Pr | Cl | 4-fluorophenyl |
| 916 | SCH(CH$_3$)$_2$ | H | O | CH$_2$—c-Pr | Cl | 4-fluorophenyl |
| 917 | OCH$_2$CH$_3$ | H | O | CH$_2$—c-Pr | Cl | 4-fluorophenyl |
| 918 | (CH$_2$)$_2$ | | O | CH$_2$—c-Pr | Cl | 4-fluorophenyl |
| 919 | (CH$_2$)$_4$ | | O | CH$_2$—c-Pr | Cl | 4-fluorophenyl |
| 920 | CH$_3$ | H | O | CH$_2$—c-Pr | Cl | 4-chlorophenyl |
| 921 | CH$_2$CH$_3$ | H | O | CH$_2$—c-Pr | Cl | 4-chlorophenyl |
| 922 | CH$_2$CF$_3$ | H | O | CH$_2$—c-Pr | Cl | 4-chlorophenyl |
| 923 | CH$_2$CH$_2$CH$_3$ | H | O | CH$_2$—c-Pr | Cl | 4-chlorophenyl |
| 924 | CH$_2$CH(CH$_3$)$_2$ | H | O | CH$_2$—c-Pr | Cl | 4-chlorophenyl |
| 925 | cyclopropylmethyl | H | O | CH$_2$—c-Pr | Cl | 4-chlorophenyl |
| 926 | SCH(CH$_3$)$_2$ | H | O | CH$_2$—c-Pr | Cl | 4-chlorophenyl |
| 927 | OCH$_2$CH$_3$ | H | O | CH$_2$—c-Pr | Cl | 4-chlorophenyl |
| 928 | (CH$_2$)$_2$ | | O | CH$_2$—c-Pr | Cl | 4-chlorophenyl |
| 929 | (CH$_2$)$_4$ | | O | CH$_2$—c-Pr | Cl | 4-chlorophenyl |
| 930 | CH$_3$ | H | O | CH$_2$—c-Pr | Cl | 4-trifluoromethylphenyl |
| 931 | CH$_2$CH$_3$ | H | O | CH$_2$—c-Pr | Cl | 4-trifluoromethylphenyl |
| 932 | CH$_2$CF$_3$ | H | O | CH$_2$—c-Pr | Cl | 4-trifluoromethylphenyl |
| 933 | CH$_2$CH$_2$CH$_3$ | H | O | CH$_2$—c-Pr | Cl | 4-trifluoromethylphenyl |
| 934 | CH$_2$CH(CH$_3$)$_2$ | H | O | CH$_2$—c-Pr | Cl | 4-trifluoromethylphenyl |
| 935 | cyclopropylmethyl | H | O | CH$_2$—c-Pr | Cl | 4-trifluoromethylphenyl |
| 936 | SCH(CH$_3$)$_2$ | H | O | CH$_2$—c-Pr | Cl | 4-trifluoromethylphenyl |
| 937 | OCH$_2$CH$_3$ | H | O | CH$_2$—c-Pr | Cl | 4-trifluoromethylphenyl |
| 938 | (CH$_2$)$_2$ | | O | CH$_2$—c-Pr | Cl | 4-trifluoromethylphenyl |
| 939 | (CH$_2$)$_4$ | | O | CH$_2$—c-Pr | Cl | 4-trifluoromethylphenyl |
| 940 | CH$_3$ | H | O | CH$_2$—c-Pr | Cl | 4-methoxyphenyl |
| 941 | CH$_2$CH$_3$ | H | O | CH$_2$—c-Pr | Cl | 4-methoxyphenyl |
| 942 | CH$_2$CF$_3$ | H | O | CH$_2$—c-Pr | Cl | 4-methoxyphenyl |
| 943 | CH$_2$CH$_2$CH$_3$ | H | O | CH$_2$—c-Pr | Cl | 4-methoxyphenyl |
| 944 | CH$_2$CH(CH$_3$)$_2$ | H | O | CH$_2$—c-Pr | Cl | 4-methoxyphenyl |
| 945 | cyclopropylmethyl | H | O | CH$_2$—c-Pr | Cl | 4-methoxyphenyl |
| 946 | SCH(CH$_3$)$_2$ | H | O | CH$_2$—c-Pr | Cl | 4-methoxyphenyl |
| 947 | OCH$_2$CH$_3$ | H | O | CH$_2$—c-Pr | Cl | 4-methoxyphenyl |
| 948 | (CH$_2$)$_2$ | | O | CH$_2$—c-Pr | Cl | 4-methoxyphenyl |
| 949 | (CH$_2$)$_4$ | | O | CH$_2$—c-Pr | Cl | 4-methoxyphenyl |
| 950 | CH$_3$ | H | O | CH$_2$—c-Pr | Cl | 3,4 dichloro phenyl |
| 951 | CH$_2$CH$_3$ | H | O | CH$_2$—c-Pr | Cl | 3,4 dichloro phenyl |
| 952 | CH$_2$CF$_3$ | H | O | CH$_2$—c-Pr | Cl | 3,4 dichloro phenyl |
| 953 | CH$_2$CH$_2$CH$_3$ | H | O | CH$_2$—c-Pr | Cl | 3,4 dichloro phenyl |
| 954 | CH$_2$CH(CH$_3$)$_2$ | H | O | CH$_2$—c-Pr | Cl | 3,4 dichloro phenyl |
| 955 | cyclopropylmethyl | H | O | CH$_2$—c-Pr | Cl | 3,4 dichloro phenyl |

TABLE 2-continued

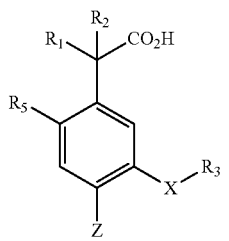

Formula V

| EX | R1 | R2 | X | R3 | R5 | Z |
|---|---|---|---|---|---|---|
| 956 | SCH(CH$_3$)$_2$ | H | O | CH$_2$—c-Pr | Cl | 3,4 dichloro phenyl |
| 957 | OCH$_2$CH$_3$ | H | O | CH$_2$—c-Pr | Cl | 3,4 dichloro phenyl |
| 958 | (CH$_2$)$_2$ | | O | CH$_2$—c-Pr | Cl | 3,4 dichloro phenyl |
| 959 | (CH$_2$)$_4$ | | O | CH$_2$—c-Pr | Cl | 3,4 dichloro phenyl |
| 960 | CH$_3$ | H | O | CH$_2$—c-Pr | Cl | 5-benzo[c][1,2,5]oxadiazolyl |
| 961 | CH$_2$CH$_3$ | H | O | CH$_2$—c-Pr | Cl | 5-benzo[c][1,2,5]oxadiazolyl |
| 962 | CH$_2$CF$_3$ | H | O | CH$_2$—c-Pr | Cl | 5-benzo[c][1,2,5]oxadiazolyl |
| 963 | CH$_2$CH$_2$CH$_3$ | H | O | CH$_2$—c-Pr | Cl | 5-benzo[c][1,2,5]oxadiazolyl |
| 964 | CH$_2$CH(CH$_3$)$_2$ | H | O | CH$_2$—c-Pr | Cl | 5-benzo[c][1,2,5]oxadiazolyl |
| 965 | cyclopropylmethyl | H | O | CH$_2$—c-Pr | Cl | 5-benzo[c][1,2,5]oxadiazolyl |
| 966 | SCH(CH$_3$)$_2$ | H | O | CH$_2$—c-Pr | Cl | 5-benzo[c][1,2,5]oxadiazolyl |
| 967 | OCH$_2$CH$_3$ | H | O | CH$_2$—c-Pr | Cl | 5-benzo[c][1,2,5]oxadiazolyl |
| 968 | (CH$_2$)$_2$ | | O | CH$_2$—c-Pr | Cl | 5-benzo[c][1,2,5]oxadiazolyl |
| 969 | (CH$_2$)$_4$ | | O | CH$_2$—c-Pr | Cl | 5-benzo[c][1,2,5]oxadiazolyl |
| 970 | CH$_3$ | H | O | CH$_2$—c-Pr | Cl | 5-benzo[c][1,2,5]thiadiazolyl |
| 971 | CH$_2$CH$_3$ | H | O | CH$_2$—c-Pr | Cl | 5-benzo[c][1,2,5]thiadiazolyl |
| 972 | CH$_2$CF$_3$ | H | O | CH$_2$—c-Pr | Cl | 5-benzo[c][1,2,5]thiadiazolyl |
| 973 | CH$_2$CH$_2$CH$_3$ | H | O | CH$_2$—c-Pr | Cl | 5-benzo[c][1,2,5]thiadiazolyl |
| 974 | CH$_2$CH(CH$_3$)$_2$ | H | O | CH$_2$—c-Pr | Cl | 5-benzo[c][1,2,5]thiadiazolyl |
| 975 | cyclopropylmethyl | H | O | CH$_2$—c-Pr | Cl | 5-benzo[c][1,2,5]thiadiazolyl |
| 976 | SCH(CH$_3$)$_2$ | H | O | CH$_2$—c-Pr | Cl | 5-benzo[c][1,2,5]thiadiazolyl |
| 977 | OCH$_2$CH$_3$ | H | O | CH$_2$—c-Pr | Cl | 5-benzo[c][1,2,5]thiadiazolyl |
| 978 | (CH$_2$)$_2$ | | O | CH$_2$—c-Pr | Cl | 5-benzo[c][1,2,5]thiadiazolyl |
| 979 | (CH$_2$)$_4$ | | O | CH$_2$—c-Pr | Cl | 5-benzo[c][1,2,5]thiadiazolyl |

TABLE 3

Compounds of Formula III

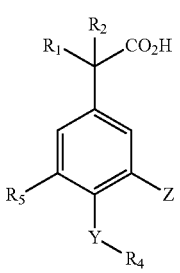

Formula III

| Ex | R1 | R2 | Y | R4 | R5 | Z |
|---|---|---|---|---|---|---|
| 980 | CH$_2$CH$_3$ | H | O | CH$_2$CF$_3$ | CF$_3$ | 4-trifluoromethylphenyl |
| 981 | CH$_2$CF$_3$ | H | O | CH$_2$CF$_3$ | CF$_3$ | 4-trifluoromethylphenyl |
| 982 | CH$_2$CH$_2$CH$_3$ | H | O | CH$_2$CF$_3$ | CF$_3$ | 4-trifluoromethylphenyl |
| 983 | CH$_2$CH(CH$_3$)$_2$ | H | O | CH$_2$CF$_3$ | CF$_3$ | 4-trifluoromethylphenyl |
| 984 | cyclopropylmethyl | H | O | CH$_2$CF$_3$ | CF$_3$ | 4-trifluoromethylphenyl |
| 985 | cyclobutylmethyl | H | O | CH$_2$CF$_3$ | CF$_3$ | 4-trifluoromethylphenyl |
| 986 | (CH$_2$)$_2$ | | O | CH$_2$CF$_3$ | CF$_3$ | 4-trifluoromethylphenyl |
| 987 | (CH$_2$)$_3$ | | O | CH$_2$CF$_3$ | CF$_3$ | 4-trifluoromethylphenyl |
| 988 | (CH$_2$)$_4$ | | O | CH$_2$CF$_3$ | CF$_3$ | 4-trifluoromethylphenyl |
| 989 | (CH$_2$)$_5$ | | O | CH$_2$CF$_3$ | CF$_3$ | 4-trifluoromethylphenyl |
| 990 | 5,5-spiro[2.3]hexane | | O | CH$_2$CF$_3$ | CF$_3$ | 4-trifluoromethylphenyl |
| 991 | Cyclopentyl | H | O | CH$_2$CF$_3$ | CF$_3$ | 4-trifluoromethylphenyl |
| 992 | CH$_2$CH$_3$ | H | O | CH$_2$CF$_3$ | CF$_3$ | 4-tolyl |
| 993 | CH$_2$CF$_3$ | H | O | CH$_2$CF$_3$ | CF$_3$ | 4-tolyl |
| 994 | CH$_2$CH$_2$CH$_3$ | H | O | CH$_2$CF$_3$ | CF$_3$ | 4-tolyl |
| 995 | CH$_2$CH(CH$_3$)$_2$ | H | O | CH$_2$CF$_3$ | CF$_3$ | 4-tolyl |
| 996 | cyclopropylmethyl | H | O | CH$_2$CF$_3$ | CF$_3$ | 4-tolyl |
| 997 | cyclobutylmethyl | H | O | CH$_2$CF$_3$ | CF$_3$ | 4-tolyl |
| 998 | (CH$_2$)$_2$ | | O | CH$_2$CF$_3$ | CF$_3$ | 4-tolyl |

TABLE 3-continued

Compounds of Formula III

Formula III $$\text{R}_1\text{-C(R}_2\text{)(CO}_2\text{H)-C}_6\text{H}_2(\text{R}_5)(\text{Z})(\text{Y-R}_4)$$

| Ex | R1 | R2 | Y | R4 | R5 | Z |
|---|---|---|---|---|---|---|
| 999 | (CH$_2$)$_3$ | | O | CH$_2$CF$_3$ | CF$_3$ | 4-tolyl |
| 1000 | (CH$_2$)$_4$ | | O | CH$_2$CF$_3$ | CF$_3$ | 4-tolyl |
| 1001 | (CH$_2$)$_5$ | | O | CH$_2$CF$_3$ | CF$_3$ | 4-tolyl |
| 1002 | 5,5-spiro[2.3]hexane | | O | CH$_2$CF$_3$ | CF$_3$ | 4-tolyl |
| 1003 | Cyclopentyl | H | O | CH$_2$CF$_3$ | CF$_3$ | 4-tolyl |
| 1004 | CH$_2$CH$_3$ | H | O | CH$_2$CF$_3$ | CF$_3$ | 4-ethyl phenyl |
| 1005 | CH$_2$CF$_3$ | H | O | CH$_2$CF$_3$ | CF$_3$ | 4-ethyl phenyl |
| 1006 | CH$_2$CH$_2$CH$_3$ | H | O | CH$_2$CF$_3$ | CF$_3$ | 4-ethyl phenyl |
| 1007 | CH$_2$CH(CH$_3$)$_2$ | H | O | CH$_2$CF$_3$ | CF$_3$ | 4-ethyl phenyl |
| 1008 | cyclopropylmethyl | H | O | CH$_2$CF$_3$ | CF$_3$ | 4-ethyl phenyl |
| 1009 | cyclobutylmethyl | H | O | CH$_2$CF$_3$ | CF$_3$ | 4-ethyl phenyl |
| 1010 | (CH$_2$)$_2$ | | O | CH$_2$CF$_3$ | CF$_3$ | 4-ethyl phenyl |
| 1011 | (CH$_2$)$_3$ | | O | CH$_2$CF$_3$ | CF$_3$ | 4-ethyl phenyl |
| 1012 | (CH$_2$)$_4$ | | O | CH$_2$CF$_3$ | CF$_3$ | 4-ethyl phenyl |
| 1013 | (CH$_2$)$_5$ | | O | CH$_2$CF$_3$ | CF$_3$ | 4-ethyl phenyl |
| 1014 | 5,5-spiro[2.3]hexane | | O | CH$_2$CF$_3$ | CF$_3$ | 4-ethyl phenyl |
| 1015 | Cyclopentyl | H | O | CH$_2$CF$_3$ | CF$_3$ | 4-ethyl phenyl |
| 1016 | CH$_2$CH$_3$ | H | O | CH$_2$CF$_3$ | CF$_3$ | 4-isopropyl phenyl |
| 1017 | CH$_2$CF$_3$ | H | O | CH$_2$CF$_3$ | CF$_3$ | 4-isopropyl phenyl |
| 1018 | CH$_2$CH$_2$CH$_3$ | H | O | CH$_2$CF$_3$ | CF$_3$ | 4-isopropyl phenyl |
| 1019 | CH$_2$CH(CH$_3$)$_2$ | H | O | CH$_2$CF$_3$ | CF$_3$ | 4-isopropyl phenyl |
| 1020 | cyclopropylmethyl | H | O | CH$_2$CF$_3$ | CF$_3$ | 4-isopropyl phenyl |
| 1021 | cyclobutylmethyl | H | O | CH$_2$CF$_3$ | CF$_3$ | 4-isopropyl phenyl |
| 1022 | (CH$_2$)$_2$ | | O | CH$_2$CF$_3$ | CF$_3$ | 4-isopropyl phenyl |
| 1023 | (CH$_2$)$_3$ | | O | CH$_2$CF$_3$ | CF$_3$ | 4-isopropyl phenyl |
| 1024 | (CH$_2$)$_4$ | | O | CH$_2$CF$_3$ | CF$_3$ | 4-isopropyl phenyl |
| 1025 | (CH$_2$)$_5$ | | O | CH$_2$CF$_3$ | CF$_3$ | 4-isopropyl phenyl |
| 1026 | 5,5-spiro[2.3]hexane | | O | CH$_2$CF$_3$ | CF$_3$ | 4-isopropyl phenyl |
| 1027 | Cyclopentyl | H | O | CH$_2$CF$_3$ | CF$_3$ | 4-isopropyl phenyl |
| 1028 | CH$_2$CH$_3$ | H | O | CH$_2$CF$_3$ | CF$_3$ | 4-thiomethylphenyl |
| 1029 | CH$_2$CF$_3$ | H | O | CH$_2$CF$_3$ | CF$_3$ | 4-thiomethylphenyl |
| 1030 | CH$_2$CH$_2$CH$_3$ | H | O | CH$_2$CF$_3$ | CF$_3$ | 4-thiomethylphenyl |
| 1031 | CH$_2$CH(CH$_3$)$_2$ | H | O | CH$_2$CF$_3$ | CF$_3$ | 4-thiomethylphenyl |
| 1032 | cyclopropylmethyl | H | O | CH$_2$CF$_3$ | CF$_3$ | 4-thiomethylphenyl |
| 1033 | cyclobutylmethyl | H | O | CH$_2$CF$_3$ | CF$_3$ | 4-thiomethylphenyl |
| 1034 | (CH$_2$)$_2$ | | O | CH$_2$CF$_3$ | CF$_3$ | 4-thiomethylphenyl |
| 1035 | (CH$_2$)$_3$ | | O | CH$_2$CF$_3$ | CF$_3$ | 4-thiomethylphenyl |
| 1036 | (CH$_2$)$_4$ | | O | CH$_2$CF$_3$ | CF$_3$ | 4-thiomethylphenyl |
| 1037 | (CH$_2$)$_5$ | | O | CH$_2$CF$_3$ | CF$_3$ | 4-thiomethylphenyl |
| 1038 | 5,5-spiro[2.3]hexane | | O | CH$_2$CF$_3$ | CF$_3$ | 4-thiomethylphenyl |
| 1039 | Cyclopentyl | H | O | CH$_2$CF$_3$ | CF$_3$ | 4-thiomethylphenyl |
| 1040 | CH$_2$CH$_3$ | H | O | CH$_2$CF$_3$ | CF$_3$ | 4-trifluoromethoxyphenyl |
| 1041 | CH$_2$CF$_3$ | H | O | CH$_2$CF$_3$ | CF$_3$ | 4-trifluoromethoxyphenyl |
| 1042 | CH$_2$CH$_2$CH$_3$ | H | O | CH$_2$CF$_3$ | CF$_3$ | 4-trifluoromethoxyphenyl |
| 1043 | CH$_2$CH(CH$_3$)$_2$ | H | O | CH$_2$CF$_3$ | CF$_3$ | 4-trifluoromethoxyphenyl |
| 1044 | cyclopropylmethyl | H | O | CH$_2$CF$_3$ | CF$_3$ | 4-trifluoromethoxyphenyl |
| 1045 | cyclobutylmethyl | H | O | CH$_2$CF$_3$ | CF$_3$ | 4-trifluoromethoxyphenyl |
| 1046 | (CH$_2$)$_2$ | | O | CH$_2$CF$_3$ | CF$_3$ | 4-trifluoromethoxyphenyl |
| 1047 | (CH$_2$)$_3$ | | O | CH$_2$CF$_3$ | CF$_3$ | 4-trifluoromethoxyphenyl |
| 1048 | (CH$_2$)$_4$ | | O | CH$_2$CF$_3$ | CF$_3$ | 4-trifluoromethoxyphenyl |
| 1049 | (CH$_2$)$_5$ | | O | CH$_2$CF$_3$ | CF$_3$ | 4-trifluoromethoxyphenyl |
| 1050 | 5,5-spiro[2.3]hexane | | O | CH$_2$CF$_3$ | CF$_3$ | 4-trifluoromethoxyphenyl |
| 1051 | Cyclopentyl | H | O | CH$_2$CF$_3$ | CF$_3$ | 4-trifluoromethoxyphenyl |
| 1052 | CH$_2$CH$_3$ | H | O | CH$_2$—c-Pr | CF$_3$ | 4-trifluoromethylphenyl |
| 1053 | CH$_2$CF$_3$ | H | O | CH$_2$—c-Pr | CF$_3$ | 4-trifluoromethylphenyl |
| 1054 | CH$_2$CH$_2$CH$_3$ | H | O | CH$_2$—c-Pr | CF$_3$ | 4-trifluoromethylphenyl |
| 1055 | CH$_2$CH(CH$_3$)$_2$ | H | O | CH$_2$—c-Pr | CF$_3$ | 4-trifluoromethylphenyl |
| 1056 | cyclopropylmethyl | H | O | CH$_2$—c-Pr | CF$_3$ | 4-trifluoromethylphenyl |
| 1057 | cyclobutylmethyl | H | O | CH$_2$—c-Pr | CF$_3$ | 4-trifluoromethylphenyl |
| 1058 | (CH$_2$)$_2$ | | O | CH$_2$—c-Pr | CF$_3$ | 4-trifluoromethylphenyl |
| 1059 | (CH$_2$)$_3$ | | O | CH$_2$—c-Pr | CF$_3$ | 4-trifluoromethylphenyl |
| 1060 | (CH$_2$)$_4$ | | O | CH$_2$—c-Pr | CF$_3$ | 4-trifluoromethylphenyl |
| 1061 | (CH$_2$)$_5$ | | O | CH$_2$—c-Pr | CF$_3$ | 4-trifluoromethylphenyl |

TABLE 3-continued

Compounds of Formula III

Formula III

| Ex | R1 | R2 | Y | R4 | R5 | Z |
|---|---|---|---|---|---|---|
| 1062 | 5,5-spiro[2.3]hexane | | O | CH$_2$—c-Pr | CF$_3$ | 4-trifluoromethylphenyl |
| 1063 | Cyclopentyl | H | O | CH$_2$—c-Pr | CF$_3$ | 4-trifluoromethylphenyl |
| 1064 | CH$_2$CH$_3$ | H | O | CH$_2$—c-Pr | CF$_3$ | 4-tolyl |
| 1065 | CH$_2$CF$_3$ | H | O | CH$_2$—c-Pr | CF$_3$ | 4-tolyl |
| 1066 | CH$_2$CH$_2$CH$_3$ | H | O | CH$_2$—c-Pr | CF$_3$ | 4-tolyl |
| 1067 | CH$_2$CH(CH$_3$)$_2$ | H | O | CH$_2$—c-Pr | CF$_3$ | 4-tolyl |
| 1068 | cyclopropylmethyl | H | O | CH$_2$—c-Pr | CF$_3$ | 4-tolyl |
| 1069 | cyclobutylmethyl | H | O | CH$_2$—c-Pr | CF$_3$ | 4-tolyl |
| 1070 | (CH$_2$)$_2$ | | O | CH$_2$—c-Pr | CF$_3$ | 4-tolyl |
| 1071 | (CH$_2$)$_3$ | | O | CH$_2$—c-Pr | CF$_3$ | 4-tolyl |
| 1072 | (CH$_2$)$_4$ | | O | CH$_2$—c-Pr | CF$_3$ | 4-tolyl |
| 1073 | (CH$_2$)$_5$ | | O | CH$_2$—c-Pr | CF$_3$ | 4-tolyl |
| 1074 | 5,5-spiro[2.3]hexane | | O | CH$_2$—c-Pr | CF$_3$ | 4-tolyl |
| 1075 | Cyclopentyl | H | O | CH$_2$—c-Pr | CF$_3$ | 4-tolyl |
| 1076 | CH$_2$CH$_3$ | H | O | CH$_2$—c-Pr | CF$_3$ | 4-ethyl phenyl |
| 1077 | CH$_2$CF$_3$ | H | O | CH$_2$—c-Pr | CF$_3$ | 4-ethyl phenyl |
| 1078 | CH$_2$CH$_2$CH$_3$ | H | O | CH$_2$—c-Pr | CF$_3$ | 4-ethyl phenyl |
| 1079 | CH$_2$CH(CH$_3$)$_2$ | H | O | CH$_2$—c-Pr | CF$_3$ | 4-ethyl phenyl |
| 1080 | cyclopropylmethyl | H | O | CH$_2$—c-Pr | CF$_3$ | 4-ethyl phenyl |
| 1081 | cyclobutylmethyl | H | O | CH$_2$—c-Pr | CF$_3$ | 4-ethyl phenyl |
| 1082 | (CH$_2$)$_2$ | | O | CH$_2$—c-Pr | CF$_3$ | 4-ethyl phenyl |
| 1083 | (CH$_2$)$_3$ | | O | CH$_2$—c-Pr | CF$_3$ | 4-ethyl phenyl |
| 1084 | (CH$_2$)$_4$ | | O | CH$_2$—c-Pr | CF$_3$ | 4-ethyl phenyl |
| 1085 | (CH$_2$)$_5$ | | O | CH$_2$—c-Pr | CF$_3$ | 4-ethyl phenyl |
| 1086 | 5,5-spiro[2.3]hexane | | O | CH$_2$—c-Pr | CF$_3$ | 4-ethyl phenyl |
| 1087 | Cyclopentyl | H | O | CH$_2$—c-Pr | CF$_3$ | 4-ethyl phenyl |
| 1088 | CH$_2$CH$_3$ | H | O | CH$_2$—c-Pr | CF$_3$ | 4-isopropyl phenyl |
| 1089 | CH$_2$CF$_3$ | H | O | CH$_2$—c-Pr | CF$_3$ | 4-isopropyl phenyl |
| 1090 | CH$_2$CH$_2$CH$_3$ | H | O | CH$_2$—c-Pr | CF$_3$ | 4-isopropyl phenyl |
| 1091 | CH$_2$CH(CH$_3$)$_2$ | H | O | CH$_2$—c-Pr | CF$_3$ | 4-isopropyl phenyl |
| 1092 | cyclopropylmethyl | H | O | CH$_2$—c-Pr | CF$_3$ | 4-isopropyl phenyl |
| 1093 | cyclobutylmethyl | H | O | CH$_2$—c-Pr | CF$_3$ | 4-isopropyl phenyl |
| 1094 | (CH$_2$)$_2$ | | O | CH$_2$—c-Pr | CF$_3$ | 4-isopropyl phenyl |
| 1095 | (CH$_2$)$_3$ | | O | CH$_2$—c-Pr | CF$_3$ | 4-isopropyl phenyl |
| 1096 | (CH$_2$)$_4$ | | O | CH$_2$—c-Pr | CF$_3$ | 4-isopropyl phenyl |
| 1097 | (CH$_2$)$_5$ | | O | CH$_2$—c-Pr | CF$_3$ | 4-isopropyl phenyl |
| 1098 | 5,5-spiro[2.3]hexane | | O | CH$_2$—c-Pr | CF$_3$ | 4-isopropyl phenyl |
| 1099 | Cyclopentyl | H | O | CH$_2$—c-Pr | CF$_3$ | 4-isopropyl phenyl |
| 1100 | CH$_2$CH$_3$ | H | O | CH$_2$—c-Pr | CF$_3$ | 4-thiomethylphenyl |
| 1101 | CH$_2$CF$_3$ | H | O | CH$_2$—c-Pr | CF$_3$ | 4-thiomethylphenyl |
| 1102 | CH$_2$CH$_2$CH$_3$ | H | O | CH$_2$—c-Pr | CF$_3$ | 4-thiomethylphenyl |
| 1103 | CH$_2$CH(CH$_3$)$_2$ | H | O | CH$_2$—c-Pr | CF$_3$ | 4-thiomethylphenyl |
| 1104 | cyclopropylmethyl | H | O | CH$_2$—c-Pr | CF$_3$ | 4-thiomethylphenyl |
| 1105 | cyclobutylmethyl | H | O | CH$_2$—c-Pr | CF$_3$ | 4-thiomethylphenyl |
| 1106 | (CH$_2$)$_2$ | | O | CH$_2$—c-Pr | CF$_3$ | 4-thiomethylphenyl |
| 1107 | (CH$_2$)$_3$ | | O | CH$_2$—c-Pr | CF$_3$ | 4-thiomethylphenyl |
| 1108 | (CH$_2$)$_4$ | | O | CH$_2$—c-Pr | CF$_3$ | 4-thiomethylphenyl |
| 1109 | (CH$_2$)$_5$ | | O | CH$_2$—c-Pr | CF$_3$ | 4-thiomethylphenyl |
| 1110 | 5,5-spiro[2.3]hexane | | O | CH$_2$—c-Pr | CF$_3$ | 4-thiomethylphenyl |
| 1111 | Cyclopentyl | H | O | CH$_2$—c-Pr | CF$_3$ | 4-thiomethylphenyl |
| 1112 | CH$_2$CH$_3$ | H | O | CH$_2$—c-Pr | CF$_3$ | 4-trifluoromethoxyphenyl |
| 1113 | CH$_2$CF$_3$ | H | O | CH$_2$—c-Pr | CF$_3$ | 4-trifluoromethoxyphenyl |
| 1114 | CH$_2$CH$_2$CH$_3$ | H | O | CH$_2$—c-Pr | CF$_3$ | 4-trifluoromethoxyphenyl |
| 1115 | CH$_2$CH(CH$_3$)$_2$ | H | O | CH$_2$—c-Pr | CF$_3$ | 4-trifluoromethoxyphenyl |
| 1116 | cyclopropylmethyl | H | O | CH$_2$—c-Pr | CF$_3$ | 4-trifluoromethoxyphenyl |
| 1117 | cyclobutylmethyl | H | O | CH$_2$—c-Pr | CF$_3$ | 4-trifluoromethoxyphenyl |
| 1118 | (CH$_2$)$_2$ | | O | CH$_2$—c-Pr | CF$_3$ | 4-trifluoromethoxyphenyl |
| 1119 | (CH$_2$)$_3$ | | O | CH$_2$—c-Pr | CF$_3$ | 4-trifluoromethoxyphenyl |
| 1120 | (CH$_2$)$_4$ | | O | CH$_2$—c-Pr | CF$_3$ | 4-trifluoromethoxyphenyl |
| 1121 | (CH$_2$)$_5$ | | O | CH$_2$—c-Pr | CF$_3$ | 4-trifluoromethoxyphenyl |
| 1122 | 5,5-spiro[2.3]hexane | | O | CH$_2$—c-Pr | CF$_3$ | 4-trifluoromethoxyphenyl |
| 1123 | Cyclopentyl | H | O | CH$_2$—c-Pr | CF$_3$ | 4-trifluoromethoxyphenyl |
| 1124 | CH$_2$CH$_3$ | H | O | CH$_2$CF$_3$ | OCH$_2$CF$_3$ | 4-trifluoromethylphenyl |

TABLE 3-continued

Compounds of Formula III

Formula III

| Ex | R1 | R2 | Y | R4 | R5 | Z |
|---|---|---|---|---|---|---|
| 1125 | CH$_2$CF$_3$ | H | O | CH$_2$CF$_3$ | OCH$_2$CF$_3$ | 4-trifluoromethylphenyl |
| 1126 | CH$_2$CH$_2$CH$_3$ | H | O | CH$_2$CF$_3$ | OCH$_2$CF$_3$ | 4-trifluoromethylphenyl |
| 1127 | CH$_2$CH(CH$_3$)$_2$ | H | O | CH$_2$CF$_3$ | OCH$_2$CF$_3$ | 4-trifluoromethylphenyl |
| 1128 | cyclopropylmethyl | H | O | CH$_2$CF$_3$ | OCH$_2$CF$_3$ | 4-trifluoromethylphenyl |
| 1129 | cyclobutylmethyl | H | O | CH$_2$CF$_3$ | OCH$_2$CF$_3$ | 4-trifluoromethylphenyl |
| 1130 | (CH$_2$)$_2$ | | O | CH$_2$CF$_3$ | OCH$_2$CF$_3$ | 4-trifluoromethylphenyl |
| 1131 | (CH$_2$)$_3$ | | O | CH$_2$CF$_3$ | OCH$_2$CF$_3$ | 4-trifluoromethylphenyl |
| 1132 | (CH$_2$)$_4$ | | O | CH$_2$CF$_3$ | OCH$_2$CF$_3$ | 4-trifluoromethylphenyl |
| 1133 | (CH$_2$)$_5$ | | O | CH$_2$CF$_3$ | OCH$_2$CF$_3$ | 4-trifluoromethylphenyl |
| 1134 | 5,5-spiro[2.3]hexane | | O | CH$_2$CF$_3$ | OCH$_2$CF$_3$ | 4-trifluoromethylphenyl |
| 1135 | Cyclopentyl | H | O | CH$_2$CF$_3$ | OCH$_2$CF$_3$ | 4-trifluoromethylphenyl |
| 1136 | CH$_2$CH$_3$ | H | O | CH$_2$CF$_3$ | OCH$_2$CF$_3$ | 4-tolyl |
| 1137 | CH$_2$CF$_3$ | H | O | CH$_2$CF$_3$ | OCH$_2$CF$_3$ | 4-tolyl |
| 1138 | CH$_2$CH$_2$CH$_3$ | H | O | CH$_2$CF$_3$ | OCH$_2$CF$_3$ | 4-tolyl |
| 1139 | CH$_2$CH(CH$_3$)$_2$ | H | O | CH$_2$CF$_3$ | OCH$_2$CF$_3$ | 4-tolyl |
| 1140 | cyclopropylmethyl | H | O | CH$_2$CF$_3$ | OCH$_2$CF$_3$ | 4-tolyl |
| 1141 | cyclobutylmethyl | H | O | CH$_2$CF$_3$ | OCH$_2$CF$_3$ | 4-tolyl |
| 1142 | (CH$_2$)$_2$ | | O | CH$_2$CF$_3$ | OCH$_2$CF$_3$ | 4-tolyl |
| 1143 | (CH$_2$)$_3$ | | O | CH$_2$CF$_3$ | OCH$_2$CF$_3$ | 4-tolyl |
| 1144 | (CH$_2$)$_4$ | | O | CH$_2$CF$_3$ | OCH$_2$CF$_3$ | 4-tolyl |
| 1145 | (CH$_2$)$_5$ | | O | CH$_2$CF$_3$ | OCH$_2$CF$_3$ | 4-tolyl |
| 1146 | 5,5-spiro[2.3]hexane | | O | CH$_2$CF$_3$ | OCH$_2$CF$_3$ | 4-tolyl |
| 1147 | Cyclopentyl | H | O | CH$_2$CF$_3$ | OCH$_2$CF$_3$ | 4-tolyl |
| 1148 | CH$_2$CH$_3$ | H | O | CH$_2$CF$_3$ | OCH$_2$CF$_3$ | 4-ethyl phenyl |
| 1149 | CH$_2$CF$_3$ | H | O | CH$_2$CF$_3$ | OCH$_2$CF$_3$ | 4-ethyl phenyl |
| 1150 | CH$_2$CH$_2$CH$_3$ | H | O | CH$_2$CF$_3$ | OCH$_2$CF$_3$ | 4-ethyl phenyl |
| 1151 | CH$_2$CH(CH$_3$)$_2$ | H | O | CH$_2$CF$_3$ | OCH$_2$CF$_3$ | 4-ethyl phenyl |
| 1152 | cyclopropylmethyl | H | O | CH$_2$CF$_3$ | OCH$_2$CF$_3$ | 4-ethyl phenyl |
| 1153 | cyclobutylmethyl | H | O | CH$_2$CF$_3$ | OCH$_2$CF$_3$ | 4-ethyl phenyl |
| 1154 | (CH$_2$)$_2$ | | O | CH$_2$CF$_3$ | OCH$_2$CF$_3$ | 4-ethyl phenyl |
| 1155 | (CH$_2$)$_3$ | | O | CH$_2$CF$_3$ | OCH$_2$CF$_3$ | 4-ethyl phenyl |
| 1156 | (CH$_2$)$_4$ | | O | CH$_2$CF$_3$ | OCH$_2$CF$_3$ | 4-ethyl phenyl |
| 1157 | (CH$_2$)$_5$ | | O | CH$_2$CF$_3$ | OCH$_2$CF$_3$ | 4-ethyl phenyl |
| 1158 | 5,5-spiro[2.3]hexane | | O | CH$_2$CF$_3$ | OCH$_2$CF$_3$ | 4-ethyl phenyl |
| 1159 | Cyclopentyl | H | O | CH$_2$CF$_3$ | OCH$_2$CF$_3$ | 4-ethyl phenyl |
| 1160 | CH$_2$CH$_3$ | H | O | CH$_2$CF$_3$ | OCH$_2$CF$_3$ | 4-isopropyl phenyl |
| 1161 | CH$_2$CF$_3$ | H | O | CH$_2$CF$_3$ | OCH$_2$CF$_3$ | 4-isopropyl phenyl |
| 1162 | CH$_2$CH$_2$CH$_3$ | H | O | CH$_2$CF$_3$ | OCH$_2$CF$_3$ | 4-isopropyl phenyl |
| 1163 | CH$_2$CH(CH$_3$)$_2$ | H | O | CH$_2$CF$_3$ | OCH$_2$CF$_3$ | 4-isopropyl phenyl |
| 1164 | cyclopropylmethyl | H | O | CH$_2$CF$_3$ | OCH$_2$CF$_3$ | 4-isopropyl phenyl |
| 1165 | cyclobutylmethyl | H | O | CH$_2$CF$_3$ | OCH$_2$CF$_3$ | 4-isopropyl phenyl |
| 1166 | (CH$_2$)$_2$ | | O | CH$_2$CF$_3$ | OCH$_2$CF$_3$ | 4-isopropyl phenyl |
| 1167 | (CH$_2$)$_3$ | | O | CH$_2$CF$_3$ | OCH$_2$CF$_3$ | 4-isopropyl phenyl |
| 1168 | (CH$_2$)$_4$ | | O | CH$_2$CF$_3$ | OCH$_2$CF$_3$ | 4-isopropyl phenyl |
| 1169 | (CH$_2$)$_5$ | | O | CH$_2$CF$_3$ | OCH$_2$CF$_3$ | 4-isopropyl phenyl |
| 1170 | 5,5-spiro[2.3]hexane | | O | CH$_2$CF$_3$ | OCH$_2$CF$_3$ | 4-isopropyl phenyl |
| 1171 | Cyclopentyl | H | O | CH$_2$CF$_3$ | OCH$_2$CF$_3$ | 4-isopropyl phenyl |
| 1172 | CH$_2$CH$_3$ | H | O | CH$_2$CF$_3$ | OCH$_2$CF$_3$ | 4-thiomethylphenyl |
| 1173 | CH$_2$CF$_3$ | H | O | CH$_2$CF$_3$ | OCH$_2$CF$_3$ | 4-thiomethylphenyl |
| 1174 | CH$_2$CH$_2$CH$_3$ | H | O | CH$_2$CF$_3$ | OCH$_2$CF$_3$ | 4-thiomethylphenyl |
| 1175 | CH$_2$CH(CH$_3$)$_2$ | H | O | CH$_2$CF$_3$ | OCH$_2$CF$_3$ | 4-thiomethylphenyl |
| 1176 | cyclopropylmethyl | H | O | CH$_2$CF$_3$ | OCH$_2$CF$_3$ | 4-thiomethylphenyl |
| 1177 | cyclobutylmethyl | H | O | CH$_2$CF$_3$ | OCH$_2$CF$_3$ | 4-thiomethylphenyl |
| 1178 | (CH$_2$)$_2$ | | O | CH$_2$CF$_3$ | OCH$_2$CF$_3$ | 4-thiomethylphenyl |
| 1179 | (CH$_2$)$_3$ | | O | CH$_2$CF$_3$ | OCH$_2$CF$_3$ | 4-thiomethylphenyl |
| 1180 | (CH$_2$)$_4$ | | O | CH$_2$CF$_3$ | OCH$_2$CF$_3$ | 4-thiomethylphenyl |
| 1181 | (CH$_2$)$_5$ | | O | CH$_2$CF$_3$ | OCH$_2$CF$_3$ | 4-thiomethylphenyl |
| 1182 | 5,5-spiro[2.3]hexane | | O | CH$_2$CF$_3$ | OCH$_2$CF$_3$ | 4-thiomethylphenyl |
| 1183 | Cyclopentyl | H | O | CH$_2$CF$_3$ | OCH$_2$CF$_3$ | 4-thiomethylphenyl |
| 1184 | CH$_2$CH$_3$ | H | O | CH$_2$CF$_3$ | OCH$_2$CF$_3$ | 4-trifluoromethoxyphenyl |
| 1185 | CH$_2$CF$_3$ | H | O | CH$_2$CF$_3$ | OCH$_2$CF$_3$ | 4-trifluoromethoxyphenyl |
| 1186 | CH$_2$CH$_2$CH$_3$ | H | O | CH$_2$CF$_3$ | OCH$_2$CF$_3$ | 4-trifluoromethoxyphenyl |
| 1187 | CH$_2$CH(CH$_3$)$_2$ | H | O | CH$_2$CF$_3$ | OCH$_2$CF$_3$ | 4-trifluoromethoxyphenyl |

TABLE 3-continued

Compounds of Formula III

Formula III $$\text{structure with } R_1, R_2, CO_2H \text{ on a carbon attached to a phenyl ring with } R_5, Z, \text{ and } Y-R_4 \text{ substituents}$$

| Ex | R1 | R2 | Y | R4 | R5 | Z |
|---|---|---|---|---|---|---|
| 1188 | cyclopropylmethyl | H | O | $CH_2CF_3$ | $OCH_2CF_3$ | 4-trifluoromethoxyphenyl |
| 1189 | cyclobutylmethyl | H | O | $CH_2CF_3$ | $OCH_2CF_3$ | 4-trifluoromethoxyphenyl |
| 1190 | $(CH_2)_2$ | | O | $CH_2CF_3$ | $OCH_2CF_3$ | 4-trifluoromethoxyphenyl |
| 1191 | $(CH_2)_3$ | | O | $CH_2CF_3$ | $OCH_2CF_3$ | 4-trifluoromethoxyphenyl |
| 1192 | $(CH_2)_4$ | | O | $CH_2CF_3$ | $OCH_2CF_3$ | 4-trifluoromethoxyphenyl |
| 1193 | $(CH_2)_5$ | | O | $CH_2CF_3$ | $OCH_2CF_3$ | 4-trifluoromethoxyphenyl |
| 1194 | 5,5-spiro[2.3]hexane | | O | $CH_2CF_3$ | $OCH_2CF_3$ | 4-trifluoromethoxyphenyl |
| 1195 | Cyclopentyl | H | O | $CH_2CF_3$ | $OCH_2CF_3$ | 4-trifluoromethoxyphenyl |
| 1196 | $CH_2CH_3$ | H | O | $CH_2$—c-Pr | $OCH_2CF_3$ | 4-trifluoromethylphenyl |
| 1197 | $CH_2CF_3$ | H | O | $CH_2$—c-Pr | $OCH_2CF_3$ | 4-trifluoromethylphenyl |
| 1198 | $CH_2CH_2CH_3$ | H | O | $CH_2$—c-Pr | $OCH_2CF_3$ | 4-trifluoromethylphenyl |
| 1199 | $CH_2CH(CH_3)_2$ | H | O | $CH_2$—c-Pr | $OCH_2CF_3$ | 4-trifluoromethylphenyl |
| 1200 | cyclopropylmethyl | H | O | $CH_2$—c-Pr | $OCH_2CF_3$ | 4-trifluoromethylphenyl |
| 1201 | cyclobutylmethyl | H | O | $CH_2$—c-Pr | $OCH_2CF_3$ | 4-trifluoromethylphenyl |
| 1202 | $(CH_2)_2$ | | O | $CH_2$—c-Pr | $OCH_2CF_3$ | 4-trifluoromethylphenyl |
| 1203 | $(CH_2)_3$ | | O | $CH_2$—c-Pr | $OCH_2CF_3$ | 4-trifluoromethylphenyl |
| 1204 | $(CH_2)_4$ | | O | $CH_2$—c-Pr | $OCH_2CF_3$ | 4-trifluoromethylphenyl |
| 1205 | $(CH_2)_5$ | | O | $CH_2$—c-Pr | $OCH_2CF_3$ | 4-trifluoromethylphenyl |
| 1206 | 5,5-spiro[2.3]hexane | | O | $CH_2$—c-Pr | $OCH_2CF_3$ | 4-trifluoromethylphenyl |
| 1207 | Cyclopentyl | H | O | $CH_2$—c-Pr | $OCH_2CF_3$ | 4-trifluoromethylphenyl |
| 1208 | $CH_2CH_3$ | H | O | $CH_2$—c-Pr | $OCH_2CF_3$ | 4-tolyl |
| 1209 | $CH_2CF_3$ | H | O | $CH_2$—c-Pr | $OCH_2CF_3$ | 4-tolyl |
| 1210 | $CH_2CH_2CH_3$ | H | O | $CH_2$—c-Pr | $OCH_2CF_3$ | 4-tolyl |
| 1211 | $CH_2CH(CH_3)_2$ | H | O | $CH_2$—c-Pr | $OCH_2CF_3$ | 4-tolyl |
| 1212 | cyclopropylmethyl | H | O | $CH_2$—c-Pr | $OCH_2CF_3$ | 4-tolyl |
| 1213 | cyclobutylmethyl | H | O | $CH_2$—c-Pr | $OCH_2CF_3$ | 4-tolyl |
| 1214 | $(CH_2)_2$ | | O | $CH_2$—c-Pr | $OCH_2CF_3$ | 4-tolyl |
| 1215 | $(CH_2)_3$ | | O | $CH_2$—c-Pr | $OCH_2CF_3$ | 4-tolyl |
| 1216 | $(CH_2)_4$ | | O | $CH_2$—c-Pr | $OCH_2CF_3$ | 4-tolyl |
| 1217 | $(CH_2)_5$ | | O | $CH_2$—c-Pr | $OCH_2CF_3$ | 4-tolyl |
| 1218 | 5,5-spiro[2.3]hexane | | O | $CH_2$—c-Pr | $OCH_2CF_3$ | 4-tolyl |
| 1219 | Cyclopentyl | H | O | $CH_2$—c-Pr | $OCH_2CF_3$ | 4-tolyl |
| 1220 | $CH_2CH_3$ | H | O | $CH_2$—c-Pr | $OCH_2CF_3$ | 4-ethyl phenyl |
| 1221 | $CH_2CF_3$ | H | O | $CH_2$—c-Pr | $OCH_2CF_3$ | 4-ethyl phenyl |
| 1222 | $CH_2CH_2CH_3$ | H | O | $CH_2$—c-Pr | $OCH_2CF_3$ | 4-ethyl phenyl |
| 1223 | $CH_2CH(CH_3)_2$ | H | O | $CH_2$—c-Pr | $OCH_2CF_3$ | 4-ethyl phenyl |
| 1224 | cyclopropylmethyl | H | O | $CH_2$—c-Pr | $OCH_2CF_3$ | 4-ethyl phenyl |
| 1225 | cyclobutylmethyl | H | O | $CH_2$—c-Pr | $OCH_2CF_3$ | 4-ethyl phenyl |
| 1226 | $(CH_2)_2$ | | O | $CH_2$—c-Pr | $OCH_2CF_3$ | 4-ethyl phenyl |
| 1227 | $(CH_2)_3$ | | O | $CH_2$—c-Pr | $OCH_2CF_3$ | 4-ethyl phenyl |
| 1228 | $(CH_2)_4$ | | O | $CH_2$—c-Pr | $OCH_2CF_3$ | 4-ethyl phenyl |
| 1229 | $(CH_2)_5$ | | O | $CH_2$—c-Pr | $OCH_2CF_3$ | 4-ethyl phenyl |
| 1230 | 5,5-spiro[2.3]hexane | | O | $CH_2$—c-Pr | $OCH_2CF_3$ | 4-ethyl phenyl |
| 1231 | Cyclopentyl | H | O | $CH_2$—c-Pr | $OCH_2CF_3$ | 4-ethyl phenyl |
| 1232 | $CH_2CH_3$ | H | O | $CH_2$—c-Pr | $OCH_2CF_3$ | 4-isopropyl phenyl |
| 1233 | $CH_2CF_3$ | H | O | $CH_2$—c-Pr | $OCH_2CF_3$ | 4-isopropyl phenyl |
| 1234 | $CH_2CH_2CH_3$ | H | O | $CH_2$—c-Pr | $OCH_2CF_3$ | 4-isopropyl phenyl |
| 1235 | $CH_2CH(CH_3)_2$ | H | O | $CH_2$—c-Pr | $OCH_2CF_3$ | 4-isopropyl phenyl |
| 1236 | cyclopropylmethyl | H | O | $CH_2$—c-Pr | $OCH_2CF_3$ | 4-isopropyl phenyl |
| 1237 | cyclobutylmethyl | H | O | $CH_2$—c-Pr | $OCH_2CF_3$ | 4-isopropyl phenyl |
| 1238 | $(CH_2)_2$ | | O | $CH_2$—c-Pr | $OCH_2CF_3$ | 4-isopropyl phenyl |
| 1239 | $(CH_2)_3$ | | O | $CH_2$—c-Pr | $OCH_2CF_3$ | 4-isopropyl phenyl |
| 1240 | $(CH_2)_4$ | | O | $CH_2$—c-Pr | $OCH_2CF_3$ | 4-isopropyl phenyl |
| 1241 | $(CH_2)_5$ | | O | $CH_2$—c-Pr | $OCH_2CF_3$ | 4-isopropyl phenyl |
| 1242 | 5,5-spiro[2.3]hexane | | O | $CH_2$—c-Pr | $OCH_2CF_3$ | 4-isopropyl phenyl |
| 1243 | Cyclopentyl | H | O | $CH_2$—c-Pr | $OCH_2CF_3$ | 4-isopropyl phenyl |
| 1244 | $CH_2CH_3$ | H | O | $CH_2$—c-Pr | $OCH_2CF_3$ | 4-thiomethylphenyl |
| 1245 | $CH_2CF_3$ | H | O | $CH_2$—c-Pr | $OCH_2CF_3$ | 4-thiomethylphenyl |
| 1246 | $CH_2CH_2CH_3$ | H | O | $CH_2$—c-Pr | $OCH_2CF_3$ | 4-thiomethylphenyl |
| 1247 | $CH_2CH(CH_3)_2$ | H | O | $CH_2$—c-Pr | $OCH_2CF_3$ | 4-thiomethylphenyl |
| 1248 | cyclopropylmethyl | H | O | $CH_2$—c-Pr | $OCH_2CF_3$ | 4-thiomethylphenyl |
| 1249 | cyclobutylmethyl | H | O | $CH_2$—c-Pr | $OCH_2CF_3$ | 4-thiomethylphenyl |
| 1250 | $(CH_2)_2$ | | O | $CH_2$—c-Pr | $OCH_2CF_3$ | 4-thiomethylphenyl |

TABLE 3-continued

Compounds of Formula III

Formula III

| Ex | R1 | R2 | Y | R4 | R5 | Z |
|---|---|---|---|---|---|---|
| 1251 | (CH$_2$)$_3$ | | O | CH$_2$—c-Pr | OCH$_2$CF$_3$ | 4-thiomethylphenyl |
| 1252 | (CH$_2$)$_4$ | | O | CH$_2$—c-Pr | OCH$_2$CF$_3$ | 4-thiomethylphenyl |
| 1253 | (CH$_2$)$_5$ | | O | CH$_2$—c-Pr | OCH$_2$CF$_3$ | 4-thiomethylphenyl |
| 1254 | 5,5-spiro[2.3]hexane | | O | CH$_2$—c-Pr | OCH$_2$CF$_3$ | 4-thiomethylphenyl |
| 1255 | Cyclopentyl | H | O | CH$_2$—c-Pr | OCH$_2$CF$_3$ | 4-thiomethylphenyl |
| 1256 | CH$_2$CH$_3$ | H | O | CH$_2$—c-Pr | OCH$_2$CF$_3$ | 4-trifluoromethoxyphenyl |
| 1257 | CH$_2$CF$_3$ | H | O | CH$_2$—c-Pr | OCH$_2$CF$_3$ | 4-trifluoromethoxyphenyl |
| 1258 | CH$_2$CH$_2$CH$_3$ | H | O | CH$_2$—c-Pr | OCH$_2$CF$_3$ | 4-trifluoromethoxyphenyl |
| 1259 | CH$_2$CH(CH$_3$)$_2$ | H | O | CH$_2$—c-Pr | OCH$_2$CF$_3$ | 4-trifluoromethoxyphenyl |
| 1260 | cyclopropylmethyl | H | O | CH$_2$—c-Pr | OCH$_2$CF$_3$ | 4-trifluoromethoxyphenyl |
| 1261 | cyclobutylmethyl | H | O | CH$_2$—c-Pr | OCH$_2$CF$_3$ | 4-trifluoromethoxyphenyl |
| 1262 | (CH$_2$)$_2$ | | O | CH$_2$—c-Pr | OCH$_2$CF$_3$ | 4-trifluoromethoxyphenyl |
| 1263 | (CH$_2$)$_3$ | | O | CH$_2$—c-Pr | OCH$_2$CF$_3$ | 4-trifluoromethoxyphenyl |
| 1264 | (CH$_2$)$_4$ | | O | CH$_2$—c-Pr | OCH$_2$CF$_3$ | 4-trifluoromethoxyphenyl |
| 1265 | (CH$_2$)$_5$ | | O | CH$_2$—c-Pr | OCH$_2$CF$_3$ | 4-trifluoromethoxyphenyl |
| 1266 | 5,5-spiro[2.3]hexane | | O | CH$_2$—c-Pr | OCH$_2$CF$_3$ | 4-trifluoromethoxyphenyl |
| 1267 | Cyclopentyl | H | O | CH$_2$—c-Pr | OCH$_2$CF$_3$ | 4-trifluoromethoxyphenyl |

TABLE 4

Compounds of Formula III

Formula III

| Ex | R1 | R2 | Y | R4 | R5 | Z |
|---|---|---|---|---|---|---|
| 1268 | cyclobutylmethyl | H | O | CH$_2$CF$_3$ | Cl | 4-trifluoromethylphenyl |
| 1269 | (CH$_2$)$_3$ | | O | CH$_2$CF$_3$ | Cl | 4-trifluoromethylphenyl |
| 1270 | (CH$_2$)$_5$ | | O | CH$_2$CF$_3$ | Cl | 4-trifluoromethylphenyl |
| 1271 | 5,5-spiro[2.3]hexane | | O | CH$_2$CF$_3$ | Cl | 4-trifluoromethylphenyl |
| 1272 | Cyclopentyl | H | O | CH$_2$CF$_3$ | Cl | 4-trifluoromethylphenyl |
| 1273 | CH$_2$CH$_3$ | H | O | CH$_2$CF$_3$ | Cl | 4-tolyl |
| 1274 | CH$_2$CF$_3$ | H | O | CH$_2$CF$_3$ | Cl | 4-tolyl |
| 1275 | CH$_2$CH$_2$CH$_3$ | H | O | CH$_2$CF$_3$ | Cl | 4-tolyl |
| 1276 | CH$_2$CH(CH$_3$)$_2$ | H | O | CH$_2$CF$_3$ | Cl | 4-tolyl |
| 1277 | cyclopropylmethyl | H | O | CH$_2$CF$_3$ | Cl | 4-tolyl |
| 1278 | cyclobutylmethyl | H | O | CH$_2$CF$_3$ | Cl | 4-tolyl |
| 1279 | (CH$_2$)$_2$ | | O | CH$_2$CF$_3$ | Cl | 4-tolyl |
| 1280 | (CH$_2$)$_3$ | | O | CH$_2$CF$_3$ | Cl | 4-tolyl |
| 1281 | (CH2)$_4$ | | O | CH$_2$CF$_3$ | Cl | 4-tolyl |
| 1282 | (CH$_2$)$_5$ | | O | CH$_2$CF$_3$ | Cl | 4-tolyl |
| 1283 | 5,5-spiro[2.3]hexane | | O | CH$_2$CF$_3$ | Cl | 4-tolyl |
| 1284 | Cyclopentyl | H | O | CH$_2$CF$_3$ | Cl | 4-tolyl |
| 1285 | CH$_2$CH$_3$ | H | O | CH$_2$CF$_3$ | Cl | 4-ethyl phenyl |
| 1286 | CH$_2$CF$_3$ | H | O | CH$_2$CF$_3$ | Cl | 4-ethyl phenyl |
| 1287 | CH$_2$CH$_2$CH$_3$ | H | O | CH$_2$CF$_3$ | Cl | 4-ethyl phenyl |
| 1288 | CH$_2$CH(CH$_3$)$_2$ | H | O | CH$_2$CF$_3$ | Cl | 4-ethyl phenyl |
| 1289 | cyclopropylmethyl | H | O | CH$_2$CF$_3$ | Cl | 4-ethyl phenyl |

TABLE 4-continued

Compounds of Formula III

Formula III

| Ex | R1 | R2 | Y | R4 | R5 | Z |
|---|---|---|---|---|---|---|
| 1290 | cyclobutylmethyl | H | O | CH$_2$CF$_3$ | Cl | 4-ethyl phenyl |
| 1291 | (CH$_2$)$_2$ | | O | CH$_2$CF$_3$ | Cl | 4-ethyl phenyl |
| 1292 | (CH$_2$)$_3$ | | O | CH$_2$CF$_3$ | Cl | 4-ethyl phenyl |
| 1293 | (CH2)$_4$ | | O | CH$_2$CF$_3$ | Cl | 4-ethyl phenyl |
| 1294 | (CH$_2$)$_5$ | | O | CH$_2$CF$_3$ | Cl | 4-ethyl phenyl |
| 1295 | 5,5-spiro[2.3]hexane | | O | CH$_2$CF$_3$ | Cl | 4-ethyl phenyl |
| 1296 | Cyclopentyl | H | O | CH$_2$CF$_3$ | Cl | 4-ethyl phenyl |
| 1297 | CH$_2$CH$_3$ | H | O | CH$_2$CF$_3$ | Cl | 4-isopropyl phenyl |
| 1298 | CH$_2$CF$_3$ | H | O | CH$_2$CF$_3$ | Cl | 4-isopropyl phenyl |
| 1299 | CH$_2$CH$_2$CH$_3$ | H | O | CH$_2$CF$_3$ | Cl | 4-isopropyl phenyl |
| 1300 | CH$_2$CH(CH$_3$)$_2$ | H | O | CH$_2$CF$_3$ | Cl | 4-isopropyl phenyl |
| 1301 | cyclopropylmethyl | H | O | CH$_2$CF$_3$ | Cl | 4-isopropyl phenyl |
| 1302 | cyclobutylmethyl | H | O | CH$_2$CF$_3$ | Cl | 4-isopropyl phenyl |
| 1303 | (CH$_2$)$_2$ | | O | CH$_2$CF$_3$ | Cl | 4-isopropyl phenyl |
| 1304 | (CH$_2$)$_3$ | | O | CH$_2$CF$_3$ | Cl | 4-isopropyl phenyl |
| 1305 | (CH$_2$)$_4$ | | O | CH$_2$CF$_3$ | Cl | 4-isopropyl phenyl |
| 1306 | (CH$_2$)$_5$ | | O | CH$_2$CF$_3$ | Cl | 4-isopropyl phenyl |
| 1307 | 5,5-spiro[2.3]hexane | | O | CH$_2$CF$_3$ | Cl | 4-isopropyl phenyl |
| 1308 | Cyclopentyl | H | O | CH$_2$CF$_3$ | Cl | 4-isopropyl phenyl |
| 1309 | CH$_2$CH$_3$ | H | O | CH$_2$CF$_3$ | Cl | 4-thiomethylphenyl |
| 1310 | CH$_2$CF$_3$ | H | O | CH$_2$CF$_3$ | Cl | 4-thiomethylphenyl |
| 1311 | CH$_2$CH$_2$CH$_3$ | H | O | CH$_2$CF$_3$ | Cl | 4-thiomethylphenyl |
| 1312 | CH$_2$CH(CH$_3$)$_2$ | H | O | CH$_2$CF$_3$ | Cl | 4-thiomethylphenyl |
| 1313 | cyclopropylmethyl | H | O | CH$_2$CF$_3$ | Cl | 4-thiomethylphenyl |
| 1314 | cyclobutylmethyl | H | O | CH$_2$CF$_3$ | Cl | 4-thiomethylphenyl |
| 1315 | (CH$_2$)$_2$ | | O | CH$_2$CF$_3$ | Cl | 4-thiomethylphenyl |
| 1316 | (CH$_2$)$_3$ | | O | CH$_2$CF$_3$ | Cl | 4-thiomethylphenyl |
| 1317 | (CH$_2$)$_4$ | | O | CH$_2$CF$_3$ | Cl | 4-thiomethylphenyl |
| 1318 | (CH$_2$)$_5$ | | O | CH$_2$CF$_3$ | Cl | 4-thiomethylphenyl |
| 1319 | 5,5-spiro[2.3]hexane | | O | CH$_2$CF$_3$ | Cl | 4-thiomethylphenyl |
| 1320 | Cyclopentyl | H | O | CH$_2$CF$_3$ | Cl | 4-thiomethylphenyl |
| 1321 | CH$_2$CH$_3$ | H | O | CH$_2$CF$_3$ | Cl | 4-trifluoromethoxyphenyl |
| 1322 | CH$_2$CF$_3$ | H | O | CH$_2$CF$_3$ | Cl | 4-trifluoromethoxyphenyl |
| 1323 | CH$_2$CH$_2$CH$_3$ | H | O | CH$_2$CF$_3$ | Cl | 4-trifluoromethoxyphenyl |
| 1324 | CH$_2$CH(CH$_3$)$_2$ | H | O | CH$_2$CF$_3$ | Cl | 4-trifluoromethoxyphenyl |
| 1325 | cyclopropylmethyl | H | O | CH$_2$CF$_3$ | Cl | 4-trifluoromethoxyphenyl |
| 1326 | cyclobutylmethyl | H | O | CH$_2$CF$_3$ | Cl | 4-trifluoromethoxyphenyl |
| 1327 | (CH$_2$)$_2$ | | O | CH$_2$CF$_3$ | Cl | 4-trifluoromethoxyphenyl |
| 1328 | (CH$_2$)$_3$ | | O | CH$_2$CF$_3$ | Cl | 4-trifluoromethoxyphenyl |
| 1329 | (CH$_2$)$_4$ | | O | CH$_2$CF$_3$ | Cl | 4-trifluoromethoxyphenyl |
| 1330 | (CH$_2$)$_5$ | | O | CH$_2$CF$_3$ | Cl | 4-trifluoromethoxyphenyl |
| 1331 | 5,5-spiro[2.3]hexane | | O | CH$_2$CF$_3$ | Cl | 4-trifluoromethoxyphenyl |
| 1332 | Cyclopentyl | H | O | CH$_2$CF$_3$ | Cl | 4-trifluoromethoxyphenyl |
| 1333 | cyclobutylmethyl | H | O | CH$_2$-c-Pr | Cl | 4-trifluoromethylphenyl |
| 1334 | (CH$_2$)$_3$ | | O | CH$_2$-c-Pr | Cl | 4-trifluoromethylphenyl |
| 1335 | (CH$_2$)$_5$ | | O | CH$_2$-c-Pr | Cl | 4-trifluoromethylphenyl |
| 1336 | 5,5-spiro[2.3]hexane | | O | CH$_2$-c-Pr | Cl | 4-trifluoromethylphenyl |
| 1337 | Cyclopentyl | H | O | CH$_2$-c-Pr | Cl | 4-trifluoromethylphenyl |
| 1338 | CH$_2$CH$_3$ | H | O | CH$_2$-c-Pr | Cl | 4-tolyl |
| 1339 | CH$_2$CF$_3$ | H | O | CH$_2$-c-Pr | Cl | 4-tolyl |
| 1340 | CH$_2$CH$_2$CH$_3$ | H | O | CH$_2$-c-Pr | Cl | 4-tolyl |
| 1341 | CH$_2$CH(CH$_3$)$_2$ | H | O | CH$_2$-c-Pr | Cl | 4-tolyl |
| 1342 | cyclopropylmethyl | H | O | CH$_2$-c-Pr | Cl | 4-tolyl |
| 1343 | cyclobutylmethyl | H | O | CH$_2$-c-Pr | Cl | 4-tolyl |
| 1344 | (CH$_2$)$_2$ | | O | CH$_2$-c-Pr | Cl | 4-tolyl |
| 1345 | (CH$_2$)$_3$ | | O | CH$_2$-c-Pr | Cl | 4-tolyl |
| 1346 | (CH$_2$)$_4$ | | O | CH$_2$-c-Pr | Cl | 4-tolyl |
| 1347 | (CH$_2$)$_5$ | | O | CH$_2$-c-Pr | Cl | 4-tolyl |
| 1348 | 5,5-spiro[2.3]hexane | | O | CH$_2$-c-Pr | Cl | 4-tolyl |
| 1349 | Cyclopentyl | H | O | CH$_2$-c-Pr | Cl | 4-tolyl |
| 1350 | CH$_2$CH$_3$ | H | O | CH$_2$-c-Pr | Cl | 4-ethyl phenyl |
| 1351 | CH$_2$CF$_3$ | H | O | CH$_2$-c-Pr | Cl | 4-ethyl phenyl |

TABLE 4-continued

Compounds of Formula III

Formula III

| Ex | R1 | R2 | Y | R4 | R5 | Z |
|---|---|---|---|---|---|---|
| 1352 | $CH_2CH_2CH_3$ | H | O | $CH_2$-c-Pr | Cl | 4-ethyl phenyl |
| 1353 | $CH_2CH(CH_3)_2$ | H | O | $CH_2$-c-Pr | Cl | 4-ethyl phenyl |
| 1354 | cyclopropylmethyl | H | O | $CH_2$-c-Pr | Cl | 4-ethyl phenyl |
| 1355 | cyclobutylmethyl | H | O | $CH_2$-c-Pr | Cl | 4-ethyl phenyl |
| 1356 | $(CH_2)_2$ | | O | $CH_2$-c-Pr | Cl | 4-ethyl phenyl |
| 1357 | $(CH_2)_3$ | | O | $CH_2$-c-Pr | Cl | 4-ethyl phenyl |
| 1358 | $(CH_2)_4$ | | O | $CH_2$-c-Pr | Cl | 4-ethyl phenyl |
| 1359 | $(CH_2)_5$ | | O | $CH_2$-c-Pr | Cl | 4-ethyl phenyl |
| 1360 | 5,5-spiro[2.3]hexane | | O | $CH_2$-c-Pr | Cl | 4-ethyl phenyl |
| 1361 | Cyclopentyl | H | O | $CH_2$-c-Pr | Cl | 4-ethyl phenyl |
| 1362 | $CH_2CH_3$ | H | O | $CH_2$-c-Pr | Cl | 4-isopropyl phenyl |
| 1363 | $CH_2CF_3$ | H | O | $CH_2$-c-Pr | Cl | 4-isopropyl phenyl |
| 1364 | $CH_2CH_2CH_3$ | H | O | $CH_2$-c-Pr | Cl | 4-isopropyl phenyl |
| 1365 | $CH_2CH(CH_3)_2$ | H | O | $CH_2$-c-Pr | Cl | 4-isopropyl phenyl |
| 1366 | cyclopropylmethyl | H | O | $CH_2$-c-Pr | Cl | 4-isopropyl phenyl |
| 1367 | cyclobutylmethyl | H | O | $CH_2$-c-Pr | Cl | 4-isopropyl phenyl |
| 1368 | $(CH_2)_2$ | | O | $CH_2$-c-Pr | Cl | 4-isopropyl phenyl |
| 1369 | $(CH_2)_3$ | | O | $CH_2$-c-Pr | Cl | 4-isopropyl phenyl |
| 1370 | $(CH_2)_4$ | | O | $CH_2$-c-Pr | Cl | 4-isopropyl phenyl |
| 1371 | $(CH_2)_5$ | | O | $CH_2$-c-Pr | Cl | 4-isopropyl phenyl |
| 1372 | 5,5-spiro[2.3]hexane | | O | $CH_2$-c-Pr | Cl | 4-isopropyl phenyl |
| 1373 | Cyclopentyl | H | O | $CH_2$-c-Pr | Cl | 4-isopropyl phenyl |
| 1374 | $CH_2CH_3$ | H | O | $CH_2$-c-Pr | Cl | 4-thiomethylphenyl |
| 1375 | $CH_2CF_3$ | H | O | $CH_2$-c-Pr | Cl | 4-thiomethylphenyl |
| 1376 | $CH_2CH_2CH_3$ | H | O | $CH_2$-c-Pr | Cl | 4-thiomethylphenyl |
| 1377 | $CH_2CH(CH_3)_2$ | H | O | $CH_2$-c-Pr | Cl | 4-thiomethylphenyl |
| 1378 | cyclopropylmethyl | H | O | $CH_2$-c-Pr | Cl | 4-thiomethylphenyl |
| 1379 | cyclobutylmethyl | H | O | $CH_2$-c-Pr | Cl | 4-thiomethylphenyl |
| 1380 | $(CH_2)_2$ | | O | $CH_2$-c-Pr | Cl | 4-thiomethylphenyl |
| 1381 | $(CH_2)_3$ | | O | $CH_2$-c-Pr | Cl | 4-thiomethylphenyl |
| 1382 | $(CH_2)_4$ | | O | $CH_2$-c-Pr | Cl | 4-thiomethylphenyl |
| 1383 | $(CH_2)_5$ | | O | $CH_2$-c-Pr | Cl | 4-thiomethylphenyl |
| 1384 | 5,5-spiro[2.3]hexane | | O | $CH_2$-c-Pr | Cl | 4-thiomethylphenyl |
| 1385 | Cyclopentyl | H | O | $CH_2$-c-Pr | Cl | 4-thiomethylphenyl |
| 1386 | $CH_2CH_3$ | H | O | $CH_2$-c-Pr | Cl | 4-trifluoromethoxyphenyl |
| 1387 | $CH_2CF_3$ | H | O | $CH_2$-c-Pr | Cl | 4-trifluoromethoxyphenyl |
| 1388 | $CH_2CH_2CH_3$ | H | O | $CH_2$-c-Pr | Cl | 4-trifluoromethoxyphenyl |
| 1389 | $CH_2CH(CH_3)_2$ | H | O | $CH_2$-c-Pr | Cl | 4-trifluoromethoxyphenyl |
| 1390 | cyclopropylmethyl | H | O | $CH_2$-c-Pr | Cl | 4-trifluoromethoxyphenyl |
| 1391 | cyclobutylmethyl | H | O | $CH_2$-c-Pr | Cl | 4-trifluoromethoxyphenyl |
| 1392 | $(CH_2)_2$ | | O | $CH_2$-c-Pr | Cl | 4-trifluoromethoxyphenyl |
| 1393 | $(CH_2)_3$ | | O | $CH_2$-c-Pr | Cl | 4-trifluoromethoxyphenyl |
| 1394 | $(CH_2)_4$ | | O | $CH_2$-c-Pr | Cl | 4-trifluoromethoxyphenyl |
| 1395 | $(CH_2)_5$ | | O | $CH_2$-c-Pr | Cl | 4-trifluoromethoxyphenyl |
| 1396 | 5,5-spiro[2.3]hexane | | O | $CH_2$-c-Pr | Cl | 4-trifluoromethoxyphenyl |
| 1397 | Cyclopentyl | H | O | $CH_2$-c-Pr | Cl | 4-trifluoromethoxyphenyl |
| 1398 | $CH_2CH_3$ | H | O | $CH_2CF_3$ | $OCH_2CF_3$ | 4-trifluoromethylphenyl |
| 1399 | $CH_2CF_3$ | H | O | $CH_2CF_3$ | $OCH_2CF_3$ | 4-trifluoromethylphenyl |
| 1400 | $CH_2CH_2CH_3$ | H | O | $CH_2CF_3$ | $OCH_2CF_3$ | 4-trifluoromethylphenyl |
| 1401 | $CH_2CH(CH_3)_2$ | H | O | $CH_2CF_3$ | $OCH_2CF_3$ | 4-trifluoromethylphenyl |
| 1402 | cyclopropylmethyl | H | O | $CH_2CF_3$ | $OCH_2CF_3$ | 4-trifluoromethylphenyl |
| 1403 | cyclobutylmethyl | H | O | $CH_2CF_3$ | $OCH_2CF_3$ | 4-trifluoromethylphenyl |
| 1404 | $(CH_2)_2$ | | O | $CH_2CF_3$ | $OCH_2CF_3$ | 4-trifluoromethylphenyl |
| 1405 | $(CH_2)_3$ | | O | $CH_2CF_3$ | $OCH_2CF_3$ | 4-trifluoromethylphenyl |
| 1406 | $(CH_2)_4$ | | O | $CH_2CF_3$ | $OCH_2CF_3$ | 4-trifluoromethylphenyl |
| 1407 | $(CH_2)_5$ | | O | $CH_2CF_3$ | $OCH_2CF_3$ | 4-trifluoromethylphenyl |
| 1408 | 5,5-spiro[2.3]hexane | | O | $CH_2CF_3$ | $OCH_2CF_3$ | 4-trifluoromethylphenyl |
| 1409 | Cyclopentyl | H | O | $CH_2CF_3$ | $OCH_2CF_3$ | 4-trifluoromethylphenyl |
| 1410 | $CH_2CH_3$ | H | O | $CH_2CF_3$ | $OCH_2CF_3$ | 4-tolyl |
| 1411 | $CH_2CF_3$ | H | O | $CH_2CF_3$ | $OCH_2CF_3$ | 4-tolyl |
| 1412 | $CH_2CH_2CH_3$ | H | O | $CH_2CF_3$ | $OCH_2CF_3$ | 4-tolyl |
| 1413 | $CH_2CH(CH_3)_2$ | H | O | $CH_2CF_3$ | $OCH_2CF_3$ | 4-tolyl |

TABLE 4-continued

Compounds of Formula III

Formula III

| Ex | R1 | R2 | Y | R4 | R5 | Z |
|---|---|---|---|---|---|---|
| 1414 | cyclopropylmethyl | H | O | $CH_2CF_3$ | $OCH_2CF_3$ | 4-tolyl |
| 1415 | cyclobutylmethyl | H | O | $CH_2CF_3$ | $OCH_2CF_3$ | 4-tolyl |
| 1416 | $(CH_2)_2$ | | O | $CH_2CF_3$ | $OCH_2CF_3$ | 4-tolyl |
| 1417 | $(CH_2)_3$ | | O | $CH_2CF_3$ | $OCH_2CF_3$ | 4-tolyl |
| 1418 | $(CH_2)_4$ | | O | $CH_2CF_3$ | $OCH_2CF_3$ | 4-tolyl |
| 1419 | $(CH_2)_5$ | | O | $CH_2CF_3$ | $OCH_2CF_3$ | 4-tolyl |
| 1420 | 5,5-spiro[2.3]hexane | | O | $CH_2CF_3$ | $OCH_2CF_3$ | 4-tolyl |
| 1421 | Cyclopentyl | H | O | $CH_2CF_3$ | $OCH_2CF_3$ | 4-tolyl |
| 1422 | $CH_2CH_3$ | H | O | $CH_2CF_3$ | $OCH_2CF_3$ | 4-ethyl phenyl |
| 1423 | $CH_2CF_3$ | H | O | $CH_2CF_3$ | $OCH_2CF_3$ | 4-ethyl phenyl |
| 1424 | $CH_2CH_2CH_3$ | H | O | $CH_2CF_3$ | $OCH_2CF_3$ | 4-ethyl phenyl |
| 1425 | $CH_2CH(CH_3)_2$ | H | O | $CH_2CF_3$ | $OCH_2CF_3$ | 4-ethyl phenyl |
| 1426 | cyclopropylmethyl | H | O | $CH_2CF_3$ | $OCH_2CF_3$ | 4-ethyl phenyl |
| 1427 | cyclobutylmethyl | H | O | $CH_2CF_3$ | $OCH_2CF_3$ | 4-ethyl phenyl |
| 1428 | $(CH_2)_2$ | | O | $CH_2CF_3$ | $OCH_2CF_3$ | 4-ethyl phenyl |
| 1429 | $(CH_2)_3$ | | O | $CH_2CF_3$ | $OCH_2CF_3$ | 4-ethyl phenyl |
| 1430 | $(CH_2)_4$ | | O | $CH_2CF_3$ | $OCH_2CF_3$ | 4-ethyl phenyl |
| 1431 | $(CH_2)_5$ | | O | $CH_2CF_3$ | $OCH_2CF_3$ | 4-ethyl phenyl |
| 1432 | 5,5-spiro[2.3]hexane | | O | $CH_2CF_3$ | $OCH_2CF_3$ | 4-ethyl phenyl |
| 1433 | Cyclopentyl | H | O | $CH_2CF_3$ | $OCH_2CF_3$ | 4-ethyl phenyl |
| 1434 | $CH_2CH_3$ | H | O | $CH_2CF_3$ | $OCH_2CF_3$ | 4-isopropyl phenyl |
| 1435 | $CH_2CF_3$ | H | O | $CH_2CF_3$ | $OCH_2CF_3$ | 4-isopropyl phenyl |
| 1436 | $CH_2CH_2CH_3$ | H | O | $CH_2CF_3$ | $OCH_2CF_3$ | 4-isopropyl phenyl |
| 1437 | $CH_2CH(CH_3)_2$ | H | O | $CH_2CF_3$ | $OCH_2CF_3$ | 4-isopropyl phenyl |
| 1438 | cyclopropylmethyl | H | O | $CH_2CF_3$ | $OCH_2CF_3$ | 4-isopropyl phenyl |
| 1439 | cyclobutylmethyl | H | O | $CH_2CF_3$ | $OCH_2CF_3$ | 4-isopropyl phenyl |
| 1440 | $(CH_2)_2$ | | O | $CH_2CF_3$ | $OCH_2CF_3$ | 4-isopropyl phenyl |
| 1441 | $(CH_2)_3$ | | O | $CH_2CF_3$ | $OCH_2CF_3$ | 4-isopropyl phenyl |
| 1442 | $(CH_2)_4$ | | O | $CH_2CF_3$ | $OCH_2CF_3$ | 4-isopropyl phenyl |
| 1443 | $(CH_2)_5$ | | O | $CH_2CF_3$ | $OCH_2CF_3$ | 4-isopropyl phenyl |
| 1444 | 5,5-spiro[2.3]hexane | | O | $CH_2CF_3$ | $OCH_2CF_3$ | 4-isopropyl phenyl |
| 1445 | Cyclopentyl | H | O | $CH_2CF_3$ | $OCH_2CF_3$ | 4-isopropyl phenyl |
| 1446 | $CH_2CH_3$ | H | O | $CH_2CF_3$ | $OCH_2CF_3$ | 4-thiomethylphenyl |
| 1447 | $CH_2CF_3$ | H | O | $CH_2CF_3$ | $OCH_2CF_3$ | 4-thiomethylphenyl |
| 1448 | $CH_2CH_2CH_3$ | H | O | $CH_2CF_3$ | $OCH_2CF_3$ | 4-thiomethylphenyl |
| 1449 | $CH_2CH(CH_3)_2$ | H | O | $CH_2CF_3$ | $OCH_2CF_3$ | 4-thiomethylphenyl |
| 1450 | cyclopropylmethyl | H | O | $CH_2CF_3$ | $OCH_2CF_3$ | 4-thiomethylphenyl |
| 1451 | cyclobutylmethyl | H | O | $CH_2CF_3$ | $OCH_2CF_3$ | 4-thiomethylphenyl |
| 1452 | $(CH_2)_2$ | | O | $CH_2CF_3$ | $OCH_2CF_3$ | 4-thiomethylphenyl |
| 1453 | $(CH_2)_3$ | | O | $CH_2CF_3$ | $OCH_2CF_3$ | 4-thiomethylphenyl |
| 1454 | $(CH_2)_4$ | | O | $CH_2CF_3$ | $OCH_2CF_3$ | 4-thiomethylphenyl |
| 1455 | $(CH_2)_5$ | | O | $CH_2CF_3$ | $OCH_2CF_3$ | 4-thiomethylphenyl |
| 1456 | 5,5-spiro[2.3]hexane | | O | $CH_2CF_3$ | $OCH_2CF_3$ | 4-thiomethylphenyl |
| 1457 | Cyclopentyl | H | O | $CH_2CF_3$ | $OCH_2CF_3$ | 4-thiomethylphenyl |
| 1458 | $CH_2CH_3$ | H | O | $CH_2CF_3$ | $OCH_2CF_3$ | 4-trifluoromethoxyphenyl |
| 1459 | $CH_2CF_3$ | H | O | $CH_2CF_3$ | $OCH_2CF_3$ | 4-trifluoromethoxyphenyl |
| 1460 | $CH_2CH_2CH_3$ | H | O | $CH_2CF_3$ | $OCH_2CF_3$ | 4-trifluoromethoxyphenyl |
| 1461 | $CH_2CH(CH_3)_2$ | H | O | $CH_2CF_3$ | $OCH_2CF_3$ | 4-trifluoromethoxyphenyl |
| 1462 | cyclopropylmethyl | H | O | $CH_2CF_3$ | $OCH_2CF_3$ | 4-trifluoromethoxyphenyl |
| 1463 | cyclobutylmethyl | H | O | $CH_2CF_3$ | $OCH_2CF_3$ | 4-trifluoromethoxyphenyl |
| 1464 | $(CH_2)_2$ | | O | $CH_2CF_3$ | $OCH_2CF_3$ | 4-trifluoromethoxyphenyl |
| 1465 | $(CH_2)_3$ | | O | $CH_2CF_3$ | $OCH_2CF_3$ | 4-trifluoromethoxyphenyl |
| 1466 | $(CH_2)_4$ | | O | $CH_2CF_3$ | $OCH_2CF_3$ | 4-trifluoromethoxyphenyl |
| 1467 | $(CH_2)_5$ | | O | $CH_2CF_3$ | $OCH_2CF_3$ | 4-trifluoromethoxyphenyl |
| 1468 | 5,5-spiro[2.3]hexane | | O | $CH_2CF_3$ | $OCH_2CF_3$ | 4-trifluoromethoxyphenyl |
| 1469 | Cyclopentyl | H | O | $CH_2CF_3$ | $OCH_2CF_3$ | 4-trifluoromethoxyphenyl |
| 1470 | $CH_2CH_3$ | H | O | $CH_2$-c-Pr | $OCH_2CF_3$ | 4-trifluoromethylphenyl |
| 1471 | $CH_2CF_3$ | H | O | $CH_2$-c-Pr | $OCH_2CF_3$ | 4-trifluoromethylphenyl |
| 1472 | $CH_2CH_2CH_3$ | H | O | $CH_2$-c-Pr | $OCH_2CF_3$ | 4-trifluoromethylphenyl |
| 1473 | $CH_2CH(CH_3)_2$ | H | O | $CH_2$-c-Pr | $OCH_2CF_3$ | 4-trifluoromethylphenyl |
| 1474 | cyclopropylmethyl | H | O | $CH_2$-c-Pr | $OCH_2CF_3$ | 4-trifluoromethylphenyl |
| 1475 | cyclobutylmethyl | H | O | $CH_2$-c-Pr | $OCH_2CF_3$ | 4-trifluoromethylphenyl |

TABLE 4-continued

Compounds of Formula III

Formula III

| Ex | R1 | R2 | Y | R4 | R5 | Z |
|---|---|---|---|---|---|---|
| 1476 | $(CH_2)_2$ | | O | $CH_2$-c-Pr | $OCH_2CF_3$ | 4-trifluoromethylphenyl |
| 1477 | $(CH_2)_3$ | | O | $CH_2$-c-Pr | $OCH_2CF_3$ | 4-trifluoromethylphenyl |
| 1478 | $(CH_2)_4$ | | O | $CH_2$-c-Pr | $OCH_2CF_3$ | 4-trifluoromethylphenyl |
| 1479 | $(CH_2)_5$ | | O | $CH_2$-c-Pr | $OCH_2CF_3$ | 4-trifluoromethylphenyl |
| 1480 | 5,5-spiro[2.3]hexane | | O | $CH_2$-c-Pr | $OCH_2CF_3$ | 4-trifluoromethylphenyl |
| 1481 | Cyclopentyl | H | O | $CH_2$-c-Pr | $OCH_2CF_3$ | 4-trifluoromethylphenyl |
| 1482 | $CH_2CH_3$ | H | O | $CH_2$-c-Pr | $OCH_2CF_3$ | 4-tolyl |
| 1483 | $CH_2CF_3$ | H | O | $CH_2$-c-Pr | $OCH_2CF_3$ | 4-tolyl |
| 1484 | $CH_2CH_2CH_3$ | H | O | $CH_2$-c-Pr | $OCH_2CF_3$ | 4-tolyl |
| 1485 | $CH_2CH(CH_3)_2$ | H | O | $CH_2$-c-Pr | $OCH_2CF_3$ | 4-tolyl |
| 1486 | cyclopropylmethyl | H | O | $CH_2$-c-Pr | $OCH_2CF_3$ | 4-tolyl |
| 1487 | cyclobutylmethyl | H | O | $CH_2$-c-Pr | $OCH_2CF_3$ | 4-tolyl |
| 1488 | $(CH_2)_2$ | | O | $CH_2$-c-Pr | $OCH_2CF_3$ | 4-tolyl |
| 1489 | $(CH_2)_3$ | | O | $CH_2$-c-Pr | $OCH_2CF_3$ | 4-tolyl |
| 1490 | $(CH_2)_4$ | | O | $CH_2$-c-Pr | $OCH_2CF_3$ | 4-tolyl |
| 1491 | $(CH_2)_5$ | | O | $CH_2$-c-Pr | $OCH_2CF_3$ | 4-tolyl |
| 1492 | 5,5-spiro[2.3]hexane | | O | $CH_2$-c-Pr | $OCH_2CF_3$ | 4-tolyl |
| 1493 | Cyclopentyl | H | O | $CH_2$-c-Pr | $OCH_2CF_3$ | 4-tolyl |
| 1494 | $CH_2CH_3$ | H | O | $CH_2$-c-Pr | $OCH_2CF_3$ | 4-ethyl phenyl |
| 1495 | $CH_2CF_3$ | H | O | $CH_2$-c-Pr | $OCH_2CF_3$ | 4-ethyl phenyl |
| 1496 | $CH_2CH_2CH_3$ | H | O | $CH_2$-c-Pr | $OCH_2CF_3$ | 4-ethyl phenyl |
| 1497 | $CH_2CH(CH_3)_2$ | H | O | $CH_2$-c-Pr | $OCH_2CF_3$ | 4-ethyl phenyl |
| 1498 | cyclopropylmethyl | H | O | $CH_2$-c-Pr | $OCH_2CF_3$ | 4-ethyl phenyl |
| 1499 | cyclobutylmethyl | H | O | $CH_2$-c-Pr | $OCH_2CF_3$ | 4-ethyl phenyl |
| 1500 | $(CH_2)_2$ | | O | $CH_2$-c-Pr | $OCH_2CF_3$ | 4-ethyl phenyl |
| 1501 | $(CH_2)_3$ | | O | $CH_2$-c-Pr | $OCH_2CF_3$ | 4-ethyl phenyl |
| 1502 | $(CH_2)_4$ | | O | $CH_2$-c-Pr | $OCH_2CF_3$ | 4-ethyl phenyl |
| 1503 | $(CH_2)_5$ | | O | $CH_2$-c-Pr | $OCH_2CF_3$ | 4-ethyl phenyl |
| 1504 | 5,5-spiro[2.3]hexane | | O | $CH_2$-c-Pr | $OCH_2CF_3$ | 4-ethyl phenyl |
| 1505 | Cyclopentyl | H | O | $CH_2$-c-Pr | $OCH_2CF_3$ | 4-ethyl phenyl |
| 1506 | $CH_2CH_3$ | H | O | $CH_2$-c-Pr | $OCH_2CF_3$ | 4-isopropyl phenyl |
| 1507 | $CH_2CF_3$ | H | O | $CH_2$-c-Pr | $OCH_2CF_3$ | 4-isopropyl phenyl |
| 1508 | $CH_2CH_2CH_3$ | H | O | $CH_2$-c-Pr | $OCH_2CF_3$ | 4-isopropyl phenyl |
| 1509 | $CH_2CH(CH_3)_2$ | H | O | $CH_2$-c-Pr | $OCH_2CF_3$ | 4-isopropyl phenyl |
| 1510 | cyclopropylmethyl | H | O | $CH_2$-c-Pr | $OCH_2CF_3$ | 4-isopropyl phenyl |
| 1511 | cyclobutylmethyl | H | O | $CH_2$-c-Pr | $OCH_2CF_3$ | 4-isopropyl phenyl |
| 1512 | $(CH_2)_2$ | | O | $CH_2$-c-Pr | $OCH_2CF_3$ | 4-isopropyl phenyl |
| 1513 | $(CH_2)_3$ | | O | $CH_2$-c-Pr | $OCH_2CF_3$ | 4-isopropyl phenyl |
| 1514 | $(CH_2)_4$ | | O | $CH_2$-c-Pr | $OCH_2CF_3$ | 4-isopropyl phenyl |
| 1515 | $(CH_2)_5$ | | O | $CH_2$-c-Pr | $OCH_2CF_3$ | 4-isopropyl phenyl |
| 1516 | 5,5-spiro[2.3]hexane | | O | $CH_2$-c-Pr | $OCH_2CF_3$ | 4-isopropyl phenyl |
| 1517 | Cyclopentyl | H | O | $CH_2$-c-Pr | $OCH_2CF_3$ | 4-isopropyl phenyl |
| 1518 | $CH_2CH_3$ | H | O | $CH_2$-c-Pr | $OCH_2CF_3$ | 4-thiomethylphenyl |
| 1519 | $CH_2CF_3$ | H | O | $CH_2$-c-Pr | $OCH_2CF_3$ | 4-thiomethylphenyl |
| 1520 | $CH_2CH_2CH_3$ | H | O | $CH_2$-c-Pr | $OCH_2CF_3$ | 4-thiomethylphenyl |
| 1521 | $CH_2CH(CH_3)_2$ | H | O | $CH_2$-c-Pr | $OCH_2CF_3$ | 4-thiomethylphenyl |
| 1522 | cyclopropylmethyl | H | O | $CH_2$-c-Pr | $OCH_2CF_3$ | 4-thiomethylphenyl |
| 1523 | cyclobutylmethyl | H | O | $CH_2$-c-Pr | $OCH_2CF_3$ | 4-thiomethylphenyl |
| 1524 | $(CH_2)_2$ | | O | $CH_2$-c-Pr | $OCH_2CF_3$ | 4-thiomethylphenyl |
| 1525 | $(CH_2)_3$ | | O | $CH_2$-c-Pr | $OCH_2CF_3$ | 4-thiomethylphenyl |
| 1526 | $(CH_2)_4$ | | O | $CH_2$-c-Pr | $OCH_2CF_3$ | 4-thiomethylphenyl |
| 1527 | $(CH_2)_5$ | | O | $CH_2$-c-Pr | $OCH_2CF_3$ | 4-thiomethylphenyl |
| 1528 | 5,5-spiro[2.3]hexane | | O | $CH_2$-c-Pr | $OCH_2CF_3$ | 4-thiomethylphenyl |
| 1529 | Cyclopentyl | | O | $CH_2$-c-Pr | $OCH_2CF_3$ | 4-thiomethylphenyl |
| | $CH_2CH_3$ | H | O | $CH_2$-c-Pr | $OCH_2CF_3$ | 4-trifluoromethoxyphenyl |
| 1530 | $CH_2CF_3$ | H | O | $CH_2$-c-Pr | $OCH_2CF_3$ | 4-trifluoromethoxyphenyl |
| 1531 | $CH_2CH_2CH_3$ | H | O | $CH_2$-c-Pr | $OCH_2CF_3$ | 4-trifluoromethoxyphenyl |
| 1532 | $CH_2CH(CH_3)_2$ | H | O | $CH_2$-c-Pr | $OCH_2CF_3$ | 4-trifluoromethoxyphenyl |
| 1533 | cyclopropylmethyl | H | O | $CH_2$-c-Pr | $OCH_2CF_3$ | 4-trifluoromethoxyphenyl |
| 1534 | cyclobutylmethyl | H | O | $CH_2$-c-Pr | $OCH_2CF_3$ | 4-trifluoromethoxyphenyl |
| 1535 | $(CH_2)_2$ | | O | $CH_2$-c-Pr | $OCH_2CF_3$ | 4-trifluoromethoxyphenyl |
| 1536 | $(CH_2)_3$ | | O | $CH_2$-c-Pr | $OCH_2CF_3$ | 4-trifluoromethoxyphenyl |

TABLE 4-continued

Compounds of Formula III

Formula III

| Ex | R1 | R2 | Y | R4 | R5 | Z |
|---|---|---|---|---|---|---|
| 1537 | $(CH_2)_4$ | | O | $CH_2$-c-Pr | $OCH_2CF_3$ | 4-trifluoromethoxyphenyl |
| 1538 | $(CH_2)_5$ | | O | $CH_2$-c-Pr | $OCH_2CF_3$ | 4-trifluoromethoxyphenyl |
| 1539 | 5,5-spiro[2.3]hexane | | O | $CH_2$-c-Pr | $OCH_2CF_3$ | 4-trifluoromethoxyphenyl |
| 1540 | Cyclopentyl | H | O | $CH_2$-c-Pr | $OCH_2CF_3$ | 4-trifluoromethoxyphenyl |

TABLE 5

Compounds of Formula IV

Formula IV

| Ex | R1 | R2 | X | R3 | R5 | Z |
|---|---|---|---|---|---|---|
| 1541 | $CH_2CH_3$ | H | O | $CH_2CF_3$ | $CF_3$ | 4-trifluoromethylphenyl |
| 1542 | $CH_2CF_3$ | H | O | $CH_2CF_3$ | $CF_3$ | 4-trifluoromethylphenyl |
| 1543 | $CH_2CH_2CH_3$ | H | O | $CH_2CF_3$ | $CF_3$ | 4-trifluoromethylphenyl |
| 1544 | $CH_2CH(CH_3)_2$ | H | O | $CH_2CF_3$ | $CF_3$ | 4-trifluoromethylphenyl |
| 1545 | cyclopropylmethyl | H | O | $CH_2CF_3$ | $CF_3$ | 4-trifluoromethylphenyl |
| 1546 | cyclobutylmethyl | H | O | $CH_2CF_3$ | $CF_3$ | 4-trifluoromethylphenyl |
| 1547 | $(CH_2)_2$ | | O | $CH_2CF_3$ | $CF_3$ | 4-trifluoromethylphenyl |
| 1548 | $(CH_2)_3$ | | O | $CH_2CF_3$ | $CF_3$ | 4-trifluoromethylphenyl |
| 1549 | $(CH2)_4$ | | O | $CH_2CF_3$ | $CF_3$ | 4-trifluoromethylphenyl |
| 1550 | $(CH_2)_5$ | | O | $CH_2CF_3$ | $CF_3$ | 4-trifluoromethylphenyl |
| 1551 | 5,5-spiro[2.3]hexane | | O | $CH_2CF_3$ | $CF_3$ | 4-trifluoromethylphenyl |
| 1552 | Cyclopentyl | H | O | $CH_2CF_3$ | $CF_3$ | 4-trifluoromethylphenyl |
| 1553 | $CH_2CH_3$ | H | O | $CH_2CF_3$ | $CF_3$ | 4-tolyl |
| 1554 | $CH_2CF_3$ | H | O | $CH_2CF_3$ | $CF_3$ | 4-tolyl |
| 1555 | $CH_2CH_2CH_3$ | H | O | $CH_2CF_3$ | $CF_3$ | 4-tolyl |
| 1556 | $CH_2CH(CH_3)_2$ | H | O | $CH_2CF_3$ | $CF_3$ | 4-tolyl |
| 1557 | cyclopropylmethyl | H | O | $CH_2CF_3$ | $CF_3$ | 4-tolyl |
| 1558 | cyclobutylmethyl | H | O | $CH_2CF_3$ | $CF_3$ | 4-tolyl |
| 1559 | $(CH_2)_2$ | | O | $CH_2CF_3$ | $CF_3$ | 4-tolyl |
| 1560 | $(CH_2)_3$ | | O | $CH_2CF_3$ | $CF_3$ | 4-tolyl |
| 1561 | $(CH2)_4$ | | O | $CH_2CF_3$ | $CF_3$ | 4-tolyl |
| 1562 | $(CH_2)_5$ | | O | $CH_2CF_3$ | $CF_3$ | 4-tolyl |
| 1563 | 5,5-spiro[2.3]hexane | | O | $CH_2CF_3$ | $CF_3$ | 4-tolyl |
| 1564 | Cyclopentyl | H | O | $CH_2CF_3$ | $CF_3$ | 4-tolyl |
| 1565 | $CH_2CH_3$ | H | O | $CH_2CF_3$ | $CF_3$ | 4-ethyl phenyl |
| 1566 | $CH_2CF_3$ | H | O | $CH_2CF_3$ | $CF_3$ | 4-ethyl phenyl |
| 1567 | $CH_2CH_2CH_3$ | H | O | $CH_2CF_3$ | $CF_3$ | 4-ethyl phenyl |
| 1568 | $CH_2CH(CH_3)_2$ | H | O | $CH_2CF_3$ | $CF_3$ | 4-ethyl phenyl |
| 1569 | cyclopropylmethyl | H | O | $CH_2CF_3$ | $CF_3$ | 4-ethyl phenyl |
| 1570 | cyclobutylmethyl | H | O | $CH_2CF_3$ | $CF_3$ | 4-ethyl phenyl |
| 1571 | $(CH_2)_2$ | | O | $CH_2CF_3$ | $CF_3$ | 4-ethyl phenyl |
| 1572 | $(CH_2)_3$ | | O | $CH_2CF_3$ | $CF_3$ | 4-ethyl phenyl |
| 1573 | $(CH_2)_4$ | | O | $CH_2CF_3$ | $CF_3$ | 4-ethyl phenyl |
| 1574 | $(CH_2)_5$ | | O | $CH_2CF_3$ | $CF_3$ | 4-ethyl phenyl |
| 1575 | 5,5-spiro[2.3]hexane | | O | $CH_2CF_3$ | $CF_3$ | 4-ethyl phenyl |

TABLE 5-continued

Compounds of Formula IV

Formula IV $$\text{R}_1\text{-C(R}_2\text{)(CO}_2\text{H)-[phenyl with R}_5, Z, X\text{-R}_3\text{]}$$

| Ex | R1 | R2 | X | R3 | R5 | Z |
|---|---|---|---|---|---|---|
| 1576 | Cyclopentyl | H | O | CH₂CF₃ | CF₃ | 4-ethyl phenyl |
| 1577 | CH₂CH₃ | H | O | CH₂CF₃ | CF₃ | 4-isopropyl phenyl |
| 1578 | CH₂CF₃ | H | O | CH₂CF₃ | CF₃ | 4-isopropyl phenyl |
| 1579 | CH₂CH₂CH₃ | H | O | CH₂CF₃ | CF₃ | 4-isopropyl phenyl |
| 1580 | CH₂CH(CH₃)₂ | H | O | CH₂CF₃ | CF₃ | 4-isopropyl phenyl |
| 1581 | cyclopropylmethyl | H | O | CH₂CF₃ | CF₃ | 4-isopropyl phenyl |
| 1582 | cyclobutylmethyl | H | O | CH₂CF₃ | CF₃ | 4-isopropyl phenyl |
| 1583 | (CH₂)₂ | | O | CH₂CF₃ | CF₃ | 4-isopropyl phenyl |
| 1584 | (CH₂)₃ | | O | CH₂CF₃ | CF₃ | 4-isopropyl phenyl |
| 1585 | (CH2)₄ | | O | CH₂CF₃ | CF₃ | 4-isopropyl phenyl |
| 1586 | (CH₂)₅ | | O | CH₂CF₃ | CF₃ | 4-isopropyl phenyl |
| 1587 | 5,5-spiro[2.3]hexane | | O | CH₂CF₃ | CF₃ | 4-isopropyl phenyl |
| 1588 | Cyclopentyl | H | O | CH₂CF₃ | CF₃ | 4-isopropyl phenyl |
| 1589 | CH₂CH₃ | H | O | CH₂CF₃ | CF₃ | 4-thiomethylphenyl |
| 1590 | CH₂CF₃ | H | O | CH₂CF₃ | CF₃ | 4-thiomethylphenyl |
| 1591 | CH₂CH₂CH₃ | H | O | CH₂CF₃ | CF₃ | 4-thiomethylphenyl |
| 1592 | CH₂CH(CH₃)₂ | H | O | CH₂CF₃ | CF₃ | 4-thiomethylphenyl |
| 1593 | cyclopropylmethyl | H | O | CH₂CF₃ | CF₃ | 4-thiomethylphenyl |
| 1594 | cyclobutylmethyl | H | O | CH₂CF₃ | CF₃ | 4-thiomethylphenyl |
| 1595 | (CH₂)₂ | | O | CH₂CF₃ | CF₃ | 4-thiomethylphenyl |
| 1596 | (CH₂)₃ | | O | CH₂CF₃ | CF₃ | 4-thiomethylphenyl |
| 1597 | (CH2)₄ | | O | CH₂CF₃ | CF₃ | 4-thiomethylphenyl |
| 1598 | (CH₂)₅ | | O | CH₂CF₃ | CF₃ | 4-thiomethylphenyl |
| 1599 | 5,5-spiro[2.3]hexane | | O | CH₂CF₃ | CF₃ | 4-thiomethylphenyl |
| 1600 | Cyclopentyl | H | O | CH₂CF₃ | CF₃ | 4-thiomethylphenyl |
| 1601 | CH₂CH₃ | H | O | CH₂CF₃ | CF₃ | 4-trifluoromethoxyphenyl |
| 1602 | CH₂CF₃ | H | O | CH₂CF₃ | CF₃ | 4-trifluoromethoxyphenyl |
| 1603 | CH₂CH₂CH₃ | H | O | CH₂CF₃ | CF₃ | 4-trifluoromethoxyphenyl |
| 1604 | CH₂CH(CH₃)₂ | H | O | CH₂CF₃ | CF₃ | 4-trifluoromethoxyphenyl |
| 1605 | cyclopropylmethyl | H | O | CH₂CF₃ | CF₃ | 4-trifluoromethoxyphenyl |
| 1606 | cyclobutylmethyl | H | O | CH₂CF₃ | CF₃ | 4-trifluoromethoxyphenyl |
| 1607 | (CH₂)₂ | | O | CH₂CF₃ | CF₃ | 4-trifluoromethoxyphenyl |
| 1608 | (CH₂)₃ | | O | CH₂CF₃ | CF₃ | 4-trifluoromethoxyphenyl |
| 1609 | (CH2)₄ | | O | CH₂CF₃ | CF₃ | 4-trifluoromethoxyphenyl |
| 1610 | (CH₂)₅ | | O | CH₂CF₃ | CF₃ | 4-trifluoromethoxyphenyl |
| 1611 | 5,5-spiro[2.3]hexane | | O | CH₂CF₃ | CF₃ | 4-trifluoromethoxyphenyl |
| 1612 | Cyclopentyl | H | O | CH₂CF₃ | CF₃ | 4-trifluoromethoxyphenyl |
| 1613 | CH₂CH₃ | H | O | CH₂-c-Pr | CF₃ | 4-trifluoromethylphenyl |
| 1614 | CH₂CF₃ | H | O | CH₂-c-Pr | CF₃ | 4-trifluoromethylphenyl |
| 1615 | CH₂CH₂CH₃ | H | O | CH₂-c-Pr | CF₃ | 4-trifluoromethylphenyl |
| 1616 | CH₂CH(CH₃)₂ | H | O | CH₂-c-Pr | CF₃ | 4-trifluoromethylphenyl |
| 1617 | cyclopropylmethyl | H | O | CH₂-c-Pr | CF₃ | 4-trifluoromethylphenyl |
| 1618 | cyclobutylmethyl | H | O | CH₂-c-Pr | CF₃ | 4-trifluoromethylphenyl |
| 1619 | (CH₂)₂ | | O | CH₂-c-Pr | CF₃ | 4-trifluoromethylphenyl |
| 1620 | (CH₂)₃ | | O | CH₂-c-Pr | CF₃ | 4-trifluoromethylphenyl |
| 1621 | (CH2)₄ | | O | CH₂-c-Pr | CF₃ | 4-trifluoromethylphenyl |
| 1622 | (CH₂)₅ | | O | CH₂-c-Pr | CF₃ | 4-trifluoromethylphenyl |
| 1623 | 5,5-spiro[2.3]hexane | | O | CH₂-c-Pr | CF₃ | 4-trifluoromethylphenyl |
| 1624 | Cyclopentyl | H | O | CH₂-c-Pr | CF₃ | 4-trifluoromethylphenyl |
| 1625 | CH₂CH₃ | H | O | CH₂-c-Pr | CF₃ | 4-tolyl |
| 1626 | CH₂CF₃ | H | O | CH₂-c-Pr | CF₃ | 4-tolyl |
| 1627 | CH₂CH₂CH₃ | H | O | CH₂-c-Pr | CF₃ | 4-tolyl |
| 1628 | CH₂CH(CH₃)₂ | H | O | CH₂-c-Pr | CF₃ | 4-tolyl |
| 1629 | cyclopropylmethyl | H | O | CH₂-c-Pr | CF₃ | 4-tolyl |
| 1630 | cyclobutylmethyl | H | O | CH₂-c-Pr | CF₃ | 4-tolyl |
| 1631 | (CH₂)₂ | | O | CH₂-c-Pr | CF₃ | 4-tolyl |
| 1632 | (CH₂)₃ | | O | CH₂-c-Pr | CF₃ | 4-tolyl |
| 1633 | (CH2)₄ | | O | CH₂-c-Pr | CF₃ | 4-tolyl |
| 1634 | (CH₂)₅ | | O | CH₂-c-Pr | CF₃ | 4-tolyl |
| 1635 | 5,5-spiro[2.3]hexane | | O | CH₂-c-Pr | CF₃ | 4-tolyl |
| 1636 | Cyclopentyl | H | O | CH₂-c-Pr | CF₃ | 4-tolyl |
| 1637 | CH₂CH₃ | H | O | CH₂-c-Pr | CF₃ | 4-ethyl phenyl |
| 1638 | CH₂CF₃ | H | O | CH₂-c-Pr | CF₃ | 4-ethyl phenyl |

TABLE 5-continued

Compounds of Formula IV

Formula IV

| Ex | R1 | R2 | X | R3 | R5 | Z |
|---|---|---|---|---|---|---|
| 1639 | $CH_2CH_2CH_3$ | H | O | $CH_2$-c-Pr | $CF_3$ | 4-ethyl phenyl |
| 1640 | $CH_2CH(CH_3)_2$ | H | O | $CH_2$-c-Pr | $CF_3$ | 4-ethyl phenyl |
| 1641 | cyclopropylmethyl | H | O | $CH_2$-c-Pr | $CF_3$ | 4-ethyl phenyl |
| 1642 | cyclobutylmethyl | H | O | $CH_2$-c-Pr | $CF_3$ | 4-ethyl phenyl |
| 1643 | $(CH_2)_2$ | | O | $CH_2$-c-Pr | $CF_3$ | 4-ethyl phenyl |
| 1644 | $(CH_2)_3$ | | O | $CH_2$-c-Pr | $CF_3$ | 4-ethyl phenyl |
| 1645 | $(CH2)_4$ | | O | $CH_2$-c-Pr | $CF_3$ | 4-ethyl phenyl |
| 1646 | $(CH_2)_5$ | | O | $CH_2$-c-Pr | $CF_3$ | 4-ethyl phenyl |
| 1647 | 5,5-spiro[2.3]hexane | | O | $CH_2$-c-Pr | $CF_3$ | 4-ethyl phenyl |
| 1648 | Cyclopentyl | H | O | $CH_2$-c-Pr | $CF_3$ | 4-ethyl phenyl |
| 1649 | $CH_2CH_3$ | H | O | $CH_2$-c-Pr | $CF_3$ | 4-isopropyl phenyl |
| 1650 | $CH_2CF_3$ | H | O | $CH_2$-c-Pr | $CF_3$ | 4-isopropyl phenyl |
| 1651 | $CH_2CH_2CH_3$ | H | O | $CH_2$-c-Pr | $CF_3$ | 4-isopropyl phenyl |
| 1652 | $CH_2CH(CH_3)_2$ | H | O | $CH_2$-c-Pr | $CF_3$ | 4-isopropyl phenyl |
| 1653 | cyclopropylmethyl | H | O | $CH_2$-c-Pr | $CF_3$ | 4-isopropyl phenyl |
| 1654 | cyclobutylmethyl | H | O | $CH_2$-c-Pr | $CF_3$ | 4-isopropyl phenyl |
| 1655 | $(CH_2)_2$ | | O | $CH_2$-c-Pr | $CF_3$ | 4-isopropyl phenyl |
| 1656 | $(CH_2)_3$ | | O | $CH_2$-c-Pr | $CF_3$ | 4-isopropyl phenyl |
| 1657 | $(CH2)_4$ | | O | $CH_2$-c-Pr | $CF_3$ | 4-isopropyl phenyl |
| 1658 | $(CH_2)_5$ | | O | $CH_2$-c-Pr | $CF_3$ | 4-isopropyl phenyl |
| 1659 | 5,5-spiro[2.3]hexane | | O | $CH_2$-c-Pr | $CF_3$ | 4-isopropyl phenyl |
| 1660 | Cyclopentyl | H | O | $CH_2$-c-Pr | $CF_3$ | 4-isopropyl phenyl |
| 1661 | $CH_2CH_3$ | H | O | $CH_2$-c-Pr | $CF_3$ | 4-thiomethylphenyl |
| 1662 | $CH_2CF_3$ | H | O | $CH_2$-c-Pr | $CF_3$ | 4-thiomethylphenyl |
| 1663 | $CH_2CH_2CH_3$ | H | O | $CH_2$-c-Pr | $CF_3$ | 4-thiomethylphenyl |
| 1664 | $CH_2CH(CH_3)_2$ | H | O | $CH_2$-c-Pr | $CF_3$ | 4-thiomethylphenyl |
| 1665 | cyclopropylmethyl | H | O | $CH_2$-c-Pr | $CF_3$ | 4-thiomethylphenyl |
| 1666 | cyclobutylmethyl | H | O | $CH_2$-c-Pr | $CF_3$ | 4-thiomethylphenyl |
| 1667 | $(CH_2)_2$ | | O | $CH_2$-c-Pr | $CF_3$ | 4-thiomethylphenyl |
| 1668 | $(CH_2)_3$ | | O | $CH_2$-c-Pr | $CF_3$ | 4-thiomethylphenyl |
| 1669 | $(CH2)_4$ | | O | $CH_2$-c-Pr | $CF_3$ | 4-thiomethylphenyl |
| 1670 | $(CH_2)_5$ | | O | $CH_2$-c-Pr | $CF_3$ | 4-thiomethylphenyl |
| 1671 | 5,5-spiro[2.3]hexane | | O | $CH_2$-c-Pr | $CF_3$ | 4-thiomethylphenyl |
| 1672 | Cyclopentyl | H | O | $CH_2$-c-Pr | $CF_3$ | 4-thiomethylphenyl |
| 1673 | $CH_2CH_3$ | H | O | $CH_2$-c-Pr | $CF_3$ | 4-trifluoromethoxyphenyl |
| 1674 | $CH_2CF_3$ | H | O | $CH_2$-c-Pr | $CF_3$ | 4-trifluoromethoxyphenyl |
| 1675 | $CH_2CH_2CH_3$ | H | O | $CH_2$-c-Pr | $CF_3$ | 4-trifluoromethoxyphenyl |
| 1676 | $CH_2CH(CH_3)_2$ | H | O | $CH_2$-c-Pr | $CF_3$ | 4-trifluoromethoxyphenyl |
| 1677 | cyclopropylmethyl | H | O | $CH_2$-c-Pr | $CF_3$ | 4-trifluoromethoxyphenyl |
| 1678 | cyclobutylmethyl | H | O | $CH_2$-c-Pr | $CF_3$ | 4-trifluoromethoxyphenyl |
| 1679 | $(CH_2)_2$ | | O | $CH_2$-c-Pr | $CF_3$ | 4-trifluoromethoxyphenyl |
| 1680 | $(CH_2)_3$ | | O | $CH_2$-c-Pr | $CF_3$ | 4-trifluoromethoxyphenyl |
| 1681 | $(CH2)_4$ | | O | $CH_2$-c-Pr | $CF_3$ | 4-trifluoromethoxyphenyl |
| 1682 | $(CH_2)_5$ | | O | $CH_2$-c-Pr | $CF_3$ | 4-trifluoromethoxyphenyl |
| 1683 | 5,5-spiro[2.3]hexane | | O | $CH_2$-c-Pr | $CF_3$ | 4-trifluoromethoxyphenyl |
| 1684 | Cyclopentyl | H | O | $CH_2$-c-Pr | $CF_3$ | 4-trifluoromethoxyphenyl |
| 1685 | $CH_2CH_3$ | H | O | $CH_2CF_3$ | $OCH_2CF_3$ | 4-trifluoromethylphenyl |
| 1686 | $CH_2CF_3$ | H | O | $CH_2CF_3$ | $OCH_2CF_3$ | 4-trifluoromethylphenyl |
| 1687 | $CH_2CH_2CH_3$ | H | O | $CH_2CF_3$ | $OCH_2CF_3$ | 4-trifluoromethylphenyl |
| 1688 | $CH_2CH(CH_3)_2$ | H | O | $CH_2CF_3$ | $OCH_2CF_3$ | 4-trifluoromethylphenyl |
| 1689 | cyclopropylmethyl | H | O | $CH_2CF_3$ | $OCH_2CF_3$ | 4-trifluoromethylphenyl |
| 1690 | cyclobutylmethyl | H | O | $CH_2CF_3$ | $OCH_2CF_3$ | 4-trifluoromethylphenyl |
| 1691 | $(CH_2)_2$ | | O | $CH_2CF_3$ | $OCH_2CF_3$ | 4-trifluoromethylphenyl |
| 1692 | $(CH_2)_3$ | | O | $CH_2CF_3$ | $OCH_2CF_3$ | 4-trifluoromethylphenyl |
| 1693 | $(CH2)_4$ | | O | $CH_2CF_3$ | $OCH_2CF_3$ | 4-trifluoromethylphenyl |
| 1694 | $(CH_2)_5$ | | O | $CH_2CF_3$ | $OCH_2CF_3$ | 4-trifluoromethylphenyl |
| 1695 | 5,5-spiro[2.3]hexane | | O | $CH_2CF_3$ | $OCH_2CF_3$ | 4-trifluoromethylphenyl |
| 1696 | Cyclopentyl | H | O | $CH_2CF_3$ | $OCH_2CF_3$ | 4-trifluoromethylphenyl |
| 1697 | $CH_2CH_3$ | H | O | $CH_2CF_3$ | $OCH_2CF_3$ | 4-tolyl |
| 1698 | $CH_2CF_3$ | H | O | $CH_2CF_3$ | $OCH_2CF_3$ | 4-tolyl |
| 1699 | $CH_2CH_2CH_3$ | H | O | $CH_2CF_3$ | $OCH_2CF_3$ | 4-tolyl |
| 1700 | $CH_2CH(CH_3)_2$ | H | O | $CH_2CF_3$ | $OCH_2CF_3$ | 4-tolyl |
| 1701 | cyclopropylmethyl | H | O | $CH_2CF_3$ | $OCH_2CF_3$ | 4-tolyl |

TABLE 5-continued

Compounds of Formula IV

Formula IV

| Ex | R1 | R2 | X | R3 | R5 | Z |
|---|---|---|---|---|---|---|
| 1702 | cyclobutylmethyl | H | O | $CH_2CF_3$ | $OCH_2CF_3$ | 4-tolyl |
| 1703 | $(CH_2)_2$ | | O | $CH_2CF_3$ | $OCH_2CF_3$ | 4-tolyl |
| 1704 | $(CH_2)_3$ | | O | $CH_2CF_3$ | $OCH_2CF_3$ | 4-tolyl |
| 1705 | $(CH2)_4$ | | O | $CH_2CF_3$ | $OCH_2CF_3$ | 4-tolyl |
| 1706 | $(CH_2)_5$ | | O | $CH_2CF_3$ | $OCH_2CF_3$ | 4-tolyl |
| 1707 | 5,5-spiro[2.3]hexane | | O | $CH_2CF_3$ | $OCH_2CF_3$ | 4-tolyl |
| 1708 | Cyclopentyl | H | O | $CH_2CF_3$ | $OCH_2CF_3$ | 4-tolyl |
| 1709 | $CH_2CH_3$ | H | O | $CH_2CF_3$ | $OCH_2CF_3$ | 4-ethyl phenyl |
| 1710 | $CH_2CF_3$ | H | O | $CH_2CF_3$ | $OCH_2CF_3$ | 4-ethyl phenyl |
| 1711 | $CH_2CH_2CH_3$ | H | O | $CH_2CF_3$ | $OCH_2CF_3$ | 4-ethyl phenyl |
| 1712 | $CH_2CH(CH_3)_2$ | H | O | $CH_2CF_3$ | $OCH_2CF_3$ | 4-ethyl phenyl |
| 1713 | cyclopropylmethyl | H | O | $CH_2CF_3$ | $OCH_2CF_3$ | 4-ethyl phenyl |
| 1714 | cyclobutylmethyl | H | O | $CH_2CF_3$ | $OCH_2CF_3$ | 4-ethyl phenyl |
| 1715 | $(CH_2)_2$ | | O | $CH_2CF_3$ | $OCH_2CF_3$ | 4-ethyl phenyl |
| 1716 | $(CH_2)_3$ | | O | $CH_2CF_3$ | $OCH_2CF_3$ | 4-ethyl phenyl |
| 1717 | $(CH2)_4$ | | O | $CH_2CF_3$ | $OCH_2CF_3$ | 4-ethyl phenyl |
| 1718 | $(CH_2)_5$ | | O | $CH_2CF_3$ | $OCH_2CF_3$ | 4-ethyl phenyl |
| 1719 | 5,5-spiro[2.3]hexane | | O | $CH_2CF_3$ | $OCH_2CF_3$ | 4-ethyl phenyl |
| 1720 | Cyclopentyl | H | O | $CH_2CF_3$ | $OCH_2CF_3$ | 4-ethyl phenyl |
| 1721 | $CH_2CH_3$ | H | O | $CH_2CF_3$ | $OCH_2CF_3$ | 4-isopropyl phenyl |
| 1722 | $CH_2CF_3$ | H | O | $CH_2CF_3$ | $OCH_2CF_3$ | 4-isopropyl phenyl |
| 1723 | $CH_2CH_2CH_3$ | H | O | $CH_2CF_3$ | $OCH_2CF_3$ | 4-isopropyl phenyl |
| 1724 | $CH_2CH(CH_3)_2$ | H | O | $CH_2CF_3$ | $OCH_2CF_3$ | 4-isopropyl phenyl |
| 1725 | cyclopropylmethyl | H | O | $CH_2CF_3$ | $OCH_2CF_3$ | 4-isopropyl phenyl |
| 1726 | cyclobutylmethyl | H | O | $CH_2CF_3$ | $OCH_2CF_3$ | 4-isopropyl phenyl |
| 1727 | $(CH_2)_2$ | | O | $CH_2CF_3$ | $OCH_2CF_3$ | 4-isopropyl phenyl |
| 1728 | $(CH_2)_3$ | | O | $CH_2CF_3$ | $OCH_2CF_3$ | 4-isopropyl phenyl |
| 1729 | $(CH2)_4$ | | O | $CH_2CF_3$ | $OCH_2CF_3$ | 4-isopropyl phenyl |
| 1730 | $(CH_2)_5$ | | O | $CH_2CF_3$ | $OCH_2CF_3$ | 4-isopropyl phenyl |
| 1731 | 5,5-spiro[2.3]hexane | | O | $CH_2CF_3$ | $OCH_2CF_3$ | 4-isopropyl phenyl |
| 1732 | Cyclopentyl | H | O | $CH_2CF_3$ | $OCH_2CF_3$ | 4-isopropyl phenyl |
| 1733 | $CH_2CH_3$ | H | O | $CH_2CF_3$ | $OCH_2CF_3$ | 4-thiomethylphenyl |
| 1734 | $CH_2CF_3$ | H | O | $CH_2CF_3$ | $OCH_2CF_3$ | 4-thiomethylphenyl |
| 1735 | $CH_2CH_2CH_3$ | H | O | $CH_2CF_3$ | $OCH_2CF_3$ | 4-thiomethylphenyl |
| 1736 | $CH_2CH(CH_3)_2$ | H | O | $CH_2CF_3$ | $OCH_2CF_3$ | 4-thiomethylphenyl |
| 1737 | cyclopropylmethyl | H | O | $CH_2CF_3$ | $OCH_2CF_3$ | 4-thiomethylphenyl |
| 1738 | cyclobutylmethyl | H | O | $CH_2CF_3$ | $OCH_2CF_3$ | 4-thiomethylphenyl |
| 1739 | $(CH_2)_2$ | | O | $CH_2CF_3$ | $OCH_2CF_3$ | 4-thiomethylphenyl |
| 1740 | $(CH_2)_3$ | | O | $CH_2CF_3$ | $OCH_2CF_3$ | 4-thiomethylphenyl |
| 1741 | $(CH2)_4$ | | O | $CH_2CF_3$ | $OCH_2CF_3$ | 4-thiomethylphenyl |
| 1742 | $(CH_2)_5$ | | O | $CH_2CF_3$ | $OCH_2CF_3$ | 4-thiomethylphenyl |
| 1743 | 5,5-spiro[2.3]hexane | | O | $CH_2CF_3$ | $OCH_2CF_3$ | 4-thiomethylphenyl |
| 1744 | Cyclopentyl | H | O | $CH_2CF_3$ | $OCH_2CF_3$ | 4-thiomethylphenyl |
| 1745 | $CH_2CH_3$ | H | O | $CH_2CF_3$ | $OCH_2CF_3$ | 4-trifluoromethoxyphenyl |
| 1746 | $CH_2CF_3$ | H | O | $CH_2CF_3$ | $OCH_2CF_3$ | 4-trifluoromethoxyphenyl |
| 1747 | $CH_2CH_2CH_3$ | H | O | $CH_2CF_3$ | $OCH_2CF_3$ | 4-trifluoromethoxyphenyl |
| 1748 | $CH_2CH(CH_3)_2$ | H | O | $CH_2CF_3$ | $OCH_2CF_3$ | 4-trifluoromethoxyphenyl |
| 1749 | cyclopropylmethyl | H | O | $CH_2CF_3$ | $OCH_2CF_3$ | 4-trifluoromethoxyphenyl |
| 1750 | cyclobutylmethyl | H | O | $CH_2CF_3$ | $OCH_2CF_3$ | 4-trifluoromethoxyphenyl |
| 1751 | $(CH_2)_2$ | | O | $CH_2CF_3$ | $OCH_2CF_3$ | 4-trifluoromethoxyphenyl |
| 1752 | $(CH_2)_3$ | | O | $CH_2CF_3$ | $OCH_2CF_3$ | 4-trifluoromethoxyphenyl |
| 1753 | $(CH2)_4$ | | O | $CH_2CF_3$ | $OCH_2CF_3$ | 4-trifluoromethoxyphenyl |
| 1754 | $(CH_2)_5$ | | O | $CH_2CF_3$ | $OCH_2CF_3$ | 4-trifluoromethoxyphenyl |
| 1755 | 5,5-spiro[2.3]hexane | | O | $CH_2CF_3$ | $OCH_2CF_3$ | 4-trifluoromethoxyphenyl |
| 1756 | Cyclopentyl | H | O | $CH_2CF_3$ | $OCH_2CF_3$ | 4-trifluoromethoxyphenyl |
| 1757 | $CH_2CH_3$ | H | O | $CH_2$-c-Pr | $OCH_2CF_3$ | 4-trifluoromethylphenyl |
| 1758 | $CH_2CF_3$ | H | O | $CH_2$-c-Pr | $OCH_2CF_3$ | 4-trifluoromethylphenyl |
| 1759 | $CH_2CH_2CH_3$ | H | O | $CH_2$-c-Pr | $OCH_2CF_3$ | 4-trifluoromethylphenyl |
| 1760 | $CH_2CH(CH_3)_2$ | H | O | $CH_2$-c-Pr | $OCH_2CF_3$ | 4-trifluoromethylphenyl |
| 1761 | cyclopropylmethyl | H | O | $CH_2$-c-Pr | $OCH_2CF_3$ | 4-trifluoromethylphenyl |
| 1762 | cyclobutylmethyl | H | O | $CH_2$-c-Pr | $OCH_2CF_3$ | 4-trifluoromethylphenyl |
| 1763 | $(CH_2)_2$ | | O | $CH_2$-c-Pr | $OCH_2CF_3$ | 4-trifluoromethylphenyl |
| 1764 | $(CH_2)_3$ | | O | $CH_2$-c-Pr | $OCH_2CF_3$ | 4-trifluoromethylphenyl |

TABLE 5-continued

Compounds of Formula IV

Formula IV

| Ex | R1 | R2 | X | R3 | R5 | Z |
|---|---|---|---|---|---|---|
| 1765 | (CH2)4 | | O | CH$_2$-c-Pr | OCH$_2$CF$_3$ | 4-trifluoromethylphenyl |
| 1766 | (CH$_2$)$_5$ | | O | CH$_2$-c-Pr | OCH$_2$CF$_3$ | 4-trifluoromethylphenyl |
| 1767 | 5,5-spiro[2.3]hexane | | O | CH$_2$-c-Pr | OCH$_2$CF$_3$ | 4-trifluoromethylphenyl |
| 1768 | Cyclopentyl | H | O | CH$_2$-c-Pr | OCH$_2$CF$_3$ | 4-trifluoromethylphenyl |
| 1769 | CH$_2$CH$_3$ | H | O | CH$_2$-c-Pr | OCH$_2$CF$_3$ | 4-tolyl |
| 1770 | CH$_2$CF$_3$ | H | O | CH$_2$-c-Pr | OCH$_2$CF$_3$ | 4-tolyl |
| 1771 | CH$_2$CH$_2$CH$_3$ | H | O | CH$_2$-c-Pr | OCH$_2$CF$_3$ | 4-tolyl |
| 1772 | CH$_2$CH(CH$_3$)$_2$ | H | O | CH$_2$-c-Pr | OCH$_2$CF$_3$ | 4-tolyl |
| 1773 | cyclopropylmethyl | H | O | CH$_2$-c-Pr | OCH$_2$CF$_3$ | 4-tolyl |
| 1774 | cyclobutylmethyl | H | O | CH$_2$-c-Pr | OCH$_2$CF$_3$ | 4-tolyl |
| 1775 | (CH$_2$)$_2$ | | O | CH$_2$-c-Pr | OCH$_2$CF$_3$ | 4-tolyl |
| 1776 | (CH$_2$)$_3$ | | O | CH$_2$-c-Pr | OCH$_2$CF$_3$ | 4-tolyl |
| 1777 | (CH2)4 | | O | CH$_2$-c-Pr | OCH$_2$CF$_3$ | 4-tolyl |
| 1778 | (CH$_2$)$_5$ | | O | CH$_2$-c-Pr | OCH$_2$CF$_3$ | 4-tolyl |
| 1779 | 5,5-spiro[2.3]hexane | | O | CH$_2$-c-Pr | OCH$_2$CF$_3$ | 4-tolyl |
| 1780 | Cyclopentyl | H | O | CH$_2$-c-Pr | OCH$_2$CF$_3$ | 4-tolyl |
| 1781 | CH$_2$CH$_3$ | H | O | CH$_2$-c-Pr | OCH$_2$CF$_3$ | 4-ethyl phenyl |
| 1782 | CH$_2$CF$_3$ | H | O | CH$_2$-c-Pr | OCH$_2$CF$_3$ | 4-ethyl phenyl |
| 1783 | CH$_2$CH$_2$CH$_3$ | H | O | CH$_2$-c-Pr | OCH$_2$CF$_3$ | 4-ethyl phenyl |
| 1784 | CH$_2$CH(CH$_3$)$_2$ | H | O | CH$_2$-c-Pr | OCH$_2$CF$_3$ | 4-ethyl phenyl |
| 1785 | cyclopropylmethyl | H | O | CH$_2$-c-Pr | OCH$_2$CF$_3$ | 4-ethyl phenyl |
| 1786 | cyclobutylmethyl | H | O | CH$_2$-c-Pr | OCH$_2$CF$_3$ | 4-ethyl phenyl |
| 1787 | (CH$_2$)$_2$ | | O | CH$_2$-c-Pr | OCH$_2$CF$_3$ | 4-ethyl phenyl |
| 1788 | (CH$_2$)$_3$ | | O | CH$_2$-c-Pr | OCH$_2$CF$_3$ | 4-ethyl phenyl |
| 1789 | (CH2)4 | | O | CH$_2$-c-Pr | OCH$_2$CF$_3$ | 4-ethyl phenyl |
| 1790 | (CH$_2$)$_5$ | | O | CH$_2$-c-Pr | OCH$_2$CF$_3$ | 4-ethyl phenyl |
| 1791 | 5,5-spiro[2.3]hexane | | O | CH$_2$-c-Pr | OCH$_2$CF$_3$ | 4-ethyl phenyl |
| 1792 | Cyclopentyl | H | O | CH$_2$-c-Pr | OCH$_2$CF$_3$ | 4-ethyl phenyl |
| 1793 | CH$_2$CH$_3$ | H | O | CH$_2$-c-Pr | OCH$_2$CF$_3$ | 4-isopropyl phenyl |
| 1794 | CH$_2$CF$_3$ | H | O | CH$_2$-c-Pr | OCH$_2$CF$_3$ | 4-isopropyl phenyl |
| 1795 | CH$_2$CH$_2$CH$_3$ | H | O | CH$_2$-c-Pr | OCH$_2$CF$_3$ | 4-isopropyl phenyl |
| 1796 | CH$_2$CH(CH$_3$)$_2$ | H | O | CH$_2$-c-Pr | OCH$_2$CF$_3$ | 4-isopropyl phenyl |
| 1797 | cyclopropylmethyl | H | O | CH$_2$-c-Pr | OCH$_2$CF$_3$ | 4-isopropyl phenyl |
| 1798 | cyclobutylmethyl | H | O | CH$_2$-c-Pr | OCH$_2$CF$_3$ | 4-isopropyl phenyl |
| 1799 | (CH$_2$)$_2$ | | O | CH$_2$-c-Pr | OCH$_2$CF$_3$ | 4-isopropyl phenyl |
| 1800 | (CH$_2$)$_3$ | | O | CH$_2$-c-Pr | OCH$_2$CF$_3$ | 4-isopropyl phenyl |
| 1801 | (CH2)4 | | O | CH$_2$-c-Pr | OCH$_2$CF$_3$ | 4-isopropyl phenyl |
| 1802 | (CH$_2$)$_5$ | | O | CH$_2$-c-Pr | OCH$_2$CF$_3$ | 4-isopropyl phenyl |
| 1803 | 5,5-spiro[2.3]hexane | | O | CH$_2$-c-Pr | OCH$_2$CF$_3$ | 4-isopropyl phenyl |
| 1804 | Cyclopentyl | H | O | CH$_2$-c-Pr | OCH$_2$CF$_3$ | 4-isopropyl phenyl |
| 1805 | CH$_2$CH$_3$ | H | O | CH$_2$-c-Pr | OCH$_2$CF$_3$ | 4-thiomethylphenyl |
| 1806 | CH$_2$CF$_3$ | H | O | CH$_2$-c-Pr | OCH$_2$CF$_3$ | 4-thiomethylphenyl |
| 1807 | CH$_2$CH$_2$CH$_3$ | H | O | CH$_2$-c-Pr | OCH$_2$CF$_3$ | 4-thiomethylphenyl |
| 1808 | CH$_2$CH(CH$_3$)$_2$ | H | O | CH$_2$-c-Pr | OCH$_2$CF$_3$ | 4-thiomethylphenyl |
| 1809 | cyclopropylmethyl | H | O | CH$_2$-c-Pr | OCH$_2$CF$_3$ | 4-thiomethylphenyl |
| 1810 | cyclobutylmethyl | H | O | CH$_2$-c-Pr | OCH$_2$CF$_3$ | 4-thiomethylphenyl |
| 1811 | (CH$_2$)$_2$ | | O | CH$_2$-c-Pr | OCH$_2$CF$_3$ | 4-thiomethylphenyl |
| 1812 | (CH$_2$)$_3$ | | O | CH$_2$-c-Pr | OCH$_2$CF$_3$ | 4-thiomethylphenyl |
| 1813 | (CH2)4 | | O | CH$_2$-c-Pr | OCH$_2$CF$_3$ | 4-thiomethylphenyl |
| 1814 | (CH$_2$)$_5$ | | O | CH$_2$-c-Pr | OCH$_2$CF$_3$ | 4-thiomethylphenyl |
| 1815 | 5,5-spiro[2.3]hexane | | O | CH$_2$-c-Pr | OCH$_2$CF$_3$ | 4-thiomethylphenyl |
| 1816 | Cyclopentyl | H | O | CH$_2$-c-Pr | OCH$_2$CF$_3$ | 4-thiomethylphenyl |
| 1817 | CH$_2$CH$_3$ | H | O | CH$_2$-c-Pr | OCH$_2$CF$_3$ | 4-trifluoromethoxyphenyl |
| 1818 | CH$_2$CF$_3$ | H | O | CH$_2$-c-Pr | OCH$_2$CF$_3$ | 4-trifluoromethoxyphenyl |
| 1819 | CH$_2$CH$_2$CH$_3$ | H | O | CH$_2$-c-Pr | OCH$_2$CF$_3$ | 4-trifluoromethoxyphenyl |
| 1820 | CH$_2$CH(CH$_3$)$_2$ | H | O | CH$_2$-c-Pr | OCH$_2$CF$_3$ | 4-trifluoromethoxyphenyl |
| 1821 | cyclopropylmethyl | H | O | CH$_2$-c-Pr | OCH$_2$CF$_3$ | 4-trifluoromethoxyphenyl |
| 1822 | cyclobutylmethyl | H | O | CH$_2$-c-Pr | OCH$_2$CF$_3$ | 4-trifluoromethoxyphenyl |
| 1823 | (CH$_2$)$_2$ | | O | CH$_2$-c-Pr | OCH$_2$CF$_3$ | 4-trifluoromethoxyphenyl |
| 1824 | (CH$_2$)$_3$ | | O | CH$_2$-c-Pr | OCH$_2$CF$_3$ | 4-trifluoromethoxyphenyl |
| 1825 | (CH2)4 | | O | CH$_2$-c-Pr | OCH$_2$CF$_3$ | 4-trifluoromethoxyphenyl |

TABLE 5-continued

Compounds of Formula IV

Formula IV

| Ex | R1 | R2 | X | R3 | R5 | Z |
|---|---|---|---|---|---|---|
| 1826 | (CH$_2$)$_5$ | | O | CH$_2$-c-Pr | OCH$_2$CF$_3$ | 4-trifluoromethoxyphenyl |
| 1827 | 5,5-spiro[2.3]hexane | | O | CH$_2$-c-Pr | OCH$_2$CF$_3$ | 4-trifluoromethoxyphenyl |
| 1828 | Cyclopentyl | H | O | CH$_2$-c-Pr | OCH$_2$CF$_3$ | 4-trifluoromethoxyphenyl |

TABLE 6

Compounds of Formula IV

Formula IV

| Ex | R1 | R2 | X | R3 | R5 | Z |
|---|---|---|---|---|---|---|
| 1829 | CH$_2$CH$_3$ | H | O | CH$_2$CF$_3$ | Cl | 4-trifluoromethylphenyl |
| 1830 | CH$_2$CF$_3$ | H | O | CH$_2$CF$_3$ | Cl | 4-trifluoromethylphenyl |
| 1831 | CH$_2$CH$_2$CH$_3$ | H | O | CH$_2$CF$_3$ | Cl | 4-trifluoromethylphenyl |
| 1832 | CH$_2$CH(CH$_3$)$_2$ | H | O | CH$_2$CF$_3$ | Cl | 4-trifluoromethylphenyl |
| 1833 | cyclopropylmethyl | H | O | CH$_2$CF$_3$ | Cl | 4-trifluoromethylphenyl |
| 1834 | cyclobutylmethyl | H | O | CH$_2$CF$_3$ | Cl | 4-trifluoromethylphenyl |
| 1835 | (CH$_2$)$_2$ | | O | CH$_2$CF$_3$ | Cl | 4-trifluoromethylphenyl |
| 1836 | (CH$_2$)$_3$ | | O | CH$_2$CF$_3$ | Cl | 4-trifluoromethylphenyl |
| 1837 | (CH$_2$)$_4$ | | O | CH$_2$CF$_3$ | Cl | 4-trifluoromethylphenyl |
| 1838 | (CH$_2$)$_5$ | | O | CH$_2$CF$_3$ | Cl | 4-trifluoromethylphenyl |
| 1839 | 5,5-spiro[2.3]hexane | | O | CH$_2$CF$_3$ | Cl | 4-trifluoromethylphenyl |
| 1840 | Cyclopentyl | H | O | CH$_2$CF$_3$ | Cl | 4-trifluoromethylphenyl |
| 1841 | CH$_2$CH$_3$ | H | O | CH$_2$CF$_3$ | Cl | 4-tolyl |
| 1842 | CH$_2$CF$_3$ | H | O | CH$_2$CF$_3$ | Cl | 4-tolyl |
| 1843 | CH$_2$CH$_2$CH$_3$ | H | O | CH$_2$CF$_3$ | Cl | 4-tolyl |
| 1844 | CH$_2$CH(CH$_3$)$_2$ | H | O | CH$_2$CF$_3$ | Cl | 4-tolyl |
| 1845 | cyclopropylmethyl | H | O | CH$_2$CF$_3$ | Cl | 4-tolyl |
| 1846 | cyclobutylmethyl | H | O | CH$_2$CF$_3$ | Cl | 4-tolyl |
| 1847 | (CH$_2$)$_2$ | | O | CH$_2$CF$_3$ | Cl | 4-tolyl |
| 1848 | (CH$_2$)$_3$ | | O | CH$_2$CF$_3$ | Cl | 4-tolyl |
| 1849 | (CH$_2$)$_4$ | | O | CH$_2$CF$_3$ | Cl | 4-tolyl |
| 1850 | (CH$_2$)$_5$ | | O | CH$_2$CF$_3$ | Cl | 4-tolyl |
| 1851 | 5,5-spiro[2.3]hexane | | O | CH$_2$CF$_3$ | Cl | 4-tolyl |
| 1852 | Cyclopentyl | H | O | CH$_2$CF$_3$ | Cl | 4-tolyl |
| 1853 | CH$_2$CH$_3$ | H | O | CH$_2$CF$_3$ | Cl | 4-ethyl phenyl |
| 1854 | CH$_2$CF$_3$ | H | O | CH$_2$CF$_3$ | Cl | 4-ethyl phenyl |
| 1855 | CH$_2$CH$_2$CH$_3$ | H | O | CH$_2$CF$_3$ | Cl | 4-ethyl phenyl |
| 1856 | CH$_2$CH(CH$_3$)$_2$ | H | O | CH$_2$CF$_3$ | Cl | 4-ethyl phenyl |
| 1857 | cyclopropylmethyl | H | O | CH$_2$CF$_3$ | Cl | 4-ethyl phenyl |
| 1858 | cyclobutylmethyl | H | O | CH$_2$CF$_3$ | Cl | 4-ethyl phenyl |
| 1859 | (CH$_2$)$_2$ | | O | CH$_2$CF$_3$ | Cl | 4-ethyl phenyl |
| 1860 | (CH$_2$)$_3$ | | O | CH$_2$CF$_3$ | Cl | 4-ethyl phenyl |
| 1861 | (CH$_2$)$_4$ | | O | CH$_2$CF$_3$ | Cl | 4-ethyl phenyl |
| 1862 | (CH$_2$)$_5$ | | O | CH$_2$CF$_3$ | Cl | 4-ethyl phenyl |
| 1863 | 5,5-spiro[2.3]hexane | | O | CH$_2$CF$_3$ | Cl | 4-ethyl phenyl |
| 1864 | Cyclopentyl | H | O | CH$_2$CF$_3$ | Cl | 4-ethyl phenyl |
| 1865 | CH$_2$CH$_3$ | H | O | CH$_2$CF$_3$ | Cl | 4-isopropyl phenyl |
| 1866 | CH$_2$CF$_3$ | H | O | CH$_2$CF$_3$ | Cl | 4-isopropyl phenyl |

TABLE 6-continued

Compounds of Formula IV

Formula IV: structure with R1, R2, CO2H on central carbon attached to phenyl ring bearing R5, Z, and X-R3 substituents.

| Ex | R1 | R2 | X | R3 | R5 | Z |
|---|---|---|---|---|---|---|
| 1867 | CH$_2$CH$_2$CH$_3$ | H | O | CH$_2$CF$_3$ | Cl | 4-isopropyl phenyl |
| 1868 | CH$_2$CH(CH$_3$)$_2$ | H | O | CH$_2$CF$_3$ | Cl | 4-isopropyl phenyl |
| 1869 | cyclopropylmethyl | H | O | CH$_2$CF$_3$ | Cl | 4-isopropyl phenyl |
| 1870 | cyclobutylmethyl | H | O | CH$_2$CF$_3$ | Cl | 4-isopropyl phenyl |
| 1871 | (CH$_2$)$_2$ | | O | CH$_2$CF$_3$ | Cl | 4-isopropyl phenyl |
| 1872 | (CH$_2$)$_3$ | | O | CH$_2$CF$_3$ | Cl | 4-isopropyl phenyl |
| 1873 | (CH$_2$)$_4$ | | O | CH$_2$CF$_3$ | Cl | 4-isopropyl phenyl |
| 1874 | (CH$_2$)$_5$ | | O | CH$_2$CF$_3$ | Cl | 4-isopropyl phenyl |
| 1875 | 5,5-spiro[2.3]hexane | | O | CH$_2$CF$_3$ | Cl | 4-isopropyl phenyl |
| 1876 | Cyclopentyl | H | O | CH$_2$CF$_3$ | Cl | 4-isopropyl phenyl |
| 1877 | CH$_2$CH$_3$ | H | O | CH$_2$CF$_3$ | Cl | 4-thiomethylphenyl |
| 1878 | CH$_2$CF$_3$ | H | O | CH$_2$CF$_3$ | Cl | 4-thiomethylphenyl |
| 1879 | CH$_2$CH$_2$CH$_3$ | H | O | CH$_2$CF$_3$ | Cl | 4-thiomethylphenyl |
| 1880 | CH$_2$CH(CH$_3$)$_2$ | H | O | CH$_2$CF$_3$ | Cl | 4-thiomethylphenyl |
| 1881 | cyclopropylmethyl | H | O | CH$_2$CF$_3$ | Cl | 4-thiomethylphenyl |
| 1882 | cyclobutylmethyl | H | O | CH$_2$CF$_3$ | Cl | 4-thiomethylphenyl |
| 1883 | (CH$_2$)$_2$ | | O | CH$_2$CF$_3$ | Cl | 4-thiomethylphenyl |
| 1884 | (CH$_2$)$_3$ | | O | CH$_2$CF$_3$ | Cl | 4-thiomethylphenyl |
| 1885 | (CH$_2$)$_4$ | | O | CH$_2$CF$_3$ | Cl | 4-thiomethylphenyl |
| 1886 | (CH$_2$)$_5$ | | O | CH$_2$CF$_3$ | Cl | 4-thiomethylphenyl |
| 1887 | 5,5-spiro[2.3]hexane | | O | CH$_2$CF$_3$ | Cl | 4-thiomethylphenyl |
| 1888 | Cyclopentyl | H | O | CH$_2$CF$_3$ | Cl | 4-thiomethylphenyl |
| 1889 | CH$_2$CH$_3$ | H | O | CH$_2$CF$_3$ | Cl | 4-trifluoromethoxyphenyl |
| 1890 | CH$_2$CF$_3$ | H | O | CH$_2$CF$_3$ | Cl | 4-trifluoromethoxyphenyl |
| 1891 | CH$_2$CH$_2$CH$_3$ | H | O | CH$_2$CF$_3$ | Cl | 4-trifluoromethoxyphenyl |
| 1892 | CH$_2$CH(CH$_3$)$_2$ | H | O | CH$_2$CF$_3$ | Cl | 4-trifluoromethoxyphenyl |
| 1893 | cyclopropylmethyl | H | O | CH$_2$CF$_3$ | Cl | 4-trifluoromethoxyphenyl |
| 1894 | cyclobutylmethyl | H | O | CH$_2$CF$_3$ | Cl | 4-trifluoromethoxyphenyl |
| 1895 | (CH$_2$)$_2$ | | O | CH$_2$CF$_3$ | Cl | 4-trifluoromethoxyphenyl |
| 1896 | (CH$_2$)$_3$ | | O | CH$_2$CF$_3$ | Cl | 4-trifluoromethoxyphenyl |
| 1897 | (CH$_2$)$_4$ | | O | CH$_2$CF$_3$ | Cl | 4-trifluoromethoxyphenyl |
| 1898 | (CH$_2$)$_5$ | | O | CH$_2$CF$_3$ | Cl | 4-trifluoromethoxyphenyl |
| 1899 | 5,5-spiro[2.3]hexane | | O | CH$_2$CF$_3$ | Cl | 4-trifluoromethoxyphenyl |
| 1900 | Cyclopentyl | H | O | CH$_2$CF$_3$ | Cl | 4-trifluoromethoxylphenyl |
| 1901 | CH$_2$CH$_3$ | H | O | CH$_2$-c-Pr | Cl | 4-trifluoromethylphenyl |
| 1902 | CH$_2$CF$_3$ | H | O | CH$_2$-c-Pr | Cl | 4-trifluoromethylphenyl |
| 1903 | CH$_2$CH$_2$CH$_3$ | H | O | CH$_2$-c-Pr | Cl | 4-trifluoromethylphenyl |
| 1904 | CH$_2$CH(CH$_3$)$_2$ | H | O | CH$_2$-c-Pr | Cl | 4-trifluoromethylphenyl |
| 1905 | cyclopropylmethyl | H | O | CH$_2$-c-Pr | Cl | 4-trifluoromethylphenyl |
| 1906 | cyclobutylmethyl | H | O | CH$_2$-c-Pr | Cl | 4-trifluoromethylphenyl |
| 1907 | (CH$_2$)$_2$ | | O | CH$_2$-c-Pr | Cl | 4-trifluoromethylphenyl |
| 1908 | (CH$_2$)$_3$ | | O | CH$_2$-c-Pr | Cl | 4-trifluoromethylphenyl |
| 1909 | (CH$_2$)$_4$ | | O | CH$_2$-c-Pr | Cl | 4-trifluoromethylphenyl |
| 1910 | (CH$_2$)$_5$ | | O | CH$_2$-c-Pr | Cl | 4-trifluoromethylphenyl |
| 1911 | 5,5-spiro[2.3]hexane | | O | CH$_2$-c-Pr | Cl | 4-trifluoromethylphenyl |
| 1912 | Cyclopentyl | H | O | CH$_2$-c-Pr | Cl | 4-trifluoromethylphenyl |
| 1913 | CH$_2$CH$_3$ | H | O | CH$_2$-c-Pr | Cl | 4-tolyl |
| 1914 | CH$_2$CF$_3$ | H | O | CH$_2$-c-Pr | Cl | 4-tolyl |
| 1915 | CH$_2$CH$_2$CH$_3$ | H | O | CH$_2$-c-Pr | Cl | 4-tolyl |
| 1916 | CH$_2$CH(CH$_3$)$_2$ | H | O | CH$_2$-c-Pr | Cl | 4-tolyl |
| 1917 | cyclopropylmethyl | H | O | CH$_2$-c-Pr | Cl | 4-tolyl |
| 1918 | cyclobutylmethyl | H | O | CH$_2$-c-Pr | Cl | 4-tolyl |
| 1919 | (CH$_2$)$_2$ | | O | CH$_2$-c-Pr | Cl | 4-tolyl |
| 1920 | (CH$_2$)$_3$ | | O | CH$_2$-c-Pr | Cl | 4-tolyl |
| 1921 | (CH$_2$)$_4$ | | O | CH$_2$-c-Pr | Cl | 4-tolyl |
| 1922 | (CH$_2$)$_5$ | | O | CH$_2$-c-Pr | Cl | 4-tolyl |
| 1923 | 5,5-spiro[2.3]hexane | | O | CH$_2$-c-Pr | Cl | 4-tolyl |
| 1924 | Cyclopentyl | H | O | CH$_2$-c-Pr | Cl | 4-tolyl |
| 1925 | CH$_2$CH$_3$ | H | O | CH$_2$-c-Pr | Cl | 4-ethyl phenyl |
| 1926 | CH$_2$CF$_3$ | H | O | CH$_2$-c-Pr | Cl | 4-ethyl phenyl |
| 1927 | CH$_2$CH$_2$CH$_3$ | H | O | CH$_2$-c-Pr | Cl | 4-ethyl phenyl |
| 1928 | CH$_2$CH(CH$_3$)$_2$ | H | O | CH$_2$-c-Pr | Cl | 4-ethyl phenyl |
| 1929 | cyclopropylmethyl | H | O | CH$_2$-c-Pr | Cl | 4-ethyl phenyl |

TABLE 6-continued

Compounds of Formula IV

Formula IV

| Ex | R1 | R2 | X | R3 | R5 | Z |
|---|---|---|---|---|---|---|
| 1930 | cyclobutylmethyl | H | O | $CH_2$-c-Pr | Cl | 4-ethyl phenyl |
| 1931 | $(CH_2)_2$ | | O | $CH_2$-c-Pr | Cl | 4-ethyl phenyl |
| 1932 | $(CH_2)_3$ | | O | $CH_2$-c-Pr | Cl | 4-ethyl phenyl |
| 1933 | $(CH_2)_4$ | | O | $CH_2$-c-Pr | Cl | 4-ethyl phenyl |
| 1934 | $(CH_2)_5$ | | O | $CH_2$-c-Pr | Cl | 4-ethyl phenyl |
| 1935 | 5,5-spiro[2.3]hexane | | O | $CH_2$-c-Pr | Cl | 4-ethyl phenyl |
| 1936 | Cyclopentyl | H | O | $CH_2$-c-Pr | Cl | 4-ethyl phenyl |
| 1937 | $CH_2CH_3$ | H | O | $CH_2$-c-Pr | Cl | 4-isopropyl phenyl |
| 1938 | $CH_2CF_3$ | H | O | $CH_2$-c-Pr | Cl | 4-isopropyl phenyl |
| 1939 | $CH_2CH_2CH_3$ | H | O | $CH_2$-c-Pr | Cl | 4-isopropyl phenyl |
| 1940 | $CH_2CH(CH_3)_2$ | H | O | $CH_2$-c-Pr | Cl | 4-isopropyl phenyl |
| 1941 | cyclopropylmethyl | H | O | $CH_2$-c-Pr | Cl | 4-isopropyl phenyl |
| 1942 | cyclobutylmethyl | H | O | $CH_2$-c-Pr | Cl | 4-isopropyl phenyl |
| 1943 | $(CH_2)_2$ | | O | $CH_2$-c-Pr | Cl | 4-isopropyl phenyl |
| 1944 | $(CH_2)_3$ | | O | $CH_2$-c-Pr | Cl | 4-isopropyl phenyl |
| 1945 | $(CH_2)_4$ | | O | $CH_2$-c-Pr | Cl | 4-isopropyl phenyl |
| 1946 | $(CH_2)_5$ | | O | $CH_2$-c-Pr | Cl | 4-isopropyl phenyl |
| 1947 | 5,5-spiro[2.3]hexane | | O | $CH_2$-c-Pr | Cl | 4-isopropyl phenyl |
| 1948 | Cyclopentyl | H | O | $CH_2$-c-Pr | Cl | 4-isopropyl phenyl |
| 1949 | $CH_2CH_3$ | H | O | $CH_2$-c-Pr | Cl | 4-thiomethylphenyl |
| 1950 | $CH_2CF_3$ | H | O | $CH_2$-c-Pr | Cl | 4-thiomethylphenyl |
| 1951 | $CH_2CH_2CH_3$ | H | O | $CH_2$-c-Pr | Cl | 4-thiomethylphenyl |
| 1952 | $CH_2CH(CH_3)_2$ | H | O | $CH_2$-c-Pr | Cl | 4-thiomethylphenyl |
| 1953 | cyclopropylmethyl | H | O | $CH_2$-c-Pr | Cl | 4-thiomethylphenyl |
| 1954 | cyclobutylmethyl | H | O | $CH_2$-c-Pr | Cl | 4-thiomethylphenyl |
| 1955 | $(CH_2)_2$ | | O | $CH_2$-c-Pr | Cl | 4-thiomethylphenyl |
| 1956 | $(CH_2)_3$ | | O | $CH_2$-c-Pr | Cl | 4-thiomethylphenyl |
| 1957 | $(CH_2)_4$ | | O | $CH_2$-c-Pr | Cl | 4-thiomethylphenyl |
| 1958 | $(CH_2)_5$ | | O | $CH_2$-c-Pr | Cl | 4-thiomethylphenyl |
| 1959 | 5,5-spiro[2.3]hexane | | O | $CH_2$-c-Pr | Cl | 4-thiomethylphenyl |
| 1960 | Cyclopentyl | H | O | $CH_2$-c-Pr | Cl | 4-thiomethylphenyl |
| 1961 | $CH_2CH_3$ | H | O | $CH_2$-c-Pr | Cl | 4-trifluoromethoxyphenyl |
| 1962 | $CH_2CF_3$ | H | O | $CH_2$-c-Pr | Cl | 4-trifluoromethoxyphenyl |
| 1963 | $CH_2CH_2CH_3$ | H | O | $CH_2$-c-Pr | Cl | 4-trifluoromethoxyphenyl |
| 1964 | $CH_2CH(CH_3)_2$ | H | O | $CH_2$-c-Pr | Cl | 4-trifluoromethoxyphenyl |
| 1965 | cyclopropylmethyl | H | O | $CH_2$-c-Pr | Cl | 4-trifluoromethoxyphenyl |
| 1966 | cyclobutylmethyl | H | O | $CH_2$-c-Pr | Cl | 4-trifluoromethoxyphenyl |
| 1967 | $(CH_2)_2$ | | O | $CH_2$-c-Pr | Cl | 4-trifluoromethoxyphenyl |
| 1968 | $(CH_2)_3$ | | O | $CH_2$-c-Pr | Cl | 4-trifluoromethoxyphenyl |
| 1969 | $(CH_2)_4$ | | O | $CH_2$-c-Pr | Cl | 4-trifluoromethoxyphenyl |
| 1970 | $(CH_2)_5$ | | O | $CH_2$-c-Pr | Cl | 4-trifluoromethoxyphenyl |
| 1971 | 5,5-spiro[2.3]hexane | | O | $CH_2$-c-Pr | Cl | 4-trifluoromethoxyphenyl |
| 1972 | Cyclopentyl | H | O | $CH_2$-c-Pr | Cl | 4-trifluoromethoxyphenyl |
| 1973 | $CH_2CH_3$ | H | O | $CH_2CF_3$ | $OCH_2CF_3$ | 4-trifluoromethylphenyl |
| 1974 | $CH_2CF_3$ | H | O | $CH_2CF_3$ | $OCH_2CF_3$ | 4-trifluoromethylphenyl |
| 1975 | $CH_2CH_2CH_3$ | H | O | $CH_2CF_3$ | $OCH_2CF_3$ | 4-trifluoromethylphenyl |
| 1976 | $CH_2CH(CH_3)_2$ | H | O | $CH_2CF_3$ | $OCH_2CF_3$ | 4-trifluoromethylphenyl |
| 1977 | cyclopropylmethyl | H | O | $CH_2CF_3$ | $OCH_2CF_3$ | 4-trifluoromethylphenyl |
| 1978 | cyclobutylmethyl | H | O | $CH_2CF_3$ | $OCH_2CF_3$ | 4-trifluoromethylphenyl |
| 1979 | $(CH_2)_2$ | | O | $CH_2CF_3$ | $OCH_2CF_3$ | 4-trifluoromethylphenyl |
| 1980 | $(CH_2)_3$ | | O | $CH_2CF_3$ | $OCH_2CF_3$ | 4-trifluoromethylphenyl |
| 1981 | $(CH_2)_4$ | | O | $CH_2CF_3$ | $OCH_2CF_3$ | 4-trifluoromethylphenyl |
| 1982 | $(CH_2)_5$ | | O | $CH_2CF_3$ | $OCH_2CF_3$ | 4-trifluoromethylphenyl |
| 1983 | 5,5-spiro[2.3]hexane | | O | $CH_2CF_3$ | $OCH_2CF_3$ | 4-trifluoromethylphenyl |
| 1984 | Cyclopentyl | H | O | $CH_2CF_3$ | $OCH_2CF_3$ | 4-trifluoromethylphenyl |
| 1985 | $CH_2CH_3$ | H | O | $CH_2CF_3$ | $OCH_2CF_3$ | 4-tolyl |
| 1986 | $CH_2CF_3$ | H | O | $CH_2CF_3$ | $OCH_2CF_3$ | 4-tolyl |
| 1987 | $CH_2CH_2CH_3$ | H | O | $CH_2CF_3$ | $OCH_2CF_3$ | 4-tolyl |
| 1988 | $CH_2CH(CH_3)_2$ | H | O | $CH_2CF_3$ | $OCH_2CF_3$ | 4-tolyl |
| 1989 | cyclopropylmethyl | H | O | $CH_2CF_3$ | $OCH_2CF_3$ | 4-tolyl |
| 1990 | cyclobutylmethyl | H | O | $CH_2CF_3$ | $OCH_2CF_3$ | 4-tolyl |
| 1991 | $(CH_2)_2$ | | O | $CH_2CF_3$ | $OCH_2CF_3$ | 4-tolyl |
| 1992 | $(CH_2)_3$ | | O | $CH_2CF_3$ | $OCH_2CF_3$ | 4-tolyl |

TABLE 6-continued

Compounds of Formula IV

Formula IV

| Ex | R1 | R2 | X | R3 | R5 | Z |
|---|---|---|---|---|---|---|
| 1993 | (CH$_2$)$_4$ | | O | CH$_2$CF$_3$ | OCH$_2$CF$_3$ | 4-tolyl |
| 1994 | (CH$_2$)$_5$ | | O | CH$_2$CF$_3$ | OCH$_2$CF$_3$ | 4-tolyl |
| 1995 | 5,5-spiro[2.3]hexane | | O | CH$_2$CF$_3$ | OCH$_2$CF$_3$ | 4-tolyl |
| 1996 | Cyclopentyl | H | O | CH$_2$CF$_3$ | OCH$_2$CF$_3$ | 4-tolyl |
| 1997 | CH$_2$CH$_3$ | H | O | CH$_2$CF$_3$ | OCH$_2$CF$_3$ | 4-ethyl phenyl |
| 1998 | CH$_2$CF$_3$ | H | O | CH$_2$CF$_3$ | OCH$_2$CF$_3$ | 4-ethyl phenyl |
| 1999 | CH$_2$CH$_2$CH$_3$ | H | O | CH$_2$CF$_3$ | OCH$_2$CF$_3$ | 4-ethyl phenyl |
| 2000 | CH$_2$CH(CH$_3$)$_2$ | H | O | CH$_2$CF$_3$ | OCH$_2$CF$_3$ | 4-ethyl phenyl |
| 2001 | cyclopropylmethyl | H | O | CH$_2$CF$_3$ | OCH$_2$CF$_3$ | 4-ethyl phenyl |
| 2002 | cyclobutylmethyl | H | O | CH$_2$CF$_3$ | OCH$_2$CF$_3$ | 4-ethyl phenyl |
| 2003 | (CH$_2$)$_2$ | | O | CH$_2$CF$_3$ | OCH$_2$CF$_3$ | 4-ethyl phenyl |
| 2004 | (CH$_2$)$_3$ | | O | CH$_2$CF$_3$ | OCH$_2$CF$_3$ | 4-ethyl phenyl |
| 2005 | (CH$_2$)$_4$ | | O | CH$_2$CF$_3$ | OCH$_2$CF$_3$ | 4-ethyl phenyl |
| 2006 | (CH$_2$)$_5$ | | O | CH$_2$CF$_3$ | OCH$_2$CF$_3$ | 4-ethyl phenyl |
| 2007 | 5,5-spiro[2.3]hexane | | O | CH$_2$CF$_3$ | OCH$_2$CF$_3$ | 4-ethyl phenyl |
| 2008 | Cyclopentyl | H | O | CH$_2$CF$_3$ | OCH$_2$CF$_3$ | 4-ethyl phenyl |
| 2009 | CH$_2$CH$_3$ | H | O | CH$_2$CF$_3$ | OCH$_2$CF$_3$ | 4-isopropyl phenyl |
| 2010 | CH$_2$CF$_3$ | H | O | CH$_2$CF$_3$ | OCH$_2$CF$_3$ | 4-isopropyl phenyl |
| 2011 | CH$_2$CH$_2$CH$_3$ | H | O | CH$_2$CF$_3$ | OCH$_2$CF$_3$ | 4-isopropyl phenyl |
| 2012 | CH$_2$CH(CH$_3$)$_2$ | H | O | CH$_2$CF$_3$ | OCH$_2$CF$_3$ | 4-isopropyl phenyl |
| 2013 | cyclopropylmethyl | H | O | CH$_2$CF$_3$ | OCH$_2$CF$_3$ | 4-isopropyl phenyl |
| 2014 | cyclobutylmethyl | H | O | CH$_2$CF$_3$ | OCH$_2$CF$_3$ | 4-isopropyl phenyl |
| 2015 | (CH$_2$)$_2$ | | O | CH$_2$CF$_3$ | OCH$_2$CF$_3$ | 4-isopropyl phenyl |
| 2016 | (CH$_2$)$_3$ | | O | CH$_2$CF$_3$ | OCH$_2$CF$_3$ | 4-isopropyl phenyl |
| 2017 | (CH$_2$)$_4$ | | O | CH$_2$CF$_3$ | OCH$_2$CF$_3$ | 4-isopropyl phenyl |
| 2018 | (CH$_2$)$_5$ | | O | CH$_2$CF$_3$ | OCH$_2$CF$_3$ | 4-isopropyl phenyl |
| 2019 | 5,5-spiro[2.3]hexane | | O | CH$_2$CF$_3$ | OCH$_2$CF$_3$ | 4-isopropyl phenyl |
| 2020 | Cyclopentyl | H | O | CH$_2$CF$_3$ | OCH$_2$CF$_3$ | 4-isopropyl phenyl |
| 2031 | CH$_2$CH$_3$ | H | O | CH$_2$CF$_3$ | OCH$_2$CF$_3$ | 4-thiomethylphenyl |
| 2032 | CH$_2$CF$_3$ | H | O | CH$_2$CF$_3$ | OCH$_2$CF$_3$ | 4-thiomethylphenyl |
| 2033 | CH$_2$CH$_2$CH$_3$ | H | O | CH$_2$CF$_3$ | OCH$_2$CF$_3$ | 4-thiomethylphenyl |
| 2034 | CH$_2$CH(CH$_3$)$_2$ | H | O | CH$_2$CF$_3$ | OCH$_2$CF$_3$ | 4-thiomethylphenyl |
| 2035 | cyclopropylmethyl | H | O | CH$_2$CF$_3$ | OCH$_2$CF$_3$ | 4-thiomethylphenyl |
| 2036 | cyclobutylmethyl | H | O | CH$_2$CF$_3$ | OCH$_2$CF$_3$ | 4-thiomethylphenyl |
| 2037 | (CH$_2$)$_2$ | | O | CH$_2$CF$_3$ | OCH$_2$CF$_3$ | 4-thiomethylphenyl |
| 2038 | (CH$_2$)$_3$ | | O | CH$_2$CF$_3$ | OCH$_2$CF$_3$ | 4-thiomethylphenyl |
| 2039 | (CH$_2$)$_4$ | | O | CH$_2$CF$_3$ | OCH$_2$CF$_3$ | 4-thiomethylphenyl |
| 2040 | (CH$_2$)$_5$ | | O | CH$_2$CF$_3$ | OCH$_2$CF$_3$ | 4-thiomethylphenyl |
| 2041 | 5,5-spiro[2.3]hexane | | O | CH$_2$CF$_3$ | OCH$_2$CF$_3$ | 4-thiomethylphenyl |
| 2042 | Cyclopentyl | H | O | CH$_2$CF$_3$ | OCH$_2$CF$_3$ | 4-thiomethylphenyl |
| 2043 | CH$_2$CH$_3$ | H | O | CH$_2$CF$_3$ | OCH$_2$CF$_3$ | 4-trifluoromethoxyphenyl |
| 2044 | CH$_2$CF$_3$ | H | O | CH$_2$CF$_3$ | OCH$_2$CF$_3$ | 4-trifluoromethoxyphenyl |
| 2045 | CH$_2$CH$_2$CH$_3$ | H | O | CH$_2$CF$_3$ | OCH$_2$CF$_3$ | 4-trifluoromethoxyphenyl |
| 2046 | CH$_2$CH(CH$_3$)$_2$ | H | O | CH$_2$CF$_3$ | OCH$_2$CF$_3$ | 4-trifluoromethoxyphenyl |
| 2047 | cyclopropylmethyl | H | O | CH$_2$CF$_3$ | OCH$_2$CF$_3$ | 4-trifluoromethoxyphenyl |
| 2048 | cyclobutylmethyl | H | O | CH$_2$CF$_3$ | OCH$_2$CF$_3$ | 4-trifluoromethoxyphenyl |
| 2049 | (CH$_2$)$_2$ | | O | CH$_2$CF$_3$ | OCH$_2$CF$_3$ | 4-trifluoromethoxyphenyl |
| 2050 | (CH$_2$)$_3$ | | O | CH$_2$CF$_3$ | OCH$_2$CF$_3$ | 4-trifluoromethoxyphenyl |
| 2051 | (CH$_2$)$_4$ | | O | CH$_2$CF$_3$ | OCH$_2$CF$_3$ | 4-trifluoromethoxyphenyl |
| 2052 | (CH$_2$)$_5$ | | O | CH$_2$CF$_3$ | OCH$_2$CF$_3$ | 4-trifluoromethoxyphenyl |
| 2053 | 5,5-spiro[2.3]hexane | | O | CH$_2$CF$_3$ | OCH$_2$CF$_3$ | 4-trifluoromethoxyphenyl |
| 2054 | Cyclopentyl | H | O | CH$_2$CF$_3$ | OCH$_2$CF$_3$ | 4-trifluoromethoxyphenyl |
| 2055 | CH$_2$CH$_3$ | H | O | CH$_2$-c-Pr | OCH$_2$CF$_3$ | 4-trifluoromethylphenyl |
| 2056 | CH$_2$CF$_3$ | H | O | CH$_2$-c-Pr | OCH$_2$CF$_3$ | 4-trifluoromethylphenyl |
| 2057 | CH$_2$CH$_2$CH$_3$ | H | O | CH$_2$-c-Pr | OCH$_2$CF$_3$ | 4-trifluoromethylphenyl |
| 2058 | CH$_2$CH(CH$_3$)$_2$ | H | O | CH$_2$-c-Pr | OCH$_2$CF$_3$ | 4-trifluoromethylphenyl |
| 2059 | cyclopropylmethyl | H | O | CH$_2$-c-Pr | OCH$_2$CF$_3$ | 4-trifluoromethylphenyl |
| 2060 | cyclobutylmethyl | H | O | CH$_2$-c-Pr | OCH$_2$CF$_3$ | 4-trifluoromethylphenyl |
| 2061 | (CH$_2$)$_2$ | | O | CH$_2$-c-Pr | OCH$_2$CF$_3$ | 4-trifluoromethylphenyl |
| 2062 | (CH$_2$)$_3$ | | O | CH$_2$-c-Pr | OCH$_2$CF$_3$ | 4-trifluoromethylphenyl |
| 2063 | (CH$_2$)$_4$ | | O | CH$_2$-c-Pr | OCH$_2$CF$_3$ | 4-trifluoromethylphenyl |
| 2064 | (CH$_2$)$_5$ | | O | CH$_2$-c-Pr | OCH$_2$CF$_3$ | 4-trifluoromethylphenyl |
| 2065 | 5,5-spiro[2.3]hexane | | O | CH$_2$-c-Pr | OCH$_2$CF$_3$ | 4-trifluoromethylphenyl |

TABLE 6-continued

Compounds of Formula IV

Formula IV

| Ex | R1 | R2 | X | R3 | R5 | Z |
|---|---|---|---|---|---|---|
| 2066 | Cyclopentyl | H | O | $CH_2$-c-Pr | $OCH_2CF_3$ | 4-trifluoromethylphenyl |
| 2067 | $CH_2CH_3$ | H | O | $CH_2$-c-Pr | $OCH_2CF_3$ | 4-tolyl |
| 2068 | $CH_2CF_3$ | H | O | $CH_2$-c-Pr | $OCH_2CF_3$ | 4-tolyl |
| 2069 | $CH_2CH_2CH_3$ | H | O | $CH_2$-c-Pr | $OCH_2CF_3$ | 4-tolyl |
| 2070 | $CH_2CH(CH_3)_2$ | H | O | $CH_2$-c-Pr | $OCH_2CF_3$ | 4-tolyl |
| 2071 | cyclopropylmethyl | H | O | $CH_2$-c-Pr | $OCH_2CF_3$ | 4-tolyl |
| 2072 | cyclobutylmethyl | H | O | $CH_2$-c-Pr | $OCH_2CF_3$ | 4-tolyl |
| 2073 | $(CH_2)_2$ | | O | $CH_2$-c-Pr | $OCH_2CF_3$ | 4-tolyl |
| 2074 | $(CH_2)_3$ | | O | $CH_2$-c-Pr | $OCH_2CF_3$ | 4-tolyl |
| 2075 | $(CH_2)_4$ | | O | $CH_2$-c-Pr | $OCH_2CF_3$ | 4-tolyl |
| 2076 | $(CH_2)_5$ | | O | $CH_2$-c-Pr | $OCH_2CF_3$ | 4-tolyl |
| 2077 | 5,5-spiro[2.3]hexane | | O | $CH_2$-c-Pr | $OCH_2CF_3$ | 4-tolyl |
| 2078 | Cyclopentyl | H | O | $CH_2$-c-Pr | $OCH_2CF_3$ | 4-tolyl |
| 2079 | $CH_2CH_3$ | H | O | $CH_2$-c-Pr | $OCH_2CF_3$ | 4-ethyl phenyl |
| 2080 | $CH_2CF_3$ | H | O | $CH_2$-c-Pr | $OCH_2CF_3$ | 4-ethyl phenyl |
| 2081 | $CH_2CH_2CH_3$ | H | O | $CH_2$-c-Pr | $OCH_2CF_3$ | 4-ethyl phenyl |
| 2082 | $CH_2CH(CH_3)_2$ | H | O | $CH_2$-c-Pr | $OCH_2CF_3$ | 4-ethyl phenyl |
| 2083 | cyclopropylmethyl | H | O | $CH_2$-c-Pr | $OCH_2CF_3$ | 4-ethyl phenyl |
| 2084 | cyclobutylmethyl | H | O | $CH_2$-c-Pr | $OCH_2CF_3$ | 4-ethyl phenyl |
| 2085 | $(CH_2)_2$ | | O | $CH_2$-c-Pr | $OCH_2CF_3$ | 4-ethyl phenyl |
| 2086 | $(CH_2)_3$ | | O | $CH_2$-c-Pr | $OCH_2CF_3$ | 4-ethyl phenyl |
| 2087 | $(CH_2)_4$ | | O | $CH_2$-c-Pr | $OCH_2CF_3$ | 4-ethyl phenyl |
| 2088 | $(CH_2)_5$ | | O | $CH_2$-c-Pr | $OCH_2CF_3$ | 4-ethyl phenyl |
| 2089 | 5,5-spiro[2.3]hexane | | O | $CH_2$-c-Pr | $OCH_2CF_3$ | 4-ethyl phenyl |
| 2090 | Cyclopentyl | H | O | $CH_2$-c-Pr | $OCH_2CF_3$ | 4-ethyl phenyl |
| 2091 | $CH_2CH_3$ | H | O | $CH_2$-c-Pr | $OCH_2CF_3$ | 4-isopropyl phenyl |
| 2092 | $CH_2CF_3$ | H | O | $CH_2$-c-Pr | $OCH_2CF_3$ | 4-isopropyl phenyl |
| 2093 | $CH_2CH_2CH_3$ | H | O | $CH_2$-c-Pr | $OCH_2CF_3$ | 4-isopropyl phenyl |
| 2094 | $CH_2CH(CH_3)_2$ | H | O | $CH_2$-c-Pr | $OCH_2CF_3$ | 4-isopropyl phenyl |
| 2095 | cyclopropylmethyl | H | O | $CH_2$-c-Pr | $OCH_2CF_3$ | 4-isopropyl phenyl |
| 2096 | cyclobutylmethyl | H | O | $CH_2$-c-Pr | $OCH_2CF_3$ | 4-isopropyl phenyl |
| 2097 | $(CH_2)_2$ | | O | $CH_2$-c-Pr | $OCH_2CF_3$ | 4-isopropyl phenyl |
| 2098 | $(CH_2)_3$ | | O | $CH_2$-c-Pr | $OCH_2CF_3$ | 4-isopropyl phenyl |
| 2099 | $(CH_2)_4$ | | O | $CH_2$-c-Pr | $OCH_2CF_3$ | 4-isopropyl phenyl |
| 2100 | $(CH_2)_5$ | | O | $CH_2$-c-Pr | $OCH_2CF_3$ | 4-isopropyl phenyl |
| 2101 | 5,5-spiro[2.3]hexane | | O | $CH_2$-c-Pr | $OCH_2CF_3$ | 4-isopropyl phenyl |
| 2102 | Cyclopentyl | H | O | $CH_2$-c-Pr | $OCH_2CF_3$ | 4-isopropyl phenyl |
| 2103 | $CH_2CH_3$ | H | O | $CH_2$-c-Pr | $OCH_2CF_3$ | 4-thiomethylphenyl |
| 2104 | $CH_2CF_3$ | H | O | $CH_2$-c-Pr | $OCH_2CF_3$ | 4-thiomethylphenyl |
| 2105 | $CH_2CH_2CH_3$ | H | O | $CH_2$-c-Pr | $OCH_2CF_3$ | 4-thiomethylphenyl |
| 2106 | $CH_2CH(CH_3)_2$ | H | O | $CH_2$-c-Pr | $OCH_2CF_3$ | 4-thiomethylphenyl |
| 2107 | cyclopropylmethyl | H | O | $CH_2$-c-Pr | $OCH_2CF_3$ | 4-thiomethylphenyl |
| 2108 | cyclobutylmethyl | H | O | $CH_2$-c-Pr | $OCH_2CF_3$ | 4-thiomethylphenyl |
| 2109 | $(CH_2)_2$ | | O | $CH_2$-c-Pr | $OCH_2CF_3$ | 4-thiomethylphenyl |
| 2110 | $(CH_2)_3$ | | O | $CH_2$-c-Pr | $OCH_2CF_3$ | 4-thiomethylphenyl |
| 2111 | $(CH_2)_4$ | | O | $CH_2$-c-Pr | $OCH_2CF_3$ | 4-thiomethylphenyl |
| 2112 | $(CH_2)_5$ | | O | $CH_2$-c-Pr | $OCH_2CF_3$ | 4-thiomethylphenyl |
| 2113 | 5,5-spiro[2.3]hexane | | O | $CH_2$-c-Pr | $OCH_2CF_3$ | 4-thiomethylphenyl |
| 2114 | Cyclopentyl | H | O | $CH_2$-c-Pr | $OCH_2CF_3$ | 4-thiomethylphenyl |
| 2115 | $CH_2CH_3$ | H | O | $CH_2$-c-Pr | $OCH_2CF_3$ | 4-trifluoromethoxyphenyl |
| 2116 | $CH_2CF_3$ | H | O | $CH_2$-c-Pr | $OCH_2CF_3$ | 4-trifluoromethoxyphenyl |
| 2117 | $CH_2CH_2CH_3$ | H | O | $CH_2$-c-Pr | $OCH_2CF_3$ | 4-trifluoromethoxyphenyl |
| 2118 | $CH_2CH(CH_3)_2$ | H | O | $CH_2$-c-Pr | $OCH_2CF_3$ | 4-trifluoromethoxyphenyl |
| 2119 | cyclopropylmethyl | H | O | $CH_2$-c-Pr | $OCH_2CF_3$ | 4-trifluoromethoxyphenyl |
| 2120 | cyclobutylmethyl | H | O | $CH_2$-c-Pr | $OCH_2CF_3$ | 4-trifluoromethoxyphenyl |
| 2121 | $(CH_2)_2$ | | O | $CH_2$-c-Pr | $OCH_2CF_3$ | 4-trifluoromethoxyphenyl |
| 2122 | $(CH_2)_3$ | | O | $CH_2$-c-Pr | $OCH_2CF_3$ | 4-trifluoromethoxyphenyl |
| 2123 | $(CH_2)_4$ | | O | $CH_2$-c-Pr | $OCH_2CF_3$ | 4-trifluoromethoxyphenyl |
| 2124 | $(CH_2)_5$ | | O | $CH_2$-c-Pr | $OCH_2CF_3$ | 4-trifluoromethoxyphenyl |
| 2125 | 5,5-spiro[2.3]hexane | | O | $CH_2$-c-Pr | $OCH_2CF_3$ | 4-trifluoromethoxyphenyl |
| 2126 | Cyclopentyl | H | O | $CH_2$-c-Pr | $OCH_2CF_3$ | 4-trifluoromethoxyphenyl |

TABLE 7

Compounds of Formula VII

Formula VII

| Ex | R1 | R2 | Y | R4 | R5 | Z |
|---|---|---|---|---|---|---|
| 2127 | $CH_2CH_3$ | H | O | $CH_2CF_3$ | $CF_3$ | 4-trifluoromethylphenyl |
| 2128 | $CH_2CF_3$ | H | O | $CH_2CF_3$ | $CF_3$ | 4-trifluoromethylphenyl |
| 2129 | $CH_2CH_2CH_3$ | H | O | $CH_2CF_3$ | $CF_3$ | 4-trifluoromethylphenyl |
| 2130 | $CH_2CH(CH_3)_2$ | H | O | $CH_2CF_3$ | $CF_3$ | 4-trifluoromethylphenyl |
| 2131 | cyclopropylmethyl | H | O | $CH_2CF_3$ | $CF_3$ | 4-trifluoromethylphenyl |
| 2132 | cyclobutylmethyl | H | O | $CH_2CF_3$ | $CF_3$ | 4-trifluoromethylphenyl |
| 2133 | $(CH_2)_2$ | | O | $CH_2CF_3$ | $CF_3$ | 4-trifluoromethylphenyl |
| 2134 | $(CH_2)_3$ | | O | $CH_2CF_3$ | $CF_3$ | 4-trifluoromethylphenyl |
| 2135 | $(CH_2)_4$ | | O | $CH_2CF_3$ | $CF_3$ | 4-trifluoromethylphenyl |
| 2136 | $(CH_2)_5$ | | O | $CH_2CF_3$ | $CF_3$ | 4-trifluoromethylphenyl |
| 2137 | 5,5-spiro[2.3]hexane | | O | $CH_2CF_3$ | $CF_3$ | 4-trifluoromethylphenyl |
| 2138 | Cyclopentyl | H | O | $CH_2CF_3$ | $CF_3$ | 4-trifluoromethylphenyl |
| 2139 | $CH_2CH_3$ | H | O | $CH_2CF_3$ | $CF_3$ | 4-tolyl |
| 2140 | $CH_2CF_3$ | H | O | $CH_2CF_3$ | $CF_3$ | 4-tolyl |
| 2141 | $CH_2CH_2CH_3$ | H | O | $CH_2CF_3$ | $CF_3$ | 4-tolyl |
| 2142 | $CH_2CH(CH_3)_2$ | H | O | $CH_2CF_3$ | $CF_3$ | 4-tolyl |
| 2143 | cyclopropylmethyl | H | O | $CH_2CF_3$ | $CF_3$ | 4-tolyl |
| 2144 | cyclobutylmethyl | H | O | $CH_2CF_3$ | $CF_3$ | 4-tolyl |
| 2145 | $(CH_2)_2$ | | O | $CH_2CF_3$ | $CF_3$ | 4-tolyl |
| 2146 | $(CH_2)_3$ | | O | $CH_2CF_3$ | $CF_3$ | 4-tolyl |
| 2147 | $(CH_2)_4$ | | O | $CH_2CF_3$ | $CF_3$ | 4-tolyl |
| 2148 | $(CH_2)_5$ | | O | $CH_2CF_3$ | $CF_3$ | 4-tolyl |
| 2149 | 5,5-spiro[2.3]hexane | | O | $CH_2CF_3$ | $CF_3$ | 4-tolyl |
| 2150 | Cyclopentyl | H | O | $CH_2CF_3$ | $CF_3$ | 4-tolyl |
| 2151 | $CH_2CH_3$ | H | O | $CH_2CF_3$ | $CF_3$ | 4-ethyl phenyl |
| 2152 | $CH_2CF_3$ | H | O | $CH_2CF_3$ | $CF_3$ | 4-ethyl phenyl |
| 2153 | $CH_2CH_2CH_3$ | H | O | $CH_2CF_3$ | $CF_3$ | 4-ethyl phenyl |
| 2154 | $CH_2CH(CH_3)_2$ | H | O | $CH_2CF_3$ | $CF_3$ | 4-ethyl phenyl |
| 2155 | cyclopropylmethyl | H | O | $CH_2CF_3$ | $CF_3$ | 4-ethyl phenyl |
| 2156 | cyclobutylmethyl | H | O | $CH_2CF_3$ | $CF_3$ | 4-ethyl phenyl |
| 2157 | $(CH_2)_2$ | | O | $CH_2CF_3$ | $CF_3$ | 4-ethyl phenyl |
| 2158 | $(CH_2)_3$ | | O | $CH_2CF_3$ | $CF_3$ | 4-ethyl phenyl |
| 2159 | $(CH_2)_4$ | | O | $CH_2CF_3$ | $CF_3$ | 4-ethyl phenyl |
| 2160 | $(CH_2)_5$ | | O | $CH_2CF_3$ | $CF_3$ | 4-ethyl phenyl |
| 2161 | 5,5-spiro[2.3]hexane | | O | $CH_2CF_3$ | $CF_3$ | 4-ethyl phenyl |
| 2162 | Cyclopentyl | H | O | $CH_2CF_3$ | $CF_3$ | 4-ethyl phenyl |
| 2163 | $CH_2CH_3$ | H | O | $CH_2CF_3$ | $CF_3$ | 4-isopropyl phenyl |
| 2164 | $CH_2CF_3$ | H | O | $CH_2CF_3$ | $CF_3$ | 4-isopropyl phenyl |
| 2165 | $CH_2CH_2CH_3$ | H | O | $CH_2CF_3$ | $CF_3$ | 4-isopropyl phenyl |
| 2166 | $CH_2CH(CH_3)_2$ | H | O | $CH_2CF_3$ | $CF_3$ | 4-isopropyl phenyl |
| 2167 | cyclopropylmethyl | H | O | $CH_2CF_3$ | $CF_3$ | 4-isopropyl phenyl |
| 2168 | cyclobutylmethyl | H | O | $CH_2CF_3$ | $CF_3$ | 4-isopropyl phenyl |
| 2169 | $(CH_2)_2$ | | O | $CH_2CF_3$ | $CF_3$ | 4-isopropyl phenyl |
| 2170 | $(CH_2)_3$ | | O | $CH_2CF_3$ | $CF_3$ | 4-isopropyl phenyl |
| 2171 | $(CH_2)_4$ | | O | $CH_2CF_3$ | $CF_3$ | 4-isopropyl phenyl |
| 2172 | $(CH_2)_5$ | | O | $CH_2CF_3$ | $CF_3$ | 4-isopropyl phenyl |
| 2173 | 5,5-spiro[2.3]hexane | | O | $CH_2CF_3$ | $CF_3$ | 4-isopropyl phenyl |
| 2174 | Cyclopentyl | H | O | $CH_2CF_3$ | $CF_3$ | 4-isopropyl phenyl |
| 2175 | $CH_2CH_3$ | H | O | $CH_2CF_3$ | $CF_3$ | 4-thiomethylphenyl |
| 2176 | $CH_2CF_3$ | H | O | $CH_2CF_3$ | $CF_3$ | 4-thiomethylphenyl |
| 2177 | $CH_2CH_2CH_3$ | H | O | $CH_2CF_3$ | $CF_3$ | 4-thiomethylphenyl |
| 2178 | $CH_2CH(CH_3)_2$ | H | O | $CH_2CF_3$ | $CF_3$ | 4-thiomethylphenyl |
| 2179 | cyclopropylmethyl | H | O | $CH_2CF_3$ | $CF_3$ | 4-thiomethylphenyl |
| 2180 | cyclobutylmethyl | H | O | $CH_2CF_3$ | $CF_3$ | 4-thiomethylphenyl |
| 2181 | $(CH_2)_2$ | | O | $CH_2CF_3$ | $CF_3$ | 4-thiomethylphenyl |
| 2182 | $(CH_2)_3$ | | O | $CH_2CF_3$ | $CF_3$ | 4-thiomethylphenyl |
| 2183 | $(CH_2)_4$ | | O | $CH_2CF_3$ | $CF_3$ | 4-thiomethylphenyl |
| 2184 | $(CH_2)_5$ | | O | $CH_2CF_3$ | $CF_3$ | 4-thiomethylphenyl |
| 2185 | 5,5-spiro[2.3]hexane | | O | $CH_2CF_3$ | $CF_3$ | 4-thiomethylphenyl |

TABLE 7-continued

Compounds of Formula VII

Formula VII

| Ex | R1 | R2 | Y | R4 | R5 | Z |
|---|---|---|---|---|---|---|
| 2186 | Cyclopentyl | H | O | CH$_2$CF$_3$ | CF$_3$ | 4-thiomethylphenyl |
| 2187 | CH$_2$CH$_3$ | H | O | CH$_2$CF$_3$ | CF$_3$ | 4-trifluoromethoxyphenyl |
| 2188 | CH$_2$CF$_3$ | H | O | CH$_2$CF$_3$ | CF$_3$ | 4-trifluoromethoxyphenyl |
| 2189 | CH$_2$CH$_2$CH$_3$ | H | O | CH$_2$CF$_3$ | CF$_3$ | 4-trifluoromethoxyphenyl |
| 2190 | CH$_2$CH(CH$_3$)$_2$ | H | O | CH$_2$CF$_3$ | CF$_3$ | 4-trifluoromethoxyphenyl |
| 2191 | cyclopropylmethyl | H | O | CH$_2$CF$_3$ | CF$_3$ | 4-trifluoromethoxyphenyl |
| 2192 | cyclobutylmethyl | H | O | CH$_2$CF$_3$ | CF$_3$ | 4-trifluoromethoxyphenyl |
| 2193 | (CH$_2$)$_2$ | | O | CH$_2$CF$_3$ | CF$_3$ | 4-trifluoromethoxyphenyl |
| 2194 | (CH$_2$)$_3$ | | O | CH$_2$CF$_3$ | CF$_3$ | 4-trifluoromethoxyphenyl |
| 2195 | (CH$_2$)$_4$ | | O | CH$_2$CF$_3$ | CF$_3$ | 4-trifluoromethoxyphenyl |
| 2196 | (CH$_2$)$_5$ | | O | CH$_2$CF$_3$ | CF$_3$ | 4-trifluoromethoxyphenyl |
| 2197 | 5,5-spiro[2.3]hexane | | O | CH$_2$CF$_3$ | CF$_3$ | 4-trifluoromethoxyphenyl |
| 2198 | Cyclopentyl | H | O | CH$_2$CF$_3$ | CF$_3$ | 4-trifluoromethoxyphenyl |
| 2199 | CH$_2$CH$_3$ | H | O | CH$_2$-c-Pr | CF$_3$ | 4-trifluoromethylphenyl |
| 2200 | CH$_2$CF$_3$ | H | O | CH$_2$-c-Pr | CF$_3$ | 4-trifluoromethylphenyl |
| 2201 | CH$_2$CH$_2$CH$_3$ | H | O | CH$_2$-c-Pr | CF$_3$ | 4-trifluoromethylphenyl |
| 2202 | CH$_2$CH(CH$_3$)$_2$ | H | O | CH$_2$-c-Pr | CF$_3$ | 4-trifluoromethylphenyl |
| 2203 | cyclopropylmethyl | H | O | CH$_2$-c-Pr | CF$_3$ | 4-trifluoromethylphenyl |
| 2204 | cyclobutylmethyl | H | O | CH$_2$-c-Pr | CF$_3$ | 4-trifluoromethylphenyl |
| 2205 | (CH$_2$)$_2$ | | O | CH$_2$-c-Pr | CF$_3$ | 4-trifluoromethylphenyl |
| 2206 | (CH$_2$)$_3$ | | O | CH$_2$-c-Pr | CF$_3$ | 4-trifluoromethylphenyl |
| 2207 | (CH$_2$)$_4$ | | O | CH$_2$-c-Pr | CF$_3$ | 4-trifluoromethylphenyl |
| 2208 | (CH$_2$)$_5$ | | O | CH$_2$-c-Pr | CF$_3$ | 4-trifluoromethylphenyl |
| 2209 | 5,5-spiro[2.3]hexane | | O | CH$_2$-c-Pr | CF$_3$ | 4-trifluoromethylphenyl |
| 2210 | Cyclopentyl | H | O | CH$_2$-c-Pr | CF$_3$ | 4-trifluoromethylphenyl |
| 2211 | CH$_2$CH$_3$ | H | O | CH$_2$-c-Pr | CF$_3$ | 4-tolyl |
| 2212 | CH$_2$CF$_3$ | H | O | CH$_2$-c-Pr | CF$_3$ | 4-tolyl |
| 2213 | CH$_2$CH$_2$CH$_3$ | H | O | CH$_2$-c-Pr | CF$_3$ | 4-tolyl |
| 2214 | CH$_2$CH(CH$_3$)$_2$ | H | O | CH$_2$-c-Pr | CF$_3$ | 4-tolyl |
| 2215 | cyclopropylmethyl | H | O | CH$_2$-c-Pr | CF$_3$ | 4-tolyl |
| 2216 | cyclobutylmethyl | H | O | CH$_2$-c-Pr | CF$_3$ | 4-tolyl |
| 2217 | (CH$_2$)$_2$ | | O | CH$_2$-c-Pr | CF$_3$ | 4-tolyl |
| 2218 | (CH$_2$)$_3$ | | O | CH$_2$-c-Pr | CF$_3$ | 4-tolyl |
| 2219 | (CH$_2$)$_4$ | | O | CH$_2$-c-Pr | CF$_3$ | 4-tolyl |
| 2220 | (CH$_2$)$_5$ | | O | CH$_2$-c-Pr | CF$_3$ | 4-tolyl |
| 2221 | 5,5-spiro[2.3]hexane | | O | CH$_2$-c-Pr | CF$_3$ | 4-tolyl |
| 2222 | Cyclopentyl | H | O | CH$_2$-c-Pr | CF$_3$ | 4-tolyl |
| 2223 | CH$_2$CH$_3$ | H | O | CH$_2$-c-Pr | CF$_3$ | 4-ethyl phenyl |
| 2224 | CH$_2$CF$_3$ | H | O | CH$_2$-c-Pr | CF$_3$ | 4-ethyl phenyl |
| 2225 | CH$_2$CH$_2$CH$_3$ | H | O | CH$_2$-c-Pr | CF$_3$ | 4-ethyl phenyl |
| 2226 | CH$_2$CH(CH$_3$)$_2$ | H | O | CH$_2$-c-Pr | CF$_3$ | 4-ethyl phenyl |
| 2227 | cyclopropylmethyl | H | O | CH$_2$-c-Pr | CF$_3$ | 4-ethyl phenyl |
| 2228 | cyclobutylmethyl | H | O | CH$_2$-c-Pr | CF$_3$ | 4-ethyl phenyl |
| 2229 | (CH$_2$)$_2$ | | O | CH$_2$-c-Pr | CF$_3$ | 4-ethyl phenyl |
| 2230 | (CH$_2$)$_3$ | | O | CH$_2$-c-Pr | CF$_3$ | 4-ethyl phenyl |
| 2231 | (CH$_2$)$_4$ | | O | CH$_2$-c-Pr | CF$_3$ | 4-ethyl phenyl |
| 2232 | (CH$_2$)$_5$ | | O | CH$_2$-c-Pr | CF$_3$ | 4-ethyl phenyl |
| 2233 | 5,5-spiro[2.3]hexane | | O | CH$_2$-c-Pr | CF$_3$ | 4-ethyl phenyl |
| 2234 | Cyclopentyl | H | O | CH$_2$-c-Pr | CF$_3$ | 4-ethyl phenyl |
| 2235 | CH$_2$CH$_3$ | H | O | CH$_2$-c-Pr | CF$_3$ | 4-isopropyl phenyl |
| 2236 | CH$_2$CF$_3$ | H | O | CH$_2$-c-Pr | CF$_3$ | 4-isopropyl phenyl |
| 2237 | CH$_2$CH$_2$CH$_3$ | H | O | CH$_2$-c-Pr | CF$_3$ | 4-isopropyl phenyl |
| 2238 | CH$_2$CH(CH$_3$)$_2$ | H | O | CH$_2$-c-Pr | CF$_3$ | 4-isopropyl phenyl |
| 2239 | cyclopropylmethyl | H | O | CH$_2$-c-Pr | CF$_3$ | 4-isopropyl phenyl |
| 2240 | cyclobutylmethyl | H | O | CH$_2$-c-Pr | CF$_3$ | 4-isopropyl phenyl |
| 2241 | (CH$_2$)$_2$ | | O | CH$_2$-c-Pr | CF$_3$ | 4-isopropyl phenyl |

TABLE 7-continued

Compounds of Formula VII

Formula VII

| Ex | R1 | R2 | Y | R4 | R5 | Z |
|---|---|---|---|---|---|---|
| 2242 | (CH$_2$)$_3$ | | O | CH$_2$-c-Pr | CF$_3$ | 4-isopropyl phenyl |
| 2243 | (CH$_2$)$_4$ | | O | CH$_2$-c-Pr | CF$_3$ | 4-isopropyl phenyl |
| 2244 | (CH$_2$)$_5$ | | O | CH$_2$-c-Pr | CF$_3$ | 4-isopropyl phenyl |
| 2245 | 5,5-spiro[2.3]hexane | | O | CH$_2$-c-Pr | CF$_3$ | 4-isopropyl phenyl |
| 2246 | Cyclopentyl | H | O | CH$_2$-c-Pr | CF$_3$ | 4-isopropyl phenyl |
| 2247 | CH$_2$CH$_3$ | H | O | CH$_2$-c-Pr | CF$_3$ | 4-thiomethylphenyl |
| 2248 | CH$_2$CF$_3$ | H | O | CH$_2$-c-Pr | CF$_3$ | 4-thiomethylphenyl |
| 2249 | CH$_2$CH$_2$CH$_3$ | H | O | CH$_2$-c-Pr | CF$_3$ | 4-thiomethylphenyl |
| 2250 | CH$_2$CH(CH$_3$)$_2$ | H | O | CH$_2$-c-Pr | CF$_3$ | 4-thiomethylphenyl |
| 2251 | cyclopropylmethyl | H | O | CH$_2$-c-Pr | CF$_3$ | 4-thiomethylphenyl |
| 2252 | cyclobutylmethyl | H | O | CH$_2$-c-Pr | CF$_3$ | 4-thiomethylphenyl |
| 2253 | (CH$_2$)$_2$ | | O | CH$_2$-c-Pr | CF$_3$ | 4-thiomethylphenyl |
| 2254 | (CH$_2$)$_3$ | | O | CH$_2$-c-Pr | CF$_3$ | 4-thiomethylphenyl |
| 2255 | (CH$_2$)$_4$ | | O | CH$_2$-c-Pr | CF$_3$ | 4-thiomethylphenyl |
| 2256 | (CH$_2$)$_5$ | | O | CH$_2$-c-Pr | CF$_3$ | 4-thiomethylphenyl |
| 2257 | 5,5-spiro[2.3]hexane | | O | CH$_2$-c-Pr | CF$_3$ | 4-thiomethylphenyl |
| 2258 | Cyclopentyl | H | O | CH$_2$-c-Pr | CF$_3$ | 4-thiomethylphenyl |
| 2259 | CH$_2$CH$_3$ | H | O | CH$_2$-c-Pr | CF$_3$ | 4-trifluoromethoxyphenyl |
| 2260 | CH$_2$CF$_3$ | H | O | CH$_2$-c-Pr | CF$_3$ | 4-trifluoromethoxyphenyl |
| 2261 | CH$_2$CH$_2$CH$_3$ | H | O | CH$_2$-c-Pr | CF$_3$ | 4-trifluoromethoxyphenyl |
| 2262 | CH$_2$CH(CH$_3$)$_2$ | H | O | CH$_2$-c-Pr | CF$_3$ | 4-trifluoromethoxyphenyl |
| 2263 | cyclopropylmethyl | H | O | CH$_2$-c-Pr | CF$_3$ | 4-trifluoromethoxyphenyl |
| 2264 | cyclobutylmethyl | H | O | CH$_2$-c-Pr | CF$_3$ | 4-trifluoromethoxyphenyl |
| 2265 | (CH$_2$)$_2$ | | O | CH$_2$-c-Pr | CF$_3$ | 4-trifluoromethoxyphenyl |
| 2266 | (CH$_2$)$_3$ | | O | CH$_2$-c-Pr | CF$_3$ | 4-trifluoromethoxyphenyl |
| 2267 | (CH$_2$)$_4$ | | O | CH$_2$-c-Pr | CF$_3$ | 4-trifluoromethoxyphenyl |
| 2268 | (CH$_2$)$_5$ | | O | CH$_2$-c-Pr | CF$_3$ | 4-trifluoromethoxyphenyl |
| 2269 | 5,5-spiro[2.3]hexane | | O | CH$_2$-c-Pr | CF$_3$ | 4-trifluoromethoxyphenyl |
| 2270 | Cyclopentyl | H | O | CH$_2$-c-Pr | CF$_3$ | 4-trifluoromethoxyphenyl |
| 2271 | CH$_2$CH$_3$ | H | O | CH$_2$CF$_3$ | OCH$_2$CF$_3$ | 4-trifluoromethylphenyl |
| 2272 | CH$_2$CF$_3$ | H | O | CH$_2$CF$_3$ | OCH$_2$CF$_3$ | 4-trifluoromethylphenyl |
| 2273 | CH$_2$CH$_2$CH$_3$ | H | O | CH$_2$CF$_3$ | OCH$_2$CF$_3$ | 4-trifluoromethylphenyl |
| 2274 | CH$_2$CH(CH$_3$)$_2$ | H | O | CH$_2$CF$_3$ | OCH$_2$CF$_3$ | 4-trifluoromethylphenyl |
| 2275 | cyclopropylmethyl | H | O | CH$_2$CF$_3$ | OCH$_2$CF$_3$ | 4-trifluoromethylphenyl |
| 2276 | cyclobutylmethyl | H | O | CH$_2$CF$_3$ | OCH$_2$CF$_3$ | 4-trifluoromethylphenyl |
| 2277 | (CH$_2$)$_2$ | | O | CH$_2$CF$_3$ | OCH$_2$CF$_3$ | 4-trifluoromethylphenyl |
| 2278 | (CH$_2$)$_3$ | | O | CH$_2$CF$_3$ | OCH$_2$CF$_3$ | 4-trifluoromethylphenyl |
| 2279 | (CH$_2$)$_4$ | | O | CH$_2$CF$_3$ | OCH$_2$CF$_3$ | 4-trifluoromethylphenyl |
| 2280 | (CH$_2$)$_5$ | | O | CH$_2$CF$_3$ | OCH$_2$CF$_3$ | 4-trifluoromethylphenyl |
| 2281 | 5,5-spiro[2.3]hexane | | O | CH$_2$CF$_3$ | OCH$_2$CF$_3$ | 4-trifluoromethylphenyl |
| 2282 | Cyclopentyl | H | O | CH$_2$CF$_3$ | OCH$_2$CF$_3$ | 4-trifluoromethylphenyl |
| 2283 | CH$_2$CH$_3$ | H | O | CH$_2$CF$_3$ | OCH$_2$CF$_3$ | 4-tolyl |
| 2284 | CH$_2$CF$_3$ | H | O | CH$_2$CF$_3$ | OCH$_2$CF$_3$ | 4-tolyl |
| 2285 | CH$_2$CH$_2$CH$_3$ | H | O | CH$_2$CF$_3$ | OCH$_2$CF$_3$ | 4-tolyl |
| 2286 | CH$_2$CH(CH$_3$)$_2$ | H | O | CH$_2$CF$_3$ | OCH$_2$CF$_3$ | 4-tolyl |
| 2287 | cyclopropylmethyl | H | O | CH$_2$CF$_3$ | OCH$_2$CF$_3$ | 4-tolyl |
| 2288 | cyclobutylmethyl | H | O | CH$_2$CF$_3$ | OCH$_2$CF$_3$ | 4-tolyl |
| 2289 | (CH$_2$)$_2$ | | O | CH$_2$CF$_3$ | OCH$_2$CF$_3$ | 4-tolyl |
| 2290 | (CH$_2$)$_3$ | | O | CH$_2$CF$_3$ | OCH$_2$CF$_3$ | 4-tolyl |
| 2291 | (CH$_2$)$_4$ | | O | CH$_2$CF$_3$ | OCH$_2$CF$_3$ | 4-tolyl |
| 2292 | (CH$_2$)$_5$ | | O | CH$_2$CF$_3$ | OCH$_2$CF$_3$ | 4-tolyl |
| 2293 | 5,5-spiro[2.3]hexane | | O | CH$_2$CF$_3$ | OCH$_2$CF$_3$ | 4-tolyl |
| 2294 | Cyclopentyl | H | O | CH$_2$CF$_3$ | OCH$_2$CF$_3$ | 4-tolyl |
| 2295 | CH$_2$CH$_3$ | H | O | CH$_2$CF$_3$ | OCH$_2$CF$_3$ | 4-ethyl phenyl |
| 2296 | CH$_2$CF$_3$ | H | O | CH$_2$CF$_3$ | OCH$_2$CF$_3$ | 4-ethyl phenyl |
| 2297 | CH$_2$CH$_2$CH$_3$ | H | O | CH$_2$CF$_3$ | OCH$_2$CF$_3$ | 4-ethyl phenyl |
| 2298 | CH$_2$CH(CH$_3$)$_2$ | H | O | CH$_2$CF$_3$ | OCH$_2$CF$_3$ | 4-ethyl phenyl |

TABLE 7-continued

Compounds of Formula VII

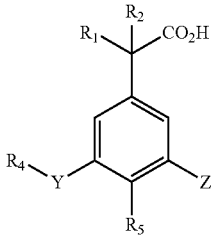

Formula VII

| Ex | R1 | R2 | Y | R4 | R5 | Z |
|---|---|---|---|---|---|---|
| 2299 | cyclopropylmethyl | H | O | $CH_2CF_3$ | $OCH_2CF_3$ | 4-ethyl phenyl |
| 2300 | cyclobutylmethyl | H | O | $CH_2CF_3$ | $OCH_2CF_3$ | 4-ethyl phenyl |
| 2301 | $(CH_2)_2$ | | O | $CH_2CF_3$ | $OCH_2CF_3$ | 4-ethyl phenyl |
| 2302 | $(CH_2)_3$ | | O | $CH_2CF_3$ | $OCH_2CF_3$ | 4-ethyl phenyl |
| 2303 | $(CH_2)_4$ | | O | $CH_2CF_3$ | $OCH_2CF_3$ | 4-ethyl phenyl |
| 2304 | $(CH_2)_5$ | | O | $CH_2CF_3$ | $OCH_2CF_3$ | 4-ethyl phenyl |
| 2305 | 5,5-spiro[2.3]hexane | | O | $CH_2CF_3$ | $OCH_2CF_3$ | 4-ethyl phenyl |
| 2306 | Cyclopentyl | H | O | $CH_2CF_3$ | $OCH_2CF_3$ | 4-ethyl phenyl |
| 2307 | $CH_2CH_3$ | H | O | $CH_2CF_3$ | $OCH_2CF_3$ | 4-isopropyl phenyl |
| 2308 | $CH_2CF_3$ | H | O | $CH_2CF_3$ | $OCH_2CF_3$ | 4-isopropyl phenyl |
| 2309 | $CH_2CH_2CH_3$ | H | O | $CH_2CF_3$ | $OCH_2CF_3$ | 4-isopropyl phenyl |
| 2310 | $CH_2CH(CH_3)_2$ | H | O | $CH_2CF_3$ | $OCH_2CF_3$ | 4-isopropyl phenyl |
| 2311 | cyclopropylmethyl | H | O | $CH_2CF_3$ | $OCH_2CF_3$ | 4-isopropyl phenyl |
| 2312 | cyclobutylmethyl | H | O | $CH_2CF_3$ | $OCH_2CF_3$ | 4-isopropyl phenyl |
| 2313 | $(CH_2)_2$ | | O | $CH_2CF_3$ | $OCH_2CF_3$ | 4-isopropyl phenyl |
| 2314 | $(CH_2)_3$ | | O | $CH_2CF_3$ | $OCH_2CF_3$ | 4-isopropyl phenyl |
| 2315 | $(CH_2)_4$ | | O | $CH_2CF_3$ | $OCH_2CF_3$ | 4-isopropyl phenyl |
| 2316 | $(CH_2)_5$ | | O | $CH_2CF_3$ | $OCH_2CF_3$ | 4-isopropyl phenyl |
| 2317 | 5,5-spiro[2.3]hexane | | O | $CH_2CF_3$ | $OCH_2CF_3$ | 4-isopropyl phenyl |
| 2318 | Cyclopentyl | H | O | $CH_2CF_3$ | $OCH_2CF_3$ | 4-isopropyl phenyl |
| 2319 | $CH_2CH_3$ | H | O | $CH_2CF_3$ | $OCH_2CF_3$ | 4-thiomethylphenyl |
| 2320 | $CH_2CF_3$ | H | O | $CH_2CF_3$ | $OCH_2CF_3$ | 4-thiomethylphenyl |
| 2321 | $CH_2CH_2CH_3$ | H | O | $CH_2CF_3$ | $OCH_2CF_3$ | 4-thiomethylphenyl |
| 2322 | $CH_2CH(CH_3)_2$ | H | O | $CH_2CF_3$ | $OCH_2CF_3$ | 4-thiomethylphenyl |
| 2323 | cyclopropylmethyl | H | O | $CH_2CF_3$ | $OCH_2CF_3$ | 4-thiomethylphenyl |
| 2324 | cyclobutylmethyl | H | O | $CH_2CF_3$ | $OCH_2CF_3$ | 4-thiomethylphenyl |
| 2325 | $(CH_2)_2$ | | O | $CH_2CF_3$ | $OCH_2CF_3$ | 4-thiomethylphenyl |
| 2326 | $(CH_2)_3$ | | O | $CH_2CF_3$ | $OCH_2CF_3$ | 4-thiomethylphenyl |
| 2327 | $(CH_2)_4$ | | O | $CH_2CF_3$ | $OCH_2CF_3$ | 4-thiomethylphenyl |
| 2328 | $(CH_2)_5$ | | O | $CH_2CF_3$ | $OCH_2CF_3$ | 4-thiomethylphenyl |
| 2329 | 5,5-spiro[2.3]hexane | | O | $CH_2CF_3$ | $OCH_2CF_3$ | 4-thiomethylphenyl |
| 2330 | Cyclopentyl | H | O | $CH_2CF_3$ | $OCH_2CF_3$ | 4-thiomethylphenyl |
| 2331 | $CH_2CH_3$ | H | O | $CH_2CF_3$ | $OCH_2CF_3$ | 4-trifluoromethoxyphenyl |
| 2332 | $CH_2CF_3$ | H | O | $CH_2CF_3$ | $OCH_2CF_3$ | 4-trifluoromethoxyphenyl |
| 2333 | $CH_2CH_2CH_3$ | H | O | $CH_2CF_3$ | $OCH_2CF_3$ | 4-trifluoromethoxyphenyl |
| 2334 | $CH_2CH(CH_3)_2$ | H | O | $CH_2CF_3$ | $OCH_2CF_3$ | 4-trifluoromethoxyphenyl |
| 2335 | cyclopropylmethyl | H | O | $CH_2CF_3$ | $OCH_2CF_3$ | 4-trifluoromethoxyphenyl |
| 2336 | cyclobutylmethyl | H | O | $CH_2CF_3$ | $OCH_2CF_3$ | 4-trifluoromethoxyphenyl |
| 2337 | $(CH_2)_2$ | | O | $CH_2CF_3$ | $OCH_2CF_3$ | 4-trifluoromethoxyphenyl |
| 2338 | $(CH_2)_3$ | | O | $CH_2CF_3$ | $OCH_2CF_3$ | 4-trifluoromethoxyphenyl |
| 2339 | $(CH_2)_4$ | | O | $CH_2CF_3$ | $OCH_2CF_3$ | 4-trifluoromethoxyphenyl |
| 2340 | $(CH_2)_5$ | | O | $CH_2CF_3$ | $OCH_2CF_3$ | 4-trifluoromethoxyphenyl |
| 2341 | 5,5-spiro[2.3]hexane | | O | $CH_2CF_3$ | $OCH_2CF_3$ | 4-trifluoromethoxyphenyl |
| 2342 | Cyclopentyl | H | O | $CH_2CF_3$ | $OCH_2CF_3$ | 4-trifluoromethoxyphenyl |
| 2343 | $CH_2CH_3$ | H | O | $CH_2$-c-Pr | $OCH_2CF_3$ | 4-trifluoromethylphenyl |
| 2344 | $CH_2CF_3$ | H | O | $CH_2$-c-Pr | $OCH_2CF_3$ | 4-trifluoromethylphenyl |
| 2345 | $CH_2CH_2CH_3$ | H | O | $CH_2$-c-Pr | $OCH_2CF_3$ | 4-trifluoromethylphenyl |
| 2346 | $CH_2CH(CH_3)_2$ | H | O | $CH_2$-c-Pr | $OCH_2CF_3$ | 4-trifluoromethylphenyl |
| 2347 | cyclopropylmethyl | H | O | $CH_2$-c-Pr | $OCH_2CF_3$ | 4-trifluoromethylphenyl |
| 2348 | cyclobutylmethyl | H | O | $CH_2$-c-Pr | $OCH_2CF_3$ | 4-trifluoromethylphenyl |
| 2349 | $(CH_2)_2$ | | O | $CH_2$-c-Pr | $OCH_2CF_3$ | 4-trifluoromethylphenyl |
| 2350 | $(CH_2)_3$ | | O | $CH_2$-c-Pr | $OCH_2CF_3$ | 4-trifluoromethylphenyl |
| 2351 | $(CH_2)_4$ | | O | $CH_2$-c-Pr | $OCH_2CF_3$ | 4-trifluoromethylphenyl |
| 2352 | $(CH_2)_5$ | | O | $CH_2$-c-Pr | $OCH_2CF_3$ | 4-trifluoromethylphenyl |
| 2353 | 5,5-spiro[2.3]hexane | | O | $CH_2$-c-Pr | $OCH_2CF_3$ | 4-trifluoromethylphenyl |

TABLE 7-continued

Compounds of Formula VII

Formula VII

| Ex | R1 | R2 | Y | R4 | R5 | Z |
|---|---|---|---|---|---|---|
| 2354 | Cyclopentyl | H | O | CH$_2$-c-Pr | OCH$_2$CF$_3$ | 4-trifluoromethylphenyl |
| 2355 | CH$_2$CH$_3$ | H | O | CH$_2$-c-Pr | OCH$_2$CF$_3$ | 4-tolyl |
| 2356 | CH$_2$CF$_3$ | H | O | CH$_2$-c-Pr | OCH$_2$CF$_3$ | 4-tolyl |
| 2357 | CH$_2$CH$_2$CH$_3$ | H | O | CH$_2$-c-Pr | OCH$_2$CF$_3$ | 4-tolyl |
| 2358 | CH$_2$CH(CH$_3$)$_2$ | H | O | CH$_2$-c-Pr | OCH$_2$CF$_3$ | 4-tolyl |
| 2359 | cyclopropylmethyl | H | O | CH$_2$-c-Pr | OCH$_2$CF$_3$ | 4-tolyl |
| 2360 | cyclobutylmethyl | H | O | CH$_2$-c-Pr | OCH$_2$CF$_3$ | 4-tolyl |
| 2361 | (CH$_2$)$_2$ | | O | CH$_2$-c-Pr | OCH$_2$CF$_3$ | 4-tolyl |
| 2362 | (CH$_2$)$_3$ | | O | CH$_2$-c-Pr | OCH$_2$CF$_3$ | 4-tolyl |
| 2363 | (CH$_2$)$_4$ | | O | CH$_2$-c-Pr | OCH$_2$CF$_3$ | 4-tolyl |
| 2364 | (CH$_2$)$_5$ | | O | CH$_2$-c-Pr | OCH$_2$CF$_3$ | 4-tolyl |
| 2365 | 5,5-spiro[2.3]hexane | | O | CH$_2$-c-Pr | OCH$_2$CF$_3$ | 4-tolyl |
| 2366 | Cyclopentyl | H | O | CH$_2$-c-Pr | OCH$_2$CF$_3$ | 4-tolyl |
| 2367 | CH$_2$CH$_3$ | H | O | CH$_2$-c-Pr | OCH$_2$CF$_3$ | 4-ethyl phenyl |
| 2368 | CH$_2$CF$_3$ | H | O | CH$_2$-c-Pr | OCH$_2$CF$_3$ | 4-ethyl phenyl |
| 2369 | CH$_2$CH$_2$CH$_3$ | H | O | CH$_2$-c-Pr | OCH$_2$CF$_3$ | 4-ethyl phenyl |
| 2370 | CH$_2$CH(CH$_3$)$_2$ | H | O | CH$_2$-c-Pr | OCH$_2$CF$_3$ | 4-ethyl phenyl |
| 2371 | cyclopropylmethyl | H | O | CH$_2$-c-Pr | OCH$_2$CF$_3$ | 4-ethyl phenyl |
| 2372 | cyclobutylmethyl | H | O | CH$_2$-c-Pr | OCH$_2$CF$_3$ | 4-ethyl phenyl |
| 2373 | (CH$_2$)$_2$ | | O | CH$_2$-c-Pr | OCH$_2$CF$_3$ | 4-ethyl phenyl |
| 2374 | (CH$_2$)$_3$ | | O | CH$_2$-c-Pr | OCH$_2$CF$_3$ | 4-ethyl phenyl |
| 2375 | (CH$_2$)$_4$ | | O | CH$_2$-c-Pr | OCH$_2$CF$_3$ | 4-ethyl phenyl |
| 2376 | (CH$_2$)$_5$ | | O | CH$_2$-c-Pr | OCH$_2$CF$_3$ | 4-ethyl phenyl |
| 2377 | 5,5-spiro[2.3]hexane | | O | CH$_2$-c-Pr | OCH$_2$CF$_3$ | 4-ethyl phenyl |
| 2378 | Cyclopentyl | H | O | CH$_2$-c-Pr | OCH$_2$CF$_3$ | 4-ethyl phenyl |
| 2379 | CH$_2$CH$_3$ | H | O | CH$_2$-c-Pr | OCH$_2$CF$_3$ | 4-isopropyl phenyl |
| 2380 | CH$_2$CF$_3$ | H | O | CH$_2$-c-Pr | OCH$_2$CF$_3$ | 4-isopropyl phenyl |
| 2381 | CH$_2$CH$_2$CH$_3$ | H | O | CH$_2$-c-Pr | OCH$_2$CF$_3$ | 4-isopropyl phenyl |
| 2382 | CH$_2$CH(CH$_3$)$_2$ | H | O | CH$_2$-c-Pr | OCH$_2$CF$_3$ | 4-isopropyl phenyl |
| 2383 | cyclopropylmethyl | H | O | CH$_2$-c-Pr | OCH$_2$CF$_3$ | 4-isopropyl phenyl |
| 2384 | cyclobutylmethyl | H | O | CH$_2$-c-Pr | OCH$_2$CF$_3$ | 4-isopropyl phenyl |
| 2385 | (CH$_2$)$_2$ | | O | CH$_2$-c-Pr | OCH$_2$CF$_3$ | 4-isopropyl phenyl |
| 2386 | (CH$_2$)$_3$ | | O | CH$_2$-c-Pr | OCH$_2$CF$_3$ | 4-isopropyl phenyl |
| 2387 | (CH$_2$)$_4$ | | O | CH$_2$-c-Pr | OCH$_2$CF$_3$ | 4-isopropyl phenyl |
| 2388 | (CH$_2$)$_5$ | | O | CH$_2$-c-Pr | OCH$_2$CF$_3$ | 4-isopropyl phenyl |
| 2389 | 5,5-spiro[2.3]hexane | | O | CH$_2$-c-Pr | OCH$_2$CF$_3$ | 4-isopropyl phenyl |
| 2390 | Cyclopentyl | H | O | CH$_2$-c-Pr | OCH$_2$CF$_3$ | 4-isopropyl phenyl |
| 2391 | CH$_2$CH$_3$ | H | O | CH$_2$-c-Pr | OCH$_2$CF$_3$ | 4-thiomethylphenyl |
| 2392 | CH$_2$CF$_3$ | H | O | CH$_2$-c-Pr | OCH$_2$CF$_3$ | 4-thiomethylphenyl |
| 2393 | CH$_2$CH$_2$CH$_3$ | H | O | CH$_2$-c-Pr | OCH$_2$CF$_3$ | 4-thiomethylphenyl |
| 2394 | CH$_2$CH(CH$_3$)$_2$ | H | O | CH$_2$-c-Pr | OCH$_2$CF$_3$ | 4-thiomethylphenyl |
| 2395 | cyclopropylmethyl | H | O | CH$_2$-c-Pr | OCH$_2$CF$_3$ | 4-thiomethylphenyl |
| 2396 | cyclobutylmethyl | H | O | CH$_2$-c-Pr | OCH$_2$CF$_3$ | 4-thiomethylphenyl |
| 2397 | (CH$_2$)$_2$ | | O | CH$_2$-c-Pr | OCH$_2$CF$_3$ | 4-thiomethylphenyl |
| 2398 | (CH$_2$)$_3$ | | O | CH$_2$-c-Pr | OCH$_2$CF$_3$ | 4-thiomethylphenyl |
| 2399 | (CH$_2$)$_4$ | | O | CH$_2$-c-Pr | OCH$_2$CF$_3$ | 4-thiomethylphenyl |
| 2400 | (CH$_2$)$_5$ | | O | CH$_2$-c-Pr | OCH$_2$CF$_3$ | 4-thiomethylphenyl |
| 2401 | 5,5-spiro[2.3]hexane | | O | CH$_2$-c-Pr | OCH$_2$CF$_3$ | 4-thiomethylphenyl |
| 2402 | Cyclopentyl | H | O | CH$_2$-c-Pr | OCH$_2$CF$_3$ | 4-thiomethylphenyl |
| 2403 | CH$_2$CH$_3$ | H | O | CH$_2$-c-Pr | OCH$_2$CF$_3$ | 4-trifluoromethoxyphenyl |
| 2404 | CH$_2$CF$_3$ | H | O | CH$_2$-c-Pr | OCH$_2$CF$_3$ | 4-trifluoromethoxyphenyl |
| 2405 | CH$_2$CH$_2$CH$_3$ | H | O | CH$_2$-c-Pr | OCH$_2$CF$_3$ | 4-trifluoromethoxyphenyl |
| 2406 | CH$_2$CH(CH$_3$)$_2$ | H | O | CH$_2$-c-Pr | OCH$_2$CF$_3$ | 4-trifluoromethoxyphenyl |
| 2407 | cyclopropylmethyl | H | O | CH$_2$-c-Pr | OCH$_2$CF$_3$ | 4-trifluoromethoxyphenyl |
| 2408 | cyclobutylmethyl | H | O | CH$_2$-c-Pr | OCH$_2$CF$_3$ | 4-trifluoromethoxyphenyl |
| 2409 | (CH$_2$)$_2$ | | O | CH$_2$-c-Pr | OCH$_2$CF$_3$ | 4-trifluoromethoxyphenyl |
| 2410 | (CH$_2$)$_3$ | | O | CH$_2$-c-Pr | OCH$_2$CF$_3$ | 4-trifluoromethoxyphenyl |
| 2411 | (CH$_2$)$_4$ | | O | CH$_2$-c-Pr | OCH$_2$CF$_3$ | 4-trifluoromethoxyphenyl |
| 2412 | (CH$_2$)$_5$ | | O | CH$_2$-c-Pr | OCH$_2$CF$_3$ | 4-trifluoromethoxyphenyl |
| 2413 | 5,5-spiro[2.3]hexane | | O | CH$_2$-c-Pr | OCH$_2$CF$_3$ | 4-trifluoromethoxyphenyl |
| 2414 | Cyclopentyl | H | O | CH$_2$-c-Pr | OCH$_2$CF$_3$ | 4-trifluoromethoxyphenyl |

TABLE 8

Formula VII

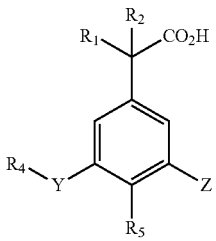

Compounds of Formula VII

| Ex | R1 | R2 | Y | R4 | R5 | Z |
|---|---|---|---|---|---|---|
| 2415 | $CH_2CH_3$ | H | O | $CH_2CF_3$ | Cl | 4-trifluoromethylphenyl |
| 2416 | $CH_2CF_3$ | H | O | $CH_2CF_3$ | Cl | 4-trifluoromethylphenyl |
| 2417 | $CH_2CH_2CH_3$ | H | O | $CH_2CF_3$ | Cl | 4-trifluoromethylphenyl |
| 2418 | $CH_2CH(CH_3)_2$ | H | O | $CH_2CF_3$ | Cl | 4-trifluoromethylphenyl |
| 2419 | cyclopropyl-methyl | H | O | $CH_2CF_3$ | Cl | 4-trifluoromethylphenyl |
| 2420 | cyclobutyl-methyl | H | O | $CH_2CF_3$ | Cl | 4-trifluoromethylphenyl |
| 2421 | $(CH_2)_2$ | | O | $CH_2CF_3$ | Cl | 4-trifluoromethylphenyl |
| 2422 | $(CH_2)_3$ | | O | $CH_2CF_3$ | Cl | 4-trifluoromethylphenyl |
| 2423 | $(CH_2)_4$ | | O | $CH_2CF_3$ | Cl | 4-trifluoromethylphenyl |
| 2424 | $(CH_2)_5$ | | O | $CH_2CF_3$ | Cl | 4-trifluoromethylphenyl |
| 2425 | 5,5-spiro[2.3]hexane | | O | $CH_2CF_3$ | Cl | 4-trifluoromethylphenyl |
| 2426 | Cyclopentyl | H | O | $CH_2CF_3$ | Cl | 4-trifluoromethylphenyl |
| 2427 | $CH_2CH_3$ | H | O | $CH_2CF_3$ | Cl | 4-tolyl |
| 2428 | $CH_2CF_3$ | H | O | $CH_2CF_3$ | Cl | 4-tolyl |
| 2429 | $CH_2CH_2CH_3$ | H | O | $CH_2CF_3$ | Cl | 4-tolyl |
| 2430 | $CH_2CH(CH_3)_2$ | H | O | $CH_2CF_3$ | Cl | 4-tolyl |
| 2431 | cyclopropyl-methyl | H | O | $CH_2CF_3$ | Cl | 4-tolyl |
| 2432 | cyclobutyl-methyl | H | O | $CH_2CF_3$ | Cl | 4-tolyl |
| 2433 | $(CH_2)_2$ | | O | $CH_2CF_3$ | Cl | 4-tolyl |
| 2434 | $(CH_2)_3$ | | O | $CH_2CF_3$ | Cl | 4-tolyl |
| 2435 | $(CH_2)_4$ | | O | $CH_2CF_3$ | Cl | 4-tolyl |
| 2436 | $(CH_2)_5$ | | O | $CH_2CF_3$ | Cl | 4-tolyl |
| 2437 | 5,5-spiro[2.3]hexane | | O | $CH_2CF_3$ | Cl | 4-tolyl |
| 2438 | Cyclopentyl | H | O | $CH_2CF_3$ | Cl | 4-tolyl |
| 2439 | $CH_2CH_3$ | H | O | $CH_2CF_3$ | Cl | 4-ethyl phenyl |
| 2440 | $CH_2CF_3$ | H | O | $CH_2CF_3$ | Cl | 4-ethyl phenyl |
| 2441 | $CH_2CH_2CH_3$ | H | O | $CH_2CF_3$ | Cl | 4-ethyl phenyl |
| 2442 | $CH_2CH(CH_3)_2$ | H | O | $CH_2CF_3$ | Cl | 4-ethyl phenyl |
| 2443 | cyclopropyl-methyl | H | O | $CH_2CF_3$ | Cl | 4-ethyl phenyl |
| 2444 | cyclobutyl-methyl | H | O | $CH_2CF_3$ | Cl | 4-ethyl phenyl |
| 2445 | $(CH_2)_2$ | | O | $CH_2CF_3$ | Cl | 4-ethyl phenyl |
| 2446 | $(CH_2)_3$ | | O | $CH_2CF_3$ | Cl | 4-ethyl phenyl |
| 2447 | $(CH_2)_4$ | | O | $CH_2CF_3$ | Cl | 4-ethyl phenyl |
| 2448 | $(CH_2)_5$ | | O | $CH_2CF_3$ | Cl | 4-ethyl phenyl |
| 2449 | 5,5-spiro[2.3]hexane | | O | $CH_2CF_3$ | Cl | 4-ethyl phenyl |
| 2450 | Cyclopentyl | H | O | $CH_2CF_3$ | Cl | 4-ethyl phenyl |
| 2451 | $CH_2CH_3$ | H | O | $CH_2CF_3$ | Cl | 4-isopropyl phenyl |
| 2452 | $CH_2CF_3$ | H | O | $CH_2CF_3$ | Cl | 4-isopropyl phenyl |
| 2453 | $CH_2CH_2CH_3$ | H | O | $CH_2CF_3$ | Cl | 4-isopropyl phenyl |
| 2454 | $CH_2CH(CH_3)_2$ | H | O | $CH_2CF_3$ | Cl | 4-isopropyl phenyl |
| 2455 | cyclopropyl-methyl | H | O | $CH_2CF_3$ | Cl | 4-isopropyl phenyl |
| 2456 | cyclobutyl-methyl | H | O | $CH_2CF_3$ | Cl | 4-isopropyl phenyl |
| 2457 | $(CH_2)_2$ | | O | $CH_2CF_3$ | Cl | 4-isopropyl phenyl |
| 2458 | $(CH_2)_3$ | | O | $CH_2CF_3$ | Cl | 4-isopropyl phenyl |
| 2459 | $(CH_2)_4$ | | O | $CH_2CF_3$ | Cl | 4-isopropyl phenyl |
| 2460 | $(CH_2)_5$ | | O | $CH_2CF_3$ | Cl | 4-isopropyl phenyl |
| 2461 | 5,5-spiro[2.3]hexane | | O | $CH_2CF_3$ | Cl | 4-isopropyl phenyl |
| 2462 | Cyclopentyl | H | O | $CH_2CF_3$ | Cl | 4-isopropyl phenyl |
| 2463 | $CH_2CH_3$ | H | O | $CH_2CF_3$ | Cl | 4-thiomethyl-phenyl |
| 2464 | $CH_2CF_3$ | H | O | $CH_2CF_3$ | Cl | 4-thiomethyl-phenyl |
| 2465 | $CH_2CH_2CH_3$ | H | O | $CH_2CF_3$ | Cl | 4-thiomethyl-phenyl |
| 2466 | $CH_2CH(CH_3)_2$ | H | O | $CH_2CF_3$ | Cl | 4-thiomethyl-phenyl |
| 2467 | cyclopropyl-methyl | H | O | $CH_2CF_3$ | Cl | 4-thiomethyl-phenyl |
| 2468 | cyclobutyl-methyl | H | O | $CH_2CF_3$ | Cl | 4-thiomethyl-phenyl |
| 2469 | $(CH_2)_2$ | | O | $CH_2CF_3$ | Cl | 4-thiomethyl-phenyl |
| 2470 | $(CH_2)_3$ | | O | $CH_2CF_3$ | Cl | 4-thiomethyl-phenyl |
| 2471 | $(CH_2)_4$ | | O | $CH_2CF_3$ | Cl | 4-thiomethyl-phenyl |
| 2472 | $(CH_2)_5$ | | O | $CH_2CF_3$ | Cl | 4-thiomethyl-phenyl |
| 2473 | 5,5-spiro[2.3]hexane | | O | $CH_2CF_3$ | Cl | 4-thiomethyl-phenyl |
| 2474 | Cyclopentyl | H | O | $CH_2CF_3$ | Cl | 4-thiomethyl-phenyl |
| 2475 | $CH_2CH_3$ | H | O | $CH_2CF_3$ | Cl | 4-trifluoromethoxyphenyl |
| 2476 | $CH_2CF_3$ | H | O | $CH_2CF_3$ | Cl | 4-trifluoromethoxyphenyl |
| 2477 | $CH_2CH_2CH_3$ | H | O | $CH_2CF_3$ | Cl | 4-trifluoromethoxyphenyl |
| 2478 | $CH_2CH(CH_3)_2$ | H | O | $CH_2CF_3$ | Cl | 4-trifluoromethoxyphenyl |
| 2479 | cyclopropyl-methyl | H | O | $CH_2CF_3$ | Cl | 4-trifluoromethoxyphenyl |
| 2480 | cyclobutyl-methyl | H | O | $CH_2CF_3$ | Cl | 4-trifluoromethoxyphenyl |
| 2481 | $(CH_2)_2$ | | O | $CH_2CF_3$ | Cl | 4-trifluoromethoxyphenyl |
| 2482 | $(CH_2)_3$ | | O | $CH_2CF_3$ | Cl | 4-trifluoromethoxyphenyl |
| 2483 | $(CH_2)_4$ | | O | $CH_2CF_3$ | Cl | 4-trifluoromethoxyphenyl |
| 2484 | $(CH_2)_5$ | | O | $CH_2CF_3$ | Cl | 4-trifluoromethoxyphenyl |
| 2485 | 5,5-spiro[2.3]hexane | | O | $CH_2CF_3$ | Cl | 4-trifluoromethoxyphenyl |

TABLE 8-continued

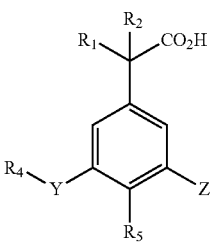

Formula VII

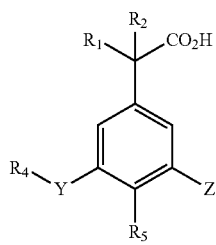

Formula VII

Compounds of Formula VII

| Ex | R1 | R2 | Y | R4 | R5 | Z |
|---|---|---|---|---|---|---|
| 2486 | Cyclopentyl | H | O | $CH_2CF_3$ | Cl | 4-trifluoromethoxyphenyl |
| 2487 | $CH_2CH_3$ | H | O | $CH_2$-c-Pr | Cl | 4-trifluoromethylphenyl |
| 2488 | $CH_2CF_3$ | H | O | $CH_2$-c-Pr | Cl | 4-trifluoromethylphenyl |
| 2489 | $CH_2CH_2CH_3$ | H | O | $CH_2$-c-Pr | Cl | 4-trifluoromethylphenyl |
| 2490 | $CH_2CH(CH_3)_2$ | H | O | $CH_2$-c-Pr | Cl | 4-trifluoromethylphenyl |
| 2491 | cyclopropylmethyl | H | O | $CH_2$-c-Pr | Cl | 4-trifluoromethylphenyl |
| 2492 | cyclobutylmethyl | H | O | $CH_2$-c-Pr | Cl | 4-trifluoromethylphenyl |
| 2493 | $(CH_2)_2$ | | O | $CH_2$-c-Pr | Cl | 4-trifluoromethylphenyl |
| 2494 | $(CH_2)_3$ | | O | $CH_2$-c-Pr | Cl | 4-trifluoromethylphenyl |
| 2495 | $(CH_2)_4$ | | O | $CH_2$-c-Pr | Cl | 4-trifluoromethylphenyl |
| 2496 | $(CH_2)_5$ | | O | $CH_2$-c-Pr | Cl | 4-trifluoromethylphenyl |
| 2497 | 5,5-spiro[2.3]hexane | | O | $CH_2$-c-Pr | Cl | 4-trifluoromethylphenyl |
| 2498 | Cyclopentyl | H | O | $CH_2$-c-Pr | Cl | 4-trifluoromethylphenyl |
| 2499 | $CH_2CH_3$ | H | O | $CH_2$-c-Pr | Cl | 4-tolyl |
| 2500 | $CH_2CF_3$ | H | O | $CH_2$-c-Pr | Cl | 4-tolyl |
| 2501 | $CH_2CH_2CH_3$ | H | O | $CH_2$-c-Pr | Cl | 4-tolyl |
| 2502 | $CH_2CH(CH_3)_2$ | H | O | $CH_2$-c-Pr | Cl | 4-tolyl |
| 2503 | cyclopropylmethyl | H | O | $CH_2$-c-Pr | Cl | 4-tolyl |
| 2504 | cyclobutylmethyl | H | O | $CH_2$-c-Pr | Cl | 4-tolyl |
| 2505 | $(CH_2)_2$ | | O | $CH_2$-c-Pr | Cl | 4-tolyl |
| 2506 | $(CH_2)_3$ | | O | $CH_2$-c-Pr | Cl | 4-tolyl |
| 2507 | $(CH_2)_4$ | | O | $CH_2$-c-Pr | Cl | 4-tolyl |
| 2508 | $(CH_2)_5$ | | O | $CH_2$-c-Pr | Cl | 4-tolyl |
| 2509 | 5,5-spiro[2.3]hexane | | O | $CH_2$-c-Pr | Cl | 4-tolyl |
| 2510 | Cyclopentyl | H | O | $CH_2$-c-Pr | Cl | 4-tolyl |
| 2511 | $CH_2CH_3$ | H | O | $CH_2$-c-Pr | Cl | 4-ethyl phenyl |
| 2512 | $CH_2CF_3$ | H | O | $CH_2$-c-Pr | Cl | 4-ethyl phenyl |
| 2513 | $CH_2CH_2CH_3$ | H | O | $CH_2$-c-Pr | Cl | 4-ethyl phenyl |
| 2514 | $CH_2CH(CH_3)_2$ | H | O | $CH_2$-c-Pr | Cl | 4-ethyl phenyl |
| 2515 | cyclopropylmethyl | H | O | $CH_2$-c-Pr | Cl | 4-ethyl phenyl |
| 2516 | cyclobutylmethyl | H | O | $CH_2$-c-Pr | Cl | 4-ethyl phenyl |
| 2517 | $(CH_2)_2$ | | O | $CH_2$-c-Pr | Cl | 4-ethyl phenyl |
| 2518 | $(CH_2)_3$ | | O | $CH_2$-c-Pr | Cl | 4-ethyl phenyl |
| 2519 | $(CH_2)_4$ | | O | $CH_2$-c-Pr | Cl | 4-ethyl phenyl |
| 2520 | $(CH_2)_5$ | | O | $CH_2$-c-Pr | Cl | 4-ethyl phenyl |
| 2521 | 5,5-spiro[2.3]hexane | | O | $CH_2$-c-Pr | Cl | 4-ethyl phenyl |
| 2522 | Cyclopentyl | H | O | $CH_2$-c-Pr | Cl | 4-ethyl phenyl |
| 2523 | $CH_2CH_3$ | H | O | $CH_2$-c-Pr | Cl | 4-isopropyl phenyl |
| 2524 | $CH_2CF_3$ | H | O | $CH_2$-c-Pr | Cl | 4-isopropyl phenyl |
| 2525 | $CH_2CH_2CH_3$ | H | O | $CH_2$-c-Pr | Cl | 4-isopropyl phenyl |
| 2526 | $CH_2CH(CH_3)_2$ | H | O | $CH_2$-c-Pr | Cl | 4-isopropyl phenyl |
| 2527 | cyclopropylmethyl | H | O | $CH_2$-c-Pr | Cl | 4-isopropyl phenyl |
| 2528 | cyclobutylmethyl | H | O | $CH_2$-c-Pr | Cl | 4-isopropyl phenyl |
| 2529 | $(CH_2)_2$ | | O | $CH_2$-c-Pr | Cl | 4-isopropyl phenyl |
| 2530 | $(CH_2)_3$ | | O | $CH_2$-c-Pr | Cl | 4-isopropyl phenyl |
| 2531 | $(CH_2)_4$ | | O | $CH_2$-c-Pr | Cl | 4-isopropyl phenyl |
| 2532 | $(CH_2)_5$ | | O | $CH_2$-c-Pr | Cl | 4-isopropyl phenyl |
| 2533 | 5,5-spiro[2.3]hexane | | O | $CH_2$-c-Pr | Cl | 4-isopropyl phenyl |
| 2534 | Cyclopentyl | H | O | $CH_2$-c-Pr | Cl | 4-isopropyl phenyl |
| 2535 | $CH_2CH_3$ | H | O | $CH_2$-c-Pr | Cl | 4-thiomethyl-phenyl |
| 2536 | $CH_2CF_3$ | H | O | $CH_2$-c-Pr | Cl | 4-thiomethyl-phenyl |
| 2537 | $CH_2CH_2CH_3$ | H | O | $CH_2$-c-Pr | Cl | 4-thiomethyl-phenyl |
| 2538 | $CH_2CH(CH_3)_2$ | H | O | $CH_2$-c-Pr | Cl | 4-thiomethyl-phenyl |
| 2539 | cyclopropylmethyl | H | O | $CH_2$-c-Pr | Cl | 4-thiomethyl-phenyl |
| 2540 | cyclobutylmethyl | H | O | $CH_2$-c-Pr | Cl | 4-thiomethyl-phenyl |
| 2541 | $(CH_2)_2$ | | O | $CH_2$-c-Pr | Cl | 4-thiomethyl-phenyl |
| 2542 | $(CH_2)_3$ | | O | $CH_2$-c-Pr | Cl | 4-thiomethyl-phenyl |
| 2543 | $(CH_2)_4$ | | O | $CH_2$-c-Pr | Cl | 4-thiomethyl-phenyl |
| 2544 | $(CH_2)_5$ | | O | $CH_2$-c-Pr | Cl | 4-thiomethyl-phenyl |
| 2545 | 5,5-spiro[2.3]hexane | | O | $CH_2$-c-Pr | Cl | 4-thiomethyl-phenyl |
| 2546 | Cyclopentyl | H | O | $CH_2$-c-Pr | Cl | 4-thiomethyl-phenyl |
| 2547 | $CH_2CH_3$ | H | O | $CH_2$-c-Pr | Cl | 4-trifluoromethoxyphenyl |
| 2548 | $CH_2CF_3$ | H | O | $CH_2$-c-Pr | Cl | 4-trifluoromethoxyphenyl |
| 2549 | $CH_2CH_2CH_3$ | H | O | $CH_2$-c-Pr | Cl | 4-trifluoromethoxyphenyl |
| 2550 | $CH_2CH(CH_3)_2$ | H | O | $CH_2$-c-Pr | Cl | 4-trifluoromethoxyphenyl |
| 2551 | cyclopropylmethyl | H | O | $CH_2$-c-Pr | Cl | 4-trifluoromethoxyphenyl |
| 2552 | cyclobutylmethyl | H | O | $CH_2$-c-Pr | Cl | 4-trifluoromethoxyphenyl |
| 2553 | $(CH_2)_2$ | | O | $CH_2$-c-Pr | Cl | 4-trifluoromethoxyphenyl |
| 2554 | $(CH_2)_3$ | | O | $CH_2$-c-Pr | Cl | 4-trifluoromethoxyphenyl |
| 2555 | $(CH_2)_4$ | | O | $CH_2$-c-Pr | Cl | 4-trifluoromethoxyphenyl |
| 2556 | $(CH_2)_5$ | | O | $CH_2$-c-Pr | Cl | 4-trifluoromethoxyphenyl |

TABLE 8-continued

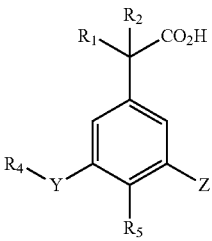

Formula VII

Compounds of Formula VII

| Ex | R1 | R2 | Y | R4 | R5 | Z |
|---|---|---|---|---|---|---|
| 2557 | 5,5-spiro[2.3]hexane | | O | $CH_2$-c-Pr | Cl | 4-trifluoromethoxyphenyl |
| 2558 | Cyclopentyl | H | O | $CH_2$-c-Pr | Cl | 4-trifluoromethoxyphenyl |
| 2559 | $CH_2CH_3$ | H | O | $CH_2CF_3$ | $OCH_2CF_3$ | 4-trifluoromethylphenyl |
| 2560 | $CH_2CF_3$ | H | O | $CH_2CF_3$ | $OCH_2CF_3$ | 4-trifluoromethylphenyl |
| 2561 | $CH_2CH_2CH_3$ | H | O | $CH_2CF_3$ | $OCH_2CF_3$ | 4-trifluoromethylphenyl |
| 2562 | $CH_2CH(CH_3)_2$ | H | O | $CH_2CF_3$ | $OCH_2CF_3$ | 4-trifluoromethylphenyl |
| 2563 | cyclopropylmethyl | H | O | $CH_2CF_3$ | $OCH_2CF_3$ | 4-trifluoromethylphenyl |
| 2564 | cyclobutylmethyl | H | O | $CH_2CF_3$ | $OCH_2CF_3$ | 4-trifluoromethylphenyl |
| 2565 | $(CH_2)_2$ | | O | $CH_2CF_3$ | $OCH_2CF_3$ | 4-trifluoromethylphenyl |
| 2566 | $(CH_2)_3$ | | O | $CH_2CF_3$ | $OCH_2CF_3$ | 4-trifluoromethylphenyl |
| 2567 | $(CH_2)_4$ | | O | $CH_2CF_3$ | $OCH_2CF_3$ | 4-trifluoromethylphenyl |
| 2568 | $(CH_2)_5$ | | O | $CH_2CF_3$ | $OCH_2CF_3$ | 4-trifluoromethylphenyl |
| 2569 | 5,5-spiro[2.3]hexane | | O | $CH_2CF_3$ | $OCH_2CF_3$ | 4-trifluoromethylphenyl |
| 2570 | Cyclopentyl | H | O | $CH_2CF_3$ | $OCH_2CF_3$ | 4-trifluoromethylphenyl |
| 2571 | $CH_2CH_3$ | H | O | $CH_2CF_3$ | $OCH_2CF_3$ | 4-tolyl |
| 2572 | $CH_2CF_3$ | H | O | $CH_2CF_3$ | $OCH_2CF_3$ | 4-tolyl |
| 2573 | $CH_2CH_2CH_3$ | H | O | $CH_2CF_3$ | $OCH_2CF_3$ | 4-tolyl |
| 2574 | $CH_2CH(CH_3)_2$ | H | O | $CH_2CF_3$ | $OCH_2CF_3$ | 4-tolyl |
| 2575 | cyclopropylmethyl | H | O | $CH_2CF_3$ | $OCH_2CF_3$ | 4-tolyl |
| 2576 | cyclobutylmethyl | H | O | $CH_2CF_3$ | $OCH_2CF_3$ | 4-tolyl |
| 2577 | $(CH_2)_2$ | | O | $CH_2CF_3$ | $OCH_2CF_3$ | 4-tolyl |
| 2578 | $(CH_2)_3$ | | O | $CH_2CF_3$ | $OCH_2CF_3$ | 4-tolyl |
| 2579 | $(CH_2)_4$ | | O | $CH_2CF_3$ | $OCH_2CF_3$ | 4-tolyl |
| 2580 | $(CH_2)_5$ | | O | $CH_2CF_3$ | $OCH_2CF_3$ | 4-tolyl |
| 2581 | 5,5-spiro[2.3]hexane | | O | $CH_2CF_3$ | $OCH_2CF_3$ | 4-tolyl |
| 2582 | Cyclopentyl | H | O | $CH_2CF_3$ | $OCH_2CF_3$ | 4-tolyl |
| 2583 | $CH_2CH_3$ | H | O | $CH_2CF_3$ | $OCH_2CF_3$ | 4-ethyl phenyl |
| 2584 | $CH_2CF_3$ | H | O | $CH_2CF_3$ | $OCH_2CF_3$ | 4-ethyl phenyl |
| 2585 | $CH_2CH_2CH_3$ | H | O | $CH_2CF_3$ | $OCH_2CF_3$ | 4-ethyl phenyl |
| 2586 | $CH_2CH(CH_3)_2$ | H | O | $CH_2CF_3$ | $OCH_2CF_3$ | 4-ethyl phenyl |
| 2587 | cyclopropylmethyl | H | O | $CH_2CF_3$ | $OCH_2CF_3$ | 4-ethyl phenyl |
| 2588 | cyclobutylmethyl | H | O | $CH_2CF_3$ | $OCH_2CF_3$ | 4-ethyl phenyl |
| 2589 | $(CH_2)_2$ | | O | $CH_2CF_3$ | $OCH_2CF_3$ | 4-ethyl phenyl |
| 2590 | $(CH_2)_3$ | | O | $CH_2CF_3$ | $OCH_2CF_3$ | 4-ethyl phenyl |
| 2591 | $(CH_2)_4$ | | O | $CH_2CF_3$ | $OCH_2CF_3$ | 4-ethyl phenyl |
| 2592 | $(CH_2)_5$ | | O | $CH_2CF_3$ | $OCH_2CF_3$ | 4-ethyl phenyl |
| 2593 | 5,5-spiro[2.3]hexane | | O | $CH_2CF_3$ | $OCH_2CF_3$ | 4-ethyl phenyl |
| 2594 | Cyclopentyl | H | O | $CH_2CF_3$ | $OCH_2CF_3$ | 4-ethyl phenyl |
| 2595 | $CH_2CH_3$ | H | O | $CH_2CF_3$ | $OCH_2CF_3$ | 4-isopropyl phenyl |
| 2596 | $CH_2CF_3$ | H | O | $CH_2CF_3$ | $OCH_2CF_3$ | 4-isopropyl phenyl |
| 2597 | $CH_2CH_2CH_3$ | H | O | $CH_2CF_3$ | $OCH_2CF_3$ | 4-isopropyl phenyl |
| 2598 | $CH_2CH(CH_3)_2$ | H | O | $CH_2CF_3$ | $OCH_2CF_3$ | 4-isopropyl phenyl |
| 2599 | cyclopropylmethyl | H | O | $CH_2CF_3$ | $OCH_2CF_3$ | 4-isopropyl phenyl |
| 2600 | cyclobutylmethyl | H | O | $CH_2CF_3$ | $OCH_2CF_3$ | 4-isopropyl phenyl |
| 2601 | $(CH_2)_2$ | | O | $CH_2CF_3$ | $OCH_2CF_3$ | 4-isopropyl phenyl |
| 2602 | $(CH_2)_3$ | | O | $CH_2CF_3$ | $OCH_2CF_3$ | 4-isopropyl phenyl |
| 2603 | $(CH_2)_4$ | | O | $CH_2CF_3$ | $OCH_2CF_3$ | 4-isopropyl phenyl |
| 2604 | $(CH_2)_5$ | | O | $CH_2CF_3$ | $OCH_2CF_3$ | 4-isopropyl phenyl |
| 2605 | 5,5-spiro[2.3]hexane | | O | $CH_2CF_3$ | $OCH_2CF_3$ | 4-isopropyl phenyl |
| 2606 | Cyclopentyl | H | O | $CH_2CF_3$ | $OCH_2CF_3$ | 4-isopropyl phenyl |
| 2607 | $CH_2CH_3$ | H | O | $CH_2CF_3$ | $OCH_2CF_3$ | 4-thiomethylphenyl |
| 2608 | $CH_2CF_3$ | H | O | $CH_2CF_3$ | $OCH_2CF_3$ | 4-thiomethylphenyl |
| 2609 | $CH_2CH_2CH_3$ | H | O | $CH_2CF_3$ | $OCH_2CF_3$ | 4-thiomethylphenyl |
| 2610 | $CH_2CH(CH_3)_2$ | H | O | $CH_2CF_3$ | $OCH_2CF_3$ | 4-thiomethylphenyl |
| 2611 | cyclopropylmethyl | H | O | $CH_2CF_3$ | $OCH_2CF_3$ | 4-thiomethylphenyl |
| 2612 | cyclobutylmethyl | H | O | $CH_2CF_3$ | $OCH_2CF_3$ | 4-thiomethylphenyl |
| 2613 | $(CH_2)_2$ | | O | $CH_2CF_3$ | $OCH_2CF_3$ | 4-thiomethylphenyl |
| 2614 | $(CH_2)_3$ | | O | $CH_2CF_3$ | $OCH_2CF_3$ | 4-thiomethylphenyl |
| 2615 | $(CH_2)_4$ | | O | $CH_2CF_3$ | $OCH_2CF_3$ | 4-thiomethylphenyl |
| 2616 | $(CH_2)_5$ | | O | $CH_2CF_3$ | $OCH_2CF_3$ | 4-thiomethylphenyl |
| 2617 | 5,5-spiro[2.3]hexane | | O | $CH_2CF_3$ | $OCH_2CF_3$ | 4-thiomethylphenyl |
| 2618 | Cyclopentyl | H | O | $CH_2CF_3$ | $OCH_2CF_3$ | 4-thiomethylphenyl |
| 2619 | $CH_2CH_3$ | H | O | $CH_2CF_3$ | $OCH_2CF_3$ | 4-trifluoromethoxyphenyl |
| 2620 | $CH_2CF_3$ | H | O | $CH_2CF_3$ | $OCH_2CF_3$ | 4-trifluoromethoxyphenyl |
| 2621 | $CH_2CH_2CH_3$ | H | O | $CH_2CF_3$ | $OCH_2CF_3$ | 4-trifluoromethoxyphenyl |
| 2622 | $CH_2CH(CH_3)_2$ | H | O | $CH_2CF_3$ | $OCH_2CF_3$ | 4-trifluoromethoxyphenyl |
| 2623 | cyclopropylmethyl | H | O | $CH_2CF_3$ | $OCH_2CF_3$ | 4-trifluoromethoxyphenyl |
| 2624 | cyclobutylmethyl | H | O | $CH_2CF_3$ | $OCH_2CF_3$ | 4-trifluoromethoxyphenyl |
| 2625 | $(CH_2)_2$ | | O | $CH_2CF_3$ | $OCH_2CF_3$ | 4-trifluoromethoxyphenyl |
| 2626 | $(CH_2)_3$ | | O | $CH_2CF_3$ | $OCH_2CF_3$ | 4-trifluoromethoxyphenyl |
| 2627 | $(CH_2)_4$ | | O | $CH_2CF_3$ | $OCH_2CF_3$ | 4-trifluoromethoxyphenyl |

TABLE 8-continued

Formula VII

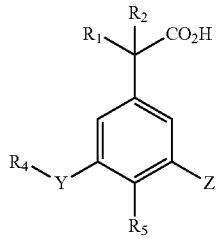

Compounds of Formula VII

| Ex | R1 | R2 | Y | R4 | R5 | Z |
|---|---|---|---|---|---|---|
| 2628 | (CH$_2$)$_5$ |  | O | CH$_2$CF$_3$ | OCH$_2$CF$_3$ | 4-trifluoro-methoxyphenyl |
| 2629 | 5,5-spiro[2.3]hexane |  | O | CH$_2$CF$_3$ | OCH$_2$CF$_3$ | 4-trifluoro-methoxyphenyl |
| 2630 | Cyclopentyl | H | O | CH$_2$CF$_3$ | OCH$_2$CF$_3$ | 4-trifluoro-methoxyphenyl |
| 2632 | CH$_2$CH$_3$ | H | O | CH$_2$-c-Pr | OCH$_2$CF$_3$ | 4-trifluoro-methylphenyl |
| 2633 | CH$_2$CF$_3$ | H | O | CH$_2$-c-Pr | OCH$_2$CF$_3$ | 4-trifluoro-methylphenyl |
| 2634 | CH$_2$CH$_2$CH$_3$ | H | O | CH$_2$-c-Pr | OCH$_2$CF$_3$ | 4-trifluoro-methylphenyl |
| 2635 | CH$_2$CH(CH$_3$)$_2$ | H | O | CH$_2$-c-Pr | OCH$_2$CF$_3$ | 4-trifluoro-methylphenyl |
| 2636 | cyclopropyl-methyl | H | O | CH$_2$-c-Pr | OCH$_2$CF$_3$ | 4-trifluoro-methylphenyl |
| 2637 | cyclobutyl-methyl | H | O | CH$_2$-c-Pr | OCH$_2$CF$_3$ | 4-trifluoro-methylphenyl |
| 2638 | (CH$_2$)$_2$ |  | O | CH$_2$-c-Pr | OCH$_2$CF$_3$ | 4-trifluoro-methylphenyl |
| 2639 | (CH$_2$)$_3$ |  | O | CH$_2$-c-Pr | OCH$_2$CF$_3$ | 4-trifluoro-methylphenyl |
| 2640 | (CH$_2$)$_4$ |  | O | CH$_2$-c-Pr | OCH$_2$CF$_3$ | 4-trifluoro-methylphenyl |
| 2641 | (CH$_2$)$_5$ |  | O | CH$_2$-c-Pr | OCH$_2$CF$_3$ | 4-trifluoro-methylphenyl |
| 2642 | 5,5-spiro[2.3]hexane |  | O | CH$_2$-c-Pr | OCH$_2$CF$_3$ | 4-trifluoro-methylphenyl |
| 2643 | Cyclopentyl | H | O | CH$_2$-c-Pr | OCH$_2$CF$_3$ | 4-trifluoro-methylphenyl |
| 2644 | CH$_2$CH$_3$ | H | O | CH$_2$-c-Pr | OCH$_2$CF$_3$ | 4-tolyl |
| 2645 | CH$_2$CF$_3$ | H | O | CH$_2$-c-Pr | OCH$_2$CF$_3$ | 4-tolyl |
| 2646 | CH$_2$CH$_2$CH$_3$ | H | O | CH$_2$-c-Pr | OCH$_2$CF$_3$ | 4-tolyl |
| 2647 | CH$_2$CH(CH$_3$)$_2$ | H | O | CH$_2$-c-Pr | OCH$_2$CF$_3$ | 4-tolyl |
| 2648 | cyclopropyl-methyl | H | O | CH$_2$-c-Pr | OCH$_2$CF$_3$ | 4-tolyl |
| 2649 | cyclobutyl-methyl | H | O | CH$_2$-c-Pr | OCH$_2$CF$_3$ | 4-tolyl |
| 2650 | (CH$_2$)$_2$ |  | O | CH$_2$-c-Pr | OCH$_2$CF$_3$ | 4-tolyl |
| 2651 | (CH$_2$)$_3$ |  | O | CH$_2$-c-Pr | OCH$_2$CF$_3$ | 4-tolyl |
| 2652 | (CH$_2$)$_4$ |  | O | CH$_2$-c-Pr | OCH$_2$CF$_3$ | 4-tolyl |
| 2653 | (CH$_2$)$_5$ |  | O | CH$_2$-c-Pr | OCH$_2$CF$_3$ | 4-tolyl |
| 2654 | 5,5-spiro[2.3]hexane |  | O | CH$_2$-c-Pr | OCH$_2$CF$_3$ | 4-tolyl |
| 2655 | Cyclopentyl | H | O | CH$_2$-c-Pr | OCH$_2$CF$_3$ | 4-tolyl |
| 2656 | CH$_2$CH$_3$ | H | O | CH$_2$-c-Pr | OCH$_2$CF$_3$ | 4-ethyl phenyl |
| 2657 | CH$_2$CF$_3$ | H | O | CH$_2$-c-Pr | OCH$_2$CF$_3$ | 4-ethyl phenyl |
| 2658 | CH$_2$CH$_2$CH$_3$ | H | O | CH$_2$-c-Pr | OCH$_2$CF$_3$ | 4-ethyl phenyl |
| 2659 | CH$_2$CH(CH$_3$)$_2$ | H | O | CH$_2$-c-Pr | OCH$_2$CF$_3$ | 4-ethyl phenyl |
| 2660 | cyclopropyl-methyl | H | O | CH$_2$-c-Pr | OCH$_2$CF$_3$ | 4-ethyl phenyl |
| 2661 | cyclobutyl-methyl | H | O | CH$_2$-c-Pr | OCH$_2$CF$_3$ | 4-ethyl phenyl |
| 2662 | (CH$_2$)$_2$ |  | O | CH$_2$-c-Pr | OCH$_2$CF$_3$ | 4-ethyl phenyl |
| 2663 | (CH$_2$)$_3$ |  | O | CH$_2$-c-Pr | OCH$_2$CF$_3$ | 4-ethyl phenyl |
| 2664 | (CH$_2$)$_4$ |  | O | CH$_2$-c-Pr | OCH$_2$CF$_3$ | 4-ethyl phenyl |
| 2665 | (CH$_2$)$_5$ |  | O | CH$_2$-c-Pr | OCH$_2$CF$_3$ | 4-ethyl phenyl |
| 2666 | 5,5-spiro[2.3]hexane |  | O | CH$_2$-c-Pr | OCH$_2$CF$_3$ | 4-ethyl phenyl |
| 2667 | Cyclopentyl | H | O | CH$_2$-c-Pr | OCH$_2$CF$_3$ | 4-ethyl phenyl |
| 2668 | CH$_2$CH$_3$ | H | O | CH$_2$-c-Pr | OCH$_2$CF$_3$ | 4-isopropyl phenyl |
| 2669 | CH$_2$CF$_3$ | H | O | CH$_2$-c-Pr | OCH$_2$CF$_3$ | 4-isopropyl phenyl |
| 2670 | CH$_2$CH$_2$CH$_3$ | H | O | CH$_2$-c-Pr | OCH$_2$CF$_3$ | 4-isopropyl phenyl |
| 2671 | CH$_2$CH(CH$_3$)$_2$ | H | O | CH$_2$-c-Pr | OCH$_2$CF$_3$ | 4-isopropyl phenyl |
| 2672 | cyclopropyl-methyl | H | O | CH$_2$-c-Pr | OCH$_2$CF$_3$ | 4-isopropyl phenyl |
| 2673 | cyclobutyl-methyl | H | O | CH$_2$-c-Pr | OCH$_2$CF$_3$ | 4-isopropyl phenyl |
| 2674 | (CH$_2$)$_2$ |  | O | CH$_2$-c-Pr | OCH$_2$CF$_3$ | 4-isopropyl phenyl |
| 2675 | (CH$_2$)$_3$ |  | O | CH$_2$-c-Pr | OCH$_2$CF$_3$ | 4-isopropyl phenyl |
| 2676 | (CH$_2$)$_4$ |  | O | CH$_2$-c-Pr | OCH$_2$CF$_3$ | 4-isopropyl phenyl |
| 2677 | (CH$_2$)$_5$ |  | O | CH$_2$-c-Pr | OCH$_2$CF$_3$ | 4-isopropyl phenyl |
| 2678 | 5,5-spiro[2.3]hexane |  | O | CH$_2$-c-Pr | OCH$_2$CF$_3$ | 4-isopropyl phenyl |
| 2679 | Cyclopentyl | H | O | CH$_2$-c-Pr | OCH$_2$CF$_3$ | 4-isopropyl phenyl |
| 2680 | CH$_2$CH$_3$ | H | O | CH$_2$-c-Pr | OCH$_2$CF$_3$ | 4-thiomethyl-phenyl |
| 2681 | CH$_2$CF$_3$ | H | O | CH$_2$-c-Pr | OCH$_2$CF$_3$ | 4-thiomethyl-phenyl |
| 2682 | CH$_2$CH$_2$CH$_3$ | H | O | CH$_2$-c-Pr | OCH$_2$CF$_3$ | 4-thiomethyl-phenyl |
| 2683 | CH$_2$CH(CH$_3$)$_2$ | H | O | CH$_2$-c-Pr | OCH$_2$CF$_3$ | 4-thiomethyl-phenyl |
| 2684 | cyclopropyl-methyl | H | O | CH$_2$-c-Pr | OCH$_2$CF$_3$ | 4-thiomethyl-phenyl |
| 2685 | cyclobutyl-methyl | H | O | CH$_2$-c-Pr | OCH$_2$CF$_3$ | 4-thiomethyl-phenyl |
| 2686 | (CH$_2$)$_2$ |  | O | CH$_2$-c-Pr | OCH$_2$CF$_3$ | 4-thiomethyl-phenyl |
| 2687 | (CH$_2$)$_3$ |  | O | CH$_2$-c-Pr | OCH$_2$CF$_3$ | 4-thiomethyl-phenyl |
| 2688 | (CH$_2$)$_4$ |  | O | CH$_2$-c-Pr | OCH$_2$CF$_3$ | 4-thiomethyl-phenyl |
| 2689 | (CH$_2$)$_5$ |  | O | CH$_2$-c-Pr | OCH$_2$CF$_3$ | 4-thiomethyl-phenyl |
| 2690 | 5,5-spiro[2.3]hexane |  | O | CH$_2$-c-Pr | OCH$_2$CF$_3$ | 4-thiomethyl-phenyl |
| 2691 | Cyclopentyl | H | O | CH$_2$-c-Pr | OCH$_2$CF$_3$ | 4-thiomethyl-phenyl |
| 2692 | CH$_2$CH$_3$ | H | O | CH$_2$-c-Pr | OCH$_2$CF$_3$ | 4-trifluoro-methoxyphenyl |
| 2693 | CH$_2$CF$_3$ | H | O | CH$_2$-c-Pr | OCH$_2$CF$_3$ | 4-trifluoro-methoxyphenyl |
| 2694 | CH$_2$CH$_2$CH$_3$ | H | O | CH$_2$-c-Pr | OCH$_2$CF$_3$ | 4-trifluoro-methoxyphenyl |
| 2695 | CH$_2$CH(CH$_3$)$_2$ | H | O | CH$_2$-c-Pr | OCH$_2$CF$_3$ | 4-trifluoro-methoxyphenyl |
| 2696 | cyclopropyl-methyl | H | O | CH$_2$-c-Pr | OCH$_2$CF$_3$ | 4-trifluoro-methoxyphenyl |
| 2697 | cyclobutyl-methyl | H | O | CH$_2$-c-Pr | OCH$_2$CF$_3$ | 4-trifluoro-methoxyphenyl |
| 2698 | (CH$_2$)$_2$ |  | O | CH$_2$-c-Pr | OCH$_2$CF$_3$ | 4-trifluoro-methoxyphenyl |
| 2699 | (CH$_2$)$_3$ |  | O | CH$_2$-c-Pr | OCH$_2$CF$_3$ | 4-trifluoro-methoxyphenyl |

TABLE 8-continued

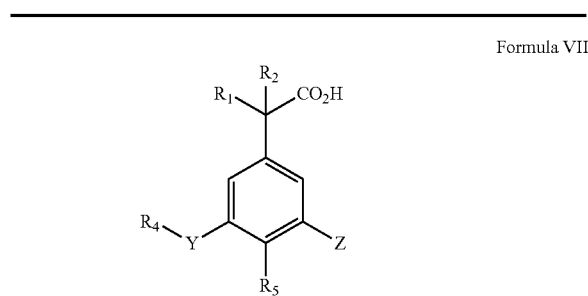

Formula VII

Compounds of Formula VII

| Ex | R1 | R2 | Y | R4 | R5 | Z |
|---|---|---|---|---|---|---|
| 2700 | (CH$_2$)$_4$ | | O | CH$_2$-c-Pr | OCH$_2$CF$_3$ | 4-trifluoromethoxyphenyl |
| 2701 | (CH$_2$)$_5$ | | O | CH$_2$-c-Pr | OCH$_2$CF$_3$ | 4-trifluoromethoxyphenyl |
| 2702 | 5,5-spiro[2.3]hexane | | O | CH$_2$-c-Pr | OCH$_2$CF$_3$ | 4-trifluoromethoxyphenyl |
| 2703 | Cyclopentyl | H | O | CH$_2$-c-Pr | OCH$_2$CF$_3$ | 4-trifluoromethoxyphenyl |

TABLE 9

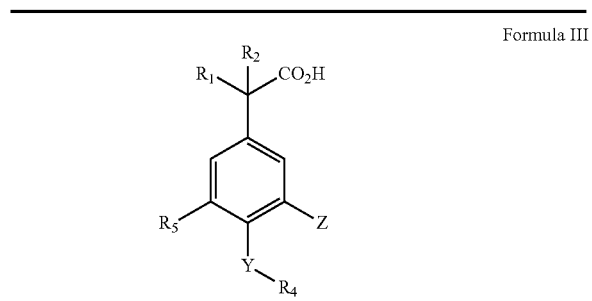

Formula III

Compounds of Formula III

| Ex | R1 | R2 | Y | R4 | R5 | Z |
|---|---|---|---|---|---|---|
| 2704 | CH$_2$CH$_3$ | H | O | CH$_2$CH$_2$CF$_3$ | Cl | 4-trifluoromethylphenyl |
| 2705 | CH$_2$CF$_3$ | H | O | CH$_2$CH$_2$CF$_3$ | Cl | 4-trifluoromethylphenyl |
| 2706 | CH$_2$CH$_2$CH$_3$ | H | O | CH$_2$CH$_2$CF$_3$ | Cl | 4-trifluoromethylphenyl |
| 2707 | CH$_2$CH(CH$_3$)$_2$ | H | O | CH$_2$CH$_2$CF$_3$ | Cl | 4-trifluoromethylphenyl |
| 2708 | cyclopropyl-methyl | H | O | CH$_2$CH$_2$CF$_3$ | Cl | 4-trifluoromethylphenyl |
| 2709 | cyclobutyl-methyl | H | O | CH$_2$CH$_2$CF$_3$ | Cl | 4-trifluoromethylphenyl |
| 2710 | (CH$_2$)$_2$ | | O | CH$_2$CH$_2$CF$_3$ | Cl | 4-trifluoromethylphenyl |
| 2711 | (CH$_2$)$_3$ | | O | CH$_2$CH$_2$CF$_3$ | Cl | 4-trifluoromethylphenyl |
| 2712 | (CH$_2$)$_4$ | | O | CH$_2$CH$_2$CF$_3$ | Cl | 4-trifluoromethylphenyl |
| 2713 | (CH$_2$)$_5$ | | O | CH$_2$CH$_2$CF$_3$ | Cl | 4-trifluoromethylphenyl |
| 2714 | 5,5-spiro[2.3]hexane | | O | CH$_2$CH$_2$CF$_3$ | Cl | 4-trifluoromethylphenyl |
| 2715 | Cyclopentyl | H | O | CH$_2$CH$_2$CF$_3$ | Cl | 4-trifluoromethylphenyl |

TABLE 10

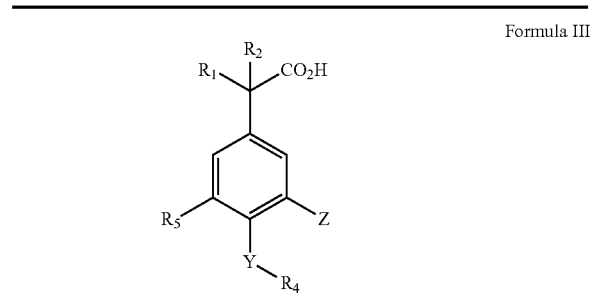

Formula III

Compounds of Formula III

| Ex | R1 | R2 | Y | R4 | R5 | Z |
|---|---|---|---|---|---|---|
| 2716 | CH$_2$CH$_3$ | H | O | CH$_2$CF$_3$ | CF$_3$ | 5-benzo[c][1,2,5]oxadiazole |
| 2717 | CH$_2$CF$_3$ | H | O | CH$_2$CF$_3$ | CF$_3$ | 5-benzo[c][1,2,5]oxadiazole |
| 2718 | CH$_2$CH$_2$CH$_3$ | H | O | CH$_2$CF$_3$ | CF$_3$ | 5-benzo[c][1,2,5]oxadiazole |
| 2719 | CH$_2$CH(CH$_3$)$_2$ | H | O | CH$_2$CF$_3$ | CF$_3$ | 5-benzo[c][1,2,5]oxadiazole |
| 2720 | cyclopropylmethyl | H | O | CH$_2$CF$_3$ | CF$_3$ | 5-benzo[c][1,2,5]oxadiazole |
| 2721 | cyclobutylmethyl | H | O | CH$_2$CF$_3$ | CF$_3$ | 5-benzo[c][1,2,5]oxadiazole |
| 2722 | (CH$_2$)$_2$ | | O | CH$_2$CF$_3$ | CF$_3$ | 5-benzo[c][1,2,5]oxadiazole |
| 2723 | (CH$_2$)$_3$ | | O | CH$_2$CF$_3$ | CF$_3$ | 5-benzo[c][1,2,5]oxadiazole |
| 2724 | (CH$_2$)$_4$ | | O | CH$_2$CF$_3$ | CF$_3$ | 5-benzo[c][1,2,5]oxadiazole |
| 2725 | (CH$_2$)$_5$ | | O | CH$_2$CF$_3$ | CF$_3$ | 5-benzo[c][1,2,5]oxadiazole |
| 2726 | 5,5-spiro[2.3]hexane | | O | CH$_2$CF$_3$ | CF$_3$ | 5-benzo[c][1,2,5]oxadiazole |
| 2727 | Cyclopentyl | H | O | CH$_2$CF$_3$ | CF$_3$ | 5-benzo[c][1,2,5]oxadiazole |
| 2733 | cyclobutylmethyl | H | O | CH$_2$CF$_3$ | F | 5-benzo[c][1,2,5]oxadiazole |
| 2735 | (CH$_2$)$_3$ | | O | CH$_2$CF$_3$ | F | 5-benzo[c][1,2,5]oxadiazole |
| 2737 | (CH$_2$)$_5$ | | O | CH$_2$CF$_3$ | F | 5-benzo[c][1,2,5]oxadiazole |
| 2738 | 5,5-spiro[2.3]hexane | | O | CH$_2$CF$_3$ | F | 5-benzo[c][1,2,5]oxadiazole |
| 2739 | Cyclopentyl | H | O | CH$_2$CF$_3$ | F | 5-benzo[c][1,2,5]oxadiazole |
| 2745 | cyclobutylmethyl | H | O | CH$_2$CF$_3$ | Cl | 5-benzo[c][1,2,5]oxadiazole |
| 2747 | (CH$_2$)$_3$ | | O | CH$_2$CF$_3$ | Cl | 5-benzo[c][1,2,5]oxadiazole |
| 2749 | (CH$_2$)$_5$ | | O | CH$_2$CF$_3$ | Cl | 5-benzo[c][1,2,5]oxadiazole |
| 2750 | 5,5-spiro[2.3]hexane | | O | CH$_2$CF$_3$ | Cl | 5-benzo[c][1,2,5]oxadiazole |
| 2751 | Cyclopentyl | H | O | CH$_2$CF$_3$ | Cl | 5-benzo[c][1,2,5]oxadiazole |
| 2752 | CH$_2$CH$_3$ | H | O | CH$_2$CF$_3$ | CF$_3$ | 5-benzo[c][1,2,5]thiadiazole |
| 2753 | CH$_2$CF$_3$ | H | O | CH$_2$CF$_3$ | CF$_3$ | 5-benzo[c][1,2,5]thiadiazole |
| 2754 | CH$_2$CH$_2$CH$_3$ | H | O | CH$_2$CF$_3$ | CF$_3$ | 5-benzo[c][1,2,5]thiadiazole |
| 2755 | CH$_2$CH(CH$_3$)$_2$ | H | O | CH$_2$CF$_3$ | CF$_3$ | 5-benzo[c][1,2,5]thiadiazole |
| 2756 | cyclopropylmethyl | H | O | CH$_2$CF$_3$ | CF$_3$ | 5-benzo[c][1,2,5]thiadiazole |
| 2757 | cyclobutylmethyl | H | O | CH$_2$CF$_3$ | CF$_3$ | 5-benzo[c][1,2,5]thiadiazole |
| 2758 | (CH$_2$)$_2$ | | O | CH$_2$CF$_3$ | CF$_3$ | 5-benzo[c][1,2,5]thiadiazole |
| 2759 | (CH$_2$)$_3$ | | O | CH$_2$CF$_3$ | CF$_3$ | 5-benzo[c][1,2,5]thiadiazole |

TABLE 10-continued

Formula III

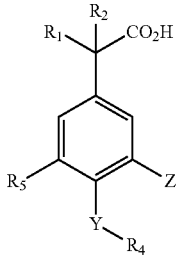

Compounds of Formula III

| Ex | R1 | R2 | Y | R4 | R5 | Z |
|---|---|---|---|---|---|---|
| 2760 | $(CH_2)_4$ |  | O | $CH_2CF_3$ | $CF_3$ | 5-benzo[c][1,2,5]thiadiazole |
| 2761 | $(CH_2)_5$ |  | O | $CH_2CF_3$ | $CF_3$ | 5-benzo[c][1,2,5]thiadiazole |
| 2762 | 5,5-spiro[2.3]hexane |  | O | $CH_2CF_3$ | $CF_3$ | 5-benzo[c][1,2,5]thiadiazole |
| 2763 | Cyclopentyl | H | O | $CH_2CF_3$ | $CF_3$ | 5-benzo[c][1,2,5]thiadiazole |
| 2769 | cyclobutylmethyl | H | O | $CH_2CF_3$ | F | 5-benzo[c][1,2,5]thiadiazole |
| 2771 | $(CH_2)_3$ |  | O | $CH_2CF_3$ | F | 5-benzo[c][1,2,5]thiadiazole |
| 2773 | $(CH_2)_5$ |  | O | $CH_2CF_3$ | F | 5-benzo[c][1,2,5]thiadiazole |
| 2774 | 5,5-spiro[2.3]hexane |  | O | $CH_2CF_3$ | F | 5-benzo[c][1,2,5]thiadiazole |
| 2775 | Cyclopentyl | H | O | $CH_2CF_3$ | F | 5-benzo[c][1,2,5]thiadiazole |
| 2781 | cyclobutylmethyl | H | O | $CH_2CF_3$ | Cl | 5-benzo[c][1,2,5]thiadiazole |
| 2783 | $(CH_2)_3$ |  | O | $CH_2CF_3$ | Cl | 5-benzo[c][1,2,5]thiadiazole |
| 2785 | $(CH_2)_5$ |  | O | $CH_2CF_3$ | Cl | 5-benzo[c][1,2,5]thiadiazole |
| 2786 | 5,5-spiro[2.3]hexane |  | O | $CH_2CF_3$ | Cl | 5-benzo[c][1,2,5]thiadiazole |
| 2787 | Cyclopentyl | H | O | $CH_2CF_3$ | Cl | 5-benzo[c][1,2,5]thiadiazole |
| 2788 | $CH_2CH_3$ | H | O | $CH_2$-c-Pr | $CF_3$ | 5-benzo[c][1,2,5]oxadiazole |
| 2789 | $CH_2CF_3$ | H | O | $CH_2$-c-Pr | $CF_3$ | 5-benzo[c][1,2,5]oxadiazole |
| 2790 | $CH_2CH_2CH_3$ | H | O | $CH_2$-c-Pr | $CF_3$ | 5-benzo[c][1,2,5]oxadiazole |
| 2791 | $CH_2CH(CH_3)_2$ | H | O | $CH_2$-c-Pr | $CF_3$ | 5-benzo[c][1,2,5]oxadiazole |
| 2792 | cyclopropylmethyl | H | O | $CH_2$-c-Pr | $CF_3$ | 5-benzo[c][1,2,5]oxadiazole |
| 2793 | cyclobutylmethyl | H | O | $CH_2$-c-Pr | $CF_3$ | 5-benzo[c][1,2,5]oxadiazole |
| 2794 | $(CH_2)_2$ |  | O | $CH_2$-c-Pr | $CF_3$ | 5-benzo[c][1,2,5]oxadiazole |
| 2795 | $(CH_2)_3$ |  | O | $CH_2$-c-Pr | $CF_3$ | 5-benzo[c][1,2,5]oxadiazole |
| 2796 | $(CH_2)_4$ |  | O | $CH_2$-c-Pr | $CF_3$ | 5-benzo[c][1,2,5]oxadiazole |
| 2797 | $(CH_2)_5$ |  | O | $CH_2$-c-Pr | $CF_3$ | 5-benzo[c][1,2,5]oxadiazole |
| 2798 | 5,5-spiro[2.3]hexane |  | O | $CH_2$-c-Pr | $CF_3$ | 5-benzo[c][1,2,5]oxadiazole |
| 2799 | Cyclopentyl | H | O | $CH_2$-c-Pr | $CF_3$ | 5-benzo[c][1,2,5]oxadiazole |
| 2805 | cyclobutylmethyl | H | O | $CH_2$-c-Pr | F | 5-benzo[c][1,2,5]oxadiazole |
| 2807 | $(CH_2)_3$ |  | O | $CH_2$-c-Pr | F | 5-benzo[c][1,2,5]oxadiazole |
| 2809 | $(CH_2)_5$ |  | O | $CH_2$-c-Pr | F | 5-benzo[c][1,2,5]oxadiazole |
| 2810 | 5,5-spiro[2.3]hexane |  | O | $CH_2$-c-Pr | F | 5-benzo[c][1,2,5]oxadiazole |
| 2811 | Cyclopentyl | H | O | $CH_2$-c-Pr | F | 5-benzo[c][1,2,5]oxadiazole |
| 2817 | cyclobutylmethyl | H | O | $CH_2$-c-Pr | Cl | 5-benzo[c][1,2,5]oxadiazole |
| 2819 | $(CH_2)_3$ |  | O | $CH_2$-c-Pr | Cl | 5-benzo[c][1,2,5]oxadiazole |
| 2821 | $(CH_2)_5$ |  | O | $CH_2$-c-Pr | Cl | 5-benzo[c][1,2,5]oxadiazole |
| 2822 | 5,5-spiro[2.3]hexane |  | O | $CH_2$-c-Pr | Cl | 5-benzo[c][1,2,5]oxadiazole |
| 2823 | Cyclopentyl | H | O | $CH_2$-c-Pr | Cl | 5-benzo[c][1,2,5]oxadiazole |
| 2824 | $CH_2CH_3$ | H | O | $CH_2$-c-Pr | $CF_3$ | 5-benzo[c][1,2,5]thiadiazole |
| 2825 | $CH_2CF_3$ | H | O | $CH_2$-c-Pr | $CF_3$ | 5-benzo[c][1,2,5]thiadiazole |
| 2826 | $CH_2CH_2CH_3$ | H | O | $CH_2$-c-Pr | $CF_3$ | 5-benzo[c][1,2,5]thiadiazole |
| 2827 | $CH_2CH(CH_3)_2$ | H | O | $CH_2$-c-Pr | $CF_3$ | 5-benzo[c][1,2,5]thiadiazole |
| 2828 | cyclopropylmethyl | H | O | $CH_2$-c-Pr | $CF_3$ | 5-benzo[c][1,2,5]thiadiazole |
| 2829 | cyclobutylmethyl | H | O | $CH_2$-c-Pr | $CF_3$ | 5-benzo[c][1,2,5]thiadiazole |
| 2830 | $(CH_2)_2$ |  | O | $CH_2$-c-Pr | $CF_3$ | 5-benzo[c][1,2,5]thiadiazole |
| 2831 | $(CH_2)_3$ |  | O | $CH_2$-c-Pr | $CF_3$ | 5-benzo[c][1,2,5]thiadiazole |
| 2832 | $(CH_2)_4$ |  | O | $CH_2$-c-Pr | $CF_3$ | 5-benzo[c][1,2,5]thiadiazole |
| 2833 | $(CH_2)_5$ |  | O | $CH_2$-c-Pr | $CF_3$ | 5-benzo[c][1,2,5]thiadiazole |
| 2834 | 5,5-spiro[2.3]hexane |  | O | $CH_2$-c-Pr | $CF_3$ | 5-benzo[c][1,2,5]thiadiazole |
| 2835 | Cyclopentyl | H | O | $CH_2$-c-Pr | $CF_3$ | 5-benzo[c][1,2,5]thiadiazole |
| 2841 | cyclobutylmethyl | H | O | $CH_2$-c-Pr | F | 5-benzo[c][1,2,5]thiadiazole |
| 2843 | $(CH_2)_3$ |  | O | $CH_2$-c-Pr | F | 5-benzo[c][1,2,5]thiadiazole |
| 2845 | $(CH_2)_5$ |  | O | $CH_2$-c-Pr | F | 5-benzo[c][1,2,5]thiadiazole |
| 2846 | 5,5-spiro[2.3]hexane |  | O | $CH_2$-c-Pr | F | 5-benzo[c][1,2,5]thiadiazole |
| 2847 | Cyclopentyl | H | O | $CH_2$-c-Pr | F | 5-benzo[c][1,2,5]thiadiazole |
| 2853 | cyclobutylmethyl | H | O | $CH_2$-c-Pr | Cl | 5-benzo[c][1,2,5]thiadiazole |
| 2855 | $(CH_2)_3$ |  | O | $CH_2$-c-Pr | Cl | 5-benzo[c][1,2,5]thiadiazole |
| 2857 | $(CH_2)_5$ |  | O | $CH_2$-c-Pr | Cl | 5-benzo[c][1,2,5]thiadiazole |
| 2858 | 5,5-spiro[2.3]hexane |  | O | $CH_2$-c-Pr | Cl | 5-benzo[c][1,2,5]thiadiazole |
| 2859 | Cyclopentyl | H | O | $CH_2$-c-Pr | Cl | 5-benzo[c][1,2,5]thiadiazole |

TABLE 11

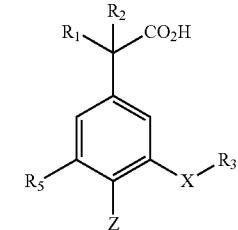

Formula IV

Compounds of Formula IV

| Ex | R1 | R2 | X | R3 | R5 | Z |
|---|---|---|---|---|---|---|
| 2860 | $CH_2CH_3$ | H | O | $CH_2CF_3$ | $CF_3$ | 5-benzo[c][1,2,5]oxadiazole |
| 2861 | $CH_2CF_3$ | H | O | $CH_2CF_3$ | $CF_3$ | 5-benzo[c][1,2,5]oxadiazole |
| 2862 | $CH_2CH_2CH_3$ | H | O | $CH_2CF_3$ | $CF_3$ | 5-benzo[c][1,2,5]oxadiazole |
| 2863 | $CH_2CH(CH_3)_2$ | H | O | $CH_2CF_3$ | $CF_3$ | 5-benzo[c][1,2,5]oxadiazole |
| 2864 | cyclopropylmethyl | H | O | $CH_2CF_3$ | $CF_3$ | 5-benzo[c][1,2,5]oxadiazole |
| 2865 | cyclobutylmethyl | H | O | $CH_2CF_3$ | $CF_3$ | 5-benzo[c][1,2,5]oxadiazole |
| 2866 | $(CH_2)_2$ | | O | $CH_2CF_3$ | $CF_3$ | 5-benzo[c][1,2,5]oxadiazole |
| 2867 | $(CH_2)_3$ | | O | $CH_2CF_3$ | $CF_3$ | 5-benzo[c][1,2,5]oxadiazole |
| 2868 | $(CH_2)_4$ | | O | $CH_2CF_3$ | $CF_3$ | 5-benzo[c][1,2,5]oxadiazole |
| 2869 | $(CH_2)_5$ | | O | $CH_2CF_3$ | $CF_3$ | 5-benzo[c][1,2,5]oxadiazole |
| 2870 | 5,5-spiro[2.3]hexane | | O | $CH_2CF_3$ | $CF_3$ | 5-benzo[c][1,2,5]oxadiazole |
| 2871 | Cyclopentyl | H | O | $CH_2CF_3$ | $CF_3$ | 5-benzo[c][1,2,5]oxadiazole |
| 2872 | $CH_2CH_3$ | H | O | $CH_2CF_3$ | F | 5-benzo[c][1,2,5]oxadiazole |
| 2873 | $CH_2CF_3$ | H | O | $CH_2CF_3$ | F | 5-benzo[c][1,2,5]oxadiazole |
| 2874 | $CH_2CH_2CH_3$ | H | O | $CH_2CF_3$ | F | 5-benzo[c][1,2,5]oxadiazole |
| 2875 | $CH_2CH(CH_3)_2$ | H | O | $CH_2CF_3$ | F | 5-benzo[c][1,2,5]oxadiazole |
| 2876 | cyclopropylmethyl | H | O | $CH_2CF_3$ | F | 5-benzo[c][1,2,5]oxadiazole |
| 2877 | cyclobutylmethyl | H | O | $CH_2CF_3$ | F | 5-benzo[c][1,2,5]oxadiazole |
| 2878 | $(CH_2)_2$ | | O | $CH_2CF_3$ | F | 5-benzo[c][1,2,5]oxadiazole |
| 2879 | $(CH_2)_3$ | | O | $CH_2CF_3$ | F | 5-benzo[c][1,2,5]oxadiazole |
| 2880 | $(CH_2)_4$ | | O | $CH_2CF_3$ | F | 5-benzo[c][1,2,5]oxadiazole |
| 2881 | $(CH_2)_5$ | | O | $CH_2CF_3$ | F | 5-benzo[c][1,2,5]oxadiazole |
| 2882 | 5,5-spiro[2.3]hexane | | O | $CH_2CF_3$ | F | 5-benzo[c][1,2,5]oxadiazole |
| 2883 | Cyclopentyl | H | O | $CH_2CF_3$ | F | 5-benzo[c][1,2,5]oxadiazole |
| 2884 | $CH_2CH_3$ | H | O | $CH_2CF_3$ | Cl | 5-benzo[c][1,2,5]oxadiazole |
| 2885 | $CH_2CF_3$ | H | O | $CH_2CF_3$ | Cl | 5-benzo[c][1,2,5]oxadiazole |
| 2886 | $CH_2CH_2CH_3$ | H | O | $CH_2CF_3$ | Cl | 5-benzo[c][1,2,5]oxadiazole |
| 2887 | $CH_2CH(CH_3)_2$ | H | O | $CH_2CF_3$ | Cl | 5-benzo[c][1,2,5]oxadiazole |
| 2888 | cyclopropylmethyl | H | O | $CH_2CF_3$ | Cl | 5-benzo[c][1,2,5]oxadiazole |
| 2889 | cyclobutylmethyl | H | O | $CH_2CF_3$ | Cl | 5-benzo[c][1,2,5]oxadiazole |
| 2890 | $(CH_2)_2$ | | O | $CH_2CF_3$ | Cl | 5-benzo[c][1,2,5]oxadiazole |
| 2891 | $(CH_2)_3$ | | O | $CH_2CF_3$ | Cl | 5-benzo[c][1,2,5]oxadiazole |
| 2892 | $(CH_2)_4$ | | O | $CH_2CF_3$ | Cl | 5-benzo[c][1,2,5]oxadiazole |
| 2893 | $(CH_2)_5$ | | O | $CH_2CF_3$ | Cl | 5-benzo[c][1,2,5]oxadiazole |
| 2894 | 5,5-spiro[2.3]hexane | | O | $CH_2CF_3$ | Cl | 5-benzo[c][1,2,5]oxadiazole |
| 2895 | Cyclopentyl | H | O | $CH_2CF_3$ | Cl | 5-benzo[c][1,2,5]oxadiazole |
| 2896 | $CH_2CH_3$ | H | O | $CH_2CF_3$ | $CF_3$ | 5-benzo[c][1,2,5]thiadiazole |
| 2897 | $CH_2CF_3$ | H | O | $CH_2CF_3$ | $CF_3$ | 5-benzo[c][1,2,5]thiadiazole |
| 2898 | $CH_2CH_2CH_3$ | H | O | $CH_2CF_3$ | $CF_3$ | 5-benzo[c][1,2,5]thiadiazole |
| 2899 | $CH_2CH(CH_3)_2$ | H | O | $CH_2CF_3$ | $CF_3$ | 5-benzo[c][1,2,5]thiadiazole |
| 2900 | cyclopropylmethyl | H | O | $CH_2CF_3$ | $CF_3$ | 5-benzo[c][1,2,5]thiadiazole |
| 2901 | cyclobutylmethyl | H | O | $CH_2CF_3$ | $CF_3$ | 5-benzo[c][1,2,5]thiadiazole |
| 2902 | $(CH_2)_2$ | | O | $CH_2CF_3$ | $CF_3$ | 5-benzo[c][1,2,5]thiadiazole |
| 2903 | $(CH_2)_3$ | | O | $CH_2CF_3$ | $CF_3$ | 5-benzo[c][1,2,5]thiadiazole |
| 2904 | $(CH_2)_4$ | | O | $CH_2CF_3$ | $CF_3$ | 5-benzo[c][1,2,5]thiadiazole |
| 2905 | $(CH_2)_5$ | | O | $CH_2CF_3$ | $CF_3$ | 5-benzo[c][1,2,5]thiadiazole |
| 2906 | 5,5-spiro[2.3]hexane | | O | $CH_2CF_3$ | $CF_3$ | 5-benzo[c][1,2,5]thiadiazole |
| 2907 | Cyclopentyl | H | O | $CH_2CF_3$ | $CF_3$ | 5-benzo[c][1,2,5]thiadiazole |
| 2908 | $CH_2CH_3$ | H | O | $CH_2CF_3$ | F | 5-benzo[c][1,2,5]thiadiazole |
| 2909 | $CH_2CF_3$ | H | O | $CH_2CF_3$ | F | 5-benzo[c][1,2,5]thiadiazole |
| 2910 | $CH_2CH_2CH_3$ | H | O | $CH_2CF_3$ | F | 5-benzo[c][1,2,5]thiadiazole |
| 2911 | $CH_2CH(CH_3)_2$ | H | O | $CH_2CF_3$ | F | 5-benzo[c][1,2,5]thiadiazole |
| 2912 | cyclopropylmethyl | H | O | $CH_2CF_3$ | F | 5-benzo[c][1,2,5]thiadiazole |
| 2913 | cyclobutylmethyl | H | O | $CH_2CF_3$ | F | 5-benzo[c][1,2,5]thiadiazole |
| 2914 | $(CH_2)_2$ | | O | $CH_2CF_3$ | F | 5-benzo[c][1,2,5]thiadiazole |
| 2915 | $(CH_2)_3$ | | O | $CH_2CF_3$ | F | 5-benzo[c][1,2,5]thiadiazole |
| 2916 | $(CH_2)_4$ | | O | $CH_2CF_3$ | F | 5-benzo[c][1,2,5]thiadiazole |
| 2917 | $(CH_2)_5$ | | O | $CH_2CF_3$ | F | 5-benzo[c][1,2,5]thiadiazole |
| 2918 | 5,5-spiro[2.3]hexane | | O | $CH_2CF_3$ | F | 5-benzo[c][1,2,5]thiadiazole |
| 2919 | Cyclopentyl | H | O | $CH_2CF_3$ | F | 5-benzo[c][1,2,5]thiadiazole |
| 2920 | $CH_2CH_3$ | H | O | $CH_2CF_3$ | Cl | 5-benzo[c][1,2,5]thiadiazole |
| 2921 | $CH_2CF_3$ | H | O | $CH_2CF_3$ | Cl | 5-benzo[c][1,2,5]thiadiazole |

TABLE 11-continued

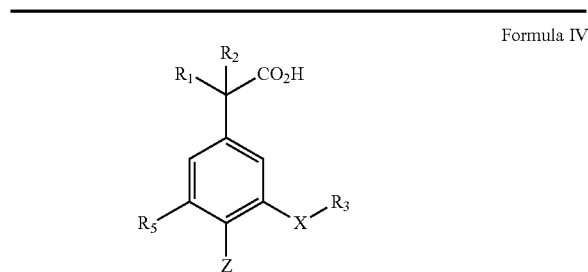

Compounds of Formula IV

| Ex | R1 | R2 | X | R3 | R5 | Z |
|---|---|---|---|---|---|---|
| 2922 | $CH_2CH_2CH_3$ | H | O | $CH_2CF_3$ | Cl | 5-benzo[c][1,2,5]thiadiazole |
| 2923 | $CH_2CH(CH_3)_2$ | H | O | $CH_2CF_3$ | Cl | 5-benzo[c][1,2,5]thiadiazole |
| 2924 | cyclopropylmethyl | H | O | $CH_2CF_3$ | Cl | 5-benzo[c][1,2,5]thiadiazole |
| 2925 | cyclobutylmethyl | H | O | $CH_2CF_3$ | Cl | 5-benzo[c][1,2,5]thiadiazole |
| 2926 | $(CH_2)_2$ | | O | $CH_2CF_3$ | Cl | 5-benzo[c][1,2,5]thiadiazole |
| 2927 | $(CH_2)_3$ | | O | $CH_2CF_3$ | Cl | 5-benzo[c][1,2,5]thiadiazole |
| 2928 | $(CH_2)_4$ | | O | $CH_2CF_3$ | Cl | 5-benzo[c][1,2,5]thiadiazole |
| 2929 | $(CH_2)_5$ | | O | $CH_2CF_3$ | Cl | 5-benzo[c][1,2,5]thiadiazole |
| 2930 | 5,5-spiro[2.3]hexane | | O | $CH_2CF_3$ | Cl | 5-benzo[c][1,2,5]thiadiazole |
| 2931 | Cyclopentyl | H | O | $CH_2CF_3$ | Cl | 5-benzo[c][1,2,5]thiadiazole |
| 2932 | $CH_2CH_3$ | H | O | $CH_2$-c-Pr | $CF_3$ | 5-benzo[c][1,2,5]oxadiazole |
| 2933 | $CH_2CF_3$ | H | O | $CH_2$-c-Pr | $CF_3$ | 5-benzo[c][1,2,5]oxadiazole |
| 2934 | $CH_2CH_2CH_3$ | H | O | $CH_2$-c-Pr | $CF_3$ | 5-benzo[c][1,2,5]oxadiazole |
| 2935 | $CH_2CH(CH_3)_2$ | H | O | $CH_2$-c-Pr | $CF_3$ | 5-benzo[c][1,2,5]oxadiazole |
| 2936 | cyclopropylmethyl | H | O | $CH_2$-c-Pr | $CF_3$ | 5-benzo[c][1,2,5]oxadiazole |
| 2937 | cyclobutylmethyl | H | O | $CH_2$-c-Pr | $CF_3$ | 5-benzo[c][1,2,5]oxadiazole |
| 2938 | $(CH_2)_2$ | | O | $CH_2$-c-Pr | $CF_3$ | 5-benzo[c][1,2,5]oxadiazole |
| 2939 | $(CH_2)_3$ | | O | $CH_2$-c-Pr | $CF_3$ | 5-benzo[c][1,2,5]oxadiazole |
| 2940 | $(CH_2)_4$ | | O | $CH_2$-c-Pr | $CF_3$ | 5-benzo[c][1,2,5]oxadiazole |
| 2941 | $(CH_2)_5$ | | O | $CH_2$-c-Pr | $CF_3$ | 5-benzo[c][1,2,5]oxadiazole |
| 2942 | 5,5-spiro[2.3]hexane | | O | $CH_2$-c-Pr | $CF_3$ | 5-benzo[c][1,2,5]oxadiazole |
| 2943 | Cyclopentyl | H | O | $CH_2$-c-Pr | $CF_3$ | 5-benzo[c][1,2,5]oxadiazole |
| 2944 | $CH_2CH_3$ | H | O | $CH_2$-c-Pr | F | 5-benzo[c][1,2,5]oxadiazole |
| 2945 | $CH_2CF_3$ | H | O | $CH_2$-c-Pr | F | 5-benzo[c][1,2,5]oxadiazole |
| 2946 | $CH_2CH_2CH_3$ | H | O | $CH_2$-c-Pr | F | 5-benzo[c][1,2,5]oxadiazole |
| 2947 | $CH_2CH(CH_3)_2$ | H | O | $CH_2$-c-Pr | F | 5-benzo[c][1,2,5]oxadiazole |
| 2948 | cyclopropylmethyl | H | O | $CH_2$-c-Pr | F | 5-benzo[c][1,2,5]oxadiazole |
| 2949 | cyclobutylmethyl | H | O | $CH_2$-c-Pr | F | 5-benzo[c][1,2,5]oxadiazole |
| 2950 | $(CH_2)_2$ | | O | $CH_2$-c-Pr | F | 5-benzo[c][1,2,5]oxadiazole |
| 2951 | $(CH_2)_3$ | | O | $CH_2$-c-Pr | F | 5-benzo[c][1,2,5]oxadiazole |
| 2952 | $(CH_2)_4$ | | O | $CH_2$-c-Pr | F | 5-benzo[c][1,2,5]oxadiazole |
| 2953 | $(CH_2)_5$ | | O | $CH_2$-c-Pr | F | 5-benzo[c][1,2,5]oxadiazole |
| 2954 | 5,5-spiro[2.3]hexane | | O | $CH_2$-c-Pr | F | 5-benzo[c][1,2,5]oxadiazole |
| 2955 | Cyclopentyl | H | O | $CH_2$-c-Pr | F | 5-benzo[c][1,2,5]oxadiazole |
| 2956 | $CH_2CH_3$ | H | O | $CH_2$-c-Pr | Cl | 5-benzo[c][1,2,5]oxadiazole |
| 2957 | $CH_2CF_3$ | H | O | $CH_2$-c-Pr | Cl | 5-benzo[c][1,2,5]oxadiazole |
| 2958 | $CH_2CH_2CH_3$ | H | O | $CH_2$-c-Pr | Cl | 5-benzo[c][1,2,5]oxadiazole |
| 2959 | $CH_2CH(CH_3)_2$ | H | O | $CH_2$-c-Pr | Cl | 5-benzo[c][1,2,5]oxadiazole |
| 2960 | cyclopropylmethyl | H | O | $CH_2$-c-Pr | Cl | 5-benzo[c][1,2,5]oxadiazole |
| 2961 | cyclobutylmethyl | H | O | $CH_2$-c-Pr | Cl | 5-benzo[c][1,2,5]oxadiazole |
| 2962 | $(CH_2)_2$ | | O | $CH_2$-c-Pr | Cl | 5-benzo[c][1,2,5]oxadiazole |
| 2963 | $(CH_2)_3$ | | O | $CH_2$-c-Pr | Cl | 5-benzo[c][1,2,5]oxadiazole |
| 2964 | $(CH_2)_4$ | | O | $CH_2$-c-Pr | Cl | 5-benzo[c][1,2,5]oxadiazole |
| 2965 | $(CH_2)_5$ | | O | $CH_2$-c-Pr | Cl | 5-benzo[c][1,2,5]oxadiazole |
| 2966 | 5,5-spiro[2.3]hexane | | O | $CH_2$-c-Pr | Cl | 5-benzo[c][1,2,5]oxadiazole |
| 2967 | Cyclopentyl | H | O | $CH_2$-c-Pr | Cl | 5-benzo[c][1,2,5]oxadiazole |
| 2968 | $CH_2CH_3$ | H | O | $CH_2$-c-Pr | $CF_3$ | 5-benzo[c][1,2,5]thiadiazole |
| 2969 | $CH_2CF_3$ | H | O | $CH_2$-c-Pr | $CF_3$ | 5-benzo[c][1,2,5]thiadiazole |
| 2970 | $CH_2CH_2CH_3$ | H | O | $CH_2$-c-Pr | $CF_3$ | 5-benzo[c][1,2,5]thiadiazole |
| 2971 | $CH_2CH(CH_3)_2$ | H | O | $CH_2$-c-Pr | $CF_3$ | 5-benzo[c][1,2,5]thiadiazole |
| 2972 | cyclopropylmethyl | H | O | $CH_2$-c-Pr | $CF_3$ | 5-benzo[c][1,2,5]thiadiazole |
| 2973 | cyclobutylmethyl | H | O | $CH_2$-c-Pr | $CF_3$ | 5-benzo[c][1,2,5]thiadiazole |
| 2974 | $(CH_2)_2$ | | O | $CH_2$-c-Pr | $CF_3$ | 5-benzo[c][1,2,5]thiadiazole |
| 2975 | $(CH_2)_3$ | | O | $CH_2$-c-Pr | $CF_3$ | 5-benzo[c][1,2,5]thiadiazole |
| 2976 | $(CH_2)_4$ | | O | $CH_2$-c-Pr | $CF_3$ | 5-benzo[c][1,2,5]thiadiazole |
| 2977 | $(CH_2)_5$ | | O | $CH_2$-c-Pr | $CF_3$ | 5-benzo[c][1,2,5]thiadiazole |
| 2978 | 5,5-spiro[2.3]hexane | | O | $CH_2$-c-Pr | $CF_3$ | 5-benzo[c][1,2,5]thiadiazole |
| 2979 | Cyclopentyl | H | O | $CH_2$-c-Pr | $CF_3$ | 5-benzo[c][1,2,5]thiadiazole |
| 2980 | $CH_2CH_3$ | H | O | $CH_2$-c-Pr | F | 5-benzo[c][1,2,5]thiadiazole |
| 2981 | $CH_2CF_3$ | H | O | $CH_2$-c-Pr | F | 5-benzo[c][1,2,5]thiadiazole |
| 2982 | $CH_2CH_2CH_3$ | H | O | $CH_2$-c-Pr | F | 5-benzo[c][1,2,5]thiadiazole |
| 2983 | $CH_2CH(CH_3)_2$ | H | O | $CH_2$-c-Pr | F | 5-benzo[c][1,2,5]thiadiazole |

TABLE 11-continued

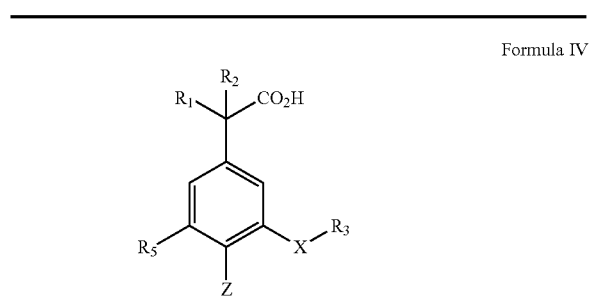

Formula IV

Compounds of Formula IV

| Ex | R1 | R2 | X | R3 | R5 | Z |
|---|---|---|---|---|---|---|
| 2984 | cyclopropylmethyl | H | O | CH$_2$-c-Pr | F | 5-benzo[c][1,2,5]thiadiazole |
| 2985 | cyclobutylmethyl | H | O | CH$_2$-c-Pr | F | 5-benzo[c][1,2,5]thiadiazole |
| 2986 | (CH$_2$)$_2$ | | O | CH$_2$-c-Pr | F | 5-benzo[c][1,2,5]thiadiazole |
| 2987 | (CH$_2$)$_3$ | | O | CH$_2$-c-Pr | F | 5-benzo[c][1,2,5]thiadiazole |
| 2988 | (CH$_2$)$_4$ | | O | CH$_2$-c-Pr | F | 5-benzo[c][1,2,5]thiadiazole |
| 2989 | (CH$_2$)$_5$ | | O | CH$_2$-c-Pr | F | 5-benzo[c][1,2,5]thiadiazole |
| 2990 | 5,5-spiro[2.3]hexane | | O | CH$_2$-c-Pr | F | 5-benzo[c][1,2,5]thiadiazole |
| 2991 | Cyclopentyl | H | O | CH$_2$-c-Pr | F | 5-benzo[c][1,2,5]thiadiazole |
| 2992 | CH$_2$CH$_3$ | H | O | CH$_2$-c-Pr | Cl | 5-benzo[c][1,2,5]thiadiazole |
| 2993 | CH$_2$CF$_3$ | H | O | CH$_2$-c-Pr | Cl | 5-benzo[c][1,2,5]thiadiazole |
| 2994 | CH$_2$CH$_2$CH$_3$ | H | O | CH$_2$-c-Pr | Cl | 5-benzo[c][1,2,5]thiadiazole |
| 2995 | CH$_2$CH(CH$_3$)$_2$ | H | O | CH$_2$-c-Pr | Cl | 5-benzo[c][1,2,5]thiadiazole |
| 2996 | cyclopropylmethyl | H | O | CH$_2$-c-Pr | Cl | 5-benzo[c][1,2,5]thiadiazole |
| 2997 | cyclobutylmethyl | H | O | CH$_2$-c-Pr | Cl | 5-benzo[c][1,2,5]thiadiazole |
| 2998 | (CH$_2$)$_2$ | | O | CH$_2$-c-Pr | Cl | 5-benzo[c][1,2,5]thiadiazole |
| 2999 | (CH$_2$)$_3$ | | O | CH$_2$-c-Pr | Cl | 5-benzo[c][1,2,5]thiadiazole |
| 3000 | (CH$_2$)$_4$ | | O | CH$_2$-c-Pr | Cl | 5-benzo[c][1,2,5]thiadiazole |
| 3001 | (CH$_2$)$_5$ | | O | CH$_2$-c-Pr | Cl | 5-benzo[c][1,2,5]thiadiazole |
| 3002 | 5,5-spiro[2.3]hexane | | O | CH$_2$-c-Pr | Cl | 5-benzo[c][1,2,5]thiadiazole |
| 3003 | Cyclopentyl | H | O | CH$_2$-c-Pr | Cl | 5-benzo[c][1,2,5]thiadiazole |

TABLE 12

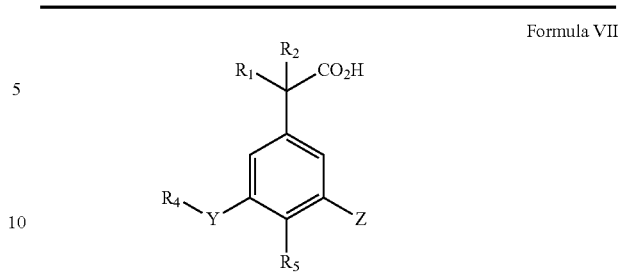

Formula VII

Compounds of Formula VII

| Ex | R1 | R2 | Y | R4 | R5 | Z |
|---|---|---|---|---|---|---|
| 3004 | CH$_2$CH$_3$ | H | O | CH$_2$CF$_3$ | CF$_3$ | 5-benzo[c][1,2,5]oxadiazole |
| 3005 | CH$_2$CF$_3$ | H | O | CH$_2$CF$_3$ | CF$_3$ | 5-benzo[c][1,2,5]oxadiazole |
| 3006 | CH$_2$CH$_2$CH$_3$ | H | O | CH$_2$CF$_3$ | CF$_3$ | 5-benzo[c][1,2,5]oxadiazole |
| 3007 | CH$_2$CH(CH$_3$)$_2$ | H | O | CH$_2$CF$_3$ | CF$_3$ | 5-benzo[c][1,2,5]oxadiazole |
| 3008 | cyclopropylmethyl | H | O | CH$_2$CF$_3$ | CF$_3$ | 5-benzo[c][1,2,5]oxadiazole |
| 3009 | cyclobutylmethyl | H | O | CH$_2$CF$_3$ | CF$_3$ | 5-benzo[c][1,2,5]oxadiazole |
| 3010 | (CH$_2$)$_2$ | | O | CH$_2$CF$_3$ | CF$_3$ | 5-benzo[c][1,2,5]oxadiazole |
| 3011 | (CH$_2$)$_3$ | | O | CH$_2$CF$_3$ | CF$_3$ | 5-benzo[c][1,2,5]oxadiazole |
| 3012 | (CH$_2$)$_4$ | | O | CH$_2$CF$_3$ | CF$_3$ | 5-benzo[c][1,2,5]oxadiazole |
| 3013 | (CH$_2$)$_5$ | | O | CH$_2$CF$_3$ | CF$_3$ | 5-benzo[c][1,2,5]oxadiazole |
| 3014 | 5,5-spiro[2.3]hexane | | O | CH$_2$CF$_3$ | CF$_3$ | 5-benzo[c][1,2,5]oxadiazole |
| 3015 | Cyclopentyl | H | O | CH$_2$CF$_3$ | CF$_3$ | 5-benzo[c][1,2,5]oxadiazole |
| 3016 | CH$_2$CH$_3$ | H | O | CH$_2$CF$_3$ | F | 5-benzo[c][1,2,5]oxadiazole |
| 3017 | CH$_2$CF$_3$ | H | O | CH$_2$CF$_3$ | F | 5-benzo[c][1,2,5]oxadiazole |
| 3018 | CH$_2$CH$_2$CH$_3$ | H | O | CH$_2$CF$_3$ | F | 5-benzo[c][1,2,5]oxadiazole |
| 3019 | CH$_2$CH(CH$_3$)$_2$ | H | O | CH$_2$CF$_3$ | F | 5-benzo[c][1,2,5]oxadiazole |
| 3020 | cyclopropylmethyl | H | O | CH$_2$CF$_3$ | F | 5-benzo[c][1,2,5]oxadiazole |
| 3021 | cyclobutylmethyl | H | O | CH$_2$CF$_3$ | F | 5-benzo[c][1,2,5]oxadiazole |
| 3022 | (CH$_2$)$_2$ | | O | CH$_2$CF$_3$ | F | 5-benzo[c][1,2,5]oxadiazole |
| 3023 | (CH$_2$)$_3$ | | O | CH$_2$CF$_3$ | F | 5-benzo[c][1,2,5]oxadiazole |
| 3024 | (CH$_2$)$_4$ | | O | CH$_2$CF$_3$ | F | 5-benzo[c][1,2,5]oxadiazole |
| 3025 | (CH$_2$)$_5$ | | O | CH$_2$CF$_3$ | F | 5-benzo[c][1,2,5]oxadiazole |
| 3026 | 5,5-spiro[2.3]hexane | | O | CH$_2$CF$_3$ | F | 5-benzo[c][1,2,5]oxadiazole |
| 3027 | Cyclopentyl | H | O | CH$_2$CF$_3$ | F | 5-benzo[c][1,2,5]oxadiazole |
| 3028 | CH$_2$CH$_3$ | H | O | CH$_2$CF$_3$ | Cl | 5-benzo[c][1,2,5]oxadiazole |
| 3029 | CH$_2$CF$_3$ | H | O | CH$_2$CF$_3$ | Cl | 5-benzo[c][1,2,5]oxadiazole |
| 3030 | CH$_2$CH$_2$CH$_3$ | H | O | CH$_2$CF$_3$ | Cl | 5-benzo[c][1,2,5]oxadiazole |
| 3031 | CH$_2$CH(CH$_3$)$_2$ | H | O | CH$_2$CF$_3$ | Cl | 5-benzo[c][1,2,5]oxadiazole |
| 3032 | cyclopropylmethyl | H | O | CH$_2$CF$_3$ | Cl | 5-benzo[c][1,2,5]oxadiazole |
| 3033 | cyclobutylmethyl | H | O | CH$_2$CF$_3$ | Cl | 5-benzo[c][1,2,5]oxadiazole |
| 3034 | (CH$_2$)$_2$ | | O | CH$_2$CF$_3$ | Cl | 5-benzo[c][1,2,5]oxadiazole |

TABLE 12-continued

Formula VII

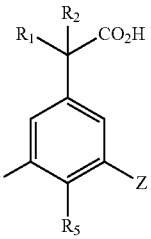

Compounds of Formula VII

| Ex | R1 | R2 | Y | R4 | R5 | Z |
|---|---|---|---|---|---|---|
| 3035 | $(CH_2)_3$ | | O | $CH_2CF_3$ | Cl | 5-benzo[c][1,2,5]oxadiazole |
| 3036 | $(CH_2)_4$ | | O | $CH_2CF_3$ | Cl | 5-benzo[c][1,2,5]oxadiazole |
| 3037 | $(CH_2)_5$ | | O | $CH_2CF_3$ | Cl | 5-benzo[c][1,2,5]oxadiazole |
| 3038 | 5,5-spiro[2.3]hexane | | O | $CH_2CF_3$ | Cl | 5-benzo[c][1,2,5]oxadiazole |
| 3039 | Cyclopentyl | H | O | $CH_2CF_3$ | Cl | 5-benzo[c][1,2,5]oxadiazole |
| 3040 | $CH_2CH_3$ | H | O | $CH_2CF_3$ | $CF_3$ | 5-benzo[c][1,2,5]thiadiazole |
| 3041 | $CH_2CF_3$ | H | O | $CH_2CF_3$ | $CF_3$ | 5-benzo[c][1,2,5]thiadiazole |
| 3042 | $CH_2CH_2CH_3$ | H | O | $CH_2CF_3$ | $CF_3$ | 5-benzo[c][1,2,5]thiadiazole |
| 3043 | $CH_2CH(CH_3)_2$ | H | O | $CH_2CF_3$ | $CF_3$ | 5-benzo[c][1,2,5]thiadiazole |
| 3044 | cyclopropylmethyl | H | O | $CH_2CF_3$ | $CF_3$ | 5-benzo[c][1,2,5]thiadiazole |
| 3045 | cyclobutylmethyl | H | O | $CH_2CF_3$ | $CF_3$ | 5-benzo[c][1,2,5]thiadiazole |
| 3046 | $(CH_2)_2$ | | O | $CH_2CF_3$ | $CF_3$ | 5-benzo[c][1,2,5]thiadiazole |
| 3047 | $(CH_2)_3$ | | O | $CH_2CF_3$ | $CF_3$ | 5-benzo[c][1,2,5]thiadiazole |
| 3048 | $(CH_2)_4$ | | O | $CH_2CF_3$ | $CF_3$ | 5-benzo[c][1,2,5]thiadiazole |
| 3049 | $(CH_2)_5$ | | O | $CH_2CF_3$ | $CF_3$ | 5-benzo[c][1,2,5]thiadiazole |
| 3050 | 5,5-spiro[2.3]hexane | | O | $CH_2CF_3$ | $CF_3$ | 5-benzo[c][1,2,5]thiadiazole |
| 3051 | Cyclopentyl | H | O | $CH_2CF_3$ | $CF_3$ | 5-benzo[c][1,2,5]thiadiazole |
| 3052 | $CH_2CH_3$ | H | O | $CH_2CF_3$ | F | 5-benzo[c][1,2,5]thiadiazole |
| 3053 | $CH_2CF_3$ | H | O | $CH_2CF_3$ | F | 5-benzo[c][1,2,5]thiadiazole |
| 3054 | $CH_2CH_2CH_3$ | H | O | $CH_2CF_3$ | F | 5-benzo[c][1,2,5]thiadiazole |
| 3055 | $CH_2CH(CH_3)_2$ | H | O | $CH_2CF_3$ | F | 5-benzo[c][1,2,5]thiadiazole |
| 3056 | cyclopropylmethyl | H | O | $CH_2CF_3$ | F | 5-benzo[c][1,2,5]thiadiazole |
| 3057 | cyclobutylmethyl | H | O | $CH_2CF_3$ | F | 5-benzo[c][1,2,5]thiadiazole |
| 3058 | $(CH_2)_2$ | | O | $CH_2CF_3$ | F | 5-benzo[c][1,2,5]thiadiazole |
| 3059 | $(CH_2)_3$ | | O | $CH_2CF_3$ | F | 5-benzo[c][1,2,5]thiadiazole |
| 3060 | $(CH_2)_4$ | | O | $CH_2CF_3$ | F | 5-benzo[c][1,2,5]thiadiazole |
| 3061 | $(CH_2)_5$ | | O | $CH_2CF_3$ | F | 5-benzo[c][1,2,5]thiadiazole |
| 3062 | 5,5-spiro[2.3]hexane | | O | $CH_2CF_3$ | F | 5-benzo[c][1,2,5]thiadiazole |
| 3063 | Cyclopentyl | H | O | $CH_2CF_3$ | F | 5-benzo[c][1,2,5]thiadiazole |
| 3064 | $CH_2CH_3$ | H | O | $CH_2CF_3$ | Cl | 5-benzo[c][1,2,5]thiadiazole |
| 3065 | $CH_2CF_3$ | H | O | $CH_2CF_3$ | Cl | 5-benzo[c][1,2,5]thiadiazole |
| 3066 | $CH_2CH_2CH_3$ | H | O | $CH_2CF_3$ | Cl | 5-benzo[c][1,2,5]thiadiazole |
| 3067 | $CH_2CH(CH_3)_2$ | H | O | $CH_2CF_3$ | Cl | 5-benzo[c][1,2,5]thiadiazole |
| 3068 | cyclopropylmethyl | H | O | $CH_2CF_3$ | Cl | 5-benzo[c][1,2,5]thiadiazole |
| 3069 | cyclobutylmethyl | H | O | $CH_2CF_3$ | Cl | 5-benzo[c][1,2,5]thiadiazole |
| 3070 | $(CH_2)_2$ | | O | $CH_2CF_3$ | Cl | 5-benzo[c][1,2,5]thiadiazole |
| 3071 | $(CH_2)_3$ | | O | $CH_2CF_3$ | Cl | 5-benzo[c][1,2,5]thiadiazole |
| 3072 | $(CH_2)_4$ | | O | $CH_2CF_3$ | Cl | 5-benzo[c][1,2,5]thiadiazole |
| 3073 | $(CH_2)_5$ | | O | $CH_2CF_3$ | Cl | 5-benzo[c][1,2,5]thiadiazole |
| 3074 | 5,5-spiro[2.3]hexane | | O | $CH_2CF_3$ | Cl | 5-benzo[c][1,2,5]thiadiazole |
| 3075 | Cyclopentyl | H | O | $CH_2CF_3$ | Cl | 5-benzo[c][1,2,5]thiadiazole |
| 3076 | $CH_2CH_3$ | H | O | $CH_2$-c-Pr | $CF_3$ | 5-benzo[c][1,2,5]oxadiazole |
| 3077 | $CH_2CF_3$ | H | O | $CH_2$-c-Pr | $CF_3$ | 5-benzo[c][1,2,5]oxadiazole |
| 3078 | $CH_2CH_2CH_3$ | H | O | $CH_2$-c-Pr | $CF_3$ | 5-benzo[c][1,2,5]oxadiazole |
| 3079 | $CH_2CH(CH_3)_2$ | H | O | $CH_2$-c-Pr | $CF_3$ | 5-benzo[c][1,2,5]oxadiazole |
| 3080 | cyclopropylmethyl | H | O | $CH_2$-c-Pr | $CF_3$ | 5-benzo[c][1,2,5]oxadiazole |
| 3081 | cyclobutylmethyl | H | O | $CH_2$-c-Pr | $CF_3$ | 5-benzo[c][1,2,5]oxadiazole |
| 3082 | $(CH_2)_2$ | | O | $CH_2$-c-Pr | $CF_3$ | 5-benzo[c][1,2,5]oxadiazole |
| 3083 | $(CH_2)_3$ | | O | $CH_2$-c-Pr | $CF_3$ | 5-benzo[c][1,2,5]oxadiazole |
| 3084 | $(CH_2)_4$ | | O | $CH_2$-c-Pr | $CF_3$ | 5-benzo[c][1,2,5]oxadiazole |
| 3085 | $(CH_2)_5$ | | O | $CH_2$-c-Pr | $CF_3$ | 5-benzo[c][1,2,5]oxadiazole |
| 3086 | 5,5-spiro[2.3]hexane | | O | $CH_2$-c-Pr | $CF_3$ | 5-benzo[c][1,2,5]oxadiazole |
| 3087 | Cyclopentyl | H | O | $CH_2$-c-Pr | $CF_3$ | 5-benzo[c][1,2,5]oxadiazole |
| 3088 | $CH_2CH_3$ | H | O | $CH_2$-c-Pr | F | 5-benzo[c][1,2,5]oxadiazole |
| 3089 | $CH_2CF_3$ | H | O | $CH_2$-c-Pr | F | 5-benzo[c][1,2,5]oxadiazole |
| 3090 | $CH_2CH_2CH_3$ | H | O | $CH_2$-c-Pr | F | 5-benzo[c][1,2,5]oxadiazole |
| 3091 | $CH_2CH(CH_3)_2$ | H | O | $CH_2$-c-Pr | F | 5-benzo[c][1,2,5]oxadiazole |
| 3092 | cyclopropylmethyl | H | O | $CH_2$-c-Pr | F | 5-benzo[c][1,2,5]oxadiazole |
| 3093 | cyclobutylmethyl | H | O | $CH_2$-c-Pr | F | 5-benzo[c][1,2,5]oxadiazole |
| 3094 | $(CH_2)_2$ | | O | $CH_2$-c-Pr | F | 5-benzo[c][1,2,5]oxadiazole |
| 3095 | $(CH_2)_3$ | | O | $CH_2$-c-Pr | F | 5-benzo[c][1,2,5]oxadiazole |
| 3096 | $(CH_2)_4$ | | O | $CH_2$-c-Pr | F | 5-benzo[c][1,2,5]oxadiazole |

TABLE 12-continued

Formula VII

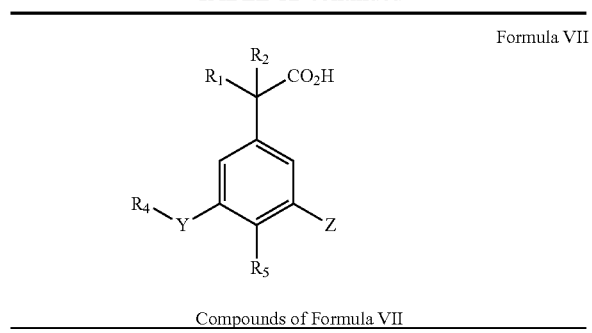

Compounds of Formula VII

| Ex | R1 | R2 | Y | R4 | R5 | Z |
|---|---|---|---|---|---|---|
| 3097 | (CH$_2$)$_5$ | | O | CH$_2$-c-Pr | F | 5-benzo[c][1,2,5]oxadiazole |
| 3098 | 5,5-spiro[2.3]hexane | | O | CH$_2$-c-Pr | F | 5-benzo[c][1,2,5]oxadiazole |
| 3099 | Cyclopentyl | H | O | CH$_2$-c-Pr | F | 5-benzo[c][1,2,5]oxadiazole |
| 3100 | CH$_2$CH$_3$ | H | O | CH$_2$-c-Pr | Cl | 5-benzo[c][1,2,5]oxadiazole |
| 3101 | CH$_2$CF$_3$ | H | O | CH$_2$-c-Pr | Cl | 5-benzo[c][1,2,5]oxadiazole |
| 3102 | CH$_2$CH$_2$CH$_3$ | H | O | CH$_2$-c-Pr | Cl | 5-benzo[c][1,2,5]oxadiazole |
| 3103 | CH$_2$CH(CH$_3$)$_2$ | H | O | CH$_2$-c-Pr | Cl | 5-benzo[c][1,2,5]oxadiazole |
| 3104 | cyclopropylmethyl | H | O | CH$_2$-c-Pr | Cl | 5-benzo[c][1,2,5]oxadiazole |
| 3105 | cyclobutylmethyl | H | O | CH$_2$-c-Pr | Cl | 5-benzo[c][1,2,5]oxadiazole |
| 3106 | (CH$_2$)$_2$ | | O | CH$_2$-c-Pr | Cl | 5-benzo[c][1,2,5]oxadiazole |
| 3107 | (CH$_2$)$_3$ | | O | CH$_2$-c-Pr | Cl | 5-benzo[c][1,2,5]oxadiazole |
| 3108 | (CH$_2$)$_4$ | | O | CH$_2$-c-Pr | Cl | 5-benzo[c][1,2,5]oxadiazole |
| 3109 | (CH$_2$)$_5$ | | O | CH$_2$-c-Pr | Cl | 5-benzo[c][1,2,5]oxadiazole |
| 3110 | 5,5-spiro[2.3]hexane | | O | CH$_2$-c-Pr | Cl | 5-benzo[c][1,2,5]oxadiazole |
| 3111 | Cyclopentyl | H | O | CH$_2$-c-Pr | Cl | 5-benzo[c][1,2,5]oxadiazole |
| 3112 | CH$_2$CH$_3$ | H | O | CH$_2$-c-Pr | CF$_3$ | 5-benzo[c][1,2,5]thiadiazole |
| 3113 | CH$_2$CF$_3$ | H | O | CH$_2$-c-Pr | CF$_3$ | 5-benzo[c][1,2,5]thiadiazole |
| 3114 | CH$_2$CH$_2$CH$_3$ | H | O | CH$_2$-c-Pr | CF$_3$ | 5-benzo[c][1,2,5]thiadiazole |
| 3115 | CH$_2$CH(CH$_3$)$_2$ | H | O | CH$_2$-c-Pr | CF$_3$ | 5-benzo[c][1,2,5]thiadiazole |
| 3116 | cyclopropylmethyl | H | O | CH$_2$-c-Pr | CF$_3$ | 5-benzo[c][1,2,5]thiadiazole |
| 3117 | cyclobutylmethyl | H | O | CH$_2$-c-Pr | CF$_3$ | 5-benzo[c][1,2,5]thiadiazole |
| 3118 | (CH$_2$)$_2$ | | O | CH$_2$-c-Pr | CF$_3$ | 5-benzo[c][1,2,5]thiadiazole |
| 3119 | (CH$_2$)$_3$ | | O | CH$_2$-c-Pr | CF$_3$ | 5-benzo[c][1,2,5]thiadiazole |
| 3120 | (CH$_2$)$_4$ | | O | CH$_2$-c-Pr | CF$_3$ | 5-benzo[c][1,2,5]thiadiazole |
| 3121 | (CH$_2$)$_5$ | | O | CH$_2$-c-Pr | CF$_3$ | 5-benzo[c][1,2,5]thiadiazole |
| 3122 | 5,5-spiro[2.3]hexane | | O | CH$_2$-c-Pr | CF$_3$ | 5-benzo[c][1,2,5]thiadiazole |
| 3123 | Cyclopentyl | H | O | CH$_2$-c-Pr | CF$_3$ | 5-benzo[c][1,2,5]thiadiazole |
| 3124 | CH$_2$CH$_3$ | H | O | CH$_2$-c-Pr | F | 5-benzo[c][1,2,5]thiadiazole |
| 3125 | CH$_2$CF$_3$ | H | O | CH$_2$-c-Pr | F | 5-benzo[c][1,2,5]thiadiazole |
| 3126 | CH$_2$CH$_2$CH$_3$ | H | O | CH$_2$-c-Pr | F | 5-benzo[c][1,2,5]thiadiazole |
| 3127 | CH$_2$CH(CH$_3$)$_2$ | H | O | CH$_2$-c-Pr | F | 5-benzo[c][1,2,5]thiadiazole |

TABLE 12-continued

Formula VII

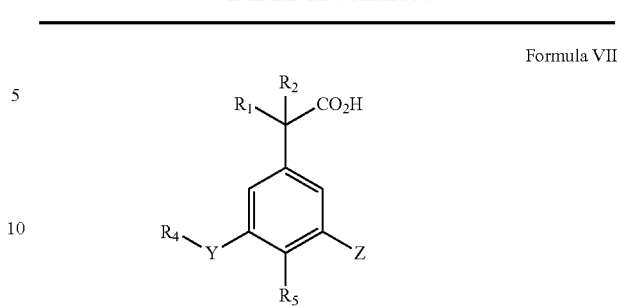

Compounds of Formula VII

| Ex | R1 | R2 | Y | R4 | R5 | Z |
|---|---|---|---|---|---|---|
| 3128 | cyclopropylmethyl | H | O | CH$_2$-c-Pr | F | 5-benzo[c][1,2,5]thiadiazole |
| 3129 | cyclobutylmethyl | H | O | CH$_2$-c-Pr | F | 5-benzo[c][1,2,5]thiadiazole |
| 3130 | (CH$_2$)$_2$ | | O | CH$_2$-c-Pr | F | 5-benzo[c][1,2,5]thiadiazole |
| 3131 | (CH$_2$)$_3$ | | O | CH$_2$-c-Pr | F | 5-benzo[c][1,2,5]thiadiazole |
| 3132 | (CH$_2$)$_4$ | | O | CH$_2$-c-Pr | F | 5-benzo[c][1,2,5]thiadiazole |
| 3133 | (CH$_2$)$_5$ | | O | CH$_2$-c-Pr | F | 5-benzo[c][1,2,5]thiadiazole |
| 3134 | 5,5-spiro[2.3]hexane | | O | CH$_2$-c-Pr | F | 5-benzo[c][1,2,5]thiadiazole |
| 3135 | Cyclopentyl | H | O | CH$_2$-c-Pr | F | 5-benzo[c][1,2,5]thiadiazole |
| 3136 | CH$_2$CH$_3$ | H | O | CH$_2$-c-Pr | Cl | 5-benzo[c][1,2,5]thiadiazole |
| 3137 | CH$_2$CF$_3$ | H | O | CH$_2$-c-Pr | Cl | 5-benzo[c][1,2,5]thiadiazole |
| 3138 | CH$_2$CH$_2$CH$_3$ | H | O | CH$_2$-c-Pr | Cl | 5-benzo[c][1,2,5]thiadiazole |
| 3139 | CH$_2$CH(CH$_3$)$_2$ | H | O | CH$_2$-c-Pr | Cl | 5-benzo[c][1,2,5]thiadiazole |
| 3140 | cyclopropylmethyl | H | O | CH$_2$-c-Pr | Cl | 5-benzo[c][1,2,5]thiadiazole |
| 3141 | cyclobutylmethyl | H | O | CH$_2$-c-Pr | Cl | 5-benzo[c][1,2,5]thiadiazole |
| 3142 | (CH$_2$)$_2$ | | O | CH$_2$-c-Pr | Cl | 5-benzo[c][1,2,5]thiadiazole |
| 3143 | (CH$_2$)$_3$ | | O | CH$_2$-c-Pr | Cl | 5-benzo[c][1,2,5]thiadiazole |
| 3144 | (CH$_2$)$_4$ | | O | CH$_2$-c-Pr | Cl | 5-benzo[c][1,2,5]thiadiazole |
| 3145 | (CH$_2$)$_5$ | | O | CH$_2$-c-Pr | Cl | 5-benzo[c][1,2,5]thiadiazole |
| 3146 | 5,5-spiro[2.3]hexane | | O | CH$_2$-c-Pr | Cl | 5-benzo[c][1,2,5]thiadiazole |
| 3147 | Cyclopentyl | H | O | CH$_2$-c-Pr | Cl | 5-benzo[c][1,2,5]thiadiazole |

Example 534

2-(6-cyclopropylmethoxy)-5-nitro-4'-(trifluoromethyl)biphenyl-3-yl)-4-methylpentanoic acid

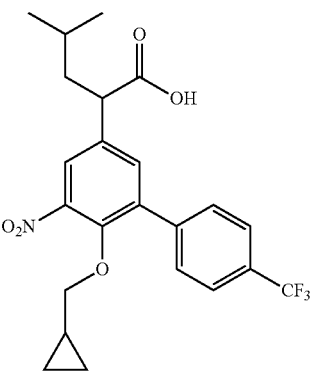 [SMILES: CC(C)CC(C(=O)O)c1cc(-c2ccc(C(F)(F)F)cc2)c(OCC2CC2)c([N+](=O)[O-])c1]

Step-1:

2-(3-Bromo-4-hydroxyphenyl)-4-methylpentanoate

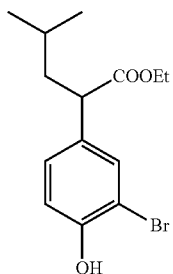 [SMILES: CCOC(=O)C(CC(C)C)c1ccc(O)c(Br)c1]

To a stirred solution of ethyl 2-(4-hydroxyphenyl)-4-methylpentanoate E-9 (15 g, 63.55 mmol) in 100 ml of glacial acetic acid at 0° C., slowly added bromine (20.26 g, 64.14 mol) and stirred at same temperature for 2.5 h. After completion the reaction, the reaction mixture was poured into water and neutralized with saturated sodium carbonate solution and extracted with ethyl acetate (300 ml×3). The organic layer was washed with water, saturated sodium bicarbonate solution and brine. The organic layer was then distilled off to yield product ethyl 2-(3-bromo-4-hydroxyphenyl)-4-methylpentanoate. Yield: (16 g, 80%). $^1$H NMR (CDCl$_3$): δ 7.20 (m 2H), 6.80 (d, J=7.9 Hz, 1H), 4.90 (bs, 1H), 4.15 (q, 2H), 3.60 (t, 1H), 1.95-2.00 (m, 1H), 1.75-1.80 (m, 1H), 1.45-1.50 (m, 1H), 1.20 (t, 3H), 1.00 (m, 6H). Mass: (315, M+1,100%).

Step-2:

2-(3-Bromo-4-hydroxy-5-nitrophenyl)-4-methylpentanoic acid

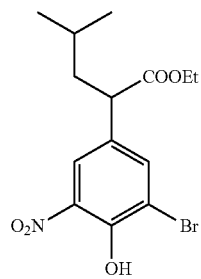 [SMILES: CCOC(=O)C(CC(C)C)c1cc(Br)c(O)c([N+](=O)[O-])c1]

Ethyl 2-(3-bromo-4-hydroxyphenyl)-4-methylpentanoate (16 g) was taken in acetic acid (100 ml) and to it added drop wise 70% nitric acid (10 ml) below 15° C. The reaction mixture was stirred for 2 h. After completion of the reaction; it was poured into 300 ml of ice water and extracted with ethyl acetate (300 ml×3). The ethyl acetate layer was washed with bicarbonate solution, water and finally brine solution. The organic layer was then distilled off and the crude residue was purified by column chromatography using Ethyl acetate:hexane (2:3) as eluent provided 12 g of 2-(3-bromo-4-hydroxy-5-nitrophenyl)-4-methylpentanoic acid. The acid was taken in 50 ml of absolute ethanol and 2 ml of concentrated sulfuric acid and refluxed for 1 h. The ethanol layer was distilled off, washed it with water and dried gave 13 g of ethyl 2-(3-bromo-4-hydroxy-5-nitrophenyl)-4-methylpentanoate intermediate. $^1$H NMR (CDCl$_3$): δ 8.20 (s 1H), 7.20 (s, 1H), 4.90 (bs, 1H), 4.15 (q, 2H), 3.60 (t, 1H), 1.95-2.00 (m, 1H), 1.75-1.80 (m, 1H), 1.45-1.50 (m, 1H), 1.20 (t, 3H), 1.00 (m, 6H). Mass: (360, M+1,100%).

Step 3

Ethyl 2-(3-bromo-4-(cyclopropylmethoxy)-5-nitrophenyl)-4-methylpentanoate

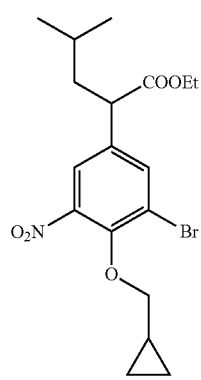 [SMILES: CCOC(=O)C(CC(C)C)c1cc(Br)c(OCC2CC2)c([N+](=O)[O-])c1]

A solution of ethyl 2-(3-bromo-4-hydroxy-5-nitrophenyl)-4-methylpentanoate (4.1 g, 11.26 mmol) was taken in 50 ml of DMSO and to it added Cs$_2$CO$_3$ (3.02 g, 12.39 mmol). The reaction mixture was stirred at room temperature for 15 minutes and then added cyclopropylmethyl bromide (1.67 g, 12.39 mmol) dropwise. After completion of addition, the reaction mixture was stirred at 70° C. for 4 h. After completion of the reaction, it was poured into water (200 ml) and extracted with ethyl acetate (100 ml×3). The ethyl acetate layer was washed with 1N HCl, water and finally brine solution. The organic layer was then distilled off and the crude residue was purified by column chromatography using Ethyl acetate:hexane (1:3) as eluent provided 3 g of ethyl 2-(3-bromo-4-(cyclopropylmethoxy)-5-nitrophenyl)-4-methylpentanoate. $^1$H NMR (CDCl$_3$): δ 8.20 (s 1H), 7.20 (s, 1H), 4.15 (q, 2H), 3.60 (t, 1H), 3.45 (d, 2H), 1.95-2.00 (m, 1H), 1.75-1.80 (m, 1H), 1.45-1.50 (m, 1H), 1.20 (t, 3H), 1.00 (m, 6H), 0.35-0.25 (m, 5H). Mass: (414, M+1,100%).

Step 4

Ethyl 2-(6-(cyclopropylmethoxy)-5-nitro-4'-(trifluoromethyl)biphenyl-3-yl)-4-methylpentanoate

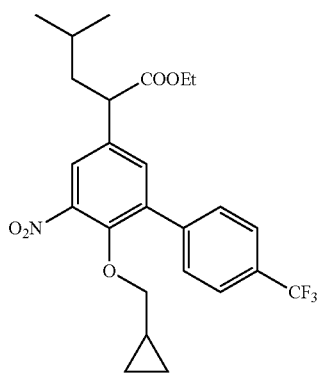 [SMILES: CCOC(=O)C(CC(C)C)c1cc(-c2ccc(C(F)(F)F)cc2)c(OCC2CC2)c([N+](=O)[O-])c1]

To a solution of ethyl 2-(3-bromo-4-(cyclopropylmethoxy)-5-nitrophenyl)-4-methylpentanoate (2 g, 4.83 mmol) in 30 ml of DMF/Water (25:5 ml) was added Pd(PPh$_3$)$_4$ (558 mg, 0.483 mmol), Cs$_2$CO$_3$ (5.5 g, 16.9 mmol) and 4-CF3-PhB(OH)$_2$ (1.01 g, 5.31 mmol) and the reaction mixture was stirred at 90° C. for 12 h. After completion of the reaction, it was poured into water (100 ml) and extracted with ethyl acetate (100 ml×3). The ethyl acetate layer was washed with 1N HCl, water and finally brine solution. The organic layer was then distilled off and the crude residue was purified by column chromatography using Ethyl acetate:hexane (2:3) as eluent provided 1.3 g of ethyl 2-(6-(cyclopropylmethoxy)-5-nitro-4'-(trifluoromethyl)biphenyl-3-yl)-4-methylpentanoate. $^1$H NMR (CDCl$_3$): δ 8.20 (s 1H), 7.40-7.20 (m, 5H), 4.15 (q, 2H), 3.60 (t, 1H), 3.45 (d, 2H), 1.95-2.00 (m, 1H), 1.75-1.80 (m, 1H), 1.45-1.50 (m, 1H), 1.20 (t, 3H), 1.00 (m, 6H), 0.35-0.25 (m, 5H). Mass: (480, M+1,100%).

Step 5

2-(6-(Cyclopropylmethoxy)-5-nitro-4'-(trifluoromethyl)biphenyl-3-yl)-4-methylpentanoic acid

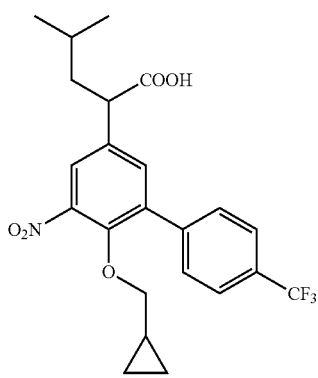

Ethyl 2-(6-(cyclopropylmethoxy)-5-nitro-4'-(trifluoromethyl)biphenyl-3-yl)-4-methylpentanoate (100 mg, 0.208 mmol) was taken in a mixture of MeOH; THF: Water (30 ml, 10:10:2) and to it added LiOH (30 mg, 0.7 mmol). The reaction mixture was stirred at room temperature for 3 h. After completion of the reaction, it was poured into water (50 ml) and extracted with ethyl acetate (100 ml×2). The ethyl acetate layer was washed with 1N HCl, water and finally brine solution. The organic layer was then distilled off and the crude residue was purified by column chromatography using Ethyl acetate:hexane (1:1) as eluent provided 70 mg of 2-(6-(cyclopropylmethoxy)-5-nitro-4'-(trifluoromethyl)biphenyl-3-yl)-4-methylpentanoic acid. $^1$H NMR (CDCl$_3$): δ 8.20 (s 1H), 7.40-7.20 (m, 5H), 3.60 (t, 1H), 3.45 (d, 2H), 1.95-2.00 (m, 1H), 1.75-1.80 (m, 1H), 1.45-1.50 (m, 1H), 1.00 (m, 6H), 0.35-0.25 (m, 5H). Mass: (452, M+1,100%).

Example 554

2-(6-cyclopropylmethoxy)-5-amino-4'-(trifluoromethyl)biphenyl-3-yl)-4-methylpentanoic acid

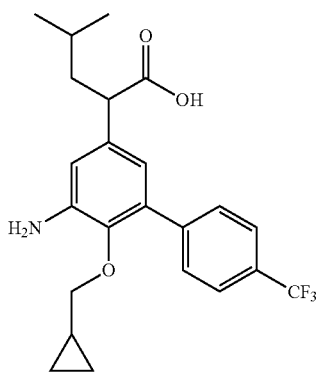

Step 1

Ethyl 2-(5-amino-6-(cyclopropylmethoxy)-4'-(trifluoromethyl)biphenyl-3-yl)-4-methylpentanoate

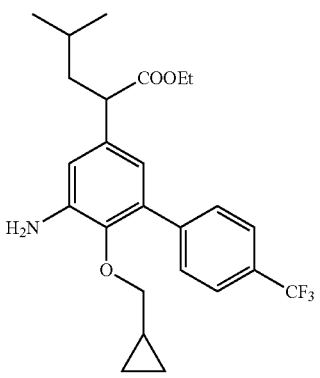

Ethyl 2-(6-(cyclopropylmethoxy)-5-nitro-4'-(trifluoromethyl)biphenyl-3-yl)-4-methylpentanoate (300 mg, 0.626 mmo) was taken in 30 ml of Toluene:Water (1:1) and to it added Fe powder (203 mg, 3.62 mmol), Ammonium formate (228 mg, 3.62 mmol). The reaction mixture was refluxed for 3 h and then filtered through celite. The toluene was distilled off under reduced pressure and the crude residue was purified by column chromatography using Ethyl acetate:hexane (2:3) as eluent provided 220 mg of ethyl 2-(5-amino-6-(cyclopropylmethoxy)-4'-(trifluoromethyl)biphenyl-3-yl)-4-methylpentanoate. $^1$H NMR (CDCl$_3$): δ 7.40-7.20 (m, 5H), 6.90 (s 1H), 4.50 (bs, 2H), 4.15 (q, 2H), 3.60 (t, 1H), 3.45 (d, 2H), 1.95-2.00 (m, 1H), 1.75-1.80 (m, 1H), 1.45-1.50 (m, 1H), 1.20 (t, 3H), 1.00 (m, 6H), 0.35-0.25 (m, 5H). Mass: (450, M+1,100%).

Step 3

2-(5-Amino-6-(cyclopropylmethoxy)-4'-(trifluoromethyl)biphenyl-3-yl)-4-methylpentanoic acid

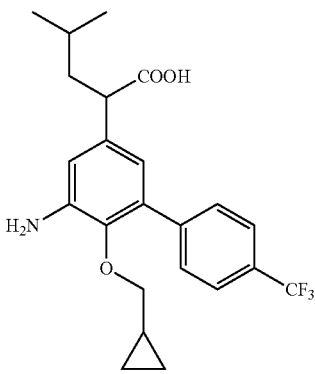 [SMILES: CC(C)CC(C(=O)O)c1cc(-c2ccc(C(F)(F)F)cc2)c(OCC2CC2)c([N+](=O)[O-])c1]

Ethyl 2-(5-amino-6-(cyclopropylmethoxy)-4'-(trifluoromethyl)biphenyl-3-yl)-4-methylpentanoate. (120 mg, 0.267 mmol) was taken in a mixture of MeOH; THF: Water (30 ml, 10:10:2) and to it added LiOH (30 mg, 0.7 mmol). The reaction mixture was stirred at room temperature for 3 h. After completion of the reaction, it was poured into water (50 ml) and extracted with ethyl acetate (100 ml×2). The ethyl acetate layer was washed with 1N HCl, water and finally brine solution. The organic layer was then distilled off and the crude residue was purified by column chromatography using Ethyl acetate:hexane (1:1) as eluent provided 80 mg of 2-(6-cyclopropylmethoxy)-5-amino-4'-(trifluoromethyl)biphenyl-3-yl)-4-methylpentanoic acid 2-(5-amino-6-(cyclopropylmethoxy)-4'-(trifluoromethyl)biphenyl-3-yl)-4-methylpentanoic acid. $^1$H NMR (CDCl$_3$): δ 7.40-7.20 (m, 5H), 7.00 (s, 1H), 3.60 (t, 1H), 3.45 (d, 2H), 1.95-2.00 (m, 1H), 1.75-1.80 (m, 1H), 1.45-1.50 (m, 1H), 1.00 (m, 6H), 0.35-0.25 (m, 5H). Mass: (422, M+1,100%).

Example 484

2-(6-cyclopropylmethoxy)-5-chloro-4'-(trifluoromethyl)biphenyl-3-yl)-4-methylpentanoic acid

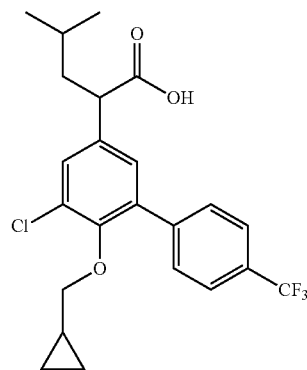 [SMILES: CC(C)CC(C(=O)O)c1cc(Cl)c(OCC2CC2)c(-c2ccc(C(F)(F)F)cc2)c1]

Step 1

Ethyl 2-(6-cyclopropylmethoxy)-5-chloro-4'-(trifluoromethyl)biphenyl-3-yl)-4-methylpentanoate

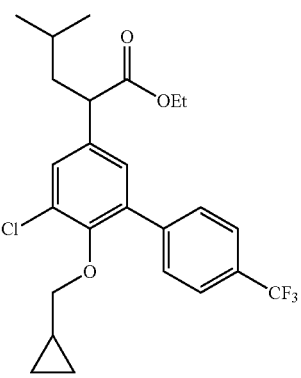 [SMILES: CCOC(=O)C(CC(C)C)c1cc(Cl)c(OCC2CC2)c(-c2ccc(C(F)(F)F)cc2)c1]

2-(6-Cyclopropylmethoxy)-5-amino-4'-(trifluoromethyl) biphenyl-3-yl)-4-methylpentanoic acid (150 mg, 0.33 mmol) was taken up in 10 ml of 6N HCl and a solution of sodium nitrite (30 mg, 0.40 mmol, 5 ml in water) was added at 0° C.

The reaction mixture was stirred for 15 minutes at 0° C. and then poured into a saturated solution of copper (II) chloride in water (25 ml) The reaction mixture was then heated at 70° C. for 3 hours. The mixture was cooled to room temperature and extracted with ethyl acetate (2×100 mL). The combined organic layers were dried (MgSO$_4$) and concentrated under reduced pressure. The crude residue obtained was purified by column chromatography using ethyl acetate:hexane (2:3) as eluent to yield 120 mg of ethyl 2-(6-cyclopropylmethoxy)-5-chloro-4'-(trifluoromethyl)biphenyl-3-yl)-4-methylpentanoate. $^1$H NMR (CDCl$_3$): δ 7.60-7.45 (m, 5H), 7.20 (s 1H), 4.15 (q, 2H), 3.60 (t, 1H), 3.45 (d, 2H), 1.95-2.00 (m, 1H), 1.75-1.80 (m, 1H), 1.45-1.50 (m, 1H), 1.20 (t, 3H), 1.00 (m, 6H), 0.35-0.25 (m, 5H). Mass: (470, M+1,100%).

Step 2

2-(6-Cyclopropylmethoxy)-5-chloro-4'-(trifluoromethyl)biphenyl-3-yl)-4-methylpentanoic acid

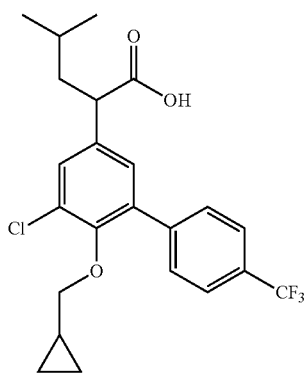 [SMILES: CC(C)CC(C(=O)O)c1cc(Cl)c(OCC2CC2)c(-c2ccc(C(F)(F)F)cc2)c1]

The ethyl 2-(6-cyclopropylmethoxy)-5-chloro-4'-(trifluoromethyl)biphenyl-3-yl)-4-methylpentanoate above (120 mg, 0.207 mmol) was taken up in a mixture of MeOH; THF: Water (30 ml, 10:10:2) and LiOH (42 mg, 0.7 mmol) was added. The reaction mixture was stirred at room temperature for 3 h. After completion of the reaction, it was poured into water (50 ml) and extracted with ethyl acetate (2×100 ml). The combined extracts were washed with 1N HCl, water and finally brine solution. The combined organic layers were dried (MgSO$_4$) and concentrated under reduced pressure. The crude residue obtained was purified by column chromatography using ethyl acetate:hexane (1:1) as eluent to yield 105 mg of 2-(6-cyclopropylmethoxy)-5-chloro-4'-(trifluoromethyl) biphenyl-3-yl)-4-methylpentanoic acid product. $^1$H NMR (CDCl$_3$): δ 7.65-7.40 (m, 5H), 7.20 (s, 1H), 3.60 (t, 1H), 3.45 (d, 2H), 1.95-2.00 (m, 1H), 1.75-1.80 (m, 1H), 1.45-1.50 (m, 1H), 1.00 (m, 6H), 0.35-0.25 (m, 5H). Mass: (442, M+1, 100%). HPLC Purity (99%).

Example 264

2-(6-cyclopropylmethoxy)-5-fluoro-4'-(trifluoromethyl)biphenyl-3-yl)-4-methylpentanoic acid

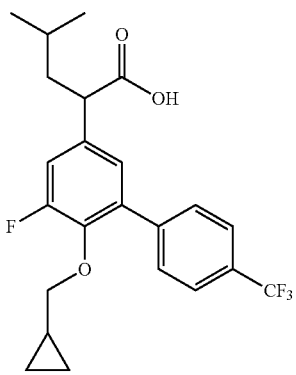 [SMILES: CC(C)CC(C(=O)O)c1cc(F)c(OCC2CC2)c(-c2ccc(C(F)(F)F)cc2)c1]

Step 1

Ethyl 2-(6-cyclopropylmethoxy)-5-amino-4'-(trifluoromethyl)biphenyl-3-yl)-4-methylpentanoate

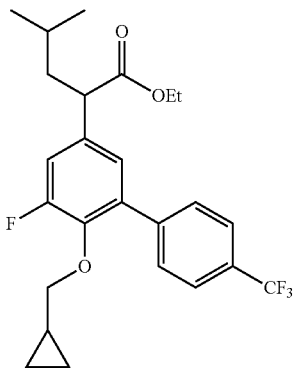 [SMILES: CC(C)CC(C(=O)O)c1cc(F)c(OCC2CC2)c(-c2ccc(C(F)(F)F)cc2)c1]

2-(6-cyclopropylmethoxy)-5-amino-4'-(trifluoromethyl) biphenyl-3-yl)-4-methylpentanoic acid (200 mg, 0.53 mmol) was taken up in 5 ml of 1,2-dichlorobenzene and a solution of BF3-etherate (1.5M, 5 ml) was added at 0° C. The reaction mixture was stirred for 15 minutes at 0° C. and t-butyl nitrite (1.5M, 3 ml) was added in a dropwise manner. The reaction mixture was then heated at 100° C. for 1 hour. The reaction mixture was cooled to room temperature and extracted with ethyl acetate (2×100 mL). The combined organic layers were dried (MgSO$_4$) and concentrated under reduced pressure. The crude residue obtained was purified by column chromatography using ethyl acetate:hexane (2:3) as eluent to provide 120 mg of ethyl 2-(6-cyclopropylmethoxy)-5-amino-4'-(trifluoromethyl)biphenyl-3-yl)-4-methylpentanoate. $^1$H NMR (CDCl$_3$): δ 7.60-7.35 (m, 5H), 7.20 (s 1H), 4.15 (q, 2H), 3.60 (t, 1H), 3.45 (d, 2H), 1.95-2.00 (m, 1H), 1.75-1.80 (m, 1H), 1.45-1.50 (m, 1H), 1.20 (t, 3H), 1.00 (m, 6H), 0.35-0.25 (m, 5H). Mass: (453, M+1,100%).

Step 2

2-(6-cyclopropylmethoxy)-5-fluoro-4'-(trifluoromethyl)biphenyl-3-yl)-4-methylpentanoic acid

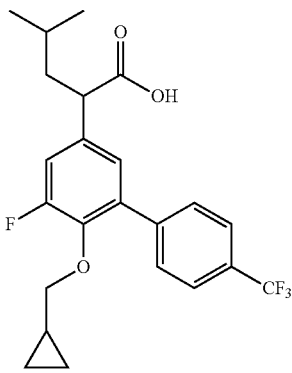

The above ethyl 2-(6-cyclopropylmethoxy)-5-amino-4'-(trifluoromethyl)biphenyl-3-yl)-4-methylpentanoate (120 mg, 0.267 mmol) was taken up in MeOH; THF: Water (20 ml, 10:10:2) and LiOH (42 mg, 0.7 mmol) was added. The reaction mixture was stirred at room temperature for 3 h. After completion, the reaction was poured into water (50 ml) and extracted with ethyl acetate (2×100 ml). The combined ethyl acetate layers were washed with 1N HCl, water and finally brine solution. The combined organic layers were dried (MgSO$_4$) and concentrated under reduced pressure. The crude residue obtained was purified by column chromatography using ethyl acetate:hexane (1:1) as eluent to yield 85 mg of 2-(6-cyclopropylmethoxy)-5-fluoro-4'-(trifluoromethyl)biphenyl-3-yl)-4-methylpentanoic acid product. $^1$H NMR (CDCl$_3$): δ 7.55-7.30 (m, 5H), 7.10 (s, 1H), 3.60 (t, 1H), 3.45 (d, 2H), 1.95-2.00 (m, 1H), 1.75-1.80 (m, 1H), 1.45-1.50 (m, 1H), 1.00 (m, 6H), 0.35-0.25 (m, 5H). Mass: (425, M+1, 100%). HPLC Purity (97%).

Example 724

2-(2-cyclopropylmethoxy-5-fluoro-4'-trifluoromethyl-biphenyl-4-yl)-4-methyl-pentanoic acid

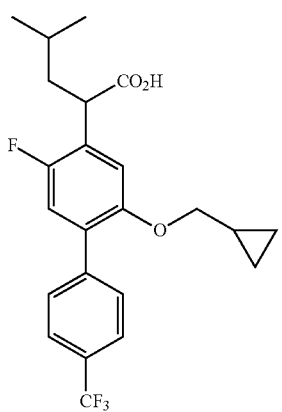 [SMILES: CC(C)CC(C(=O)O)c1cc(OCC2CC2)c(-c2ccc(C(F)(F)F)cc2)cc1F]

Step 1

Diethyl 2-(2,5-difluoro-4-nitrophenyl)-2-isobutylmalonate

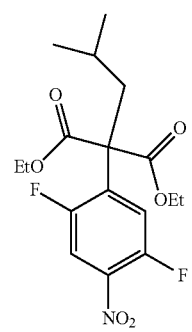

2-Isobutylmalonic acid diethyl ester (40.0 g, 0.185 mol) in DMF (50 mL) was added dropwise to a stirred suspension of sodium hydride (60% in mineral oil, 8.0 g, 0.33 mol) in 200 mL DMF (200 mL) over 20 min. at 0° C. under nitrogen. The mixture was stirred for 0.5 h at room temperature, cooled to 0° C. and 1,2,4-trifluoro-5-nitro-benzene (30.0 g, 169.5 mmol) in DMF (150 mL) was added dropwise. The resulting reaction mixture was stirred at room temperature for 16 h, poured into ice water (200 mL) and extracted with EtOAc (3×100 mL). The combined organic phases were washed with water (3×100 mL), brine (100 mL) and dried (MgSO$_4$). Evaporation of solvent under reduced pressure gave a brown oil which was purified by column chromatography over silica gel (Heptane-EtOAc, gradient) to give 57.0 g (90%) of 2-(2,5-difluoro-4-nitrophenyl)-2-isobutylmalonic acid diethyl ester as yellow oil. $^1$H NMR (300 MHz, CDCl$_3$/TMS): δ 7.87 (dd, J=12.3, 6.0 Hz, 1H), 7.79 (dd, J=10.1, 6.4 Hz, 1H), 4.30-4.18 (m, 4H), 2.27 (d, J=5.8 Hz, 2H), 1.60-1.50 (m, 1H), 1.26 (t, J=7.1 Hz, 6H), 0.82 (d, J=7.0 Hz, 6H); $^{13}$C NMR (75 MHz, CDCl$_3$/TMS): δ 168.2, 155.1 (d, $^1J_{CF}$=252.3 Hz), 150.9 (d, $^1J_{CF}$=263.2 Hz), 135.7, 135.1, 120.0 (dd, $^2J_{CF}$=26.0, $^3J_{CF}$=4.0 Hz), 113.0 (d, $^2J_{CF}$=29.0 Hz), 62.3, 43.1, 24.9, 23.8, 13.8.

Step 2

2-(2,5-Difluoro-4-nitro-phenyl)-4-methyl-pentanoic acid

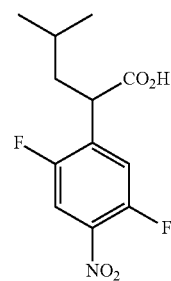 [SMILES: CC(C)CC(C(=O)O)c1cc(F)c([N+](=O)[O-])cc1F]

The above 2-(2,5-difluoro-4-nitrophenyl)-2-isobutylmalonic acid diethyl ester (57.0 g, 152.8 mmol) was dissolved in AcOH/H₂O/EtOH (400 mL/120 mL/50 mL) and the reaction mixture was heated under reflux for 96 h. After cooling the solvent was evaporated under reduced pressure and water (200 mL) was added. The reaction mixture was extracted with EtOAc (3×100 mL), and the combined extracts were washed with water (3×100 mL), brine (100 mL) and dried (MgSO₄). Evaporation of solvent under reduced pressure gave a yellow oil which crystallized on standing to yield 27 g of 2-(2,5-difluoro-4-nitro-phenyl)-4-methyl-pentanoic acid. Chromatography of the residual oil (Heptane-EtOAc gradient) gave an additional 3 g of product (72% combined yield). ¹H NMR (300 MHz, CDCl₃/TMS): δ 9.63 (br s, 1H), 7.82 (dd, J=8.8, 6.0 Hz, 1H), 7.38 (dd, J=11.0, 5.8 Hz, 1H), 4.14-4.08 (m, 1H), 2.05-1.95 (m, 1H), 1.76-1.66 (m, 1H), 1.52-1.43 (m, 1H), 0.95-0.92 (m, 6H); ¹³C NMR (75 MHz, CDCl₃/TMS): δ 177.6, 158.2 (d, $^1J_{CF}$=232.5 Hz), 150.9 (d, $^1J_{CF}$=262.5 Hz), 136.0, 134.7, 119.0 (d, $^2J_{CF}$=20.0, Hz), 113.1 (d, $^2J_{CF}$=29.4 Hz), 41.7, 41.3, 26.0, 22.6, 21.9.

Step 3

2-(2,5-Difluoro-4-nitro-phenyl)-4-methyl-pentanoic acid ethyl ester

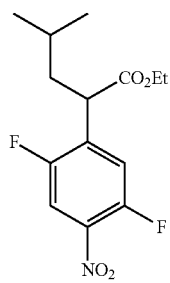

2-(2,5-difluoro-4-nitro-phenyl)-4-methyl-pentanoic acid (29.0 g, 0.11 mol) was dissolved in EtOH (200 mL) and H₂SO₄ (96%) 10 mL added. The reaction mixture was refluxed for 3 h and the solvent evaporated to an oil which was dissolved in EtOAc. Water (150 mL) added and the reaction mixture was extracted with EtOAc (3×100 mL). Organic phases washed with saturated NaHCO₃ (50 mL), water (100 mL) and brine (100 mL) then dried under MgSO₄. The evaporation of solvent under reduced pressure gave 2-(2,5-difluoro-4-nitro-phenyl)-4-methyl-pentanoic acid ethyl ester as yellow oil 32.0 g, (97%), which was used for the next step without purification. ¹H NMR (300 MHz, CDCl₃/TMS): δ 7.81 (dd, J=8.8, 6.2 Hz, 1H), 7.41 (dd, J=11.1, 5.6 Hz, 1H), 4.23-4.05 (m, 3H), 2.04-1.94 (m, 1H), 1.71-1.62 (m, 1H), 1.51-1.42 (m, 1H), 1.25 (t, J=7.1 Hz, 3H), 0.95-0.92 (m, 6H); ¹³C NMR (75 MHz, CDCl₃/TMS): δ 171.6, 155.0 (d, $^1J_{CF}$=246.0 Hz), 151.5 (d, $^1J_{CF}$=261.3 Hz), 145.5, 135.7, 118.8 (dd, $^2J_{CF}$=24.0, $^3J_{CF}$=4.0 Hz), 113.0 (d, $^2J_{CF}$=20.0 Hz), 61.6, 41.8, 26.1, 22.5, 22.0, 14.1.

Step 4

2-(5-cyclopropylmethoxy-2-fluoro-4-iodo-phenyl)-4-methyl-pentanoic acid cyclopropylmethyl ester

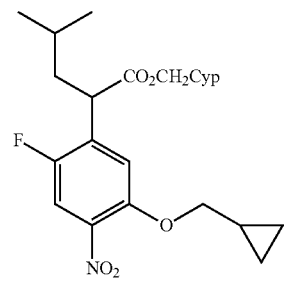

Cyclopropylmethanol (10.0 g, 138.8 mmol) was treated with n-BuLi (2.5M in hexane 7.4 g, 46 mL, 115.6 mmol) at −15° C. under nitrogen, and the reaction mixture was stirred 1 h at 25° C. To the mixture was added 2-(2,5-difluoro-4-nitro-phenyl)-4-methyl-pentanoic acid ethyl ester (29 g, 96 mmol) in Cyclopropylmethanol (30 mL) dropwise at 25° C. and the reaction mixture stirred for an additional 16 h. Water (100 mL) was added and the reaction mixture was extracted with EtOAc (3×100 mL). The combined organic phases washed with water (3×100 mL), brine (100 mL) and dried (MgSO₄). Evaporation of the solvent under reduced pressure gave a brown oil which was purified by column chromatography over silica gel (Heptane-EtOAc gradient) to give 29.5 g, (81%) of 2-(5-cyclopropylmethoxy-2-fluoro-4-nitro-phenyl)-4-methyl-pentanoic acid cyclopropylmethyl ester as a yellow oil. ¹H NMR (300 MHz, CDCl₃/TMS): δ 7.60 (d, J=9.0 Hz, 1H), 7.15 (d, J=5.7 Hz, 1H), 4.07 (t, J=7.7 Hz, 1H), 4.00-3.80 (m, 4H), 2.01-1.92 (m, 1H), 1.68-1.60 (m, 1H), 1.52-1.43 (m, 1H), 1.34-1.20 (m, 1H), 1.19-1.00 (m, 1H), 0.94 (d, J=6.3 Hz, 6H), 0.65 (d, J=7.7 Hz, 2H), 0.54 (d, J=7.7 Hz, 2H), 0.39 (d, J=4.4 Hz, 2H), 0.25 (d, J=4.4 Hz, 2H); ¹³C NMR (75 MHz, CDCl₃/TMS): δ 172.6, 152.7 (d, $^1J_{CF}$=243.4 Hz), 148.8, 138.1, 133.3 (d, $^2J_{CF}$=15.7 Hz), 115.8, 112.6 (d, $^2J_{CF}$=29.5 Hz), 75.1, 70.0, 42.1, 41.7, 26.1, 22.5, 22.2, 10.0, 9.8, 3.4.

Step 5

2-(5-Cyclopropylmethoxy-2-fluoro-4-amino-phenyl)-4-methyl-pentanoic acid cyclopropylmethyl ester

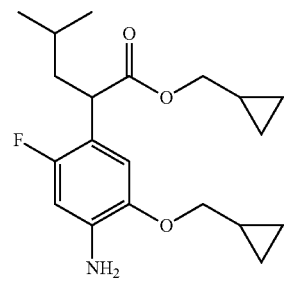 [SMILES: CC(C)CC(C(=O)OCC1CC1)c1cc(OCC2CC2)c(N)cc1F]

2-(5-cyclopropylmethoxy-2-fluoro-4-nitro-phenyl)-4-methyl-pentanoic acid cyclopropylmethyl ester (10.0 g, 26.4 mmol) was dissolved in EtOH (200 mL) and hydrogenated at 50 psi, 25° C. for 24 h over 10% Pd—C (1 g). The mixture was filtered and the solvent evaporated to give crude a brown oi, which was purified by column chromatography over silica gel (Heptane-EtOAc gradient) to give 6.7 g, (72%) of 2-(5-cyclopropylmethoxy-2-fluoro-4-amino-phenyl)-4-methyl-pentanoic acid cyclopropylmethyl ester as a yellow oil. $^1$H NMR (300 MHz, CDCl$_3$/TMS): δ 6.73 (d, J=6.9 Hz, 1H), 6.40 (d, J=11.0 Hz, 1H), 4.00-3.70 (m, 5H), 1.91-1.81 (m, 1H), 1.65-1.56 (m, 1H), 1.51-1.39 (m, 1H), 1.28-1.18 (m, 1H), 1.12-1.00 (m, 1H), 0.90 (d, J=6.6 Hz, 6H), 0.63-0.57 (m, 2H), 0.53-047 (m, 2H), 0.35-0.28 (m, 2H), 0.25-0.18 (m, 2H); $^{13}$C NMR (75 MHz, CDCl$_3$/TMS): δ 174.2, 154.8 (d, $^1J_{CF}$=236.0 Hz), 142.6, 136.6 (d, $^3J_{CF}$=11.5 Hz), 114.1 (d, $^2J_{CF}$=16.8 Hz), 111.6 (d, $^3J_{CF}$=4.8 Hz), 101.6 (d, $^2J_{CF}$=28.2 Hz), 73.8, 69.2, 42.1, 40.8, 25.9, 22.7, 22.2, 10.5, 9.8, 3.2.

Step 6

2-(5-Cyclopropylmethoxy-2-fluoro-4-iodo-phenyl)-4-methyl-pentanoic acid cyclopropylmethyl ester

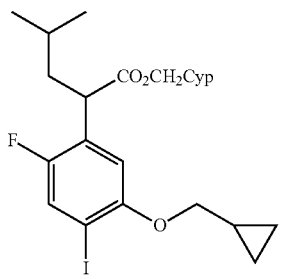

2-(5-cyclopropylmethoxy-2-fluoro-4-amino-phenyl)-4-methyl-pentanoic acid cyclopropylmethyl ester (2.9 g, 8.3 mmol) was dissolved in a mixture of EtOH/H$_2$O/H$_2$SO$_4$ (96%) 50 mL/100 mL/2.5 mL at 0° C. A solution of NaNO$_2$ (0.63 g, 9.1 mmol) in water (20 mL) was added dropwise at 0° C. and the reaction mixture was stirred for 20 min. A solution of KI (4.0 g, 24.1 mmol) in water (20 mL) was added dropwise at 0° C. and the reaction mixture was heated 50-60° C. for 2.5 h. The reaction mixture was extracted with EtOAc (3×50 mL). The combined organic layers were washed with 10% sodium thiosulfate (30 mL) followed by brine (30 mL) and then dried over MgSO$_4$. and solvent evaporated to give crude brown oil, which was purified by column chromatography over silica gel (Heptane-EtOAc gradient) to give 2.2 g, (57%) of 2-(5-cyclopropylmethoxy-2-fluoro-4-iodo-phenyl)-4-methyl-pentanoic acid cyclopropylmethyl ester as a yellow oil. $^1$H NMR (300 MHz, CDCl$_3$/TMS): δ 7.46 (d, J=8.8 Hz, 1H), 6.83 (d, J=6.3 Hz, 1H), 4.01-3.83 (m, 5H), 1.96-1.86 (m, 1H), 1.69-1.58 (m, 1H), 1.51-1.39 (m, 1H), 1.28-1.18 (m, 1H), 1.12-1.00 (m, 1H), 0.91 (d, J=6.3 Hz, 6H), 0.66-0.60 (m, 2H), 0.55-047 (m, 2H), 0.42-0.34 (m, 2H), 0.26-0.18 (m, 2H); $^{13}$C NMR (75 MHz, CDCl$_3$/TMS): δ 173.2, 154.3 (d, $^1J_{CF}$=243.4 Hz), 154.1, 127.1 (d, $^2J_{CF}$=16.2 Hz), 125.5 (d, $^2J_{CF}$=26.4 Hz), 112.3 (d, $^3J_{CF}$=3.6 Hz), 84.6 (d, $^3J_{CF}$=8.4 Hz), 74.5, 69.6, 41.9, 41.5, 26.0, 22.7, 22.2, 10.2, 9.8, 3.3.

Step 7

2-(2-Cyclopropylmethoxy-5-fluoro-4'-trifluoromethyl-biphenyl-4-yl)-4-methyl-pentanoic acid cyclopropylmethyl ester

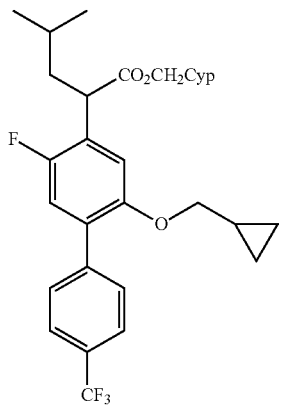

To a solution of 2-(5-cyclopropylmethoxy-2-fluoro-4-iodo-phenyl)-4-methyl-pentanoic acid cyclopropylmethyl ester (0.2 g, 0.43 mmol) in anhydrous DME (10 mL) under argon was added 4-trifluoromethylphenylboronic acid (0.1 g, 0.53 mmol), CsF (0.16 g, 1.05 mmol), and Pd(PPh$_3$)$_4$ (0.015 g, 0.013 mmol). The reaction mixture was refluxed for 18 h, a water/EtOAc 15/15 mL mixture was added and the organic phase was separated and dried over MgSO$_4$. The solvent was then evaporated to give a yellow oil which was purified by column chromatography over silica gel (Heptane-EtOAc gradient) to give 0.18 of 2-(2-cyclopropylmethoxy-5-fluoro-4'-trifluoromethyl-biphenyl-4-yl)-4-methyl-pentanoic acid cyclopropylmethyl ester as a light yellow oil. $^1$H NMR (300 MHz, CDCl$_3$/TMS): δ 7.70-7.64 (m, 4H), 7.05 (d, J=10.4 Hz, 1H), 7.01 (d, J=6.1 Hz, 1H), 4.09 (t, J=7.7 Hz, 1H), 4.02-3.87 (m, 2H), 3.78 (d, J=6.6 Hz, 2H), 2.04-1.90 (m, 1H), 1.74-1.65 (m, 1H), 1.60-1.45 (m, 1H), 1.25-1.05 (m, 2H), 0.95 (d, J=6.3 Hz, 6H), 0.60-0.40 (m, 4H), 0.30-0.10 (m, 4H). $^{13}$C NMR (75 MHz, CDCl$_3$/TMS): δ 173.5, 154.3 (d, $^1J_{CF}$=239.7 Hz), 151.9, 140.7, 132.0, 129.5, 126.6 (d, $^2J_{CF}$=16.9 Hz), 124.8 (q, $^3J_{CF}$=3.7 Hz), 124.0 (q, $^1J_{CF}$=271.6 Hz), 117.0 (d, $^2J_{CF}$=24.6 Hz), 113.6, 74.1, 69.6, 41.1, 41.5, 26.1, 22.7, 22.2, 10.2, 9.8, 3.2.

Step 8

2-(2-Cyclopropylmethoxy-5-fluoro-4'-trifluoromethyl-biphenyl-4-yl)-4-methyl-pentanoic acid

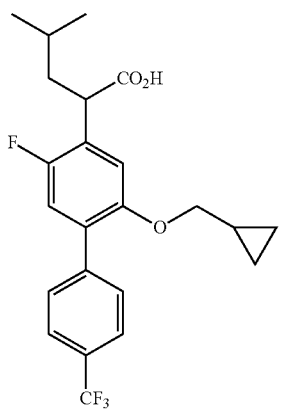 [SMILES: CC(C)CC(C(=O)O)c1cc(OCC2CC2)c(-c2ccc(C(F)(F)F)cc2)cc1F]

2-(2-cyclopropylmethoxy-5-fluoro-4'-trifluoromethyl-biphenyl-4-yl)-4-methyl-pentanoic acid cyclopropylmethyl ester (0.14 g, 0.29 mmol) was dissolved in a mixture of EtOH/H$_2$O (9 ml/1 ml) and KOH 0.3 g added. The reaction mixture was refluxed for 2 h and after cooling the solvent was evaporated. Water (10 mL) was added and the reaction mixture was extracted with EtOAc (3×10 mL). The combined organic extracts were dried over MgSO$_4$ and evaporated under reduced pressure to an oil which was purified by column chromatography over silica gel (Heptane-EtOAc gradient) to give 0.12 g of a white solid. A second chromatography of the solid gave 0.03 g (25%) of pure 2-(2-cyclopropylmethoxy-5-fluoro-4'-trifluoromethyl-biphenyl-4-yl)-4-methyl-pentanoic acid product as a crystalline white solid. M.P.=110-111° C., $^1$HNMR (300 MHz, CDCl$_3$/TMS): δ 8.99 (br s 1H), 7.66 (br s, 4H), 7.05 (d, J=9.9 Hz, 1H), 6.94 (d, J=5.2 Hz, 1H), 4.08 (t, J=7.7 Hz, 1H), 3.76 (d, J=6.6 Hz, 2H), 2.04-1.90 (m, 1H), 1.81-1.65 (m, 1H), 1.60-1.45 (m, 1H), 1.32-1.05 (m, 2H), 0.94 (d, J=6.0 Hz, 6H), 0.54 (d, J=7.4 Hz, 2H), 0.24 (d, J=3.9 Hz, 2H). $^{13}$C NMR (75 MHz, CDCl$_3$/TMS): δ 179.2, 154.7 (d, $^1J_{CF}$=239.8 Hz), 152.0, 140.6, 132.0, 129.9, 129.6, 125.7 (d, $^2J_{CF}$=16.2 Hz), 124.8 (q, $^3J_{CF}$=3.6 Hz), 124.0 (q, $^1J_{CF}$=270 Hz), 117.2 (d, $^2J_{CF}$=25.2 Hz), 113.9, 74.2, 41.3, 29.8, 25.9, 22.8, 22.1, 10.3, 3.2.

Example 485

2-(5-chloro-6-(cyclopropylmethoxy)-4'-(trifluoromethyl)biphenyl-3-yl)-3-cyclopropylpropanoic acid

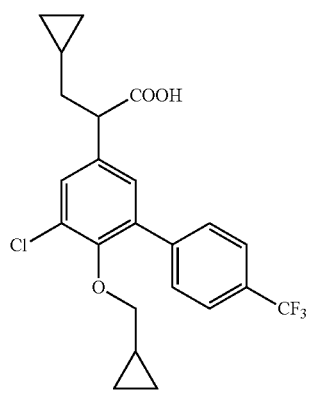

Step 1

Ethyl 2-(3-bromo-4-hydroxyphenyl)acetate

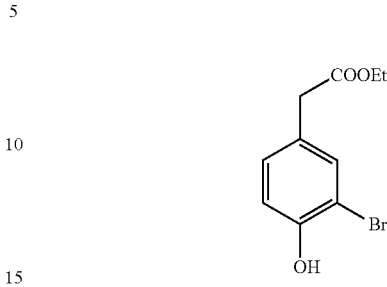

To a stirred solution of ethyl 2-(4-hydroxyphenyl)acetate (20 g, 0.11 mol) in 200 ml of CCl$_4$, was slowly added bromine (18.8 g, 0.11 mol) dissolved in 10 ml of CCl$_4$ at 0° C. for 30 min. The reaction mass was stirred for another 30 min at 0° C. After completion of the reaction, the mixture was poured onto crushed ice and extracted with DCM (×2). The combined organic layers were washed with water, and 10% sodium bi-sulfite solution, dried over Na$_2$SO$_4$, filtered and concentrated in vacuo to give ethyl 2-(3-bromo-4-hydroxyphenyl)acetate in 78% yield. (22.4 g). $^1$HNMR (CDCl$_3$): 7.42 (s, 1H); 7.14 (d, 1H); 6.97 (d, 1H); 5.53 (bs, 1H); 4.13 (q, 2H); 3.52 (s, 2H); 1.16 (t, 3H).

Step 2

Ethyl 2-(3-bromo-5-chloro-4-hydroxyphenyl)acetate

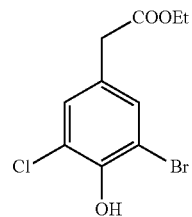 [SMILES: CCOC(=O)Cc1cc(Cl)c(O)c(Br)c1]

To a stirred solution of ethyl 2-(3-bromo-4-hydroxyphenyl)acetate (20 g, 0.076 molo) in 200 ml of DCM was added MeOH (3.4 ml, 0.84 mol) and the mixture was refluxed. Sulfuryl chloride (6.8 ml 0.846 mol) was slowly added under over a period of 10 min. The reaction mixture was refluxed for a further 5 h. Upon completion of reaction, the mixture was poured onto crushed ice and extracted with DCM (×2). The combined organic layer were washed with 10% NaHCO$_3$ solution and water, dried over Na$_2$SO$_4$, filtered and evaporated under vacuum to give ethyl 2-(3-bromo-5-chloro-4-hydroxyphenyl)acetate in 60% yield. (13.6 g). $^1$HNMR (CDCl3): 7.37 (s, 1H); 7.27 (s, 1H); 5.68 (bs, 1H); 4.16 (q, 2H); 3.48 (s, 2H); 1.29 (t, 3H).

Step 3

Ethyl 2-(3-bromo-5-chloro-4-(cyclopropylmethoxy)phenyl)acetate

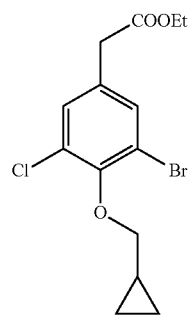 [SMILES: CCOC(=O)Cc1cc(Cl)c(OCC2CC2)c(Br)c1]

To a stirred solution of ethyl 2-(3-bromo-5-chloro-4-hydroxyphenyl)acetate (4 g, 0.011 mol) and $K_2CO_3$ (2.8 g, 0.02 mol) in 100 ml of DMSO was slowly added cyclopropyl methylbromide (1.46 ml, 0.017 mol) at room temperature. Upon completion of the addition, the reaction mixture was heated at 60° C. for 4 h. Upon completion of the reaction, the mixture was poured onto water and extracted with EtOAc (×2). The combined organic layers were washed with water, dried over $Na_2SO_4$, filtered and concentrated in vacuo to give ethyl 2-(3-bromo-5-chloro-4-(cyclopropylmethoxy)phenyl)acetate in 72% yield. (93.4 g). $^1$HNMR (CDCl$_3$): 7.38 (bs, 1H); 7.28 (s, 1H); 4.16 (q, 2H); 3.87 (d, 2H); 3.58 (s, 2H); 1.38 (m, 1H); 1.28 (t, 3H); 0.63 (m, 2H); 0.38 (m, 2H).

Step 4

Ethyl 2-(5-chloro-6-(cyclopropylmethoxy)-4'-(trifluoromethyl)biphenyl-3-yl)acetate

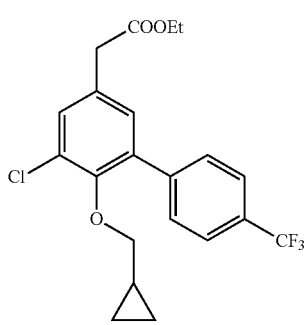 [SMILES: CCOC(=O)Cc1cc(Cl)c(OCC2CC2)c(-c2ccc(C(F)(F)F)cc2)c1]

A mixture of ethyl 2-(3-bromo-5-chloro-4-(cyclopropylmethoxy)phenyl)acetate (4 g, 0.011 mol), 4-Trifluoromethyl phenylboronic acid (2.6 g, 0.012 mol), Palladium Tetrakis (triphenylphosphine) (1.3 g, 0.001 mol), Cesium carbonate (13.1 g, 0.04 mol) in DMF/water mixture (100 ml/5 ml) was stirred overnight at 100° C. Upon completion of reaction, the precipitate were removed by filtration. The filtrate was diluted with water and extracted with EtOAc twice. The combined organic layers were washed with water and brine, dried over $Na_2SO_4$ and concentrated in vacuo. The residue was purified by Flash Column Chromatography to give ethyl 2-(5-chloro-6-(cyclopropylmethoxy)-4'-(trifluoromethyl)biphenyl-3-yl)acetate in 57% yield. (2.7 g). $^1$HNMR (CDCl$_3$): 7.69 (bs, 4H); 7.36 (s, 1H); 7.17 (s, 1H); 4.18 (q, 2H); 3.59 (s, 2H); 3.39 (d, 2H); 1.28 (t, 3H); 0.96 (m, 1H); 0.41 (m, 2H); 0.01 (m, 2H).

Step 5

Ethyl 2-(5-chloro-6-(cyclopropylmethoxy)-4'-(trifluoromethyl)biphenyl-3-yl)-3-cyclopropylpropanoate

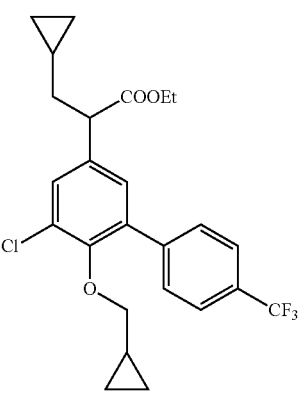 [SMILES: O=C(O)C(CC1CC1)c1cc(Cl)c(OCC2CC2)c(-c2ccc(C(F)(F)F)cc2)c1]

To a suspension of NaH (37 mg, 50% suspension, 0.79 mmol) in 25 ml of DMF was slowly added a mixture of ethyl 2-(5-chloro-6-(cyclopropylmethoxy)-4'-(trifluoromethyl)biphenyl-3-yl)acetate (300 mg, 0.719 mmol) and cyclopropylmethyl bromide (108 mg, 0.782 mmol) in 20 ml of DMF at 0° C. for 15 min under nitrogen atmosphere. Upon completion of the addition, the mixture was stirred for 15 min at 0° C. The reaction mixture was poured onto crushed ice and extracted with EtOAc (×2). The combined organic layers were washed with water and brine, dried over $Na_2SO_4$ and concentrated in vacuo. The residue was purified by Flash column Chromatography to give ethyl 2-(5-chloro-6-(cyclopropylmethoxy)-4'-(trifluoromethyl)biphenyl-3-yl)-3-cyclopropylpropanoate in 62% yield. (0.210 g). $^1$HNMR (CDCl$_3$): 7.69 (s, 4H); 7.41 (s, 1H); 7.21 (s, 1H); 4.19 (q, 2H); 3.63 (t, 1H); 3.41 (d, 2H); 1.94 (m, 1H); 1.78 (m, 1H); 1.27 (t, 3H); 0.97 (bs, 1H); 0.72 (bs, 1H); 0.42 (m, 4H); 0.13 (m, 2H); 0.1 (m, 2H).

Step 6

2-(5-chloro-6-(cyclopropylmethoxy)-4'-(trifluoromethyl)biphenyl-3-yl)-3-cyclopropylpropanoic acid

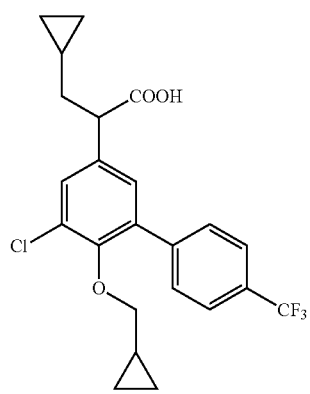

A mixture of ethyl 2-(5-chloro-6-(cyclopropylmethoxy)-4'-(trifluoromethyl)biphenyl-3-yl)-3-cyclopropylpropanoate (100 mg, 0.214 mmol) and lithium hydroxide monohydrate (27 mg, 0.642 mmol) in a MeOH/THF/Water solvent mixture (5 ml/5 ml5/ml) was stirred for 3 h at room temperature. Upon completion of reaction, the volatiles were removed under reduced pressure. The residue was diluted with water, acidified with 5% HCl solution and extracted with EtOAc (×2). The combined organic layers were washed with water, dried over $Na_2SO_4$, filtered and concentrated in vacuo. The residue was purified by Flash Column Chromatography to give 2-(5-chloro-6-(cyclopropylmethoxy)-4'-(trifluoromethyl)biphenyl-3-yl)-3-cyclopropylpropanoic acid in 56% yield. (52.6 mg). $^1$HNMR ($CDCl_3$): 7.71 (s, 4H); 7.42 (s, 1H); 7.23 (s, 1H); 3.68 (t, 1H); 3.41 (d, 2H); 1.93 (m, 1H); 1.77 (m, 1H); 0.97 (bs, 1H); 0.71 (bs, 1H); 0.42 (m, 4H); 0.12 (m, 2H); 0.1 (m, 2H).

Example 414

2-(5-chloro-6-(2,2,2-trifluoroethoxy)-4'-(trifluoromethyl)biphenyl-3-yl)-4-methylpentanoic acid

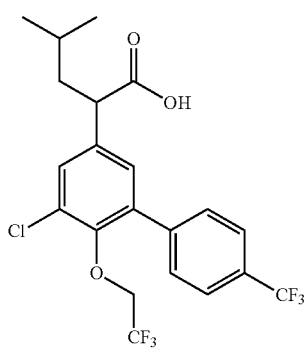 [SMILES: CC(C)CC(C(=O)O)c1cc(Cl)c(OCC(F)(F)F)c(-c2ccc(C(F)(F)F)cc2)c1]

Step 1

Ethyl 2-(3-amino-5-bromo-4-hydroxyphenyl)-4-methylpentanoate

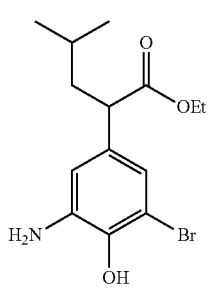 [SMILES: CCOC(=O)C(CC(C)C)c1cc(N)c(O)c(Br)c1]

To a stirred solution compound ethyl 2-(3-bromo-4-hydroxy-5-nitrophenyl)-4-methylpentanoate (6 g), in dry methanol (100 mL) was added Pd(OH)$_2$ under an atmosphere of nitrogen. The reaction mixture was stirred for 5 h under an atmosphere of hydrogen. The reaction mixture was filtered through Celite™, washed with methanol and concentrated to dryness under reduced pressure. The crude material was purified by column chromatography to yield ethyl 2-(3-amino-5-bromo-4-hydroxyphenyl)-4-methylpentanoate (4 g, 72%). $^1$HNMR ($CDCl_3$, 200 MHz): 6.80 (s, 1H); 6.62 (s, 1H); 5.35 (bs, 1H); 4.13 (q, 2H); 3.41 (t, 1H); 1.93-1.56 (m, 2H); 1.51 (m, 1H); 1.21 (t, 3H), 0.97 (d, 6H).

Step 2

Ethyl 2-(3-bromo-5-chloro-4-hydroxyphenyl)-4-methylpentanoate

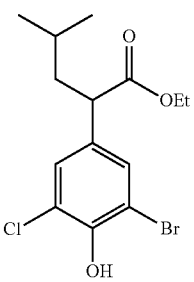 [SMILES: CCOC(=O)C(CC(C)C)c1cc(Cl)c(O)c(Br)c1]

Ethyl 2-(3-amino-5-bromo-4-hydroxyphenyl)-4-methylpentanoate 1 (4 g, 0.012 mol) was dissolved in a mixture of ACN/H$_2$O/HCl 60 mL/30 mL/8 mL at 0° C. A solution of NaNO$_2$ (0.919 g, 1.1 eq) in water (10 mL) was added dropwise at 0° C. and the reaction mixture was stirred for 1 h at 0° C. A solution of CuCl (5.99 g, 0.060 mol) in water (10 mL) was added dropwise to the reaction mixture at 0° C. The reaction mixture was then heated to 50° C. for 2.5 h. upon which the mixture was poured into ice water, extracted with ethyl acetate (3×100 mL) The combined organic layers were washed with water (200 mL) and brine (100 mL), dried over NaSO$_4$ and concentrated in vacuo to give crude black oil which was purified by chromatography over silica gel (hexane/EtOAc) to give ethyl 2-(3-bromo-5-chloro-4-hydroxyphenyl)-4-methylpentanoate as yellow oil 2.2 g, (47.3%). $^1$HNMR ($CDCl_3$, 200 MHz): 7.38 (s, 1H); 7.4 (s, 1H); 5.80 (bs, 1H); 4.13 (q, 2H); 3.51 (t, 1H); 1.93-1.56 (m, 2H); 1.51 (m, 1H); 1.21 (t, 3H), 0.97 (d, 6H);

Step 3

Ethyl 2-(3-bromo-5-chloro-4-(2,2,2-trifluoroethoxy)phenyl)-4-methyl pentanoate

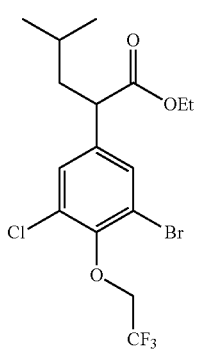 [SMILES: CCOC(=O)C(CC(C)C)c1cc(Cl)c(OCC(F)(F)F)c(Br)c1]

To a stirred solution of ethyl 2-(3-bromo-5-chloro-4-hydroxyphenyl)-4-methylpentanoate (2 g, 0.57 mmol) and K₂CO₃ (1.58 g, 0.011 mol) in dry DMF (20 mL), slowly added trifluoroethyl iodide (7.2 g, 3.39 ml, 0.034 mol) at room temperature. Upon completion of the addition, the reaction mixture was slowly heated to 100° C. for 4 h. Upon completion, the reaction mixture was poured into water and extracted with ethyl acetate (2×50 mL). The combined organic layer were washed with water, dried over Na₂SO₄ and concentrated under reduced pressure. The residue was purified by flash column chromatography over silica gel (hexane/EtOAc) to give ethyl 2-(3-bromo-5-chloro-4-(2,2,2-trifluoroethoxy)phenyl)-4-methylpentanoate (1.4 g, 60% yield). ¹HNMR (CDCl₃, 400 MHz): 7.43 (s, 1H); 7.34 (s, 1H); 4.4 (q, 2H), 4.13 (q, 2H); 3.55 (t, 1H); 1.93 (m, 1H); 1.58 (m, 1H); 1.45 (m, 1H); 1.24 (t, 3H), 0.92 (d, 6H);

Step 4

Ethyl 2-(5-chloro-6-(2,2,2-trifluoroethoxy)-4'-(trifluoromethyl)biphenyl-3-yl)-4-methylpentanoate

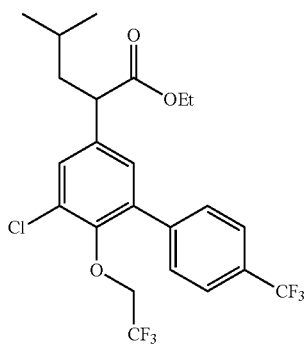 [SMILES: CCOC(=O)C(CC(C)C)c1cc(Cl)c(OCC(F)(F)F)c(-c2ccc(C(F)(F)F)cc2)c1]

A mixture of ethyl 2-(3-bromo-5-chloro-4-(2,2,2-trifluoroethoxy)phenyl)-4-methylpentanoate (1 g, 1 eq), 4-Trifluoromethyl phenylboronic acid (2.6 g, 1.4 eq), Pd(PPh₃)₄ (1.3 g, 0.1 eq) and Cesium Fluoride (13.1 g, 2 eq) in DME (30 ml) was stirred for overnight at 100° C. Upon completion, the precipitate was removed by filtration. The filtrate was diluted with water and extracted with ethyl acetate (2×50 mL). The combined organic layers were washed with water followed by brine, dried over Na₂SO₄ and concentrated under vacuo. The residue was purified by Flash Column Chromatography to give ethyl 2-(5-chloro-6-(2,2,2-trifluoroethoxy)-4'-(trifluoromethyl)biphenyl-3-yl)-4-methylpentanoate in 74% yield (1.08 g). ¹HNMR (CDCl₃, 400 MHz): 7.68 (m, 5H), 7.43 (s, 1H); 7.24 (s, 1H); 4.4 (q, 2H), 4.13 (q, 2H); 3.55 (t, 1H); 1.93 (m, 1H), 1.58 (m, 1H); 1.45 (m, 1H); 1.24 (t, 3H), 0.92 (d, 6H);

Step 5

2-(5-chloro-6-(2,2,2-trifluoroethoxy)-4'-(trifluoromethyl)biphenyl-3-yl)-4-methylpentanoic acid

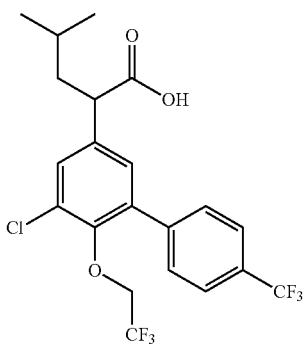 [SMILES: CC(C)CC(C(=O)O)c1cc(Cl)c(OCC(F)(F)F)c(-c2ccc(C(F)(F)F)cc2)c1]

A mixture of ethyl 2-(5-chloro-6-(2,2,2-trifluoroethoxy)-4'-(trifluoromethyl)biphenyl-3-yl)-4-methylpentanoate (800 mg, mmol) and lithium hydroxide monohydrate (27 mg, 0.642 mmol) in a MeOH/THF/Water solvent mixture (5 ml/5 ml5/ml) was stirred for 3 h at room temperature. Upon completion of the reaction, the volatiles were removed under reduced pressure. The residue was diluted with water, acidified with 5% HCl solution and extracted with ethyl acetate (3×50 mL). The combined organic layers were washed with water, dried over Na₂SO₄, filtered and evaporated under reduced pressure. The residue was purified by Flash Column Chromatography to give 2-(5-chloro-6-(2,2,2-trifluoroethoxy)-4'-(trifluoromethyl)biphenyl-3-yl)-4-methylpentanoic acid in 88% yield (670 mg).

Or alternatively example 414 may be synthesized via the following procedures:

Step 1

Ethyl 2-(5-chloro-6-(2,2,2-trifluoroethoxy)-4'-(trifluoromethyl)biphenyl-3-yl)-4-methylpentanoate

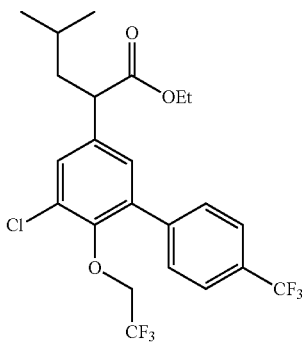 [SMILES: CCOC(=O)C(CC(C)C)c1cc(Cl)c(OCC(F)(F)F)c(-c2ccc(C(F)(F)F)cc2)c1]

Ethyl 2-(5-chloro-6-(2,2,2-trifluoroethoxy)-4'-(trifluoromethyl)biphenyl-3-yl)acetate (0.75 g, 1.70 mmol) was dissolved in anhydrous DMF (20 mL), NaH (60% wt. in paraffin oil, 0.049 g, 2.04 mmol) was added at 0° C. The reaction mixture was stirred for 30 min at room temperature, upon which isobutyl bromide (0.2 mL, 1.87 mmol), was added in a drop wise manner at 0° C. The reaction mixture was stirred an additional 1 h at 0° C. and then saturated NH₄Cl solution (10 mL) was added. The reaction mixture was extracted with EtOAc (3×20 mL) and the combined organic layers were washed with water (2×10 mL) and brine (10 mL), dried over Na$_2$SO$_4$, filtered and concentrated under reduced pressure to give a colorless oil, witch was purified by flash column chromatography to give ethyl 2-(5-chloro-6-(2,2,2-trifluoroethoxy)-4'-(trifluoromethyl)biphenyl-3-yl)-4-methylpentanoate (0.5 g, 59% yield) as a thick liquid.

Step 2

2-(5-Chloro-6-(2,2,2-trifluoroethoxy)-4'-(trifluoromethyl)biphenyl-3-yl)-4-methyl pentanoic acid

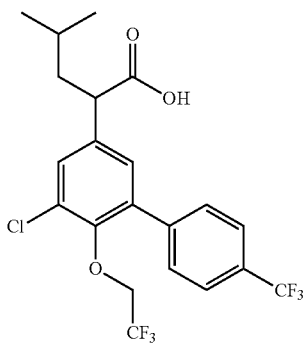 [SMILES: CC(C)CC(C(=O)O)c1cc(Cl)c(OCC(F)(F)F)c(-c2ccc(C(F)(F)F)cc2)c1]

A mixture of ethyl 2-(5-chloro-6-(2,2,2-trifluoroethoxy)-4'-(trifluoromethyl)biphenyl-3-yl)-4-methylpentanoate (0.6 g, 1.21 mmol) and lithium hydroxide monohydrate (0.509 g, 12.1 mmol) in MeOH/THF/Water a solvent mixture (10 mL/10 mL/10 mL) was stirred for 4 h at room temperature. After completion of reaction volatiles were removed under reduced pressure. The residue was diluted with water, acidified with 5% HCl solution and extracted with ethyl acetate (3×20 mL). The combined organic layers washed with water, dried over Na$_2$SO$_4$, filtered and evaporated under reduced pressure. The residue was purified by Flash Column Chromatography to give 2-(5-chloro-6-(2,2,2-trifluoroethoxy)-4'-(trifluoromethyl)biphenyl-3-yl)-4-methyl pentanoic acid (0.4 g, 72% yield) as a white solid.

Example 1055

2-(6-Cyclopropylmethoxy-5,4'-bis-trifluoromethyl-biphenyl-3-yl)-4-methyl-pentanoic Acid Step 1

Diethyl 2-isobutyl-2-(4-nitro-3-(trifluoromethyl)phenyl)malonate

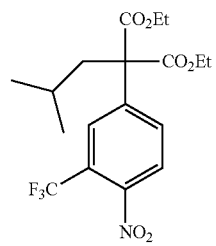 [SMILES: CCOC(=O)C(CC(C)C)(C(=O)OCC)c1ccc([N+](=O)[O-])c(C(F)(F)F)c1]

To a solution of diethyl isobutylmalonate (50.0 g, 231 mmol) in anhydrous DMF (200 mL) cooled in an ice bath was added NaH (60%, 11.1 g, 277 mmol) in small portions. After the addition, the reaction mixture was stirred at 0° C. for 10 min and then at room temperature for 30 min. 5-Chloro-2-nitrobenzotrifluoride (47.3 g, 210 mmol) in anhydrous DMF (50 mL) was added dropwise and the mixture was stirred at room temperature for two days. The DMF was removed under high vacuum and the residue was diluted with ethyl acetate (400 mL). Water (400 mL) was added dropwise; ammonium chloride (25 g) was added and the layers were separated. The organic layer was washed with brine (400 mL), dried over sodium sulfate, and concentrated under reduced pressure to give a red-brown oil, which was purified by silica-gel flash chromatography eluting with heptane/ethyl acetate (12:1) to give the desired product diethyl 2-isobutyl-2-(4-nitro-3-(trifluoromethyl)phenyl)malonate (74.4 g, 87%) as a yellow oil: $^1$H NMR (300 MHz, CDCl$_3$): δ 8.07 (s, 1H), 7.94 (d, 2H, J=8.7 Hz), 7.88 (d, 2H, J=8.7 Hz), 4.25 (m, 4H), 2.33 (d, 2H, J=6.6 Hz), 1.51 (m, 1H), 1.26 (t, 6H, J=7.2 Hz), 0.84 (d, 6H, J=6.6 Hz); $^{13}$C NMR (75 MHz, CDCl$_3$): δ 169.23, 146.71, 142.86, 132.94, 127.94 (q, J=5 Hz), 124.55, 123.12 (q, J=33 Hz), 121.79 (q, J=272 Hz), 62.19, 61.59, 44.16, 24.66, 23.66, 13.89.

Step 2

4-Methyl-2-(4-nitro-3-trifluoromethyl-phenyl)-pentanoic acid

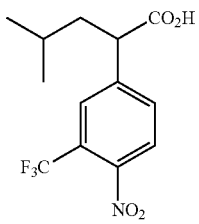 [SMILES: CC(C)CC(C(=O)O)c1ccc([N+](=O)[O-])c(C(F)(F)F)c1]

To a solution of diethyl 2-isobutyl-2-(4-nitro-3-(trifluoromethyl)phenyl)malonate (74.4 g, 184 mmol) in acetic acid (500 mL) were added water (157 mL) and concentrated H$_2$SO$_4$ (55 mL) carefully. The reaction mixture was refluxed for three days and then concentrated under reduced pressure. The residue was diluted with water (400 mL) and extracted with ethyl acetate (6×100 mL). The combined organic extracts were washed with water (400 mL), dried over sodium sulfate, and concentrated under reduced pressure to give a brown oil. The residue was purified by silica-gel flash chromatography eluting with heptane/EtOAc (5:1 and then 2:1) to give 4-methyl-2-(4-nitro-3-trifluoromethyl-phenyl)-pentanoic acid (42.5 g, 76%) as a yellowish oil: $^1$H NMR (300 MHz, CDCl$_3$): δ 11.51 (s, 1H, br), 7.87 (d, 1H, J=8.4 Hz), 7.78 (s, 1H), 7.71 (d, 1H, J=8.4 Hz), 3.84 (t, 1H, J=7.8 Hz), 2.06 (m, 1H), 1.72 (m, 1H), 1.49 (m, 1H), 0.95 (d, 3H, J=6.6 Hz), 0.94 (d, 3H, J=6.3 Hz); $^{13}$C NMR (75 MHz, CDCl$_3$): δ 178.76, 147.09, 143.94, 132.66, 127.70 (q, J=5 Hz), 125.40, 123.95 (q, J=34 Hz), 121.74 (q, J=271 Hz), 42.16, 25.96, 22.44, 22.09.

Step 3

4-Methyl-2-(4-nitro-3-trifluoromethyl-phenyl)-pentanoic acid ethyl ester

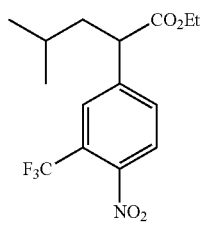

To a solution of 4-methyl-2-(4-nitro-3-trifluoromethyl-phenyl)-pentanoic acid (42.3 g, 139 mmol) in absolute ethanol (300 mL) was added concentrated sulfuric acid (95-98%, 9.0 mL) and the solution was heated at reflux overnight. The reaction mixture was concentrated under reduced pressure; the residue was treated with a solution of sodium carbonate (5%, 300 mL) and the mixture was extracted with ethyl acetate (300 mL). The organic layer was washed with brine (300 mL), dried over sodium sulfate, and concentrated under reduced pressure. Purification by silica-gel flash chromatography eluting with heptane/EtOAc (10:1) gave 4-methyl-2-(4-nitro-3-trifluoromethyl-phenyl)-pentanoic acid ethyl ester (38.4 g, 83%) as a yellowish oil: $^1$H NMR (300 MHz, CDCl$_3$): δ 7.90 (d, 1H, J=8.4 Hz), 7.82 (s, 1H), 7.74 (dd, 1H, J=8.4, 1.5 Hz), 4.18 (m, 2H), 3.83 (t, 1H, J=7.5 Hz), 2.06 (m, 1H), 1.70 (m, 1H), 1.50 (m, 1H), 1.27 (t, 3H, J=7.2 Hz), 0.97 (d, 3H, J=6.6 Hz), 0.96 (d, 3H, J=6.3 Hz); $^{13}$C NMR (75 MHz, CDCl$_3$): δ 172.24, 146.83, 145.04, 132.40, 127.51 (q, J=5 Hz), 125.28, 123.80 (q, J=32 Hz), 121.78 (q, J=272 Hz), 61.45, 49.45, 42.65, 26.03, 22.41, 22.17, 14.10.

Step 4

2-(4-Amino-3-trifluoromethyl-phenyl)-4-methyl-pentanoic acid ethyl ester

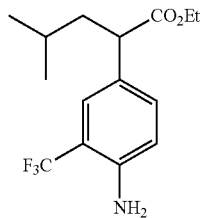 [SMILES: CCOC(=O)C(CC(C)C)c1ccc(N)c(C(F)(F)F)c1]

A suspension of 4-methyl-2-(4-nitro-3-trifluoromethyl-phenyl)-pentanoic acid ethyl ester (38.3 g, 115 mmol), tin (II) chloride (87.2 g, 460 mmol) and water (16.6 g, 920 mmol) in ethanol (500 mL) was heated at reflux for four hours. The reaction mixture was concentrated under reduced pressure; the residue was treated with ethyl acetate (300 mL) and aqueous NaOH solution (1 N, 2.5 L). The aqueous layer was extracted with ethyl acetate (3×600 mL). The combined organic layers were washed with brine (1 L), dried over Na$_2$SO$_4$, and concentrated under reduced pressure. The residue was purified by silica-gel flash chromatography eluting with heptane/ethyl acetate (10:1) to give 2-(4-amino-3-trifluoromethyl-phenyl)-4-methyl-pentanoic acid ethyl ester (31.1 g, 89%) as a yellow oil: $^1$H NMR (300 MHz, CDCl$_3$): δ 7.35 (d, 1H, J=2.1 Hz), 7.27 (dd, 1H, J=8.4, 2.1 Hz), 6.69 (d, 1H, J=8.4 Hz), 4.10 (m, 4H), 3.54 (t, 1H, J=7.8 Hz), 1.91 (m, 1H), 1.58 (m, 1H), 1.44 (m, 1H), 1.21 (t, 3H, J=6.9 Hz), 0.90 (d, 3H, J=6.6 Hz), 0.89 (d, 3H, J=6.6 Hz); $^{13}$C NMR (75 MHz, CDCl$_3$): δ 174.14, 143.45, 132.22, 128.58, 125.91 (q, J=4 Hz), 124.80 (q, J=271 Hz), 117.35, 113.60 (q, J=29 Hz), 60.60, 48.54, 42.35, 25.77, 22.46, 22.18, 14.04.

Step 5

2-(4-Hydroxy-3-nitro-5-trifluoromethyl-phenyl)-4-methyl-pentanoic acid ethyl ester

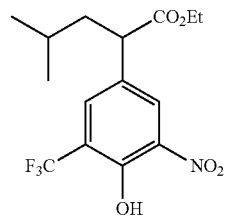 [SMILES: CCOC(=O)C(CC(C)C)c1cc([N+](=O)[O-])c(O)c(C(F)(F)F)c1]

To sulfuric acid (95-98%, 20.0 mL) was added 2-(4-amino-3-trifluoromethyl-phenyl)-4-methyl-pentanoic acid ethyl ester (6.06 g, 20.0 mmol). The mixture was cooled to 0° C. and water (30.0 mL) was added dropwise. A solution of NaNO$_2$ (1.66 g, 24.0 mmol) in water (12 mL) was added dropwise and the mixture was stirred for additional 20 min. A few crystals of urea were added to decompose any excess NaNO$_2$. A solution of cupric nitrate (466 g, 2.00 mol) in water (880 mL) was added, followed by addition of Cu$_2$O (2.86 g, 20.0 mmol). The mixture was stirred for 5 min and diethyl ether (1 L) was added. The organic extract was washed with brine (500 mL), dried over Na$_2$SO$_4$, and concentrated under reduced pressure. The residue was purified by silica-gel flash chromatography eluting with heptane/ethyl acetate (20:1) to give 2-(4-hydroxy-3-nitro-5-trifluoromethyl-phenyl)-4-methyl-pentanoic acid ethyl ester (2.20 g, 31%) as a yellow oil: HRMS (DIP-CI-MS): calcd for C$_{15}$H$_{19}$NO$_5$F$_3$ (M+H)$^+$: 350.1215, found 350.1240; $^1$H NMR (300 MHz, CDCl$_3$): δ 11.13 (s, 1H), 8.29 (s, 1H), 7.90 (s, 1H), 4.15 (m, 2H), 3.69 (t, 1H, J=7.8 Hz), 2.00 (m, 1H), 1.62 (m, 1H), 1.47 (m, 1H), 1.25 (t, 3H, J=7.2 Hz), 0.94 (d, 3H, J=6.3 Hz), 0.93 (d, 3H, J=6.6 Hz); $^{13}$C NMR (75 MHz, CDCl$_3$): δ 172.75, 152.45, 134.67 (q, J=5 Hz), 134.29, 131.40, 127.90, 122.35, (q, J=271 Hz), 121.42 (q, J=32 Hz), 61.51, 48.76, 42.76, 26.23, 22.60, 22.42, 14.32.

Step 6

2-(4-Cyclopropylmethoxy-3-nitro-5-trifluoromethyl-phenyl)-4-methyl-pentanoic acid ethyl ester

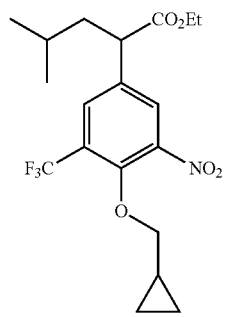 [SMILES: CCOC(=O)C(CC(C)C)c1cc([N+](=O)[O-])c(OCC2CC2)c(C(F)(F)F)c1]

To a solution of 2-(4-hydroxy-3-nitro-5-trifluoromethyl-phenyl)-4-methyl-pentanoic acid ethyl ester (2.66 g, 7.62 mmol), cyclopropanemethanol (0.60 g, 8.38 mmol) and triphenylphosphine (2.40 g, 9.14 mmol) in anhydrous THF (32 mL) was added diethyl azodicarboxylate (40 wt % solution in toluene, 3.98 g, 9.14 mmol) dropwise. The reaction mixture was stirred at room temperature for two days and then concentrated under reduced pressure. The residue was triturated with THF/hexane (1:5, 3×15 mL). The combined extracts were concentrated under reduced pressure to give a yellow solid, which was purified by silica-gel flash chromatography eluting with heptane/ethyl acetate (60:1 and then 10:1) to give 2-(4-cyclopropylmethoxy-3-nitro-5-trifluoromethyl-phenyl)-4-methyl-pentanoic acid ethyl ester (1.89 g, 61%) as a colorless oil: $^1$H NMR (300 MHz, CDCl$_3$): δ 7.92 (s, 1H), 7.73 (s, 1H), 4.06 (m, 2H), 3.79 (d, 2H, J=7.2 Hz), 3.64 (t, 1H, J=7.5 Hz), 1.93 (m, 1H), 1.55 (m, 1H), 1.40 (m, 1H), 1.24 (m, 1H), 1.17 (t, 3H, J=6.9 Hz), 0.86 (m, 6H), 0.56 (d, 2H, J=6.6 Hz), 0.27 (m, 2H); $^{13}$C NMR (75 MHz, CDCl$_3$): δ 172.49, 149.98, 144.40, 135.55, 130.96 (q, J=5 Hz), 128.29, 126.77, (q, J=31 Hz), 122.37 (q, J=272 Hz), 82.03, 61.37, 48.74, 42.66, 26.04, 22.36, 22.32, 14.14, 10.66, 3.39.

Step 7

2-(3-Amino-4-cyclopropylmethoxy-5-trifluoromethyl-phenyl)-4-methyl-pentanoic acid ethyl ester

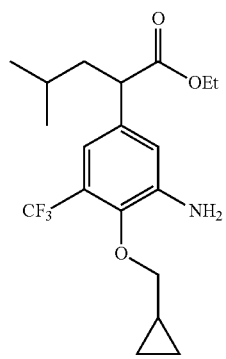 [SMILES: CCOC(=O)C(CC(C)C)c1cc(N)c(OCC2CC2)c(C(F)(F)F)c1]

A mixture of 2-(4-cyclopropylmethoxy-3-nitro-5-trifluoromethyl-phenyl)-4-methyl-pentanoic acid ethyl ester (1.85 g, 4.59 mmol) and Pd/C (1.85 g) in ethanol and 1 N HCl (4.60 mL) was hydrogenated under 36 psi H$_2$ in a Parr apparatus. After 4 h, the reaction mixture was filtered through Celite 521®. The filtrate was concentrated under reduced pressure to give a yellow oil. The residue was treated with an aqueous solution of sodium carbonate (3 g in 100 mL of water) and the resulting solution was extracted with ethyl acetate (100 mL). The organic layer was dried over sodium sulfate and concentrated under reduced pressure to give a brown oil, which was purified by silica-gel flash chromatography eluting with a gradient of heptane/ethyl acetate (from 10:1 to 2:1) to give 2-(3-amino-4-cyclopropylmethoxy-5-trifluoromethyl-phenyl)-4-methyl-pentanoic acid ethyl ester (0.88 g, 51%) as a light pink oil: $^1$H NMR (300 MHz, CDCl$_3$): δ 6.83 (s, 1H), 6.80 (s, 1H), 4.04 (m, 2H), 3.85 (s, 2H), 3.66 (d, 2H, J=6.9 Hz), 3.45 (t, 1H, J=7.8 Hz), 1.84 (m, 1H), 1.49 (m, 1H), 1.39 (m, 1H), 1.22 (m, 1H), 1.14 (t, 3H, J=7.2 Hz), 0.82 (m, 6H), 0.56 (d, 2H, J=7.5 Hz), 0.27 (d, 2H, J=4.5 Hz); $^{13}$C NMR (75 MHz, CDCl$_3$): δ 173.61, 142.71, 141.25, 135.51, 123.75 (q, J=30 Hz), 123.52 (q, J=271 Hz), 118.46, 115.52 (q, J=5 Hz), 77.88, 60.70, 49.03, 42.53, 25.86, 22.40, 22.31, 14.07, 10.98, 3.19.

Step 8

2-(4-Cyclopropylmethoxy-3-iodo-5-trifluoromethyl-phenyl)-4-methyl-pentanoic acid ethyl ester

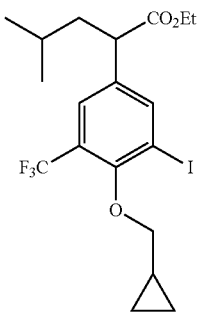 [SMILES: CCOC(=O)C(CC(C)C)c1cc(I)c(OCC2CC2)c(C(F)(F)F)c1]

To a solution of p-toluenesulfonic acid monohydrate (0.308 g, 1.62 mmol) in acetonitrile (2.3 mL) was added 2-(3-amino-4-cyclopropylmethoxy-5-trifluoromethyl-phenyl)-4-methyl-pentanoic acid ethyl ester (0.20 g, 0.54 mmol). The resulting suspension of the amine salt was cooled in an ice bath. A solution of sodium nitrite (0.0745 g, 1.08 mmol) in water (0.32 mL) was added dropwise, followed by addition of a solution of KI (1.79 g, 10.8 mmol) in water (2.0 mL). The reaction mixture was stirred in the ice bath for one hour and then at room temperature for one hour. TLC showed that the reaction was completed. Water (20 mL) was added and then an aqueous solution of sodium bicarbonate (1 M) to adjust the pH to 8. Ethyl acetate (20 mL) was added for extraction. The organic layer was washed with aqueous Na$_2$S$_2$O$_4$ solution (10%, 20 mL) and brine (20 mL), dried over Na$_2$SO$_4$, and concentrated under reduced pressure to give a brown oil, which was purified by silica-gel flash chromatography eluting with heptane/ethyl acetate (30:1) to give 2-(4-cyclopropylmethoxy-3-iodo-5-trifluoromethyl-phenyl)-4-methyl-pentanoic acid ethyl ester (0.15 g, 57%) as a yellowish oil: $^1$H NMR (300 MHz, CDCl$_3$): δ 7.93 (s, 1H), 7.52 (s, 1H), 4.11 (m, 2H), 3.83 (d, 2H, J=7.2 Hz), 3.59 (t, 1H, J=7.5 Hz), 1.95 (m, 1H), 1.50 (m, 3H), 1.22 (t, 3H, J=6.9 Hz), 0.91 (d, 3H, J=6.3 Hz), 0.90 (d, 3H, J=6.3 Hz), 0.64 (m, 2H), 0.43 (m, 2H); $^{13}$C NMR (75 MHz, CDCl$_3$): δ 172.96, 155.55, 142.66, 136.98, 126.94 (q, J=5 Hz), 124.87 (q, J=30 Hz), 122.64 (q, J=272 Hz), 93.73, 79.79, 61.06, 48.53, 42.65, 26.01, 22.39, 14.16, 10.75, 3.36.

Step 9

2-(6-Cyclopropylmethoxy-5,4'-bis-trifluoromethyl-biphenyl-3-yl)-4-methyl-pentanoic acid ethyl ester

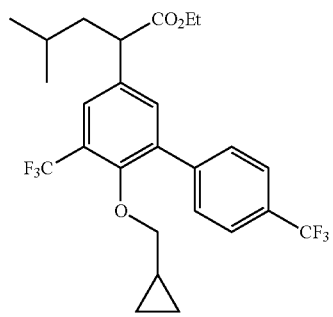 [SMILES: CCOC(=O)C(CC(C)C)c1cc(-c2ccc(C(F)(F)F)cc2)c(OCC2CC2)c(C(F)(F)F)c1]

A mixture of 2-(4-cyclopropylmethoxy-3-iodo-5-trifluoromethyl-phenyl)-4-methyl-pentanoic acid ethyl ester (0.14 g, 0.29 mmol), 4-(trifluoromethyl)benzeneboronic acid (0.089 g, 0.47 mmol), Pd(dppf)Cl$_2$ (0.023 g, 0.031 mmol) and a solution of aqueous sodium carbonate (2 M, 0.31 mL, 0.62 mmol) in 1,4-dioxane (4 mL) was degassed and heated at 100° C. for ten days. The reaction mixture was concentrated under reduced pressure; the residue was treated with water (30 mL) and ethyl acetate (30 mL). The organic layer was washed with brine (30 mL), dried over sodium sulfate, and concentrated under reduced pressure. The residue was purified by silica gel flash chromatography eluting with heptane/ethyl acetate (100:1) to give a colorless oil (0.11 g), which was further purified by flash chromatography on silica gel 100 C$_B$-reversed phase eluting with MeOH/H$_2$O (5:1 to 20:3) to give 2-(6-cyclopropylmethoxy-5,4'-bis-trifluoromethyl-biphenyl-3-yl)-4-methyl-pentanoic acid ethyl ester (0.05 g, 34%) as a white solid: $^1$H NMR (300 MHz, CDCl$_3$/TMS): δ 7.73 (m, 4H), 7.58 (s, 1H), 7.48 (s, 1H), 4.13 (m, 2H), 3.70 (t, 1H, J=7.5 Hz), 3.27 (d, 2H, J=7.2 Hz), 2.00 (m, 1H), 1.67 (m, 2H), 1.51 (m, 1H), 1.25 (t, 3H, J=7.2 Hz), 0.93 (m, 8H), 0.45 (d, 2H, J=7.5 Hz); $^{13}$C NMR (75 MHz, CDCl$_3$/TMS): δ 173.35, 153.80, 140.99, 135.48, 135.40, 134.05, 130.05 (q, J=32 Hz), 129.88 (q, J=32 Hz), 129.42, 126.41 (q, J=5 Hz), 125.33 (q, J=4 Hz), 124.06 (q, J=270 Hz), 123.48 (q, J=270 Hz), 79.47, 60.98, 49.21, 42.87, 26.19, 22.46, 14.22, 10.56, 3.13.

Step 10

2-(6-Cyclopropylmethoxy-5,4'-bis-trifluoromethyl-biphenyl-3-yl)-4-methyl-pentanoic acid

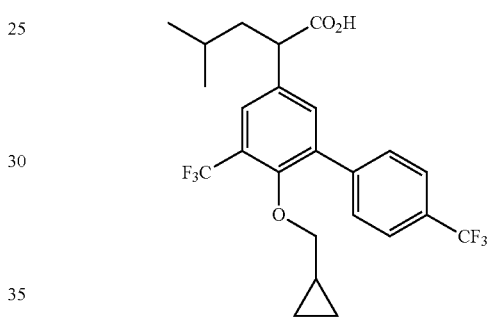

A mixture of 2-(6-cyclopropylmethoxy-5,4'-bis-trifluoromethyl-biphenyl-3-yl)-4-methyl-pentanoic acid ethyl ester (0.04 g, 0.08 mmol) and aqueous KOH (1.4 M, 0.4 mL) in ethanol (5 mL) was stirred at room temperature for two days. After the solvent was removed under reduced pressure, the residue was diluted with water (30 mL), acidified with 1 N HCl to pH 1, and then extracted with ethyl acetate (30 mL). The organic layer was dried over sodium sulfate, concentrated under reduced pressure and freeze-dried overnight to give the desired carboxylic acid 2-(6-cyclopropylmethoxy-5,4'-bis-trifluoromethyl-biphenyl-3-yl)-4-methyl-pentanoic acid (0.04 g, 100%) as a white solid: mp 148-149° C.; HRMS (ESI-TOF): calcd for $C_{24}H_{23}O_3F_6Na_2$ (M−H+2 Na)$^+$: 519.1341, found 519.1366; $^1$H NMR (300 MHz, CDCl$_3$/TMS): δ 7.72 (m, 4H), 7.59 (s, 1H), 7.48 (s, 1H), 3.73 (m, 1H), 3.27 (d, 2H, J=6.9 Hz), 2.02 (m, 1H), 1.69 (m, 1H), 1.56 (m, 1H), 1.28 (m, 1H), 0.94 (m, 8H), 0.46 (m, 2H); the proton of COOH was not observed; $^{13}$C NMR (75 MHz, CDCl$_3$/TMS): δ 178.95, 154.12, 140.82, 135.61, 134.49, 134.24, 130.18 (q, J=32 Hz), 129.44 (q, J=32 Hz), 129.40, 126.50 (q, J=5 Hz), 125.39 (q, J=4 Hz), 124.04 (q, J=270 Hz), 123.40 (q, J=271 Hz), 79.55, 48.91, 42.35, 26.07, 22.49, 22.35, 10.58, 3.15; HPLC purity: 95.2%, retention time=11.78 min.

Example 754

2-(4-(benzo[c][1,2,5]oxadiazol-5-yl)-5-(cyclopropyl-methoxy)-2-fluorophenyl)-4-methylpentanoic acid

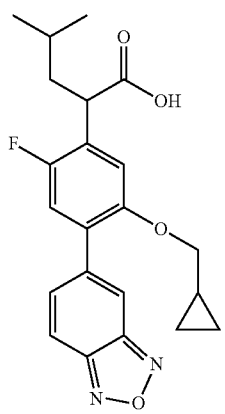 [SMILES: CC(C)CC(C(=O)O)c1cc(OCC2CC2)c(-c2ccc3nonc3c2)cc1F]

Step 1.

Cyclopropylmethyl 2-(4-(benzo[c][1,2,5]oxadiazol-5-yl)-5-(cyclopropylmethoxy)-2-fluorophenyl)-4-methylpentanoate

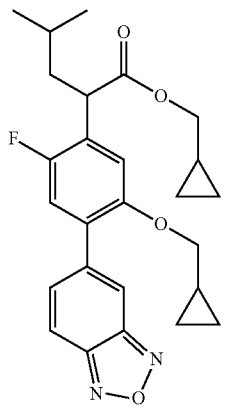

To a solution of 2-(5-cyclopropylmethoxy-2-fluoro-4-iodo-phenyl)-4-methyl-pentanoic acid cyclopropylmethyl ester (0.2 g, 0.43 mmol) in DME (anhydrous, 10 mL) under argon atmosphere was added 4-trifluoromethylphenylboronic acid (0.1 g, 0.53 mmol), CsF (0.16 g, 1.05 mmol), and Pd(PPh$_3$)$_4$ (0.015 g, 0.013 mmol). The reaction mixture was refluxed for 18 h (oil bath, 100° C.). A mixture of water and EtOAc (15 mL/15 mL) was added and the layers were separated. The organic phase was dried over MgSO$_4$ and evaporated to give a crude yellow oil, which was purified by silica gel gradient column chromatograph using Heptane-EtOAc (60:1-9:1) to give cyclopropylmethyl 2-(4-(benzo[c][1,2,5] oxadiazol-5-yl)-5-(cyclopropylmethoxy)-2-fluorophenyl)-4-methylpentanoate as a yellowish oil (0.18 g, 90%). $^1$H NMR (300 MHz, CDCl$_3$/TMS): δ 7.70-7.64 (m, 4H), 7.05 (d, J=10.4 Hz, 1H), 7.01 (d, J=6.1 Hz, 1H), 4.09 (t, J=7.7 Hz, 1H), 4.02-3.87 (m, 2H), 3.78 (d, J=6.6 Hz, 2H), 2.04-1.90 (m, 1H), 1.74-1.65 (m, 1H), 1.60-1.45 (m, 1H), 1.25-1.05 (m, 2H), 0.95 (d, J=6.3 Hz, 6H), 0.60-0.40 (m, 4H), 0.30-0.10 (m, 4H). $^{13}$C NMR (75 MHz, CDCl$_3$/TMS): δ 173.5, 154.3 (d, $^1J_{CF}$=239.7 Hz), 151.9, 140.7, 132.0, 129.5, 126.6 (d, $^2J_{CF}$=16.9 Hz), 124.8 (q, $^3J_{CF}$=3.7 Hz), 124.0 (q, $^1J_{CF}$=271.6 Hz), 117.0 (d, $^2J_{CF}$=24.6 Hz), 113.6, 74.1, 69.6, 41.1, 41.5, 26.1, 22.7, 22.2, 10.2, 9.8, 3.2.

Step 2

2-(4-benzo[1,2,5]oxadiazol-5-yl-5-cyclopropyl-methoxy-2-fluoro-phenyl)-4-methylpentanoic acid

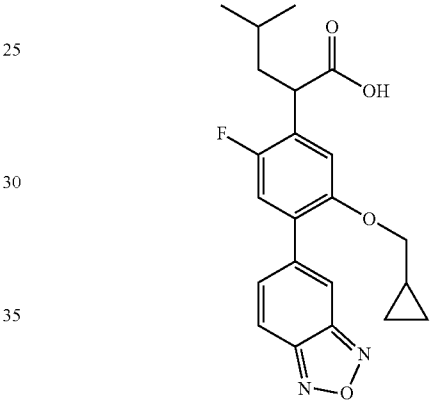

Cyclopropylmethyl 2-(4-(benzo[c][1,2,5]oxadiazol-5-yl)-5-(cyclopropylmethoxy)-2-fluorophenyl)-4-methylpentanoate (0.14 g, 0.29 mmol) was dissolved in a mixture of EtOH/H$_2$O (9 mL/1 mL) and KOH (0.3 g) was added. The reaction mixture was refluxed for 2 h and after cooling the solvent was evaporated. Then, 6 N HCl was added to adjust the pH to 5, and the reaction mixture was extracted with EtOAc (3×10 mL). The combined organic phases were dried over MgSO$_4$ and evaporated under reduced pressure to give a colorless oil. Purification by gradient column chromatography on silica gel Heptane-EtOAc (50:1-9:1) gave 2-(4-(benzo[c][1,2,5]oxadiazol-5-yl)-5-(cyclopropylmethoxy)-2-fluorophenyl)-4-methylpentanoic acid as a white solid (0.12 g, quantitative); pure portion (0.03 g, 25%); white microcrystals, M.P.=110-111° C., $^1$H NMR (300 MHz, CDCl$_3$/TMS): δ 8.99 (br s, 1H), 7.66 (br s, 4H), 7.05 (d, J=9.9 Hz, 1H), 6.94 (d, J=5.2 Hz, 1H), 4.08 (t, J=7.7 Hz, 1H), 3.76 (d, J=6.6 Hz, 2H), 2.04-1.90 (m, 1H), 1.81-1.65 (m, 1H), 1.60-1.45 (m, 1H), 1.32-1.05 (m, 2H), 0.94 (d, J=6.0 Hz, 6H), 0.54 (d, J=7.4 Hz, 2H), 0.24 (d, J=3.9 Hz, 2H). $^{13}$C NMR (75 MHz, CDCl$_3$/TMS): δ 179.2, 154.7 (d, $^1J_{CF}$=239.8 Hz), 152.0, 140.6, 132.0, 129.9, 129.6, 125.7 (d, $^2J_{CF}$=16.2 Hz), 124.8 (q, $^3J_{CF}$=3.6 Hz), 124.0 (q, $^1J_{CF}$=270 Hz), 117.2 (d, $^2J_{CF}$=25.2 Hz), 113.9, 74.2, 41.3, 29.8, 25.9, 22.8, 22.1, 10.3, 3.2.

Example 2959

2-(4-benzo[1,2,5]oxadiazol-5-yl-3-chloro-5-cyclopropylmethoxy-phenyl)-4-methyl-pentanoic acid

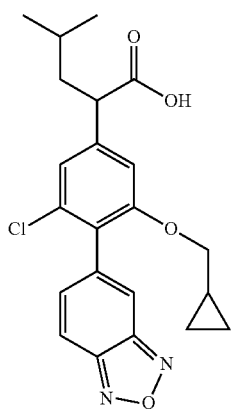 [SMILES: CC(C)CC(C(=O)O)c1cc(Cl)c(-c2ccc3nonc3c2)c(OCC2CC2)c1]

Step 1

2-(3-Fluoro-4-nitro-phenyl)-2-isobutyl-malonic acid diethyl ester

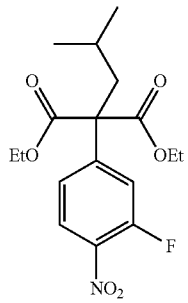 [SMILES: CCOC(=O)C(CC(C)C)(C(=O)OCC)c1ccc([N+](=O)[O-])c(F)c1]

To a solution of 2-isobutylmalonic acid diethyl ester (75.0 g, 0.35 mol) in DMF (200 mL) was added sodium hydride (60% in mineral oil, 13.0 g, 0.57 mol) over 20 min. at 0° C. The reaction mixture was stirred at 0° C. for 0.5 h, then warmed to 25° C. The reaction mixture was cooled down to 0° C. again and a solution of 2,4-difluoronitro-benzene (50.0 g, 0.31 mol) in DMF (150 mL) was added dropwise at 0° C. The reaction mixture was stirred at 25° C. for 16 h. After cooling, the reaction mixture was poured into ice water (200 mL) and extracted with EtOAc (3×100 mL). The combined organic phases washed with water (3×100 mL), brine (100 mL), and dried (MgSO$_4$). Evaporation of the solvent under reduced pressure gave a brown oil. The crude product (92.0 g, 82%) was used for the next step without purification. $^1$H NMR (300 MHz, CDCl$_3$/TMS): δ 8.03 (t, J=8.4 Hz, 1H), 7.70 (dd, J=12.9, 1.7 Hz, 1H), 7.47 (d, J=8.5 Hz, 1H), 4.25-4.18 (m, 4H), 2.28 (d, J=6.3 Hz, 2H), 1.54-1.45 (m, 1H), 1.25 (t, J=7.0 Hz, 6H), 0.82 (d, J=7.0 Hz, 6H); $^{13}$C NMR (75 MHz, CDCl$_3$/TMS): δ 169.2, 154.5 (d, $^1J_{CF}$=263.1 Hz), 146.9 (d, unresolved), 125.3, 124.1 (d, $^3J_{CF}$=3.6 Hz), 118.6 (d, $^2J_{CF}$=23.3 Hz), 62.0, 60.3, 44.1, 24.7, 23.6, 13.9.

Step 2

2-(3-fluoro-4-nitro-phenyl)-4-methyl-pentanoic acid

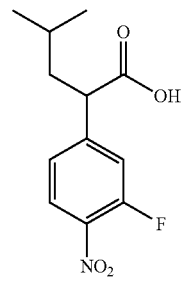 [SMILES: CC(C)CC(C(=O)O)c1ccc([N+](=O)[O-])c(F)c1]

2-(3-Fluoro-4-nitro-phenyl)-2-isobutyl-malonic acid diethyl ester (92.0 g, 0.26 mol) was dissolved in AcOH/H$_2$O/H$_2$SO$_4$ (96%) (500 mL/200 mL/70 mL) and the reaction mixture was refluxed for 24 h. After cooling and evaporation, water (300 mL) was added. The reaction mixture was extracted with EtOAc (3×100 mL). The combined organic phases were washed with water (3×100 mL), brine (100 mL) and dried (MgSO$_4$). The evaporation of solvent under reduced pressure gave a brown oil (61 g, quantitative), which was used for the next step without purification. $^1$H NMR (300 MHz, CDCl$_3$/TMS): δ 8.07-8.01 (m, 1H), 7.33-7.26 (m, 2H), 3.79-3.73 (m, 1H), 2.05-1.95 (m, 1H), 1.76-1.66 (m, 1H), 1.52-1.43 (m, 1H), 0.95-0.92 (m, 6H); $^{13}$C NMR (75 MHz, CDCl$_3$/TMS): δ 178.3, 156.0 (d, $^1J_{CF}$=232.5 Hz), 147.0, 136.0, 126.2, 124.3, 118.1 (d, $^2J_{CF}$=30 Hz), 49.3, 42.0, 25.8, 22.4, 22.0.

Step 3

2-(3-Fluoro-4-nitro-phenyl)-4-methyl-pentanoic acid ethyl ester

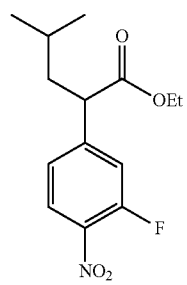 [SMILES: CCOC(=O)C(CC(C)C)c1ccc([N+](=O)[O-])c(F)c1]

2-(3-Fluoro-4-nitro-phenyl)-4-methyl-pentanoic acid (29.0 g, 0.12 mmol) was dissolved in EtOH (100 mL) and H$_2$SO$_4$ (96%, 5 mL) was added. The reaction mixture was refluxed for 3 h and the solvent evaporated. Water (100 mL) was added and the reaction mixture was extracted with EtOAc (3×100 mL). The combined organic phases were washed with saturated NaHCO₃ solution (50 mL), water (100 mL) and brine (100 mL), and then dried over MgSO₄. Evaporation of the solvent under reduced pressure gave a brown oil (31.0 g, 97%), which was used for the next step without purification. ¹H NMR (300 MHz, CDCl₃/TMS): δ 8.03 (t, J=8.4 Hz, 1H), 7.33-7.26 (m, 2H), 4.17-4.11 (m, 2H), 3.73 (t, J=7.6 Hz, 1H), 2.10-1.94 (m, 1H), 1.71-1.62 (m, 1H), 1.51-1.42 (m, 1H), 1.25 (t, J=7.0 Hz, 3H), 0.95-0.92 (m, 6H); ¹³C NMR (75 MHz, CDCl₃/TMS): δ 172.2, 155.3 (d, $^1J_{CF}$=265.0 Hz), 148.3 (d, $^3J_{CF}$=8.4 Hz), 136.5, 126.1, 124.1 (d, $^3J_{CF}$=3.6 Hz), 117.8 (d, $^2J_{CF}$=21.6 Hz), 61.3, 49.4, 42.3, 25.9, 22.5, 22.1, 14.1.

Step 4

2-(3-Cyclopropylmethoxy-4-nitro-phenyl)-4-methyl-pentanoic acid cyclopropylmethyl ester

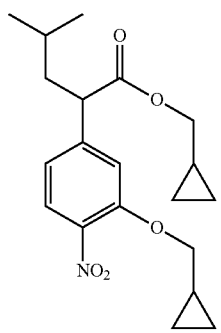

Cyclopropylmethanol (80.0 g, 1.11 mol) was treated with n-BuLi (2.5 M in hexane, 9.1 g, 57 mL, 0.14 mol) at a temperature ranging from −15 to 0° C. The reaction mixture was stirred for 1 h at 25° C. Then, a solution of 2-(3-fluoro-4-nitro-phenyl)-4-methyl-pentanoic acid ethyl ester in cyclopropylmethanol (30 mL) was added at 25° C. and the reaction mixture was stirred for 16 h. Water (100 mL) was added and the reaction mixture was extracted with EtOAc (3×100 mL). The combined organic phases were washed with water (3×100 mL), brine (100 mL), and dried (MgSO₄). Evaporation of the solvent under reduced pressure gave a brown oil, which was purified by silica gel gradient column chromatography by use of Heptane-EtOAc (9:1-4:1) to give 2-(3-cyclopropylmethoxy-4-nitro-phenyl)-4-methyl-pentanoic acid cyclopropylmethyl ester as a yellow oil (34.0 g, 93%). ¹H NMR (300 MHz, CDCl₃/TMS): δ 7.78 (d, J=8.4 Hz, 1H), 7.06 (s, 1H), 6.97 (d, J=8.4 Hz, 1H), 4.00-3.83 (m, 4H), 3.69 (t, J=8.0 Hz, 1H), 2.07-1.92 (m, 1H), 1.69-1.60 (m, 1H), 1.52-1.42 (m, 1H), 1.32-1.20 (m, 1H), 1.19-1.00 (m, 1H), 0.92 (d, J=6.3 Hz, 6H), 0.68-0.62 (m, 2H), 0.56-0.48 (m, 2H), 0.42-0.38 (m, 2H), 0.26-0.21 (m, 2H); ¹³C NMR (75 MHz, CDCl₃/TMS): δ 172.9, 152.3, 146.2, 138.8, 125.6, 119.8, 114.4, 74.2, 69.8, 49.8, 42.6, 26.0, 22.5, 22.2, 10.0, 9.7, 3.3.

Step 5

2-(4-Amino-3-cyclopropylmethoxy-phenyl)-4-methyl-pentanoic acid cyclopropylmethyl ester

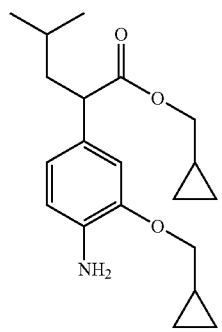 [SMILES: CC(C)CC(C(=O)OCC1CC1)c1ccc([N+](=O)[O-])c(OCC2CC2)c1]

2-(3-Cyclopropylmethoxy-4-nitro-phenyl)-4-methyl-pentanoic acid cyclopropylmethyl ester (34.0 g, 94.2 mmol) was dissolved in AcOH (300 mL) and water (20 mL). Then, Zn powder (60.0 g, 923 mmol) was added in portions. The reaction mixture was refluxed for 1 h and after cooling the precipitate was filtered. The solvent was evaporated and water (150 mL) was added. The reaction mixture was extracted with EtOAc (3×100 mL) and the combined organic phases were washed with water (3×100 mL) and brine (100 mL). Drying of the organic phase was performed with magnesium sulfate. The evaporation of the solvent gave crude product as a brown oil, which was purified by silica gel gradient column chromatography by use of Heptane-EtOAc to give 2-(4-amino-3-cyclopropylmethoxy-phenyl)-4-methyl-pentanoic acid cyclopropylmethyl ester as a yellow oil (23 g, 75%). ¹H NMR (300 MHz, CDCl₃/TMS): δ 6.73-6.61 (m, 3H), 3.94-3.78 (m, 6H), 3.53 (t, J=7.7 Hz, 1H), 1.94-1.85 (m, 1H), 1.65-1.56 (m, 1H), 1.52-1.43 (m, 1H), 1.28-1.18 (m, 1H), 1.11-1.03 (m, 1H), 0.90 (d, J=6.6 Hz, 6H), 0.64-0.58 (m, 2H), 0.53-0.47 (m, 2H), 0.36-0.33 (m, 2H), 0.24-0.21 (m, 2H); ¹³C NMR (75 MHz, CDCl₃/TMS): δ 174.6, 146.4, 135.3, 129.3, 120.5, 114.6, 111.2, 73.1, 69.0, 49.2, 42.7, 25.8, 22.6, 22.4, 10.4, 9.8, 3.2.

Step 6

2-(4-Amino-3-chloro-5-cyclopropylmethoxy-phenyl)-4-methyl-pentanoic acid cyclopropylmethyl ester

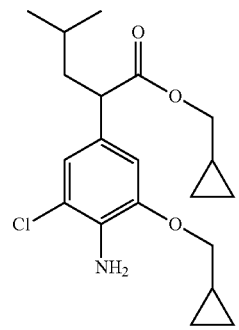 [SMILES: CC(C)CC(C(=O)OCC1CC1)c1cc(Cl)c(N)c(OCC2CC2)c1]

2-(4-Amino-3-cyclopropylmethoxy-phenyl)-4-methyl-pentanoic acid cyclopropylmethyl ester (16.3 g, 49.1 mmol)

was dissolved in chloroform (200 mL) and N-chlorosuccinimide (5.3 g, 0.75 equiv, 39.6 mmol) was added. The reaction mixture was refluxed for 1 h and after cooling treated with 10% potassium carbonate solution (100 mL). The reaction mixture was extracted with EtOAc (3×50 mL) and the combined organic phases were dried over magnesium sulfate. Evaporation of the solvent gave the crude product as a brown oil, which was purified by silica gel gradient column chromatography by use of Heptane-EtOAc to give 2-(4-amino-3-chloro-5-cyclopropylmethoxy-phenyl)-4-methyl-pentanoic acid cyclopropylmethyl ester as a yellow oil (5 g, 36%). $^1$H NMR (300 MHz, CDCl$_3$/TMS): δ 6.85 (s, 1H), 6.66 (s, 1H), 3.95-3.80 (m, 4H), 3.49 (t, J=7.7 Hz, 1H), 1.94-1.82 (m, 1H), 1.63-1.52 (m, 1H), 1.50-1.40 (m, 1H), 1.28-1.18 (m, 1H), 1.11-1.03 (m, 1H), 0.90 (d, J=6.6 Hz, 6H), 0.66-0.58 (m, 2H), 0.53-0.47 (m, 2H), 0.37-0.32 (m, 2H), 0.25-0.20 (m, 2H); $^{13}$C NMR (75 MHz, CDCl$_3$/TMS): δ 174.2, 146.8, 132.6, 128.7, 120.6, 118.3, 109.4, 73.6, 69.3, 49.0, 42.6, 25.9, 22.6, 22.4, 10.4, 9.8, 3.3.

Step 7

2-(3-Chloro-5-cyclopropylmethoxy-4-iodo-phenyl)-4-methyl-pentanoic acid cyclopropylmethyl ester

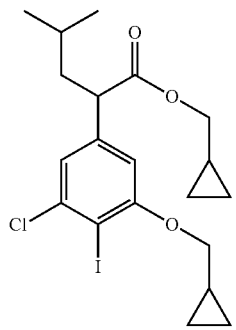 [SMILES: CC(C)CC(C(=O)OCC1CC1)c1cc(Cl)c(I)c(OCC2CC2)c1]

2-(4-Amino-3-chloro-5-cyclopropylmethoxy-phenyl)-4-methyl-pentanoic acid cyclopropylmethyl ester (5.0 g, 13.7 mmol) was dissolved in a mixture of EtOH/H$_2$O/H$_2$SO$_4$ (96%) (65 mL/100 mL/2.5 mL) and the reaction mixture was cooled down to 0° C. A solution of NaNO$_2$ (0.95 g, 13.7 mmol) in water (5 mL) was added dropwise at 0° C. and the reaction mixture was stirred for 30 min. A solution of KI (7.0 g, 42.2 mmol) in water (20 mL) was added dropwise at 0° C. The reaction mixture was heated to 50-60° C. for 2.5 h. The reaction mixture was extracted with EtOAc (3×50 mL). The organic layers were combined and washed with 10% sodium thiosulfate solution (30 mL) followed by brine (30 mL). The organic phase was dried over MgSO$_4$ and the solvent evaporated to give a crude brown oil, which was purified by silica gel gradient column chromatography by use of Heptane-EtOAc (20:1-9:1) to give 2-(3-Chloro-5-cyclopropylmethoxy-4-iodo-phenyl)-4-methyl-pentanoic acid cyclopropylmethyl ester as a yellow oil (4.0 g, 62%). $^1$H NMR (300 MHz, CDCl$_3$/TMS): δ 7.07 (s, 1H), 6.66 (s, 1H), 3.95-3.80 (m, 4H), 3.58 (t, J=7.7 Hz, 1H), 1.96-1.89 (m, 1H), 1.66-1.52 (m, 1H), 1.50-1.40 (m, 1H), 1.28-1.18 (m, 1H), 1.11-1.03 (m, 1H), 0.91 (d, J=6.6 Hz, 6H), 0.67-0.61 (m, 2H), 0.56-0.50 (m, 2H), 0.45-0.40 (m, 2H), 0.26-0.21 (m, 2H); $^{13}$C NMR (75 MHz, CDCl$_3$/TMS): δ 173.2, 159.2, 141.6, 139.4, 121.4, 109.8, 90.4, 74.0, 69.7, 49.4, 42.5, 26.0, 22.6, 22.3, 10.2, 9.8, 3.3.

Step 8

2-(4-benzo[1,2,5]oxadiazol-5-yl-3-chloro-5-cyclopropylmethoxy-phenyl)-4-methyl-pentanoic acid cyclopropylmethyl ester

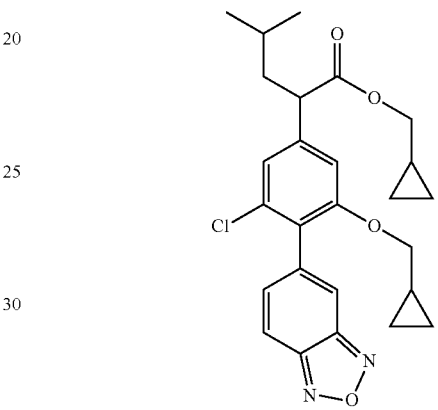

To a solution of 2-(3-chloro-5-cyclopropylmethoxy-4-iodo-phenyl)-4-methyl-pentanoic acid cyclopropylmethyl ester (0.27 g, 0.57 mmol) in DME (anhydrous, 10 mL) under argon atmosphere were added 5-(4,4,5,5-tetramethyl-[1,3,2]dioxaborolan-2-yl)-benzo[1,2,5]oxadiazole (0.15 g, 0.61 mmol), CsF (0.2 g, 1.32 mmol), and [1,1'-bis(diphenylphosphino)ferrocene]dichloropalladium (II) (0.021 g, 0.029 mmol, need 0.06 mmol to complete the reaction!). The reaction mixture was refluxed for 18 h (oil bath, 100° C.). A mixture water/EtOAc (15 mL/15 mL) was added and the layers were separated. The organic phase was dried over MgSO$_4$, then evaporated to give a crude yellow oil, which was purified by silica gel gradient column chromatography using Heptane-EtOAc (20:1-9:1) to give 2-(4-benzo[1,2,5]oxadiazol-5-yl-3-chloro-5-cyclopropylmethoxy-phenyl)-4-methyl-pentanoic acid cyclopropylmethyl ester (0.11 g, 41%) of as a yellowish oil. $^1$H NMR (300 MHz, CDCl$_3$/TMS): δ 7.83 (d, J=9.3 Hz, 1H), 7.77 (s, 1H), 7.36-7.33 (m, 1H), 7.11 (s, 1H), 6.91 (s, 1H), 4.02-3.81 (m, 4H), 3.67 (t, J=7.7 Hz, 1H), 2.03-1.96 (m, 1H), 1.74-1.65 (m, 1H), 1.60-1.45 (m, 1H), 1.20-1.05 (m, 2H), 0.96 (d, J=6.3 Hz, 6H), 0.57-0.47 (m, 4H), 0.28 (br s, 2H), 0.19 (br s, 2H). $^{13}$C NMR (75 MHz, CDCl$_3$/TMS): δ 173.4, 157.0, 149.2, 148.3, 142.0, 138.7, 135.4, 133.5, 126.4, 121.6, 117.4, 114.9, 110.6, 73.4, 69.8, 49.8, 42.8, 26.1, 22.5, 22.4, 10.0, 9.8, 3.3, 3.1

Step 9

2-(4-benzo[1,2,5]oxadiazol-5-yl-3-chloro-5-cyclopropylmethoxy-phenyl)-4-methyl-pentanoic acid

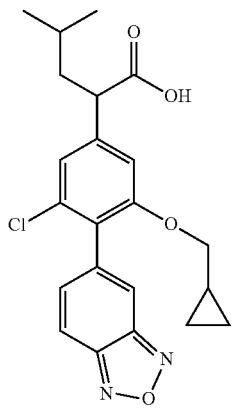 [SMILES: CC(C)CC(C(=O)O)c1cc(Cl)c(-c2ccc3nonc3c2)c(OCC2CC2)c1]

2-(4-Benzo[1,2,5]oxadiazol-5-yl-3-chloro-5-cyclopropylmethoxy-phenyl)-4-methyl-pentanoic acid cyclopropylmethyl ester (0.11 g, 0.23 mmol) was dissolved in a mixture of EtOH/H$_2$O (9 mL/1 mL) and KOH (0.1 g, 1.76 mmol) was added. The reaction mixture was refluxed for 2 h and after cooling the solvent was evaporated. Then, 6 N HCl was added to adjust the pH to 5, and the reaction mixture was extracted with EtOAc (3×10 mL). The combined organic phases were dried over MgSO$_4$ and evaporated under reduced pressure to give 2-(4-benzo[1,2,5]oxadiazol-5-yl-3-chloro-5-cyclopropylmethoxy-phenyl)-4-methyl-pentanoic acid as a yellow oil (0.068 g, 70%). $^1$H NMR (300 MHz, CDCl$_3$/TMS): δ 8.40 (br s, 1H), 7.70 (d, J=9.3 Hz, 1H), 7.62 (s, 1H), 7.19 (d, J=9.3 Hz, 1H), 6.97 (s, 1H), 6.73 (s, 1H), 3.67 (d, J=6.6 Hz, 2H), 3.52 (t, J=7.7 Hz, 1H), 1.90-1.81 (m, 1H), 1.62-1.53 (m, 1H), 1.50-1.39 (m, 1H), 0.98-0.68 (m, 1H), 0.81 (d, J=6.1 Hz, 6H), 0.37-0.31 (m, 2H), 0.15-0.10 (m, 2H). $^{13}$C NMR (75 MHz, CDCl$_3$/TMS): δ 179.1, 157.1, 149.1, 148.3, 141.0, 138.6, 135.3, 133.7, 126.8, 121.6, 117.4, 115.0, 110.9, 73.4, 49.4, 41.9, 25.9, 22.6, 22.3, 10.0, 3.1.

Example 2995

2-(4-Benzo[1,2,5]thiadiazol-5-yl-3-chloro-5-cyclopropylmethoxy-phenyl)-4-methyl-pentanoic acid

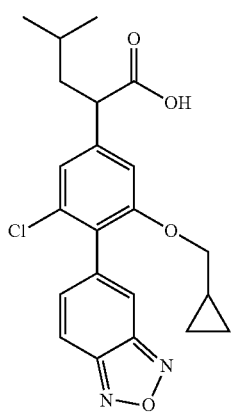 [SMILES: CC(C)CC(C(=O)O)c1cc(Cl)c(-c2ccc3nonc3c2)c(OCC2CC2)c1]

Step 1

2-(4-Benzo[1,2,5]thiadiazol-5-yl-3-chloro-5-cyclopropylmethoxy-phenyl)-4-methyl-pentanoic acid cyclopropylmethyl ester

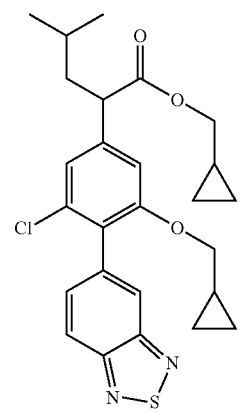 [SMILES: CC(C)CC(C(=O)OCC1CC1)c1cc(Cl)c(-c2ccc3nsnc3c2)c(OCC2CC2)c1]

To a solution of 2-(3-chloro-5-cyclopropylmethoxy-4-iodo-phenyl)-4-methyl-pentanoic acid cyclopropylmethyl ester (0.18 g, 0.38 mmol) in DME (anhydrous, 10 mL) under argon atmosphere were added 5-(4,4,5,5-tetramethyl-[1,3,2]dioxaborolan-2-yl)-benzo[1,2,5]thiodiazole (0.15 g, 0.57 mmol), CsF (0.14 g, 0.92 mmol), and [1,1'-bis(diphenylphosphino)ferrocene]dichloropalladium (II) (0.02 g, 0.027 mmol). The reaction mixture was refluxed for 18 h (oil bath, 100° C.). A mixture of water and EtOAc (15 mL/15 mL) was added and the layers were separated. The combined organic phases were dried over MgSO$_4$ and evaporated to give a crude yellow oil, which was purified by silica gel gradient column chromatography by use of Heptane-EtOAc (20:1-9:1) to give 2-(4-benzo[1,2,5]thiadiazol-5-yl-3-chloro-5-cyclopropylmethoxy-phenyl)-4-methyl-pentanoic acid cyclopropylmethyl ester (0.08 g, 50%) as a yellow oil. $^1$H NMR (300 MHz, CDCl$_3$/TMS): δ 7.83 (d, J=9.3 Hz, 1H), 7.77 (s, 1H), 7.36-7.33 (m, 1H), 7.11 (s, 1H), 6.91 (s, 1H), 4.02-3.81 (m, 4H), 3.67 (t, J=7.7 Hz, 1H), 2.03-1.96 (m, 1H), 1.74-1.65 (m, 1H), 1.60-1.45 (m, 1H), 1.20-1.05 (m, 2H), 0.96 (d, J=6.3 Hz, 6H), 0.57-0.47 (m, 4H), 0.28 (br s, 2H), 0.19 (br s, 2H). $^{13}$C NMR (75 MHz, CDCl$_3$/TMS): δ 173.5, 157.1, 154.7, 154.0, 141.4, 136.8, 133.7, 132.9, 126.9, 122.8, 121.6, 120.0, 110.8, 73.3, 69.7, 49.7, 42.7, 26.1, 22.5, 22.5, 10.0, 9.8, 3.3, 3.1.

Step 2

2-(4-Benzo[1,2,5]thiadiazol-5-yl-3-chloro-5-cyclopropylmethoxy-phenyl)-4-methyl-pentanoic acid

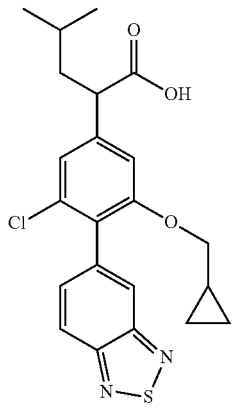 [SMILES: CC(C)CC(C(=O)O)c1cc(Cl)c(-c2ccc3nsnc3c2)c(OCC2CC2)c1]

2-(4-Benzo[1,2,5]thiadiazol-5-yl-3-chloro-5-cyclopropylmethoxy-phenyl)-4-methyl-pentanoic acid cyclopropylmethyl ester (0.08 g, 0.19 mmol) was dissolved in a mixture of EtOH and $H_2O$ (9 mL/1 mL) and KOH (0.1 g, 1.76 mmol) was added. The reaction mixture was refluxed for 2 h and after cooling the solvent was evaporated. Then, 6 N HCl was added to adjust the pH to 5, and the reaction mixture was extracted with EtOAc (3×10 mL). The combined organic phases were dried over $MgSO_4$ and evaporated under reduced pressure to give 2-(4-benzo[1,2,5]thiadiazol-5-yl-3-chloro-5-cyclopropylmethoxy-phenyl)-4-methyl-pentanoic acid as a yellow oil (0.038 g, 55%). $^1$H NMR (300 MHz, $CDCl_3$/TMS): δ 8.02 (d, J=9.0 Hz, 1H), 7.96 (s, 1H), 7.53 (d, J=9.0 Hz, 1H), 7.13 (s, 1H), 6.89 (s, 1H), 3.81 (d, J=6.4 Hz, 2H), 3.68 (t, J=7.6 Hz, 1H), 2.04-1.96 (m, 1H), 1.78-1.69 (m, 1H), 1.63-1.55 (m, 1H), 1.10-1.00 (m, 1H), 0.97 (d, J=6.4 Hz, 6H), 0.50-0.39 (m, 2H), 0.22-0.12 (m, 2H). $^{13}$C NMR (75 MHz, $CDCl_3$/TMS): δ 179.1, 157.2, 154.6, 154.0, 140.5, 136.7, 134.0, 132.9, 127.8, 122.9, 121.6, 120.1, 111.0, 73.4, 49.4, 42.0, 25.9, 22.6, 22.3, 10.0, 3.1.

Example 1904

2-(2-Chloro-6-cyclopropylmethoxy-4'-trifluoromethyl-biphenyl-4-yl)-4-methyl-pentanoic acid

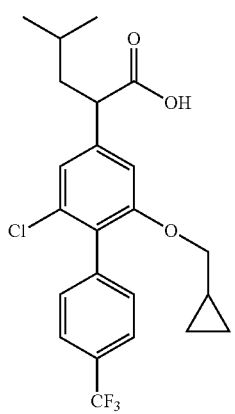 [SMILES: CC(C)CC(C(=O)O)c1cc(Cl)c(-c2ccc(C(F)(F)F)cc2)c(OCC2CC2)c1]

Step 1

2-(2-Chloro-6-cyclopropylmethoxy-4'-trifluoromethyl-biphenyl-4-yl)-4-methyl-pentanoic acid cyclopropylmethyl ester To a solution of 2-(3-chloro-5-cyclopropylmethoxy-4-iodo-phenyl)-4-methyl-pentanoic acid cyclopropylmethyl ester (0.09 g, 0.19 mmol) in DME (anhydrous, 10 mL) under argon atmosphere were added 4-trifluoromethylphenylboronic acid (0.04 g, 0.2 mmol), CsF (0.07 g, 0.46 mmol), and [1,1'-bis(diphenylphosphino)ferrocene]dichloropalladium (II) (0.06 g, 0.08 mmol). The reaction mixture was refluxed for 18 h (oil bath, 100° C.). A mixture of water and EtOAc (15 mL/15 mL) was added and the layers were separated. The organic phase was dried over $MgSO_4$, then evaporated to give a crude yellow oil, which was purified by silica gel gradient column chromatography by use of Heptane-EtOAc (20:1-9:1) to give 2-(2-chloro-6-cyclopropylmethoxy-4'-trifluoromethyl-biphenyl-4-yl)-4-methyl-pentanoic acid cyclopropylmethyl ester (0.063 g, 70%) as a yellowish oil. $^1$H NMR (300 MHz, $CDCl_3$/TMS): δ 7.66 (d, J=8.0 Hz, 2H), 7.43 (d, J=8.0 Hz, 2H), 7.08 (s, 1H), 6.88 (s, 1H), 4.01-3.86 (m, 2H), 3.77 (d, J=6.6 Hz, 2H), 3.65 (t, J=7.9 Hz, 1H), 2.04-1.95 (m, 1H), 1.71-1.62 (m, 1H), 1.59-1.48 (m, 1H), 1.20-1.02 (m, 2H), 0.96-0.94 (m, 6H), 0.56-0.46 (m, 4H), 0.27-0.25 (m, 2H), 0.16-0.15 (m, 2H). $^{13}$C NMR (75 MHz, $CDCl_3$/TMS): δ 173.5, 157.0, 141.2, 138.9, 133.6, 130.8 (two signals), 127.8, 124.5 (q), 124.3 (q, $^1J_{CF}$=271.0 Hz), 121.6, 111.0, 73.3, 69.7, 49.6, 42.7, 26.1, 22.6, 22.4, 10.0, 9.8, 3.3, 3.1.

Step 2

2-(2-Chloro-6-cyclopropylmethoxy-4'-trifluorom-
ethyl-biphenyl-4-yl)-4-methyl-pentanoic acid

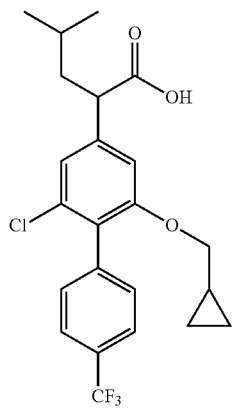 [SMILES: CC(C)CC(C(=O)O)c1cc(Cl)c(-c2ccc(C(F)(F)F)cc2)c(OCC2CC2)c1]

2-(2-Chloro-6-cyclopropylmethoxy-4'-trifluoromethyl-biphenyl-4-yl)-4-methyl-pentanoic acid cyclopropylmethyl ester (0.06 g, 0.12 mmol) was dissolved in a mixture of EtOH and H$_2$O (9 mL/1 mL) and KOH (0.1 g, 1.76 mmol) was added. The reaction mixture was refluxed for 2 h and after cooling the solvent was evaporated. Then, 6 N HCl was added to adjust the pH to 5 and the reaction mixture was extracted with EtOAc (3×10 mL). The combined organic phases were dried over MgSO$_4$ and evaporated under reduced pressure to give 2-(2-chloro-6-cyclopropylmethoxy-4'-trifluoromethyl-biphenyl-4-yl)-4-methyl-pentanoic acid as a yellowish solid (0.046 g, 85%). M.p.=115-116° C. $^1$H NMR (300 MHz, CDCl$_3$/TMS): δ 7.67 (d, J=8.0 Hz, 2H), 7.42 (d, J=8.0 Hz, 2H), 7.08 (s, 1H), 6.85 (s, 1H), 3.77 (d, J=6.4 Hz, 2H), 3.65 (t, J=7.7 Hz, 1H), 2.04-1.94 (m, 1H), 1.75-1.66 (m, 1H), 1.60-1.52 (m, 1H), 1.15-0.89 (m, 1H), 0.95 (d, J=6.4 Hz, 6H), 0.54-0.40 (m, 2H), 0.20-0.10 (m, 2H). $^{13}$C NMR (75 MHz, CDCl$_3$/TMS): δ 179.0, 157.1, 140.3, 138.8, 133.8, 130.8, 129.3 (q), 128.2, 124.6, 124.3 (q, $^1J_{CF}$=271.0 Hz), 121.6, 111.2, 73.4, 49.4, 42.0, 25.9, 22.6, 22.3, 10.0, 3.0.

Example 3200

2-(2,4'-Dichloro-6-cyclopropylmethoxy-biphenyl-4-
yl)-4-methyl-pentanoic acid

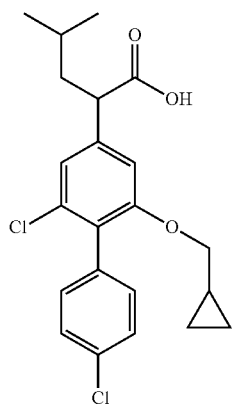 [SMILES: CC(C)CC(C(=O)O)c1cc(Cl)c(-c2ccc(Cl)cc2)c(OCC2CC2)c1]

Step 1

2-(2,4'-Dichloro-6-cyclopropylmethoxy-biphenyl-4-
yl)-4-methyl-pentanoic acid cyclopropylmethyl ester

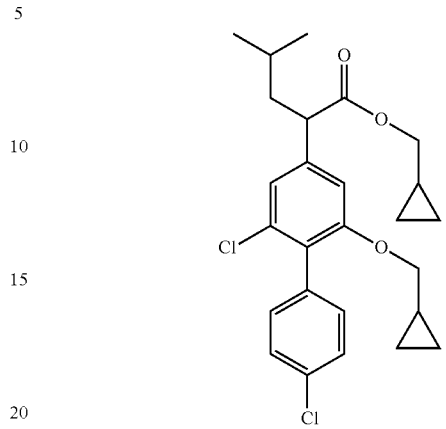

To a solution of 2-(3-chloro-5-cyclopropylmethoxy-4-iodo-phenyl)-4-methyl-pentanoic acid cyclopropylmethyl ester (0.32 g, 0.67 mmol) in DME (anhydrous, 20 mL) under argon atmosphere were added 4-chlorophenylboronic acid (0.13 g, 0.83 mmol), CsF (0.24 g, 1.58 mmol), and [1,1'-bis(diphenylphosphino)ferrocene]dichloropalladium (II) (0.05 g, 0.07 mmol). The reaction mixture was refluxed for 18 h (oil bath, 100° C.). A mixture of water and EtOAc (15 mL/15 mL) was added and the layers were separated. The organic phase was dried over MgSO$_4$ and evaporated to give a crude yellow oil, which was purified by silica gel gradient column chromatography by use of Heptane-EtOAc (20:1-9:1) to give 2-(2,4'-dichloro-6-cyclopropylmethoxy-biphenyl-4-yl)-4-methyl-pentanoic acid cyclopropylmethyl ester (0.26 g, 87%) as a yellowish oil. $^1$H NMR (300 MHz, CDCl$_3$/TMS): δ 7.37 (d, J=8.0 Hz, 2H), 7.24 (d, J=8.2 Hz, 2H), 7.07 (s, 1H), 6.86 (s, 1H), 3.96-3.89 (m, 2H), 3.76 (d, J=6.3 Hz, 2H), 3.63 (t, J=7.7 Hz, 1H), 2.04-1.95 (m, 1H), 1.71-1.48 (m, 2H), 1.21-1.00 (m, 2H), 0.94 (d, J=6.3 Hz, 6H), 0.55-0.48 (m, 4H), 0.27-0.15 (m, 4H). $^{13}$C NMR (75 MHz, CDCl$_3$/TMS): δ 173.5, 157.1, 140.8, 133.7, 133.5, 133.0, 131.8, 128.1, 127.8, 121.5, 111.1, 73.2, 69.6, 49.6, 42.6, 26.1, 22.6, 22.5, 10.0, 9.8, 3.3, 3.0.

Step 2

2-(2,4'-Dichloro-6-cyclopropylmethoxy-biphenyl-4-
yl)-4-methyl-pentanoic acid

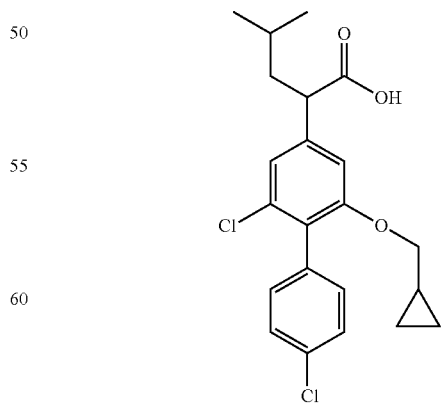

2-(2,4'-Dichloro-6-cyclopropylmethoxy-biphenyl-4-yl)-4-methyl-pentanoic acid cyclopropylmethyl ester (0.18 g, 0.36 mmol) was dissolved in a mixture of EtOH and H$_2$O (9 mL/1 mL) and KOH (0.2 g, 3.6 mmol) was added. The reaction mixture was refluxed for 2 h and after cooling the solvent was evaporated. Then, 6 N HCl was added to adjust the pH to 5 and the reaction mixture was extracted with EtOAc (3×10 mL). The organic phase was dried over MgSO$_4$ and evaporated under reduced pressure to give 2-(2,4'-dichloro-6-cyclopropylmethoxy-biphenyl-4-yl)-4-methyl-pentanoic acid as a yellowish solid (0.15 g, 93%). M.p.=52-53° C. $^1$H NMR (300 MHz, CDCl$_3$/TMS): δ 10.60 (br s, 1H), 7.37 (d, J=8.4 Hz, 1H), 7.22 (d, J=8.4 Hz, 1H), 7.07 (s, 1H), 6.83 (s, 1H), 3.75 (d, J=6.3 Hz, 2H), 3.63 (t, J=7.3 Hz, 1H), 1.99-1.93 (m, 1H), 1.74-1.65 (m, 1H), 1.59-1.51 (m, 1H), 1.11-1.00 (m, 1H), 0.94 (d, J=6.3 Hz, 6H), 0.54-0.40 (m, 2H), 0.22-0.12 (m, 2H). $^{13}$C NMR (75 MHz, CDCl$_3$/TMS): δ 179.7, 157.2, 139.7, 134.0, 133.4, 133.1, 131.8, 128.5, 127.9, 121.6, 111.3, 73.3, 49.4, 42.0, 25.9, 22.6, 22.3, 10.0, 3.0.

Example 3201

4-Methyl-2-(2,3',4'-trichloro-6-cyclopropylmethoxy-biphenyl-4-yl)-pentanoic acid

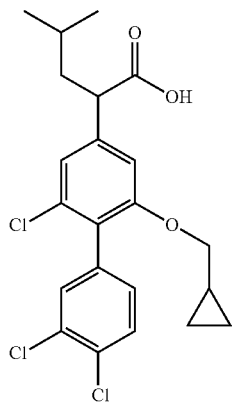 [SMILES: CC(C)CC(C(=O)O)c1cc(Cl)c(-c2ccc(Cl)c(Cl)c2)c(OCC2CC2)c1]

Step 1

4-Methyl-2-(2,3',4'-trichloro-6-cyclopropylmethoxy-biphenyl-4-yl)-pentanoic acid cyclopropylmethyl ester

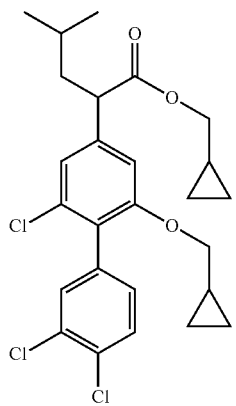 [SMILES: CC(C)CC(C(=O)OCC1CC1)c1cc(Cl)c(-c2ccc(Cl)c(Cl)c2)c(OCC2CC2)c1]

To a solution of 2-(3-chloro-5-cyclopropylmethoxy-4-iodo-phenyl)-4-methyl-pentanoic acid cyclopropylmethyl ester (0.53 g, 1.11 mmol) in DME (anhydrous, 20 mL) under argon atmosphere were added 4-chlorophenylboronic acid (0.25 g, 1.30 mmol), CsF (0.41 g, 2.70 mmol), and [1,1'-bis(diphenylphosphino)ferrocene]dichloropalladium (II) (0.24 g, 0.33 mmol). The reaction mixture was refluxed for 18 h (oil bath, 100° C.). A mixture water and EtOAc (15 mL/15 mL) was added and the layers were separated. The organic phase was dried over MgSO$_4$ and evaporated to give a crude yellow oil, which was purified by silica gel gradient column chromatography by use of Heptane-EtOAc (20:1-9:1) to give 4-methyl-2-(2,3',4'-trichloro-6-cyclopropylmethoxy-biphenyl-4-yl)-pentanoic acid cyclopropylmethyl ester (0.37 g, 70%) as a yellowish oil. $^1$H NMR (300 MHz, CDCl$_3$/TMS): δ 7.48-7.42 (m, 2H), 7.17-7.14 (m, 2H), 7.07 (s, 1H), 6.86 (s, 1H), 4.07-3.87 (m, 2H), 3.78 (d, J=6.3 Hz, 2H), 3.64 (t, J=7.7 Hz, 1H), 2.03-1.93 (m, 1H), 1.70-1.49 (m, 2H), 1.21-1.00 (m, 2H), 0.95-0.93 (m, 6H), 0.56-0.49 (m, 4H), 0.27-0.19 (m, 4H). $^{13}$C NMR (75 MHz, CDCl$_3$/TMS): δ 173.4, 156.9, 141.3, 134.9, 133.6, 132.5, 131.6, 131.2, 129.9, 129.5, 126.6, 121.5, 110.8, 73.2, 69.6, 49.6, 42.6, 26.1, 22.6, 22.4, 10.0, 9.8, 3.3, 3.1.

Step 2

4-Methyl-2-(2,3',4'-trichloro-6-cyclopropylmethoxy-biphenyl-4-yl)-pentanoic acid

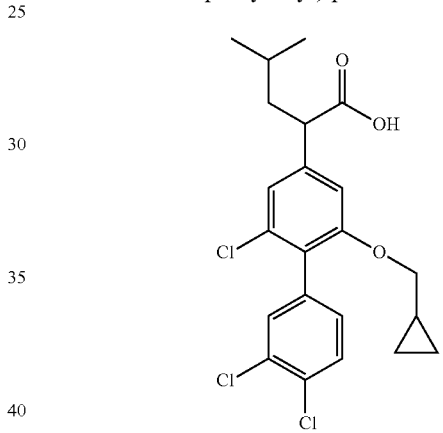

4-Methyl-2-(2,3',4'-trichloro-6-cyclopropylmethoxy-biphenyl-4-yl)-pentanoic acid cyclopropylmethyl ester (0.37 g, 0.75 mmol) was dissolved in a mixture of EtOH and H$_2$O (9 mL/1 mL) and KOH (0.2 g, 3.6 mmol) was added. The reaction mixture was refluxed for 2 h and after cooling the solvent was evaporated. Then, 6 N HCl was added to adjust the pH to 5, and the reaction mixture was extracted with EtOAc (3×10 mL). The organic phase was dried over MgSO$_4$ and evaporated under reduced pressure to give 4-methyl-2-(2,3',4'-trichloro-6-cyclopropylmethoxy-biphenyl-4-yl)-pentanoic acid as a white solid (0.30 g, 90%). M.p.=118-119° C. $^1$H NMR (300 MHz, CDCl$_3$/TMS): δ 9.70 (br s, 1H), 7.47 (d, J=8.3 Hz, 1H), 7.42 (d, J=1.6 Hz, 1H), 7.53 (dd, J=8.2, 1.4 Hz, 1H), 7.07 (s, 1H), 6.83 (s, 1H), 3.78 (d, J=6.3 Hz, 2H), 3.63 (t, J=7.3 Hz, 1H), 2.02-1.93 (m, 1H), 1.74-1.65 (m, 1H), 1.59-1.51 (m, 1H), 1.11-1.00 (m, 1H), 0.94 (d, J=6.3 Hz, 6H), 0.54-0.47 (m, 2H), 0.24-0.16 (m, 2H). $^{13}$C NMR (75 MHz, CDCl$_3$/TMS): δ 179.4, 157.0, 140.3, 134.8, 133.9, 132.5, 131.6, 131.3, 129.9, 129.6, 127.0, 121.5, 111.1, 73.3, 49.4, 42.0, 25.9, 22.6, 22.3, 10.0, 3.1.

Example 1976

2-[2,6-Bis-(2,2,2-trifluoro-ethoxy)-4'-trifluoromethyl-biphenyl-4-yl]-4-methyl-pentanoic acid

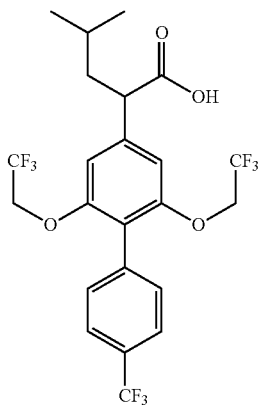

Step 1

5-Fluoro-2-nitro-1,3-bis-(2,2,2-trifluoro-ethoxy)-benzene

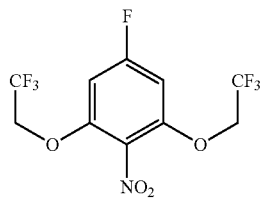 [SMILES: O=[N+]([O-])c1c(OCC(F)(F)F)cc(F)cc1OCC(F)(F)F]

To a solution of 2,2,2-trifluoroethanol (28.2 g, 282.0 mmol) in toluene (120 mL) n-BuLi (1.6 M in hexane, 8.0 g, 80 mL, 125.0 mmol) was added at 0° C. and the reaction mixture warmed up to 25° C. A solution of 1,3,5-trifluoronitrobenzene (10.0 g, 56.5 mmol) in toluene (50 mL) was added dropwise. The reaction mixture was refluxed for 30 h and then poured into water (100 mL). The reaction mixture was extracted with EtOAc (3×100 mL). The organic layers were combined and dried over MgSO$_4$. The solvent was evaporated under reduced pressure to give 5-fluoro-2-nitro-1,3-bis-(2,2,2-trifluoro-ethoxy)-benzene as a brown oil (18.0 g, 95%). The product was used for the next step without purification. $^1$H NMR (300 MHz, CDCl$_3$/TMS): δ 6.47 (d, J=9.4 Hz, 2H), 4.40 (q, J=8.0 Hz, 4H).

Step 2

2-[4-Nitro-3,5-bis-(2,2,2-trifluoro-ethoxy)-phenyl]-malonic acid diethyl ester

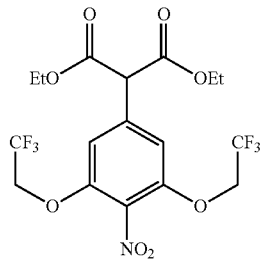 [SMILES: CCOC(=O)C(C(=O)OCC)c1cc(OCC(F)(F)F)c([N+](=O)[O-])c(OCC(F)(F)F)c1]

To a solution of diethyl malonate (18.0 g, 114.9 mmol) in DMF (50 mL) was added sodium hydride (60% in mineral oil, 3.0 g, 125.0 mmol) at 0° C. The reaction mixture was stirred at 25° C. for 0.5 h and a solution of 5-fluoro-2-nitro-1,3-bis-(2,2,2-trifluoro-ethoxy)-benzene (18.0 g, 53.4 mmol) in DMF (30 mL) was added dropwise. The reaction mixture was heated 100° C. for 24 h. After cooling the reaction mixture was poured into water (300 mL) and extracted with EtOAc (3×50 mL). The combined organic phases were washed with water (3×100 mL), brine (100 mL) and dried (MgSO$_4$). Evaporation of the solvent under reduced pressure gave 2-[4-nitro-3,5-bis-(2,2,2-trifluoro-ethoxy)-phenyl]-malonic acid diethyl ester as a brown oil (20.8 g, 80%). The crude product was used for the next step without purification. $^1$H NMR (300 MHz, CDCl$_3$/TMS): δ 6.91 (s, 2H), 4.62 (s, 1H), 4.48 (q, J=8.0 Hz, 4H), 4.28-4.16 (m, 4H), 1.31-1.25 (m, 6H). $^{13}$C NMR (75 MHz, CDCl$_3$/TMS): δ 166.4, 149.2, 136.7, 132.3, 122.3 (q, $^1J_{CF}$=276.6 Hz), 109.5 (two signals), 67.0 (q, $^2J_{CF}$=36.7 Hz), 61.4, 41.6, 14.0.

Step 3

[4-Nitro-3,5-bis-(2,2,2-trifluoro-ethoxy)-phenyl] acetic acid ethyl ester

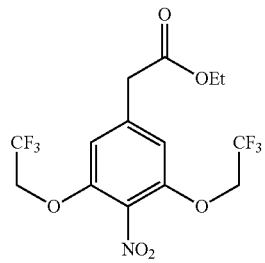 [SMILES: CCOC(=O)Cc1cc(OCC(F)(F)F)c([N+](=O)[O-])c(OCC(F)(F)F)c1]

Crude 2-[4-nitro-3,5-bis-(2,2,2-trifluoro-ethoxy)-phenyl]-malonic acid diethyl ester (20.8 g, 43.6 mmol) was dissolved in a mixture of AcOH/12 N HCl (150 mL/150 mL) and the reaction mixture was refluxed for 16 h. The solvent was evaporated and water (100 mL) was added. The reaction mixture was extracted with EtOAc (3×100 mL). The organic layers were combined, washed with water (3×100 mL), and dried over MgSO$_4$. The solvent was evaporated under reduced pressure to give a brown solid, which was washed with a mixture of Heptane/Et$_2$O (100 mL/100 mL) to give [4-nitro-3,5-bis-(2,2,2-trifluoro-ethoxy)-phenyl]-acetic acid ethyl ester as a solid (10.0 g, 57%). $^1$H NMR (300 MHz, CDCl$_3$/TMS): δ 6.71 (s, 2H), 4.45 (q, J=7.7 Hz, 4H), 4.18 (q, J=7.2 Hz, 2H), 3.63 (s, 2H), 1.28 (t, J=7.1 Hz, 6H). $^{13}$C NMR (75 MHz, CDCl$_3$/TMS): δ 169.7, 149.6, 138.5, 132.4, 122.4 (q, $^1J_{CF}$=277.6 Hz), 109.4 (two signals), 67.0 (q, $^2J_{CF}$=37.2 Hz), 61.6, 41.4, 14.2.

Step 4

[4-Amino-3,5-bis-(2,2,2-trifluoro-ethoxy)-phenyl] acetic acid ethyl ester

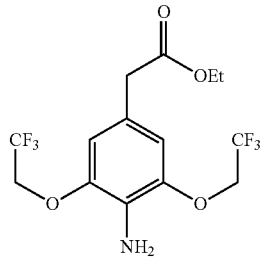

[4-Nitro-3,5-bis-(2,2,2-trifluoro-ethoxy)-phenyl]-acetic acid ethyl ester (10.0 g, 24.7 mmol) was dissolved in EtOH (200 mL) and hydrogenated at 50 psi, 25° C. for 16 h in the presence of Pd—C catalyst (10%, 1 g). The catalyst was filtered off and the solvent evaporated to give a crude brown oil, which was purified by silica gel gradient column chromatography by use of Heptane-EtOAc to give [4-amino-3,5-bis-(2,2,2-trifluoro-ethoxy)-phenyl]-acetic acid ethyl ester as a yellow oil (8.3 g, 90%). $^1$H NMR (300 MHz, CDCl$_3$/TMS): δ 6.52 (s, 2H), 4.37 (q, J=8.0 Hz, 4H), 4.14 (q, J=7.2 Hz, 2H), 3.90 (br s, 2H), 3.48 (s, 2H), 1.25 (t, J=7.2 Hz, 3H). $^{13}$C NMR (75 MHz, CDCl$_3$/TMS): δ 171.4, 145.0, 126.3, 123.2, (q, $^1J_{CF}$=277.6 Hz), 122.6, 110.0, 109.8 (two signals), 66.8 (q, $^2J_{CF}$=35.5 Hz), 61.0, 41.0, 14.2.

Step 5

[4-Iodo-3,5-bis-(2,2,2-trifluoro-ethoxy)-phenyl]acetic acid ethyl ester

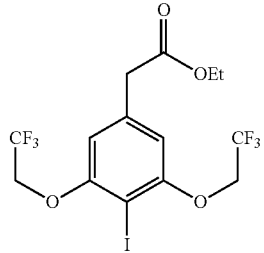 [SMILES: CCOC(=O)Cc1cc(OCC(F)(F)F)c(I)c(OCC(F)(F)F)c1]

[4-Amino-3,5-bis-(2,2,2-trifluoro-ethoxy)-phenyl]-acetic acid ethyl ester (7.1 g, 18.9 mmol) was dissolved in MeCN (50 mL) and p-TsOH×H$_2$O (11.0 g, 57.9 mmol) was added. The reaction mixture was cooled down to −15° C. and NaNO$_2$ (1.6 g, 23.2 mmol) in water (1 mL) was added. The reaction mixture was stirred at −15° C. for 0.5 h; then a solution of KI (15.0 g, 93.8 mmol) in water (10 mL) was added. The reaction mixture was stirred at −15° C. for additional 0.5 h and quenched with 1 N NaHCO$_3$ solution to pH 9-10. After addition of 10% NaHSO$_3$ solution (20 mL), the reaction mixture was extracted with EtOAc (3×50 mL). The combined organic phases were washed with saturated NaCl solution, dried (MgSO$_4$) and evaporated to give crude a brown oil (9.0 g), which was purified by gradient column chromatography on silica gel eluting with Heptane-EtOAc (9:1-3:1) to give [4-iodo-3,5-bis-(2,2,2-trifluoro-ethoxy)-phenyl]-acetic acid ethyl ester as a white solid (3.8 g, 41%). $^1$H NMR (300 MHz, CDCl$_3$/TMS): δ 6.53 (s, 2H), 4.40 (q, J=8.0 Hz, 4H), 4.16 (q, J=7.1 Hz, 2H), 3.56 (s, 2H), 1.26 (t, J=7.2 Hz, 3H). $^{13}$C NMR (75 MHz, CDCl$_3$/TMS): δ 170.3, 157.7, 136.7, 122.8 (q, $^1J_{CF}$=277.6 Hz), 108.9 (two signals), 78.3, 67.0 (q, $^2J_{CF}$=36.0 Hz), 61.3, 41.2, 14.2.

Step 6

[2,6-Bis-(2,2,2-trifluoro-ethoxy)-4'-trifluoromethyl-biphenyl-4-yl]-acetic acid ethyl ester

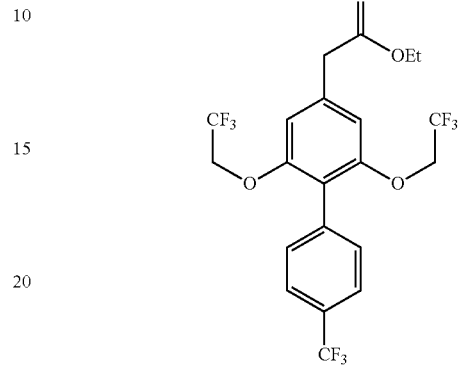

To a solution of [4-iodo-3,5-bis-(2,2,2-trifluoro-ethoxy)-phenyl]-acetic acid ethyl ester (0.8 g, 1.65 mmol) in DME (anhydrous, 15 mL) under argon atmosphere were added 4-trifluoromethylphenylboronic acid (0.4 g, 2.10 mmol), CsF (0.6 g, 3.95 mmol), and Pd(PPh$_3$)$_4$ (0.3 g, 0.26 mmol). The reaction mixture was refluxed for 18 h (oil bath, 100° C.). A mixture of water and EtOAc (15 mL/15 mL) was added and the layers were separated. The organic phase was dried over MgSO$_4$ and evaporated to give a crude yellow oil, which was purified by silica gel gradient column chromatography by use of Heptane-EtOAc (20:1-9:1) to give [2,6-bis-(2,2,2-trifluoro-ethoxy)-4'-trifluoromethyl-biphenyl-4-yl]-acetic acid ethyl ester (0.54 g, 70%) as a yellowish oil. $^1$H NMR (300 MHz, CDCl$_3$/TMS): δ 7.64 (d, J=8.2 Hz, 2H), 7.46 (d, J=8.0 Hz, 2H), 6.68 (s, 2H), 4.28-4.16 (6H), 3.63 (s, 2H), 1.29 (t, J=7.2 Hz, 3H). $^{13}$C NMR (75 MHz, CDCl$_3$/TMS): δ 170.6, 155.3, 136.1, 135.5, 131.0, 129.4, 129.0, 124.4 (q, $^3J_{CF}$=3.9 Hz), 124.2, 122.9, 119.0, 109.2 (two signals), 66.5 (q, $^2J_{CF}$=35.5 Hz), 61.3, 41.5, 14.2.

Step 7

2-[2,6-Bis-(2,2,2-trifluoro-ethoxy)-4'-trifluoromethyl-biphenyl-4-yl]-4-methyl-pentanoic acid

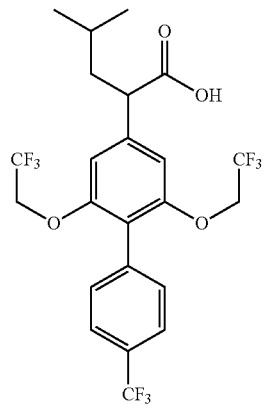 [SMILES: CC(C)CC(C(=O)O)c1cc(OCC(F)(F)F)c(-c2ccc(C(F)(F)F)cc2)c(OCC(F)(F)F)c1]

[2,6-Bis-(2,2,2-trifluoro-ethoxy)-4'-trifluoromethyl-biphenyl-4-yl]-acetic acid ethyl ester (0.52 g, 1.03 mmol) was dissolved in anhydrous DMF (5 mL) and sodium hydride (60% in oil, 0.05 g, 2.08 mmol) was added at 0° C. The reaction mixture was stirred at 0° C. for 20 min and isobutyl bromide (0.15 g, 1.09 mmol) was added. The reaction mixture was stirred for 1 h at the same temperature and at 25° C. for 15 min., followed by addition of saturated ammonium chloride solution (10 mL). The reaction mixture was extracted with ethyl acetate (2×20 mL) and the combined organic phases were washed with water (3×20 mL), saturated sodium chloride solution (10 mL) and dried over magnesium sulfate. Evaporation gave the crude yellow oil (0.56 g), which was purified by silica gel column chromatography with Heptane/EtOAc to give a white solid (0.24 g). The resulting solid was dissolved in EtOH (10 mL), and H$_2$O (1 mL) and potassium hydroxide (0.2 g) were added. The reaction mixture was refluxed for 2 h and solvent evaporated. Then, 6 N HCl was added to adjust the pH to 3-5 and the mixture was extracted with EtOAc (3×10 mL). The combined organic phases were dried over MgSO$_4$ and evaporated to give 2-[2,6-Bis-(2,2,2-trifluoro-ethoxy)-4'-trifluoromethyl-biphenyl-4-yl]-4-methyl-pentanoic acid as a white solid (0.2 g, 40%). $^1$H NMR (300 MHz, CDCl$_3$/TMS): δ 7.65 (d, J=8.1 Hz, 2H), 7.46 (d, J=8.1 Hz, 2H), 6.72 (s, 2H), 4.24 (q, J=8.0 Hz, 4H), 3.69 (t, J=7.7 Hz, 1H), 2.03-1.96 (m, 1H), 1.76-1.67 (m, 1H), 1.60-1.52 (m, 1H), 0.96 (d, J=6.3 Hz, 6H). $^{13}$C NMR (75 MHz, CDCl$_3$/TMS): δ 179.3, 155.4, 140.6, 135.3, 130.9, 129.6, 129.1, 124.5 (q, $^3J_{CF}$=4 Hz), 124.2 (q, $^1J_{CF}$=272 Hz), 122.9 (q, $^1J_{CF}$=278 Hz), 119.8, 107.9, 66.5 (q, $^2J_{CF}$=36 Hz), 49.7, 42.2, 25.9, 22.6, 22.3.

Example 2420

2-[6-Chloro-5-(2,2,2-trifluoro-ethoxy)-4'-trifluoromethyl-biphenyl-3-yl]-3-cyclobutyl-propionic acid

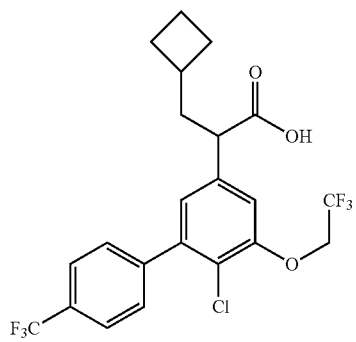

Step 1

4-Fluoro-1-nitro-2-(2,2,2-trifluoro-ethoxy)-benzene

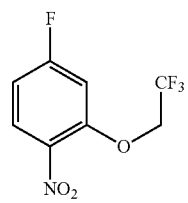 [SMILES: O=[N+]([O-])c1ccc(F)cc1OCC(F)(F)F]

To a solution of 2,4-difluoronitrobenzene (300.0 g, 1.89 mol) and 2,2,2-trifluoroethanol (245.0 g, 2.45 mol) in toluene (600 mL) was added sodium hydroxide (90.5 g, 2.26 mol) in portions over 30 min to keep the temperature between 30 and 40° C. After the temperature had dropped to 30° C., the reaction mixture was heated to 45-50° C. using an oil bath for additional 16 h. After cooling, water (500 mL) and 2.5 N H$_2$SO$_4$ (200-300 mL, for adjustment of pH to 5) were added and the organic layer was separated. The water layer was extracted with EtOAc (2×300 mL). The combined organic layers were washed with saturated sodium chloride solution (100 mL) and dried over magnesium sulfate. The solvent was evaporated to give a yellow oil, which solidified after 30 min to give a yellowish solid (450.0 g, quantitative). The crude product was used in the next step without purification. $^1$H NMR (300 MHz, CDCl$_3$/TMS): δ 8.03-7.98 (m, 1H), 6.93-6.82 (m, 2H), 4.49 (q, J=7.7 Hz, 2H). $^{13}$C NMR (75 MHz, CDCl$_3$/TMS): δ 165.0 (d, $^1J_{CF}$=259.6 Hz), 152.3 (d, $^3J_{CF}$=13.1 Hz), 128.2 (d, $^3J_{CF}$=11.9 Hz), 122.4 (d, $^1J_{CF}$=273.4 Hz), 110.1 (d, $^2J_{CF}$=22.5 Hz), 105.9 (q, $^1J_{CF}$=242.6 Hz), 104.3 (d, $^2J_{CF}$=26.1 Hz), 67.6 (q, $^1J_{CF}$=36.7 Hz).

Step 2

[4-Nitro-3-(2,2,2-trifluoro-ethoxy)-phenyl]acetic acid

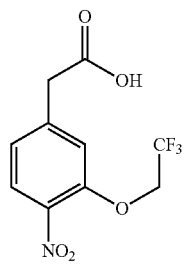 [SMILES: O=C(O)Cc1ccc([N+](=O)[O-])c(OCC(F)(F)F)c1]

Potassium hydroxide (≥85%, 176 g, ≥2.67 mmol) was added to a solution of 4-fluoro-1-nitro-2-(2,2,2-trifluoro-ethoxy)-benzene (412 g, ~90% purity, 1.56 mmol) and diethyl malonate (503.0 g, 3.14 mmol) in DMSO (700 mL) in portions to keep the temperature at ~40° C. The reaction mixture became deep red in color. The reaction mixture was stirred at 40° C. overnight. Monitoring was performed by TLC (EtOAc:Hept., 1:3).

Acetic acid (1 L) was added to the warm reaction mixture followed by a mixture of concentrated sulfuric acid (325 mL) in water (1 L) in one portion. A precipitate, which was formed initially, dissolved at the end of the addition. Effective stirring was required for this reaction. The reaction mixture was heated at reflux overnight. The reaction mixture was cooled to room temperature and EtOAc (1000 mL) and water (1000 mL) were added. The organic layer (bottom layer!) was separated. The aqueous solution was extracted with EtOAc (500 mL), the organic phases were combined, washed with water (3×2000 mL), brine (500 mL), and dried over MgSO$_4$ with charcoal. The solvent was evaporated and the solid residue was washed by stirring with heptane/EtOAc (20:1, 500 mL). The solid was filtered and dried in vacuum. The yield of 2-(4-nitro-3-(2,2,2-trifluoro-ethoxy)phenyl)acetic acid was 256 g (65%). $^1$H NMR (300 MHz, CDCl$_3$/TMS): δ 7.80 (d, J=8.3 Hz, 1H), 7.25 (s, 1H), 7.10 (d, J=8.3 Hz, 1H), 5.07 (s, 1H), 4.67 (q, J=8.2 Hz, 2H), 3.70 (s, 2H). $^{13}$C NMR (75 MHz, CDCl₃/TMS): δ 175.0, 151.5, 144.0, 140.3, 126.4, 125.0, 122.2 (d, $^1J_{CF}$=273.0 Hz), 118.0, 67.6 (q, $^1J_{CF}$=36.0 Hz), 42.5.

Step 3

[4-Nitro-3-(2,2,2-trifluoro-ethoxy)-phenyl]acetic acid methyl ester

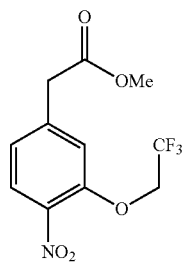 [SMILES: COC(=O)Cc1ccc([N+](=O)[O-])c(OCC(F)(F)F)c1]

Concentrated sulfuric acid (50 mL) was added slowly to a solution of 2-(4-nitro-3-(2,2,2-trifluoro-ethoxy)phenyl)acetic acid (180 g, 0.64 mol) in MeOH (500 mL). The reaction mixture was stirred at room temperature overnight. The methanol was evaporated and EtOAc (500 mL) was added. The solution was washed with water (2×200 mL) and brine and dried over MgSO₄. The solvent was evaporated, the solid residue was stirred with heptane (200 mL), and the solid was filtered. Yield 182.2 g (96%). ¹H NMR (300 MHz, CDCl₃/TMS): δ 7.82 (d, J=8.7 Hz, 1H), 7.07-7.05 (m, 2H), 4.47 (q, J=8.0 Hz, 2H), 3.68 (s, 3H), 3.67 (s, 2H). ¹³C NMR (75 MHz, CDCl₃/TMS): δ 170.1, 150.4, 141.2, 139.4, 125.9, 123.9, 122.6 (d, $^1J_{CF}$=277.6 Hz), 117.5, 67.6 (q, $^1J_{CF}$=36.7 Hz), 52.4, 41.0.

Step 4

3-Cyclobutyl-2-[4-nitro-3-(2,2,2-trifluoro-ethoxy)-phenyl]-propionic acid methyl ester

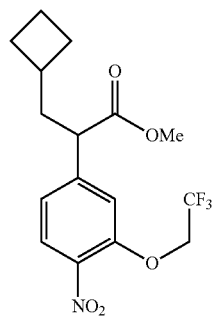 [SMILES: COC(=O)C(CC1CCC1)c1ccc([N+](=O)[O-])c(OCC(F)(F)F)c1]

[4-Nitro-3-(2,2,2-trifluoro-ethoxy)-phenyl]-acetic acid methyl ester (33 g, 94.5 mmol) and (bromomethyl)cyclobutane (17 g, 114.1 mmol) were mixed in DMSO (50 mL) and KOH (6.4 g, 114.1 mmol) was added in portions over 15 min. The reaction mixture was stirred for 16 h and water (100 mL) was added. The reaction mixture was extracted with EtOAc (3×50 mL). The combined organic phases were dried over MgSO₄ and evaporated to give a crude yellow oil, which was purified by silica gel gradient column chromatography using Heptane-EtOAc (9:1-4:1) to give 15 g (40%) of the product as a yellow oil. (The synthesis was repeated with temperature kept at 40° C. over 16 h to give the product in quantitative yield). ¹H NMR (300 MHz, CDCl₃/TMS): δ 7.86 (d, J=8.0 Hz, 1H), 7.12-7.09 (m, 2H), 4.50 (q, J=7.7 Hz, 2H), 3.68 (s, 3H), 3.55 (t, J=7.3 Hz, 1H), 2.22-2.10 (m, 2H), 2.03-1.75 (m, 5H), 1.70-1.55 (m, 2H). ¹³C NMR (75 MHz, CDCl₃/TMS): δ 172.9, 150.5, 146.4, 139.4, 126.0, 122.7, 122.6 (d, $^1J_{CF}$=277.6 Hz), 116.0, 67.5 (q, $^1J_{CF}$=36.7 Hz), 52.3, 49.6, 40.7, 33.9, 28.2, 27.9, 18.4.

Step 5

2-[4-Amino-3-(2,2,2-trifluoro-ethoxy)-phenyl]-3-cyclobutyl-propionic acid methyl ester

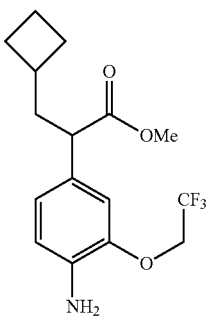

A solution of the 3-cyclobutyl-2-[4-nitro-3-(2,2,2-trifluoro-ethoxy)-phenyl]-propionic acid methyl ester (15 g, 36.0 mmol) in EtOH (150 mL) was hydrogenated at 50 psi and 25° C. for 16 h in the presence of Pd—C catalyst (10%, 1.5 g). On the next day, the catalyst was filtered off and the solvent evaporated to give the crude product (12.3 g, 88%) as a yellow oil, which was used without purification for the next step. ¹H NMR (300 MHz, CDCl₃/TMS): δ 6.79-6.73 (m, 2H), 6.66 (d, J=8.0 Hz, 1H), 4.36 (q, J=8.3 Hz, 2H), 3.80 (br s, 2H), 3.63 (s, 3H), 3.35 (t, J=7.7 Hz, 1H), 2.20-1.86 (m, 4H), 1.85-1.70 (m, 3H), 1.67-1.51 (m, 2H). ¹³C NMR (75 MHz, CDCl₃/TMS): δ 174.7, 146.7, 135.7, 129.1, 123.3 (d, $^1J_{CF}$=277.6 Hz), 122.7, 115.4, 112.2, 66.4 (q, $^1J_{CF}$=35.4 Hz), 51.9, 48.9, 40.8, 34.0, 28.3, 28.1, 18.5.

Step 6

2-[4-Amino-3-bromo-5-(2,2,2-trifluoro-ethoxy)-phenyl]-3-cyclobutyl-propionic acid methyl ester

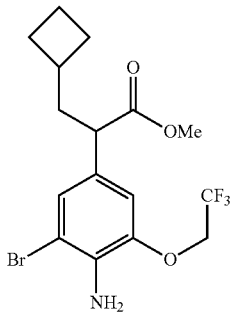 [SMILES: COC(=O)C(CC1CCC1)c1cc(Br)c(N)c(OCC(F)(F)F)c1]

To a solution of the 2-[4-amino-3-(2,2,2-trifluoro-ethoxy)-phenyl]-3-cyclobutyl-propionic acid methyl ester (12.3 g, 31.8 mmol) in chloroform (150 mL) was added N-bromosuccinimide (7 g, 39.3 mmol). The reaction mixture was stirred at 25° C. for 16 h and a mixture of water and methylene chloride (100 mL/100 mL) was added. The reaction mixture was extracted with methylene chloride (2×50 mL) and the organic phases were separated. The combined organic phases were dried over MgSO₄ and evaporated to give a crude yellow oil, which was purified by a short silica gel column chromatography eluting with heptane-EtOAc (4:1) to give the product (13.9 g, 94%) as a yellowish oil. ¹H NMR (300 MHz, CDCl₃/TMS): δ 7.06 (d, J=1.1 Hz, 1H), 6.70 (d, J=1.2 Hz, 1H), 4.37 (q, J=8.0 Hz, 2H), 4.21 (br s, 2H), 3.64 (s, 3H), 3.31 (t, J=7.7 Hz, 1H), 2.20-1.89 (m, 4H), 1.81-1.75 (m, 3H), 1.67-1.51 (m, 2H). ¹³C NMR (75 MHz, CDCl₃/TMS): δ 174.2, 144.6, 134.4, 128.9, 125.7, 123.0 (d, $^1J_{CF}$=277.6 Hz), 110.9, 108.7, 66.5 (q, $^1J_{CF}$=36.0 Hz), 52.0, 48.6, 40.7, 33.9, 28.3, 28.0, 18.5.

Step 7

2-[6-Amino-5-(2,2,2-trifluoro-ethoxy)-4'-trifluoromethyl-biphenyl-3-yl]-3-cyclobutyl-propionic acid methyl ester

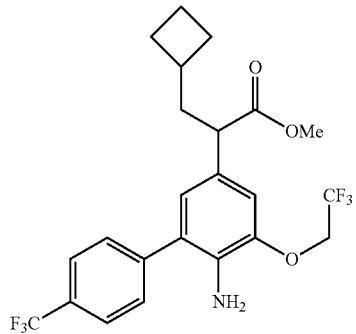

To a solution of 2-[4-amino-3-bromo-5-(2,2,2-trifluoroethoxy)-phenyl]-3-cyclobutyl-propionic acid methyl ester (13.8 g, 29.6 mmol) in DME (anhydrous, 100 mL) under argon atmosphere were added 4-trifluoromethylphenylboronic acid (6.8 g, 35.8 mmol), CsF (11 g, 72.3 mmol), and Pd(PPh₃)₄ (3.4 g, 2.94 mmol). The reaction mixture was refluxed for 18 h (oil bath, 100° C.). On the next day, a mixture water and EtOAc (100 mL/100 mL) was added and the layers were separated. The organic phase was dried over MgSO₄ and evaporated to give a crude yellow oil, which was purified by a short silica gel column chromatography by use of Heptane-EtOAc (4:1) to give the product (14.7 g, 94%) as a yellowish oil. ¹H NMR (300 MHz, CDCl₃/TMS): δ 7.70 (d, J=8.2 Hz, 2H), 7.59 (d, J=8.0 Hz, 2H), 6.78 (dd, J=9.6, 1.4 Hz, 2H), 4.43 (q, J=8.0 Hz, 2H), 3.95 (br s, 2H), 3.66 (s, 3H), 3.39 (t, J=7.7 Hz, 1H), 2.25-2.07 (m, 2H), 2.03-1.91 (m, 2H), 1.88-1.75 (m, 3H), 1.69-1.52 (m, 2H). ¹³C NMR (75 MHz, CDCl₃/TMS): δ 174.6, 144.8, 133.1, 129.2, 128.6, 126.3, 125.7 (q, $^3J_{CF}$=3.6 Hz), 123.8, 123.3 (q, $^1J_{CF}$=277.6 Hz), 111.4, 66.5 (q, $^1J_{CF}$=35.4 Hz), 52.0, 49.0, 40.9, 34.1, 28.3, 28.1, 18.5.

Step 8

2-[6-Chloro-5-(2,2,2-trifluoro-ethoxy)-4'-trifluoromethyl-biphenyl-3-yl]-3-cyclobutyl-propionic acid methyl ester

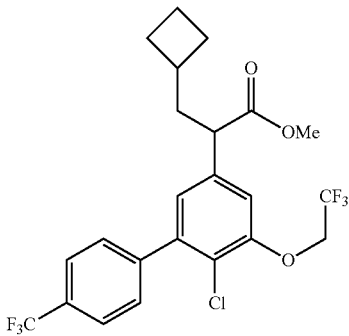

To a solution of 2-[6-amino-5-(2,2,2-trifluoro-ethoxy)-4'-trifluoromethyl-biphenyl-3-yl]-3-cyclobutyl-propionic acid methyl ester (14.7 g, 27.7 mmol) in a mixture of MeCN and H₂O (120 mL/120 mL), concentrated HCl (25 mL) was added. The reaction mixture was cooled down to 0-5° C. and a solution of NaNO₂ (2.9 g, 42.0 mmol) in water (3 mL) was added dropwise. The reaction mixture was stirred at 0-5° C. for 40 min and CuCl (I) (27 g, 272.7 mmol) was added at once. The reaction mixture was heated at 50° C. for additional 3 h and the solvent was evaporated. The reaction mixture was extracted with EtOAc (3×50 mL) and the combined organic phases were washed with water (200 mL) and brine (100 mL). The organic phase was dried over MgSO₄ and evaporated to give the product (14.5 g, 95%) as a yellow oil. ¹H NMR (300 MHz, CDCl₃/TMS): δ 7.70 (d, J=8.2 Hz, 2H), 7.53 (d, J=8.0 Hz, 2H), 6.98 (dd, J=6.1, 1.6 Hz, 2H), 4.47 (q, J=8.0 Hz, 2H), 3.68 (s, 3H), 3.48 (t, J=7.7 Hz, 1H), 2.20-2.10 (m, 2H), 2.03-1.75 (m, 5H), 1.70-1.52 (m, 2H). ¹³C NMR (75 MHz, CDCl₃/TMS): δ 173.6, 153.5, 142.2, 141.0, 138.9, 129.7, 125.0 (q, $^3J_{CF}$=3.6 Hz), 124.8, 124.0 (q, $^1J_{CF}$=271.6 Hz), 126.6 (q, $^1J_{CF}$=278.8 Hz), 121.4, 114.0, 67.3 (q, $^1J_{CF}$=35.4 Hz), 52.2, 49.3, 40.8, 34.0, 28.3, 28.0, 18.5.

Step 9

2-[6-Chloro-5-(2,2,2-trifluoro-ethoxy)-4'-trifluoromethyl-biphenyl-3-yl]-3-cyclobutyl-propionic acid

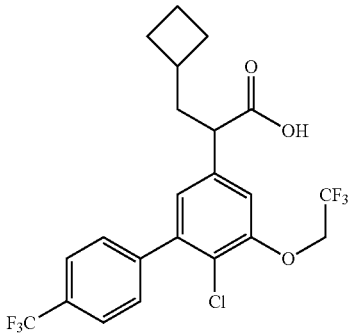

To a solution of the 2-[6-chloro-5-(2,2,2-trifluoro-ethoxy)-4'-trifluoromethyl-biphenyl-3-yl]-3-cyclobutyl-propionic acid methyl ester (8.0 g, 14.5 mmol) in a mixture of the EtOH (100 mL) and H$_2$O (15 mL) was added potassium hydroxide (10 g, 178.5 mmol). The reaction mixture was refluxed for 3 h and the solvent evaporated. Then, 6 N HCl was added to adjust the pH to 3-5 and the mixture was extracted with EtOAc (3×50 mL). The combined organic phases were dried over MgSO$_4$ and evaporated to give 2-[6-chloro-5-(2,2,2-trifluoro-ethoxy)-4'-trifluoromethyl-biphenyl-3-yl]-3-cyclobutyl-propionic acid as a white solid (7.0 g, 90%). $^1$H NMR (300 MHz, CDCl$_3$/TMS): δ 7.70 (d, J=8.2 Hz, 2H), 7.53 (d, J=8.2 Hz, 2H), 6.98 (s, 2H), 4.47 (q, J=8.0 Hz, 2H), 3.49 (t, J=7.7 Hz, 1H), 2.27-2.13 (m, 2H), 2.06-1.73 (m, 5H), 1.71-1.52 (m, 2H). $^{13}$C NMR (75 MHz, CDCl$_3$/TMS): δ 179.1, 153.6, 142.1, 141.2, 138.0, 129.7, 125.0 (q, $^3J_{CF}$=3.6 Hz), 124.9, 124.0 (q, $^1J_{CF}$=262.5 Hz), 123.0 (q, $^1J_{CF}$=277.6 Hz), 121.8, 114.3, 67.3 (q, $^1J_{CF}$=36.0 Hz), 49.3, 40.3, 33.9, 28.3, 28.0, 18.5.

Example 415

2-(5-Chloro-6-(2,2,2-trifluoroethoxy)-4'-(trifluoromethyl)biphenyl-3-yl)-3-cyclopropylpropanoic acid

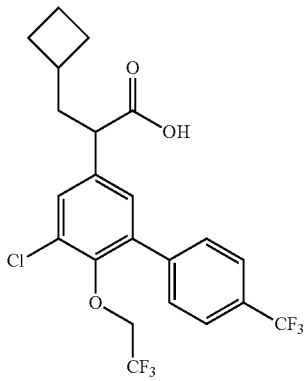 [SMILES: O=C(O)C(CC1CCC1)c1cc(Cl)c(OCC(F)(F)F)c(-c2ccc(C(F)(F)F)cc2)c1]

Step 1

Ethyl 2-(3-chloro-4-hydroxyphenyl)acetate

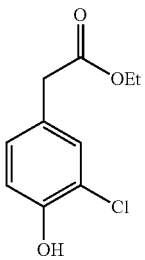

To a stirred solution of ethyl 2-(4-hydroxyphenyl)acetate (20 g, 0.076 molo) in 200 ml of DCM was added MeOH (3.4 ml, 0.84 mol). The mixture was brought to reflux and sulfuryl chloride (6.8 ml 0.846 mol) dissolved in DCM (50 mL) was slowly added under over 10 min. The reaction mixture was refluxed further for 5 h, upon which the reaction mixture was poured onto crushed ice and extracted with DCM (×2). The combined organic layers were washed with 10% NaHCO$_3$ solution and water. The organic layer was dried over Na$_2$SO$_4$, filtered and evaporated under vacuum to give compound ethyl 2-(3-chloro-4-hydroxyphenyl)acetate in 60% yield. (13.6 g).

Step 2

Ethyl 2-(3-bromo-5-chloro-4-hydroxyphenyl)acetate

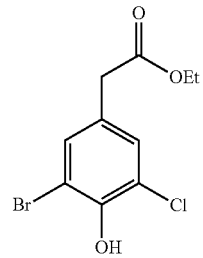 [SMILES: CCOC(=O)Cc1cc(Cl)c(O)c(Br)c1]

To a stirred solution of compound ethyl 2-(3-chloro-4-hydroxyphenyl)acetate (11 g, 51 mmol) in 200 ml of CCl$_4$, was slowly added bromine (8.22 g, 51 mmol) as a solution CCl$_4$ (100 ml) at 0° C. over a period of 30 min. The reaction mixture was stirred for a further 30 min at 0° C. Upon which the reaction mixture was poured onto crushed ice and extracted with DCM (2×100 mL). The combined organic layers were washed with water followed by 10% sodium bisulfite solution, dried over Na$_2$SO$_4$ filtered and evaporated under reduced pressure to give ethyl 2-(3-bromo-5-chloro-4-hydroxyphenyl)acetate (12.2 g) as a white solid in 80% yield. $^1$HNMR (CDCl$_3$): 7.37 (s, 1H); 7.27 (s, 1H); 5.68 (bs, 1H); 4.16 (q, 2H); 3.48 (s, 2H); 1.29 (t, 3H).

Step 3

Ethyl 2-(3-bromo-5-chloro-4-(2,2,2-trifluoroethoxy)phenyl)-acetate

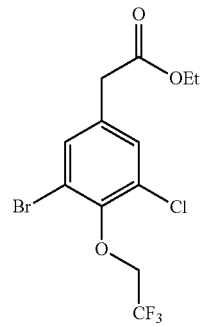 [SMILES: CCOC(=O)Cc1cc(Cl)c(OCC(F)(F)F)c(Br)c1]

To a stirred solution of ethyl 2-(3-bromo-5-chloro-4-hydroxyphenyl)acetate (2 g, 6.8 mmol), potassium carbonate (2.35 g, 17.0 mmol) in dry DMF (20 mL), was slowly added trifluoro ethyl iodide (8.58 g, 4.0 mL, 40.8 mmol) at room temperature, the reaction mixture was slowly heated to 100° C. and heating was continued for 4 h. Upon which the reaction mixture was poured onto water and extracted with ethyl acetate (2×50 mL). The combined organic layers were washed with water, dried over Na$_2$SO$_4$ and evaporated under reduced pressure. Purification by column chromatography over silica gel (hexane/EtOAc) to gave compound ethyl 2-(3-bromo-5-chloro-4-(2,2,2-trifluoroethoxy)phenyl)-acetate (0.750 g, 30% yield). $^1$HNMR (CDCl$_3$, 400 MHz): 7.43 (s, 1H); 7.34 (s, 1H); 4.4 (q, 2H), 4.13 (q, 2H); 3.55 (t, 1H); 1.93 (m, 1H), 1.58 (m, 1H); 1.45 (m, 1H); 1.24 (t, 3H), 0.92 (d, 6H);

Step 4

Ethyl 2-(5-chloro-6-(2,2,2-trifluoroethoxy)-4'-(trifluoromethyl)biphenyl-3-yl)acetate

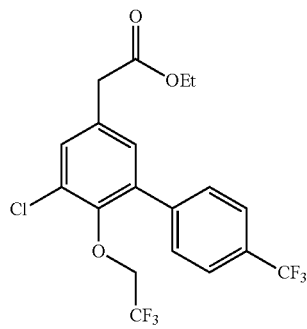 [SMILES: CCOC(=O)Cc1cc(Cl)c(OCC(F)(F)F)c(-c2ccc(C(F)(F)F)cc2)c1]

A mixture of 2-(3-bromo-5-chloro-4-(2,2,2-trifluoroethoxy)phenyl)-acetate (0.750 g, 2.0 mmol), 4-trifluoromethyl phenylboronic acid (0.567 g, 3.0 mmol), Pd (PPh$_3$)$_4$ (0.231 g, 0.2 mmol), cesium fluoride (0.604 g, 4.0 mmol) in DME (10 ml) was stirred overnight at 100° C., upon which the precipitates were removed by filtration. The filtrate was diluted with water and extracted with ethyl acetate (2×50 mL). The combined organic layers were washed with water followed by brine and dried over Na$_2$SO$_4$. The crude residue was purified by flash column chromatography to give ethyl 2-(5-chloro-6-(2,2,2-trifluoroethoxy)-4'-(trifluoromethyl)biphenyl-3-yl)acetate (0.525 g, 73.6%) as an off white solid.

Step 5

Ethyl 2-(5-chloro-6-(2,2,2-trifluoroethoxy)-4'-(trifluoromethyl)biphenyl-3-yl)-3-cyclopropylpropanoate

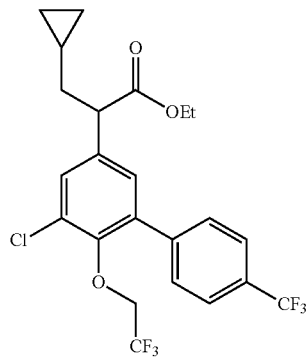 [SMILES: CCOC(=O)C(CC1CC1)c1cc(Cl)c(OCC(F)(F)F)c(-c2ccc(C(F)(F)F)cc2)c1]

Ethyl 2-(5-chloro-6-(2,2,2-trifluoroethoxy)-4'-(trifluoromethyl)biphenyl-3-yl)acetate (1.0 g, 2.27 mmol) was dissolved in anhydrous DMF (80 mL), NaH (60% wt. in paraffin oil, 0.109 g, 2.72 mmol) was added at 0° C. The reaction mixture was stirred for 30 min at room temperature, upon which cyclopropyl methyl bromide (0.24 mL, 2.5 mmol) was added in a dropwise manner at 0° C. The reaction mixture was stirred an additional 1 h at 0° C. upon which saturated NH$_4$Cl solution (10 mL) was added. The reaction mixture was extracted with EtOAc (3×50 mL) and the combined organic phases were washed with water (3×20 mL) and brine (20 mL), dried over Na$_2$SO$_4$, filtered and evaporated under reduced pressure to give colorless oil, which was purified by flash column chromatography to yield compound ethyl 2-(5-chloro-6-(2,2,2-trifluoroethoxy)-4'-(trifluoromethyl)biphenyl-3-yl)-3-cyclopropylpropanoate (0.68 g).

Step 6

2-(5-Chloro-6-(2,2,2-trifluoroethoxy)-4'-(trifluoromethyl)biphenyl-3-yl)-3-cyclopropylpropanoic acid

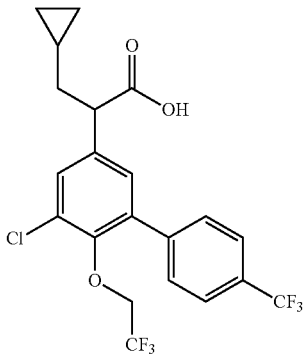 [SMILES: O=C(O)C(CC1CC1)c1cc(Cl)c(OCC(F)(F)F)c(-c2ccc(C(F)(F)F)cc2)c1]

A mixture of ethyl 2-(5-chloro-6-(2,2,2-trifluoroethoxy)-4'-(trifluoromethyl)biphenyl-3-yl)-3-cyclopropylpropanoate (0.68 g, 0.4 mmol) and lithium hydroxide monohydrate (100 mg, 4.6 mmol) in a MeOH/THF/Water solvent mixture (15 ml/15 ml/15/ml) was stirred for 3 h at room temperature. After completion of reaction, the volatiles were removed under reduced pressure. The residue was diluted with water, acidified with 5% HCl solution and extracted with ethyl acetate (3×50 mL). The combined organic layers were washed with water, dried over Na$_2$SO$_4$, filtered and evaporated under reduced pressure. The residue was purified by Flash Column Chromatography to give 2-(5-Chloro-6-(2,2,2-trifluoroethoxy)-4'-(trifluoromethyl)biphenyl-3-yl)-3-cyclopropylpropanoic acid in 88% yield (0.4 g). $^1$H-NMR (CDCl$_3$, 500 MHz): 7.72 (d, 2H); 7.65 (d, 2H), 7.43 (s, 1H); 7.24 (s, 1H); 3.98 (q, 2H); 3.72 (t, 1H); 1.94 (m, 1H), 1.78 (m, 1H); 0.71 (m, 1H), 0.46 (m, 2H), 0.02-0.19 (m, 2H).

Example 1269

1-(5-Chloro-6-(2,2,2-trifluoroethoxy)-4'-(trifluoromethyl)biphenyl-3-yl)-cyclobutane carboxylic acid Step 1

Ethyl-1-(5-chloro-6-(2,2,2-trifluoroethoxy)-4'-(Trifluoromethyl)biphenyl-3-yl)-cyclo butane carboxylate

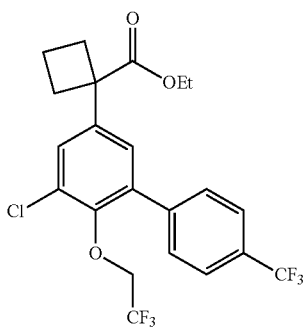 [SMILES: CCOC(=O)C1(c2cc(Cl)c(OCC(F)(F)F)c(-c3ccc(C(F)(F)F)cc3)c2)CCC1]

Ethyl 2-(5-chloro-6-(2,2,2-trifluoroethoxy)-4'-(trifluoromethyl)biphenyl-3-yl)acetate (1.5 g, 3.4 mmol) was dissolved in anhydrous DMF (30 mL), NaH (60% wt. in paraffin oil, 0.163 g, 6.8 mmol) was added at 0° C. The reaction mixture was stirred for 30 min at room temperature and 1,3-dibromopropane (0.757 g, 3.7 mmol) was added drop wise at 0° C. The reaction mixture was stirred for an additional 1 h at 0° C. and saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$. The volatiles were removed under reduced pressure and the residue was purified by flash column chromatography to yield compound ethyl-1-(5-chloro-6-(2,2,2-trifluoroethoxy)-4'-(trifluoromethyl)biphenyl-3-yl)-cyclo butane carboxylate (400 mg).

Step 2

1-(5-Chloro-6-(2,2,2-trifluoroethoxy)-4'-(trifluoromethyl)biphenyl-3-yl)-cyclobutane carboxylic acid

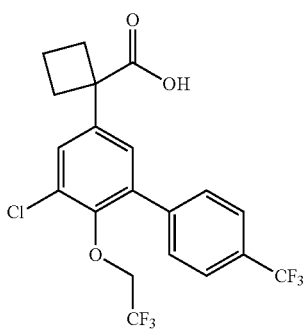 [SMILES: O=C(O)C1(c2cc(Cl)c(OCC(F)(F)F)c(-c3ccc(C(F)(F)F)cc3)c2)CCC1]

A mixture of ethyl-1-(5-chloro-6-(2,2,2-trifluoroethoxy)-4'-(trifluoromethyl)biphenyl-3-yl)-cyclo butane carboxylate (400 mg, 0.83 mmol) and lithium hydroxide monohydrate (0.2 g, 8.3 mmol) in a MeOH/THF/Water solvent mixture (10 ml/10 ml/10 ml) was stirred for 3 h at room temperature. Upon completion of the reaction, the volatiles were removed under reduced pressure. The residue was diluted with water, acidified with 5% HCl solution and extracted with ethyl acetate (3×50 mL). The combined organic layers were washed with water, dried over Na$_2$SO$_4$, filtered and evaporated under reduced pressure. The residue was purified by column chromatography to give 1-(5-chloro-6-(2,2,2-trifluoroethoxy)-4'-(trifluoromethyl)biphenyl-3-yl)-cyclobutane carboxylic acid in 88% yield (0.21 g). $^1$H-NMR (CDCl$_3$, 400 MHz): 7.72 (d, 2H); 7.65 (d, 2H), 7.39 (s, 1H); 7.26 (s, 1H); 3.98 (q, 2H); 2.86 (m, 2H); 2.52 (m, 2H); 2.16 (m, 1H), 1.91 (m, 1H).

Example 419

1-(5-Chloro-6-(2,2,2-trifluoroethoxy)-4'-(trifluoromethyl)biphenyl-3-yl)-cyclopentane carboxylic acid Step 1

Ethyl 1-(5-chloro-6-(2,2,2-trifluoroethoxy)-4'-(trifluoromethyl)biphenyl-3-yl)-cyclo pentane carboxylate

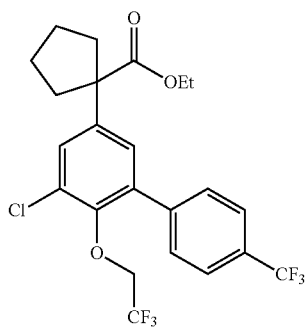 [SMILES: CCOC(=O)C1(c2cc(Cl)c(OCC(F)(F)F)c(-c3ccc(C(F)(F)F)cc3)c2)CCCC1]

Ethyl 2-(5-chloro-6-(2,2,2-trifluoroethoxy)-4'-(trifluoromethyl)biphenyl-3-yl)acetate (0.8 g, 1.81 mmol) was dissolved in anhydrous DMF (30 mL), NaH (60% wt. in paraffin oil, 0.109 g, 4.5 mmol) was added at 0° C. The reaction mixture was stirred for 30 min at room temperature and 1,4-dibromobutane (0.432 g, 1.99 mmol) was added drop wise at 0° C. The reaction mixture was stirred an additional 1 h at 0° C. upon which saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$. The volatiles were removed under reduced pressure and the residue was purified by flash column chromatography to yield compound ethyl 1-(5-chloro-6-(2,2,2-trifluoroethoxy)-4'-(trifluoromethyl)biphenyl-3-yl)-cyclo pentane carboxylate (400 mg) as a thick liquid.

Step 2

1-(5-Chloro-6-(2,2,2-trifluoroethoxy)-4'-(trifluoromethyl)biphenyl-3-yl)-cyclopentane carboxylic acid

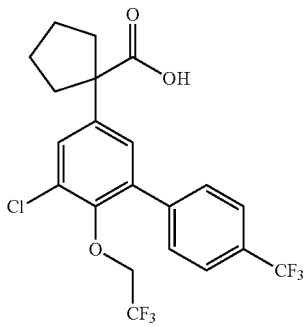 [SMILES: O=C(O)C1(c2cc(Cl)c(OCC(F)(F)F)c(-c3ccc(C(F)(F)F)cc3)c2)CCCC1]

A mixture of compound ethyl 1-(5-chloro-6-(2,2,2-trifluoroethoxy)-4'-(trifluoromethyl)biphenyl-3-yl)-cyclo pentane carboxylate (100 mg, 0.21 mmol) and lithium hydroxide monohydrate (96 mg, 2.1 mmol) in a MeOH/THF/Water solvent mixture (5 ml/5 ml5/ml) was stirred for 3 h at room temperature. After completion of reaction, the volatiles were removed under reduced pressure. The residue was diluted with water, acidified with 5% HCl solution and extracted with ethyl acetate (3×50 mL). The combined organic layers were washed with water, dried over $Na_2SO_4$, filtered and evaporated under reduced pressure. The residue was purified by Flash Column Chromatography to give 1-(5-chloro-6-(2,2,2-trifluoroethoxy)-4'-(trifluoromethyl)biphenyl-3-yl)-cyclopentane carboxylic acid (0.05 g). $^1$H-NMR ($CDCl_3$, 500 MHz): 7.72 (d, 2H); 7.65 (d, 2H), 7.56 (s, 1H); 7.34 (s, 1H); 3.98 (q, 2H); 2.68 (m, 2H); 1.94 (m, 2H); 1.78 (m, 4H).

Example 3202

4-(5-Chloro-6-(2,2,2-trifluoroethoxy)-4'-(trifluoromethyl)biphenyl-3-yl)tetrahydro-2H-pyran-4-carboxylic acid Step 1

Ethyl 4-(5-chloro-6-(2,2,2-trifluoroethoxy)-4'-(trifluoromethyl)biphenyl-3-yl)tetrahydro-2H-pyran-4-carboxylate

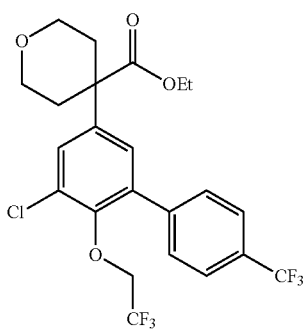

Ethyl 2-(5-chloro-6-(2,2,2-trifluoroethoxy)-4'-(trifluoromethyl)biphenyl-3-yl)acetate (0.4 g, 3.4 mmol) was dissolved in anhydrous DMF (30 mL), NaH (60% wt. in paraffin oil, 0.163 g, 6.8 mmol) was added at 0° C. The reaction mixture was stirred for 30 min at room temperature and 1-iodo-2-(2-iodoethoxy)ethane (1.2 g, 3.7 mmol) was added drop wise at 0° C. The reaction mixture was stirred an additional 1 h at 0° C. and saturated $NH_4Cl$ solution (10 mL) was added. The reaction mixture was extracted with EtOAc (3×20 mL) and the combined organic phases were washed with water (3×20 mL) and brine (20 mL), and dried over $MgSO_4$. The volatiles were removed under reduced pressure and the residue was purified by flash column chromatography to yield ethyl 4-(5-chloro-6-(2,2,2-trifluoroethoxy)-4'-(trifluoromethyl)biphenyl-3-yl)tetrahydro-2H-pyran-4-carboxylate (400 mg).

Step 2

4-(5-Chloro-6-(2,2,2-trifluoroethoxy)-4'-(trifluoromethyl)biphenyl-3-yl)tetrahydro-2H-pyran-4-carboxylic acid

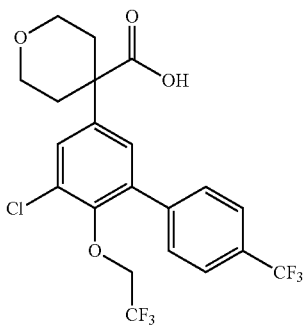 [SMILES: CCOC(=O)C1(c2cc(Cl)c(OCC(F)(F)F)c(-c3ccc(C(F)(F)F)cc3)c2)CCOCC1]

A mixture of ethyl 4-(5-chloro-6-(2,2,2-trifluoroethoxy)-4'-(trifluoromethyl)biphenyl-3-yl)tetrahydro-2H-pyran-4-carboxylate (400 mg, 0.78 mmol) and lithium hydroxide monohydrate (0.188 g, 7.8 mmol) in a MeOH/THF/Water solvent mixture (5 ml/5 ml5/ml) was stirred for 3 h at room temperature. After completion of reaction volatiles were removed under reduced pressure. Residue was diluted with water, acidified with 5% HCl solution and extracted with ethyl acetate (3×50 mL). Combined organic layer was washed with water, dried over $Na_2SO_4$, filtered and evaporated under reduced pressure. The residue was purified by Flash Column Chromatography to give 4-(5-chloro-6-(2,2,2-trifluoroethoxy)-4'-(trifluoromethyl)biphenyl-3-yl)tetrahydro-2H-pyran-4-carboxylic acid (100 mg). $^1$H-NMR ($CDCl_3$, 400 MHz): 7.72 (d, 2H); 7.65 (d, 2H), 7.56 (s, 1H); 7.34 (s, 1H); 3.98 (q, 2H); 3.61 (t, 2H); 2.53 (dd, 2H); 1.99 (m, 2H).

Example 3203

1-(5-Chloro-6-(2,2,2-trifluoroethoxy)-4'-(trifluoromethyl)biphenyl-3-yl)-4,4-dimethylcyclohexanecarboxylic acid Step 1

Ethyl 1-(5-chloro-6-(2,2,2-trifluoroethoxy)-4'-(trifluoromethyl)biphenyl-3-yl)-4,4-dimethylcyclohexanecarboxylate

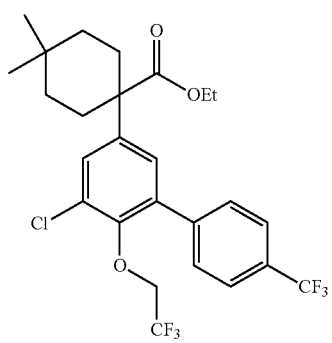

Ethyl 2-(5-chloro-6-(2,2,2-trifluoroethoxy)-4'-(trifluoromethyl)biphenyl-3-yl)acetate (0.5 g, 1.13 mmol) was dissolved in anhydrous DMF (30 mL), NaH (60% wt. in paraffin oil, 0.113 g, 2.8 mmol) was added at 0° C. The reaction mixture was stirred for 30 min at room temperature and 3,3-dimethyl-1,5-dibromopentane (0.322 g, 1.25 mmol) was added drop wise at 0° C. The reaction mixture was stirred an additional 1 h at 0° C. and saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$. The volatiles were removed under reduced pressure and the residue was purified by flash column chromatography to yield compound ethyl 1-(5-chloro-6-(2,2,2-trifluoroethoxy)-4'-(trifluoromethyl)biphenyl-3-yl)-4,4-dimethylcyclohexanecarboxylate (230 mg).

Step 2

1-(5-Chloro-6-(2,2,2-trifluoroethoxy)-4'-(trifluoromethyl)biphenyl-3-yl)-4,4-dimethylcyclohexanecarboxylic acid

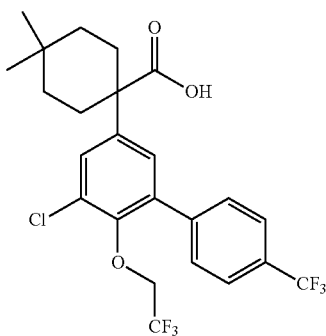 [SMILES: CCOC(=O)C1(c2cc(Cl)c(OCC(F)(F)F)c(-c3ccc(C(F)(F)F)cc3)c2)CCC(C)(C)CC1]

A mixture of compound ethyl 1-(5-chloro-6-(2,2,2-trifluoroethoxy)-4'-(trifluoromethyl)biphenyl-3-yl)-4,4-dimethylcyclohexanecarboxylate (200 mg, 0.37 mmol) and lithium hydroxide monohydrate (88 mg, 3.7 mmol) in a MeOH/THF/Water solvent mixture (5 ml/5 ml5/ml) was stirred for 3 h at room temperature. After completion of the reaction, the volatiles were removed under reduced pressure. The residue was diluted with water, acidified with 5% HCl solution and extracted with ethyl acetate (3×50 mL). The combined organic layers were washed with water, dried over Na$_2$SO$_4$, filtered and evaporated under reduced pressure. The residue was purified by Flash Column Chromatography to give 1-(5-chloro-6-(2,2,2-trifluoroethoxy)-4'-(trifluoromethyl)biphenyl-3-yl)-4,4-dimethylcyclohexanecarboxylic acid in 67% yield (150 mg). $^1$H-NMR (CDCl$_3$, 400 MHz): 7.72 (d, 2H); 7.65 (d, 2H), 7.56 (s, 1H); 7.34 (s, 1H); 3.98 (q, 2H); 2.48 (dd, 2H); 1.88 (m, 2H); 1.41 (m, 4H), 0.98 (s, 3H), 0.91 (s, 3H).

Example 1270

1-(5-chloro-6-(2,2,2-trifluoroethoxy)-4'-(trifluoromethyl)biphenyl-3-yl)-cyclohexane carboxylic acid Step 1

Ethyl 1-(5-chloro-6-(2,2,2-trifluoroethoxy)-4'-(trifluoromethyl)biphenyl-3-yl)-cyclohexanecarboxylate

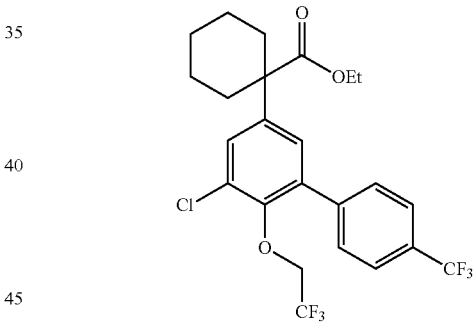

Ethyl 2-(5-chloro-6-(2,2,2-trifluoroethoxy)-4'-(trifluoromethyl)biphenyl-3-yl)acetate (0.5 g, 1.13 mmol) was dissolved in anhydrous DMF (30 mL), NaH (60% wt. in paraffin oil, 0.113 g, 2.8 mmol) was added at 0° C. The reaction mixture was stirred for 30 min at room temperature and 1,5-dibromopentane (0.19 g, 1.24 mmol) was added drop wise at 0° C. The reaction mixture was stirred an additional 1 h at 0° C. and saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$. The volatiles were removed under reduced pressure and the residue was purified by flash column chromatography to yield compound ethyl 1-(5-chloro-6-(2,2,2-trifluoroethoxy)-4'-(trifluoromethyl)biphenyl-3-yl)-cyclohexanecarboxylate (0.37 g) as a thick liquid.

Step 2

1-(5-chloro-6-(2,2,2-trifluoroethoxy)-4'-(trifluoromethyl)biphenyl-3-yl)-cyclohexane carboxylic acid

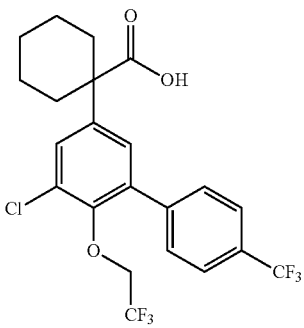

A mixture of ethyl 1-(5-chloro-6-(2,2,2-trifluoroethoxy)-4'-(trifluoromethyl)biphenyl-3-yl)-cyclohexanecarboxylate (0.37 g, 0.72 mmol) and lithium hydroxide monohydrate (0.174 g, 7.28 mmol) in a MeOH/THF/Water solvent mixture (10 ml/10 ml/10 ml) was stirred for 3 h at room temperature. After completion of reaction volatiles were removed under reduced pressure. The residue was diluted with water, acidified with 5% HCl solution and extracted with ethyl acetate (3×50 mL). The combined organic layers were washed with water, dried over $Na_2SO_4$, filtered and evaporated under reduced pressure. The residue was purified by Flash Column Chromatography to give 1-(5-chloro-6-(2,2,2-trifluoroethoxy)-4'-(trifluoromethyl)biphenyl-3-yl)-cyclohexane carboxylic acid (0.25 g) as a white solid. $^1$H-NMR ($CDCl_3$, 400 MHz): 7.72 (d, 2H); 7.65 (d, 2H), 7.55 (s, 1H); 7.34 (s, 1H); 3.98 (q, 2H); 2.48 (dd, 2H); 1.52-1.81 (m, 6H); 1.33 (m, 2H).

Example 1271

5-(5-Chloro-6-(2,2,2-trifluoroethoxy)-4'-(trifluoromethyl)biphenyl-3-yl)-spiro[2,3]hexane-5-carboxylic acid Step 1

Ethyl 5-(5-chloro-6-(2,2,2-trifluoroethoxy)-4'-(trifluoromethyl)biphenyl-3-yl)-Spiro[2,3]hexane-5-carboxylate

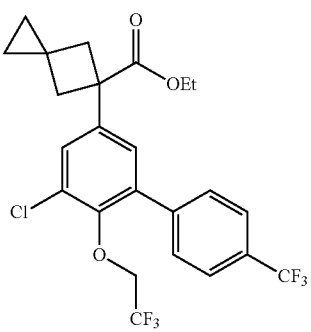 [SMILES: CCOC(=O)C1(c2cc(Cl)c(OCC(F)(F)F)c(-c3ccc(C(F)(F)F)cc3)c2)CC2(CC2)C1]

Ethyl 2-(5-chloro-6-(2,2,2-trifluoroethoxy)-4'-(trifluoromethyl)biphenyl-3-yl)acetate (0.6 g, 1.36 mmol) was dissolved in anhydrous DMF (30 mL), NaH (60% wt. in paraffin oil, 0.136 g, 3.4 mmol) was added at 0° C. The reaction mixture was stirred for 30 min at room temperature and 1,1-bis(bromomethyl)cyclopropane (0.482 g, 1.4 mmol, for preparation see J. Org. Chem 1993, 58, 4122-26) was added drop wise at 0° C. The reaction mixture was stirred an additional 1 h at 0° C. and saturated $NH_4Cl$ solution (10 mL) was added. The reaction mixture was extracted with EtOAc (3×20 mL) and the combined organic phases were washed with water (3×20 mL) and brine (20 mL), and dried over $MgSO_4$. The volatiles were removed under reduced pressure and the residue was purified by flash column chromatography to yield compound ethyl 5-(5-chloro-6-(2,2,2-trifluoroethoxy)-4'-(trifluoromethyl)biphenyl-3-yl)-spiro[2,3]hexane-5-carboxylate (150 mg) as a low melting solid.

Step 2

5-(5-Chloro-6-(2,2,2-trifluoroethoxy)-4'-(trifluoromethyl)biphenyl-3-yl)-spiro[2,3]hexane-5-carboxylic acid

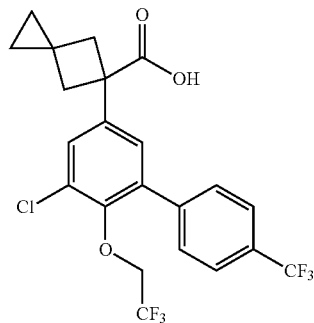 [SMILES: O=C(O)C1(c2cc(Cl)c(OCC(F)(F)F)c(-c3ccc(C(F)(F)F)cc3)c2)CC2(CC2)C1]

A mixture of ethyl 5-(5-chloro-6-(2,2,2-trifluoroethoxy)-4'-(trifluoromethyl)biphenyl-3-yl)-spiro[2,3]hexane-5-carboxylate (0.5 g, 0.9 mmol) and lithium hydroxide monohydrate (0.415 g, 9.88 mmol) in a MeOH/THF/Water solvent mixture (10 ml/10 ml/10 ml) was stirred for 3 h at room temperature. After completion of reaction volatiles were removed under reduced pressure. Residue was diluted with water, acidified with 5% HCl solution and extracted with ethyl acetate (3×50 mL). The combined organic layer was washed with water, dried over $Na_2SO_4$, filtered and evaporated under reduced pressure. The residue was purified by Flash Column Chromatography to give 5-(5-chloro-6-(2,2,2-trifluoroethoxy)-4'-(trifluoromethyl)biphenyl-3-yl)-spiro[2,3]hexane-5-carboxylic acid (0.29 g). $^1$H-NMR ($CDCl_3$, 400 MHz): 7.72 (d, 2H); 7.65 (d, 2H), 7.41 (s, 1H); 7.21 (s, 1H); 3.98 (q, 2H); 2.95 (d, 2H); 2.75 (d, 2H), 0.58 (t, 2H), 0.48 (t, 2H).

Example 1268

2-(5-Chloro-6-(2,2,2-trifluoroethoxy)-4'-(trifluoromethyl)biphenyl-3-yl)-3-cyclobutylpropanoic acid Step 1

Ethyl 2-(5-chloro-6-(2,2,2-trifluoroethoxy)-4'-(trifluoromethyl)biphenyl-3-yl)-3-cyclobutylpropanoate

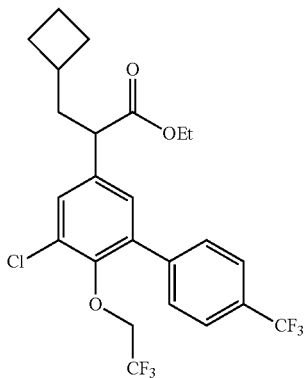

Ethyl 2-(5-chloro-6-(2,2,2-trifluoroethoxy)-4'-(trifluoromethyl)biphenyl-3-yl)acetate (0.6 g, 0.49 mmol) was dissolved in anhydrous DMF (30 mL), NaH (60% wt. in paraffin oil, 0.039 g, 1.69 mmol) was added at 0° C. The reaction mixture was stirred for 30 min at room temperature and cyclobutylmethyl bromide (0.223 g, 1.49 mmol) was added drop wise at 0° C. The reaction mixture was stirred an additional 1 h at 0° C. and saturated NH₄Cl solution (10 mL) was added. The reaction mixture was extracted with EtOAc (3×20 mL) and the combined organic phases were washed with water (3×20 mL) and brine (20 mL), and dried over MgSO₄ The volatiles were removed under reduced pressure and the residue was purified by flash column chromatography to yield ethyl 2-(5-chloro-6-(2,2,2-trifluoroethoxy)-4'-(trifluoromethyl)biphenyl-3-yl)-3-cyclobutylpropanoate (0.25 g) as a colorless liquid.

Step 2

2-(5-Chloro-6-(2,2,2-trifluoroethoxy)-4'-(trifluoromethyl)biphenyl-3-yl)-3-cyclobutylpropanoic acid

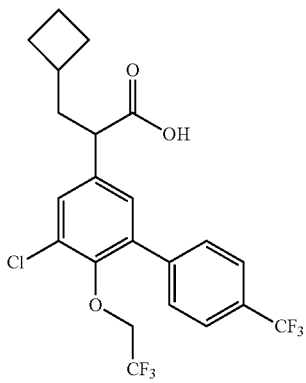

A mixture of ethyl 2-(5-chloro-6-(2,2,2-trifluoroethoxy)-4'-(trifluoromethyl)biphenyl-3-yl)-3-cyclobutylpropanoate (0.25 g, 0.49 mmol) and lithium hydroxide monohydrate (0.206 g, 4.9 mmol) in a MeOH/THF/Water solvent mixture (10 ml/10 ml/10 ml) was stirred for 3 h at room temperature. After completion of reaction volatiles were removed under reduced pressure. Residue was diluted with water, acidified with 5% HCl solution and extracted with ethyl acetate (3×50 mL). The combined organic layers were washed with water, dried over Na₂SO₄, filtered and evaporated under reduced pressure. The residue was purified by Flash Column Chromatography to give 2-(5-chloro-6-(2,2,2-trifluoroethoxy)-4'-(trifluoromethyl)biphenyl-3-yl)-3-cyclobutylpropanoic acid (0.106 g) as a white solid. ¹H-NMR (CDCl₃, 400 MHz): 7.72 (d, 2H); 7.65 (d, 2H); 7.41 (s, 1H); 7.18 (s, 1H); 3.98 (q, 2H); 3.51 (t, 1H); 2.15-2.28 (m, 2H); 1.55-2.15 (m, 7H).

Example 1272

2-(5-Chloro-6-(2,2,2-trifluoroethoxy)-4'-(trifluoromethyl)biphenyl-3-yl)-2-cyclopentylacetic acid Step 1

Ethyl 2-(5-chloro-6-(2,2,2-trifluoroethoxy)-4'-(trifluoromethyl)biphenyl-3-yl)-2-cyclopentylacetate

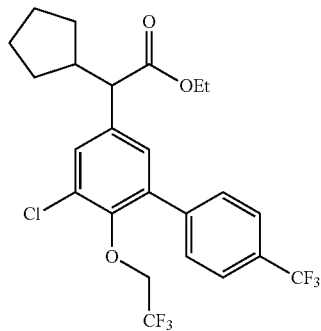 [SMILES: CCOC(=O)C(c1cc(Cl)c(OCC(F)(F)F)c(-c2ccc(C(F)(F)F)cc2)c1)C1CCCC1]

Ethyl 2-(5-chloro-6-(2,2,2-trifluoroethoxy)-4'-(trifluoromethyl)biphenyl-3-yl)acetate (0.8 g, 1.8 mmol) was dissolved in anhydrous DMF (40 mL), NaH (60% wt. in paraffin oil, 0.052 g, 2.18 mmol) was added at 0° C. The reaction mixture was stirred for 30 min at room temperature and cyclopentyl bromide (0.298 g, 1.99 mmol) was added drop wise at 0° C. The reaction mixture was stirred an additional 1 h at 0° C. and saturated NH₄Cl solution (10 mL) was added. The reaction mixture was extracted with EtOAc (3×50 mL) and the combined organic phases were washed with water (3×20 mL) and brine (20 mL), and dried over MgSO₄. The volatiles were removed under reduced pressure and the residue was purified by flash column chromatography to yield compound ethyl 2-(5-chloro-6-(2,2,2-trifluoroethoxy)-4'-(trifluoromethyl)biphenyl-3-yl)-2-cyclopentylacetate (0.4 mg) as a thick liquid.

Step 2

2-(5-Chloro-6-(2,2,2-trifluoroethoxy)-4'-(trifluoromethyl)biphenyl-3-yl)-2-cyclopentylacetic acid

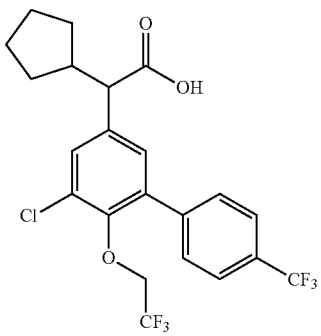 [SMILES: O=C(O)C(c1cc(Cl)c(OCC(F)(F)F)c(-c2ccc(C(F)(F)F)cc2)c1)C1CCCC1]

A mixture of ethyl 2-(5-chloro-6-(2,2,2-trifluoroethoxy)-4'-(trifluoromethyl)biphenyl-3-yl)-2-cyclopentylacetate (400 mg, 0.78 mmol) and lithium hydroxide monohydrate (0.330 g, 7.87 mmol) in a MeOH/THF/Water solvent mixture (10 ml/10 ml/10 ml) was stirred for 3 h at room temperature. After completion of reaction volatiles were removed under reduced pressure. The residue was diluted with water, acidified with 5% HCl solution and extracted with ethyl acetate (3×50 mL). The combined organic layers were washed with water, dried over $Na_2SO_4$, filtered and evaporated under reduced pressure. The residue was purified by Flash Column Chromatography to give 2-(5-chloro-6-(2,2,2-trifluoroethoxy)-4'-(trifluoromethyl)biphenyl-3-yl)-2-cyclopentylacetic acid (0.08 g). $^1$H-NMR ($CDCl_3$, 400 MHz): 12.5 (s, 1H), 7.84 (d, 2H); 7.70 (d, 2H), 7.55 (s, 1H); 7.35 (s, 1H); 4.22 (q, 2H); 3.3.35 (d, 1H); 1.82 (m, 1H); 1.18-1.68 (m, 7H); 1.08 (m, 1H).

Example 3204

2-(5-Chloro-6-(2,2,2-trifluoroethoxy)-4'-(trifluoromethyl)biphenyl-3-yl)-3-(4-fluorophenyl)propanoic acid Step 1

Ethyl 2-(5-chloro-6-(2,2,2-trifluoroethoxy)-4'-(trifluoromethyl)biphenyl-3-yl)-3-(4-fluorophenyl)propanoate

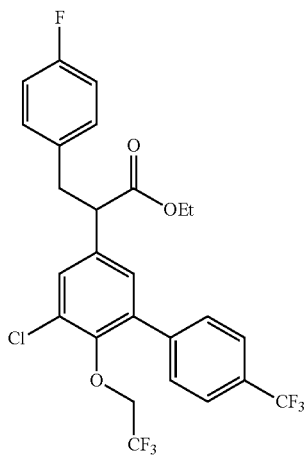 [SMILES: CCOC(=O)C(Cc1ccc(F)cc1)c1cc(Cl)c(OCC(F)(F)F)c(-c2ccc(C(F)(F)F)cc2)c1]

Ethyl 2-(5-chloro-6-(2,2,2-trifluoroethoxy)-4'-(trifluoromethyl)biphenyl-3-yl)acetate (0.6 g, 1.36 mmol) was dissolved in anhydrous DMF (30 mL), NaH (60% wt. in paraffin oil, 0.039 g, 1.36 mmol) was added at 0° C. The reaction mixture was stirred for 30 min at room temperature and cyclopentyl bromide (0.283 g, 1.49 mmol) was added drop wise at 0° C. The reaction mixture was stirred an additional 1 h at 0° C. and saturated $NH_4Cl$ solution (10 mL) was added. The reaction mixture was extracted with EtOAc (3×20 mL) and the combined organic phases were washed with water (3×20 mL) and brine (20 mL), and dried over $MgSO_4$. The volatiles were removed under reduced pressure and the residue was purified by flash column chromatography to yield compound ethyl 2-(5-chloro-6-(2,2,2-trifluoroethoxy)-4'-(trifluoromethyl)biphenyl-3-yl)-3-(4-fluorophenyl)propanoate (0.29 g) as a colorless liquid.

Step 2

2-(5-Chloro-6-(2,2,2-trifluoroethoxy)-4'-(trifluoromethyl)biphenyl-3-yl)-3-(4-fluorophenyl)propanoic acid

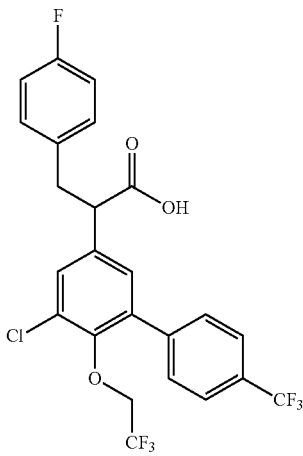 [SMILES: O=C(O)C(Cc1ccc(F)cc1)c1cc(Cl)c(OCC(F)(F)F)c(-c2ccc(C(F)(F)F)cc2)c1]

A mixture of ethyl 2-(5-chloro-6-(2,2,2-trifluoroethoxy)-4'-(trifluoromethyl)biphenyl-3-yl)-3-(4-fluorophenyl)propanoate (400 mg, 0.719 mmol) and lithium hydroxide monohydrate (0.306 g, 7.29 mmol) in a MeOH/THF/Water solvent mixture (10 ml/10 ml/10 ml) was stirred for 3 h at room temperature. After completion of reaction volatiles were removed under reduced pressure. The residue was diluted with water, acidified with 5% HCl solution and extracted with ethyl acetate (3×50 mL). The combined organic layers were washed with water, dried over $Na_2SO_4$, filtered and evaporated under reduced pressure. The residue was purified by Flash Column Chromatography to give 2-(5-chloro-6-(2,2,2-trifluoroethoxy)-4'-(trifluoromethyl)biphenyl-3-yl)-3-(4-fluorophenyl)propanoic acid (0.1 g). $^1$H-NMR ($CDCl_3$, 400 MHz): 7.55-7.78 (m, 4H); 7.42 (s, 1H), 7.18 (s, 1H); 6.92-7.16 (m, 4H); 3.98 (q, 2H); 3.84 (t, 1H); 3.41 (dd, 1H), 3.02 (dd, 1H).

Example 1905

2-(2-chloro-6-(cyclopropylmethoxy)-4'-(trifluoromethyl)biphenyl-4-yl)-3-cyclopropylpropanoic acid

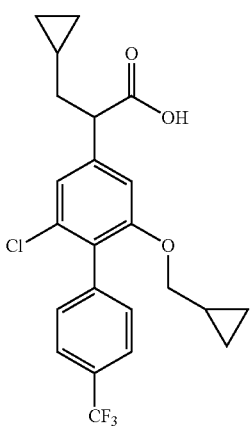 [SMILES: O=C(O)C(CC1CC1)c1cc(Cl)c(-c2ccc(C(F)(F)F)cc2)c(OCC2CC2)c1]

Step 1

2-(Cyclopropylmethoxy)-4-fluoro-1-nitrobenzene

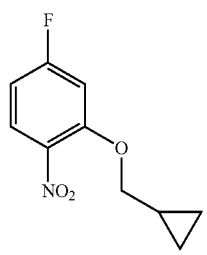 [SMILES: O=[N+]([O-])c1ccc(F)cc1OCC1CC1]

Cyclopropyl methanol (15 g, 207 mmol) was added to a stirred suspension of NaH (60% in mineral oil, 8.37 g) in 200 mL THF over a period of 15 min at 0° C. under an atmosphere of nitrogen. The reaction mixture was allowed to warm to room temperature and stirred for 1 h at RT. The mixture was cooled to 0° C. and a solution of 2,4-difluoro-1-nitrobenzene (30 g, 187 mmol) in 200 mL THF was added in a drop wise manner. The reaction mixture was stirred at 0° C. for 2 h and then poured onto ice water. The mixture was extracted with ethyl acetate (3×100 mL). The combined organic layers were dried over MgSO$_4$ and concentrated under reduced pressure to give 22.0 g of 2-(cyclopropylmethoxy)-4-fluoro-1-nitrobenzene as an orange oil (86%).

Step 2

Diethyl 2-(3-(cyclopropylmethoxy)-4-nitrophenyl)malonate

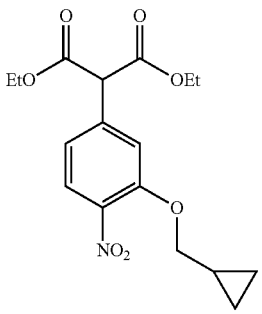 [SMILES: CCOC(=O)C(C(=O)OCC)c1ccc([N+](=O)[O-])c(OCC2CC2)c1]

Diethyl malonate (9.8 g, 1.1 eq) was added to a stirred suspension of sodium hydride (60% in mineral oil, 2.09 g) in DMF (88 mL) over 15 min. at 0° C. under nitrogen. The reaction mixture was allowed to warm to room temperature and stirred for 1 h. A solution of 2-cyclopropylmethoxy-4-fluoro-1-nitrobenzene (10 g, 1 eq) in DMF (88 mL) was added drop wise at 0° C., and the reaction mixture was heated to 100° C. for 3 h. The reaction mixture was allowed to cool to room temperature, poured into ice water and extracted with EtOAc (3×100 mL). The combined organic phases were washed with water (3×100 mL) and brine (100 mL), dried (MgSO$_4$) and filtered. Evaporation of the volatiles under reduced pressure gave 10.0 g of crude product which was purified by chromatography over silica gel (hexane/EtOAc) gave of diethyl 2-(3-(cyclopropylmethoxy)-4-nitrophenyl) malonate (7.0 g). $^1$H-NMR (CDCl$_3$, 200 MHz): 0.4 (m, 2H), 0.71 (m, 2H), 1.3 (m, 1H), 1.3 (t, 6H), 3.96 (d, 2H), 4.25 (q, 4H), 4.5 (s, 1H), 7.02 (d, 1H), 7.18 (s, 1H), 7.81 (d, 2H).

Step 3

2-(3-(cyclopropylmethoxy)-4-nitrophenyl)acetic acid

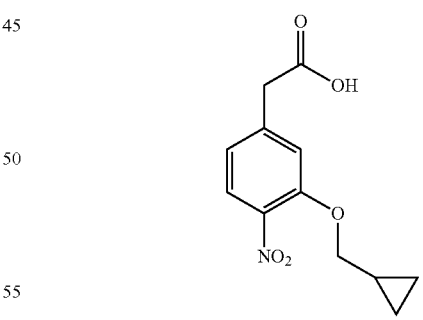

Compound diethyl 2-(3-(cyclopropylmethoxy)-4-nitrophenyl)malonate (10 g) was dissolved in 100 mL ethanol and cooled to 0° C., NaOH solution (4 eq) was added slowly to the reaction mixture for about 15 min. The reaction mixture was heated gently up to 60° C. for 5 h. Progress of the reaction was monitored by TLC analysis. After complete conversion of starting material solvent was evaporated under reduced pressure, residue dissolved in H$_2$O, acidified with 6N HCl to pH-2. Filtered the solid material washed with water, dried under reduced pressure to give 2-(3-(cyclopropylmethoxy)-

4-nitrophenyl)acetic acid (6.5 g) as a yellow solid. ¹H-NMR (CDCl₃, 200 MHz): 0.36 (m, 2H), 0.58 (m, 2H), 1.28 (m, 1H), 3.71 (s, 2H), 4.01 (d, 2H), 7.02 (d, 1H), 7.23 (s, 1H), 7.81 (d, 1H).

Step 4

Ethyl 2-(3-(cyclopropylmethoxy)-4-nitrophenyl)acetate

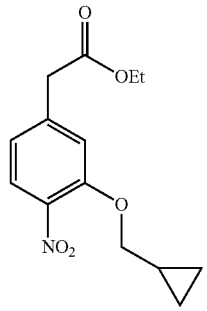

2-(3-(cyclopropylmethoxy)-4-nitrophenyl)acetic acid (40 g, 143 mmol) was dissolved in 20% EtOH—HCl solution (200 ml) and refluxed for 3 h to convert the starting material to ester. The volatiles were removed under reduced pressure and the residue was extracted with ethyl acetate (×2). The combined organic extracts were washed with water, dried (Na₂SO₄), filtered and concentrated under reduced pressure. The crude material was purified by re crystallization to ethyl 2-(3-(cyclopropylmethoxy)-4-nitrophenyl)acetate (38 g) as pale yellow solid.

Step 5

Ethyl 2-(4-amino-3-(cyclopropylmethoxy)phenyl)acetate

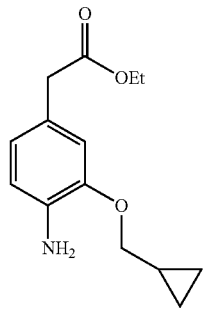 [SMILES: CCOC(=O)Cc1ccc([N+](=O)[O-])c(OCC2CC2)c1]

To a stirred solution of compound ethyl 2-(3-(cyclopropylmethoxy)-4-nitrophenyl)acetate (10 g), in dry MeOH (100 mL), Pd(OH)₂ (2 g) was added and the mixture was reduced under an H₂ atmosphere for 6 h at room temperature. The mixture was filtered a pad of Celite™ washing with MeOH. The combined filtrates were concentrated under reduced pressure to yield ethyl 2-(4-amino-3-(cyclopropylmethoxy)phenyl)acetate (7.5 g) as a thick liquid. ¹H-NMR (CDCl₃, 200 MHz): 0.38 (m, 2H), 0.61 (m, 2H), 1.23 (m, 1H), 1.23 (t, 3H), 3.51 (s, 2H), 3.80 (d, 2H), 4.16 (q, 2H), 6.72 (m, 3H).

Step 6

Ethyl 2-(4-amino-3-chloro-5-(cyclopropylmethoxy)phenyl)acetate

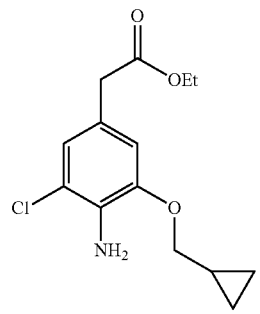 [SMILES: CCOC(=O)Cc1cc(Cl)c(N)c(OCC2CC2)c1]

To a stirred solution of ethyl 2-(4-amino-3-(cyclopropylmethoxy)phenyl)acetate (1.2 g, 4.0 mmol) in dry CCl₄ (60 mL), NCS (0.427 g, 3.2 mmol) was added at 0° C. The reaction mixture was allowed to stir for 3 h at room temperature. The reaction mixture was diluted with water and extracted with DCM (2×50 mL). The combined organic layers were dried over Na₂SO₄, filtered and the volatiles removed in vacuo. The crude reaction mixture was purified by column chromatography to give ethyl 2-(4-amino-3-chloro-5-(cyclopropylmethoxy)phenyl)acetate (920 mg) as a yellow solid.

Step 7

Ethyl 2-(3-chloro-5-(cyclopropylmethoxy)-4-iodophenyl)acetate

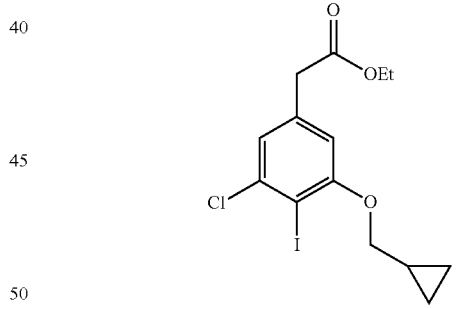

Ethyl-2-(4-amino-3-chloro-5-(cyclopropylmethoxy)phenyl)-acetate (2.5 g, 10.0 mmol) was dissolved in a mixture of EtOH/H₂O/H₂SO₄ (96%) 200 mL/400 mL/10 mL at 0° C. A solution of NaNO₂ (3.2 g, 1.16 eq) in water (40 mL) was added drop wise at 0° C., and the reaction mixture was stirred for 40 min at the same temperature. A solution of KI (30 g, 30.1 mmol) in water (80 mL) was added drop wise at 0° C. The reaction mixture was heated to 50° C. for 2.5 h upon which the volatiles were removed under reduced pressure. The reaction mixture was extracted with EtOAc (3×50 mL), and the combined organic layers were washed with 10% sodium thiosulfate (2×50 mL), water (300 mL) and brine (300 mL). The organic solution was dried over Na₂SO₄ and concentrated under reduced pressure to give a crude black oil which was purified by chromatography over silica gel (hexane/EtOAc) to give the product ethyl 2-(3-chloro-5-(cyclopropylmethoxy)-4-iodophenyl)acetate as a yellow oil (8.7 g).
Step 8

Ethyl 2-(2-chloro-6-(cyclopropylmethoxy)-4'-(trifluoromethyl)biphenyl-4-yl)acetate

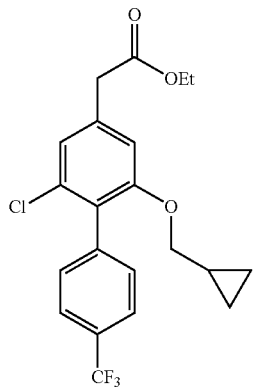 [SMILES: CCOC(=O)Cc1cc(Cl)c(-c2ccc(C(F)(F)F)cc2)c(OCC2CC2)c1]

A mixture of compound ethyl 2-(3-chloro-5-(cyclopropylmethoxy)-4-iodophenyl)acetate (5.1 g, 14 mmol), 4-trifluoromethylphenylboronic acid (3.36 g, 17 mmol), CsF (0.28 g, 1.84 mmol) and Pd (PPh$_3$)$_4$ (0.410 g, 0.4 mmol) in 75 mL anhydrous 1,2-dimethoxy ethane was refluxed for 8 h under argon. The reaction mixture was cooled to RT and 75 mL of EtOAc and 75 mL of water were added. The organic phase was separated, dried over NaSO$_4$, filtered and concentrated under reduced pressure to give a yellow oil. The oil was purified by chromatography over silica gel (hexane/EtOAc) to give ethyl 2-(2-chloro-6-(cyclopropylmethoxy)-4'-(trifluoromethyl)biphenyl-4-yl)acetate (4.6 g) as a yellow oil. $^1$H-NMR (CDCl$_3$, 200 MHz): 0.41 (m, 2H), 0.62 (m, 2H), 1.22 (t, 3H), 1.23 (m, 1H), 3.58 (s, 2H), 3.89 (d, 2H), 4.17 (q, 2H), 6.96 (m, 2H), 7.31 (s, 1H), 7.64 (m, 4H).
Step 9

2-(2-chloro-6-(cyclopropylmethoxy)-4'-(trifluoromethyl)biphenyl-4-yl)-3-cyclopropylpropanoic acid

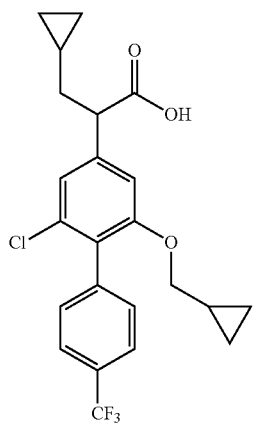 [SMILES: O=C(O)C(CC1CC1)c1cc(Cl)c(-c2ccc(C(F)(F)F)cc2)c(OCC2CC2)c1]

Ethyl 2-(2-chloro-6-(cyclopropylmethoxy)-4'-(trifluoromethyl)biphenyl-4-yl)acetate (1.1 g, 2.4 mmol) was dissolved in 10 mL anhydrous DMF and NaH (60% wt. in oil, 0.9 g) was added at 0° C. The reaction mixture was stirred for 0.5 h at 25° C. and cyclopropyl methyl bromide (1.25 mL) was added drop wise at 0° C. The reaction mixture was stirred for an additional 1 h at 0° C. upon which saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$, filtered and the volatiles removed under reduced pressure to give 0.85 g of a colorless oil. The oil was dissolved in 10 mL of EtOH/H$_2$O (9:1, v/v) and (1.0 g) LiOH added. The reaction mixture was refluxed for 5 h and concentrated under reduced pressure. Water (10 mL) was added and the reaction mixture was extracted with EtOAc (3×10 mL). The combined organic phases were dried over MgSO$_4$ and evaporated under reduced pressure. Purification by column chromatography over silica gel (hexane/EtOAc 9:1) gave 2-(2-chloro-6-(cyclopropylmethoxy)-4'-(trifluoromethyl)biphenyl-4-yl)-3 cyclopropylpropanoic acid (0.42 g) as a white solid, L-21-1 (56%). $^1$H NMR (300 MHz, CDCl$_3$): δ 7.65 (d, 2H), 7.38 (d, 2H), 7.08 (s, 1H), 6.83 (s, 1H), 3.75 (d, 2H), 3.62 (t, 1H), 1.96 (m, 1H), 1.08 (m, 1H), 0.84 (m, 1H), 0.44 (m, 4H), 0.16 (m, 4H).

Example 1908

1-(2-chloro-6-(cyclopropylmethoxy)-4'-(trifluoromethyl)biphenyl-4-yl)-cyclobutanecarboxylic acid

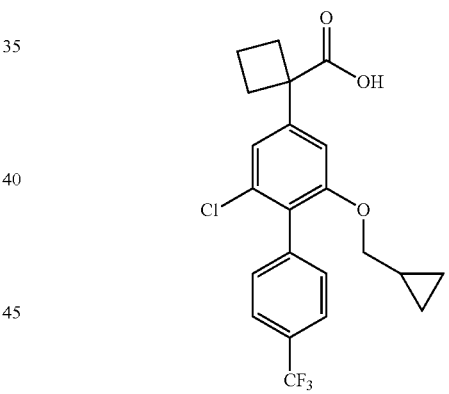

Ethyl 2-(2-chloro-6-(cyclopropylmethoxy)-4'-(trifluoromethyl)biphenyl-4-yl)acetate (0.5 g) was dissolved in 10 mL anhydrous DMF and NaH (60% wt. in oil, 0.13 g, mmol) was added at 0° C. The reaction mixture was stirred for 0.5 h at 25° C. and 1,3-dibromopropane (1.5 mL) was added drop wise at 0° C. The reaction mixture was stirred at 0° C. for 1 h and upon which saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$, filtered and concentrated under reduced pressure to give 240 mg of a colorless oil. The oil was dissolved in 10 mL of EtOH/H₂O (9:1, v/v) and 0.42 g LiOH added. The reaction mixture was refluxed for 5 h and concentrated under reduced pressure. Water (10 mL) was added and the reaction mixture was extracted with EtOAc (3×10 mL). The combined organic phases were dried over MgSO₄, filtered and concentrated under reduced pressure. The residue was purified via column chromatography over silica gel (hexane/EtOAc 9:1) to give 1-(2-chloro-6-(cyclopropylmethoxy)-4'-(trifluoromethyl)biphenyl-4-yl)-cyclobutanecarboxylic acid (0.210 g) as a white solid (52% yield). ¹H NMR (300 MHz, CDCl₃): δ 7.68 (d, 2H), 7.41 (d, 2H), 7.06 (s, 1H), 6.89 (s, 1H), 3.78 (d, 2H), 2.88 (m, 2H), 2.58 (m, 2H), 2.16 (m, 1H), 1.97 (m, 1H), 1.03 (m, 1H), 0.46 (m, 2H), 0.18 (m, 2H).

Example 1909

1-(2-chloro-6-(cyclopropylmethoxy)-4'-(trifluoromethyl)biphenyl-4-yl)-cyclopentanecarboxylic acid

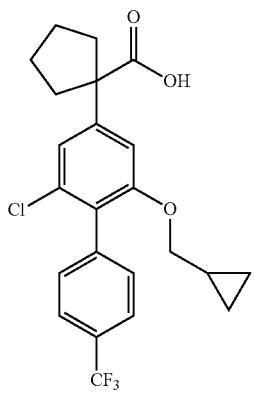 [SMILES: O=C(O)C1(c2cc(Cl)c(-c3ccc(C(F)(F)F)cc3)c(OCC3CC3)c2)CCCC1]

Ethyl 2-(2-chloro-6-(cyclopropylmethoxy)-4'-(trifluoromethyl)biphenyl-4-yl)acetate (0.5 g) was dissolved in 10 mL anhydrous DMF and NaH (60% wt. in oil, 0.13 g, mmol) was added at 0° C. The reaction mixture was stirred for 0.5 h at 25° C. and 1,4-dibromobutane (0.24 g) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), and dried over MgSO₄, filtered and concentrated under reduced pressure to give 380 mg of colorless oil. The oil was dissolved in 10 mL of EtOH/H₂O (9:1, v/v) and 1.0 g LiOH added. The reaction mixture was refluxed for 5 h and concentrated under reduced pressure. Water (10 mL) was added and the reaction mixture was extracted with EtOAc (3×10 mL). The combined organic phases were dried over MgSO₄ filtered and concentrated under reduced pressure. Purification by column chromatography over silica gel (hexane/EtOAc 9:1) gave 1-(2-chloro-6-(cyclopropylmethoxy)-4'-(trifluoromethyl)biphenyl-4-yl)-cyclopentanecarboxylic acid (0.210 g) as a white solid (60%). ¹H NMR (500 MHz, CDCl₃): δ 7.68 (d, 2H), 7.41 (d, 2H), 7.16 (s, 1H), 6.91 (s, 1H), 3.78 (d, 2H), 2.66 (m, 2H), 1.97 (m, 2H), 1.79 (m, 4H), 1.03 (m, 1H), 0.46 (d, 2H), 0.18 (d, 2H).

Example 2491

2-(6-Chloro-5-(cyclopropylmethoxy)-4'-(trifluoromethyl)biphenyl-3-yl)-3-cyclopropylpropanoic acid

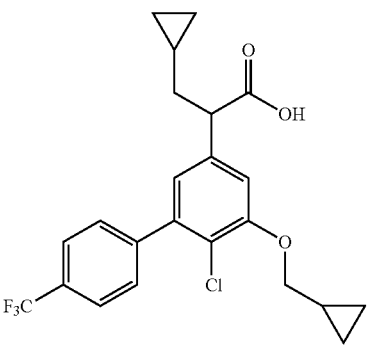

Step 1

Ethyl 3-cyclopropyl-2-(3(cyclopropylmethoxy)-4-nitrophenyl)propanoate

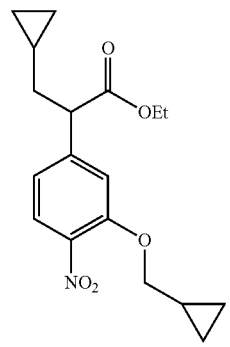

Ethyl 2-(3-(cyclopropylmethoxy)-4-nitrophenyl)acetate (5 g, 17.9 mmol) was dissolved in 50 mL anhydrous DMF, NaH (60% wt. in oil, 0.475 g, 19.7 mmol) was added at 0° C. The reaction mixture was stirred for 0.5 h at 25° C. and cyclopropylmethyl bromide (2.67 g, 19.7 mmol) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), dried over MgSO₄, filtered and concentrated under reduced pressure to give ethyl 3-cyclopropyl-2-(3(cyclopropylmethoxy)-4-nitrophenyl)propanoate (4 g) as a colorless oil.

Step 2

Ethyl 2-(4-amino-3-(cyclopropylmethoxy)phenyl)-3-cyclopropylpropanoate

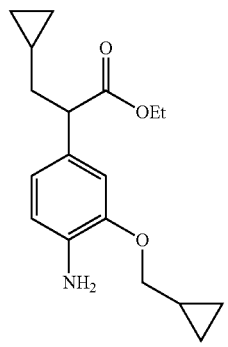 [SMILES: CCOC(=O)C(CC1CC1)c1ccc([N+](=O)[O-])c(OCC2CC2)c1]

To a stirred solution of ethyl 3-cyclopropyl-2-(3(cyclopropylmethoxy)-4-nitrophenyl)propanoate (4.0 g), in dry MeOH (100 mL), Pd(OH)$_2$ (2 g) was added and the mixture was reduced under an atmosphere of H$_2$ for 6 h at room temperature. The reaction mixture was filtered through a pad of Celite™ washing with MeOH. The combined filtrates were concentrated under reduced pressure to yield ethyl 2-(4-amino-3-(cyclopropylmethoxy)phenyl)-3-cyclopropylpropanoate (3.5 g) as a thick liquid.

Step 3

Ethyl 2-(4-amino-3-bromo-5-(Cyclopropylmethoxy)phenyl)-3-cyclopropyl propanoate

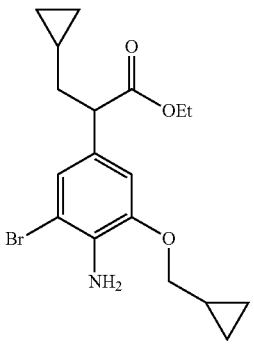 [SMILES: CCOC(=O)C(CC1CC1)c1cc(Br)c(N)c(OCC2CC2)c1]

To a stirred solution of ethyl 2-(4-amino-3-(cyclopropylmethoxy)phenyl)-3-cyclopropylpropanoate (3.0 g, 9.8 mmol) in dry CHCl$_3$ (50 mL), NBS (1.4 g, 7.8 mmol) was added at 0° C. The reaction mixture was allowed to stir for 3 h at room temperature. The reaction mixture was diluted with water and extracted with DCM (2×50 mL). The combined organic extracts were dried over Na$_2$SO$_4$, filtered and concentrated under reduced pressure. The crude reaction mixture was purified by column chromatography to yield the ethyl 2-(4-amino-3-bromo-5-(Cyclopropylmethoxy)phenyl)-3-cyclopropyl propanoate (1.5 g) as a yellow solid.

Step 4

Ethyl 2-(6-amino-5-(cyclopropylmethoxy)-4'-(trifluoromethyl)biphenyl-3-yl)-3-cyclopropylpropanoate

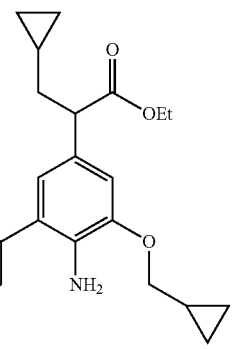

A mixture of ethyl 2-(4-amino-3-bromo-5-(Cyclopropylmethoxy)phenyl)-3-cyclopropyl propanoate (2.8 g, 7.2 mmol), 4-trifluoromethylphenylboronic acid (2.05 g, 18.8 mmol), CsF (2.19 g, 14.5 mmol) and Pd (PPh$_3$)$_4$ (0.837 g, 0.72 mmol) in 30 mL anhydrous 1,2-dimethoxy ethane was refluxed for 8 h under argon. The reaction mixture was cooled to RT, and 75 mL of EtOAc and 75 mL of water were added. The organic phase was separated, dried over NaSO$_4$, filtered and concentrated under reduced pressure to give a yellow oil. The oil was purified by chromatography over silica gel (hexane/EtOAc) to give ethyl 2-(6-amino-5-(cyclopropylmethoxy)-4'-(trifluoromethyl)biphenyl-3-yl)-3-cyclopropylpropanoate (2.5 g) as a yellow oil.

Step 5

Ethyl 2-(6-chloro-5-(cyclopropylmethoxy)-4'-(trifluoromethyl)biphenyl-3-yl)-3-cyclopropylpropanoate

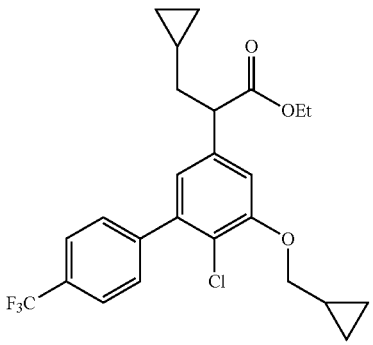

Ethyl 2-(6-amino-5-(cyclopropylmethoxy)-4'-(trifluoromethyl)biphenyl-3-yl)-3-cyclopropylpropanoate (1 g, 2.2 mmol) was dissolved in a mixture of MeCN/H$_2$O/HCl 30 mL/30 mL/2 mL at 0° C. A solution of NaNO$_2$ (0.200 g, 2.9 mmol) in water (10 mL) was added drop wise at 0° C., and the reaction mixture was stirred for 40 min, at the same temperature. A solution of CuCl (1.1 g, 11.1 mmol) in water (10 mL) was added drop wise at 0° C. The reaction mixture was heated to 90° C. for 2.0 h and the mixture was concentrated under reduced pressure. The reaction mixture was extracted with EtOAc (3×50 mL), the combined organic layers were washed with water (50 mL) followed by brine (50 mL), was dried over Na₂SO₄, filtered and concentrated under reduced pressure to give a crude black oil. The oil was purified by chromatography over silica gel (hexane/EtOAc) to give ethyl 2-(6-chloro-5-(cyclopropylmethoxy)-4'-(trifluoromethyl)biphenyl-3-yl)-3-cyclopropylpropanoate (1.1 g) as a yellow oil.

Step 6

2-(6-Chloro-5-(cyclopropylmethoxy)-4'-(trifluoromethyl)biphenyl-3-yl)-3-cyclopropylpropanoic acid

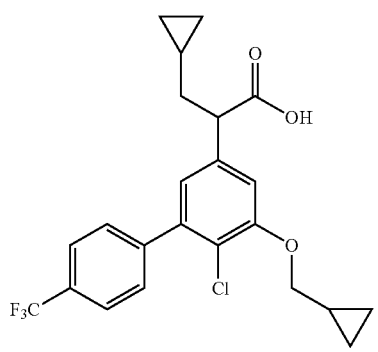 [SMILES: CCOC(=O)C(CC1CC1)c1cc(OCC2CC2)c(Cl)c(-c2ccc(C(F)(F)F)cc2)c1]

2-(6-chloro-5-(cyclopropylmethoxy)-4'-(trifluoromethyl) biphenyl-3-yl)-3-cyclopropylpropanoate (80 mg) was dissolved in 10 mL of MeOH/THF/H₂O (10 mL/10 mL/5 mL) and 57 mg LiOH added. The reaction mixture was stirred at room temperature for 5 h and then concentrated under reduced pressure. Water (10 mL) was added and the reaction mixture was extracted with EtOAc (3×10 mL). The combined organic phases were dried over MgSO₄, filtered and concentrated under reduced pressure. Purification by column chromatography over silica gel (hexane/EtOAc 9:1) gave compound 2-(6-chloro-5-(cyclopropylmethoxy)-4'-(trifluoromethyl)biphenyl-3-yl)-3-cyclopropylpropanoic acid (45 mg) as a white solid. ¹H-NMR (500 MHz, CDCl₃): 7.71 (d, 2H), 7.54 (d, 2H), 6.95 (d, 1H), 6.87 (s, 1H), 3.97 (d, 2H), 3.64 (t, 1H), 2.55 (m, 2H), 1.96 (m, 1H), 1.08 (m, 1H), 0.84 (m, 1H), 0.44 (m, 4H), 0.16 (m, 4H).

Example 2494

1-(6-chloro-5-(cyclopropylmethoxy)-4'-(trifluoromethyl)biphenyl-3-yl)cyclobutanecarboxylic acid

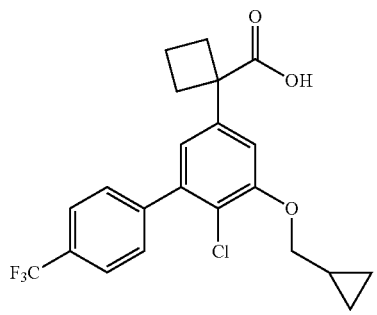 [SMILES: O=C(O)C1(c2cc(OCC3CC3)c(Cl)c(-c3ccc(C(F)(F)F)cc3)c2)CCC1]

Step 1

Ethyl 1-(3-(cyclopropylmethoxy)-4-nitrophenyl)cyclobutanecarboxylate

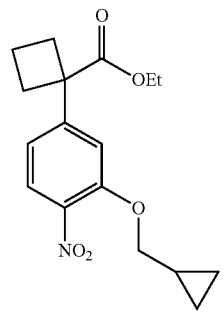

Ethyl 2-(3-(cyclopropylmethoxy)-4-nitrophenyl)acetate (5 g, 17.9 mmol) was dissolved in 50 mL anhydrous DMF, NaH (60% wt. in oil, 1.43 g, 35.9 mmol) was added at 0° C. The reaction mixture was stirred for 0.5 h at 25° C. and 1,3-dibromopropane (1.91 mL, 17.9 mmol) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), dried over MgSO₄, filtered and concentrated under reduced pressure to give ethyl 1-(3-(cyclopropylmethoxy)-4-nitrophenyl)cyclobutanecarboxylate (2.8 g) as a colorless oil.

Step 2

Ethyl 1-(4-amino-3-(cyclopropylmethoxy)phenyl)cyclobutanecarboxylate

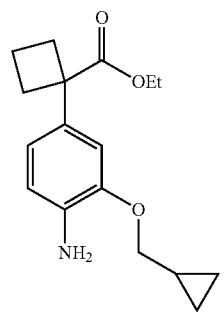 [SMILES: CCOC(=O)C1(c2ccc(N)c(OCC3CC3)c2)CCC1]

To a stirred solution of ethyl 1-(3-(cyclopropylmethoxy)-4-nitrophenyl)cyclobutanecarboxylate (2.8 g), in dry MeOH (100 mL), Pd(OH)₂ (1.2 g) was added and the reaction mixture was reduced under an atmosphere of H₂ for 6 h at room temperature. The reaction mixture was filtered through a pad of Celite™ washing with MeOH. The combined filtrates were concentrated under reduced pressure to yield ethyl 1-(4-amino-3-(cyclopropylmethoxy)phenyl)cyclobutanecarboxylate (2.4 g) as a thick liquid.

Step 3

Ethyl 1-(4-amino-3-bromo-5-(cyclopropylmethoxy)phenyl)cyclobutanecarboxylate

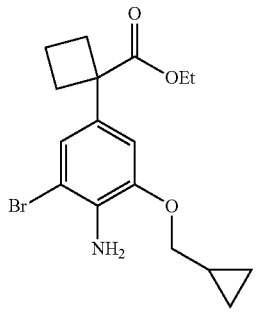 [SMILES: CCOC(=O)C1(c2cc(Br)c(N)c(OCC3CC3)c2)CCC1]

To a stirred solution of ethyl 1-(4-amino-3-(cyclopropylmethoxy)phenyl)cyclobutanecarboxylate (2.4 g, 8.3 mmol) in dry CHCl$_3$ (50 mL), NBS (1.4 g, 7.8 mmol) was added at 0° C. The reaction mixture was allowed to stir for 3 h at room temperature. The reaction mixture was diluted with water, extracted with DCM (2×50 mL), the combined organic extracts were dried over Na$_2$SO$_4$, filtered and concentrated under reduced pressure. The crude reaction mixture was purified by column chromatography to yield ethyl 1-(4-amino-3-bromo-5-(cyclopropylmethoxy)phenyl)cyclobutanecarboxylate (1.5 g) as a yellow solid.

Step 4

Ethyl 1-(6-amino-5-(cyclopropylmethoxy)-4'-(trifluoromethyl)biphenyl-3-yl)cyclobutanecarboxylate

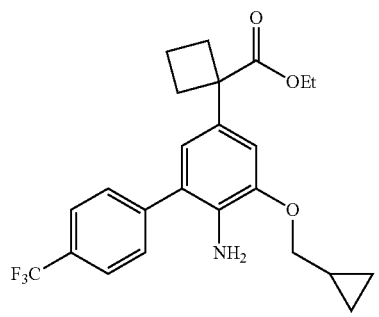 [SMILES: CCOC(=O)C1(c2cc(OCC3CC3)c(N)c(-c3ccc(C(F)(F)F)cc3)c2)CCC1]

A mixture of ethyl 1-(4-amino-3-bromo-5-(cyclopropylmethoxy)phenyl)cyclobutanecarboxylate (0.32 g, 0.86 mmol), 4-trifluoromethylphenylboronic acid (0.246 g, 1.3 mmol), CsF (0.262 g, 1.7 mmol) and Pd (PPh$_3$)$_4$ (0.1 g, 0.08 mmol) in 10 mL anhydrous 1,2-dimethoxy ethane was refluxed for 8 h under argon. The reaction mixture was cooled to RT and 25 mL of EtOAc and 75 mL of water were added. The organic phase was separated, dried over Na$_2$SO$_4$, filtered and concentrated under reduced pressure to give a yellow oil. The oil was purified by chromatography over silica gel (hexane/EtOAc) to give ethyl 1-(6-amino-5-(cyclopropylmethoxy)-4'-(trifluoromethyl)biphenyl-3-yl)cyclobutanecarboxylate (0.290 g) as a yellow oil.

Step 5

Ethyl 1-(6-chloro-5-(cyclopropylmethoxy)-4'-(trifluoromethyl)biphenyl-3-yl)cyclobutanecarboxylate

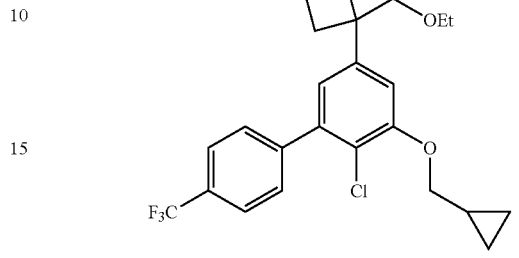

Ethyl 1-(6-amino-5-(cyclopropylmethoxy)-4'-(trifluoromethyl)biphenyl-3-yl)cyclobutanecarboxylate (0.280 g, 0.64 mmol) was dissolved in a mixture of MeCN/H$_2$O/HCl 10 mL/10 mL/4 mL at 0° C. A solution of NaNO$_2$ (0.066 g, 0.96 mmol) in water (2 mL) was added drop wise at 0° C., and the reaction mixture was stirred for 40 min, at the same temperature. A solution of CuCl (0.32 g, 3.2 mmol) in water (2 mL) was added drop wise at 0° C. The reaction mixture was heated to 70° C. for 1 h and the solvent was evaporated under reduced pressure. The reaction mixture was extracted with EtOAc (3×50 mL), and the combined organic layers were washed with water (50 mL) followed by brine (50 mL). The solution was dried over Na$_2$SO$_4$, filtered and concentrated to give crude black oil which was purified by chromatography over silica gel (hexane/EtOAc) to give ethyl 1-(6-chloro-5-(cyclopropylmethoxy)-4'-(trifluoromethyl)biphenyl-3-yl)cyclobutanecarboxylate (0.110 g) as yellow oil.

Step 6

1-(6-chloro-5-(cyclopropylmethoxy)-4'-(trifluoromethyl)biphenyl-3-yl)cyclobutanecarboxylic acid

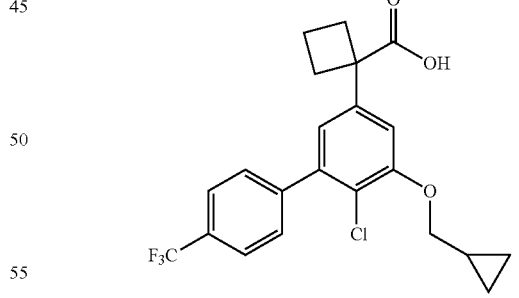

Ethyl 1-(6-chloro-5-(cyclopropylmethoxy)-4'-(trifluoromethyl)biphenyl-3-yl)cyclobutanecarboxylate (0.1 g) dissolved in MeOH/THF/H$_2$O (10 mL/10 mL/5 mL) and 70 mg LiOH added. The reaction mixture was stirred at room temperature for 5 h and concentrated under reduced pressure. Water (10 mL) was added and the reaction mixture was extracted with EtOAc (3×10 mL). The combined organic extracts were dried over MgSO$_4$, filtered and evaporated under reduced pressure. Purification by column chromatography over silica gel (hexane/EtOAc 9:1) gave 1-(6-chloro- 5-(cyclopropylmethoxy)-4'-(trifluoromethyl)biphenyl-3-yl)cyclobutanecarboxylic acid (75 mg) as a white solid. ¹H-NMR (500 MHz, CDCl₃): 7.71 (d, 2H), 7.54 (d, 2H), 6.86 (s, 1H), 6.85 (s, 1H), 3.97 (d, 2H), 2.85 (m, 2H), 2.54 (m, 2H), 2.13 (m, 1H), 1.92 (m, 1H), 1.35 (t, 1H), 0.47 (m, 2H), 0.41 (m, 2H).

Example 2495

1-(6-chloro-5-(cyclopropylmethoxy)-4'-(trifluoromethyl)biphenyl-3-yl)cyclopentanecarboxylic acid

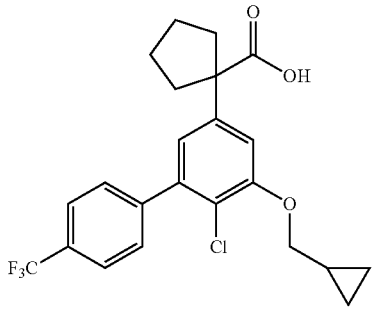 [SMILES: O=C(O)C1(c2cc(OCC3CC3)c(Cl)c(-c3ccc(C(F)(F)F)cc3)c2)CCCC1]

Step 1

Ethyl 1-(3-(cyclopropylmethoxy)-4-nitrophenyl)cyclopentanecarboxylate

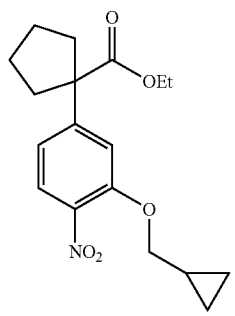 [SMILES: CCOC(=O)C1(c2ccc([N+](=O)[O-])c(OCC3CC3)c2)CCCC1]

Ethyl 2-(3-(cyclopropylmethoxy)-4-nitrophenyl)acetate (0.5 g) was dissolved in 10 mL anhydrous DMF and NaH (60% wt. in oil, 0.13 g, mmol) was added at 0° C. The reaction mixture was stirred for 0.5 h at 25° C. and 1,4-dibromobutane (0.24 g, mmol) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), and dried over MgSO₄, filtered and concentrated under reduced pressure to give ethyl 1-(3-(cyclopropylmethoxy)-4-nitrophenyl)cyclopentanecarboxylate (380 mg) as a colorless oil.

Step 2

Ethyl 1-(4-amino-3-(cyclopropylmethoxy)phenyl)cyclopentanecarboxylate

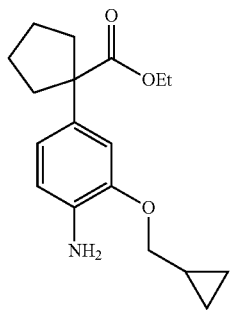 [SMILES: CCOC(=O)C1(c2ccc(N)c(OCC3CC3)c2)CCCC1]

To a stirred solution of ethyl 1-(3-(cyclopropylmethoxy)-4-nitrophenyl)cyclopentanecarboxylate (10 g), in dry MeOH (100 mL) Pd (OH)₂ (2 g) was added and the mixture was reduced under an atmosphere of H₂ for 6 h at room temperature. The mixture was filtered through a pad of Celite™, washing with MeOH. The combined filtrates were concentrated under reduced pressure to yield ethyl 1-(4-amino-3-(cyclopropylmethoxy)phenyl)cyclopentanecarboxylate (7.5 g) as a thick liquid.

Step 3

Ethyl 1-(4-amino-3-bromo-5-(cyclopropylmethoxy)phenyl)cyclopentanecarboxylate

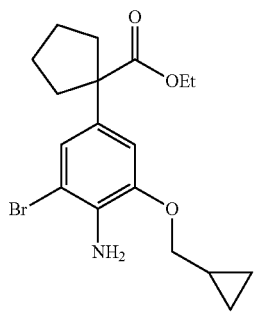 [SMILES: CCOC(=O)C1(c2cc(Br)c(N)c(OCC3CC3)c2)CCCC1]

To a stirred solution of ethyl 1-(4-amino-3-(cyclopropylmethoxy)phenyl)cyclopentanecarboxylate (1.2 g, 4.0 mmol) in dry CCl₄ (60 mL), NBS (0.427 g, 3.2 mmol) was added at 0° C. The reaction mixture was allowed to stir for 3 at room temperature to complete the reaction. The reaction mixture was diluted with water, extracted with DCM (2×50 mL), the combined organic extracts were dried over Na₂SO₄, filtered and concentrated under reduced pressure. The crude reaction mixture was purified by column chromatography to yield ethyl 1-(4-amino-3-bromo-5-(cyclopropylmethoxy)phenyl)cyclopentanecarboxylate (920 mg) as a yellow solid.

Step 4

Ethyl 1-(6-amino-5-(cyclopropylmethoxy)-4'-(trifluoromethyl)biphenyl-3-yl)cyclopentanecarboxylate

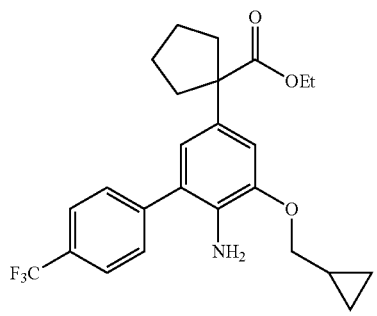

A mixture of ethyl 1-(4-amino-3-bromo-5-(cyclopropylmethoxy)phenyl)cyclopentanecarboxylate (5.1 g, 14 mmol), 4-trifluoromethylphenylboronic acid (3.36 g, 17 mmol), CsF (0.28 g, 1.84 mmol) and Pd (PPh$_3$)$_4$ (0.410 g, 0.4 mmol) in 75 mL anhydrous 1,2-dimethoxy ethane was refluxed for 8 h under argon. The reaction mixture was cooled, and 75 mL of EtOAc and 75 mL of water were added. The organic phase was separated, dried over Na$_2$SO$_4$, filtered and concentrated under reduced pressure to yellow oil. The oil was purified by chromatography over silica gel (hexane/EtOAc) to give ethyl 1-(6-amino-5-(cyclopropylmethoxy)-4'-(trifluoromethyl)biphenyl-3-yl)cyclopentanecarboxylate (4.6 g) as a yellow oil.

Step 5

Ethyl 1-(6-chloro-5-(cyclopropylmethoxy)-4'-(trifluoromethyl)biphenyl-3-yl)cyclopentanecarboxylate

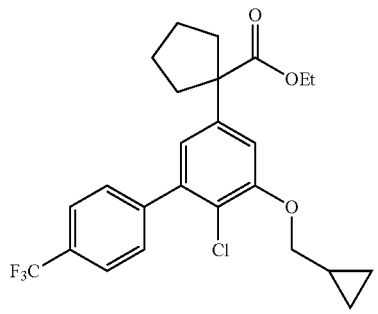

Ethyl 1-(6-amino-5-(cyclopropylmethoxy)-4'-(trifluoromethyl)biphenyl-3-yl)cyclopentanecarboxylate (1 g, 2.2 mmol) was dissolved in a mixture of MeCN/H$_2$O/HCl 30 mL/30 mL/2 mL at 0° C. A solution of NaNO$_2$ (0.200 g, 2.9 mmol) in water (10 mL) was added drop wise at 0° C., and the reaction mixture was stirred for 40 min, at the same temperature. A solution of CuCl (1.1 g, 11.1 mmol) in water (10 mL) was added drop wise at 0° C. The reaction mixture was heated to 90° C. for 2.0 h and the solvent was evaporated. The reaction mixture was extracted with EtOAc (3×50 mL), and the combined organic layers were washed with water (50 mL) followed by brine (50 mL). The solution was dried over Na$_2$SO$_4$, filtered and concentrated under reduced pressure to give a crude black oil. The oil was purified by chromatography over silica gel (hexane/EtOAc) to give ethyl 1-(6-chloro-5-(cyclopropylmethoxy)-4'-(trifluoromethyl)biphenyl-3-yl)cyclopentanecarboxylate as yellow oil (1.1 g).

Step 6

1-(6-chloro-5-(cyclopropylmethoxy)-4'-(trifluoromethyl)biphenyl-3-yl)cyclopentanecarboxylic acid

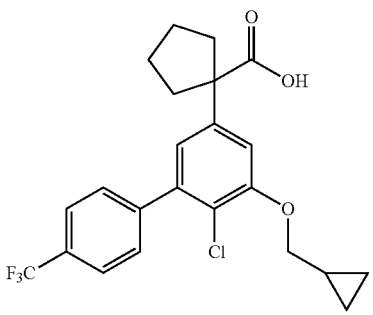 [SMILES: O=C(O)C1(c2cc(OCC3CC3)c(Cl)c(-c3ccc(C(F)(F)F)cc3)c2)CCCC1]

Ethyl 1-(6-chloro-5-(cyclopropylmethoxy)-4'-(trifluoromethyl)biphenyl-3-yl)cyclopentanecarboxylate (80 mg) dissolved in 10 mL of MeOH/THF/H$_2$O (10 mL/10 mL/5 mL) and 57 mg LiOH added. The reaction mixture was stirred at room temperature for 5 h and concentrated under reduced pressure. Water (10 mL) was added and the reaction mixture was extracted with EtOAc (3×10 mL). The combined organic phases were dried over MgSO$_4$, filtered and concentrated under reduced pressure. Purification by column chromatography over silica gel (hexane/EtOAc 9:1) gave 1-(6-chloro-5-(cyclopropylmethoxy)-4'-(trifluoromethyl)biphenyl-3-yl) cyclopentane carboxylic acid (45 mg) as a white solid. $^1$H-NMR (500 MHz, CDCl$_3$): 7.68 (d, 2H), 7.55 (d, 2H), 6.99 (s, 1H), 6.97 (s, 1H), 3.97 (d, 2H), 2.64 (m, 2H), 1.95 (m, 2H), 1.77 (m, 4H), 1.21 (m, 1H), 0.45 (m, 2H), 0.18 (m, 2H);

Example 2419

2-(6-Chloro-5-(2,2,2-trifluoroethoxy)-4'-(trifluoromethyl)biphenyl-3-yl)-3-cyclopropylpropanoic acid

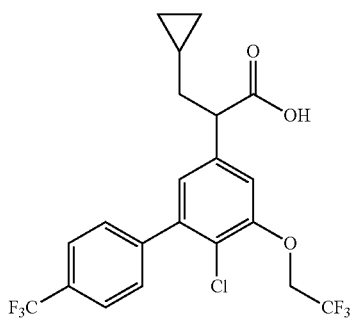 [SMILES: O=C(O)C(CC1CC1)c1cc(OCC(F)(F)F)c(Cl)c(-c2ccc(C(F)(F)F)cc2)c1]

Step 1

Ethyl 3-cyclopropyl-2-(4-nitro-3-(2,2,2-trifluoroethoxy)phenyl)propanoate

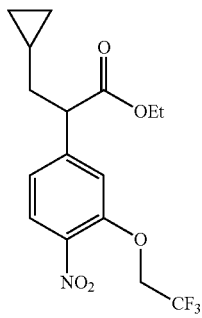 [SMILES: CCOC(=O)C(CC1CC1)c1ccc([N+](=O)[O-])c(OCC(F)(F)F)c1]

Ethyl 2-(4-nitro-3-(2,2,2-trifluoroethoxy)phenyl)acetate (2 g, 6.5 mmol) was dissolved in 50 mL anhydrous DMF, NaH (60% wt. in oil, 0.171 g, 7.1 mmol) was added at 0° C. The reaction mixture was stirred for 0.5 h at 25° C. and cyclopropylmethyl bromide (0.967 g, 7.16 mmol) was added drop wise at 0° C. The reaction mixture was stirred at 0° C. for 1 h and saturated NH$_4$Cl solution (10 mL) was added. The reaction mixture was extracted with EtOAc (3×20 mL) and the combined organic phases were washed with water (3×20 mL) and brine (20 mL), dried over MgSO$_4$, filtered and concentrated under reduced pressure to give ethyl 3-cyclopropyl-2-(4-nitro-3-(2,2,2-trifluoroethoxy)phenyl)propanoate (1.05 g) as a colorless oil.

Step 2

Ethyl 2-(4-amino-3-(2,2,2-trifluoroethoxy)phenyl)-3-cyclopropylpropanoate

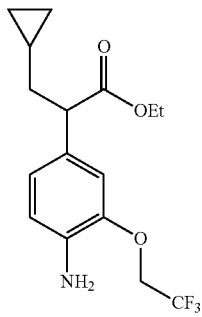

To a stirred solution of ethyl 3-cyclopropyl-2-(4-nitro-3-(2,2,2-trifluoroethoxy)phenyl)propanoate (1.0 g), in dry MeOH (100 mL) Pd(OH)$_2$ (500 mg) was added and the mixture was reduced under an atmosphere of H$_2$ for 6 h at room temperature. The mixture was filtered off through a pad of Celite™, washing with MeOH. The combined filtrates were concentrated under reduced pressure to give ethyl 2-(4-amino-3-(2,2,2-trifluoroethoxy)phenyl)-3-cyclopropylpropanoate (0.9 g) as a thick liquid.

Step 3

Ethyl 2-(4-amino-3-bromo-5-(2,2,2-trifluoroethoxy)phenyl)-3-cyclopropylpropanoate

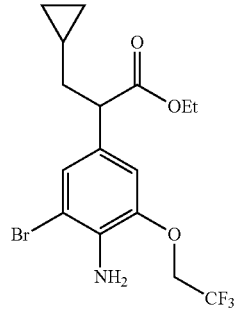

To a stirred solution of ethyl 2-(4-amino-3-(2,2,2-trifluoroethoxy)phenyl)-3-cyclopropylpropanoate (0.9 g, 2.7 mmol) in dry CHCl$_3$ (50 mL), NBS (0.412 g, 2.3 mmol) was added at 0° C. The reaction mixture was allowed to stir for 3 h at room temperature to complete the reaction. The reaction mixture was diluted with water, extracted with DCM (2×50 mL), the combined organic solvents was dried over Na$_2$SO$_4$, filtered and concentrated under reduced pressure. The crude reaction mixture was purified by column chromatography to give ethyl 2-(4-amino-3-bromo-5-(2,2,2-trifluoroethoxy)phenyl)-3-cyclopropylpropanoate (1.02 g) as a yellow solid.

Step 4

Ethyl 2-(6-amino-5-(2,2,2-trifluoroethoxy)-4'-(trifluoromethyl)biphenyl-3-yl)-3-cyclopropylpropanoate

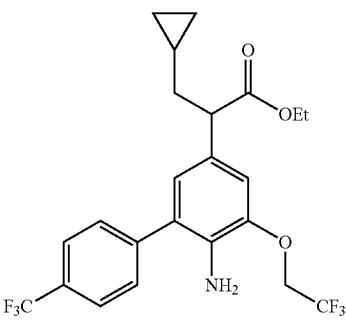 [SMILES: CCOC(=O)C(CC1CC1)c1cc(OCC(F)(F)F)c(N)c(-c2ccc(C(F)(F)F)cc2)c1]

A mixture of ethyl 2-(4-amino-3-bromo-5-(2,2,2-trifluoroethoxy)phenyl)-3-cyclopropylpropanoate (1.1, 3.3 mmol), 4-trifluoromethylphenylboronic acid (1.26 g, 6.7 mmol), CsF (1.26 g, 8.3 mmol) and Pd (PPh$_3$)$_4$ (0.38 g, 0.33 mmol) in 50 mL anhydrous 1,2-dimethoxy ethane was refluxed for 8 h under argon. The reaction mixture was cooled, and 50 mL of EtOAc and 50 mL of water were added. The organic phase was separated, dried over Na$_2$SO$_4$, filtered and concentrated under reduced pressure to give a yellow oil. The oil was purified by chromatography over silica gel (hexane/EtOAc) to give ethyl 2-(6-amino-5-(2,2,2-trifluoroethoxy)-4'-(trifluoromethyl)biphenyl-3-yl)-3-cyclopropylpropanoate (0.85 g, 82% yield) as a white solid.

Step 5

Ethyl 2-(6-chloro-5-(2,2,2-trifluoroethoxy)-4'-(trifluoromethyl)biphenyl-3-yl)-3-cyclopropylpropanoate

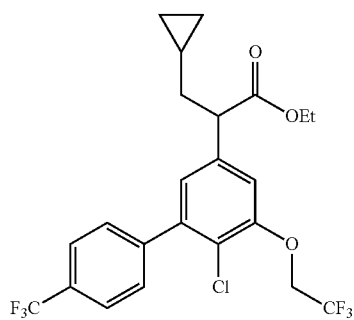 [SMILES: O=C(O)C(CC1CC1)c1cc(OCC(F)(F)F)c(Cl)c(-c2ccc(C(F)(F)F)cc2)c1]

Ethyl 2-(6-amino-5-(2,2,2-trifluoroethoxy)-4'-(trifluoromethyl)biphenyl-3-yl)-3-cyclopropylpropanoate (0.85 g, 1.78 mmol) was dissolved in a mixture of MeCN/H₂O/HCl 15 mL/15 mL/2 mL at 0° C. A solution of NaNO₂ (0.185 g, 2.68 mmol) in water (2 mL) was added drop wise at 0° C., and the reaction mixture was stirred for 40 min, at the same temperature. A solution of CuCl (1.8 g, 17.8 mmol) in water (10 mL) was added drop wise at 0° C. The reaction mixture was heated to 90° C. for 2 h. The reaction mixture was extracted with EtOAc (3×50 mL), and the combined organic layers were washed with water (50 mL) followed by brine (50 mL). The solution was dried over Na₂SO₄, filtered and concentrated under reduced pressure to give an oil. The oil was purified by chromatography over silica gel (hexane/EtOAc) to give ethyl 2-(6-chloro-5-(2,2,2-trifluoroethoxy)-4'-(trifluoromethyl)biphenyl-3-yl)-3-cyclopropylpropanoate (0.528 g) as a yellow oil.

Step 6

2-(6-Chloro-5-(2,2,2-trifluoroethoxy)-4'-(trifluoromethyl)biphenyl-3-yl)-3-cyclopropylpropanoic acid

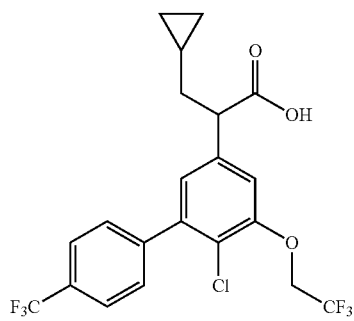

The ethyl 2-(6-chloro-5-(2,2,2-trifluoroethoxy)-4'-(trifluoromethyl)biphenyl-3-yl)-3-cyclopropylpropanoate (500 mg, 1.01 mmol) dissolved in 20 mL of MeOH/THF/H₂O (10 mL/10 mL/5 mL) and LiOH (57 mg) was added. The reaction mixture was stirred at room temperature for 5 h and concentrated under reduced pressure. Water (10 mL) was added and the reaction mixture was extracted with EtOAc (3×10 mL). The combined organic phases were dried over MgSO₄, filtered and concentrated under reduced pressure. Purification by column chromatography over silica gel (hexane/EtOAc 9:1) gave 2-(6-chloro-5-(2,2,2-trifluoroethoxy)-4'-(trifluoromethyl)biphenyl-3-yl)-cyclopropylpropanoic acid (250 mg) as a white solid. ¹H-NMR (500 MHz, CDCl₃): 7.72 (d, 2H), 7.54 (d, 2H), 7.02 (d, 2H), 4.44 (q, 2H), 3.72 (t, 1H), 1.92 (m, 1H), 1.79 (m, 1H), 1.08 (m, 1H), 0.66 (m, 1H), 0.44 (m, 2H), 0.16 (m, 2H).

Example 2422

Ethyl 1-(6-chloro-5-(2,2,2-trifluoroethoxy)-4'-(trifluoromethyl)biphenyl-3-yl)cyclobutanecarboxylate

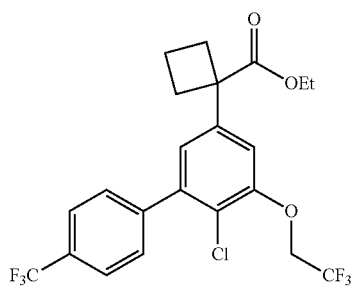

Step 1

Ethyl 1-(4-nitro-3-(2,2,2-trifluoroethoxy)phenyl)cyclobutanecarboxylate

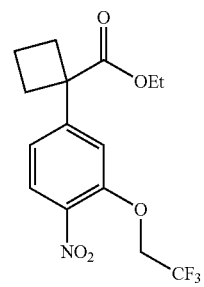 [SMILES: CCOC(=O)C1(c2ccc([N+](=O)[O-])c(OCC(F)(F)F)c2)CCC1]

Ethyl 2-(4-nitro-3-(2,2,2-trifluoroethoxy)phenyl)acetate (3 g, 9.7 mmol) was dissolved in 50 mL anhydrous DMF, NaH (60% wt. in oil, 0.514 g, 10.7 mmol) was added at 0° C. The reaction mixture was stirred for 0.5 h at 25° C. and 1,3-dibromopropane (1.03 mL, 9.7 mmol) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), dried over MgSO₄, filtered and concentrated under reduced pressure to give ethyl 1-(4-nitro-3-(2,2,2-trifluoroethoxy)phenyl)cyclobutanecarboxylate (900 mg) as a colorless oil.

Step 2

Ethyl 1-(4-amino-3-(2,2,2-trifluoroethoxy)phenyl)cyclobutanecarboxylate

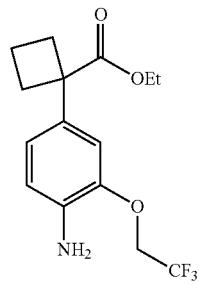

To a stirred solution of ethyl 1-(4-nitro-3-(2,2,2-trifluoroethoxy)phenyl)cyclobutanecarboxylate (900 mg), in dry MeOH (50 mL), Pd(OH)$_2$ (400 mg) was added and the mixture reduced under an atmosphere of H$_2$ for 6 h at room temperature. The mixture was filtered through a pad of Celite™ washing with MeOH, the combined filtrates were concentrated under reduced pressure to yield ethyl 1-(4-amino-3-(2,2,2-trifluoroethoxy)phenyl)cyclobutanecarboxylate (800 mg) as a thick liquid.

Step 3

Ethyl 1-(4-amino-3-bromo-5-(2,2,2-trifluoroethoxy)phenyl)cyclobutanecarboxylate

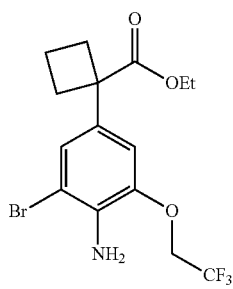

To a stirred solution of ethyl 1-(4-amino-3-(2,2,2-trifluoroethoxy)phenyl)cyclobutanecarboxylate (2.4 g, 8.3 mmol) in dry CHCl$_3$ (50 mL), NBS (1.4 g, 7.8 mmol) was added at 0° C. The reaction mixture was allowed to stir for 3 h at room temperature to complete the reaction. The reaction mixture was diluted with water, extracted with DCM (2×50 mL), the combined organic solvents were dried over Na$_2$SO$_4$, filtered and concentrated under educed pressure. The crude reaction mixture was purified by column chromatography to give ethyl 1-(4-amino-3-bromo-5-(2,2,2-trifluoroethoxy)phenyl)cyclobutanecarboxylate (1.5 g) as a yellow solid.

Step 4

Ethyl 1-(6-amino-5-(2,2,2-trifluoroethoxy)-4'-(trifluoromethyl)biphenyl-3-yl)cyclobutanecarboxylate

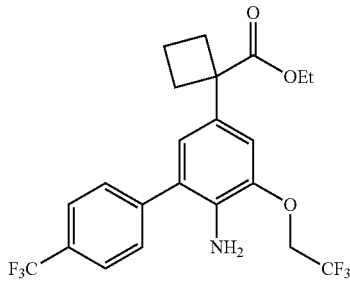 [SMILES: CCOC(=O)C1(c2cc(OCC(F)(F)F)c(N)c(-c3ccc(C(F)(F)F)cc3)c2)CCC1]

A mixture of ethyl 1-(4-amino-3-bromo-5-(2,2,2-trifluoroethoxy)phenyl)cyclobutanecarboxylate (0.32 g, 0.86 mmol), 4-trifluoromethylphenylboronic acid (0.246 g, 1.3 mmol), CsF (0.262 g, 1.7 mmol) and Pd (PPh$_3$)$_4$ (0.1 g, 0.08 mmol) in 10 mL anhydrous 1,2-dimethoxy ethane was refluxed for 8 h under argon. The reaction mixture was cooled, and 25 mL of EtOAc and 75 mL of water were added. The organic phase was separated, dried over Na$_2$SO$_4$, filtered and concentrated under reduced pressure to give a yellow oil. The oil was purified by chromatography over silica gel (hexane/EtOAc) to give ethyl 1-(6-amino-5-(2,2,2-trifluoroethoxy)-4'-(trifluoromethyl)biphenyl-3-yl)cyclobutanecarboxylate (0.290 g) as a yellow oil.

Step 5

Ethyl 1-(6-chloro-5-(2,2,2-trifluoroethoxy)-4'-(trifluoromethyl)biphenyl-3-yl)cyclobutanecarboxylate

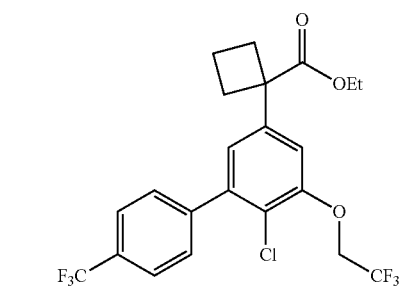 [SMILES: O=C(O)C1(c2cc(OCC(F)(F)F)c(Cl)c(-c3ccc(C(F)(F)F)cc3)c2)CCC1]

Ethyl 1-(6-amino-5-(2,2,2-trifluoroethoxy)-4'-(trifluoromethyl)biphenyl-3-yl)cyclobutanecarboxylate (0.280 g, 0.64 mmol) was dissolved in a mixture of MeCN/H$_2$O/HCl 10 mL/10 mL/4 mL at 0° C. A solution of NaNO$_2$ (0.066 g, 0.96 mmol) in water (2 mL) was added drop wise at 0° C., and the reaction mixture was stirred for 40 min, at the same temperature. A solution of CuCl (0.32 g, 3.2 mmol) in water (2 mL) was added drop wise at 0° C. The reaction mixture was heated to 70° C. for 1 h and the solvent was evaporated. The reaction mixture was extracted with EtOAc (3×50 mL), and the combined organic layers were washed with water (50 mL) followed by brine (50 mL). The solution was dried over Na$_2$SO$_4$, filtered and concentrated to give oil. The oil was purified by chromatography over silica gel (hexane/EtOAc) to give ethyl 1-(6-chloro-5-(2,2,2-trifluoroethoxy)-4'-(trifluoromethyl)biphenyl-3-yl)cyclobutanecarboxylate as a yellow oil (0.110 g).

Step 6

1-(6-chloro-5-(2,2,2-trifluoroethoxy)-4'-(trifluoromethyl)biphenyl-3-yl)cyclobutanecarboxylic acid

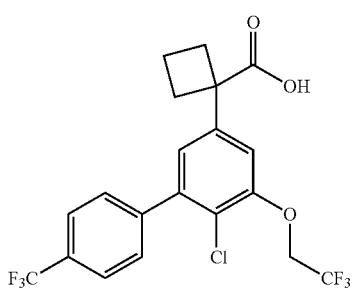

Ethyl 1-(6-chloro-5-(2,2,2-trifluoroethoxy)-4'-(trifluoromethyl)biphenyl-3-yl)cyclobutanecarboxylate (0.1 g) dissolved in MeOH/THF/H$_2$O (10 mL/10 mL/5 mL) and 70 mg LiOH added. The reaction mixture was stirred at room temperature for 5 h and concentrated under reduced pressure. Water (10 mL) was added and the reaction mixture was extracted with EtOAc (3×10 mL). The combined organic phases were dried over MgSO$_4$, filtered and evaporated under reduced pressure. Purification by column chromatography over silica gel (hexane/EtOAc 9:1) gave 1-(6-chloro-5-(2,2, 2-trifluoroethoxy)-4'-(trifluoromethyl)biphenyl-3-yl)cyclobutanecarboxylic acid (75 mg) of the product as a white solid. $^1$H-NMR (500 MHz, CDCl$_3$): 7.74 (d, 2H), 7.53 (d, 2H), 6.99 (s, 1H), 6.97 (s, 1H), 4.43 (q, 2H), 2.88 (m, 2H), 2.54 (m, 2H), 2.15 (m, 1H), 1.93 (m, 1H)

Example 2423

1-(6-Chloro-5-(2,2,2-trifluoroethoxy)-4'-(trifluoromethyl)biphenyl-3-yl)cyclopentanecarboxylic acid

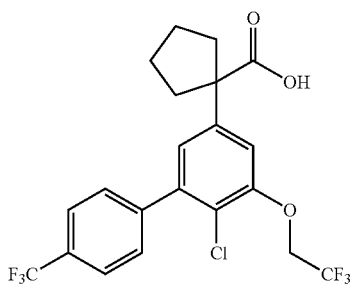 [SMILES: O=C(O)C1(c2cc(OCC(F)(F)F)c(Cl)c(-c3ccc(C(F)(F)F)cc3)c2)CCCC1]

Step 1

Ethyl 1-(4-nitro-3-(2,2,2-trifluoroethoxy)phenyl)cyclopentanecarboxylate

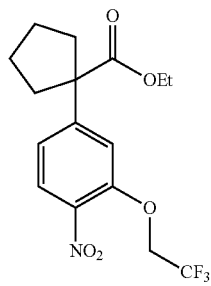 [SMILES: CCOC(=O)C1(c2ccc([N+](=O)[O-])c(OCC(F)(F)F)c2)CCCC1]

Ethyl 2-(4-nitro-3-(2,2,2-trifluoroethoxy)phenyl)acetate (0.5 g, mmol) was dissolved in 10 mL anhydrous DMF and NaH (60% wt. in oil, 0.13 g, mmol) was added at 0° C. The reaction mixture was stirred for 0.5 h at 25° C. and 1,4-dibromobutane (0.24 g, mmol) was added drop wise at 0° C. The reaction mixture was stirred at 0° C. for 1 h and saturated NH$_4$Cl solution (10 mL) was added. The reaction mixture was extracted with EtOAc (3×20 mL) and the combined organic phases were washed with water (3×20 mL) and brine (20 mL), dried over MgSO$_4$, filtered and concentrated under reduced pressure to give ethyl 1-(4-nitro-3-(2,2,2-trifluoroethoxy) phenyl)cyclopentane carboxylate (380 mg) as a colorless oil.

Step 2

Ethyl 1-(4-amino-3-(2,2,2-trifluoroethoxy)phenyl)cyclopentanecarboxylate

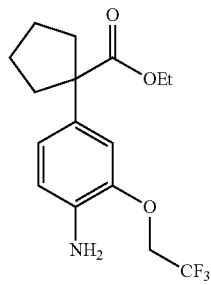 [SMILES: CCOC(=O)C1(c2ccc(N)c(OCC(F)(F)F)c2)CCCC1]

To a stirred solution of ethyl 1-(4-nitro-3-(2,2,2-trifluoroethoxy)phenyl)cyclopentane carboxylate (10 g), in dry MeOH (100 mL) Pd(OH)$_2$ (2 g) was added and reduced under an atmosphere of H$_2$ for 6 h at room temperature. The mixture was filtered through a pad of Celite™ washing with MeOH. The combined filtrates were concentrated under reduced pressure to yield ethyl 1-(4-amino-3-(2,2,2-trifluoroethoxy) phenyl)cyclopentanecarboxylate (7.5 g) as a thick liquid.

Step 3

Ethyl 1-(4-amino-3-bromo-5-(2,2,2-trifluoroethoxy)phenyl)cyclopentanecarboxylate

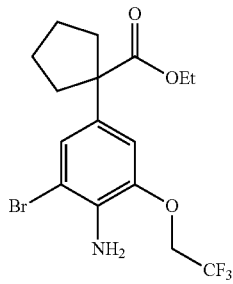

To a stirred solution of ethyl 1-(4-amino-5-(2,2,2-trifluoroethoxy)phenyl)cyclopentanecarboxylate (1.2 g, 4.0 mmol) in dry CCl$_4$ (60 mL), NBS (0.427 g, 3.2 mmol) was added at 0° C. The reaction mixture was allowed to stir for 3 h at room temperature. The reaction mixture was diluted with water, extracted with DCM (2×50 mL), the combined organic solvents was dried over Na$_2$SO$_4$, filtered and concentrated under reduced pressure. The crude reaction mixture was purified by column chromatography to give ethyl 1-(4-amino-3-bromo-5-(2,2,2-trifluoroethoxy)phenyl)cyclopentanecarboxylate (920 mg) as a yellow solid.

Step 4

Ethyl 1-(6-amino-5-(2,2,2-trifluoroethoxy)-4'-(trifluoromethyl)biphenyl-3-yl)cyclopentanecarboxylate

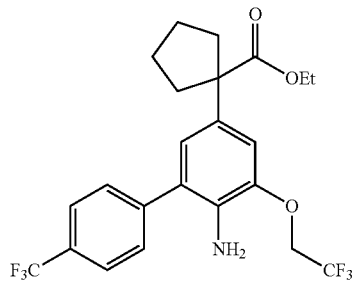 [SMILES: CCOC(=O)C1(c2cc(OCC(F)(F)F)c(N)c(-c3ccc(C(F)(F)F)cc3)c2)CCCC1]

A mixture of ethyl 1-(4-amino-3-bromo-5-(2,2,2-trifluoroethoxy)phenyl)cyclopentanecarboxylate (5.1 g, 14 mmol), 4-trifluoromethylphenylboronic acid (3.36 g, 17 mmol), CsF (0.28 g, 1.84 mmol) and Pd(PPh$_3$)$_4$ (0.410 g, 0.4 mmol) in 75 mL anhydrous 1,2-dimethoxy ethane was refluxed for 8 h under argon. The reaction mixture was cooled, and 75 mL of EtOAc and 75 mL of water were added. The organic phase was separated, dried over Na$_2$SO$_4$, filtered and concentrated under reduced pressure to yellow oil. The oil was purified by chromatography over silica gel (hexane/EtOAc) to give ethyl 1-(6-amino-5-(2,2,2-trifluoroethoxy)-4'-(trifluoromethyl)biphenyl-3-yl)cyclopentanecarboxylate (4.6 g) as a yellow oil.

Step 5

Ethyl 1-(6-chloro-5-(2,2,2-trifluoroethoxy)-4'-(trifluoromethyl)biphenyl-3-yl)cyclopentanecarboxylate

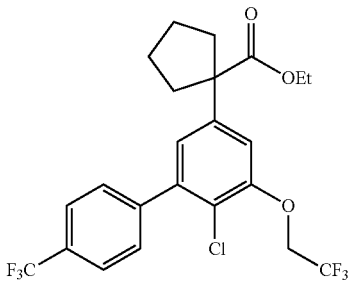 [SMILES: O=C(O)C1(c2cc(OCC(F)(F)F)c(Cl)c(-c3ccc(C(F)(F)F)cc3)c2)CCCC1]

Ethyl 1-(6-amino-5-(2,2,2-trifluoroethoxy)-4'-(trifluoromethyl)biphenyl-3-yl)cyclopentanecarboxylate (1 g, 2.2 mmol) was dissolved in a mixture of MeCN/H$_2$O/HCl 30 mL/30 mL/2 mL at 0° C. A solution of NaNO$_2$ (0.200 g, 2.9 mmol) in water (10 mL) was added drop wise at 0° C., and the reaction mixture was stirred for 40 min, at the same temperature. A solution of CuCl (1.1 g, 11.1 mmol) in water (10 mL) was added drop wise at 0° C. The reaction mixture was heated to 90° C. for 2.0 h and the solvent was evaporated. The reaction mixture was extracted with EtOAc (3×50 mL), and the combined organic layers were washed with water (50 mL) followed by brine (50 mL). The solution was dried over Na$_2$SO$_4$, filtered and concentrated under reduced pressure to give an oil. The oil was purified by chromatography over silica gel (hexane/EtOAc) to give the ethyl 1-(6-chloro-5-(2,2,2-trifluoroethoxy)-4'-(trifluoromethyl)biphenyl-3-yl)cyclopentane carboxylate (1.1 g) as yellow oil.

Step 6

1-(6-Chloro-5-(2,2,2-trifluoroethoxy)-4'-(trifluoromethyl)biphenyl-3-yl)cyclopentanecarboxylic acid

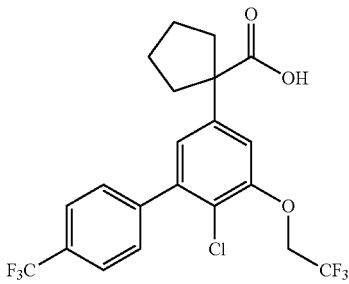

The ethyl 1-(6-chloro-5-(2,2,2-trifluoroethoxy)-4'-(trifluoromethyl)biphenyl-3-yl)cyclopentane carboxylate (80 mg) dissolved in 10 mL of MeOH/THF/H$_2$O (10 mL/10 mL/5 mL) and 57 mg LiOH added. The reaction mixture was stirred at room temperature for 5 h and concentrated under reduced pressure. Water (10 mL) was added and the reaction mixture was extracted with EtOAc (3×10 mL). The combined organic phases were dried over MgSO$_4$, filtered and concentrated under reduced pressure. Purification by column chromatography over silica gel (hexane/EtOAc 9:1) gave 1-(6-Chloro-5-(2,2,2-trifluoroethoxy)-4'-(trifluoromethyl)biphenyl-3-yl) cyclopentane carboxylic acid (45 mg) as a white solid.

¹H-NMR (500 MHz, CDCl₃): 7.74 (d, 2H), 7.55 (d, 2H), 7.08 (s, 1H), 4.44 (q, 2H), 2.66 (m, 2H), 1.98 (m, 2H), 1.78 (m, 4H).

Example 2418

2-(6-Chloro-5-(2,2,2-trifluoroethoxy)-4'-(trifluoromethyl)biphenyl-3-yl)-4-methylpentanoic acid

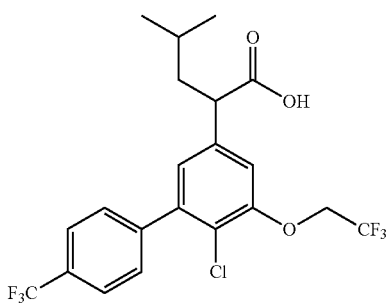 [SMILES: CC(C)CC(C(=O)O)c1cc(OCC(F)(F)F)c(Cl)c(-c2ccc(C(F)(F)F)cc2)c1]

Step 1

Ethyl 4-methyl-2-(4-nitro-3-(2,2,2-trifluoroethoxy)phenyl)pentanoate

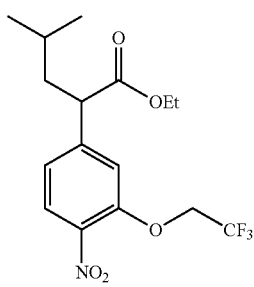

Ethyl 2-(4-nitro-3-(2,2,2-trifluoroethoxy)phenyl)acetate (4 g, 16.2 mmol) was dissolved in 50 mL anhydrous DMF and NaH (60% wt. in oil, 0.846 g, 21.1 mmol) was added at 0° C. The reaction mixture was stirred for 0.5 h at 25° C. and isobutyl bromide (2.12 mL, 19.5 mmol) was added drop wise at 0° C. The reaction mixture was stirred at 0° C. for 1 h and saturated NH₄Cl solution was added. The reaction mixture was extracted with EtOAc (3×20 mL) and the combined organic phases were washed with water (3×20 mL) and brine (20 mL), dried over MgSO₄, filtered and concentrated under reduced pressure to give ethyl 4-methyl-2-(4-nitro-3-(2,2,2-trifluoroethoxy)phenyl)pentanoate (1.5 g) as a colorless oil.

Step 2

Ethyl 2-(4-amino-3-(2,2,2-trifluoroethoxy)phenyl)-4-methylpentanoate

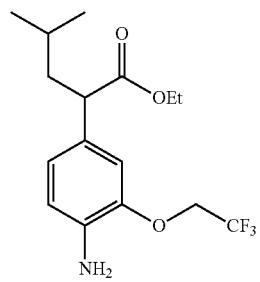 [SMILES: CCOC(=O)C(CC(C)C)c1ccc([N+](=O)[O-])c(OCC(F)(F)F)c1]

To a stirred solution of ethyl 4-methyl-2-(4-nitro-3-(2,2,2-trifluoroethoxy)phenyl)pentanoate (1.5 g), in dry MeOH (100 mL), Pd(OH)₂ (500 mg) was added and the mixture reduced under an atmosphere of H₂ for 6 h at room temperature. The mixture was filtered through a pad of Celite™ washing with MeOH. The combined filtrates were concentrated under reduced pressure to give ethyl 2-(4-amino-3-(2,2,2-trifluoroethoxy)phenyl)-4-methylpentanoate (1.2 g) as a thick liquid.

Step 3

Ethyl 2-(4-amino-3-bromo-5-(2,2,2-trifluoroethoxy)phenyl)-4-methylpentanoate

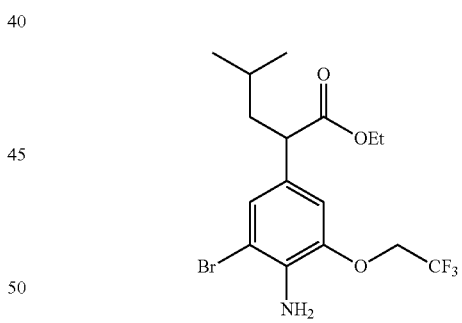

To a stirred solution of ethyl 2-(4-amino-3-(2,2,2-trifluoroethoxy)phenyl)-4-methylpentanoate (0.750 g, 2.2 mmol) in dry CHCl₃ (100 mL), NBS (0.320 g, 1.8 mmol) was added at 0° C. The reaction mixture was allowed to stir for 3 h at room temperature. The reaction mixture was diluted with water, extracted with DCM (2×50 mL), the combined organic solvents was dried over Na₂SO₄, filtered and concentrated under reduced pressure. The crude reaction mixture was purified by column chromatography to give ethyl 2-(4-amino-3-bromo-5-(2,2,2-trifluoroethoxy)phenyl)-4-methylpentanoate (700 mg) as a yellow solid.

Step 4

Ethyl 2-(6-amino-5-(2,2,2-trifluoroethoxy)-4'-(trifluoromethyl)biphenyl-3-yl)-4-methylpentanoate

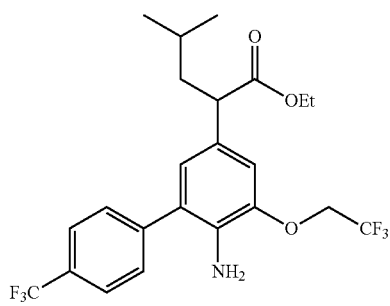 [SMILES: CCOC(=O)C(CC(C)C)c1cc(OCC(F)(F)F)c(N)c(-c2ccc(C(F)(F)F)cc2)c1]

A mixture of ethyl 2-(4-amino-3-bromo-5-(2,2,2-trifluoroethoxy)phenyl)-4-methylpentanoate (0.70 g, 1.6 mmol), 4-trifluoromethylphenylboronic acid (0.642 g, 3.39 mmol), CsF (0.641 g, 4.2 mmol) and Pd(PPh$_3$)$_4$ (0.196 g, 0.16 mmol) in 40 mL anhydrous 1,2-dimethoxy ethane was refluxed for 8 h under argon. The reaction mixture was cooled, and 35 mL of EtOAc and 35 mL of water were added. The organic phase was separated, dried over Na$_2$SO$_4$, filtered and concentrated under reduced pressure to yellow oil. The oil was purified by chromatography over silica gel (hexane/EtOAc) to give ethyl 2-(6-amino-5-(2,2,2-trifluoroethoxy)-4'-(trifluoromethyl)biphenyl-3-yl)-4-methylpentanoate (650 mg) as a colorless liquid.

Step 5

Ethyl 2-(6-chloro-5-(2,2,2-trifluoroethoxy)-4'-(trifluoromethyl)biphenyl-3-yl)-4-methylpentanoate

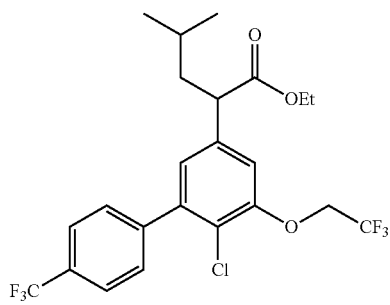 [SMILES: CC(C)CC(C(=O)O)c1cc(OCC(F)(F)F)c(Cl)c(-c2ccc(C(F)(F)F)cc2)c1]

Ethyl 2-(6-amino-5-(2,2,2-trifluoroethoxy)-4'-(trifluoromethyl)biphenyl-3-yl)-4-methylpentanoate (640 mg, 1.3 mmol) was dissolved in a mixture of MeCN/H$_2$O/HCl 15 mL/15 mL/1 mL at 0° C. A solution of NaNO$_2$ (0.138 g, 2.0 mmol) in water (2 mL) was added drop wise at 0° C., and the reaction mixture was stirred for 40 min, at the same temperature. A solution of CuCl (1.32 g, 13.4 mmol) in water (5 mL) was added drop wise at 0° C. The reaction mixture was heated to 80° C. for 2 h and the mixture was concentrated under reduced pressure. The reaction mixture was extracted with EtOAc (3×50 mL), and the combined organic layers were washed with water (50 mL) followed by brine (50 mL). The solution was dried over Na$_2$SO$_4$, filtered and concentrated to give crude black oil which was purified by chromatography over silica gel (hexane/EtOAc) to give the ethyl 2-(6-chloro-5-(2,2,2-trifluoroethoxy)-4'-(trifluoromethyl)biphenyl-3-yl)-4-methylpentanoate (380 mg) as a yellow solid.

Step 6

2-(6-Chloro-5-(2,2,2-trifluoroethoxy)-4'-(trifluoromethyl)biphenyl-3-yl)-4-methylpentanoic acid

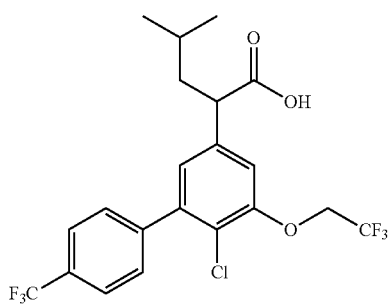

Ethyl 2-(6-chloro-5-(2,2,2-trifluoroethoxy)-4'-(trifluoromethyl)biphenyl-3-yl)-4-methylpentanoate (320 mg, 0.647 mmol) was dissolved in a MeOH/THF/H$_2$O (10 mL/10 mL/5 mL) mixture, LiOH (163 mg, 3.88 mmol) was added. The reaction mixture was stirred at room temperature for 5 h and then concentrated under reduced pressure. Water (10 mL) was added and the reaction mixture was extracted with EtOAc (3×10 mL). The combined organic phases were dried over MgSO$_4$, filtered and evaporated under reduced pressure. Purification was achieved by re-crystallization in hexane/ether mixture to give 2-(6-chloro-5-(2,2,2-trifluoroethoxy)-4'-(trifluoromethyl)biphenyl-3-yl)-4-methylpentanoic acid (220 mg) as a white solid. $^1$H-NMR (500 MHz, CDCl$_3$): 7.74 (d, 2H), 7.55 (d, 2H), 7.01 (s, 2H), 4.44 (q, 2H), 3.68 (t, 1H), 1.98 (m, 2H), 1.61 (m, 1H), 1.54 (m, 1H), 0.95 (d, 6H)

Example 1277

2-(5-Chloro-4'-methyl-6-(2,2,2-trifluoroethoxy)biphenyl-3-yl)-3-cyclopropyl propanoic acid

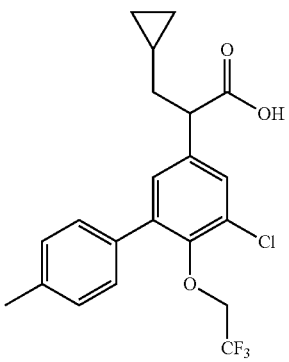 [SMILES: Cc1ccc(-c2cc(C(CC3CC3)C(=O)O)cc(Cl)c2OCC(F)(F)F)cc1]

Step 1

Ethyl 2-(3-chloro-4-hydroxyphenyl)acetate

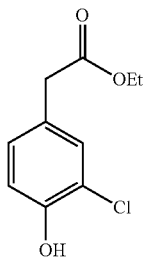

To a stirred solution of ethyl 2-(4-hydroxyphenyl)acetate (25 g, 138 mmol) in 375 ml of DCM, sulfuryl chloride (9.48 mL 118 mmol) was slowly added at 0° C. over a period of 30 min. Diethyl ether (19.6 mL) was slowly added reaction mixture at 0° C. and stirring was continued for 30 min at 0° C. The reaction mixture was slowly warmed to 15° C. for 1 h. After completion of reaction, the mixture was poured onto crushed ice and extracted with DCM (×2). The combined organic layers were washed with 10% NaHCO$_3$ solution followed by water. The organic layer was dried over Na$_2$SO$_4$, filtered and evaporated under vacuum to give compound ethyl 2-(3-chloro-4-hydroxyphenyl)acetate (15 g) as a thick oil.

Step 2

Ethyl 2-(3-bromo-5-chloro-4-hydroxyphenyl)acetate

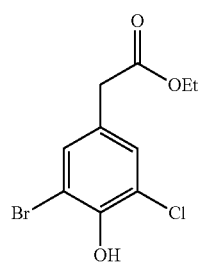

To a stirred solution of ethyl 2-(3-chloro-4-hydroxyphenyl)acetate (15 g, 69 mmol) in CCl$_4$ (270 mL), bromine (11.1 g, 69 mmol) was added slowly (dissolved in 140 mL of CCl$_4$) at −10° C. over a period of 30 min. The reaction mixture was stirred for another 1 h at −10° C. Upon completion of the reaction, the mixture was poured onto crushed ice and extracted with DCM (×2). The combined organic layers were washed with saturated Na$_2$S$_2$O$_3$ solution, water, dried over Na$_2$SO$_4$, filtered and concentrated under reduced pressure. The crude compound was purified by re-crystallization using hexane to yield compound ethyl 2-(3-bromo-5-chloro-4-hydroxyphenyl)acetate (7 g, 7 g starting material recovered) as a white solid.

Step 3

Ethyl 2-(3-bromo-5-chloro-4-(2,2,2-trifluoroethoxy)phenyl)acetate

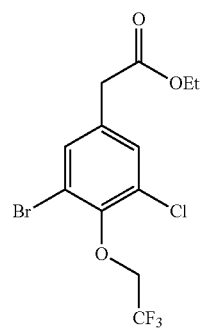 [SMILES: CCOC(=O)Cc1cc(Cl)c(OCC(F)(F)F)c(Br)c1]

To a stirred solution of ethyl 2-(3-bromo-5-chloro-4-hydroxyphenyl)acetate (6.5 g, 22 mmol), in DMF (100 mL), K$_2$CO$_3$ (7.67 g, 55.6 mmol) was added. Trifluoroethyl iodide (13.16 mL, 133 mmol) was added in a drop wise manner to the reaction mixture at RT. The mixture was then heated at 60° C. for 4 h. After completion of reaction, the mixture was poured into water and extracted with ethyl acetate (2×100 mL). The combined organic layers were washed with water, dried over Na$_2$SO$_4$ and concentrated under reduced pressure. The crude compound was purified by column chromatography to give compound ethyl 2-(3-bromo-5-chloro-4-(2,2,2-trifluoroethoxy)phenyl)acetate (6.5 g) as a white solid.

Step 4

Ethyl 2-(3-bromo-5-chloro-4-(2,2,2-trifluoroethoxy)phenyl)-3-cyclopropylpropanoate

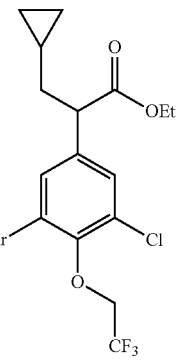

To a suspension of NaH (0.327 g, 60% in paraffin oil, 8.1 mmol) in DMF (100 mL), slowly added a mixture of ethyl 2-(3-bromo-5-chloro-4-(2,2,2-trifluoroethoxy)phenyl)acetate (3.0 g, 6.8 mmol) and cyclopropyl methylbromide (0.718 mL, 7.5 mmol) dissolved in DMF (20 mL) at 0° C. for 15 min under an atmosphere of nitrogen. The reaction mixture was allowed stir at 0° C. for 15 min, upon which the mixture was poured onto crushed ice and extracted with ethyl acetate (2×50 mL). The combined organic layers were washed with water, brine, dried over Na$_2$SO$_4$ and evaporated. The residue was purified by Flash column chromatography to give compound ethyl 2-(3-bromo-5-chloro-4-(2,2,2-trifluoroethoxy)phenyl)-3-cyclopropylpropanoate (2.35 g) as a thick syrup.

Step 5

Ethyl 2-(5-chloro-4'-methyl-6-(2,2,2-trifluoroethoxy)biphenyl-3-yl)-3-cyclopropylpropanoate

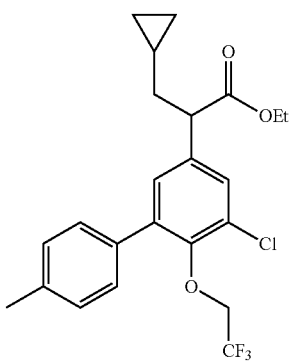 [SMILES: CCOC(=O)C(CC1CC1)c1cc(Cl)c(OCC(F)(F)F)c(-c2ccc(C)cc2)c1]

A mixture of compound ethyl 2-(3-bromo-5-chloro-4-(2,2,2-trifluoroethoxy)phenyl)-3-cyclopropylpropanoate (500 mg, 1.15 mmol), 4-methyl phenylboronic acid (0.237 g, 1.74 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 2-(5-chloro-4'-methyl-6-(2,2,2-trifluoroethoxy)biphenyl-3-yl)-3-cyclopropylpropanoate (375 mg) as a thick oil.

Step 7

2-(5-Chloro-4'-methyl-6-(2,2,2-trifluoroethoxy)biphenyl-3-yl)-3-cyclopropylpropanoic acid

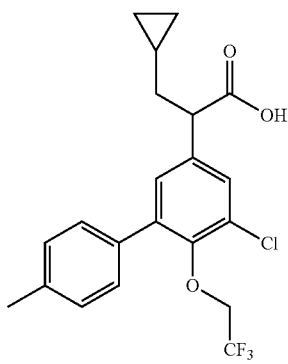 [SMILES: Cc1ccc(-c2cc(C(CC3CC3)C(=O)O)cc(Cl)c2OCC(F)(F)F)cc1]

A mixture of ethyl 2-(5-chloro-4'-methyl-6-(2,2,2-trifluoroethoxy)biphenyl-3-yl)-3-cyclopropylpropanoate (370 mg, 0.84 mmol) and lithium hydroxide monohydrate (282 mg, 6.7 mmol) in MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 2-(5-chloro-4'-methyl-6-(2,2,2-trifluoroethoxy)biphenyl-3-yl)-3-cyclopropylpropanoic acid (200 mg) as a white solid. $^1$HNMR (CDCl$_3$): 7.21-7.42 (m, 6H); 3.87 (q, 2H); 3.65 (t, 1H); 2.39 (s, 3H); 1.93 (m, 1H); 1.88 (m, 1H); 0.66 (m, 1H); 0.42 (m, 2H); 0.12 (m, 1H); 0.1 (m, 1H).

Example 1289

2-(5-chloro-4'-ethyl-6-(2,2,2-trifluoroethoxy)biphenyl-3-yl)-3-cyclopropylpropanoic acid Step 1

Ethyl 2-(5-chloro-4'-ethyl-6-(2,2,2-trifluoroethoxy)biphenyl-3-yl)-3-cyclopropyl propanoate

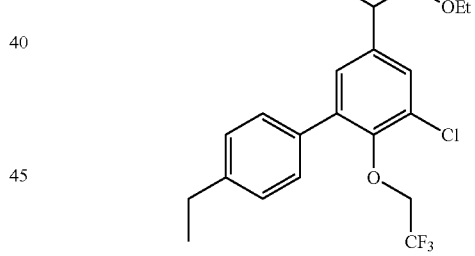

A mixture of compound ethyl 2-(3-bromo-5-chloro-4-(2,2,2-trifluoroethoxy)phenyl)-3-cyclopropylpropanoate (500 mg, 1.15 mmol), 4-ethyl phenylboronic acid (225 mg, 1.74 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 2-(5-chloro-4'-ethyl-6-(2,2,2-trifluoroethoxy)biphenyl-3-yl)-3-cyclopropyl propanoate (400 mg) as a thick oil.

Step 2

2-(5-chloro-4'-ethyl-6-(2,2,2-trifluoroethoxy)biphenyl-3-yl)-3-cyclopropylpropanoic acid

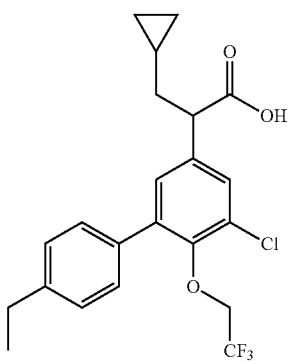 [SMILES: CCc1ccc(-c2cc(C(CC3CC3)C(=O)O)cc(Cl)c2OCC(F)(F)F)cc1]

A mixture of ethyl 2-(5-chloro-4'-ethyl-6-(2,2,2-trifluoroethoxy)biphenyl-3-yl)-3-cyclopropyl propanoate (400 mg, 0.88 mmol) and lithium hydroxide monohydrate (222 mg, 5.2 mmol) in MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 2-(5-chloro-4'-ethyl-6-(2,2,2-trifluoroethoxy)biphenyl-3-yl)-3-cyclopropylpropanoic acid (200 mg) as a white solid. $^1$HNMR ($CDCl_3$): 7.42 (d, 2H), 7.38 (s, 1H), 7.22 (d, 2H) 7.20 (s, 1H), 3.85 (q, 2H); 3.66 (t, 1H); 2.73 (q, 2H), 1.93 (m, 1H); 1.88 (m, 1H); 1.29 (t, 3H), 0.66 (m, 1H); 0.42 (m, 2H); 0.12 (m, 1H); 0.05 (m, 1H).

Example 1313

2-(5-chloro-4'-(methylthio)-6-(2,2,2-trifluoroethoxy)biphenyl-3-yl)-3-cyclopropyl propanoic acid Step 1

Ethyl 2-(5-chloro-4'-(methylthio)-6-(2,2,2-trifluoroethoxy)biphenyl-3-yl)-3-cyclopropyl propanoate

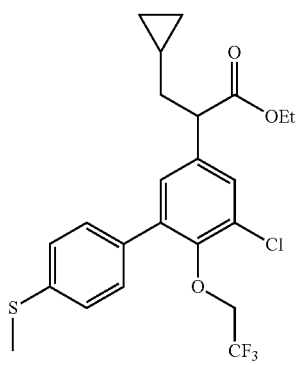 [SMILES: CCOC(=O)C(CC1CC1)c1cc(Cl)c(OCC(F)(F)F)c(-c2ccc(SC)cc2)c1]

A mixture of compound ethyl 2-(3-bromo-5-chloro-4-(2,2,2-trifluoroethoxy)phenyl)-3-cyclopropylpropanoate (500 mg, 1.15 mmol), 4-thiomethyl phenylboronic acid (293 mg, 1.7 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 2-(5-chloro-4'-(methylthio)-6-(2,2,2-trifluoroethoxy)biphenyl-3-yl)-3-cyclopropyl propanoate (360 mg) as a thick oil.

Step 2

2-(5-chloro-4'-(methylthio)-6-(2,2,2-trifluoroethoxy)biphenyl-3-yl)-3-cyclopropyl propanoic acid

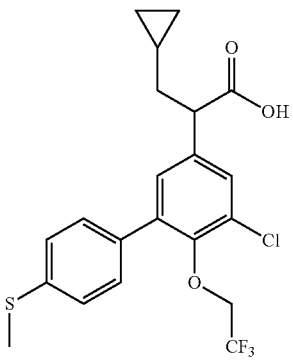 [SMILES: CSc1ccc(-c2cc(C(CC3CC3)C(=O)O)cc(Cl)c2OCC(F)(F)F)cc1]

A mixture of ethyl 2-(5-chloro-4'-(methylthio)-6-(2,2,2-trifluoroethoxy)biphenyl-3-yl)-3-cyclopropyl propanoate (350 mg, 0.74 mmol) and lithium hydroxide monohydrate (186 mg, 4.44 mmol) in MeOH/THF/Water solvent mixture (10 ml/10 ml/10/ml) was stirred for 3 h at room temperature. After completion of the reaction, the volatiles were removed under reduced pressure. Residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 2-(5-chloro-4'-(methylthio)-6-(2,2,2-trifluoroethoxy)biphenyl-3-yl)-3-cyclopropyl propanoic acid (310 mg) as a white solid. $^1$HNMR ($CDCl_3$): 7.46 (d, 2H), 7.38 (s, 1H), 7.32 (d, 2H), 7.22 (s, 1H), 3.93 (q, 2H); 3.68 (t, 1H); 2.56 (s, 3H), 1.93 (m, 1H); 1.78 (m, 1H); 1.29 (t, 3H), 0.65 (m, 1H); 0.42 (m, 2H); 0.12 (m, 1H); 0.05 (m, 1H).

Example 1325

2-(5-chloro-6-(2,2,2-trifluoroethoxy)-4'-(trifluoromethoxy)biphenyl-3-yl)-3-cyclopropyl propanoic acid Step 1

Ethyl 2-(5-chloro-6-(2,2,2-trifluoroethoxy)-4'-(trifluoromethoxy)biphenyl-3-yl)-3-cyclopropyl propanoate

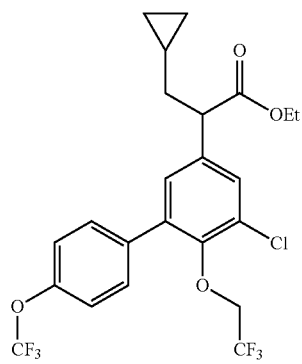 [SMILES: CCOC(=O)C(CC1CC1)c1cc(Cl)c(OCC(F)(F)F)c(-c2ccc(OC(F)(F)F)cc2)c1]

A mixture of compound ethyl 2-(3-bromo-5-chloro-4-(2,2,2-trifluoroethoxy)phenyl)-3-cyclopropylpropanoate (500 mg, 1.15 mmol), 4-trifluoromethoxy phenylboronic acid (310 mg, 1.65 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 2-(5-chloro-6-(2,2,2-trifluoroethoxy)-4'-(trifluoromethoxy)biphenyl-3-yl)-3-cyclopropyl propanoate (260 mg) as a thick oil.

Step 2

2-(5-chloro-6-(2,2,2-trifluoroethoxy)-4'-(trifluoromethoxy)biphenyl-3-yl)-3-cyclopropyl propanoic acid

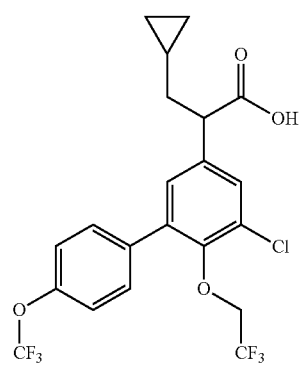 [SMILES: O=C(O)C(CC1CC1)c1cc(Cl)c(OCC(F)(F)F)c(-c2ccc(OC(F)(F)F)cc2)c1]

A mixture of ethyl 2-(5-chloro-6-(2,2,2-trifluoroethoxy)-4'-(trifluoromethoxy)biphenyl-3-yl)-3-cyclopropyl propanoate (260 mg, 0.50 mmol) and lithium hydroxide monohydrate (186 mg, 4.44 mmol) in a MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 2-(5-chloro-6-(2,2,2-trifluoroethoxy)-4'-(trifluoromethoxy)biphenyl-3-yl)-3-cyclopropyl propanoic acid (180 mg) as white solid. $^1HNMR$ ($CDCl_3$): 7.56 (d, 2H), 7.40 (s, 1H), 7.25 (m, 3H), 3.98 (q, 2H); 3.68 (t, 1H); 2.56 (s, 3H), 1.913 (m, 1H); 1.76 (m, 1H); 1.29 (t, 3H), 0.62 (m, 1H); 0.41 (m, 2H); 0.12 (m, 1H); 0.05 (m, 1H).

Example 1301

2-(5-chloro-4'-isopropyl-6-(2,2,2-trifluoroethoxy)biphenyl-3-yl)-3-cyclopropyl propanoic acid Step 1

Ethyl 2-(5-chloro-4'-isopropyl-6-(2,2,2-trifluoroethoxy)biphenyl-3-yl)-3-cyclopropyl propanoate

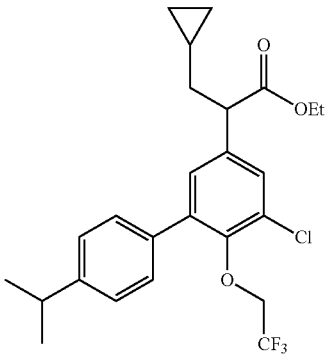 [SMILES: CCOC(=O)C(CC1CC1)c1cc(Cl)c(OCC(F)(F)F)c(-c2ccc(C(C)C)cc2)c1]

A mixture of compound ethyl 2-(3-bromo-5-chloro-4-(2,2,2-trifluoroethoxy)phenyl)-3-cyclopropylpropanoate (500 mg, 1.15 mmol), 4-isopropyl phenylboronic acid (225 mg, 1.74 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 2-(5-chloro-4'-isopropyl-6-(2,2,2-trifluoroethoxy)biphenyl-3-yl)-3-cyclopropyl propanoate (400 mg) as thick oil.

Step 2

2-(5-chloro-4'-isopropyl-6-(2,2,2-trifluoroethoxy)biphenyl-3-yl)-3-cyclopropyl propanoic acid

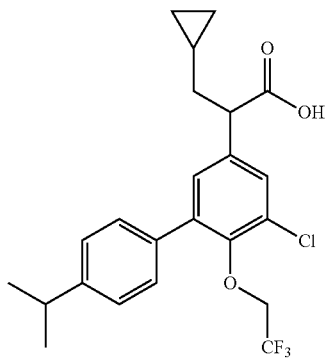 [SMILES: CC(C)c1ccc(-c2cc(C(CC3CC3)C(=O)O)cc(Cl)c2OCC(F)(F)F)cc1]

A mixture of ethyl 2-(5-chloro-4'-isopropyl-6-(2,2,2-trifluoroethoxy)biphenyl-3-yl)-3-cyclopropyl propanoate (400 mg, 0.85 mmol) and lithium hydroxide monohydrate (215 mg, 5.1 mmol) in MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with Na$_2$SO$_4$, filtered and concentrated under reduced pressure. The residue was purified by Flash Column Chromatography to give 2-(5-chloro-4'-isopropyl-6-(2,2,2-trifluoroethoxy)biphenyl-3-yl)-3-cyclopropyl propanoic acid (180 mg) as white solid. $^1$HNMR (CDCl$_3$): 7.44 (d, 2H), 7.38 (s, 1H), 7.31 (d, 2H) 7.21 (s, 1H), 3.86 (q, 2H); 3.67 (t, 1H); 2.98 (m, 1H); 1.93 (m, 1H); 1.78 (m, 1H); 1.28 (d, 6H), 0.66 (m, 1H); 0.43 (m, 2H); 0.12 (m, 1H); 0.05 (m, 1H).

Example 1280

1-(5-chloro-4'-methyl-6-(2,2,2-trifluoroethoxy)biphenyl-3-yl)cyclobutane carboxylic acid

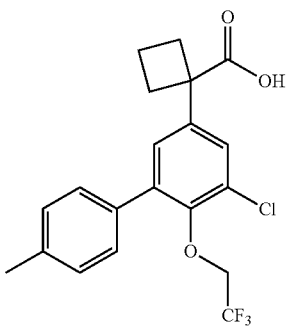 [SMILES: Cc1ccc(-c2cc(C3(C(=O)O)CCC3)cc(Cl)c2OCC(F)(F)F)cc1]

Step 1

Ethyl 1-(3-bromo-5-chloro-4-(2,2,2-trifluoroethoxy)phenyl)cyclobutanecarboxylate

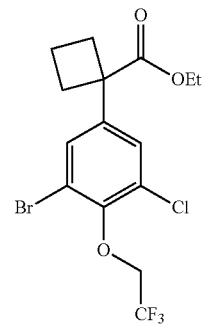 [SMILES: CCOC(=O)C1(c2cc(Cl)c(OCC(F)(F)F)c(Br)c2)CCC1]

To a suspension of NaH (0.65 g, 60% in paraffin oil) in DMF (100 mL), slowly added a mixture of ethyl 2-(3-bromo-5-chloro-4-(2,2,2-trifluoroethoxy)phenyl)acetate (3.0 g, 6.8 mmol) and 1,3-dibromo propane (1.61 g, 8.0 mmol) dissolved in DMF (20 mL) at 0° C. for 15 min under an atmosphere of nitrogen. The reaction mixture was allowed stir at 0° C. for 15 min, upon which the reaction mixture was poured onto crushed ice and extracted with ethyl acetate (2×50 mL). The combined organic layers were washed with water, brine, dried over Na$_2$SO$_4$ and concentrated in vacuo. The residue was purified by Flash column chromatography to give ethyl 1-(3-bromo-5-chloro-4-(2,2,2-trifluoroethoxy)phenyl)cyclobutanecarboxylate (2.12 g) as a thick syrup.

Step 2

Ethyl 1-(5-chloro-4'-methyl-6-(2,2,2-trifluoroethoxy)biphenyl-3-yl)cyclobutanecarboxylate

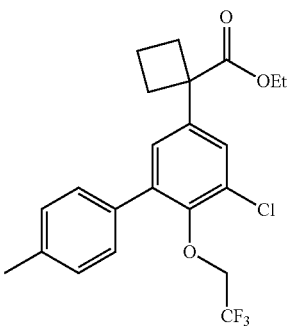 [SMILES: CCOC(=O)C1(c2cc(Cl)c(OCC(F)(F)F)c(-c3ccc(C)cc3)c2)CCC1]

A mixture of compound ethyl 1-(3-bromo-5-chloro-4-(2,2,2-trifluoroethoxy)phenyl)cyclobutanecarboxylate (500 mg, 1.2 mmol), 4-methyl phenylboronic acid (0.237 g, 1.68 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over Na$_2$SO$_4$, filtered and concentrated under reduced pressure. The crude material was purified by column chromatography to yield ethyl 1-(5-chloro-4'-methyl-6-(2,2,2-trifluoroethoxy)biphenyl-3-yl)cyclobutanecarboxylate (325 mg) as thick oil.

Step 3

1-(5-chloro-4'-methyl-6-(2,2,2-trifluoroethoxy)biphenyl-3-yl)cyclobutane carboxylic acid

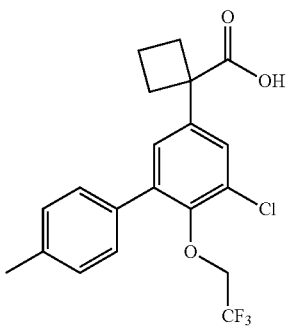 [SMILES: Cc1ccc(-c2cc(C3(C(=O)O)CCC3)cc(Cl)c2OCC(F)(F)F)cc1]

A mixture of ethyl 1-(5-chloro-4'-methyl-6-(2,2,2-trifluoroethoxy)biphenyl-3-yl)cyclobutanecarboxylate (300 mg, 0.70 mmol) and lithium hydroxide monohydrate (280 mg, 11.6 mmol) in a MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 1-(5-chloro-4'-methyl-6-(2,2,2-trifluoroethoxy)biphenyl-3-yl)cyclobutane carboxylic acid (185 mg, 66%) as white solid. $^1$HNMR ($CDCl_3$): 7.42 (m, 2H); 7.32 (s, 1H), 7.23 (d, 2H), 7.18 (s, 1H), 3.87 (q, 2H); 2.85 (m, 2H), 2.54 (m, 2H), 2.39 (s, 3H), 2.12 (m, 1H); 1.83 (m, 1H).

Step 4

Ethyl 1-(5-chloro-4'-ethyl-6-(2,2,2-trifluoroethoxy)biphenyl-3-yl)cyclobutane carboxylate

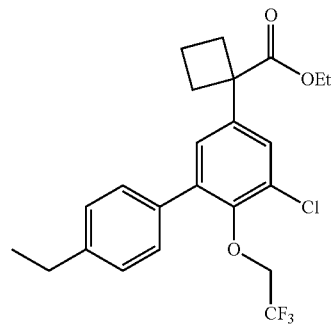 [SMILES: CCOC(=O)C1(c2cc(Cl)c(OCC(F)(F)F)c(-c3ccc(CC)cc3)c2)CCC1]

A mixture of compound ethyl 2-(3-bromo-5-chloro-4-(2,2,2-trifluoroethoxy)phenyl)acetate (500 mg, 1.2 mmol), 4-ethyl phenylboronic acid (225 mg, 1.74 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 1-(5-chloro-4'-ethyl-6-(2,2,2-trifluoroethoxy)biphenyl-3-yl)cyclobutane carboxylate (360 mg) as a thick oil.

Step 5

1-(5-chloro-4'-ethyl-6-(2,2,2-trifluoroethoxy)biphenyl-3-yl)cyclobutane carboxylic acid

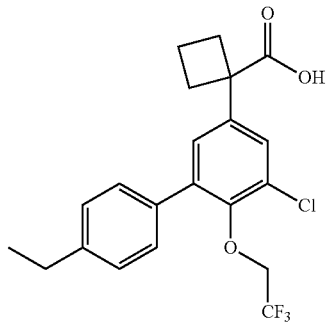 [SMILES: CCc1ccc(-c2cc(C3(C(=O)O)CCC3)cc(Cl)c2OCC(F)(F)F)cc1]

A mixture of ethyl 1-(5-chloro-4'-ethyl-6-(2,2,2-trifluoroethoxy)biphenyl-3-yl)cyclobutane carboxylate (350 mg, 0.84 mmol) and lithium hydroxide monohydrate (222 mg, 9.2 mmol) in a MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 1-(5-chloro-4'-ethyl-6-(2,2,2-trifluoroethoxy)biphenyl-3-yl)cyclobutane carboxylic acid (260 mg) as white solid. $^1$HNMR ($CDCl_3$, 500 MHz): 7.42 (d, 2H), 7.38 (s, 1H), 7.22 (d, 2H) 7.20 (s, 1H), 3.85 (q, 2H); 2.82 (m, 2H), 2.71 (q, 2H), 2.52 (m, 2H), 2.15 (m, 1H), 1.91 (m, 1H); 1.27 (t, 3H).

Example 1316

1-(5-chloro-4'-(methylthio)-6-(2,2,2-trifluoroethoxy)biphenyl-3-yl)cyclobutane carboxylic acid Step 1

Ethyl 1-(5-chloro-4'-(methylthio)-6-(2,2,2-trifluoroethoxy)biphenyl-3-yl)cyclobutane carboxylate

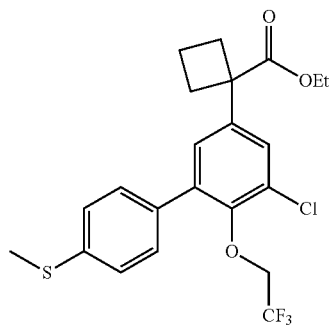 [SMILES: CCOC(=O)C1(c2cc(Cl)c(OCC(F)(F)F)c(-c3ccc(SC)cc3)c2)CCC1]

A mixture of ethyl 2-(3-bromo-5-chloro-4-(2,2,2-trifluoroethoxy)phenyl)acetate (500 mg, 1.2 mmol), 4-thiomethyl phenylboronic acid (293 mg, 1.7 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 1-(5-chloro-4'-(methylthio)-6-(2,2,2-trifluoroethoxy)biphenyl-3-yl)cyclobutane carboxylate (342 mg) as thick oil.

Step 2

1-(5-chloro-4'-(methylthio)-6-(2,2,2-trifluoroethoxy)biphenyl-3-yl)cyclobutane carboxylic acid

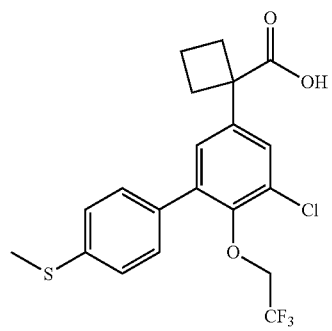 [SMILES: CSc1ccc(-c2cc(C3(C(=O)O)CCC3)cc(Cl)c2OCC(F)(F)F)cc1]

A mixture of ethyl 1-(5-chloro-4'-(methylthio)-6-(2,2,2-trifluoroethoxy)biphenyl-3-yl)cyclobutane carboxylate (325 mg, 0.70 mmol) and lithium hydroxide monohydrate (186 mg, 4.44 mmol) in MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 1-(5-chloro-4'-(methylthio)-6-(2,2,2-trifluoroethoxy)biphenyl-3-yl)cyclobutane carboxylic acid (265 mg) as a white solid. $^1$HNMR ($CDCl_3$): 7.46 (d, 2H), 7.38 (s, 1H), 7.32 (d, 2H), 7.19 (s, 1H), 3.93 (q, 2H); 2.83 (m, 2H), 2.53 (s, 3H), 2.32 (m, 2H), 2.13 (m, 1H), 1.93 (m, 1H).

Example 1304

1-(5-chloro-4'-isopropyl-6-(2,2,2-trifluoroethoxy)biphenyl-3-yl)cyclobutane carboxylic acid Step 1

Ethyl 1-(5-chloro-4'-isopropyl-6-(2,2,2-trifluoroethoxy)biphenyl-3-yl)cyclobutane carboxylate

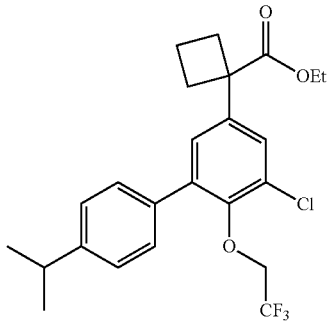 [SMILES: CCOC(=O)C1(c2cc(Cl)c(OCC(F)(F)F)c(-c3ccc(C(C)C)cc3)c2)CCC1]

A mixture of ethyl 2-(3-bromo-5-chloro-4-(2,2,2-trifluoroethoxy)phenyl)acetate (500 mg, 1.2 mmol), 4-isopropyl phenylboronic acid (245 mg, 1.68 mmol), Palladium Tetrakis (triphenylphosphine) (0.134 g, 0.116 mmol), Cesium fluoride (0.354 g, 2.23 mmol) in DME (30 ml) was stirred for overnight at 100° C. After completion of the reaction, the precipitate was removed by filtration. The filtrate was diluted with water and extracted with ethyl acetate (2×100 mL). The combined organic layers were washed with water, brine, dried over $Na_2SO_4$, filtered and concentrated under reduced pressure. The crude material was purified by column chromatography to yield ethyl 1-(5-chloro-4'-isopropyl-6-(2,2,2-trifluoroethoxy)biphenyl-3-yl)cyclobutane carboxylate (425 mg) as thick oil.

Step 2

1-(5-chloro-4'-isopropyl-6-(2,2,2-trifluoroethoxy)
biphenyl-3-yl)cyclobutane carboxylic acid

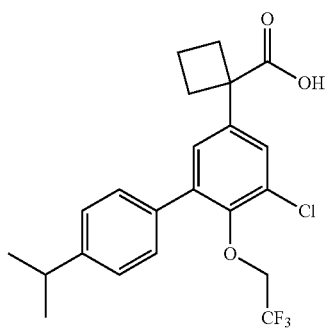 [SMILES: CC(C)c1ccc(-c2cc(C3(C(=O)O)CCC3)cc(Cl)c2OCC(F)(F)F)cc1]

A mixture of ethyl 1-(5-chloro-4'-isopropyl-6-(2,2,2-trifluoroethoxy)biphenyl-3-yl)cyclobutane carboxylate (400 mg, 0.88 mmol) and lithium hydroxide monohydrate (215 mg, 5.1 mmol) in MeOH/THF/Water solvent mixture (10 ml/10 ml/10/ml) was stirred for 3 h at room temperature. After completion of the reaction, the volatiles were removed under reduced pressure. The residue was diluted with water, acidified with 5% HCl solution and extracted with ethyl acetate (2×25 mL). The combined organic layers were washed with water, dried with $Na_2SO_4$, filtered and concentrated under reduced pressure. The residue was purified by Flash Column Chromatography to give 1-(5-chloro-4'-isopropyl-6-(2,2,2-trifluoroethoxy)biphenyl-3-yl)cyclobutane carboxylic acid (289 mg) as white solid. $^1$HNMR ($CDCl_3$): 7.44 (d, 2H), 7.38 (s, 1H), 7.31 (d, 2H) 7.21 (s, 1H), 3.86 (q, 2H); 2.99 (m, 1H), 2.86 (m, 2H), 2.52 (m, 2H), 2.13 (m, 1H), 1.92 (m, 1H); 1.28 (d, 6H).

Example 1833

2-(2-chloro-6-(2,2,2-trifluoroethoxy)-4'-(trifluoromethyl)biphenyl-4-yl)-3-cyclopropylpropanoic acid

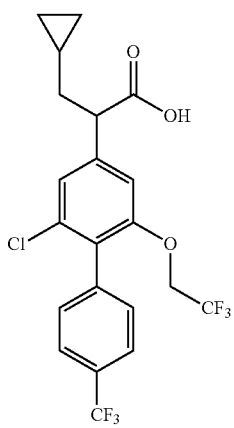 [SMILES: O=C(O)C(CC1CC1)c1cc(Cl)c(-c2ccc(C(F)(F)F)cc2)c(OCC(F)(F)F)c1]

Step 1

Ethyl-2-(4-amino-3-chloro-5-(2,2,2-trifluoroethoxy)
phenyl)-3-cyclopropyl propanoate

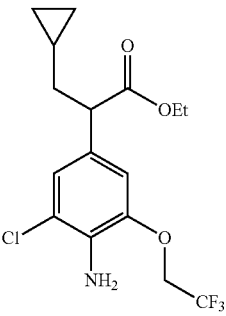 [SMILES: CCOC(=O)C(CC1CC1)c1cc(Cl)c(N)c(OCC(F)(F)F)c1]

To a stirred solution of ethyl 2-(4-amino-3-(2,2,2-trifluoroethoxy)phenyl)-3-cyclopropylpropanoate (1.2 g, 4.0 mmol) in dry $CCl_4$ (60 mL), NCS (0.427 g, 3.2 mmol) was added at 0° C. The reaction mixture was allowed to stir for 3 h at room temperature to complete the reaction. The reaction mixture was diluted with water, extracted with DCM (2×50 mL), the combined organic solvents was dried over $Na_2SO_4$, filtered and concentrated in vacuo. The crude reaction mixture was purified by column chromatography to yield compound ethyl-2-(4-amino-3-chloro-5-(2,2,2-trifluoroethoxy)phenyl)-3-cyclopropyl propanoate (0.920 g) as a yellow solid.

Step 2

Ethyl 2-(3-chloro-4-iodo-5-(2,2,2-trifluoroethoxy)
phenyl)-3-cyclopropylpropanoate

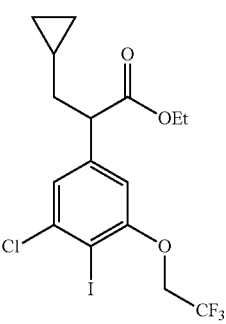 [SMILES: CCOC(=O)C(CC1CC1)c1cc(Cl)c(I)c(OCC(F)(F)F)c1]

Ethyl-2-(4-amino-3-chloro-5-(2,2,2-trifluoroethoxy)phenyl)-3-cyclopropyl propanoate (0.9 g, 2.6 mmol) was dissolved in a mixture of AcCN/$H_2O$/HCl (96%) 25 mL/25 mL/1 mL at 0° C. A solution of $NaNO_2$ (0.277 g, 4.02 mmol) in water (2 mL) was added drop wise at 0° C., and the reaction mixture was stirred for 40 min, at the same temperature. A solution of KI (4.5 g, 26.8 mmol) in water (10 mL) was added drop wise at 0° C. The reaction mixture was heated to 70° C. for 1 h. The reaction mixture was extracted with EtOAc (3×50 mL), and the combined organic layers were washed with 10% sodium thiosulfate (2×50 mL), water (100 mL) followed by brine (100 mL). The solution was dried over $Na_2SO_4$, filtered and concentrated to give crude black oil which was purified by column chromatography over silica gel (hexane/EtOAc, 95:5) to give ethyl 2-(3-chloro-4-iodo-5-(2,2,2-trifluoroethoxy)phenyl)-3-cyclopropylpropanoate (1.1 g, 90.9%) as yellow oil.

Step 3

Ethyl-2-(2-chloro-6-(2,2,2-trifluoroethoxy)-4'-(trifluoromethyl)biphenyl-4-yl)-3-cyclopropyl propanoate

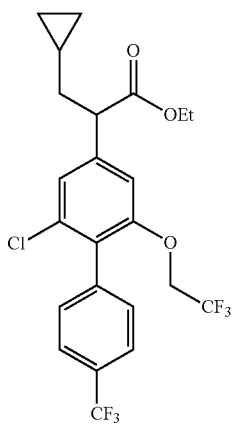 [SMILES: CCOC(=O)C(CC1CC1)c1cc(Cl)c(-c2ccc(C(F)(F)F)cc2)c(OCC(F)(F)F)c1]

A mixture of ethyl 2-(3-chloro-4-iodo-5-(2,2,2-trifluoroethoxy)phenyl)-3-cyclopropylpropanoate (1.1 g, 2.4 mmol), 4-trifluoromethylphenylboronic acid (0.928 g, 4.9 mmol), CsF (0.926 g, 6.1 mmol) and Pd (PPh$_3$)$_4$ (0.283 g, 0.245 mmol) in 50 mL anhydrous 1,2-dimethoxy ethane was refluxed for 8 h under argon. The reaction mixture was cooled, and 40 mL of EtOAc and 40 mL of water were added. The organic phase was separated, dried over Na$_2$SO$_4$, filtered and concentrated under reduced pressure to give a yellow oil. The oil was purified by column chromatography over silica gel (hexane/EtOAc, 95:5) to give ethyl-2-(2-chloro-6-(2,2,2-trifluoroethoxy)-4'-(trifluoromethyl)biphenyl-4-yl)-3-cyclopropyl propanoate (0.650 g) as a yellow oil.

Step 4

2-(2-chloro-6-(2,2,2-trifluoroethoxy)-4'-(trifluoromethyl)biphenyl-4-yl)-3-cyclopropylpropanoic acid

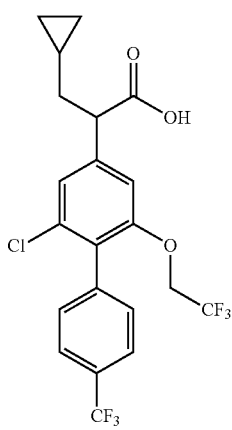 [SMILES: O=C(O)C(CC1CC1)c1cc(Cl)c(-c2ccc(C(F)(F)F)cc2)c(OCC(F)(F)F)c1]

Ethyl-2-(2-chloro-6-(2,2,2-trifluoroethoxy)-4'-(trifluoromethyl)biphenyl-4-yl)-3-cyclopropyl propanoate (0.65 g, 1.31 mmol) was dissolved in 25 mL of MeOH/THF/H$_2$O (10:10:5, vvl), LiOH (0.252 g, 10.5 mmol) was added. The reaction mixture was stirred for 5 h at room temperature and concentrated under reduced pressure. Water (10 mL) was added and the reaction mixture was extracted with EtOAc (3×10 mL). The combined organic phases were dried over Na$_2$SO$_4$, filtered and evaporated under reduced pressure. Purification by column chromatography over silica gel (DCM/MeOH, 95:5) gave the 2-(2-chloro-6-(2,2,2-trifluoroethoxy)-4'-(trifluoromethyl)biphenyl-4-yl)-3-cyclopropylpropanoic acid (0.585 g) as a white solid. $^1$H NMR (500 MHz, CDCl$_3$/TMS): δ 7.71 (d, 2H), 7.39 (d, 2H), 7.22 (s, 1H), 6.91 (s, 1H), 4.23 (q, 2H), 3.72 (t, 1H), 1.93 (m, 1H), 1.82 (m, 1H), 0.81 (m, 1H), 0.52 (m, 2H), 0.15 (m, 2H).

Example 1836

1-(2-chloro-6-(2,2,2-trifluoroethoxy)-4'-(trifluoromethyl)biphenyl-4-yl)cyclobutane carboxylic acid

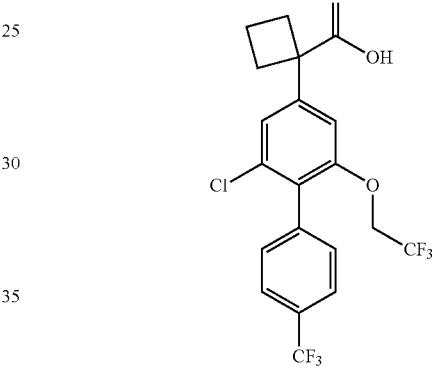

Step 1

Ethyl 1-(4-amino-3-chloro-5-(2,2,2-trifluoroethoxy)phenyl)cyclobutanecarboxylate

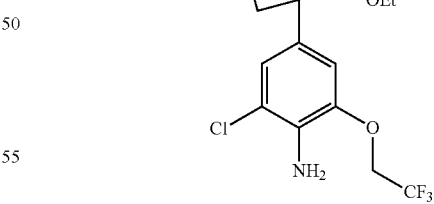

To a stirred solution of ethyl 1-(4-amino-3-(2,2,2-trifluoroethoxy)phenyl)cyclobutanecarboxylate (2.0 g, 6.3 mmol) in dry CHCl$_3$ (30 mL), NCS (0.842 g, 6.3 mmol) was added at 0° C. The reaction mixture was allowed to stir for 3 at room temperature to complete the reaction. The reaction mixture was diluted with water, extracted with DCM (2×100 mL), the combined organic solvents was dried over Na$_2$SO$_4$, filtered and concentrated in vacuo. The crude reaction mixture was purified by Flash column chromatography to yield ethyl 1-(4- amino-3-chloro-5-(2,2,2-trifluoroethoxy)phenyl)cyclobutanecarboxylate (0.4 g) as thick syrup.

Step 2

Ethyl 1-(3-chloro-4-iodo-5-(2,2,2-trifluoroethoxy)phenyl)cyclobutanecarboxylate

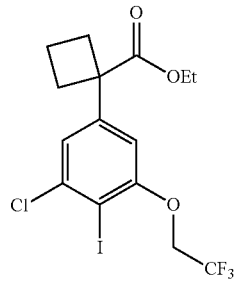 [SMILES: CCOC(=O)C1(c2cc(Cl)c(I)c(OCC(F)(F)F)c2)CCC1]

Ethyl 1-(4-amino-3-chloro-5-(2,2,2-trifluoroethoxy)phenyl)cyclobutanecarboxylate (0.45 g, 1.27 mmol) was dissolved in a mixture of AcCN/H$_2$O/HCl (96%) 15 mL/10 mL/3.1 mL at 0° C. A solution of NaNO$_2$ (0.132 g, 1.91 mmol) in water (1 mL) was added drop wise at 0° C., and the reaction mixture was stirred for 40 min, at the same temperature. A solution of KI (2.11 g, 12.7 mmol) in water (10 mL) was added drop wise at 0° C. The reaction mixture was heated to 80° C. for 1 h. The reaction mixture was extracted with EtOAc (3×50 mL), and the combined organic layers were washed with 10% sodium thiosulfate (2×50 mL), water (100 mL) followed by brine (100 mL). The solution was dried over Na$_2$SO$_4$, filtered and concentrated to give crude black oil which was purified by column chromatography over silica gel (hexane/EtOAc, 95:5) to give ethyl 1-(3-chloro-4-iodo-5-(2,2,2-trifluoroethoxy)phenyl)cyclobutanecarboxylate (0.350 g) as yellow oil.

Step 3

Ethyl-1-(2-chloro-6-(2,2,2-trifluoroethoxy)-4'-(trifluoromethyl)biphenyl-4-yl)cyclobutanecarboxylate

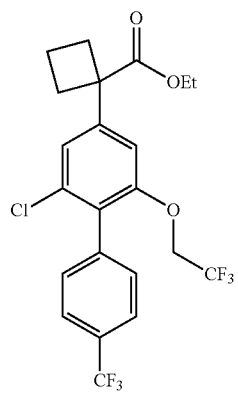 [SMILES: CCOC(=O)C1(c2cc(Cl)c(-c3ccc(C(F)(F)F)cc3)c(OCC(F)(F)F)c2)CCC1]

A mixture of ethyl 1-(3-chloro-4-iodo-5-(2,2,2-trifluoroethoxy)phenyl)cyclobutanecarboxylate (0.35, 7.35 mmol), 4-trifluoromethylphenylboronic acid (0.277 g, 1.47 mmol), CsF (0.277 g, 1.83 mmol) and Pd (PPh$_3$)$_4$ (0.084 g, 0.36 mmol) in 20 mL anhydrous 1,2-dimethoxy ethane was refluxed for 8 h under argon. The reaction mixture was cooled, and 20 mL of EtOAc and 20 mL of water were added. The organic phase was separated, dried over Na$_2$SO$_4$, filtered and concentrated under reduced pressure to yellow oil. The oil was purified by column chromatography over silica gel (hexane/EtOAc, 95:5) to give ethyl-1-(2-chloro-6-(2,2,2-trifluoroethoxy)-4'-(trifluoromethyl)biphenyl-4-yl)cyclobutanecarboxylate (0.182 g) as a colorless oil.

Step 4

1-(2-chloro-6-(2,2,2-trifluoroethoxy)-4'-(trifluoromethyl)biphenyl-4-yl)cyclobutanecarboxylic acid

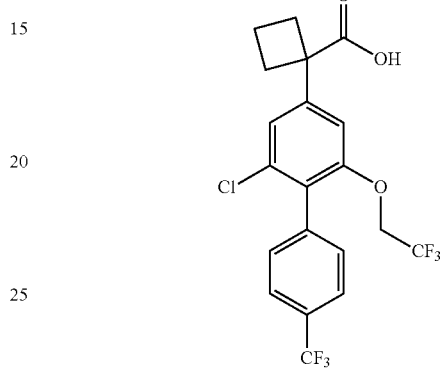

Ethyl-1-(2-chloro-6-(2,2,2-trifluoroethoxy)-4'-(trifluoromethyl)biphenyl-4-yl)cyclobutanecarboxylate (0.2 g, 0.41 mmol) was dissolved in 25 mL of MeOH/THF/H$_2$O (10:10:5, v/v/v), LiOH (0.10 g, 4.1 mmol) was added. The reaction mixture was stirred for 5 h at room temperature and concentrated under reduced pressure. Water (10 mL) was added and the reaction mixture was extracted with EtOAc (3×10 mL). The combined organic phases were dried over Na$_2$SO$_4$, filtered and evaporated under reduced pressure. Purification by column chromatography over silica gel (DCM/MeOH, 95:5) gave the compound 1-(2-chloro-6-(2,2,2-trifluoroethoxy)-4'-(trifluoromethyl)biphenyl-4-yl)cyclobutanecarboxylic acid (0.06 g) as a white solid. $^1$H NMR (500 MHz, CDCl$_3$/TMS): δ 7.72 (d, 2H), 7.41 (d, 2H), 7.19 (s, 1H), 6.79 (s, 1H), 4.23 (q, 2H), 3.92 (m, 2H), 2.58 (m, 2H), 2.19 (m, 1H), 1.97 (m, 1H);

Example 1837

Ethyl-1-(2-chloro-6-(2,2,2-trifluoroethoxy)-4'-(trifluoromethyl)biphenyl-4-yl)cyclopentanecarboxylate

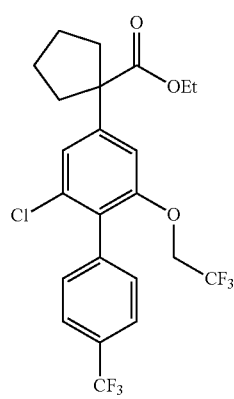 [SMILES: CCOC(=O)C1(c2cc(Cl)c(-c3ccc(C(F)(F)F)cc3)c(OCC(F)(F)F)c2)CCCC1]

257

Step 1

Ethyl 1-(4-amino-3-chloro-5-(2,2,2-trifluoroethoxy)phenyl)cyclopentanecarboxylate

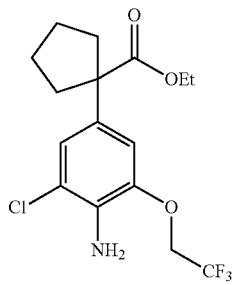 [SMILES: CCOC(=O)C1(c2cc(Cl)c(N)c(OCC(F)(F)F)c2)CCCC1]

To a stirred solution of ethyl 1-(4-amino-3-(2,2,2-trifluoroethoxy)phenyl)cyclopentanecarboxylate (1.2 g, 3.6 mmol) in dry $CHCl_3$ (60 mL), NCS (0.411 g, 3.08 mmol) was added at 0° C. The reaction mixture was allowed to stir for 3 at room temperature to complete the reaction. The reaction mixture was diluted with water, extracted with DCM (2×100 mL), the combined organic solvents was dried over $Na_2SO_4$, filtered and concentrated in vacuo. The crude reaction mixture was purified by Flash column chromatography to yield ethyl 1-(4-amino-3-chloro-5-(2,2,2-trifluoroethoxy)phenyl)cyclopentanecarboxylate (0.860 g) as a thick syrup.

Step 2

Ethyl 1-(3-chloro-4-iodo-5-(2,2,2-trifluoroethoxy)phenyl)cyclopentanecarboxylate

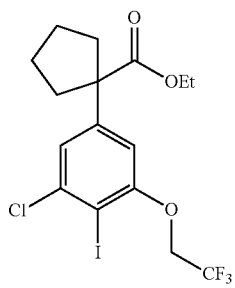 [SMILES: CCOC(=O)C1(c2cc(Cl)c(I)c(OCC(F)(F)F)c2)CCCC1]

Ethyl 1-(4-amino-3-chloro-5-(2,2,2-trifluoroethoxy)phenyl)cyclopentanecarboxylate (0.86 g, 2.3 mmol) was dissolved in a mixture of $AcCN/H_2O/HCl$ (96%) 10 mL/8 mL/2.1 mL at 0° C. A solution of $NaNO_2$ (0.243 g, 3.5 mmol) in water (1 mL) was added drop wise at 0° C., and the reaction mixture was stirred for 40 min, at the same temperature. A solution of KI (3.9 g, 23.5 mmol) in water (10 mL) was added drop wise at 0° C. The reaction mixture was heated to 80° C. for 1 h. The reaction mixture was extracted with EtOAc (3×50 mL), and the combined organic layers were washed with 10% sodium thiosulfate (2×50 mL), water (100 mL) followed by brine (100 mL). The solution was dried over $Na_2SO_4$, filtered and concentrated to give crude black oil which was purified by column chromatography over silica gel (hexane/EtOAc, 95:5) to give ethyl 1-(3-chloro-4-iodo-5-(2,2,2-trifluoroethoxy)phenyl)cyclopentanecarboxylate (0.580 g) as pale yellow oil.

258

Step 3

Ethyl-1-(2-chloro-6-(2,2,2-trifluoroethoxy)-4'-(trifluoromethyl)biphenyl-4-yl)cyclopentanecarboxylate

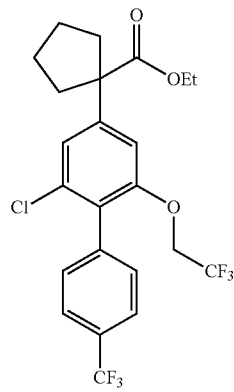 [SMILES: CCOC(=O)C1(c2cc(Cl)c(-c3ccc(C(F)(F)F)cc3)c(OCC(F)(F)F)c2)CCCC1]

A mixture of ethyl 1-(3-chloro-4-iodo-5-(2,2,2-trifluoroethoxy)phenyl)cyclopentanecarboxylate (0.58, 1.2 mmol), 4-trifluoromethylphenylboronic acid (0.56 g, 2.4 mmol), CsF (0.46 g, 3.0 mmol) and Pd $(PPh_3)_4$ (0.14 g, 0.12 mmol) in 20 mL anhydrous 1,2-dimethoxy ethane was refluxed for 8 h under argon. The reaction mixture was cooled, and 25 mL of EtOAc and 25 mL of water were added. The organic phase was separated, dried over $Na_2SO_4$, filtered and concentrated under reduced pressure to yellow oil. The oil was purified by column chromatography over silica gel (hexane/EtOAc, 95:5) to give ethyl-1-(2-chloro-6-(2,2,2-trifluoroethoxy)-4'-(trifluoromethyl)biphenyl-4-yl)cyclopentanecarboxylate (0.480 g) as a color less oil.

Step 4

1-(2-chloro-6-(2,2,2-trifluoroethoxy)-4'-(trifluoromethyl)biphenyl-4-yl)cyclopentanecarboxylic acid

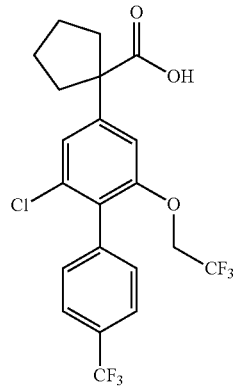 [SMILES: O=C(O)C1(c2cc(Cl)c(-c3ccc(C(F)(F)F)cc3)c(OCC(F)(F)F)c2)CCCC1]

Ethyl-1-(2-chloro-6-(2,2,2-trifluoroethoxy)-4'-(trifluoromethyl)biphenyl-4-yl)cyclopentane carboxylate (0.32 g, 0.64 mmol) was dissolved in 25 mL of $MeOH/THF/H_2O$ (10:10:5, vvl), LiOH (0.163 g, 3.88 mmol) was added. The reaction mixture was stirred for 5 h at room temperature and concentrated under reduced pressure. Water (10 mL) was added and the reaction mixture was extracted with EtOAc (3×10 mL). The combined organic phases were dried over Na₂SO₄, filtered and evaporated under reduced pressure. Purification by column chromatography over silica gel (DCM/MeOH, 95:5) gave the 1-(2-chloro-6-(2,2,2-trifluoroethoxy)-4'-(trifluoromethyl)biphenyl-4-yl)cyclopentanecarboxylic acid (0.220 g, 73%) as a white solid. ¹H NMR (500 MHz, CDCl₃): δ 7.69 (d, 2H), 7.41 (d, 2H), 7.26 (s, 1H), 6.92 (s, 1H), 4.22 (q, 2H), 3.71 (m, 2H), 1.98 (m, 2H), 1.81 (m, 4H).

Example 1832

2-(2-chloro-6-(2,2,2-trifluoroethoxy)-4'-(trifluoromethyl)biphenyl-4-yl)-4-methylpentanoic acid

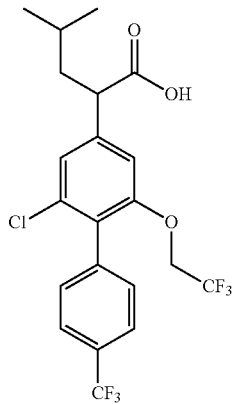 [SMILES: CC(C)CC(C(=O)O)c1cc(Cl)c(-c2ccc(C(F)(F)F)cc2)c(OCC(F)(F)F)c1]

Step 1

Ethyl 2-(4-amino-3-chloro-5-(2,2,2-trifluoroethoxy)phenyl)-4-methylpentanoate

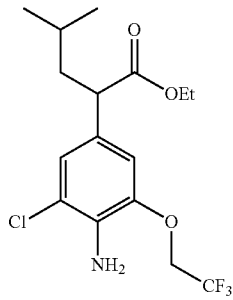 [SMILES: CCOC(=O)C(CC(C)C)c1cc(Cl)c(N)c(OCC(F)(F)F)c1]

To a stirred solution of ethyl 2-(4-amino-3-(2,2,2-trifluoroethoxy)phenyl)-4-methylpentanoate (0.25 g, 0.75 mmol) in dry CHCl₃ (20 mL), NCS (0.08 g, 0.6 mmol) was added at 0° C. The reaction mixture was allowed to stir for 3 at room temperature to complete the reaction. The reaction mixture was diluted with water, extracted with DCM (2×100 mL), the combined organic solvents was dried over Na₂SO₄, filtered and concentrated in vacuo. The crude reaction mixture was purified by Flash column chromatography to yield ethyl 2-(4-amino-3-chloro-5-(2,2,2-trifluoroethoxy)phenyl)-4-methylpentanoate (0.15 g) as thick syrup.

Step 2

Ethyl-2-(3-chloro-4-iodo-5-(2,2,2-trifluoroethoxy)phenyl)-4-methylpentanoate

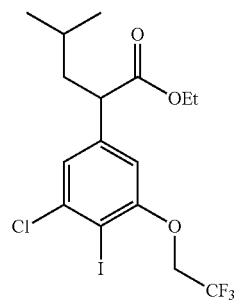 [SMILES: CCOC(=O)C(CC(C)C)c1cc(Cl)c(I)c(OCC(F)(F)F)c1]

Ethyl 2-(4-amino-3-chloro-5-(2,2,2-trifluoroethoxy)phenyl)-4-methylpentanoate (0.7 g, 1.9 mmol) was dissolved in a mixture of AcCN/H₂O/HCl (96%) 20 mL/20 mL/1.3 mL at 0° C. A solution of NaNO₂ (0.197 g, 2.8 mmol) in water (2 mL) was added drop wise at 0° C., and the reaction mixture was stirred for 40 min, at the same temperature. A solution of KI (3.16 g, 19.0 mmol) in water (10 mL) was added drop wise at 0° C. The reaction mixture was heated to 80° C. for 1 h. The reaction mixture was extracted with EtOAc (3×100 mL), and the combined organic layers were washed with 10% sodium thiosulfate (2×50 mL), water (100 mL) followed by brine (100 mL). The solution was dried over Na₂SO₄, filtered and concentrated to give crude black oil which was purified by column chromatography over silica gel (hexane/EtOAc, 95:5) to give ethyl-2-(3-chloro-4-iodo-5-(2,2,2-trifluoroethoxy)phenyl)-4-methylpentanoate (0.35 g) as pale yellow oil.

Step 3

Ethyl-2-(2-chloro-6-(2,2,2-trifluoroethoxy)-4'-(trifluoromethyl)biphenyl-4-yl)-4-methylpentanoate

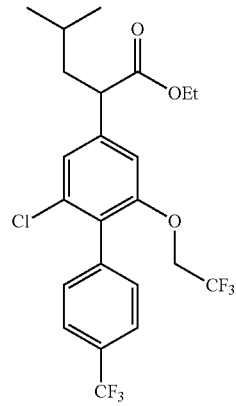 [SMILES: CCOC(=O)C(CC(C)C)c1cc(Cl)c(-c2ccc(C(F)(F)F)cc2)c(OCC(F)(F)F)c1]

A mixture of ethyl-2-(3-chloro-4-iodo-5-(2,2,2-trifluoroethoxy)phenyl)-4-methylpentanoate (0.5, 1.04 mmol), 4-trifluoromethylphenylboronic acid (0.96 g, 2.09 mmol), CsF (0.395 g, 2.6 mmol) and Pd (PPh₃)₄ (0.121 g, 0.104 mmol) in 50 mL anhydrous 1,2-dimethoxy ethane was refluxed for 8 h under argon. The reaction mixture was cooled, and 25 mL of EtOAc and 25 mL of water were added. The organic phase was separated, dried over Na₂SO₄, filtered and concentrated under reduced pressure to yellow oil. The oil was purified by column chromatography over silica gel (hexane/EtOAc, 95:5) to give ethyl-2-(2-chloro-6-(2,2,2-trifluoroethoxy)-4'-

(trifluoromethyl)biphenyl-4-yl)-4-methylpentanoate (0.265 g) as a colorless oil.

Step 4

2-(2-chloro-6-(2,2,2-trifluoroethoxy)-4'-(trifluoromethyl)biphenyl-4-yl)-4-methylpentanoic acid

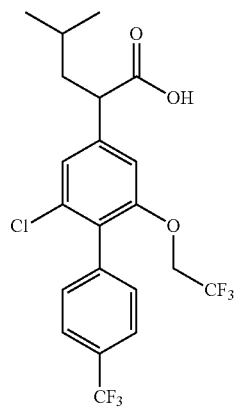 [SMILES: CC(C)CC(C(=O)O)c1cc(Cl)c(-c2ccc(C(F)(F)F)cc2)c(OCC(F)(F)F)c1]

Ethyl-2-(2-chloro-6-(2,2,2-trifluoroethoxy)-4'-(trifluoromethyl)biphenyl-4-yl)-4-methylpentanoate (0.35 g, 0.733 mmol) was dissolved in 25 mL of MeOH/THF/H$_2$O (10:10:5, v:v:l), LiOH (0.176 g, 7.33 mmol) was added. The reaction mixture was stirred for 5 h at room temperature and concentrated under reduced pressure. Water (10 mL) was added and the reaction mixture was extracted with EtOAc (3×10 mL). The combined organic phases were dried over Na$_2$SO$_4$, filtered and evaporated under reduced pressure. Purification by column chromatography over silica gel (DCM/MeOH, 95:5) gave the compound 2-(2-chloro-6-(2,2,2-trifluoroethoxy)-4'-(trifluoromethyl)biphenyl-4-yl)-4-methylpentanoic acid (0.085 g) as a white solid. $^1$H NMR (500 MHz, CDCl$_3$): δ 7.69 (d, 2H), 7.41 (d, 2H), 7.20 (s, 1H), 6.86 (s, 1H), 4.23 (q, 2H), 3.71 (t, 1H), 2.01 (m, 1H), 1.73 (m, 1H), 1.58 (m, 1H), 0.98 (d, 6H).

Example 1908

1-(2-chloro-6-(cyclopropylmethoxy)-4'-(trifluoromethyl)biphenyl-4-yl)cyclobutane carboxylic acid

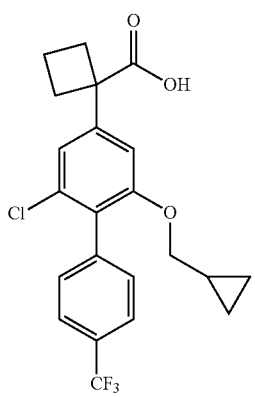 [SMILES: O=C(O)C1(c2cc(Cl)c(-c3ccc(C(F)(F)F)cc3)c(OCC3CC3)c2)CCC1]

2-(Cyclopropylmethoxy)-4-fluoro-1-nitrobenzene

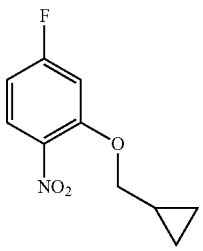 [SMILES: O=[N+]([O-])c1ccc(F)cc1OCC1CC1]

Cyclopropylmethanol (15 g, 207 mmol) was added to a stirred suspension of NaH (60% in mineral oil, 8.37 g) in 200 mL THF over 15 min at 0° C. under nitrogen. The reaction mixture was allowed to warm to room temperature and stirred for 1 h. A solution of 2,4-difluoro-1-nitrobenzene (30 g, 187 mmol) in 200 mL THF was added drop wise at 0° C. The reaction mixture was stirred at 0° C. for 2 h and then poured into ice water. The reaction mixture was extracted with ethyl acetate (3×100 mL). The combined organic layers were dried over MgSO$_4$ and concentrated under reduced pressure to give 22.0 g of product as orange oil (86%).

Step 2

Diethyl 2-(3-(cyclopropylmethoxy)-4-nitrophenyl)malonate

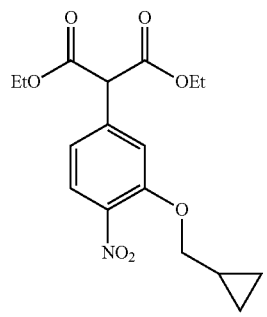 [SMILES: CCOC(=O)C(C(=O)OCC)c1ccc([N+](=O)[O-])c(OCC2CC2)c1]

Diethyl malonate (9.8 g, 1.1 eq.) was added to a stirred suspension of sodium hydride (60% in mineral oil, 2.09 g) in 88 mL DMF over 15 min. at 0° C. under nitrogen. The reaction mixture was allowed to warm to room temperature and stirred for 1 h. A solution of 2-cyclopropylmethoxy-4-fluoro-1-nitrobenzene (10 g, 1 eq.) in DMF (88 mL) was added drop wise at 0° C., and the reaction mixture was heated to 100° C. for 3 h. The reaction mixture was allowed to cool to room temperature, poured into ice water and extracted with EtOAc (3×100 mL). The combined organic phases were washed with water (3×100 mL), brine (100 mL) and dried (MgSO$_4$). Evaporation of solvent under reduced pressure gave 10.0 g of crude product which was purified by silica gel chromatography (hexane/EtOAc) gave 7.0 g of the desired product (42%)

$^1$H-NMR (CDCl$_3$, 200 MHz): 0.4 (m, 2H), 0.71 (m, 2H), 1.3 (m, 1H), 1.3 (t, 6H), 3.96 (d, 2H), 4.25 (q, 4H), 4.5 (s, 1H), 7.02 (d, 1H), 7.18 (s, 1H), 7.81 (d, 2H).

Step 3

Ethyl 2-(3-(cyclopropylmethoxy)-4-nitrophenyl)acetate

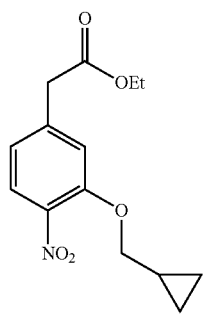 [SMILES: CCOC(=O)Cc1ccc([N+](=O)[O-])c(OCC2CC2)c1]

i) Diethyl 2-(3-(cyclopropylmethoxy)-4-nitrophenyl)malonate (10 g) was dissolved in 100 mL ethanol and cooled to 0° C., NaOH solution (4 eq) was added slowly to the reaction mixture for about 15 min. The reaction mixture was heated gently up to 60° C. for 5 h. Progress of the reaction was monitored by TLC analysis. After complete conversion of starting material solvent was evaporated under reduced pressure, the residue dissolved in H$_2$O, acidified with 6N HCl to pH-2. The solid material was collected via filtration, washed with water, dried under reduced pressure to yield 6.5 g (90%) of 2-(3-(cyclopropylmethoxy)-4-nitrophenyl)acetic acid as a yellow solid.

$^1$H-NMR (CDCl$_3$, 200 MHz): 0.36 (m, 2H), 0.58 (m, 2H), 1.28 (m, 1H), 3.71 (s, 2H), 4.01 (d, 2H), 7.02 (d, 1H), 7.23 (s, 1H), 7.81 (d, 1H).

ii) 2-(3-(Cyclopropylmethoxy)-4-nitrophenyl)acetic acid (6.5 g) was taken up in an ethanolic HCl solution (50 mL, 25%) and refluxed for 4 h, monitored by TLC. The reaction mixture was concentrated in vacuo to dryness and dissolved in ethyl acetate. The mixture was washed with NaHCO$_3$ solution, dried over NaSO$_4$ and concentrated in vacuo to give crude yellow solid which was purified by recrystallization to give the desired product (4.2 g).

$^1$H-NMR (CDCl$_3$, 200 MHz): 0.36 (m, 2H), 0.58 (m, 2H), 1.12 (t, 3H), 1.28 (m, 1H), 3.71 (s, 2H), 4.01 (d, 2H), 4.21 (q, 2H), 7.02 (d, 1H), 7.23 (s, 1H), 7.81 (d, 1H).

Step 4

Ethyl 2-(4-amino-3-(cyclopropylmethoxy)phenyl)acetate

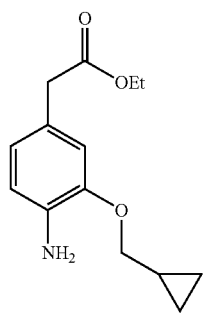

To a stirred solution of ethyl 2-(3-(cyclopropylmethoxy)-4-nitrophenyl)acetate (10 g), in dry MeOH (100 mL) was added Pd(OH)$_2$ (2 g). The mixture was hydrogenated under a H$_2$ atmosphere for 6 h at room temperature. The reaction mixture was filtered through a pad of Celite™, washing with MeOH. The combined filtrates were concentrated under reduced pressure to yield 7.5 g of the desired product as an oil.

$^1$H-NMR (CDCl$_3$, 200 MHz): 0.38 (m, 2H), 0.61 (m, 2H), 1.23 (m, 1H), 1.23 (t, 3H), 3.51 (s, 2H), 3.80 (d, 2H), 4.16 (q, 2H), 6.72 (m, 3H).

Step 5

Ethyl 2-(4-amino-3-chloro-5-(cyclopropylmethoxy)phenyl)acetate

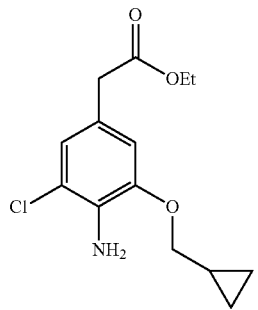 [SMILES: CCOC(=O)Cc1cc(Cl)c(N)c(OCC2CC2)c1]

To a stirred solution of ethyl 2-(4-amino-3-(cyclopropylmethoxy)phenyl)acetate (1.2 g, 4.0 mmol) in dry CCl$_4$ (60 mL), NCS (0.427 g, 3.2 mmol) was added at 0° C. The reaction mixture was allowed to stir for 3 h at room temperature to complete the reaction. The reaction mixture was diluted with water, extracted with DCM (2×50 mL), the combined organic solvents was dried over Na$_2$SO$_4$, filtered and concentrated in vacuo. The crude reaction mixture was purified by column chromatography to yield Ethyl 2-(4-amino-3-chloro-5-(cyclopropylmethoxy)phenyl)acetate (920 mg) as a yellow solid.

Step 6

Ethyl 2-(3-chloro-5-(cyclopropylmethoxy)-4-iodophenyl)acetate

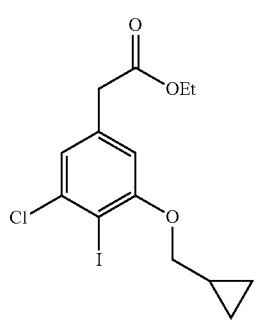 [SMILES: CCOC(=O)Cc1cc(Cl)c(I)c(OCC2CC2)c1]

Ethyl-2-(4-amino-3-chloro-5-(cyclopropylmethoxy)phenyl)-acetate (2.5 g, 10.0 mmol) was dissolved in a mixture of AcCN/H$_2$O/HCl (96%) 50 mL/50 mL/25 mL at 0° C. A solution of NaNO₂ (3.2 g, 1.16 eq) in water (40 mL) was added drop wise at 0° C., and the reaction mixture was stirred for 40 min, at the same temperature. A solution of KI (30 g, 30.1 mmol) in water (80 mL) was added drop wise at 0° C. The reaction mixture was heated to 50° C. for 2.5 h and the solvent was evaporated. The reaction mixture was extracted with EtOAc (3×50 mL), and the combined organic layers were washed with 10% sodium thiosulfate (2×50 mL), water (300 mL) followed by brine (300 mL). The solution was dried over Na₂SO₄, filtered and concentrated in vacuo to give crude black oil which was purified by chromatography over silica gel (hexane/EtOAc) to give the ethyl 2-(3-chloro-5-(cyclopropylmethoxy)-4-iodophenyl)acetate (1.2 g)

Step 7

Ethyl 2-(2-chloro-6-(cyclopropylmethoxy)-4'-(trifluoromethyl)biphenyl-4-yl)acetate

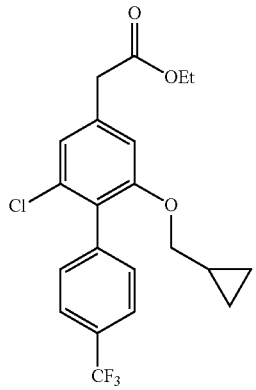 [SMILES: CCOC(=O)Cc1cc(Cl)c(-c2ccc(C(F)(F)F)cc2)c(OCC2CC2)c1]

A mixture of compound ethyl 2-(3-chloro-5-(cyclopropylmethoxy)-4-iodophenyl)acetate (5.1 g, 12.9 mmol), 4-trifluoromethylphenylboronic acid (3.66 g, 19 mmol), CsF (3.9 g, 25.8 mmol) and Pd (PPh₃)₄ (1.5 g, 1.3 mmol) in 100 mL anhydrous 1,2-dimethoxy ethane was refluxed for 8 h under argon. The reaction mixture was cooled, and 75 mL of EtOAc and 75 mL of water were added. The organic phase was separated, dried over Na₂SO₄, filtered and concentrated under reduced pressure to yellow oil. The oil was purified by column chromatography over silica gel (hexane/EtOAc) to give ethyl 2-(2-chloro-6-(cyclopropylmethoxy)-4'-(trifluoromethyl)biphenyl-4-yl)acetate (3.2 g) as yellow oil.

Step 8

1-(2-chloro-6-(cyclopropylmethoxy)-4'-(trifluoromethyl)biphenyl-4-yl)cyclobutane carboxylic acid

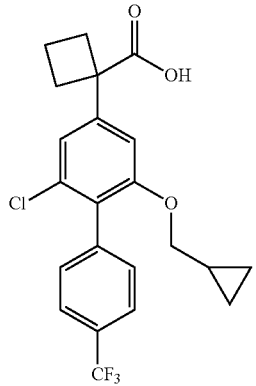 [SMILES: O=C(O)C1(c2cc(Cl)c(-c3ccc(C(F)(F)F)cc3)c(OCC3CC3)c2)CCC1]

Ethyl 2-(2-chloro-6-(cyclopropylmethoxy)-4'-(trifluoromethyl)biphenyl-4-yl)acetate (0.5 g, 1.2 mmol) was dissolved in 10 mL anhydrous DMF, NaH (60% wt. in oil, 0.058 g, 2.4 mmol) was added at 0° C. The reaction mixture was stirred for 0.5 h at 25° C. and 1,3-dibromopropane (1.5 mL) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), and dried over MgSO₄, filtered and concentrated under reduced pressure to give a (320 mg) of colorless oil. The oil was dissolved in 10 mL of EtOH/H₂O (9:1, vvl) and 0.163 g LiOH added. The reaction mixture was refluxed for 5 h and concentrated under reduced pressure. Water (10 mL) was added and the reaction mixture was extracted with EtOAc (3×10 mL). The combined organic phases were dried over MgSO₄, filtered and concentrated under reduced pressure. Purification by column chromatography over silica gel (hexane/EtOAc 9:1) gave 1-(2-chloro-6-(cyclopropylmethoxy)-4'-(trifluoromethyl)biphenyl-4-yl) cyclobutane carboxylic acid (0.210 g) as a white solid. ¹H NMR (300 MHz, CDCl₃): δ 7.68 (d, 2H), 7.41 (d, 2H), 7.06 (s, 1H), 6.78 (s, 1H), 3.78 (d, 2H), 2.86 (m, 2H), 2.58 (m, 2H), 2.16 (m, 1H), 1.95 (m, 1H), 1.03 (m, 1H), 0.46 (m, 2H), 0.18 (m, 2H).

Example 1909

1-(2-chloro-6-(cyclopropylmethoxy)-4'-(trifluoromethyl)biphenyl-4-yl)cyclopentane carboxylic acid 1-(2-chloro-6-(cyclopropylmethoxy)-4'-(trifluoromethyl)biphenyl-4-yl)cyclopentane carboxylic acid

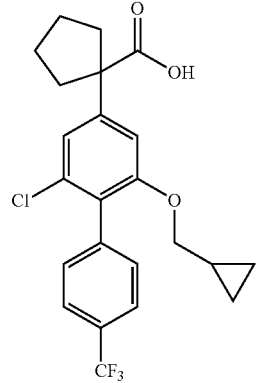 [SMILES: O=C(O)C1(c2cc(Cl)c(-c3ccc(C(F)(F)F)cc3)c(OCC3CC3)c2)CCCC1]

Ethyl 2-(2-chloro-6-(cyclopropylmethoxy)-4'-(trifluoromethyl)biphenyl-4-yl)acetate (0.5 g) was dissolved in 10 mL anhydrous DMF and NaH (60% wt. in oil, 0.058 g, 2.4 mmol) was added at 0° C. The reaction mixture was stirred for 0.5 h at 25° C. and 1,4-dibromobutane (0.24 g) was added drop wise at 0° C. The reaction mixture was stirred at 0° C. for 1 h and saturated NH₄Cl solution (10 mL) was added. The reaction mixture was extracted with EtOAc (3×20 mL) and the combined organic phases were washed with water (3×20 mL) and brine (20 mL), and dried over MgSO₄, filtered and concentrated under reduced pressure to give a (320 mg, 0.64 mmol) of colorless oil. The oil was dissolved in 10 mL of EtOH/H₂O (9:1, vvl) and LiOH (0.163 g, 3.88 mmol) added. The reaction mixture was refluxed for 5 h and concentrated under reduced pressure. Water (10 mL) was added and the reaction mixture was extracted with EtOAc (3×10 mL). The combined organic phases were dried over MgSO₄, filtered and concentrated under reduced pressure. Purification by column chromatography over silica gel (hexane/EtOAc 9:1) to give 1-(2-chloro-6-(cyclopropylmethoxy)-4'-(trifluoromethyl)biphenyl-4-yl)cyclopentane carboxylic acid (220 mg) as a white solid. $^1$H NMR (500 MHz, CDCl$_3$): δ 7.68 (d, 2H), 7.41 (d, 2H), 7.16 (s, 1H), 6.91 (s, 1H), 3.78 (d, 2H), 2.66 (m, 2H), 1.97 (m, 2H), 1.79 (m, 4H), 1.03 (m, 1H), 0.46 (d, 2H), 0.18 (d, 2H);

Example 2418

2-(6-chloro-5-(cyclopropylmethoxy)-4'-(trifluoromethyl)biphenyl-3-yl)-4-methylpentanoic acid

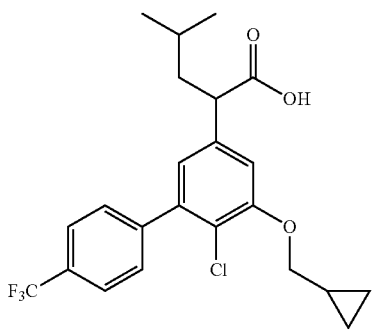 [SMILES: CC(C)CC(C(=O)O)c1cc(OCC2CC2)c(Cl)c(-c2ccc(C(F)(F)F)cc2)c1]

Step 1

Ethyl 2-(3-(cyclopropylmethoxy)-4-nitrophenyl)-4-methylpentanoate

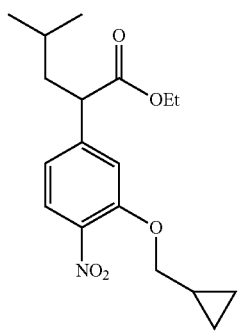 [SMILES: CCOC(=O)C(CC(C)C)c1ccc([N+](=O)[O-])c(OCC2CC2)c1]

Ethyl 2-(3-(cyclopropylmethoxy)-4-nitrophenyl)acetate (2.2 g, 7.8 mmol) was dissolved in 20 mL anhydrous DMF and NaH (60% wt. in oil, 0.189 g, 7.8 mmol) was added at 0° C. The reaction mixture was stirred for 0.5 h at 25° C. and isobutyl bromide (1.08 g, 7.8 mmol) was added drop wise at 0° C. The reaction mixture was stirred at 0° C. for 1 h and saturated NH$_4$Cl solution (10 mL) was added. The reaction mixture was extracted with EtOAc (3×20 mL) and the combined organic phases were washed with water (3×20 mL) and brine (20 mL), and dried over MgSO$_4$, filtered and concentrated under reduced pressure to give ethyl 2-(3-(cyclopropylmethoxy)-4-nitrophenyl)-4-methylpentanoate (2.06 g) of colorless oil.

Step 2

Ethyl 2-(4-amino-3-(cyclopropylmethoxy)phenyl)-4-methylpentanoate

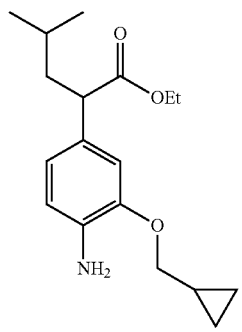

To a stirred solution of ethyl 2-(3-(cyclopropylmethoxy)-4-nitrophenyl)-4-methylpentanoate (2.0 g, 5.9 mmol), in dry MeOH (50 mL) Pd(OH)$_2$ (1.1 g) was added. The mixture was reduced under an atmosphere of H$_2$ for 6 h at room temperature. The reaction mixture was filtered off through a pad of Celite™, washing with MeOH. The combined filtrates were concentrated under reduced pressure to yield ethyl 2-(4-amino-3-(cyclopropylmethoxy)phenyl)-4-methylpentanoate (1.69 g) as a thick liquid.

Step 3

Ethyl 2-(4-amino-3-bromo-5-(cyclopropylmethoxy)phenyl)-4-methylpentanoate

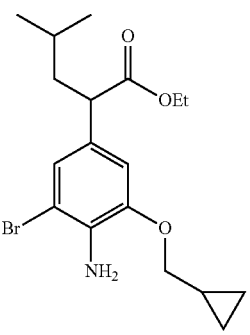 [SMILES: CCOC(=O)C(CC(C)C)c1cc(Br)c(N)c(OCC2CC2)c1]

To a stirred solution of ethyl 2-(4-amino-3-(cyclopropylmethoxy)phenyl)-4-methylpentanoate (1.65 g, 5.4 mmol) in dry CCl$_4$ (60 mL), NBS (0.96 g, 5.4 mmol) was added at 0° C. The reaction mixture was allowed to stir for 3 at room temperature to complete the reaction. The reaction mixture was diluted with water, extracted with DCM (2×50 mL), the combined organic solvents was dried over Na$_2$SO$_4$, filtered and concentrated in vacuo. The crude reaction mixture was purified by column chromatography to yield ethyl 2-(4-amino-3-bromo-5-(cyclopropylmethoxy)phenyl)-4-methylpentanoate (1.5 g) as a yellow solid.

Step 4

Ethyl-2-(6-amino-5-(cyclopropylmethoxy)-4'-(trifluoromethyl)biphenyl-3-yl)-4-methylpentanoate

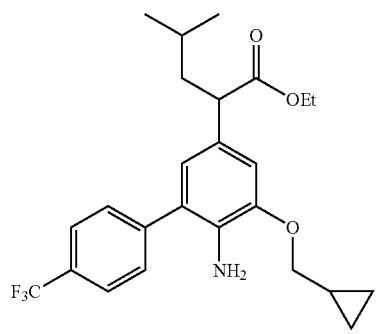 [SMILES: CCOC(=O)C(CC(C)C)c1cc(OCC2CC2)c(N)c(-c2ccc(C(F)(F)F)cc2)c1]

A mixture of ethyl 2-(4-amino-3-bromo-5-(cyclopropylmethoxy)phenyl)-4-methylpentanoate (1.5 g, 3.9 mmol), 4-trifluoromethylphenylboronic acid (1.1 g, 5.8 mmol), CsF (1.47 g, 7.8 mmol) and Pd (PPh$_3$)$_4$ (0.45 g, 0.39 mmol) in 75 mL anhydrous 1,2-dimethoxy ethane was refluxed for 8 h under argon. The reaction mixture was cooled, and 75 mL of EtOAc and 75 mL of water were added. The organic phase was separated, dried over Na$_2$SO$_4$, filtered and concentrated under reduced pressure to yellow oil. The oil was purified by chromatography over silica gel (hexane/EtOAc) to give ethyl-2-(6-amino-5-(cyclopropylmethoxy)-4'-(trifluoromethyl)biphenyl-3-yl)-4-methyl pentanoate (1.2 g) as a yellow oil.

Step 5

Ethyl-2-(6-chloro-5-(cyclopropylmethoxy)-4'-(trifluoromethyl)biphenyl-3-yl)-4-methylpentanoate

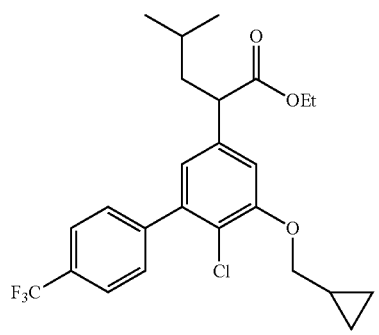

Ethyl-2-(6-amino-5-(cyclopropylmethoxy)-4'-(trifluoromethyl)biphenyl-3-yl)-4-methyl pentanoate (0.2 g, 0.44 mmol) was dissolved in a mixture of AcCN/H$_2$O/HCl 10 mL/10 mL/1 mL at 0° C. A solution of NaNO$_2$ (0.039 g, 0.53 mmol) in water (1 mL) was added drop wise at 0° C., and the reaction mixture was stirred for 40 min, at the same temperature. A solution of CuCl (0.22 g, 2.2 mmol) in water (5 mL) was added drop wise at 0° C. The reaction mixture was heated to 40° C. for 2.0 h and the solvent was evaporated. The reaction mixture was extracted with EtOAc (3×50 mL), and the combined organic layers were washed with water (30 mL) followed by brine (20 mL). The solution was dried over Na$_2$SO$_4$, filtered and concentrated in vacuo to give crude black oil which was purified by chromatography over silica gel (hexane/EtOAc) to give ethyl-2-(6-chloro-5-(cyclopropylmethoxy)-4'-(trifluoromethyl)biphenyl-3-yl)-4-methylpentanoate (0.12 g) as a thick oil.

Step 6

2-(6-chloro-5-(cyclopropylmethoxy)-4'-(trifluoromethyl)biphenyl-3-yl)-4-methylpentanoic acid

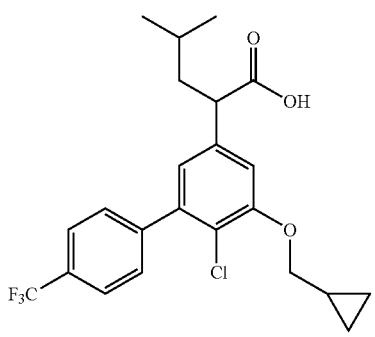

The ethyl-2-(6-chloro-5-(cyclopropylmethoxy)-4'-(trifluoromethyl)biphenyl-3-yl)-4-methylpentanoate (120 mg, 0.255 mmol) dissolved in 10 mL of MeOH/THF/H$_2$O (10 mL/10 mL/5 mL) and LiOH (30 mg, 1.2 mmol) was added. The reaction mixture was stirred at room temperature for 5 h and concentrated under reduced pressure. Water (10 mL) was added and the reaction mixture was extracted with EtOAc (3×10 mL). The combined organic phases were dried over MgSO$_4$, filtered and evaporated under reduced pressure. Purification by column chromatography over silica gel (DCM: MeOH 9:1) gave 2-(6-chloro-5-(cyclopropylmethoxy)-4'-(trifluoromethyl)biphenyl-3-yl)-4-methylpentanoic acid (89 mg) as a white solid. $^1$H-NMR (500 MHz, CDCl$_3$): 7.68 (d, 2H), 7.55 (d, 2H), 6.92 (s, 1H), 6.85 (s, 1H), 3.96 (d, 2H), 3.64 (t, 1H), 1.98 (m, 1H), 1.68 (m, 1H), 1.55 (m, 1H), 1.32 (m, 1H), 0.91 (d, 6H), 0.64 (m, 2H), 0.42 (m, 2H);

Example 3205

2-(5-chloro-6-(cyclopropylmethoxy)-4'-(trifluoromethyl)biphenyl-3-yl)-4-methoxybutanoic acid

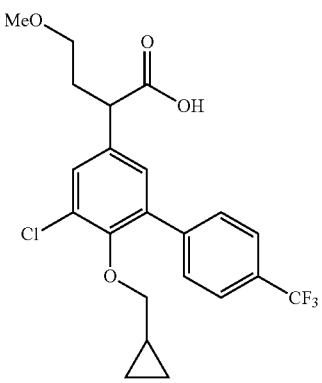 [SMILES: COCCC(C(=O)O)c1cc(Cl)c(OCC2CC2)c(-c2ccc(C(F)(F)F)cc2)c1]

Step 1

Ethyl 2-(3-bromo-5-chloro-4-(cyclopropylmethoxy)phenyl)acetate

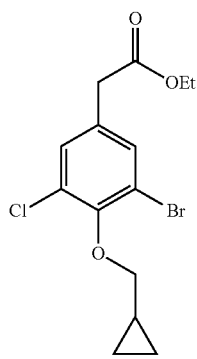 [SMILES: CCOC(=O)Cc1cc(Cl)c(OCC2CC2)c(Br)c1]

To a stirred solution of ethyl 2-(3-bromo-5-chloro-4-hydroxyphenyl)acetate (12 g, 40.816 mmol) in DMSO (80 mL) were added $K_2CO_3$ (14.08 g, 102.020 mmol) and cyclopropylmethylbromide (5 mL, 4.880 mmol) at RT under inert atmosphere. The reaction mixture was stirred at 80° C. temperature over a period of 14 h. After completion of starting material (by TLC), the reaction mixture was cooled to RT and quenched with water and extracted with EtOAc (3×100 mL). Combined organic layers were washed with water (3×75 mL), brine and dried over $Na_2SO_4$. After filtration and concentration under reduced pressure, the crude material was purified by column chromatography to afford ethyl 2-(3-bromo-5-chloro-4-(cyclopropylmethoxy)phenyl)acetate (10 g) yellow solid.

Step 2

Ethyl 2-(3-bromo-5-chloro-4-(cyclopropylmethoxy)-phenyl)-4-methoxybutanoate

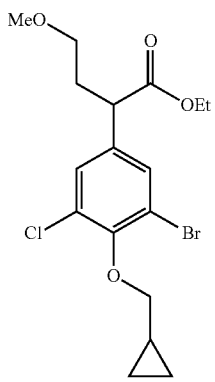 [SMILES: CCOC(=O)C(CCOC)c1cc(Cl)c(OCC2CC2)c(Br)c1]

To a stirred solution of NaH (0.3 g, 12.5 mmol) in DMF (10 mL) was added ethyl 2-(3-bromo-5-chloro-4-(cyclopropylmethoxy)phenyl)acetate (2.0 g, 5.70 mmol) at 0° C. The reaction mixture was stirred at 0° C. over a period of 30 min. To the reaction mixture was added 2-bromo ethyl methyl ether (0.87 g, 6.25 mmol) and stirred at 0° C. for 30 min. After completion of starting material (by TLC), the reaction mixture was diluted with water (20 mL), acidified with 1N HCl (pH=5) and extracted with EtOAc (3×50 mL). Combined organic layers were washed with water (3×25 mL), brine and dried over anhydrous $Na_2SO_4$. After filtration and concentration under reduced pressure, the crude material was purified by column chromatography to afford ethyl 2-(3-bromo-5-chloro-4-(cyclopropylmethoxy)-phenyl)-4-methoxybutanoate (560 mg) as an off white solid.

Step 3

Ethyl 2-(5-chloro-6-(cyclopropylmethoxy)-4'-(trifluoromethyl)biphenyl-3-yl)-4-methoxybutanoate

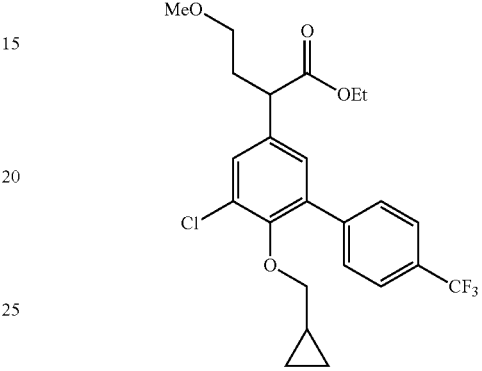

To a stirred solution of ethyl 2-(3-bromo-5-chloro-4-(cyclopropylmethoxy)-phenyl)-4-methoxybutanoate (2.3 g, 5.660 mmol) in a mixture of DMF (50 mL) and water (5 mL) were added $Cs_2CO_3$ (6.4 g, 19.815 mmol), $Pd(TPP)_4$ (1.3 g, 1.120 mmol) and 4-(trifluoromethyl)phenyl boronic acid (1.29 g, 6.780 mmol) at RT under $N_2$ atmosphere and the resulting mixture was stirred at 80° C. for 14 h. After completion of starting material (by TLC), filtered off the catalyst and celite bed was washed with EtOAc and extracted with EtOAc (3×100 mL). Combined organic layers were washed with water (3×50 mL), brine and dried over anhydrous $Na_2SO_4$. After filtration and concentration under reduced pressure, the crude material was purified by column chromatography to afford ethyl 2-(5-chloro-6-(cyclopropylmethoxy)-4'-(trifluoromethyl)biphenyl-3-yl)-4-methoxybutanoate (1.2 g) as an off white solid.

Step 4

2-(5-chloro-6-(cyclopropylmethoxy)-4'-(trifluoromethyl)biphenyl-3-yl)-4-methoxybutanoic acid

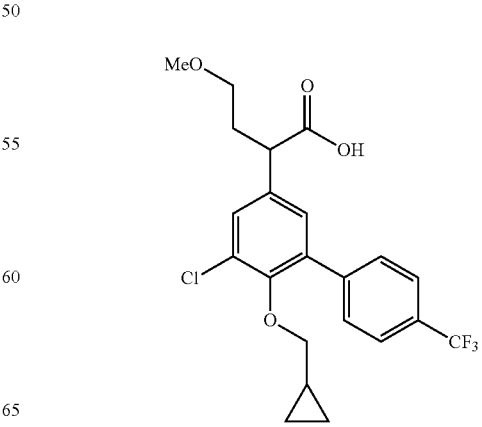

To a stirred solution of ethyl 2-(5-chloro-6-(cyclopropylmethoxy)-4'-(trifluoromethyl)biphenyl-3-yl)-4-methoxybutanoate (0.3 g, 0.638 mmol) in a mixture of THF (10 mL), methanol (10 mL) and water (5 mL) was added LiOH.H$_2$O (53 mg, 12.030 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (20 mL), brine (30 mL), dried over anhydrous Na$_2$SO$_4$ and concentrated in vacuo. The crude material was purified by column chromatography to afford 2-(5-chloro-6-(cyclopropylmethoxy)-4'-(trifluoromethyl)biphenyl-3-yl)-4-methoxybutanoic acid (100 mg) as an off white solid. $^1$HNMR (500 MHz) (CDCl$_3$): δ ppm 7.68 (m, 4H), 7.40 (s, 1H), 7.20 (s, 1H), 3.80 (t, 1H), 3.41 (d, 2H), 3.25 (m, 5H), 2.39 (m, 1H), 1.99 (m, 1H), 0.95 (m, 1H), 0.4 (d, 2H), 0.0 (m, 2H).

Example 3206

2-(3-(benzo[d]thiazol-6-yl)-5-chloro-4-(cyclopropylmethoxy)phenyl)-4-methylpentanoic acid

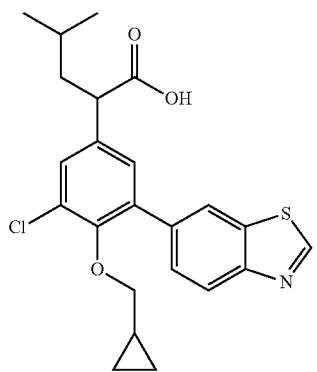 [SMILES: CC(C)CC(C(=O)O)c1cc(Cl)c(OCC2CC2)c(-c2ccc3ncsc3c2)c1]

Step 1

Ethyl 2-(3-bromo-5-chloro-4-(cyclopropylmethoxy)-phenyl)-4-methyl pentanoate

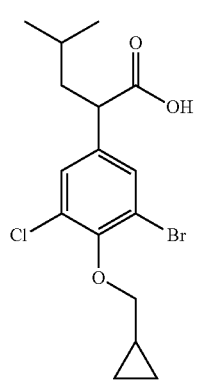 [SMILES: CC(C)CC(C(=O)O)c1cc(Cl)c(OCC2CC2)c(Br)c1]

To a stirred solution of NaH (0.76 g, 15.82 mmol) in DMF (50 mL) was added compound 2-(3-bromo-5-chloro-4-hydroxyphenyl)-4-methylpentanoic acid (5.0 g, 14.4 mmol) at 0° C. The reaction mixture was stirred at 0° C. over a period of 30 min. To the reaction mixture was added isobutyl bromide (2.93 g, 21.57 mmol) and stirred at 0° C. for 1 h. After completion of starting material (by TLC), diluted with water (40 mL), acidified with 1N HCl (pH=5) and extracted with EtOAc (3×100 mL). Combined organic layers were washed with water (3×50 mL), brine and dried over anhydrous Na$_2$SO$_4$. After filtration and concentration under reduced pressure, the crude material was purified by column chromatography to afford ethyl 2-(3-bromo-5-chloro-4-(cyclopropylmethoxy)-phenyl)-4-methyl pentanoate (5.0 g) as a liquid.

Step 2

Ethyl 2-(3-(benzo[d]thiazol-6-yl)-5-chloro-4-(cyclopropylmethoxy)phenyl)-4-methylpentanoate

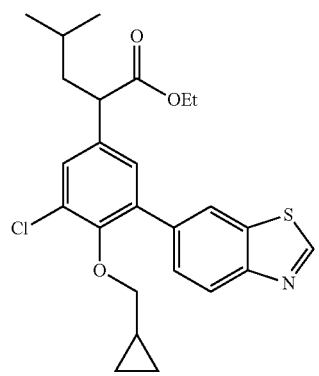 [SMILES: CCOC(=O)C(CC(C)C)c1cc(Cl)c(OCC2CC2)c(-c2ccc3ncsc3c2)c1]

To a stirred solution of ethyl 2-(3-bromo-5-chloro-4-(cyclopropylmethoxy)-phenyl)-4-methyl pentanoate (0.5 g, 1.239 mmol) in a mixture of DMF (10 mL) and water (5 mL) were added Cs$_2$CO$_3$ (1.4 g, 4.325 mmol), Pd (TPP)$_4$ (286 mg, 2.475 mmol) and 6-(4,4,5,5-tetramethyl-1,3,2-dioxaborolan-2-yl)benzo[d]thiazole (355 mg, 1.363 mmol) at RT under N$_2$ atmosphere and the resulting mixture was stirred at 80° C. for 14 h. After completion of starting material (by TLC), the solids were removed via filtration through a bed of Celite™ was washing with EtOAc (3×100 mL). The combined organic layers were washed with water (3×50 mL), brine and dried over anhydrous Na$_2$SO$_4$, filtered and concentrated under reduced pressure. The crude material was purified by column chromatography to afford ethyl 2-(3-(benzo[d]thiazol-6-yl)-5-chloro-4-(cyclopropylmethoxy)phenyl)-4-methylpentanoate (100 mg) as an off white solid.

Step 3

2-(3-(benzo[d]thiazol-6-yl)-5-chloro-4-(cyclopropylmethoxy)phenyl)-4-methylpentanoic acid

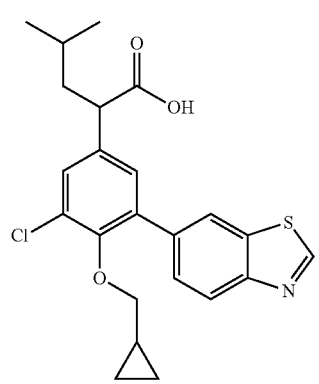 [SMILES: CC(C)CC(C(=O)O)c1cc(Cl)c(OCC2CC2)c(-c2ccc3ncsc3c2)c1]

To a stirred solution of ethyl 2-(3-(benzo[d]thiazol-6-yl)-5-chloro-4-(cyclopropylmethoxy)phenyl)-4-methylpentanoate (0.1 g, 0.218 mmol) in a mixture of THF (10 mL), methanol (10 mL) and water (5 mL) was added LiOH.H$_2$O (45 mg, 1.090 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous Na$_2$SO$_4$, filtered and concentrated in vacuo. The crude material was purified by column chromatography to afford 2-(3-(benzo[d]thiazol-6-yl)-5-chloro-4-(cyclopropylmethoxy)phenyl)-4-methylpentanoic acid (39 mg) as an off white solid. $^1$HNMR (500 MHz) (CDCl$_3$): δ (ppm) 9.05 (s, 1H), 8.2 (m, 2H), 7.73 (m, 1H), 7.40 (s, 1H), 7.30 (s, 1H), 3.63 (t, 1H), 3.40 (d, 2H), 1.99 (m, 1H), 1.65 (m, 1H), 1.55 (m, 1H), 0.93 (m, 7H), 0.38 (d, 2H), −0.5 (d, 2H).

Example 514

2-(3-(benzo[c][1,2,5]oxadiazol-5-yl)-5-chloro-4-(cyclopropylmethoxy)phenyl)-4-methylpentanoic acid Step 1

Ethyl 2-(3-(benzo[c][1,2,5]oxadiazol-5-yl)-5-chloro-4-(cyclopropylmethoxy)phenyl)-4-methylpentanoate

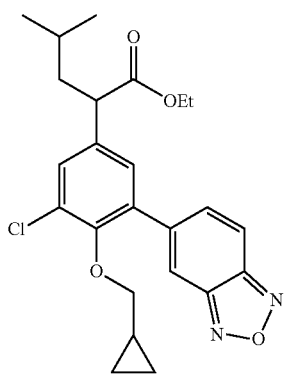 [SMILES: CCOC(=O)C(CC(C)C)c1cc(Cl)c(OCC2CC2)c(-c2ccc3nonc3c2)c1]

To a stirred solution of ethyl 2-(3-bromo-5-chloro-4-(cyclopropylmethoxy)phenyl)-4-methylpentanoate (0.5 g, 1.240 mmol) in a mixture of DMF (20 mL) and water (5 mL) were added Cs$_2$CO$_3$ (1.4 g, 4.342 mmol), Pd(TPP)$_4$ (286 mg, 2.480 mmol) and 5-(4,4,5,5,-tetramethyl-1,3,2-dioxaborolan-2-yl)benzo[c][1,2,5]oxadiazole (355 mg, 1.364 mmol) at RT under N$_2$ atmosphere and the resulting mixture was stirred at 80° C. for 14 h. After completion of starting material (by TLC), the solids were removed via filtration through a bed of Celite™ was washing with EtOAc (3×100 mL). The combined organic layers were washed with water (3×50 mL), brine and dried over anhydrous Na$_2$SO$_4$, filtered and concentrated under reduced pressure. The crude material was purified by column chromatography to afford ethyl 2-(3-(benzo[c][1,2,5]oxadiazol-5-yl)-5-chloro-4-(cyclopropylmethoxy)phenyl)-4-methylpentanoate (250 mg) as an off white solid.

2-(3-(benzo[c][1,2,5]oxadiazol-5-yl)-5-chloro-4-(cyclopropylmethoxy)phenyl)-4-methylpentanoic acid

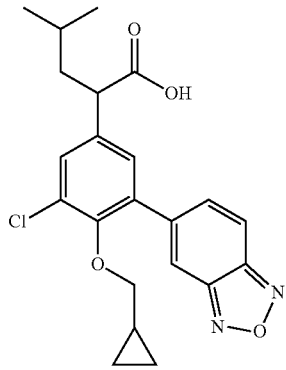 [SMILES: CC(C)CC(C(=O)O)c1cc(Cl)c(OCC2CC2)c(-c2ccc3nonc3c2)c1]

To a stirred solution of ethyl 2-(3-(benzo[c][1,2,5]oxadiazol-5-yl)-5-chloro-4-(cyclopropylmethoxy)phenyl)-4-methylpentanoate (0.25 g, 0.565 mmol) in a mixture of THF (10 mL), methanol (10 mL) and water (5 mL) was added LiOH.H$_2$O (118.7 mg, 2.828 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous Na$_2$SO$_4$, filtered and concentrated in vacuo. The crude material was purified by column chromatography to afford compound-2-(3-(benzo[c][1,2,5]oxadiazol-5-yl)-5-chloro-4-(cyclopropylmethoxy)phenyl)-4-methylpentanoic acid (152 mg) as an off white solid. $^1$HNMR (500 MHz) (CDCl$_3$): δ (ppm) 7.92 (s, 1H), 7.85 (m, 1H), 7.72 (m, 1H), 7.46 (s, 1H), 7.25 (s, 1H), 3.65 (t, 1H), 3.48 (d, 2H), 1.95 (m, 1H), 1.65 (m, 1H), 1.55 (m, 1H), 1.22 (m, 1H0, 0.93 (d, 6H), 0.39 (d, 2H), 0.0 (m, 2H).

Example 524

2-(3-(benzo[c][1,2,5]thiadiazol-5-yl)-5-chloro-4-(cyclopropylmethoxy)phenyl)-4-methylpentanoic acid Step 1

Ethyl 2-(3-(benzo[c][1,2,5]thiadiazol-5-yl)-5-chloro-4-(cyclopropylmethoxy)phenyl)-4-methylpentanoate

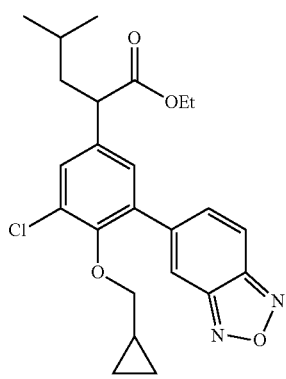 [SMILES: CCOC(=O)C(CC(C)C)c1cc(Cl)c(OCC2CC2)c(-c2ccc3nonc3c2)c1]

To a stirred solution of ethyl 2-(3-bromo-5-chloro-4-(cyclopropylmethoxy)phenyl)-4-methylpentanoate (0.5 g, 1.239 mmol) in a mixture of DMF (10 mL) and water (5 mL) were added Cs$_2$CO$_3$ (1.4 g, 4.325 mmol), Pd(TPP)$_4$ (286 mg, 2.475 mmol) and 5-(4,4,5,5,-tetramethyl-1,3,2-dioxaborolan-2-yl) benzo[c][1,2,5]thiazdiazole (355 mg, 1.363 mmol) at RT under N$_2$ atmosphere and the resulting mixture was stirred at 80° C. for 14 h. After completion of starting material (by TLC), the solids were removed via filtration through a bed of Celite™ was washing with EtOAc (3×100 mL). The combined organic layers were washed with water (3×50 mL), brine and dried over anhydrous Na$_2$SO$_4$, filtered and concentrated under reduced pressure. The crude material was purified by column chromatography to afford ethyl 2-(3-(benzo[c][1,2,5]thiadiazol-5-yl)-5-chloro-4-(cyclopropylmethoxy)phenyl)-4-methylpentanoate (222 mg) as an off white solid.

Step 2

2-(3-(benzo[c][1,2,5]thiadiazol-5-yl)-5-chloro-4-(cyclopropylmethoxy)phenyl)-4-methylpentanoic acid

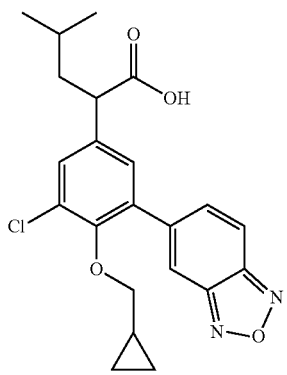 [SMILES: CC(C)CC(C(=O)O)c1cc(Cl)c(OCC2CC2)c(-c2ccc3nonc3c2)c1]

To a stirred solution of ethyl 2-(3-(benzo[c][1,2,5]thiadiazol-5-yl)-5-chloro-4-(cyclopropylmethoxy)phenyl)-4-methylpentanoate (0.22 g, 0.479 mmol) in a mixture of THF (5 mL), methanol (5 mL) and water (2 mL) was added LiOH.H$_2$O (60.3 mg, 1.438 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous Na$_2$SO$_4$ and concentrated in vacuo. The crude material was purified by column chromatography to afford 2-(3-(benzo[c][1,2,5]thiadiazol-5-yl)-5-chloro-4-(cyclopropylmethoxy) phenyl)-4-methyl pentanoic acid (105 mg, 50.0%) as an off white solid. $^1$HNMR (500 MHz) (CDCl$_3$): δ (ppm) 8.18 (s, 1H), 8.03 (d, 1H), 7.96 (d, 1H), 7.42 (s, 1H), 7.18 (s, 1H), 3.68 (t, 1H), 3.43 (d, 2H), 2.00 (m, 1H), 1.70 (m, 1H), 1.58 (m, 1H), 0.98 (d, 6H), 0.88 (m, 1H), 0.38 (d, 2H), 0.0 (m, 2H).

Example 3207

2-(6-(cyclopropylmethoxy)-5-(N,N-dimethylsulfamoyl)-4'-(trifluoromethyl)biphenyl-3-yl)-4-methylpentanoic acid

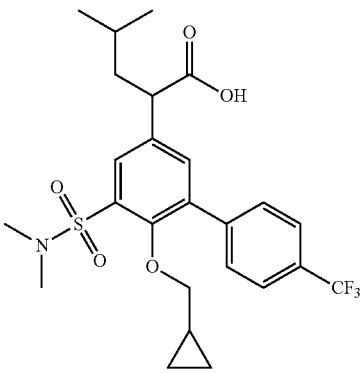 [SMILES: CC(C)CC(C(=O)O)c1cc(-c2ccc(C(F)(F)F)cc2)c(OCC2CC2)c(S(=O)(=O)N(C)C)c1]

Step 1

Ethyl 2-(3-bromo-5-(chlorosulfonyl)-4-hydroxyphenyl)-4-methyl pentanoate

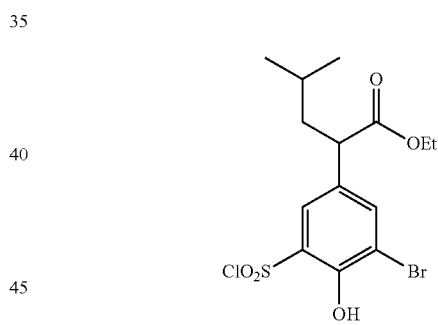

To a stirred compound ethyl 2-(3-bromo-4-hydroxyphenyl)-4-methylpentanoate (1.0 g, 3.174 mmol) in DCM (15 ml) chlorosulfonicacid (2 mL, 28.571 mmol) was added. The reaction mixture was stirred for 14 h at 80° C. under N$_2$ atmosphere. After completion of starting material (by TLC), the reaction mixture was quenched with NaHCO$_3$ solution and extracted with DCM (3×100 mL). Combined organic layers were washed with water (3×75 mL), brine and dried over Na$_2$SO$_4$, filtered and concentrated in vacuo to give ethyl 2-(3-bromo-5-(chlorosulfonyl)-4-hydroxyphenyl)-4-methyl pentanoate (0.5 g) as a liquid.

Step 2

Ethyl 2-(3-bromo-5-(N,N-dimethylsulfamoyl)-4-hydroxyphenyl)-4-methylpentanoate

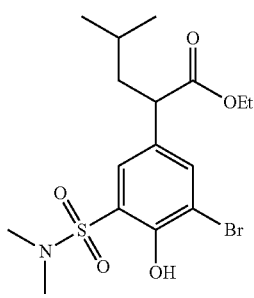 [SMILES: CCOC(=O)C(CC(C)C)c1cc(Br)c(O)c(S(=O)(=O)N(C)C)c1]

To a stirred solution of ethyl 2-(3-bromo-5-(chlorosulfonyl)-4-hydroxyphenyl)-4-methyl pentanoate (0.73 g, 1.765 mmol) in THF (20 mL) was added N,N-dimethylamine solution (5.2 mL, 10.592 mmol) at RT under inert atmosphere. The reaction mixture was stirred at RT over a period of 14 h. After completion of starting material (by TLC), the reaction mixture was quenched with water and extracted with EtOAc (3×100 mL). The combined organic layers were washed with water (3×75 mL), brine and dried over $Na_2SO_4$. After filtration and concentration under reduced pressure, the crude material was purified by column chromatography to afford ethyl 2-(3-bromo-5-(N,N-dimethylsulfamoyl)-4-hydroxyphenyl)-4-methylpentanoate (0.6 g) as a pale yellow liquid.

Step 3

Ethyl 2-(3-bromo-4-(cyclopropylmethoxy)-5-(N,N-dimethylsulfamoyl)phenyl)-4-methylpentanoate

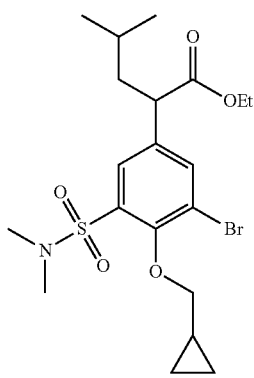 [SMILES: CCOC(=O)C(CC(C)C)c1cc(Br)c(OCC2CC2)c(S(=O)(=O)N(C)C)c1]

To a stirred solution of ethyl 2-(3-bromo-5-(N,N-dimethylsulfamoyl)-4-hydroxyphenyl)-4-methylpentanoate (0.75 g, 1.77 mmol) in DMSO (25 mL) were added $K_2CO_3$ (367 mg, 2.106 mmol) and cyclopropylmethylbromide (0.2 mL, 2.13 mmol) at RT under inert atmosphere. The reaction mixture was stirred at 80° C. temperature over a period of 14 h. After completion of starting material (by TLC), the reaction mixture was cooled to RT and quenched with water and extracted with EtOAc (3×100 mL). Combined organic layers were washed with water (3×75 mL), brine and dried over $Na_2SO_4$. After filtration and evaporation, the crude material was purified by column chromatography to afford ethyl 2-(3-bromo-4-(cyclopropylmethoxy)-5-(N,N-dimethylsulfamoyl)phenyl)-4-methylpentanoate (350 mg) as a liquid.

Step 4

2-(6-(cyclopropylmethoxy)-5-(N,N-dimethylsulfamoyl)-4'-(trifluoromethyl)biphenyl-3-yl)-4-methylpentanoic acid

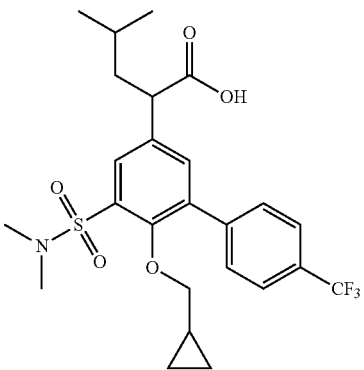 [SMILES: CC(C)CC(C(=O)O)c1cc(-c2ccc(C(F)(F)F)cc2)c(OCC2CC2)c(S(=O)(=O)N(C)C)c1]

To a stirred solution of 2-(3-bromo-4-(cyclopropylmethoxy)-5-(N,N-dimethylsulfamoyl)phenyl)-4-methylpentanoate (0.5 g, 1.049 mmol) in a mixture of DMF (10 mL) and water (5 mL) were added $Cs_2CO_3$ (1.19 g, 3.670 mmol), $Pd(TPP)_4$ (243 mg, 0.209 mmol) and 4-(trifluoromethyl)phenylbornate (220 mg, 1.150 mmol) at RT under $N_2$ atmosphere and the resulting mixture was stirred at 80° C. for 14 h. After completion of starting material (by TLC), filtered off the catalyst and celite bed was washed with EtOAc and extracted with EtOAc (3×100 mL). The combined organic layers were washed with water (3×50 mL), brine and dried over anhydrous $Na_2SO_4$. After filtration and concentration in vacuo, the crude material was purified by column chromatography to afford 2-(6-(cyclopropylmethoxy)-5-(N,N-dimethylsulfamoyl)-4'-(trifluoromethyl)biphenyl-3-yl)-4-methylpentanoic acid (100 mg) as an off white solid. $^1$HNMR (500 MHz) (CDCl$_3$): δ (ppm) 7.83 (s, 1H), 7.72 (m, 4H), 7.51 (s, 1H), 3.73 (m, 1H), 3.38 (d, 2H), 2.95 (s, 3H), 2.87 (s, 3H), 2.01 (m, 1H), 1.65 (m, 1H), 1.51 (m, 1H), 0.91 (m, 7H), 0.40 (d, 2H), 0.00 (m, 2H).

Step 5

Ethyl 2-(6-(cyclopropylmethoxy)-5-iodo-4'-(trifluoromethyl)biphenyl-3-yl)-4-methylpentanoate

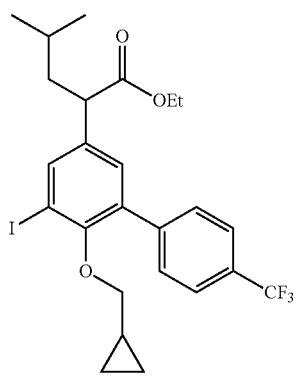 [SMILES: CCOC(=O)C(CC(C)C)c1cc(I)c(OCC2CC2)c(-c2ccc(C(F)(F)F)cc2)c1]

To a stirred solution of ethyl 2-(5-amino-6-(cyclopropylmethoxy)-4'-(trifluoromethyl)biphenyl-3-yl)-4-methylpentanoate (1.0 g, 2.227 mmol) in a mixture of HCl: H2O (0.81 mL, 6.681 mmol) was added NaNO₂ (0.180 g, 2.672 mmol). After being stirred for 1 h at 0° C. then added KI (3.69 g, 22.271 mmol) at 0° C. under inert atmosphere. The reaction mixture was stirred at 100° C. temperature over a period of 2 h. After completion of starting material (by TLC), the reaction mixture was cooled to RT and extracted with EtOAc (3×100 mL). The combined organic layers were washed with water (3×75 mL), brine and dried over Na₂SO₄. After filtration and concentration in vacuo, the crude material was purified by column chromatography to afford ethyl 2-(6-(cyclopropylmethoxy)-5-iodo-4'-(trifluoromethyl)biphenyl-3-yl)-4-methylpentanoate (0.93 g) as a solid.

Example 3210

2-(5-cyano-6-(cyclopropylmethoxy)-4'-(trifluoromethyl)biphenyl-3-yl)-4-methylpentanoic acid

Step 1

Ethyl 2-(5-cyano-6-(cyclopropylmethoxy)-4'-(trifluoromethyl)biphenyl-3-yl)-4-methylpentanoate

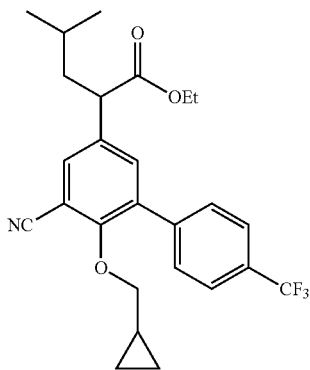 [SMILES: CCOC(=O)C(CC(C)C)c1cc(C#N)c(OCC2CC2)c(-c2ccc(C(F)(F)F)cc2)c1]

To a stirred solution of ethyl 2-(6-(cyclopropylmethoxy)-5-iodo-4'-(trifluoromethyl)biphenyl-3-yl)-4-methylpentanoate (0.25 g, 0.447 mmol) in NMP (10 mL) was added CuCN (50 mg, 0.536 mmol) at RT under inert atmosphere. The reaction mixture was stirred at 200° C. temperature over a period of 2 h. After completion of starting material (by TLC), the reaction mixture was cooled to RT and extracted with EtOAc (3×20 mL). Combined organic layers were washed with water (3×15 mL), brine and dried over Na₂SO₄. After filtration and evaporation, the crude material was purified by column chromatography to afford ethyl 2-(5-cyano-6-(cyclopropylmethoxy)-4'-(trifluoromethyl)biphenyl-3-yl)-4-methylpentanoate (0.125 g) a solid.

Step 2

2-(5-cyano-6-(cyclopropylmethoxy)-4'-(trifluoromethyl)biphenyl-3-yl)-4-methylpentanoic acid

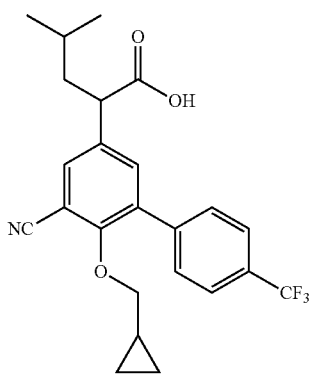 [SMILES: CC(C)CC(C(=O)O)c1cc(C#N)c(OCC2CC2)c(-c2ccc(C(F)(F)F)cc2)c1]

To a stirred solution of ethyl 2-(5-cyano-6-(cyclopropylmethoxy)-4'-(trifluoromethyl)biphenyl-3-yl)-4-methylpentanoate (0.125 g, 0.272 mmol) in a mixture of THF (5 mL), methanol (5 mL) and water (2 mL) was added LiOH.H₂O (34 mg, 0.816 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous Na₂SO₄ and concentrated under reduced pressure. The crude material was purified by column chromatography to afford 2-(5-cyano-6-(cyclopropylmethoxy)-4'-(trifluoromethyl)biphenyl-3-yl)-4-methylpentanoic acid (50 mg) as an off white solid. $^1$HNMR (500 MHz) (CDCl₃): δ (ppm) 7.70 (m, 4H), 7.61 (s, 1H), 7.51 (s, 1H), 3.71 (t, 1H), 3.55 (m, 2H), 2.00 (m, 1H), 1.67 (m, 1H), 1.51 (m, 1H), 1.02 (m, 1H), 0.91 (d, 6H), 0.45 (m, 2H), 0.05 (m, 2H).

Example 3208

2-(6-(cyclopropylmethoxy)-5-(methylthio)-4'-(trifluoromethyl)biphenyl-3-yl)-4-methylpentanoic acid

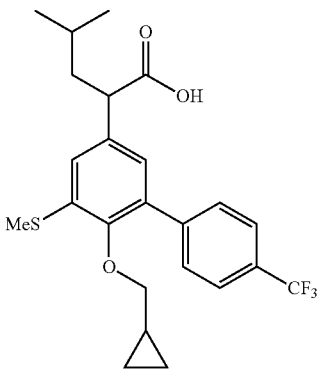 [SMILES: CSc1cc(C(CC(C)C)C(=O)O)cc(-c2ccc(C(F)(F)F)cc2)c1OCC1CC1]

Step 1

Ethyl 2-(6-(cyclopropylmethoxy)-5-(methylthio)-4'-(trifluoromethyl)biphenyl-3-yl)-4-methylpentanoate

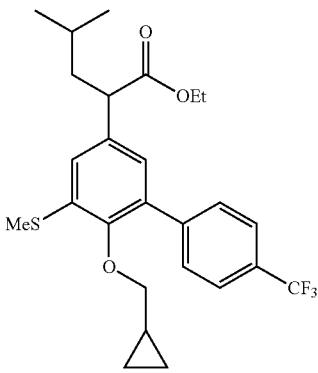 [SMILES: CCOC(=O)C(CC(C)C)c1cc(SC)c(OCC2CC2)c(-c2ccc(C(F)(F)F)cc2)c1]

To a stirred solution of ethyl 2-(5-amino-6-(cyclopropylmethoxy)-4'-(trifluoromethyl)biphenyl-3-yl)-4-methylpentanoate (1.0 g, 2.604 mmol) in a mixture of HCl: $H_2O$ (0.86 mL, 10.4 mmol) and THF (10 mL) was added $NaNO_2$ (0.215 g, 3.92 mmol). After being stirred for 1 h at 0° C. then added NaSMe (368 mg, 0.260 mmol) at 0° C. under an inert atmosphere. The reaction mixture was stirred at RT over a period of 14 h. After complete consumption of starting material (by TLC), the reaction mixture was extracted with EtOAc (3×100 mL). The combined organic layers were washed with water (3×75 mL), brine and dried over $Na_2SO_4$. After filtration and concentration under vacuo, the crude material was purified by column chromatography to afford ethyl 2-(6-(cyclopropylmethoxy)-5-(methylthio)-4'-(trifluoromethyl)biphenyl-3-yl)-4-methylpentanoate (0.93 g) as a solid.

Step 2

2-(6-(cyclopropylmethoxy)-5-(methylthio)-4'-(trifluoromethyl)biphenyl-3-yl)-4-methylpentanoic acid

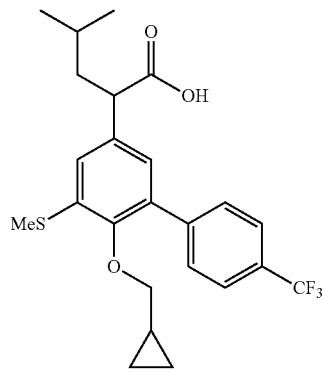 [SMILES: CSc1cc(C(CC(C)C)C(=O)O)cc(-c2ccc(C(F)(F)F)cc2)c1OCC1CC1]

To a stirred solution of ethyl 2-(6-(cyclopropylmethoxy)-5-(methylthio)-4'-(trifluoromethyl)biphenyl-3-yl)-4-methylpentanoate (80 mg, 0.166 mmol) in a mixture of THF (10 mL), methanol (10 mL) and water (5 mL) was added $LiOH.H_2O$ (20 mg, 0.832 mmol) at room temperature and the mixture was stirred at RT for 2 h. After complete consumption of starting material as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous $Na_2SO_4$, filtered and concentrated under vacuo. The crude material was purified by column chromatography to afford 2-(6-(cyclopropylmethoxy)-5-(methylthio)-4'-(trifluoromethyl)biphenyl-3-yl)-4-methylpentanoic acid (38 mg) as an off white solid. $^1$HNMR (500 MHz) ($CDCl_3$): δ (ppm) 7.75 (d, 2H), 7.65 (d, 2H), 7.31 (s, 1H), 7.23 (s, 1H), 3.65 (t, 1H), 3.60 (d, 2H), 2.82 (s, 3H), 1.98 (m, 1H), 1.65 (m, 1H), 1.5 (m, 1H), 1.22 (m, 1H), 0.9 (d, 6H), 0.38 (d, 2H), 0.01 (d, 2H).

Example 3209

2-(5-chloro-6-(cyclopropylmethoxy)-4'-(trifluoromethyl)biphenyl-3-yl)-3-methylbutanoic acid

Step 1

Ethyl 2-(3-bromo-5-chloro-4-(cyclopropylmethoxy)phenyl)-3-methylbutanoate

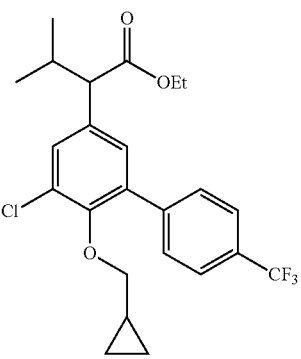 [SMILES: CCOC(=O)C(c1cc(Cl)c(OCC2CC2)c(-c2ccc(C(F)(F)F)cc2)c1)C(C)C]

285

To a stirred solution of NaH (40 mg, 0.830 mmol) in DMF (5 mL) was added compound ethyl 2-(5-chloro-6-(cyclopropylmethoxy)-4'-(trifluoromethyl)biphenyl-3-yl)acetate (300 mg, 0.728 mmol) and stirred at 0° C. for 1 h. To the reaction mixture at 0° C. was added isopropyl bromide (0.08 mL, 0.880 mmol) and continued stirring at 0° C. over a period of 30 min. After complete consumption of the starting material (by TLC), the reaction mixture was diluted with water (20 mL), acidified with 1N Hcl (pH=5) and extracted with EtOAc (3×30 mL). The combined organic layers were washed with water (3×15 mL), brine and dried over anhydrous Na₂SO₄. After filtration and concentration under educed pressure, the crude material was purified by column chromatography to afford ethyl 2-(3-bromo-5-chloro-4-(cyclopropylmethoxy)phenyl)-3-methylbutanoate (120 mg) as a liquid.

Step 2

2-(5-chloro-6-(cyclopropylmethoxy)-4'-(trifluoromethyl)biphenyl-3-yl)-3-methylbutanoic acid

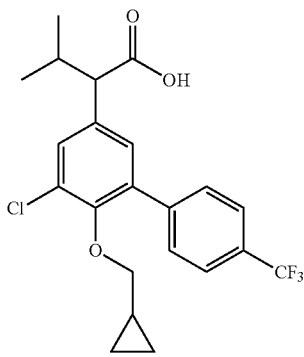 [SMILES: CC(C)C(C(=O)O)c1cc(Cl)c(OCC2CC2)c(-c2ccc(C(F)(F)F)cc2)c1]

To a stirred solution of ethyl 2-(3-bromo-5-chloro-4-(cyclopropylmethoxy)phenyl)-3-methylbutanoate (0.12 g, 0.260 mmol) in a mixture of THF (5 mL), methanol (5 mL) and water (2 mL) was added LiOH.H₂O (75 mg, 1.320 mmol) at room temperature and the mixture was stirred at RT for 2 h. After complete consumption of the starting material, as monitored by TLC, the reaction mixture was diluted with water (10 mL) and acidified using 1 N HCl at 0° C. The aqueous layer was extracted with EtOAc (2×20 mL); combined organic extracts were washed with water (10 mL), brine (20 mL), dried over anhydrous Na₂SO₄ and concentrated in vacuo. The crude material was purified by column chromatography to afford ethyl 2-(5-chloro-6-(cyclopropylmethoxy)-4'-(trifluoromethyl)biphenyl-3-yl)-3-methylbutanoate (100 mg) as an off white solid. $^1$HNMR (500 MHz) (CDCl₃): δ (ppm) 7.66 (m, 4H), 7.41 (s, 1H), 7.20 (s, 1H), 3.41 (d, 2H), 3.15 (d, 1H), 2.3 (m, 1H), 1.12 (d, 3H), 0.97 (m, 1H), 0.72 (d, 3H), 0.40 (d, 2H), 0.00 (d, 2H).

286

Example 482

2-(5-chloro-6-(cyclopropylmethoxy)-4'-(trifluoromethyl)biphenyl-3-yl)-4,4,4-trifluorobutanoic acid Step 1

Ethyl 2-(5-chloro-6-(cyclopropylmethoxy)-4'-(trifluoromethyl)biphenyl-3-yl)-4,4,4-trifluorobutanoate

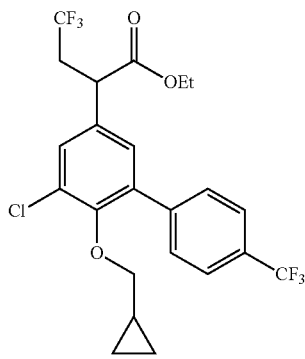 [SMILES: CCOC(=O)C(CC(F)(F)F)c1cc(Cl)c(OCC2CC2)c(-c2ccc(C(F)(F)F)cc2)c1]

To a stirred solution of NaH (64 mg, 0.13 mmol) in DMF (15 mL) was added ethyl 2-(5-chloro-6-(cyclopropylmethoxy)-4'-(trifluoromethyl)biphenyl-3-yl)acetate (500 mg, 0.12 mmol) and 1,1,1-trifluoro-2-iodoethane (0.304 mL, 0.15 mmol) at 0° C. The reaction mixture was stirred at 0° C. over a period of 30 min. After completion of starting material (by TLC), diluted with water (20 mL), acidified with 1N HCl (pH=5) and extracted with EtOAc (3×30 mL). Combined organic layers were washed with water (3×15 mL), brine and dried over anhydrous Na₂SO₄. After filtration and evaporation, the crude material was purified by column chromatography to afford ethyl 2-(5-chloro-6-(cyclopropylmethoxy)-4'-(trifluoromethyl)biphenyl-3-yl)-4,4,4-trifluorobutanoate (300 mg) as liquid.

Step 2

2-(5-chloro-6-(cyclopropylmethoxy)-4'-(trifluoromethyl)biphenyl-3-yl)-4,4,4-trifluorobutanoic acid

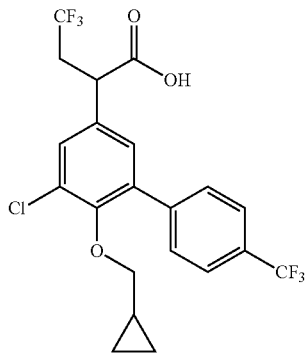 [SMILES: O=C(O)C(CC(F)(F)F)c1cc(Cl)c(OCC2CC2)c(-c2ccc(C(F)(F)F)cc2)c1]

To a stirred solution of ethyl 2-(5-chloro-6-(cyclopropylmethoxy)-4'-(trifluoromethyl)biphenyl-3-yl)-4,4,4-trifluorobutanoate (0.1 g, 0.404 mmol) in a mixture of THF (10 mL), methanol (10 mL) and water (5 mL) was added LiOH.H₂O (85 mg, 2.024 mmol) at room temperature and the mixture was stirred at RT for 2 h. After complete consumption of the starting material as monitored by TLC, the reaction mixture was diluted with water (10 mL) and acidified using 1 N HCl at 0° C. The aqueous layer was extracted with EtOAc (2×20 mL) the combined organic extracts were washed with water (10 mL), brine (20 mL), dried over anhydrous $Na_2SO_4$ and evaporated under vacuum. The crude material was purified by column chromatography to 2-(5-chloro-6-(cyclopropylmethoxy)-4'-(trifluoromethyl)biphenyl-3-yl)-4,4,4-trifluorobutanoic acid (38 mg) as sticky syrup. $^1$HNMR (500 MHz) ($CDCl_3$): δ (ppm) 7.71 (m, 4H), 7.39 (s, 1H), 7.19 (s, 1H), 3.92 (m, 1H), 3.41 (d, 2H), 3.08 (m, 1H), 2.54 (m, 1H), 0.96 (m, 1H), 0.40 (d, 2H), 0.00 (m, 2H).

The following examples can also be made using analogous procedures as described previously, substituting the appropriate reagents known to those of ordinary skill in the art.

Example 3211

2-(5-chloro-6-(cyclopropylmethoxy)biphenyl-3-yl)-4-methylpentanoic acid

Example 3212

2-(5-chloro-6-(2-methoxyethoxy)-4'-(trifluoromethyl)biphenyl-3-yl)-4-methylpentanoic acid Example 3213

2-(5-chloro-6-(cyclopropylmethoxy)-3'-(trifluoromethyl)biphenyl-3-yl)-4-methylpentanoic acid Example 3214

2-(5-bromo-6-(cyclopropylmethoxy)-4'-(trifluoromethyl)biphenyl-3-yl)-4-methylpentanoic acid Example 3215

2-(5-chloro-6-(cyclopropylmethoxy)-4'-(trifluoromethyl)biphenyl-3-yl)-3-methylpentanoic acid Example 3216

2-(5-chloro-6-(cyclopropylmethoxy)-4'-(trifluoromethyl)biphenyl-3-yl)-3-phenylpropanoic acid Example 3217

2-(3-(benzo[d]thiazol-5-yl)-5-chloro-4-(cyclopropylmethoxy)phenyl)-4-methylpentanoic acid The following examples can also be made using analogous procedures as described previously, substituting the appropriate reagents known to those of ordinary skill in the art.

Examples 464, 474, 480, 481, 483, 485, 488, 489, 494, 504, 1292, 1334, 2490, 2708, 3211, 3212, 3213, 3214, 3215, 3216 and 3217

Pharmacology Experimental

Measurement of Aβ In Vitro

The Aβ peptide is proteolytically derived from a larger integral membrane amyloid precursor protein (APP). The production of Aβ is derived from proteolytic cleavages at its N- and C-termini within β-APP by the β and γ-secretase activities, respectively. Transfected cells overexpressing β-APP or its equivalent producing the Aβ peptide can be used to monitor the effects of synthetic compounds on the production of Aβ.

To analyze a compound's effects on the concentrations of the various products of the γ-secretase cleavage activity, the Aβ peptides, various methods known to a person skilled in the art are available. Examples of such methods, but not limited to, include mass-spectrometric identification as described by Wang et al, 1996, J. Biol. Chem. 271:31894-31902) or detection by specific antibodies using, for example, ELISA's.

Examples of such assays for measuring the production of $Aβ_{total}$, $Aβ_{40}$ and $Aβ_{42}$ by ELISA include but are not limited to those described by Vassar et al., 1999, Science 286:735-741. Suitable kits containing the necessary antibodies and reagents for such an analysis are available, for example, but not limited to the Genetics Company, Wako, Covance, and Innogenetics. The kits are essentially used according to the manufacturers recommendations similar to the assay that is described by Citron et al., (1997) Nature Medicine 3:67-72 and the original assay described by Seubert et al., (1992) Nature 359:325-327.

Screening was carried out using the human embryonic kidney cell line HEK-293 overexpressing an amyloid precursor protein (APP) transgene grown in Pro-293a CDM media (BioWhittaker). Cells were grown to approximately 70-80% confluency subsequent to the addition of test compounds. The growth media was aspirated or removed, the cells washed, and replaced with 100 μl of compound, appropriately diluted in serum free media. The plates are then incubated for 16-18 hours at 37° C.

Conditioned Medium samples are removed for analysis/quantitation of the various Aβ peptide levels by differential ELISA's as described in accompanying instructions to the kits. Those compounds examined which do not demonstrate any overt toxicity or non-specific inhibitory properties are investigated further for their Aβ inhibitory effects and form the basis of medicinal chemistry efforts and to study the effect of the compounds in different experimental conditions and configurations.

Table 14 shows representative in vitro data (HEK 293) $EC_{50}$ data for compounds of the disclosure where:

A indicates a compound has an $EC_{50}$ for lowering Aβ342 of <1 μM

B indicates a compound has an $EC_{50}$ for lowering Aβ42 of >1 μM but <5 μM

C indicates a compound has an $EC_{50}$ for lowering Aβ42 of >5 μM

TABLE 14

| Example # | Activity |
|---|---|
| 264 | A |
| 414 | A |
| 415 | A |
| 419 | A |
| 464 | A |
| 474 | A |
| 480 | A |
| 481 | A |
| 482 | A |
| 483 | A |
| 484 | A |
| 485 | A |
| 488 | A |
| 489 | A |
| 494 | A |
| 504 | A |
| 514 | A |
| 524 | A |

TABLE 14-continued

| Example # | Activity |
|---|---|
| 534 | A |
| 554 | A |
| 724 | A |
| 754 | B |
| 1055 | A |
| 1268 | A |
| 1269 | A |
| 1270 | A |
| 1271 | A |
| 1272 | A |
| 1277 | A |
| 1280 | A |
| 1289 | A |
| 1292 | A |
| 1301 | A |
| 1304 | A |
| 1313 | A |
| 1316 | A |
| 1325 | A |
| 1334 | A |
| 1832 | A |
| 1833 | A |
| 1836 | A |
| 1837 | A |
| 1904 | A |
| 1905 | A |
| 1908 | A |
| 1909 | A |
| 1976 | A |
| 2418 | A |
| 2419 | A |
| 2422 | A |
| 2423 | A |
| 2490 | A |
| 2491 | A |
| 2494 | A |
| 2495 | A |
| 2708 | A |
| 2959 | A |
| 2995 | A |
| 3200 | A |
| 3201 | A |
| 3202 | B |
| 3203 | A |
| 3204 | A |
| 3205 | A |
| 3206 | A |
| 3207 | B |
| 3208 | A |
| 3209 | A |
| 3210 | A |
| 3211 | A |
| 3212 | A |
| 3213 | A |
| 3214 | A |
| 3215 | A |
| 3216 | A |
| 3217 | B |

Table 15 shows individual $EC_{50}$ values for representative compounds of the disclosure.

TABLE 15

| Example # | Compounds Name | $EC_{50}$ (Aβ42) HEK 293 (μM) |
|---|---|---|
| 484 | 2-(5-chloro-6-(cyclopropylmethoxy)-4'-(trifluoromethyl)biphenyl-3-yl)-4-methylpentanoic acid | 0.069 |
| 514 | 2-(3-(benzo[c][1,2,5]oxadiazol-5-yl)-5-chloro-4-(cyclopropylmethoxy)phenyl)-4-methylpentanoic acid | 0.274 |
| 2959 | 2-(4-(benzo[c][1,2,5]oxadiazol-5-yl)-3-chloro-5-(2-cyclopropylethyl)phenyl)-4-methylpentanoic acid | 0.298 |
| 2995 | 2-(4-(benzo[c][1,2,5]thiadiazol-5-yl)-3-chloro-5-(2-cyclopropylethyl)phenyl)-4-methylpentanoic acid | 0.220 |
| 3210 | 2-(5-cyano-6-(cyclopropylmethoxy)-4'-(trifluoromethyl)biphenyl-3-yl)-4-methylpentanoic acid | 0.275 |

Experimental Procedures for Rat Primary Cortical Culture-Based $Abeta_{1-42/1-x}$ ELISAs Rat primary neocortical cultures are established through the dissection of the neocortices from 10-12 E17 embryos harvested from time-pregnant SD (Sprague Dawley) rats (Charles River Laboratories). Following dissection, the combined neocortical tissue specimen volume is brought up to 5 mL with dissection medium (DM; 1×HBSS (Invitrogen Corp., cat#14185-052)/10 mM HEPES (Invitrogen Corp., cat#15630-080)/1 mM Sodium Pyruvate (Invitrogen Corp., cat#11360-070)) supplemented with 100 uL Trypsin (0.25%; Invitrogen Corp., cat#15090-046) and 100 uL DNase I (0.1% stock solution in DM, Roche Diagnostics Corp., cat#0104159), undergoing digestion via incubation at 37° C. for 10 minutes. Digested tissue is washed once in plating medium (PM; NeuroBasal (Invitrogen Corp., cat#21103-049)/10% Horse Serum (Sigma-Aldrich Co., cat#H1138)/0.5 mM L-Glutamine (Invitrogen Corp., cat#25030-081)), then resuspended in a fresh 10 mL PM volume for trituration. Trituration consists of 18 cycles with a 5 mL-serological pipet, followed by 18 cycles with a flame-polished glass Pasteur pipet. The volume is elevated to 50 mL with PM, the contents then passed over a 70 um cell-strainer (BD Biosciences, cat#352350) and transferred directly to a wet-ice bath. The cell-density is quantified using a hemacytometer, and diluted to allow for the plating of 50000 cells/well/100 uL in pre-coated 96-well PDL-coated plates (Corning, Inc., cat#3665). Cells are incubated for 4-5 hours at 37° C./5% $CO_2$, after which time the entire volume is exchanged to feeding medium (FM; NeuroBasal/2% B-27 Serum-free supplement (Invitrogen Corp., cat#17504-044)/0.5 mM L-Glutamine/1% Penicillin-Streptomycin (Invitrogen Corp., cat#15140-122)). The cultures undergo two 50% fresh FM exchanges, after 3 days in vitro (DIV3), and again at DIV7.

Human C-terminal recognition-site $Abeta_{1-42}$ and Rat N-terminal recognition-site $Abeta_{1-x}$ capture-antibodies, diluted 1:300 in 0.05M Carbonate-Bicarbonate buffer (Sigma-Aldrich Co., C-3041), are use to coat (100 uL/well) flat-bottomed F96 MicroWell™ (MaxiSorp™ surface) plates (Nalge Nunc International, cat#439454), and incubated overnight at 4° C. for eventual use in the ELISA assay. Compounds to be screened are solubilized in dimethyl sulphoxide (DMSO, Sigma-Aldrich Co., cat#15493-8), and further diluted in DMSO in an eight-point dose-response format. Into 96-well plates, dose-response compound dilutions (1000× the desired final concentration) are stamped out at 2 uL/well, in duplicate (up to 3 compounds/plate), as a daughter plate. In addition, DMSO and N—[N-(3,5-difluorophenacetyl)-L-alanyl]-S-phenylglycine t-butyl ester (DAPT), a gamma-secretase inhibitor (GSI), are incorporated as solvent and positive controls, respectively. With the assistance of liquid-handling automation, the compound daughter plate is diluted 1:500 with warmed FM, and two DIV8 culture plates are leveled to 60 uL/well, and immediately overlaid with 60 uL/well of the 2× diluted daughter plate. The plates are returned to the 37° C./5% $CO_2$-incubator for 24 hours.

Each coated capture-antibody ELISA plate undergoes 4×250 uL/well Phosphate-buffered saline with 0.05% Tween®-20 SigmaUltra (PBS-T; Fluka, cat#79383/Sigma-Aldrich Co., cat#P7949) washes. The ELISA plates are then overlaid with 120 uL/well PBS-T supplemented with 1% Bovine Serum Albumin Diluent/Blocking solution (BSA; Kirkegaard & Perry Laboratories (KPL), Inc., cat#50-61-01) and incubate at room-temperature on an orbital shaker for a minimum of 2 hours.

Rat $Abeta_{1-42}$ and rat $Abeta_{1-40}$ peptide (American Peptide Co., cat#62-0-84/62-0-86A) DMSO stock solutions are serially-diluted 1:2 in FM yielding a final concentration range of 0-500 pg/mL, to be plated on the respective ELISA plates for determination of the corresponding standard curve, from which concentrations of specific or total Abeta peptides in the presence of a particular drug concentration can be calculated. The conditioned medium from the duplicate culture plates are collected and combined into one round-bottom 96-well transfer plate which is incubated on wet-ice. The culture plates are rinsed once with 120 ul/well FM, and replenished immediately with 100 uL/well FM, being returned to the incubator for 10 minutes. Cell-viability is evaluated by adding 20 uL/well of warmed CellTiter 96® $Aq_{ueous}$ One Solution (MTS/PES; Promega Corp., cat#G3581), and returning the plates to the incubator for 30-90 minutes. Plate absorbance at 492 nm is read on a spectrophotometer, and from which, the ratio of absorbance of compound-treated cells to absorbance of solvent (DMSO)-treated control cells is calculated. The calculation of the corresponding $EC_{50}$ values is performed following non-linear curve-fitting using GraphPad Prism® software.

For each ELISA plate, a corresponding transfer-plate is created containing 120 uL/well of either the rat $Abeta_{1-42}$ or rat $Abeta_{1-40}$ peptide standard solutions, in duplicate, and 110-115 uL/well of the collected conditioned-medium plate, half designated for the $Abeta_{1-42}$ ELISA, and the other half for the $Abeta_{1-x}$ ELISA. The ELISA plates undergo a second set of 4×250 uL/well PBS-T washes, immediately followed by being overlaid with their designated transfer-plate. The ELISA plates incubate on an orbital-shaker for 16-18 hours at 4° C.

Detection antibody solution is prepared by diluting beta-Amyloid 17-24 (4G8) biotinylated monoclonal antibody (Covance, Inc., cat#SIG-39240-200) 1:1500 in PBS-T supplemented with 0.67% BSA. The ELISA plates undergo 4×250 uL/well PBS-T washes, and are overlaid with 100 uL/well of 4G8 diluted detection-antibody solution. The $Abeta_{1-42}$ ELISA plates are incubated on an orbital-shaker at room-temperature for 90 minutes, the $Abeta_{1-x}$ ELISA plates for 60 minutes.

In order to conjugate the biotinylated monoclonal 4G8 antibody, following 4×250 uL/well PBS-T washes, the ELISA plates undergo a one-hour incubation at 100 ul/well with a 1:15000 dilution of Streptavidin-HRP conjugate (Jackson ImmunoResearch Laboratories, Inc., cat#016-030-0840) on an orbital-shaker at room temperature.

Following a final set of 4×250 uL/well PBS-T washes, the ELISA plates are overlaid with 100 ul/well SureBlue 3,3',5,5'-Tetramethylbenzidine (TMB) Microwell Peroxidase substrate solution (Kirkegaard & Perry Laboratories, Inc., cat#52-00-02), protected from light, and incubate for 20-45 minutes at room temperature. At the point the desired level of development is attained, 100 ul/well of TMB Stop solution (Kirkegaard & Perry Laboratories, Inc., cat#50-85-05) is added, and the plate thoroughly shaken in preparation for reading on a spectrophotometer. SureBlue TMB Microwell Substrate develops a deep blue color in the presence of a peroxidase-labeled conjugate, and turns yellow when stopped by acidification, allowing for plate absorbance at 450 nm to be read. From the calculation of the standard curve, the compound dose-response curves, normalized to DAPT performance, are plotted as % DMSO using GraphPad Prism® software, and the corresponding $EC_{50}$ values calculated.

Measurement of Aβ 42 In Vivo

Compounds of the invention can be used to treat AD in mammal such as a human or alternatively in a validated animal model such as the mouse, rat, or guinea pig. The mammal may not be diagnosed with AD, or may not have a genetic predisposition for AD, but may be transgenic such that it overproduces and eventually deposits Aβ in a manner similar to that seen in the human. Additionally, non-transgenic animals may also be used to determine the biochemical efficacy of the compound, with an appropriate assay.

Compounds can be administered in any standard form using any standard method. For example, but not limited to, compounds can be in the form of liquid, tablets or capsules that are taken orally or by injection. Compounds can be administered at any dose that is sufficient to significantly reduce, for example, levels of $Aβ_{total}$ or more specifically $Aβ_{42}$ in the blood plasma, cerebrospinal fluid (CSF), or brain.

To determine whether acute administration of the compound would reduce $Aβ_{42}$ levels in-vivo, two-three month old Tg2576 transgenic mice expressing $APP_{695}$ containing the "Swedish" variant could be used or any other appropriately validated transgenic model. This transgenic mouse displays spontaneous, progressive accumulation of β-amyloid (Aβ) in brain, eventually resulting in amyloid plaques within the subiculum, hippocampus and cortex. Animals of this age have high levels of Aβ in the brain but no detectable Aβ deposition. Mice treated with the compound would be examined and compared to those untreated or treated with vehicle and brain levels of soluble Aβ42 and total Aβ would be quantitated by standard techniques, for example, using ELISA. Treatments may be acute or sub-chronic and treatment periods may vary from hours to days or longer and can be adjusted based on the results of the biochemical endpoint once a time course of onset of effect can be established.

A typical protocol for measuring Aβ or $Aβ_{42}$ levels from in-vivo samples is shown but it is only one of many variations that could used to detect the levels of Aβ. For example, aliquots of compounds can be dissolved in DMSO (volume equal to 1/10th of the final formulation volume), vortexed and further diluted (1:10) with a 10% (w/v) hydroxypropyl β cyclodextrin (HBC, Aldrich, Ref N° 33, 260-7) solution in PBS, where after they are sonicated for 20 seconds.

Compounds may be administered as a single oral dose given three to four hours before sacrifice and subsequent analysis or alternatively could be given over a course of days and the animals sacrificed three to four hours after the administration of the final dose Tg2576 mice can be anesthetized with a mixture of ketamine/xylazine (80/16 mg/kg intraperitoneally). When a deep level of anesthesia is reached, the mouse's head is secured in a stereotaxic frame. The skin on the back of the neck is retracted and the muscles on the back of the neck are removed to expose the cisterna magna. CSF is collected from the cisterna magna using a pulled 10 μl micropipette taking care not to contaminate the CSF with blood. The CSF is immediately diluted 1:10 in 1% 3-[3-cholamidopropyl)-dimethyl-ammonio]-1-propane sulfonate (CHAPS) [weight per volume in phosphate buffered saline (w/v in PBS)] containing protease inhibitors (PI's) (Complete, Mini protease inhibitor cocktail tablets-Roche), quick frozen in liquid nitrogen and stored at −80° C. until ready for biochemical analysis.

Blood is collected via cardiac puncture using a 25 gauge needle attached to a 1 ml syringe and was dispensed into a 0.6 ml microtainer tube containing ethylenediaminetetraacetic acid (EDTA). The blood was centrifuged immediately at 4° C. for 5 minutes at 1500×G. The resulting plasma was aliquoted into 0.5 ml microcentrifuge tubes, the aliquots are quick frozen in liquid nitrogen and are stored at −80° C.

The brain is removed after removing the skull and is rinsed with PBS. The cerebellum/brain-stem is removed, frozen, and retained for drug exposure analysis; the remaining brain section was quartered. The rear right quarter, which contained cortex and hippocampus, is weighed, frozen in liquid nitrogen and stored at −80° C. until ELISA analysis. The remaining brain tissue is frozen in liquid nitrogen and stored at −80° C.

For total Aβ or $A\beta_{40}$ analysis brain tissue is homogenized at a volume of 24 ml/g in cold 1% CHAPS containing protease inhibitors and the resulting homogenates are centrifuged for 1 hour at 100,000×g at 4° C. The supernatant is removed and transferred to a fresh tube and further diluted to 240 ml/g in CHAPS with protease inhibitors.

For $A\beta_{42}$ analysis brain tissue is homogenized at a volume of 50 ml/g in cold 1% CHAPS containing PI's. Homogenates were spun for 1 hour at 100,000×g at 4° C. The supernatant is removed and transferred to a fresh tube and further to diluted to a final volume 66.7 ml/g in 1% CHAPS with protease inhibitors.

To quantify the amount of human $A\beta_{42}$ in the soluble fraction of the brain homogenates, commercially available Enzyme-Linked-Immunosorbent-Assay (ELISA) kits can be used (h Amyloid Aβ42 ELISA high sensitive, The Genetics Company, Zurich, Switzerland is just one of many examples). The ELISA is performed according to the manufacturer's protocol. Briefly, the standard (a dilution of synthetic Aβ1-42) and samples are prepared in a 96-well polypropylene plate without protein binding capacity (Greiner bio-one, Frickenhausen, Germany). The standard dilutions with final concentrations of 1000, 500, 250, 125, 62.5, 31.3 and 15.6 pg/ml and the samples are prepared in the sample diluent, furnished with the ELISA kit, to a final volume of 60 µl. Samples, standards and blanks (50 µl) are added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate is added, followed 30 minutes later by an addition of TMB/peroxide mixture, resulting in the conversion of the substrate into a colored product. This reaction is stopped by the addition of sulfuric acid (1M) and the color intensity is measured by means of photometry with an ELISA-reader with a 450 nm filter. Quantification of the Aβ content of the samples is obtained by comparing absorbance to a standard curve made with synthetic Aβ1-42.

Similar analysis, with minor modification, can be carried out with CSF (Diluted 1:10 (for a final loading dilution of 1:100) in 1% CHAPS containing PI and plasma samples (Diluted 1:15 in 0.1% CHAPS [w/v in PBS]).

Certain compounds of the disclosure may lower Aβ42 by >15%, in some cases certain compounds may lower Aβ42>25% and in further cases certain compounds may lower Aβ42>40% relative to basal levels.

In Vivo Studies (Rats)

Male Sprague Dawley rats from Harlan, 230-350 g, were used for studies. Fasted rats were dosed via oral gavage, with vehicle (15% Solutol HS 15, 10% EtOH, 75% Water) or compound, at a volume of 10 ml/kg. For PK studies, at fixed time points after dosing, the rats were euthanized with an excess of $CO_2$. Terminal blood was collected through cardiac puncture, mixed in EDTA tubes, immediately spun (3 min at 11,000 rpm at 4° C.), and snap frozen for plasma collection. A piece of frontal cortex was collected and snap frozen for compound level determination. For A-beta lowering studies, at a determined time point after dosing (Cmax if it is ≥3 hr), rats were euthanized as in the PK studies and plasma was collected as described above. Cerebellum was removed and saved for compound level determination, and the remaining brain was divided into 4 quadrants, snap frozen and saved to examine A-beta peptide levels.

Solutol HS 15 was purchased from Mutchler Inc.

Practitioners will also know that similar methods can also be applied to other species such as mice (including transgenic strains such as Tg2576), guinea pig, dog and monkey.

Analysis of In Vivo Aβ Lowering Studies

Compounds of the invention can be used to treat AD in mammal such as a human or alternatively in a validated animal model such as the mouse, rat, or guinea pig. The mammal may not be diagnosed with AD, or may not have a genetic predisposition for AD, but may be transgenic such that it overproduces and eventually deposits Aβ in a manner similar to that seen in the human. Alternatively, non-transgenic animals may also be used to determine the biochemical efficacy of the compound, that is, the effect on the Aβ biomarker, with an appropriate assay.

Compounds can be administered in any standard form using any standard method. For example, but not limited to, compounds can be in the form of liquid, tablets or capsules that are taken orally or by injection. Compounds can be administered at any dose that is sufficient to significantly reduce, for example, levels of $A\beta_{total}$ or more specifically $A\beta_{42}$ in the blood plasma, cerebrospinal fluid (CSF), or brain.

To determine whether acute administration of the compound would reduce $A\beta_{42}$ levels in-vivo, two-three month old non-transgenic Sprague-Dawley rats were used. Rats treated with the compound would be examined and compared to those untreated or treated with vehicle and brain levels of soluble $A\beta_{42}$ and $A\beta_{total}$ would be quantitated by standard techniques, for example, using an immunoassay such as an ELISA. Treatments may be acute or sub-chronic and treatment periods may vary from hours to days or longer and can be adjusted based on the results of the biochemical endpoint once a time course of onset of effect can be established.

A typical protocol for measuring Aβ or $A\beta_{42}$ levels from in-vivo samples is shown but it is only one of many variations that could used to detect the levels of Aβ.

Compounds may be administered as a single oral dose given three to four hours before sacrifice and subsequent analysis or alternatively could be given over a course of days and the animals sacrificed three to four hours after the administration of the final dose.

For total Aβ or $A\beta_{42}$ analysis brain tissue is homogenized in ten volumes of ice cold 0.4% DEA/50 mM NaCl containing protease inhibitors, e.g., for 0.1 g of brain 1 ml of homogenization buffer is added. Homogenization is achieved either by sonciation for 30 seconds at 3-4 W of power or with a polytron homogenizer at three-quarters speed for 10-15 seconds. Homogenates (1.2 ml) are transferred to pre-chilled centrifuge tubes (Beckman 343778 polycarbonate tubes) are placed into a Beckman TLA120.2 rotor. Homogenates are centrifuged for 1 hour at 100,000 rpm (355,040×g) at 4° C. The resulting supernatants are transferred to fresh sample tubes and placed on ice (the pellets are discarded).

The samples are further concentrated and purified by passage over Waters 60 mg HLB Oasis columns according to the methods described (Lanz and Schachter (2006) J. Neurosci Methods. 157(1):71-81; Lanz and Schachter (2008). J. Neurosci Methods. 169(1):16-22). Briefly, using a vacuum manifold (Waters#WAT200607) the columns are attached and conditioned with 1 ml of methanol at a flow rate of 1 ml/minute. Columns are then equilibrated with 1 ml of water. Samples are loaded (800 µl) into individual columns (the Aβ will attach to the column resin).

The columns are washed sequentially with 1 ml of 5% methanol followed by 1 ml of 30% methanol. After the final wash the eluates are collected in 13×100 mm tubes by passing 800 µl of solution of 90% methanol/2% ammonium hydroxide) over the columns at 1 ml/minute. The samples are transferred to 1.5 ml non-siliconized sample tubes are dried in a speed-vac concentrator at medium heat for at least 2 hours or until dry.

The dried samples are either stored at −80° C. or are used immediately by resuspending the pellets in 80 µl of Ultra-Culture serum-free media (Lonza) supplemented with protease inhibitors by vortexing for 10 seconds. Sixty microliters of each sample is transferred to a pre-coated immunoassay plate coated with an affinity purified rabbit polyclonal antibody specific to $A\beta_{42}$ (x-42). Sixty microliters of fresh supplemented ultraculture is added to the remaining sample and 60 microliters is transferred to a pre-coated and BSA blocked immunoassay plate coated with an affinity purified rabbit polyclonal antibody specific to total rodent Aβ (1-x). Additional standard samples of rodent Aβ/rodent $A\beta_{42}$ are also added to the plates with final concentrations of 1000, 500, 250, 125, 62.5, 31.3 and 15.6 pg/ml. The samples are incubated overnight at 4° C. in order to allow formation of the antibody-Amyloid-antibody-complex. The following day the plates are washed 3-4 times with 150 microliters of phosphate buffered saline containing 0.05% Tween 20. After removal of the final wash 100 µl of the monoclonal antibody 4G8 conjugated to biotin (Covance) diluted 1:1000 in PBS-T containing 0.67% BSA was added and the plates incubated at room temperature for 1-2 hours. The plates are again washed 3-4 times with PBS-T and 100 µl of a Streptavidin-Peroxidase-Conjugate diluted 1:10,000 from a 0.5 mg/ml stock in PBS-T contained 0.67% BSA is added and the plates incubated for at least 30 minutes. Following a final set of washes in PBS-T, a TMB/peroxide mixture is added, resulting in the conversion of the substrate into a colored product. This reaction is stopped by the addition of sulfuric acid (1M) and the color intensity is measured by means of photometry with an microplate reader with a 450 nm filter. Quantification of the Aβ content of the samples is obtained by comparing absorbance to a standard curve made with synthetic Aβ. This is one example of a number of possible measureable endpoints for the immunoassay which would give similar results.

FIG. 1 demonstrates the desirable effect on Aβ after the administration of example 1301 (2-(5-chloro-4'-isopropyl-6-(2,2,2-trifluoroethoxy)biphenyl-3-yl)-3-cyclopropylpropanoic acid) to in C57BL/6 mice when give one dose at 30 mg/kg in a Solutol HS 15: Ethanol:Water (15:10:75) formulation (measuring Aβ at 3 hours).

Pharmacokinetic Analysis
Sample Preparation

Plasma samples and standards were prepared for analysis by treating with a 3× volume of acetonitrile containing 500 ng/mL of internal standard (a selected aryl propionic acid). Typically 150 µL of acetonitrile with internal standard was added to 50 µL of plasma. Acetonitrile was added first to each well of a 96-well Phenomenex Strata Impact protein precipitation filter plate followed by the addition of the plasma sample or standard. The filter plate was allowed to sit for at least 15 minutes at room temperature before a vacuum was applied to filter the samples into a clean 96-well plate.

If sample concentrations were observed or predicted to be greater than 1000 ng/mL, plasma samples were diluted with blank plasma 10-150 fold depending on the anticipated concentration and upper limit of quantitation of the analytical method.

Samples of frontal cortex or cerebellum were homogenized then treated in similar manner. To each brain sample, a 4× volume of PBS (pH 7.4) buffer was added along with a 15× volume of acetonitrile (containing internal standard) in a 2 mL screw-cap plastic tube. The tubes were then filled one third of the way with 1 mm zirconia/silica beads (Biospec) and placed in a Mini Bead Beater for 3 minutes. The samples were inspected and if any visible pieces of brain remained, they were returned to the Bead Beater for another 2-3 minutes of shaking. The resulting suspension was considered to be a 5-fold dilution treated with a 3× volume of acetonitrile (with internal standard). Calibration standards were prepared in 5-fold diluted blank brain homogenate and precipitated with a 3× volume of acetonitrile immediately after the addition of the appropriate spiking solution (see below). All brain standards and samples were allowed to sit for at least 15 minutes prior to filtering them through a Phenomenex Strata Impact protein precipitation filter plate into a clean 96-well plate.

Spiking solutions for plasma and brain calibration standards were prepared at concentrations of 0.02, 0.1, 0.2, 1, 2, 10, 20, 100 and 200 µg/mL in 50:50 acetonitrile/water. Calibration standards were prepared by taking 190 µL of blank matrix (plasma or brain homogenate) and adding 10 µL of spiking solution resulting in final concentrations of 1, 5, 10, 50, 100, 500, 1000, 5000 and 10,000 ng/mL.

LC-MS/MS Analysis

Precipitated plasma and brain samples were analyzed by LC-MS/MS using a Shimadzu LC system consisting of two LC-10AD pumps and a SIL-HTc autosampler connected to an Applied Biosystems MDS/Sciex API 3200 QTRAP mass spectrometer.

For chromatographic separation, a Phenomenex Luna C-18 3 µM (2×20 mm) column was used with an acetonitrile-based gradient mobile phase. The two mobile phase components were:

Mobile phase A: water with 0.05% (v/v) formic acid and 0.05% (v/v) 5 N ammonium hydroxide.

Mobile phase B: 95:5 acetonitrile/water with 0.05% (v/v) formic acid and 0.05% (v/v) 5 N ammonium hydroxide.

The gradient for each analysis was optimized for the specific compound, but generally, the run started with between 0% and 40% of mobile phase B, ramped up to 100% of mobile phase B over 1-2 minutes, then held there for 2-3 minutes before returning to the initial conditions for 4 minutes to re-equilibrate.

The API 3200 QTRAP mass spectrometer was used in MRM mode with negative electrospray ionization. MRM transitions and mass spec settings were optimized for each compound.

Standard curves were created by quadratic or linear regression with 1/x*x weighting. Calibration standards were prepared 1-10,000 ng/mL, but the highest (and sometimes lowest) standards were often not acceptable for quantitation and only those standards with reasonable back-calculated accuracies were included in the calibration curve. Ideally, only standards with +/−15% of nominal concentration would be included in the fitted standard curve, but occasionally larger deviations were accepted after careful consideration. Sample concentrations below the quantitation range were reported as "BQL". Concentrations above the curve were usually re-run with larger sample dilutions Glucuronidation Protocols Microsomal glucuronidation reactions were conducted using the UGT Reaction Mix solutions (A and B) from BD Biosciences and following the vendor's protocol. 10 µM of test article or control compound was incubated with 0.5 mg/mL of human or rat liver microsomes. Samples were taken at 0 and 60 minutes and acetonitrile was added to terminate the reactions. Samples were analyzed by LC/MS, monitoring for the loss of parent compound and the appearance of glucuronide. Control reactions were run for each compound substituting water for the glucuronic acid solution to monitor for any loss of parent compound due to degradation or unanticipated microsomal reactions.

Hepatocyte experiments were run using cryopreserved human hepatocytes (single donor) obtained from Celsis/In Vitro Technologies. Cells were thawed and counted according to the vendor's protocols using the trypan blue exclusion method to obtain the count of live cells. Test article and control compounds were incubated at a concentration of 5 uM in KHB buffer (Celsis/In Vitro Technologies) containing 1 million cells per mL. Samples were taken at 0, 60 and 120 minutes. The reactions were terminated with addition of acetonitrile. Samples were analyzed by LC/MS, monitoring for the loss of parent compound and the appearance of glucuronide.

Pharmacology

Compounds of the disclosure are gamma secretase modulators (GSMs), i.e., compounds that act to shift the relative levels of Aβ peptides produced by γ-secretase. In some cases the compounds alter the relative levels of Aβ peptides produced by γ-secretase without significantly changing the total level of Aβ peptides produced. Certain compounds of the disclosure modulate γ-secretase activity with respect to APP proteolytic processing and in so doing lower the production of $A\beta_{42}$ both in vitro in cells and in vivo in animals. In some cases this effect occurs at concentrations that do not significantly impair the viability of cells in vitro and at doses that are well tolerated in vivo. Certain compounds of the disclosure lower $A\beta_{42}$ secretion in native neuronal and cellular construct assay systems with $EC_{50}$ values that are below 1 micromolar (Class A compounds, Table 14) while others have $EC_{50}$ values from 1-5 micromolar (Class B compounds, Table 14) and others have $EC_{50}$ values greater than 5 micromolar (Class C compounds). Certain compounds of the disclosure do not appear to significantly interfere with γ-secretase related Notch processing activity. Compounds that significantly interfere with γ-secretase related Notch processing activity have been associated with toxic side-effects. Certain compounds of the disclosure have favorable pharmacokinetic (PK) properties in animals. Thus, certain of the compounds are orally bioavailable, penetrate into the brain and have favorable PK parameters including half-life and clearance supporting pharmaceutical application in humans. In turn, certain compounds of the disclosure significantly lower $A\beta_{42}$ production in the brains of non-transgenic and transgenic animals after single dose and multi-dose oral administration with no overt side effects. For certain compounds of the disclosure single oral doses of <30 milligrams/kilogram are efficacious at lowering $A\beta_{42}$ production in the brains of rats (e.g. Sprague-Dawley) and wild type mice (e.g. C57BL/6). Certain compounds of the disclosure which lower $A\beta_{42}$ at doses of <30 milligrams/kilogram appear to be well tolerated and show no overt or clinical chemical toxicity after sub-chronic 14-day administration at doses >30 milligrams/kilogram/day. Certain compounds of the disclosure have favorable absorption-distribution-metabolism and excretion (ADME) properties. Moreover, certain compounds of the disclosure do not appear to significantly bio-accumulate in tissues especially in the brain. Compounds of Formulas I-IX wherein $A=CO_2H$ show favorable profiles with respect to acylglucoronide ($A=CO_2Glu$) metabolite formation. The potential for acylglucoronide metabolites to cause of toxicity has been described particularly for non-steroidal anti-inflammatory drugs (NSAIDs) containing carboxylic acid groups (Ebner et al Drug Metabolism and Disposition 1999, 27(10), 1143-49). Several such NSAIDs have been removed from the market due to idiosyncratic toxicity in humans and it has been speculated that NSAID idiosyncratic toxicity is related to the relative load and relative reactivity of acylglucoronide metabolites. Therefore, carboxylic acid compounds which are less prone to acylgluconoride formation are expected to be less toxic. As measured using established in vitro assay systems, certain desirable compounds of the disclosure are less prone to acylglucoronidation than NSAID compounds that remain on the market are regarded as safe (e.g., flurbiprofen).

Dosage and Administration

The present disclosure includes pharmaceutical composition for treating a subject having a neurological disorder comprising a therapeutically effective amount of a compound of Formulas I-IX, a derivative or a pharmaceutically acceptable salt thereof, and a pharmaceutically acceptable excipient, carrier or diluent.

The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (i.v.) administration. The formulations for administration will commonly comprise a solution of the compound of the Formulas I-IX dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formulas I-IX in these formulations can vary widely, and will be selected primarily based on fluid volumes, viscosities, body weight, and the like, in accordance with the particular mode of administration selected and the patient's needs. For i.v. administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formulas I-IX can be administered by introduction into the central nervous system of the subject, e.g., into the cerbrospinal fluid of the subject. The formulations for administration will commonly comprise a solution of the compound of Formulas I-IX dissolved in a pharmaceutically acceptable carrier. In certain aspects, the compound of Formulas I-IX is introduced intrathecally, e.g., into a cerebral ventricle, the lumbar area, or the cisterna magna. In another aspect, the compound of Formulas I-IX is introduced intraocullarly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formulas I-IX is administered into a subject intrathecally. As used herein, the term "intrathecal administration" is intended to include delivering a pharmaceutical composition comprising a compound of Formulas I-IX directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formulas I-IX to any of the above mentioned sites can be achieved by direct injection of the pharmaceutical composition comprising the compound of Formulas I-IX or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formulas I-IX is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formulas I-IX with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethylcellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formulas I-IX in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formulas I-IX in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.01 to 100 mg per kilogram body weight of the recipient per day, preferably in the range of 0.2 to 10 mg per kilogram body weight per day. The desired dose is preferably presented once daily, but may be dosed as two, three, four, five, six or more subdoses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated.

Details on techniques for formulation and administration are well described in the scientific and patent literature, see, e.g., the latest edition of Remington's Pharmaceutical Sciences, Maack Publishing Co, Easton Pa. ("Remington's After a pharmaceutical composition has been formulated in an acceptable carrier, it can be placed in an appropriate container and labeled for treatment of an indicated condition. For administration of the compounds of Formulas I-IX, such labeling would include, e.g., instructions concerning the amount, frequency and method of administration.

What is claimed is:
1. A compound of Formula III

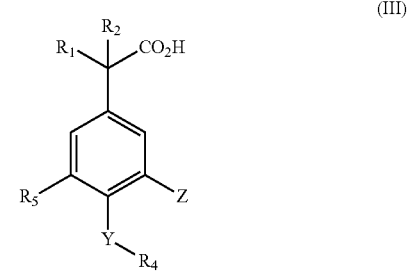

or a pharmaceutically acceptable salt thereof,
wherein:
$R_1$ and $R_2$ are independently selected from the group consisting of (a) H, (b) F, (c) OH, (d) $OR_6$, (e) $SR_6$, (f)

($C_2$-$C_6$)alkyl, (g) a $C_1$-$C_6$ alkyl that is independently interrupted by one or more —O—, —S—, —S(O)—, or —S(O)$_2$— groups, (h) ($C_0$-$C_3$)alkyl-($C_3$-$C_7$)cycloalkyl, (i) heterocycloalkylalkyl and (j) (CH$_2$)$_n$Q wherein n=0-2 and wherein Q is a monocyclic or bicyclic aromatic or heteroaromatic ring system having 5 to 10 ring atoms independently selected from the group consisting of C, N, O and S, provided that not more than 3 ring atoms in any single ring are other than C, and wherein Q is optionally independently substituted with up to 3 groups selected from the group consisting of alkyl, halogen, CF$_3$, OH, OCF$_3$, alkoxy, OCH$_2$CH$_2$OCH$_3$, NH$_2$, alkylamino, dialkylamino, morpholino, CN, NO$_2$, alkylthio and alkylsulfonyl, provided that both R$_1$ and R$_2$ are not H, wherein each alkyl or cycloalkyl of R$_1$ and R$_2$ is optionally independently substituted with one or more groups selected from the group consisting of halo, hydroxy, cyano, CF$_3$ and C$_1$-C$_4$ alkyl, or R$_1$ and R$_2$ taken together with the carbon to which they are attached form a 3-7 membered cycloalkyl or heterocycloalkyl ring which optionally bears a C$_1$-C$_4$ alkyl substituent that can be optionally independently substituted with one or more groups selected from the group consisting of halo, hydroxy, oxo, cyano, CF$_3$ and C$_1$-C$_4$ alkyl;

or

R$_1$ and R$_2$ are taken together with the carbon to which they are attached form a 3-7 membered cycloalkyl ring substituted with R$_{20}$ and R$_{21}$ wherein R$_{20}$ and R$_{21}$ taken together with the carbon or carbons to which they are attached form a 3-7 membered cycloalkyl ring wherein each cycloalkyl is optionally independently substituted with one or more groups selected from the group consisting of halo, hydroxy, cyano, CF$_3$ and C$_1$-C$_4$ alkyl;

R$_6$ is selected from the group consisting of
(a) C$_1$-C$_6$ alkyl optionally and independently interrupted by one or more —O—, —S(O)—, or —S(O)$_2$— groups,
(b) (C$_0$-C$_3$)alkyl-(C$_3$-C$_7$)cycloalkyl,
(c) heterocycloalkylalkyl and
(d) (CH$_2$)$_n$Q wherein n=0-2 and wherein Q is a monocyclic or bicyclic aromatic or heteroaromatic ring system having 5 to 10 ring atoms independently selected from the group consisting of C, N, O and S, provided that not more than 3 ring atoms in any single ring are other than C, and wherein Q is optionally independently substituted with up to 3 groups selected from the group consisting of alkyl, halogen, CF$_3$, OH, OCF$_3$, alkoxy, OCH$_2$CH$_2$OCH$_3$, NH$_2$, alkylamino, dialkylamino, morpholino, CN, NO$_2$, alkylthio and alkylsulfonyl;

each R$_7$ is independently selected from the group consisting of C$_1$-C$_6$ alkyl, alkoxyethyl, (C$_3$-C$_7$)cycloalkyl, (C$_0$-C$_3$)alkyl-(C$_3$-C$_7$)cycloalkyl and heterocycloalkylalkyl;

Y is —O—;

R$_4$ is selected from the group consisting of
(a) C$_1$-C$_7$ alkyl group optionally and independently interrupted by one or more —O—, —S—, —S(O)—, or —S(O)$_2$— groups,
(b) (C$_0$-C$_3$)alkyl-(C$_3$-C$_7$)cycloalkyl,
(c) heterocycloalkylalkyl,
(d) trifluoroethyl and
(e) trifluoropropyl;

Z is aryl or heteroaryl having 5 to 10 ring atoms independently selected from the group consisting of C, N, O and S, provided that not more than 3 ring atoms in any single ring are other than C, said ring system optionally bearing up to 3 substituents independently selected from the group consisting of halogen, R$_6$, CF$_3$, CN, NO$_2$, OH, (C$_1$-C$_4$)alkoxy, aryloxy, heteroaryloxy, OCH$_2$CH$_2$OCH$_3$, OC(O)R$_6$, OC(O)OR$_6$, OC(O)NHR$_7$, OC(O)N(R$_7$)$_2$, SR$_6$, S(O)R$_6$, S(O)$_2$R$_6$, S(O)$_2$NHR$_7$, S(O)$_2$N(R$_7$)$_2$, NHR$_7$, N(R$_7$)$_2$, NHC(O)R$_6$, N(R$_7$)C(O)R$_6$, NHC(O)OR$_6$, N(R$_7$)C(O)OR$_6$, N(R$_7$)C(O)NH(R$_7$), N(R$_7$)C(O)NH(R$_7$)$_2$, C(O)NH$_2$, C(O)NHR$_7$, C(O)N(R$_7$)$_2$, CO$_2$H, CO$_2$R$_6$ and COR$_6$; and R$_5$ is selected from the group consisting of NO$_2$, NH$_2$, CF$_3$, F, Cl, Br, SR$_6$, S(O)$_2$R$_6$, S(O)$_2$N(R$_7$)$_2$ and (C$_1$-C$_4$) alkoxy substituted with halo or CF$_3$.

2. The compound of claim 1, wherein R$_1$ and R$_2$ are independently selected from the group consisting of (a) H, (b) (C$_2$-C$_6$)alkyl and (c) (C$_0$-C$_3$)alkyl-(C$_3$-C$_7$)cycloalkyl provided that both R$_1$ and R$_2$ are not H, wherein each alkyl or cycloalkyl of R$_1$ and R$_2$ is optionally independently substituted with one or more groups selected from the group consisting of halo, hydroxy, cyano, CF$_3$ and (C$_1$-C$_4$)alkyl, or R$_1$ and R$_2$ taken together with the carbon to which they are attached form a 3-7 membered cycloalkyl or heterocycloalkyl ring which optionally bears a C$_1$-C$_4$ alkyl substituent that can be optionally independently substituted with one or more groups selected from the group consisting of halo, hydroxy, oxo, cyano, CF$_3$ and (C$_1$-C$_4$) alkyl, or R$_1$ and R$_2$ are taken together with the carbon to which they are attached form a 3-7 membered cycloalkyl ring substituted with R$_{20}$ and R$_{21}$ wherein R$_{20}$ and R$_{21}$ taken together with the carbon or carbons to which they are attached form a 3-7 membered cycloalkyl ring wherein each cycloalkyl is optionally independently substituted with one or more groups selected from the group consisting of halo, hydroxy, cyano, CF$_3$ and (C$_1$-C$_4$)alkyl;

Y is —O—,

R$_4$ is selected from the group consisting of
(a) (C$_0$-C$_3$)alkyl(C$_3$-C$_7$)cycloalkyl,
(b) trifluoroethyl and
(c) trifluoropropyl;

Z is a phenyl ring optionally bearing up to 3 substituents independently selected from the group consisting of halogen, R$_6$, CF$_3$, CN, NO$_2$, OH, (C$_1$-C$_4$)alkoxy, OCH$_2$CH$_2$OCH$_3$, SR$_6$, S(O)R$_6$ and S(O)$_2$R$_6$;

R$_5$ is selected from the group consisting of CF$_3$, F, Cl and Br; and

R$_6$ is selected from the group consisting of
(a) (C$_1$-C$_6$)alkyl optionally and independently interrupted by one or more —O—, —S—, —S(O), or —S(O)$_2$— groups;
(b)(C$_0$-C$_3$)alkyl(C$_3$-C$_7$)cycloalkyl and
(c) heterocycloalkylalkyl;

or a pharmaceutically acceptable salt thereof.

3. The compound of claim 1, wherein R$_1$ and R$_2$ are independently selected from the group consisting of H, OR$_6$, SR$_6$, —O—(C$_1$-C$_6$)alkyl optionally substituted with CF$_3$, (C$_2$-C$_6$) alkyl and (C$_0$-C$_3$)alkyl-(C$_3$-C$_7$)cycloalkyl, provided that both R$_1$ and R$_2$ are not H, and wherein each alkyl group and cycloalkyl group in R$_1$ and R$_2$ is optionally, independently substituted with one or more groups selected from the group consisting of halo and C$_1$-C$_4$ alkyl; or a pharmaceutically acceptable salt thereof.

4. The compound of claim 1, wherein R$_1$ and R$_2$ are taken together with the carbon to which they are attached to form a 3-7 membered cycloalkyl or heterocycloalkyl ring which optionally bears a $C_1$-$C_4$ alkyl substituent that can be optionally independently substituted with one or more halo, hydroxyl or oxo; or a pharmaceutically acceptable salt thereof.

5. The compound of claim 1, wherein $R_1$ and $R_2$ are taken together with the carbon to which they are attached form a 3-7 membered cycloalkyl ring substituted with $R_{20}$ and $R_{21}$, wherein $R_{20}$ and $R_{21}$ are taken together with the carbon or carbons to which they are attached form a 3-7 membered cycloalkyl ring wherein each cycloalkyl is optionally independently substituted with one or more halo, hydroxy, oxo, cyano, $CF_3$, or $C_1$-$C_4$ alkyl; or a pharmaceutically acceptable salt thereof.

6. The compound of claim 5, wherein $R_{20}$ and $R_{21}$ are bound to the same carbon; or a pharmaceutically acceptable salt thereof.

7. The compound of claim 1, wherein one of $R_1$ and $R_2$ is $(C_1$-$C_3)$alkyl-$(C_3$-$C_7)$cycloalkyl, wherein each alkyl group and cycloalkyl group in $R_1$ and $R_2$ is optionally, independently substituted with one or more substituents selected from the group consisting of halo and $(C_1$-$C_4)$alkyl; or a pharmaceutically acceptable salt thereof.

8. The compound of claim 1, wherein $R_1$ and $R_2$ are independently selected from the group consisting of (a) H, (b) F, (c) OH, (d) $OR_6$, (e) $SR_6$, (f) $(C_2$-$C_6)$alkyl, (g) $(C_0$-$C_3)$alkyl-$(C_3$-$C_7)$cycloalkyl and (h) $(CH_2)_nQ$ wherein n=0-2 and wherein Q is a monocyclic or bicyclic aromatic or heteroaromatic ring system having 5 to 10 ring atoms independently selected from the group consisting of C, N, O and S, provided that not more than 3 ring atoms in any single ring are other than C, and wherein Q is optionally independently substituted with up to 3 groups selected from the group consisting of alkyl, halogen, $CF_3$, OH, $OCF_3$, alkoxy, $OCH_2CH_2OCH_3$, $NH_2$, alkylamino, dialkylamino, morpholino, CN, $NO_2$, alkylthio and alkylsulfonyl, provided that both $R_1$ and $R_2$ are not H;
or a pharmaceutically acceptable salt thereof.

9. The compound of claim 1, wherein Z is monocyclic; or a pharmaceutically acceptable salt thereof.

10. The compound of claim 1, wherein Z is an aryl group; or a pharmaceutically acceptable salt thereof.

11. The compound of claim 1, wherein Z is an optionally substituted phenyl bearing up to 3 substituents independently selected from the group consisting of halogen, $R_6$, $CF_3$, CN, $NO_2$, OH, $(C_1$-$C_4)$alkoxy, aryloxy, heteroaryloxy, $OCH_2CH_2OCH_3$, $OC(O)R_6$, $OC(O)OR_6$, $SR_6$, $S(O)R_6$, $S(O)_2R_6$, $NHC(O)R_6$, $NHC(O)OR_6$, $CO_2H$, $CO_2R_6$ and $COR_6$; or a pharmaceutically acceptable salt thereof.

12. The compound of claim 1, wherein $R_5$ is $CF_3$, $NO_2$, $NH_2$, F, Cl, Br or $(C_1$-$C_4)$alkoxy substituted with halo or $CF_3$; or a pharmaceutically acceptable salt thereof.

13. The compound of claim 1, wherein $R_5$ is F or Cl; or a pharmaceutically acceptable salt thereof.

14. The compound of claim 1, wherein Q is phenyl; or a pharmaceutically acceptable salt thereof.

15. The compound of claim 1, wherein $R_6$ is selected from the group consisting of
(a) $C_1$-$C_6$ alkyl,
(b) $(C_0$-$C_3)$alkyl-$(C_3$-$C_7)$cycloalkyl and
(c) heterocycloalkylalkyl;
or a pharmaceutically acceptable salt thereof.

16. The compound of claim 1, wherein $R_4$ is selected from the group consisting of
(a) $(C_1$-$C_7)$alkyl,
(b) $(C_0$-$C_3)$alkyl-$(C_3$-$C_7)$cycloalkyl,
(c) heterocycloalkylalkyl,
(d) trifluoroethyl, and
(e) trifluoropropyl;
or a pharmaceutically acceptable salt thereof.

17. The compound of claim 1, wherein $R_4$ is $(C_0$-$C_3)$alkyl-$(C_3$-$C_7)$cycloalkyl, trifluoroethyl, or trifluoropropyl; or a pharmaceutically acceptable salt thereof.

18. The compound of claim 1, wherein $R_4$ is $(C_0$-$C_3)$alkyl $(C_3$-$C_7)$cycloalkyl; or a pharmaceutically acceptable salt thereof.

19. The compound of claim 1, wherein $R_4$ is trifluoroethyl or trifluoropropyl; or a pharmaceutically acceptable salt thereof.

20. The compound of claim 19, wherein $R_4$ is trifluoroethyl; or a pharmaceutically acceptable salt thereof.

21. The compound of claim 20, wherein Z is a phenyl ring optionally bearing up to 3 substituents independently selected from the group consisting of halogen, $R_6$, $CF_3$, CN, $NO_2$, OH and $(C_1$-$C_4)$alkoxy; or a pharmaceutically acceptable salt thereof.

22. The compound of claim 21, wherein $R_5$ is $CF_3$, F, Cl, or Br; or a pharmaceutically acceptable salt thereof.

23. The compound of claim 22, wherein $R_1$ and $R_2$ are independently selected from the group consisting of (a) H, (b) $(C_2$-$C_6)$alkyl and (c) $(C_0$-$C_1)$alkyl-$(C_3$-$C_5)$cycloalkyl, provided that both $R_1$ and $R_2$ are not H and wherein each alkyl or cycloalkyl of $R_1$ and $R_2$ is optionally independently substituted with one or more groups selected from the group consisting of halo, hydroxy, cyano, $CF_3$ and $(C_1$-$C_4)$alkyl; or a pharmaceutically acceptable salt thereof.

24. The compound of claim 23, wherein $R_1$ and $R_2$ are independently selected from the group consisting of (a) H and (b) $(C_0$-$C_1)$alkyl-$(C_3$-$C_5)$cycloalkyl, provided that both $R_1$ and $R_2$ are not H and wherein each alkyl or cycloalkyl of $R_1$ and $R_2$ is optionally independently substituted with one or more groups selected from the group consisting of halo, hydroxy, cyano, $CF_3$ and $(C_1$-$C_4)$alkyl; or a pharmaceutically acceptable salt thereof.

25. The compound of claim 2, wherein $R_1$ and $R_2$ are independently selected from the group consisting of H, $(C_2$-$C_6)$alkyl and $(C_0$-$C_3)$alkyl-$(C_3$-$C_7)$cycloalkyl, provided that both $R_1$ and $R_2$ are not H, and wherein each alkyl group and cycloalkyl group in $R_1$ and $R_2$ is optionally, independently substituted with one or more groups selected from the group consisting of halo and $(C_1$-$C_4)$alkyl; or a pharmaceutically acceptable salt thereof.

26. The compound of claim 25, wherein at least one of $R_1$ and $R_2$ is a $(C_2$-$C_6)$alkyl that is substituted with halo or $(C_1$-$C_4)$alkyl; or a pharmaceutically acceptable salt thereof.

27. The compound of claim 25, wherein at least one of $R_1$ and $R_2$ is $(C_0$-$C_3)$alkyl-$(C_3$-$C_7)$cycloalkyl substituted with halo or $(C_1$-$C_4)$alkyl; or a pharmaceutically acceptable salt thereof.

28. The compound of claim 27, wherein at least one of $R_1$ and $R_2$ is $(C_0$-$C_3)$alkyl-$(C_3$-$C_7)$cycloalkyl and the $(C_3$-$C_7)$ cycloalkyl portion of the $(C_0$-$C_3)$alkyl-$(C_3$-$C_7)$cycloalkyl group is substituted with halo or $(C_1$-$C_4)$alkyl; or a pharmaceutically acceptable salt thereof.

29. The compound of claim 25, wherein at least one of $R_1$ and $R_2$ is $(C_1$-$C_3)$alkyl-$(C_3$-$C_7)$cycloalkyl and the $(C_1$-$C_3)$ alkyl portion of the $(C_1$-$C_3)$alkyl-$(C_3$-$C_7)$cycloalkyl group is substituted with halo or $(C_1$-$C_4)$alkyl; or a pharmaceutically acceptable salt thereof.

30. A compound selected from the group consisting of examples 100-389, 400-413, 416-559, 980-982, 985-1267, 1269-1271, 1273-1299, 1303-1307, 1309-1311, 1315-1319, 1321-1529, 1529a, 1530-1540, 2704-2718, 2721-2754 and 2757-2859

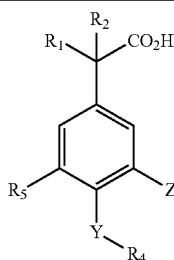

| Example | R₁ | R₂ | Y | R₄ | R₅ | Z |
|---|---|---|---|---|---|---|
| 100 | CH₃ | H | O | CH₂CH₃ | F | 4-fluorophenyl |
| 101 | CH₂CH₃ | H | O | CH₂CH₃ | F | 4-fluorophenyl |
| 102 | CH₂CH₃ | H | O | CH₂CH₃ | F | 4-fluorophenyl |
| 103 | CH₂CH₂CH₃ | H | O | CH₂CH₃ | F | 4-fluorophenyl |
| 104 | CH₂CH(CH₃)₂ | H | O | CH₂CH₃ | F | 4-fluorophenyl |
| 105 | cyclopropylmethyl | H | O | CH₂CH₃ | F | 4-fluorophenyl |
| 106 | SCH(CH₃)₂ | H | O | CH₂CH₃ | F | 4-fluorophenyl |
| 107 | OCH₂CH₃ | H | O | CH₂CH₃ | F | 4-fluorophenyl |
| 108 | (CH₂)₂ | | O | CH₂CH₃ | F | 4-fluorophenyl |
| 109 | (CH₂)₄ | | O | CH₂CH₃ | F | 4-fluorophenyl |
| 110 | CH₃ | H | O | CH₂CH₃ | F | 4-chlorophenyl |
| 111 | CH₂CH₃ | H | O | CH₂CH₃ | F | 4-chlorophenyl |
| 112 | CH₂CH₃ | H | O | CH₂CH₃ | F | 4-chlorophenyl |
| 113 | CH₂CH₂CH₃ | H | O | CH₂CH₃ | F | 4-chlorophenyl |
| 114 | CH₂CH(CH₃)₂ | H | O | CH₂CH₃ | F | 4-chlorophenyl |
| 115 | cyclopropylmethyl | H | O | CH₂CH₃ | F | 4-chlorophenyl |
| 116 | SCH(CH₃)₂ | H | O | CH₂CH₃ | F | 4-chlorophenyl |
| 117 | OCH₂CH₃ | H | O | CH₂CH₃ | F | 4-chlorophenyl |
| 118 | (CH₂)₂ | | O | CH₂CH₃ | F | 4-chlorophenyl |
| 119 | (CH₂)₄ | | O | CH₂CH₃ | F | 4-chlorophenyl |
| 120 | CH₃ | H | O | CH₂CH₃ | F | 4-trifluoromethylphenyl |
| 121 | CH₂CH₃ | H | O | CH₂CH₃ | F | 4-trifluoromethylphenyl |
| 122 | CH₂CH₃ | H | O | CH₂CH₃ | F | 4-trifluoromethylphenyl |
| 123 | CH2CH2CH3 | H | O | CH₂CH₃ | F | 4-trifluoromethylphenyl |
| 124 | CH2CH(CH3)2 | H | O | CH₂CH₃ | F | 4-trifluoromethylphenyl |
| 125 | cyclopropylmethyl | H | O | CH₂CH₃ | F | 4-trifluoromethylphenyl |
| 126 | SCH(CH₃)₂ | H | O | CH₂CH₃ | F | 4-trifluoromethylphenyl |
| 127 | OCH₂CH₃ | H | O | CH₂CH₃ | F | 4-trifluoromethylphenyl |
| 128 | (CH₂)₂ | | O | CH₂CH₃ | F | 4-trifluoromethylphenyl |
| 129 | (CH₂)₄ | | O | CH₂CH₃ | F | 4-trifluoromethylphenyl |
| 130 | CH₃ | H | O | CH₂CH₃ | F | 4-methoxyphenyl |
| 131 | CH₂CH₃ | H | O | CH₂CH₃ | F | 4-methoxyphenyl |
| 132 | CH₂CH₃ | H | O | CH₂CH₃ | F | 4-methoxyphenyl |
| 133 | CH₂CH₂CH₃ | H | O | CH₂CH₃ | F | 4-methoxyphenyl |
| 134 | CH₂CH(CH₃)₂ | H | O | CH₂CH₃ | F | 4-methoxyphenyl |
| 135 | cyclopropylmethyl | H | O | CH₂CH₃ | F | 4-methoxyphenyl |
| 136 | SCH(CH₃)₂ | H | O | CH₂CH₃ | F | 4-methoxyphenyl |
| 137 | OCH₂CH₃ | H | O | CH₂CH₃ | F | 4-methoxyphenyl |
| 138 | (CH₂)₂ | | O | CH₂CH₃ | F | 4-methoxyphenyl |
| 139 | (CH₂)₄ | | O | CH₂CH₃ | F | 4-methoxyphenyl |
| 140 | CH₃ | H | O | CH₂CH₃ | F | 3,4 dichloro phenyl |
| 141 | CH₂CH₃ | H | O | CH₂CH₃ | F | 3,4 dichloro phenyl |
| 142 | CH₂CF₃ | H | O | CH₂CH₃ | F | 3,4 dichloro phenyl |
| 143 | CH₂CH₂CH₃ | H | O | CH₂CH₃ | F | 3,4 dichloro phenyl |
| 144 | CH₂CH(CH₃)₂ | H | O | CH₂CH₃ | F | 3,4 dichloro phenyl |
| 145 | cyclopropylmethyl | H | O | CH₂CH₃ | F | 3,4 dichloro phenyl |
| 146 | SCH(CH₃)₂ | H | O | CH₂CH₃ | F | 3,4 dichloro phenyl |
| 147 | OCH₂CH₃ | H | O | CH₂CH₃ | F | 3,4 dichloro phenyl |
| 148 | (CH₂)₂ | | O | CH₂CH₃ | F | 3,4 dichloro phenyl |
| 149 | (CH₂)₄ | | O | CH₂CH₃ | F | 3,4 dichloro phenyl |
| 150 | CH₃ | H | O | CH₂CH₃ | F | 5-benzo[c][1,2,5]oxadiazolyl |
| 151 | CH₂CH₃ | H | O | CH₂CH₃ | F | 5-benzo[c][1,2,5]oxadiazolyl |
| 152 | CH₂CF₃ | H | O | CH₂CH₃ | F | 5-benzo[c][1,2,5]oxadiazolyl |
| 153 | CH₂CH₂CH₃ | H | O | CH₂CH₃ | F | 5-benzo[c][1,2,5]oxadiazolyl |
| 154 | CH₂CH(CH₃)₂ | H | O | CH₂CH₃ | F | 5-benzo[c][1,2,5]oxadiazolyl |
| 155 | cyclopropylmethyl | H | O | CH₂CH₃ | F | 5-benzo[c][1,2,5]oxadiazolyl |
| 156 | SCH(CH₃)₂ | H | O | CH₂CH₃ | F | 5-benzo[c][1,2,5]oxadiazolyl |
| 157 | OCH₂CH₃ | H | O | CH₂CH₃ | F | 5-benzo[c][1,2,5]oxadiazolyl |
| 158 | (CH₂)₂ | | O | CH₂CH₃ | F | 5-benzo[c][1,2,5]oxadiazolyl |
| 159 | (CH₂)₄ | | O | CH₂CH₃ | F | 5-benzo[c][1,2,5]oxadiazolyl |
| 160 | CH₃ | H | O | CH₂CH₃ | F | 5-benzo[c][1,2,5]thiadiazolyl |
| 161 | CH₂CH₃ | H | O | CH₂CH₃ | F | 5-benzo[c][1,2,5]thiadiazolyl |
| 162 | CH₂CF₃ | H | O | CH₂CH₃ | F | 5-benzo[c][1,2,5]thiadiazolyl |
| 163 | CH₂CH₂CH₃ | H | O | CH₂CH₃ | F | 5-benzo[c][1,2,5]thiadiazolyl |

-continued

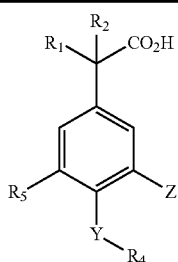

| Example | R₁ | R₂ | Y | R₄ | R₅ | Z |
|---|---|---|---|---|---|---|
| 164 | CH₂CH(CH₃)₂ | H | O | CH₂CH₃ | F | 5-benzo[c][1,2,5]thiadiazolyl |
| 165 | cyclopropylmethyl | H | O | CH₂CH₃ | F | 5-benzo[c][1,2,5]thiadiazolyl |
| 166 | SCH(CH₃)₂ | H | O | CH₂CH₃ | F | 5-benzo[c][1,2,5]thiadiazolyl |
| 167 | OCH₂CH₃ | H | O | CH₂CH₃ | F | 5-benzo[c][1,2,5]thiadiazolyl |
| 168 | (CH₂)₂ | | O | CH₂CH₃ | F | 5-benzo[c][1,2,5]thiadiazolyl |
| 169 | (CH₂)₄ | | O | CH₂CH₃ | F | 5-benzo[c][1,2,5]thiadiazolyl |
| 170 | CH₃ | H | O | CH₂CF₃ | F | 4-fluorophenyl |
| 171 | CH₂CH₃ | H | O | CH₂CF₃ | F | 4-fluorophenyl |
| 172 | CH₂CF₃ | H | O | CH₂CF₃ | F | 4-fluorophenyl |
| 173 | CH₂CH₂CH₃ | H | O | CH₂CF₃ | F | 4-fluorophenyl |
| 174 | CH₂CH(CH₃)₂ | H | O | CH₂CF₃ | F | 4-fluorophenyl |
| 175 | cyclopropylmethyl | H | O | CH₂CF₃ | F | 4-fluorophenyl |
| 176 | SCH(CH₃)₂ | H | O | CH₂CF₃ | F | 4-fluorophenyl |
| 177 | OCH₂CH₃ | H | O | CH₂CF₃ | F | 4-fluorophenyl |
| 178 | (CH₂)₂ | | O | CH₂CF₃ | F | 4-fluorophenyl |
| 179 | (CH₂)₄ | | O | CH₂CF₃ | F | 4-fluorophenyl |
| 180 | CH₃ | H | O | CH₂CF₃ | F | 4-chlorophenyl |
| 181 | CH₂CH₃ | H | O | CH₂CF₃ | F | 4-chlorophenyl |
| 182 | CH₂CF₃ | H | O | CH₂CF₃ | F | 4-chlorophenyl |
| 183 | CH₂CH₂CH₃ | H | O | CH₂CF₃ | F | 4-chlorophenyl |
| 184 | CH₂CH(CH₃)₂ | H | O | CH₂CF₃ | F | 4-chlorophenyl |
| 185 | cyclopropylmethyl | H | O | CH₂CF₃ | F | 4-chlorophenyl |
| 186 | SCH(CH₃)₂ | H | O | CH₂CF₃ | F | 4-chlorophenyl |
| 187 | OCH₂CH₃ | H | O | CH₂CF₃ | F | 4-chlorophenyl |
| 188 | (CH₂)₂ | | O | CH₂CF₃ | F | 4-chlorophenyl |
| 189 | (CH₂)₄ | | O | CH₂CF₃ | F | 4-chlorophenyl |
| 190 | CH₃ | H | O | CH₂CF₃ | F | 4-trifluoromethylphenyl |
| 191 | CH₂CH₃ | H | O | CH₂CF₃ | F | 4-trifluoromethylphenyl |
| 192 | CH₂CF₃ | H | O | CH₂CF₃ | F | 4-trifluoromethylphenyl |
| 193 | CH₂CH₂CH₃ | H | O | CH₂CF₃ | F | 4-trifluoromethylphenyl |
| 194 | CH₂CH(CH₃)₂ | H | O | CH₂CF₃ | F | 4-trifluoromethylphenyl |
| 195 | cyclopropylmethyl | H | O | CH₂CF₃ | F | 4-trifluoromethylphenyl |
| 196 | SCH(CH₃)₂ | H | O | CH₂CF₃ | F | 4-trifluoromethylphenyl |
| 197 | OCH₂CH₃ | H | O | CH₂CF₃ | F | 4-trifluoromethylphenyl |
| 198 | (CH₂)₂ | | O | CH₂CF₃ | F | 4-trifluoromethylphenyl |
| 199 | (CH₂)₄ | | O | CH₂CF₃ | F | 4-trifluoromethylphenyl |
| 200 | CH₃ | H | O | CH₂CF₃ | F | 4-methoxyphenyl |
| 201 | CH₂CH₃ | H | O | CH₂CF₃ | F | 4-methoxyphenyl |
| 202 | CH₂CF₃ | H | O | CH₂CF₃ | F | 4-methoxyphenyl |
| 203 | CH₂CH₂CH₃ | H | O | CH₂CF₃ | F | 4-methoxyphenyl |
| 204 | CH₂CH(CH₃)₂ | H | O | CH₂CF₃ | F | 4-methoxyphenyl |
| 205 | cyclopropylmethyl | H | O | CH₂CF₃ | F | 4-methoxyphenyl |
| 206 | SCH(CH₃)₂ | H | O | CH₂CF₃ | F | 4-methoxyphenyl |
| 207 | OCH₂CH₃ | H | O | CH₂CF₃ | F | 4-methoxyphenyl |
| 208 | (CH₂)₂ | | O | CH₂CF₃ | F | 4-methoxyphenyl |
| 209 | (CH₂)₄ | | O | CH₂CF₃ | F | 4-methoxyphenyl |
| 210 | CH₃ | H | O | CH₂CF₃ | F | 3,4 dichloro phenyl |
| 211 | CH₂CH₃ | H | O | CH₂CF₃ | F | 3,4 dichloro phenyl |
| 212 | CH₂CF₃ | H | O | CH₂CF₃ | F | 3,4 dichloro phenyl |
| 213 | CH₂CH₂CH₃ | H | O | CH₂CF₃ | F | 3,4 dichloro phenyl |
| 214 | CH₂CH(CH₃)₂ | H | O | CH₂CF₃ | F | 3,4 dichloro phenyl |
| 215 | cyclopropylmethyl | H | O | CH₂CF₃ | F | 3,4 dichloro phenyl |
| 216 | SCH(CH₃)₂ | H | O | CH₂CF₃ | F | 3,4 dichloro phenyl |
| 217 | OCH₂CH₃ | H | O | CH₂CF₃ | F | 3,4 dichloro phenyl |
| 218 | (CH₂)₂ | | O | CH₂CF₃ | F | 3,4 dichloro phenyl |
| 219 | (CH₂)₄ | | O | CH₂CF₃ | F | 3,4 dichloro phenyl |
| 220 | CH₃ | H | O | CH₂CF₃ | F | 5-benzo[c][1,2,5]oxadiazolyl |
| 221 | CH₂CH₃ | H | O | CH₂CF₃ | F | 5-benzo[c][1,2,5]oxadiazolyl |
| 222 | CH₂CF₃ | H | O | CH₂CF₃ | F | 5-benzo[c][1,2,5]oxadiazolyl |
| 223 | CH₂CH₂CH₃ | H | O | CH₂CF₃ | F | 5-benzo[c][1,2,5]oxadiazolyl |
| 224 | CH₂CH(CH₃)₂ | H | O | CH₂CF₃ | F | 5-benzo[c][1,2,5]oxadiazolyl |
| 225 | cyclopropylmethyl | H | O | CH₂CF₃ | F | 5-benzo[c][1,2,5]oxadiazolyl |
| 226 | SCH(CH₃)₂ | H | O | CH₂CF₃ | F | 5-benzo[c][1,2,5]oxadiazolyl |
| 227 | OCH₂CH₃ | H | O | CH₂CF₃ | F | 5-benzo[c][1,2,5]oxadiazolyl |

-continued

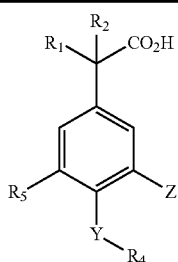

| Example | R₁ | R₂ | Y | R₄ | R₅ | Z |
|---|---|---|---|---|---|---|
| 228 | (CH₂)₂ | | O | CH₂CF₃ | F | 5-benzo[c][1,2,5]oxadiazolyl |
| 229 | (CH₂)₄ | | O | CH₂CF₃ | F | 5-benzo[c][1,2,5]oxadiazolyl |
| 230 | CH₃ | H | O | CH₂CF₃ | F | 5-benzo[c][1,2,5]thiadiazolyl |
| 231 | CH₂CH₃ | H | O | CH₂CF₃ | F | 5-benzo[c][1,2,5]thiadiazolyl |
| 232 | CH₂CF₃ | H | O | CH₂CF₃ | F | 5-benzo[c][1,2,5]thiadiazolyl |
| 233 | CH₂CH₂CH₃ | H | O | CH₂CF₃ | F | 5-benzo[c][1,2,5]thiadiazolyl |
| 234 | CH₂CH(CH₃)₂ | H | O | CH₂CF₃ | F | 5-benzo[c][1,2,5]thiadiazolyl |
| 235 | cyclopropylmethyl | H | O | CH₂CF₃ | F | 5-benzo[c][1,2,5]thiadiazolyl |
| 236 | SCH(CH₃)₂ | H | O | CH₂CF₃ | F | 5-benzo[c][1,2,5]thiadiazolyl |
| 237 | OCH₂CH₃ | H | O | CH₂CF₃ | F | 5-benzo[c][1,2,5]thiadiazolyl |
| 238 | (CH₂)₂ | | O | CH₂CF₃ | F | 5-benzo[c][1,2,5]thiadiazolyl |
| 239 | (CH₂)₄ | | O | CH₂CF₃ | F | 5-benzo[c][1,2,5]thiadiazolyl |
| 240 | CH₃ | H | O | CH₂-c-Pr | F | 4-fluorophenyl |
| 241 | CH₂CH₃ | H | O | CH₂-c-Pr | F | 4-fluorophenyl |
| 242 | CH₂CF₃ | H | O | CH₂-c-Pr | F | 4-fluorophenyl |
| 243 | CH₂CH₂CH₃ | H | O | CH₂-c-Pr | F | 4-fluorophenyl |
| 244 | CH₂CH(CH₃)₂ | H | O | CH₂-c-Pr | F | 4-fluorophenyl |
| 245 | cyclopropylmethyl | H | O | CH₂-c-Pr | F | 4-fluorophenyl |
| 246 | SCH(CH₃)₂ | H | O | CH₂-c-Pr | F | 4-fluorophenyl |
| 247 | OCH₂CH₃ | H | O | CH₂-c-Pr | F | 4-fluorophenyl |
| 248 | (CH₂)₂ | | O | CH₂-c-Pr | F | 4-fluorophenyl |
| 249 | (CH₂)₄ | | O | CH₂-c-Pr | F | 4-fluorophenyl |
| 250 | CH₃ | H | O | CH₂-c-Pr | F | 4-chlorophenyl |
| 251 | CH₂CH₃ | H | O | CH₂-c-Pr | F | 4-chlorophenyl |
| 252 | CH₂CF₃ | H | O | CH₂-c-Pr | F | 4-chlorophenyl |
| 253 | CH₂CH₂CH₃ | H | O | CH₂-c-Pr | F | 4-chlorophenyl |
| 254 | CH₂CH(CH₃)₂ | H | O | CH₂-c-Pr | F | 4-chlorophenyl |
| 255 | cyclopropylmethyl | H | O | CH₂-c-Pr | F | 4-chlorophenyl |
| 256 | SCH(CH₃)₂ | H | O | CH₂-c-Pr | F | 4-chlorophenyl |
| 257 | OCH₂CH₃ | H | O | CH₂-c-Pr | F | 4-chlorophenyl |
| 258 | (CH₂)₂ | | O | CH₂-c-Pr | F | 4-chlorophenyl |
| 259 | (CH₂)₄ | | O | CH₂-c-Pr | F | 4-chlorophenyl |
| 260 | CH₃ | H | O | CH₂-c-Pr | F | 4-trifluoromethylphenyl |
| 261 | CH₂CH₃ | H | O | CH₂-c-Pr | F | 4-trifluoromethylphenyl |
| 262 | CH₂CF₃ | H | O | CH₂-c-Pr | F | 4-trifluoromethylphenyl |
| 263 | CH₂CH₂CH₃ | H | O | CH₂-c-Pr | F | 4-trifluoromethylphenyl |
| 264 | CH₂CH(CH₃)₂ | H | O | CH₂-c-Pr | F | 4-trifluoromethylphenyl |
| 265 | cyclopropylmethyl | H | O | CH₂-c-Pr | F | 4-trifluoromethylphenyl |
| 266 | SCH(CH₃)₂ | H | O | CH₂-c-Pr | F | 4-trifluoromethylphenyl |
| 267 | OCH₂CH₃ | H | O | CH₂-c-Pr | F | 4-trifluoromethylphenyl |
| 268 | (CH₂)₂ | | O | CH₂-c-Pr | F | 4-trifluoromethylphenyl |
| 269 | (CH₂)₄ | | O | CH₂-c-Pr | F | 4-trifluoromethylphenyl |
| 270 | CH₃ | H | O | CH₂-c-Pr | F | 4-methoxyphenyl |
| 271 | CH₂CH₃ | H | O | CH₂-c-Pr | F | 4-methoxyphenyl |
| 272 | CH₂CF₃ | H | O | CH₂-c-Pr | F | 4-methoxyphenyl |
| 273 | CH₂CH₂CH₃ | H | O | CH₂-c-Pr | F | 4-methoxyphenyl |
| 274 | CH₂CH(CH₃)₂ | H | O | CH₂-c-Pr | F | 4-methoxyphenyl |
| 275 | cyclopropylmethyl | H | O | CH₂-c-Pr | F | 4-methoxyphenyl |
| 276 | SCH(CH₃)₂ | H | O | CH₂-c-Pr | F | 4-methoxyphenyl |
| 277 | OCH₂CH₃ | H | O | CH₂-c-Pr | F | 4-methoxyphenyl |
| 278 | (CH₂)₂ | | O | CH₂-c-Pr | F | 4-methoxyphenyl |
| 279 | (CH₂)₄ | | O | CH₂-c-Pr | F | 4-methoxyphenyl |
| 280 | CH₃ | H | O | CH₂-c-Pr | F | 3,4 dichloro phenyl |
| 281 | CH₂CH₃ | H | O | CH₂-c-Pr | F | 3,4 dichloro phenyl |
| 282 | CH₂CF₃ | H | O | CH₂-c-Pr | F | 3,4 dichloro phenyl |
| 283 | CH₂CH₂CH₃ | H | O | CH₂-c-Pr | F | 3,4 dichloro phenyl |
| 284 | CH₂CH(CH₃)₂ | H | O | CH₂-c-Pr | F | 3,4 dichloro phenyl |
| 285 | cyclopropylmethyl | H | O | CH₂-c-Pr | F | 3,4 dichloro phenyl |
| 286 | SCH(CH₃)₂ | H | O | CH₂-c-Pr | F | 3,4 dichloro phenyl |
| 287 | OCH₂CH₃ | H | O | CH₂-c-Pr | F | 3,4 dichloro phenyl |
| 288 | (CH₂)₂ | | O | CH₂-c-Pr | F | 3,4 dichloro phenyl |
| 289 | (CH₂)₄ | | O | CH₂-c-Pr | F | 3,4 dichloro phenyl |
| 290 | CH₃ | H | O | CH₂-c-Pr | F | 5-benzo[c][1,2,5]oxadiazolyl |
| 291 | CH₂CH₃ | H | O | CH₂-c-Pr | F | 5-benzo[c][1,2,5]oxadiazolyl |

-continued

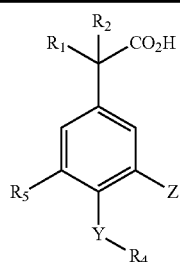

| Example | R₁ | R₂ | Y | R₄ | R₅ | Z |
|---|---|---|---|---|---|---|
| 292 | CH₂CF₃ | H | O | CH₂-c-Pr | F | 5-benzo[c][1,2,5]oxadiazolyl |
| 293 | CH₂CH₂CH₃ | H | O | CH₂-c-Pr | F | 5-benzo[c][1,2,5]oxadiazolyl |
| 294 | CH₂CH(CH₃)₂ | H | O | CH₂-c-Pr | F | 5-benzo[c][1,2,5]oxadiazolyl |
| 295 | cyclopropylmethyl | H | O | CH₂-c-Pr | F | 5-benzo[c][1,2,5]oxadiazolyl |
| 296 | SCH(CH₃)₂ | H | O | CH₂-c-Pr | F | 5-benzo[c][1,2,5]oxadiazolyl |
| 297 | OCH₂CH₃ | H | O | CH₂-c-Pr | F | 5-benzo[c][1,2,5]oxadiazolyl |
| 298 | (CH₂)₂ | | O | CH₂-c-Pr | F | 5-benzo[c][1,2,5]oxadiazolyl |
| 299 | (CH₂)₄ | | O | CH₂-c-Pr | F | 5-benzo[c][1,2,5]oxadiazolyl |
| 300 | CH₃ | H | O | CH₂-c-Pr | F | 5-benzo[c][1,2,5]thiadiazolyl |
| 301 | CH₂CH₃ | H | O | CH₂-c-Pr | F | 5-benzo[c][1,2,5]thiadiazolyl |
| 302 | CH₂CF₃ | H | O | CH₂-c-Pr | F | 5-benzo[c][1,2,5]thiadiazolyl |
| 303 | CH₂CH₂CH₃ | H | O | CH₂-c-Pr | F | 5-benzo[c][1,2,5]thiadiazolyl |
| 304 | CH₂CH(CH₃)₂ | H | O | CH₂-c-Pr | F | 5-benzo[c][1,2,5]thiadiazolyl |
| 305 | cyclopropylmethyl | H | O | CH₂-c-Pr | F | 5-benzo[c][1,2,5]thiadiazolyl |
| 306 | SCH(CH₃)₂ | H | O | CH₂-c-Pr | F | 5-benzo[c][1,2,5]thiadiazolyl |
| 307 | OCH₂CH₃ | H | O | CH₂-c-Pr | F | 5-benzo[c][1,2,5]thiadiazolyl |
| 308 | (CH₂)₂ | | O | CH₂-c-Pr | F | 5-benzo[c][1,2,5]thiadiazolyl |
| 309 | (CH₂)₄ | | O | CH₂-c-Pr | F | 5-benzo[c][1,2,5]thiadiazolyl |
| 310 | CH₃ | H | O | CH₂CH₃ | Cl | 4-fluorophenyl |
| 311 | CH₂CH₃ | H | O | CH₂CH₃ | Cl | 4-fluorophenyl |
| 312 | CH₂CF₃ | H | O | CH₂CH₃ | Cl | 4-fluorophenyl |
| 313 | CH₂CH₂CH₃ | H | O | CH₂CH₃ | Cl | 4-fluorophenyl |
| 314 | CH₂CH(CH₃)₂ | H | O | CH₂CH₃ | Cl | 4-fluorophenyl |
| 315 | cyclopropylmethyl | H | O | CH₂CH₃ | Cl | 4-fluorophenyl |
| 316 | SCH(CH₃)₂ | H | O | CH₂CH₃ | Cl | 4-fluorophenyl |
| 317 | OCH₂CH₃ | H | O | CH₂CH₃ | Cl | 4-fluorophenyl |
| 318 | (CH₂)₂ | | O | CH₂CH₃ | Cl | 4-fluorophenyl |
| 319 | (CH₂)₄ | | O | CH₂CH₃ | Cl | 4-fluorophenyl |
| 320 | CH₃ | H | O | CH₂CH₃ | Cl | 4-chlorophenyl |
| 321 | CH₂CH₃ | H | O | CH₂CH₃ | Cl | 4-chlorophenyl |
| 322 | CH₂CF₃ | H | O | CH₂CH₃ | Cl | 4-chlorophenyl |
| 323 | CH₂CH₂CH₃ | H | O | CH₂CH₃ | Cl | 4-chlorophenyl |
| 324 | CH₂CH(CH₃)₂ | H | O | CH₂CH₃ | Cl | 4-chlorophenyl |
| 325 | cyclopropylmethyl | H | O | CH₂CH₃ | Cl | 4-chlorophenyl |
| 326 | SCH(CH₃)₂ | H | O | CH₂CH₃ | Cl | 4-chlorophenyl |
| 327 | OCH₂CH₃ | H | O | CH₂CH₃ | Cl | 4-chlorophenyl |
| 328 | (CH₂)₂ | | O | CH₂CH₃ | Cl | 4-chlorophenyl |
| 329 | (CH₂)₄ | | O | CH₂CH₃ | Cl | 4-chlorophenyl |
| 330 | CH₃ | H | O | CH₂CH₃ | Cl | 4-trifluoromethylphenyl |
| 331 | CH₂CH₃ | H | O | CH₂CH₃ | Cl | 4-trifluoromethylphenyl |
| 332 | CH₂CF₃ | H | O | CH₂CH₃ | Cl | 4-trifluoromethylphenyl |
| 333 | CH₂CH₂CH₃ | H | O | CH₂CH₃ | Cl | 4-trifluoromethylphenyl |
| 334 | CH₂CH(CH₃)₂ | H | O | CH₂CH₃ | Cl | 4-trifluoromethylphenyl |
| 335 | cyclopropylmethyl | H | O | CH₂CH₃ | Cl | 4-trifluoromethylphenyl |
| 336 | SCH(CH₃)₂ | H | O | CH₂CH₃ | Cl | 4-trifluoromethylphenyl |
| 337 | OCH₂CH₃ | H | O | CH₂CH₃ | Cl | 4-trifluoromethylphenyl |
| 338 | (CH₂)₂ | | O | CH₂CH₃ | Cl | 4-trifluoromethylphenyl |
| 339 | (CH₂)₄ | | O | CH₂CH₃ | Cl | 4-trifluoromethylphenyl |
| 340 | CH₃ | H | O | CH₂CH₃ | Cl | 4-methoxyphenyl |
| 341 | CH₂CH₃ | H | O | CH₂CH₃ | Cl | 4-methoxyphenyl |
| 342 | CH₂CF₃ | H | O | CH₂CH₃ | Cl | 4-methoxyphenyl |
| 343 | CH₂CH₂CH₃ | H | O | CH₂CH₃ | Cl | 4-methoxyphenyl |
| 344 | CH₂CH(CH₃)₂ | H | O | CH₂CH₃ | Cl | 4-methoxyphenyl |
| 345 | cyclopropylmethyl | H | O | CH₂CH₃ | Cl | 4-methoxyphenyl |
| 346 | SCH(CH₃)₂ | H | O | CH₂CH₃ | Cl | 4-methoxyphenyl |
| 347 | OCH₂CH₃ | H | O | CH₂CH₃ | Cl | 4-methoxyphenyl |
| 348 | (CH₂)₂ | | O | CH₂CH₃ | Cl | 4-methoxyphenyl |
| 349 | (CH₂)₄ | | O | CH₂CH₃ | Cl | 4-methoxyphenyl |
| 350 | CH₃ | H | O | CH₂CH₃ | Cl | 3,4 dichloro phenyl |
| 351 | CH₂CH₃ | H | O | CH₂CH₃ | Cl | 3,4 dichloro phenyl |
| 352 | CH₂CF₃ | H | O | CH₂CH₃ | Cl | 3,4 dichloro phenyl |
| 353 | CH₂CH₂CH₃ | H | O | CH₂CH₃ | Cl | 3,4 dichloro phenyl |
| 354 | CH₂CH(CH₃)₂ | H | O | CH₂CH₃ | Cl | 3,4 dichloro phenyl |
| 355 | cyclopropylmethyl | H | O | CH₂CH₃ | Cl | 3,4 dichloro phenyl |

-continued

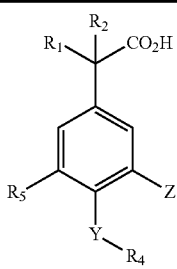

| Example | R₁ | R₂ | Y | R₄ | R₅ | Z |
|---|---|---|---|---|---|---|
| 356 | SCH(CH₃)₂ | H | O | CH₂CH₃ | Cl | 3,4 dichloro phenyl |
| 357 | OCH₂CH₃ | H | O | CH₂CH₃ | Cl | 3,4 dichloro phenyl |
| 358 | (CH₂)₂ | | O | CH₂CH₃ | Cl | 3,4 dichloro phenyl |
| 359 | (CH₂)₄ | | O | CH₂CH₃ | Cl | 3,4 dichloro phenyl |
| 360 | CH₃ | H | O | CH₂CH₃ | Cl | 5-benzo[c][1,2,5]oxadiazolyl |
| 361 | CH₂CH₃ | H | O | CH₂CH₃ | Cl | 5-benzo[c][1,2,5]oxadiazolyl |
| 362 | CH₂CF₃ | H | O | CH₂CH₃ | Cl | 5-benzo[c][1,2,5]oxadiazolyl |
| 363 | CH₂CH₂CH₃ | H | O | CH₂CH₃ | Cl | 5-benzo[c][1,2,5]oxadiazolyl |
| 364 | CH₂CH(CH₃)₂ | H | O | CH₂CH₃ | Cl | 5-benzo[c][1,2,5]oxadiazolyl |
| 365 | cyclopropylmethyl | H | O | CH₂CH₃ | Cl | 5-benzo[c][1,2,5]oxadiazolyl |
| 366 | SCH(CH₃)₂ | H | O | CH₂CH₃ | Cl | 5-benzo[c][1,2,5]oxadiazolyl |
| 367 | OCH₂CH₃ | H | O | CH₂CH₃ | Cl | 5-benzo[c][1,2,5]oxadiazolyl |
| 368 | (CH₂)₂ | | O | CH₂CH₃ | Cl | 5-benzo[c][1,2,5]oxadiazolyl |
| 369 | (CH₂)₄ | | O | CH₂CH₃ | Cl | 5-benzo[c][1,2,5]oxadiazolyl |
| 370 | CH₃ | H | O | CH₂CH₃ | Cl | 5-benzo[c][1,2,5]thiadiazolyl |
| 371 | CH₂CH₃ | H | O | CH₂CH₃ | Cl | 5-benzo[c][1,2,5]thiadiazolyl |
| 372 | CH₂CF₃ | H | O | CH₂CH₃ | Cl | 5-benzo[c][1,2,5]thiadiazolyl |
| 373 | CH₂CH₂CH₃ | H | O | CH₂CH₃ | Cl | 5-benzo[c][1,2,5]thiadiazolyl |
| 374 | CH₂CH(CH₃)₂ | H | O | CH₂CH₃ | Cl | 5-benzo[c][1,2,5]thiadiazolyl |
| 375 | cyclopropylmethyl | H | O | CH₂CH₃ | Cl | 5-benzo[c][1,2,5]thiadiazolyl |
| 376 | SCH(CH₃)₂ | H | O | CH₂CH₃ | Cl | 5-benzo[c][1,2,5]thiadiazolyl |
| 377 | OCH₂CH₃ | H | O | CH₂CH₃ | Cl | 5-benzo[c][1,2,5]thiadiazolyl |
| 378 | (CH₂)₂ | | O | CH₂CH₃ | Cl | 5-benzo[c][1,2,5]thiadiazolyl |
| 379 | (CH₂)₄ | | O | CH₂CH₃ | Cl | 5-benzo[c][1,2,5]thiadiazolyl |
| 380 | CH₃ | H | O | CH₂CF₃ | Cl | 4-fluorophenyl |
| 381 | CH₂CH₃ | H | O | CH₂CF₃ | Cl | 4-fluorophenyl |
| 382 | CH₂CF₃ | H | O | CH₂CF₃ | Cl | 4-fluorophenyl |
| 383 | CH₂CH₂CH₃ | H | O | CH₂CF₃ | Cl | 4-fluorophenyl |
| 384 | CH₂CH(CH₃)₂ | H | O | CH₂CF₃ | Cl | 4-fluorophenyl |
| 385 | cyclopropylmethyl | H | O | CH₂CF₃ | Cl | 4-fluorophenyl |
| 386 | SCH(CH₃)₂ | H | O | CH₂CF₃ | Cl | 4-fluorophenyl |
| 387 | OCH₂CH₃ | H | O | CH₂CF₃ | Cl | 4-fluorophenyl |
| 388 | (CH₂)₂ | O | O | CH₂CF₃ | Cl | 4-fluorophenyl |
| 389 | (CH₂)₄ | O | O | CH₂CF₃ | Cl | 4-fluorophenyl |
| 400 | CH₃ | H | O | CH₂CF₃ | Cl | 4-chlorophenyl |
| 401 | CH₂CH₃ | H | O | CH₂CF₃ | Cl | 4-chlorophenyl |
| 402 | CH₂CF₃ | H | O | CH₂CF₃ | Cl | 4-chlorophenyl |
| 403 | CH₂CH₂CH₃ | H | O | CH₂CF₃ | Cl | 4-chlorophenyl |
| 404 | CH₂CH(CH₃)₂ | H | O | CH₂CF₃ | Cl | 4-chlorophenyl |
| 405 | cyclopropylmethyl | H | O | CH₂CF₃ | Cl | 4-chlorophenyl |
| 406 | SCH(CH₃)₂ | H | O | CH₂CF₃ | Cl | 4-chlorophenyl |
| 407 | OCH₂CH₃ | H | O | CH₂CF₃ | Cl | 4-chlorophenyl |
| 408 | (CH₂)₂ | | O | CH₂CF₃ | Cl | 4-chlorophenyl |
| 409 | (CH₂)₄ | | O | CH₂CF₃ | Cl | 4-chlorophenyl |
| 410 | CH₃ | H | O | CH₂CF₃ | Cl | 4-trifluoromethylphenyl |
| 411 | CH₂CH₃ | H | O | CH₂CF₃ | Cl | 4-trifluoromethylphenyl |
| 412 | CH₂CF₃ | H | O | CH₂CF₃ | Cl | 4-trifluoromethylphenyl |
| 413 | CH₂CH₂CH₃ | H | O | CH₂CF₃ | Cl | 4-trifluoromethylphenyl |
| 416 | SCH(CH₃)₂ | H | O | CH₂CF₃ | Cl | 4-trifluoromethylphenyl |
| 417 | OCH₂CH₃ | H | O | CH₂CF₃ | Cl | 4-trifluoromethylphenyl |
| 418 | (CH₂)₂ | | O | CH₂CF₃ | Cl | 4-trifluoromethylphenyl |
| 419 | (CH₂)₄ | | O | CH₂CF₃ | Cl | 4-trifluoromethylphenyl |
| 420 | CH₃ | H | O | CH₂CF₃ | Cl | 4-methoxyphenyl |
| 421 | CH₂CH₃ | H | O | CH₂CF₃ | Cl | 4-methoxyphenyl |
| 422 | CH₂CF₃ | H | O | CH₂CF₃ | Cl | 4-methoxyphenyl |
| 423 | CH₂CH₂CH₃ | H | O | CH₂CF₃ | Cl | 4-methoxyphenyl |
| 424 | CH₂CH(CH₃)₂ | H | O | CH₂CF₃ | Cl | 4-methoxyphenyl |
| 425 | cyclopropylmethyl | H | O | CH₂CF₃ | Cl | 4-methoxyphenyl |
| 426 | SCH(CH₃)₂ | H | O | CH₂CF₃ | Cl | 4-methoxyphenyl |
| 427 | OCH₂CH₃ | H | O | CH₂CF₃ | Cl | 4-methoxyphenyl |
| 428 | (CH₂)₂ | | O | CH₂CF₃ | Cl | 4-methoxyphenyl |
| 429 | (CH₂)₄ | | O | CH₂CF₃ | Cl | 4-methoxyphenyl |
| 430 | CH₃ | H | O | CH₂CF₃ | Cl | 3,4 dichloro phenyl |
| 431 | CH₂CH₃ | H | O | CH₂CF₃ | Cl | 3,4 dichloro phenyl |

-continued

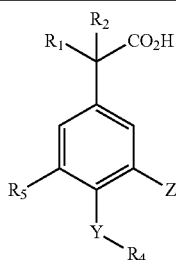

| Example | R₁ | R₂ | Y | R₄ | R₅ | Z |
|---|---|---|---|---|---|---|
| 432 | CH₂CF₃ | H | O | CH₂CF₃ | Cl | 3,4 dichloro phenyl |
| 433 | CH₂CH₂CH₃ | H | O | CH₂CF₃ | Cl | 3,4 dichloro phenyl |
| 434 | CH₂CH(CH₃)₂ | H | O | CH₂CF₃ | Cl | 3,4 dichloro phenyl |
| 435 | cyclopropylmethyl | H | O | CH₂CF₃ | Cl | 3,4 dichloro phenyl |
| 436 | SCH(CH₃)₂ | H | O | CH₂CF₃ | Cl | 3,4 dichloro phenyl |
| 437 | OCH₂CH₃ | H | O | CH₂CF₃ | Cl | 3,4 dichloro phenyl |
| 438 | (CH₂)₂ | | O | CH₂CF₃ | Cl | 3,4 dichloro phenyl |
| 439 | (CH₂)₄ | | O | CH₂CF₃ | Cl | 3,4 dichloro phenyl |
| 440 | CH₃ | H | O | CH₂CF₃ | Cl | 5-benzo[c][1,2,5]oxadiazolyl |
| 441 | CH₂CH₃ | H | O | CH₂CF₃ | Cl | 5-benzo[c][1,2,5]oxadiazolyl |
| 442 | CH₂CF₃ | H | O | CH₂CF₃ | Cl | 5-benzo[c][1,2,5]oxadiazolyl |
| 443 | CH₂CH₂CH₃ | H | O | CH₂CF₃ | Cl | 5-benzo[c][1,2,5]oxadiazolyl |
| 444 | CH₂CH(CH₃)₂ | H | O | CH₂CF₃ | Cl | 5-benzo[c][1,2,5]oxadiazolyl |
| 445 | cyclopropylmethyl | H | O | CH₂CF₃ | Cl | 5-benzo[c][1,2,5]oxadiazolyl |
| 446 | SCH(CH₃)₂ | H | O | CH₂CF₃ | Cl | 5-benzo[c][1,2,5]oxadiazolyl |
| 447 | OCH₂CH₃ | H | O | CH₂CF₃ | Cl | 5-benzo[c][1,2,5]oxadiazolyl |
| 448 | (CH₂)₂ | | O | CH₂CF₃ | Cl | 5-benzo[c][1,2,5]oxadiazolyl |
| 449 | (CH₂)₄ | | O | CH₂CF₃ | Cl | 5-benzo[c][1,2,5]oxadiazolyl |
| 450 | CH₃ | H | O | CH₂CF₃ | Cl | 5-benzo[c][1,2,5]thiadiazolyl |
| 451 | CH₂CH₃ | H | O | CH₂CF₃ | Cl | 5-benzo[c][1,2,5]thiadiazolyl |
| 452 | CH₂CF₃ | H | O | CH₂CF₃ | Cl | 5-benzo[c][1,2,5]thiadiazolyl |
| 453 | CH₂CH₂CH₃ | H | O | CH₂CF₃ | Cl | 5-benzo[c][1,2,5]thiadiazolyl |
| 454 | CH₂CH(CH₃)₂ | H | O | CH₂CF₃ | Cl | 5-benzo[c][1,2,5]thiadiazolyl |
| 455 | cyclopropylmethyl | H | O | CH₂CF₃ | Cl | 5-benzo[c][1,2,5]thiadiazolyl |
| 456 | SCH(CH₃)₂ | H | O | CH₂CF₃ | Cl | 5-benzo[c][1,2,5]thiadiazolyl |
| 457 | OCH₂CH₃ | H | O | CH₂CF₃ | Cl | 5-benzo[c][1,2,5]thiadiazolyl |
| 458 | (CH₂)₂ | | O | CH₂CF₃ | Cl | 5-benzo[c][1,2,5]thiadiazolyl |
| 459 | (CH₂)₄ | | O | CH₂CF₃ | Cl | 5-benzo[c][1,2,5]thiadiazolyl |
| 460 | CH₃ | H | O | CH₂-c-Pr | Cl | 4-fluorophenyl |
| 461 | CH₂CH₃ | H | O | CH₂-c-Pr | Cl | 4-fluorophenyl |
| 462 | CH₂CF₃ | H | O | CH₂-c-Pr | Cl | 4-fluorophenyl |
| 463 | CH₂CH₂CH₃ | H | O | CH₂-c-Pr | Cl | 4-fluorophenyl |
| 464 | CH₂CH(CH₃)₂ | H | O | CH₂-c-Pr | Cl | 4-fluorophenyl |
| 465 | cyclopropylmethyl | H | O | CH₂-c-Pr | Cl | 4-fluorophenyl |
| 466 | SCH(CH₃)₂ | H | O | CH₂-c-Pr | Cl | 4-fluorophenyl |
| 467 | OCH₂CH₃ | H | O | CH₂-c-Pr | Cl | 4-fluorophenyl |
| 468 | (CH₂)₂ | | O | CH₂-c-Pr | Cl | 4-fluorophenyl |
| 469 | (CH₂)₄ | | O | CH₂-c-Pr | Cl | 4-fluorophenyl |
| 470 | CH₃ | H | O | CH₂-c-Pr | Cl | 4-chlorophenyl |
| 471 | CH₂CH₃ | H | O | CH₂-c-Pr | Cl | 4-chlorophenyl |
| 472 | CH₂CF₃ | H | O | CH₂-c-Pr | Cl | 4-chlorophenyl |
| 473 | CH₂CH₂CH₃ | H | O | CH₂-c-Pr | Cl | 4-chlorophenyl |
| 474 | CH₂CH(CH₃)₂ | H | O | CH₂-c-Pr | Cl | 4-chlorophenyl |
| 475 | cyclopropylmethyl | H | O | CH₂-c-Pr | Cl | 4-chlorophenyl |
| 476 | SCH(CH₃)₂ | H | O | CH₂-c-Pr | Cl | 4-chlorophenyl |
| 477 | OCH₂CH₃ | H | O | CH₂-c-Pr | Cl | 4-chlorophenyl |
| 478 | (CH₂)₂ | | O | CH₂-c-Pr | Cl | 4-chlorophenyl |
| 479 | (CH₂)₄ | | O | CH₂-c-Pr | Cl | 4-chlorophenyl |
| 480 | CH₃ | H | O | CH₂-c-Pr | Cl | 4-trifluoromethylphenyl |
| 481 | CH₂CH₃ | H | O | CH₂-c-Pr | Cl | 4-trifluoromethylphenyl |
| 482 | CH₂CF₃ | H | O | CH₂-c-Pr | Cl | 4-trifluoromethylphenyl |
| 483 | CH₂CH₂CH₃ | H | O | CH₂-c-Pr | Cl | 4-trifluoromethylphenyl |
| 484 | CH₂CH(CH₃)₂ | H | O | CH₂-c-Pr | Cl | 4-trifluoromethylphenyl |
| 485 | cyclopropylmethyl | H | O | CH₂-c-Pr | Cl | 4-trifluoromethylphenyl |
| 486 | SCH(CH₃)₂ | H | O | CH₂-c-Pr | Cl | 4-trifluoromethylphenyl |
| 487 | OCH₂CH₃ | H | O | CH₂-c-Pr | Cl | 4-trifluoromethylphenyl |
| 488 | (CH₂)₂ | | O | CH₂-c-Pr | Cl | 4-trifluoromethylphenyl |
| 489 | (CH₂)₄ | | O | CH₂-c-Pr | Cl | 4-trifluoromethylphenyl |
| 490 | CH₃ | H | O | CH₂-c-Pr | Cl | 4-methoxyphenyl |
| 491 | CH₂CH₃ | H | O | CH₂-c-Pr | Cl | 4-methoxyphenyl |
| 492 | CH₂CF₃ | H | O | CH₂-c-Pr | Cl | 4-methoxyphenyl |
| 493 | CH₂CH₂CH₃ | H | O | CH₂-c-Pr | Cl | 4-methoxyphenyl |
| 494 | CH₂CH(CH₃)₂ | H | O | CH₂-c-Pr | Cl | 4-methoxyphenyl |
| 495 | cyclopropylmethyl | H | O | CH₂-c-Pr | Cl | 4-methoxyphenyl |

-continued

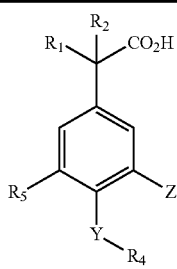

| Example | R₁ | R₂ | Y | R₄ | R₅ | Z |
|---|---|---|---|---|---|---|
| 496 | SCH(CH₃)₂ | H | O | CH₂-c-Pr | Cl | 4-methoxyphenyl |
| 497 | OCH₂CH₃ | H | O | CH₂-c-Pr | Cl | 4-methoxyphenyl |
| 498 | (CH₂)₂ | | O | CH₂-c-Pr | Cl | 4-methoxyphenyl |
| 499 | (CH₂)₄ | | O | CH₂-c-Pr | Cl | 4-methoxyphenyl |
| 500 | CH₃ | H | O | CH₂-c-Pr | Cl | 3,4 dichloro phenyl |
| 501 | CH₂CH₃ | H | O | CH₂-c-Pr | Cl | 3,4 dichloro phenyl |
| 502 | CH₂CF₃ | H | O | CH₂-c-Pr | Cl | 3,4 dichloro phenyl |
| 503 | CH₂CH₂CH₃ | H | O | CH₂-c-Pr | Cl | 3,4 dichloro phenyl |
| 504 | CH₂CH(CH₃)₂ | H | O | CH₂-c-Pr | Cl | 3,4 dichloro phenyl |
| 505 | cyclopropylmethyl | H | O | CH₂-c-Pr | Cl | 3,4 dichloro phenyl |
| 506 | SCH(CH₃)₂ | H | O | CH₂-c-Pr | Cl | 3,4 dichloro phenyl |
| 507 | OCH₂CH₃ | H | O | CH₂-c-Pr | Cl | 3,4 dichloro phenyl |
| 508 | (CH₂)₂ | | O | CH₂-c-Pr | Cl | 3,4 dichloro phenyl |
| 509 | (CH₂)₄ | | O | CH₂-c-Pr | Cl | 3,4 dichloro phenyl |
| 510 | CH₃ | H | O | CH₂-c-Pr | Cl | 5-benzo[c][1,2,5]oxadiazolyl |
| 511 | CH₂CH₃ | H | O | CH₂-c-Pr | Cl | 5-benzo[c][1,2,5]oxadiazolyl |
| 512 | CH₂CF₃ | H | O | CH₂-c-Pr | Cl | 5-benzo[c][1,2,5]oxadiazolyl |
| 513 | CH₂CH₂CH₃ | H | O | CH₂-c-Pr | Cl | 5-benzo[c][1,2,5]oxadiazolyl |
| 514 | CH₂CH(CH₃)₂ | H | O | CH₂-c-Pr | Cl | 5-benzo[c][1,2,5]oxadiazolyl |
| 515 | cyclopropylmethyl | H | O | CH₂-c-Pr | Cl | 5-benzo[c][1,2,5]oxadiazolyl |
| 516 | SCH(CH₃)₂ | H | O | CH₂-c-Pr | Cl | 5-benzo[c][1,2,5]oxadiazolyl |
| 517 | OCH₂CH₃ | H | O | CH₂-c-Pr | Cl | 5-benzo[c][1,2,5]oxadiazolyl |
| 518 | (CH₂)₂ | | O | CH₂-c-Pr | Cl | 5-benzo[c][1,2,5]oxadiazolyl |
| 519 | (CH₂)₄ | | O | CH₂-c-Pr | Cl | 5-benzo[c][1,2,5]oxadiazolyl |
| 520 | CH₃ | H | O | CH₂-c-Pr | Cl | 5-benzo[c][1,2,5]thiadiazolyl |
| 521 | CH₂CH₃ | H | O | CH₂-c-Pr | Cl | 5-benzo[c][1,2,5]thiadiazolyl |
| 522 | CH₂CF₃ | H | O | CH₂-c-Pr | Cl | 5-benzo[c][1,2,5]thiadiazolyl |
| 523 | CH₂CH₂CH₃ | H | O | CH₂-c-Pr | Cl | 5-benzo[c][1,2,5]thiadiazolyl |
| 524 | CH₂CH(CH₃)₂ | H | O | CH₂-c-Pr | Cl | 5-benzo[c][1,2,5]thiadiazolyl |
| 525 | cyclopropylmethyl | H | O | CH₂-c-Pr | Cl | 5-benzo[c][1,2,5]thiadiazolyl |
| 526 | SCH(CH₃)₂ | H | O | CH₂-c-Pr | Cl | 5-benzo[c][1,2,5]thiadiazolyl |
| 527 | OCH₂CH₃ | H | O | CH₂-c-Pr | Cl | 5-benzo[c][1,2,5]thiadiazolyl |
| 528 | (CH₂)₂ | | O | CH₂-c-Pr | Cl | 5-benzo[c][1,2,5]thiadiazolyl |
| 529 | (CH₂)₄ | | O | CH₂-c-Pr | Cl | 5-benzo[c][1,2,5]thiadiazolyl |
| 530 | CH₃ | H | O | CH₂-c-Pr | NO₂ | 4-trifluoromethylphenyl |
| 531 | CH₂CH₃ | H | O | CH₂-c-Pr | NO₂ | 4-trifluoromethylphenyl |
| 532 | CH₂CF₃ | H | O | CH₂-c-Pr | NO₂ | 4-trifluoromethylphenyl |
| 533 | CH₂CH₂CH₃ | H | O | CH₂-c-Pr | NO₂ | 4-trifluoromethylphenyl |
| 534 | CH₂CH(CH₃)₂ | H | O | CH₂-c-Pr | NO₂ | 4-trifluoromethylphenyl |
| 535 | cyclopropylmethyl | H | O | CH₂-c-Pr | NO₂ | 4-trifluoromethylphenyl |
| 536 | SCH(CH₃)₂ | H | O | CH₂-c-Pr | NO₂ | 4-trifluoromethylphenyl |
| 537 | OCH₂CH₃ | H | O | CH₂-c-Pr | NO₂ | 4-trifluoromethylphenyl |
| 538 | (CH₂)₂ | | O | CH₂-c-Pr | NO₂ | 4-trifluoromethylphenyl |
| 539 | (CH₂)₄ | | O | CH₂-c-Pr | NO₂ | 4-trifluoromethylphenyl |
| 540 | CH₃ | H | O | CH₂-c-Pr | NO₂ | 5-benzo[c][1,2,5]oxadiazolyl |
| 541 | CH₂CH₃ | H | O | CH₂-c-Pr | NO₂ | 5-benzo[c][1,2,5]oxadiazolyl |
| 542 | CH₂CF₃ | H | O | CH₂-c-Pr | NO₂ | 5-benzo[c][1,2,5]oxadiazolyl |
| 543 | CH₂CH₂CH₃ | H | O | CH₂-c-Pr | NO₂ | 5-benzo[c][1,2,5]oxadiazolyl |
| 544 | CH₂CH(CH₃)₂ | H | O | CH₂-c-Pr | NO₂ | 5-benzo[c][1,2,5]oxadiazolyl |
| 545 | cyclopropylmethyl | H | O | CH₂-c-Pr | NO₂ | 5-benzo[c][1,2,5]oxadiazolyl |
| 546 | SCH(CH₃)₂ | H | O | CH₂-c-Pr | NO₂ | 5-benzo[c][1,2,5]oxadiazolyl |
| 547 | OCH₂CH₃ | H | O | CH₂-c-Pr | NO₂ | 5-benzo[c][1,2,5]oxadiazolyl |
| 548 | (CH₂)₂ | | O | CH₂-c-Pr | NO₂ | 5-benzo[c][1,2,5]oxadiazolyl |
| 549 | (CH₂)₄ | | O | CH₂-c-Pr | NO₂ | 5-benzo[c][1,2,5]oxadiazolyl |
| 550 | CH₃ | H | O | CH₂-c-Pr | NH₂ | 4-trifluoromethylphenyl |
| 551 | CH₂CH₃ | H | O | CH₂-c-Pr | NH₂ | 4-trifluoromethylphenyl |
| 552 | CH₂CF₃ | H | O | CH₂-c-Pr | NH₂ | 4-trifluoromethylphenyl |
| 553 | CH₂CH₂CH₃ | H | O | CH₂-c-Pr | NH₂ | 4-trifluoromethylphenyl |
| 554 | CH₂CH(CH₃)₂ | H | O | CH₂-c-Pr | NH₂ | 4-trifluoromethylphenyl |
| 555 | cyclopropylmethyl | H | O | CH₂-c-Pr | NH₂ | 4-trifluoromethylphenyl |
| 556 | SCH(CH₃)₂ | H | O | CH₂-c-Pr | NH₂ | 4-trifluoromethylphenyl |
| 557 | OCH₂CH₃ | H | O | CH₂-c-Pr | NH₂ | 4-trifluoromethylphenyl |
| 558 | (CH₂)₂ | | O | CH₂-c-Pr | NH₂ | 4-trifluoromethylphenyl |
| 559 | (CH₂)₄ | | O | CH₂-c-Pr | NH₂ | 4-trifluoromethylphenyl |

-continued

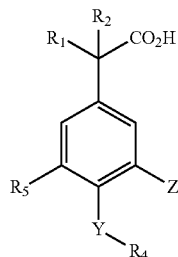

| Example | R₁ | R₂ | Y | R₄ | R₅ | Z |
|---|---|---|---|---|---|---|
| 980 | CH₂CH₃ | H | O | CH₂CF₃ | CF₃ | 4-trifluoromethylphenyl |
| 981 | CH₂CF₃ | H | O | CH₂CF₃ | CF₃ | 4-trifluoromethylphenyl |
| 982 | CH₂CH₂CH₃ | H | O | CH₂CF₃ | CF₃ | 4-trifluoromethylphenyl |
| 985 | cyclobutylmethyl | H | O | CH₂CF₃ | CF₃ | 4-trifluoromethylphenyl |
| 986 | (CH₂)₂ | | O | CH₂CF₃ | CH₂CF₃ | 4-trifluoromethylphenyl |
| 987 | (CH₂)₃ | | O | CH₂CF₃ | CH₂CF₃ | 4-trifluoromethylphenyl |
| 988 | (CH₂)₄ | | O | CH₂CF₃ | CH₂CF₃ | 4-trifluoromethylphenyl |
| 989 | (CH₂)₅ | | O | CH₂CF₃ | CH₂CF₃ | 4-trifluoromethylphenyl |
| 990 | 5,5-spiro[2.3]hexane | | O | CH₂CF₃ | CH₂CF₃ | 4-trifluoromethylphenyl |
| 991 | Cyclopentyl | H | O | CH₂CF₃ | CF₃ | 4-trifluoromethylphenyl |
| 992 | CH₂CH₃ | H | O | CH₂CF₃ | CF₃ | 4-tolyl |
| 993 | CH₂CF₃ | H | O | CH₂CF₃ | CF₃ | 4-tolyl |
| 994 | CH₂CH₂CH₃ | H | O | CH₂CF₃ | CF₃ | 4-tolyl |
| 995 | CH₂CH(CH₃)₂ | H | O | CH₂CF₃ | CF₃ | 4-tolyl |
| 996 | cyclopropylmethyl | H | O | CH₂CF₃ | CF₃ | 4-tolyl |
| 997 | cyclobutylmethyl | H | O | CH₂CF₃ | CF₃ | 4-tolyl |
| 998 | (CH₂)₂ | | O | CH₂CF₃ | CH₂CF₃ | 4-tolyl |
| 999 | (CH₂)₃ | | O | CH₂CF₃ | CH₂CF₃ | 4-tolyl |
| 1000 | (CH₂)₄ | | O | CH₂CF₃ | CH₂CF₃ | 4-tolyl |
| 1001 | (CH₂)₅ | | O | CH₂CF₃ | CH₂CF₃ | 4-tolyl |
| 1002 | 5,5-spiro[2.3]hexane | | O | CH₂CF₃ | CH₂CF₃ | 4-tolyl |
| 1003 | Cyclopentyl | H | O | CH₂CF₃ | CF₃ | 4-tolyl |
| 1004 | CH₂CH₃ | H | O | CH₂CF₃ | CF₃ | 4-ethyl phenyl |
| 1005 | CH₂CF₃ | H | O | CH₂CF₃ | CF₃ | 4-ethyl phenyl |
| 1006 | CH₂CH₂CH₃ | H | O | CH₂CF₃ | CF₃ | 4-ethyl phenyl |
| 1007 | CH₂CH(CH₃)₂ | H | O | CH₂CF₃ | CF₃ | 4-ethyl phenyl |
| 1008 | cyclopropylmethyl | H | O | CH₂CF₃ | CF₃ | 4-ethyl phenyl |
| 1009 | cyclobutylmethyl | H | O | CH₂CF₃ | CF₃ | 4-ethyl phenyl |
| 1010 | (CH₂)₂ | | O | CH₂CF₃ | CH₂CF₃ | 4-ethyl phenyl |
| 1011 | (CH₂)₃ | | O | CH₂CF₃ | CH₂CF₃ | 4-ethyl phenyl |
| 1012 | (CH₂)₄ | | O | CH₂CF₃ | CH₂CF₃ | 4-ethyl phenyl |
| 1013 | (CH₂)₅ | | O | CH₂CF₃ | CH₂CF₃ | 4-ethyl phenyl |
| 1014 | 5,5-spiro[2.3]hexane | | O | CH₂CF₃ | CH₂CF₃ | 4-ethyl phenyl |
| 1015 | Cyclopentyl | H | O | CH₂CF₃ | CF₃ | 4-ethyl phenyl |
| 1016 | CH₂CH₃ | H | O | CH₂CF₃ | CF₃ | 4-isopropyl phenyl |
| 1017 | CH₂CF₃ | H | O | CH₂CF₃ | CF₃ | 4-isopropyl phenyl |
| 1018 | CH₂CH₂CH₃ | H | O | CH₂CF₃ | CF₃ | 4-isopropyl phenyl |
| 1019 | CH₂CH(CH₃)₂ | H | O | CH₂CF₃ | CF₃ | 4-isopropyl phenyl |
| 1020 | cyclopropylmethyl | H | O | CH₂CF₃ | CF₃ | 4-isopropyl phenyl |
| 1021 | cyclobutylmethyl | H | O | CH₂CF₃ | CF₃ | 4-isopropyl phenyl |
| 1022 | (CH₂)₂ | | O | CH₂CF₃ | CH₂CF₃ | 4-isopropyl phenyl |
| 1023 | (CH₂)₃ | | O | CH₂CF₃ | CH₂CF₃ | 4-isopropyl phenyl |
| 1024 | (CH₂)₄ | | O | CH₂CF₃ | CH₂CF₃ | 4-isopropyl phenyl |
| 1025 | (CH₂)₅ | | O | CH₂CF₃ | CH₂CF₃ | 4-isopropyl phenyl |
| 1026 | 5,5-spiro[2.3]hexane | | O | CH₂CF₃ | CH₂CF₃ | 4-isopropyl phenyl |
| 1027 | Cyclopentyl | H | O | CH₂CF₃ | CF₃ | 4-isopropyl phenyl |
| 1028 | CH₂CH₃ | H | O | CH₂CF₃ | CF₃ | 4-thiomethylphenyl |
| 1029 | CH₂CF₃ | H | O | CH₂CF₃ | CF₃ | 4-thiomethylphenyl |
| 1030 | CH₂CH₂CH₃ | H | O | CH₂CF₃ | CF₃ | 4-thiomethylphenyl |
| 1031 | CH₂CH(CH₃)₂ | H | O | CH₂CF₃ | CF₃ | 4-thiomethylphenyl |
| 1032 | cyclopropylmethyl | H | O | CH₂CF₃ | CF₃ | 4-thiomethylphenyl |
| 1033 | cyclobutylmethyl | H | O | CH₂CF₃ | CF₃ | 4-thiomethylphenyl |
| 1034 | (CH₂)₂ | | O | CH₂CF₃ | CH₂CF₃ | 4-thiomethylphenyl |
| 1035 | (CH₂)₃ | | O | CH₂CF₃ | CH₂CF₃ | 4-thiomethylphenyl |
| 1036 | (CH₂)₄ | | O | CH₂CF₃ | CH₂CF₃ | 4-thiomethylphenyl |
| 1037 | (CH₂)₅ | | O | CH₂CF₃ | CH₂CF₃ | 4-thiomethylphenyl |
| 1038 | 5,5-spiro[2.3]hexane | | O | CH₂CF₃ | CH₂CF₃ | 4-thiomethylphenyl |
| 1039 | Cyclopentyl | H | O | CH₂CF₃ | CF₃ | 4-thiomethylphenyl |
| 1040 | CH₂CH₃ | H | O | CH₂CF₃ | CF₃ | 4-trifluoromethoxyphenyl |
| 1041 | CH₂CF₃ | H | O | CH₂CF₃ | CF₃ | 4-trifluoromethoxyphenyl |
| 1042 | CH₂CH₂CH₃ | H | O | CH₂CF₃ | CF₃ | 4-trifluoromethoxyphenyl |
| 1043 | CH₂CH(CH₃)₂ | H | O | CH₂CF₃ | CF₃ | 4-trifluoromethoxyphenyl |
| 1044 | cyclopropylmethyl | H | O | CH₂CF₃ | CF₃ | 4-trifluoromethoxyphenyl |
| 1045 | cyclobutylmethyl | H | O | CH₂CF₃ | CF₃ | 4-trifluoromethoxyphenyl |

-continued

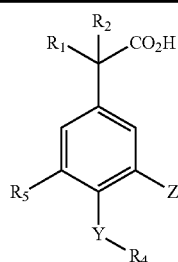

| Example | R$_1$ | R$_2$ | Y | R$_4$ | R$_5$ | Z |
|---|---|---|---|---|---|---|
| 1046 | (CH$_2$)$_2$ | | O | CH$_2$CF$_3$ | CH$_2$CF$_3$ | 4-trifluoromethoxyphenyl |
| 1047 | (CH$_2$)$_3$ | | O | CH$_2$CF$_3$ | CH$_2$CF$_3$ | 4-trifluoromethoxyphenyl |
| 1048 | (CH$_2$)$_4$ | | O | CH$_2$CF$_3$ | CH$_2$CF$_3$ | 4-trifluoromethoxyphenyl |
| 1049 | (CH$_2$)$_5$ | | O | CH$_2$CF$_3$ | CH$_2$CF$_3$ | 4-trifluoromethoxyphenyl |
| 1050 | 5,5-spiro[2.3]hexane | | O | CH$_2$CF$_3$ | CH$_2$CF$_3$ | 4-trifluoromethoxyphenyl |
| 1051 | Cyclopentyl | H | O | CH$_2$CF$_3$ | CF$_3$ | 4-trifluoromethoxyphenyl |
| 1052 | CH$_2$CH$_3$ | H | O | CH$_2$-c-Pr | CF$_3$ | 4-trifluoromethylphenyl |
| 1053 | CH$_2$CF$_3$ | H | O | CH$_2$-c-Pr | CF$_3$ | 4-trifluoromethylphenyl |
| 1054 | CH$_2$CH$_2$CH$_3$ | H | O | CH$_2$-c-Pr | CF$_3$ | 4-trifluoromethylphenyl |
| 1055 | CH$_2$CH(CH$_3$)$_2$ | H | O | CH$_2$-c-Pr | CF$_3$ | 4-trifluoromethylphenyl |
| 1056 | cyclopropylmethyl | H | O | CH$_2$-c-Pr | CF$_3$ | 4-trifluoromethylphenyl |
| 1057 | cyclobutylmethyl | H | O | CH$_2$-c-Pr | CF$_3$ | 4-trifluoromethylphenyl |
| 1058 | (CH$_2$)$_2$ | | O | CH$_2$-c-Pr | CF$_3$ | 4-trifluoromethylphenyl |
| 1059 | (CH$_2$)$_3$ | | O | CH$_2$-c-Pr | CF$_3$ | 4-trifluoromethylphenyl |
| 1060 | (CH$_2$)$_4$ | | O | CH$_2$-c-Pr | CF$_3$ | 4-trifluoromethylphenyl |
| 1061 | (CH$_2$)$_5$ | | O | CH$_2$-c-Pr | CF$_3$ | 4-trifluoromethylphenyl |
| 1062 | 5,5-spiro[2.3]hexane | | O | CH$_2$-c-Pr | CF$_3$ | 4-trifluoromethylphenyl |
| 1063 | Cyclopentyl | H | O | CH$_2$-c-Pr | CF$_3$ | 4-trifluoromethylphenyl |
| 1064 | CH$_2$CH$_3$ | H | O | CH$_2$-c-Pr | CF$_3$ | 4-tolyl |
| 1065 | CH$_2$CF$_3$ | H | O | CH$_2$-c-Pr | CF$_3$ | 4-tolyl |
| 1066 | CH$_2$CH$_2$CH$_3$ | H | O | CH$_2$-c-Pr | CF$_3$ | 4-tolyl |
| 1067 | CH$_2$CH(CH$_3$)$_2$ | H | O | CH$_2$-c-Pr | CF$_3$ | 4-tolyl |
| 1068 | cyclopropylmethyl | H | O | CH$_2$-c-Pr | CF$_3$ | 4-tolyl |
| 1069 | cyclobutylmethyl | H | O | CH$_2$-c-Pr | CF$_3$ | 4-tolyl |
| 1070 | (CH$_2$)$_2$ | | O | CH$_2$-c-Pr | CF$_3$ | 4-tolyl |
| 1071 | (CH$_2$)$_3$ | | O | CH$_2$-c-Pr | CF$_3$ | 4-tolyl |
| 1072 | (CH$_2$)$_4$ | | O | CH$_2$-c-Pr | CF$_3$ | 4-tolyl |
| 1073 | (CH$_2$)$_5$ | | O | CH$_2$-c-Pr | CF$_3$ | 4-tolyl |
| 1074 | 5,5-spiro[2.3]hexane | | O | CH$_2$-c-Pr | CF$_3$ | 4-tolyl |
| 1075 | Cyclopentyl | H | O | CH$_2$-c-Pr | CF$_3$ | 4-tolyl |
| 1076 | CH$_2$CH$_3$ | H | O | CH$_2$-c-Pr | CF$_3$ | 4-ethyl phenyl |
| 1077 | CH$_2$CF$_3$ | H | O | CH$_2$-c-Pr | CF$_3$ | 4-ethyl phenyl |
| 1078 | CH$_2$CH$_2$CH$_3$ | H | O | CH$_2$-c-Pr | CF$_3$ | 4-ethyl phenyl |
| 1079 | CH$_2$CH(CH$_3$)$_2$ | H | O | CH$_2$-c-Pr | CF$_3$ | 4-ethyl phenyl |
| 1080 | cyclopropylmethyl | H | O | CH$_2$-c-Pr | CF$_3$ | 4-ethyl phenyl |
| 1081 | cyclobutylmethyl | H | O | CH$_2$-c-Pr | CF$_3$ | 4-ethyl phenyl |
| 1082 | (CH$_2$)$_2$ | | O | CH$_2$-c-Pr | CF$_3$ | 4-ethyl phenyl |
| 1083 | (CH$_2$)$_3$ | | O | CH$_2$-c-Pr | CF$_3$ | 4-ethyl phenyl |
| 1084 | (CH$_2$)$_4$ | | O | CH$_2$-c-Pr | CF$_3$ | 4-ethyl phenyl |
| 1085 | (CH$_2$)$_5$ | | O | CH$_2$-c-Pr | CF$_3$ | 4-ethyl phenyl |
| 1086 | 5,5-spiro[2.3]hexane | | O | CH$_2$-c-Pr | CF$_3$ | 4-ethyl phenyl |
| 1087 | Cyclopentyl | H | O | CH$_2$-c-Pr | CF$_3$ | 4-ethyl phenyl |
| 1088 | CH$_2$CH$_3$ | H | O | CH$_2$-c-Pr | CF$_3$ | 4-isopropyl phenyl |
| 1089 | CH$_2$CF$_3$ | H | O | CH$_2$-c-Pr | CF$_3$ | 4-isopropyl phenyl |
| 1090 | CH$_2$CH$_2$CH$_3$ | H | O | CH$_2$-c-Pr | CF$_3$ | 4-isopropyl phenyl |
| 1091 | CH$_2$CH(CH$_3$)$_2$ | H | O | CH$_2$-c-Pr | CF$_3$ | 4-isopropyl phenyl |
| 1092 | cyclopropylmethyl | H | O | CH$_2$-c-Pr | CF$_3$ | 4-isopropyl phenyl |
| 1093 | cyclobutylmethyl | H | O | CH$_2$-c-Pr | CF$_3$ | 4-isopropyl phenyl |
| 1094 | (CH$_2$)$_2$ | | O | CH$_2$-c-Pr | CF$_3$ | 4-isopropyl phenyl |
| 1095 | (CH$_2$)$_3$ | | O | CH$_2$-c-Pr | CF$_3$ | 4-isopropyl phenyl |
| 1096 | (CH$_2$)$_4$ | | O | CH$_2$-c-Pr | CF$_3$ | 4-isopropyl phenyl |
| 1097 | (CH$_2$)$_5$ | | O | CH$_2$-c-Pr | CF$_3$ | 4-isopropyl phenyl |
| 1098 | 5,5-spiro[2.3]hexane | | O | CH$_2$-c-Pr | CF$_3$ | 4-isopropyl phenyl |
| 1099 | Cyclopentyl | H | O | CH$_2$-c-Pr | CF$_3$ | 4-isopropyl phenyl |
| 1100 | CH$_2$CH$_3$ | H | O | CH$_2$-c-Pr | CF$_3$ | 4-thiomethylphenyl |
| 1101 | CH$_2$CF$_3$ | H | O | CH$_2$-c-Pr | CF$_3$ | 4-thiomethylphenyl |
| 1102 | CH$_2$CH$_2$CH$_3$ | H | O | CH$_2$-c-Pr | CF$_3$ | 4-thiomethylphenyl |
| 1103 | CH$_2$CH(CH$_3$)$_2$ | H | O | CH$_2$-c-Pr | CF$_3$ | 4-thiomethylphenyl |
| 1104 | cyclopropylmethyl | H | O | CH$_2$-c-Pr | CF$_3$ | 4-thiomethylphenyl |
| 1105 | cyclobutylmethyl | H | O | CH$_2$-c-Pr | CF$_3$ | 4-thiomethylphenyl |
| 1106 | (CH$_2$)$_2$ | | O | CH$_2$-c-Pr | CF$_3$ | 4-thiomethylphenyl |
| 1107 | (CH$_2$)$_3$ | | O | CH$_2$-c-Pr | CF$_3$ | 4-thiomethylphenyl |
| 1108 | (CH$_2$)$_4$ | | O | CH$_2$-c-Pr | CF$_3$ | 4-thiomethylphenyl |
| 1109 | (CH$_2$)$_5$ | | O | CH$_2$-c-Pr | CF$_3$ | 4-thiomethylphenyl |

-continued

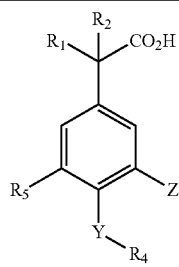

| Example | R₁ | R₂ | Y | R₄ | R₅ | Z |
|---|---|---|---|---|---|---|
| 1110 | 5,5-spiro[2.3]hexane | | O | CH₂-c-Pr | CF₃ | 4-thiomethylphenyl |
| 1111 | Cyclopentyl | H | O | CH₂-c-Pr | CF₃ | 4-thiomethylphenyl |
| 1112 | CH₂CH₃ | H | O | CH₂-c-Pr | CF₃ | 4-trifluoromethoxyphenyl |
| 1113 | CH₂CF₃ | H | O | CH₂-c-Pr | CF₃ | 4-trifluoromethoxyphenyl |
| 1114 | CH₂CH₂CH₃ | H | O | CH₂-c-Pr | CF₃ | 4-trifluoromethoxyphenyl |
| 1115 | CH₂CH(CH₃)₂ | H | O | CH₂-c-Pr | CF₃ | 4-trifluoromethoxyphenyl |
| 1116 | cyclopropylmethyl | H | O | CH₂-c-Pr | CF₃ | 4-trifluoromethoxyphenyl |
| 1117 | cyclobutylmethyl | H | O | CH₂-c-Pr | CF₃ | 4-trifluoromethoxyphenyl |
| 1118 | (CH₂)₂ | | O | CH₂-c-Pr | CF₃ | 4-trifluoromethoxyphenyl |
| 1119 | (CH₂)₃ | | O | CH₂-c-Pr | CF₃ | 4-trifluoromethoxyphenyl |
| 1120 | (CH₂)₄ | | O | CH₂-c-Pr | CF₃ | 4-trifluoromethoxyphenyl |
| 1121 | (CH₂)₅ | | O | CH₂-c-Pr | CF₃ | 4-trifluoromethoxyphenyl |
| 1122 | 5,5-spiro[2.3]hexane | | O | CH₂-c-Pr | CF₃ | 4-trifluoromethoxyphenyl |
| 1123 | Cyclopentyl | H | O | CH₂-c-Pr | CF₃ | 4-trifluoromethoxyphenyl |
| 1124 | CH₂CH₃ | H | O | CH₂CF₃ | OCH₂CF₃ | 4-trifluoromethylphenyl |
| 1125 | CH₂CF₃ | H | O | CH₂CF₃ | OCH₂CF₃ | 4-trifluoromethylphenyl |
| 1126 | CH₂CH₂CH₃ | H | O | CH₂CF₃ | OCH₂CF₃ | 4-trifluoromethylphenyl |
| 1127 | CH₂CH(CH₃)₂ | H | O | CH₂CF₃ | OCH₂CF₃ | 4-trifluoromethylphenyl |
| 1128 | cyclopropylmethyl | H | O | CH₂CF₃ | OCH₂CF₃ | 4-trifluoromethylphenyl |
| 1129 | cyclobutylmethyl | H | O | CH₂CF₃ | OCH₂CF₃ | 4-trifluoromethylphenyl |
| 1130 | (CH₂)₂ | | O | CH₂CF₃ | OCH₂CF₃ | 4-trifluoromethylphenyl |
| 1131 | (CH₂)₃ | | O | CH₂CF₃ | OCH₂CF₃ | 4-trifluoromethylphenyl |
| 1132 | (CH₂)₄ | | O | CH₂CF₃ | OCH₂CF₃ | 4-trifluoromethylphenyl |
| 1133 | (CH₂)₅ | | O | CH₂CF₃ | OCH₂CF₃ | 4-trifluoromethylphenyl |
| 1134 | 5,5-spiro[2.3]hexane | | O | CH₂CF₃ | OCH₂CF₃ | 4-trifluoromethylphenyl |
| 1135 | Cyclopentyl | H | O | CH₂CF₃ | OCH₂CF₃ | 4-trifluoromethylphenyl |
| 1136 | CH₂CH₃ | H | O | CH₂CF₃ | OCH₂CF₃ | 4-tolyl |
| 1137 | CH₂CF₃ | H | O | CH₂CF₃ | OCH₂CF₃ | 4-tolyl |
| 1138 | CH₂CH₂CH₃ | H | O | CH₂CF₃ | OCH₂CF₃ | 4-tolyl |
| 1139 | CH₂CH(CH₃)₂ | H | O | CH₂CF₃ | OCH₂CF₃ | 4-tolyl |
| 1140 | cyclopropylmethyl | H | O | CH₂CF₃ | OCH₂CF₃ | 4-tolyl |
| 1141 | cyclobutylmethyl | H | O | CH₂CF₃ | OCH₂CF₃ | 4-tolyl |
| 1142 | (CH₂)₂ | | O | CH₂CF₃ | OCH₂CF₃ | 4-tolyl |
| 1143 | (CH₂)₃ | | O | CH₂CF₃ | OCH₂CF₃ | 4-tolyl |
| 1144 | (CH₂)₄ | | O | CH₂CF₃ | OCH₂CF₃ | 4-tolyl |
| 1145 | (CH₂)₅ | | O | CH₂CF₃ | OCH₂CF₃ | 4-tolyl |
| 1146 | 5,5-spiro[2.3]hexane | | O | CH₂CF₃ | OCH₂CF₃ | 4-tolyl |
| 1147 | Cyclopentyl | H | O | CH₂CF₃ | OCH₂CF₃ | 4-tolyl |
| 1148 | CH₂CH₃ | H | O | CH₂CF₃ | OCH₂CF₃ | 4-ethyl phenyl |
| 1149 | CH₂CF₃ | H | O | CH₂CF₃ | OCH₂CF₃ | 4-ethyl phenyl |
| 1150 | CH₂CH₂CH₃ | H | O | CH₂CF₃ | OCH₂CF₃ | 4-ethyl phenyl |
| 1151 | CH₂CH(CH₃)₂ | H | O | CH₂CF₃ | OCH₂CF₃ | 4-ethyl phenyl |
| 1152 | cyclopropylmethyl | H | O | CH₂CF₃ | OCH₂CF₃ | 4-ethyl phenyl |
| 1153 | cyclobutylmethyl | H | O | CH₂CF₃ | OCH₂CF₃ | 4-ethyl phenyl |
| 1154 | (CH₂)₂ | | O | CH₂CF₃ | OCH₂CF₃ | 4-ethyl phenyl |
| 1155 | (CH₂)₃ | | O | CH₂CF₃ | OCH₂CF₃ | 4-ethyl phenyl |
| 1156 | (CH₂)₄ | | O | CH₂CF₃ | OCH₂CF₃ | 4-ethyl phenyl |
| 1157 | (CH₂)₅ | | O | CH₂CF₃ | OCH₂CF₃ | 4-ethyl phenyl |
| 1158 | 5,5-spiro[2.3]hexane | | O | CH₂CF₃ | OCH₂CF₃ | 4-ethyl phenyl |
| 1159 | Cyclopentyl | H | O | CH₂CF₃ | OCH₂CF₃ | 4-ethyl phenyl |
| 1160 | CH₂CH₃ | H | O | CH₂CF₃ | OCH₂CF₃ | 4-isopropyl phenyl |
| 1161 | CH₂CF₃ | H | O | CH₂CF₃ | OCH₂CF₃ | 4-isopropyl phenyl |
| 1162 | CH₂CH₂CH₃ | H | O | CH₂CF₃ | OCH₂CF₃ | 4-isopropyl phenyl |
| 1163 | CH₂CH(CH₃)₂ | H | O | CH₂CF₃ | OCH₂CF₃ | 4-isopropyl phenyl |
| 1164 | cyclopropylmethyl | H | O | CH₂CF₃ | OCH₂CF₃ | 4-isopropyl phenyl |
| 1165 | cyclobutylmethyl | H | O | CH₂CF₃ | OCH₂CF₃ | 4-isopropyl phenyl |
| 1166 | (CH₂)₂ | | O | CH₂CF₃ | OCH₂CF₃ | 4-isopropyl phenyl |
| 1167 | (CH₂)₃ | | O | CH₂CF₃ | OCH₂CF₃ | 4-isopropyl phenyl |
| 1168 | (CH₂)₄ | | O | CH₂CF₃ | OCH₂CF₃ | 4-isopropyl phenyl |
| 1169 | (CH₂)₅ | | O | CH₂CF₃ | OCH₂CF₃ | 4-isopropyl phenyl |
| 1170 | 5,5-spiro[2.3]hexane | | O | CH₂CF₃ | OCH₂CF₃ | 4-isopropyl phenyl |
| 1171 | Cyclopentyl | H | O | CH₂CF₃ | OCH₂CF₃ | 4-isopropyl phenyl |
| 1172 | CH₂CH₃ | H | O | CH₂CF₃ | OCH₂CF₃ | 4-thiomethylphenyl |
| 1173 | CH₂CF₃ | H | O | CH₂CF₃ | OCH₂CF₃ | 4-thiomethylphenyl |

-continued

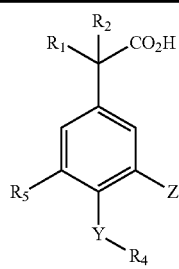

| Example | R₁ | R₂ | Y | R₄ | R₅ | Z |
|---|---|---|---|---|---|---|
| 1174 | $CH_2CH_2CH_3$ | H | O | $CH_2CF_3$ | $OCH_2CF_3$ | 4-thiomethylphenyl |
| 1175 | $CH_2CH(CH_3)_2$ | H | O | $CH_2CF_3$ | $OCH_2CF_3$ | 4-thiomethylphenyl |
| 1176 | cyclopropylmethyl | H | O | $CH_2CF_3$ | $OCH_2CF_3$ | 4-thiomethylphenyl |
| 1177 | cyclobutylmethyl | H | O | $CH_2CF_3$ | $OCH_2CF_3$ | 4-thiomethylphenyl |
| 1178 | $(CH_2)_2$ | | O | $CH_2CF_3$ | $OCH_2CF_3$ | 4-thiomethylphenyl |
| 1179 | $(CH_2)_3$ | | O | $CH_2CF_3$ | $OCH_2CF_3$ | 4-thiomethylphenyl |
| 1180 | $(CH_2)_4$ | | O | $CH_2CF_3$ | $OCH_2CF_3$ | 4-thiomethylphenyl |
| 1181 | $(CH_2)_5$ | | O | $CH_2CF_3$ | $OCH_2CF_3$ | 4-thiomethylphenyl |
| 1182 | 5,5-spiro[2.3]hexane | | O | $CH_2CF_3$ | $OCH_2CF_3$ | 4-thiomethylphenyl |
| 1183 | Cyclopentyl | H | O | $CH_2CF_3$ | $OCH_2CF_3$ | 4-thiomethylphenyl |
| 1184 | $CH_2CH_3$ | H | O | $CH_2CF_3$ | $OCH_2CF_3$ | 4-trifluoromethoxyphenyl |
| 1185 | $CH_2CF_3$ | H | O | $CH_2CF_3$ | $OCH_2CF_3$ | 4-trifluoromethoxyphenyl |
| 1186 | $CH_2CH_2CH_3$ | H | O | $CH_2CF_3$ | $OCH_2CF_3$ | 4-trifluoromethoxyphenyl |
| 1187 | $CH_2CH(CH_3)_2$ | H | O | $CH_2CF_3$ | $OCH_2CF_3$ | 4-trifluoromethoxyphenyl |
| 1188 | cyclopropylmethyl | H | O | $CH_2CF_3$ | $OCH_2CF_3$ | 4-trifluoromethoxyphenyl |
| 1189 | cyclobutylmethyl | H | O | $CH_2CF_3$ | $OCH_2CF_3$ | 4-trifluoromethoxyphenyl |
| 1190 | $(CH_2)_2$ | | O | $CH_2CF_3$ | $OCH_2CF_3$ | 4-trifluoromethoxyphenyl |
| 1191 | $(CH_2)_3$ | | O | $CH_2CF_3$ | $OCH_2CF_3$ | 4-trifluoromethoxyphenyl |
| 1192 | $(CH_2)_4$ | | O | $CH_2CF_3$ | $OCH_2CF_3$ | 4-trifluoromethoxyphenyl |
| 1193 | $(CH_2)_5$ | | O | $CH_2CF_3$ | $OCH_2CF_3$ | 4-trifluoromethoxyphenyl |
| 1194 | 5,5-spiro[2.3]hexane | | O | $CH_2CF_3$ | $OCH_2CF_3$ | 4-trifluoromethoxyphenyl |
| 1195 | Cyclopentyl | H | O | $OCH_2CF_3$ | $OCH_2CF_3$ | 4-trifluoromethoxyphenyl |
| 1196 | $CH_2CH_3$ | H | O | $OCH_2CF_3$ | $OCH_2CF_3$ | 4-trifluoromethylphenyl |
| 1197 | $CH_2CF_3$ | H | O | $OCH_2CF_3$ | $OCH_2CF_3$ | 4-trifluoromethylphenyl |
| 1198 | $CH_2CH_2CH_3$ | H | O | $OCH_2CF_3$ | $OCH_2CF_3$ | 4-trifluoromethylphenyl |
| 1199 | $CH_2CH(CH_3)_2$ | H | O | $OCH_2CF_3$ | $OCH_2CF_3$ | 4-trifluoromethylphenyl |
| 1200 | cyclopropylmethyl | H | O | $OCH_2CF_3$ | $OCH_2CF_3$ | 4-trifluoromethylphenyl |
| 1201 | cyclobutylmethyl | H | O | $OCH_2CF_3$ | $OCH_2CF_3$ | 4-trifluoromethylphenyl |
| 1202 | $(CH_2)_2$ | | O | $CH_2$-c-Pr | $OCH_2CF_3$ | 4-trifluoromethylphenyl |
| 1203 | $(CH_2)_3$ | | O | $CH_2$-c-Pr | $OCH_2CF_3$ | 4-trifluoromethylphenyl |
| 1204 | $(CH_2)_4$ | | O | $CH_2$-c-Pr | $OCH_2CF_3$ | 4-trifluoromethylphenyl |
| 1205 | $(CH_2)_5$ | | O | $CH_2$-c-Pr | $OCH_2CF_3$ | 4-trifluoromethylphenyl |
| 1206 | 5,5-spiro[2.3]hexane | | O | $CH_2$-c-Pr | $OCH_2CF_3$ | 4-trifluoromethylphenyl |
| 1207 | Cyclopentyl | H | O | $OCH_2CF_3$ | $OCH_2CF_3$ | 4-trifluoromethylphenyl |
| 1208 | $CH_2CH_3$ | H | O | $OCH_2CF_3$ | $OCH_2CF_3$ | 4-tolyl |
| 1209 | $CH_2CF_3$ | H | O | $OCH_2CF_3$ | $OCH_2CF_3$ | 4-tolyl |
| 1210 | $CH_2CH_2CH_3$ | H | O | $OCH_2CF_3$ | $OCH_2CF_3$ | 4-tolyl |
| 1211 | $CH_2CH(CH_3)_2$ | H | O | $OCH_2CF_3$ | $OCH_2CF_3$ | 4-tolyl |
| 1212 | cyclopropylmethyl | H | O | $OCH_2CF_3$ | $OCH_2CF_3$ | 4-tolyl |
| 1213 | cyclobutylmethyl | H | O | $OCH_2CF_3$ | $OCH_2CF_3$ | 4-tolyl |
| 1214 | $(CH_2)_2$ | | O | $CH_2$-c-Pr | $OCH_2CF_3$ | 4-tolyl |
| 1215 | $(CH_2)_3$ | | O | $CH_2$-c-Pr | $OCH_2CF_3$ | 4-tolyl |
| 1216 | $(CH_2)_4$ | | O | $CH_2$-c-Pr | $OCH_2CF_3$ | 4-tolyl |
| 1217 | $(CH_2)_5$ | | O | $CH_2$-c-Pr | $OCH_2CF_3$ | 4-tolyl |
| 1218 | 5,5-spiro[2.3]hexane | | O | $CH_2$-c-Pr | $OCH_2CF_3$ | 4-tolyl |
| 1219 | Cyclopentyl | H | O | $OCH_2CF_3$ | $OCH_2CF_3$ | 4-tolyl |
| 1220 | $CH_2CH_3$ | H | O | $OCH_2CF_3$ | $OCH_2CF_3$ | 4-ethyl phenyl |
| 1221 | $CH_2CF_3$ | H | O | $OCH_2CF_3$ | $OCH_2CF_3$ | 4-ethyl phenyl |
| 1222 | $CH_2CH_2CH_3$ | H | O | $OCH_2CF_3$ | $OCH_2CF_3$ | 4-ethyl phenyl |
| 1223 | $CH_2CH(CH_3)_2$ | H | O | $OCH_2CF_3$ | $OCH_2CF_3$ | 4-ethyl phenyl |
| 1224 | cyclopropylmethyl | H | O | $OCH_2CF_3$ | $OCH_2CF_3$ | 4-ethyl phenyl |
| 1225 | cyclobutylmethyl | H | O | $OCH_2CF_3$ | $OCH_2CF_3$ | 4-ethyl phenyl |
| 1226 | $(CH_2)_2$ | | O | $CH_2$-c-Pr | $OCH_2CF_3$ | 4-ethyl phenyl |
| 1227 | $(CH_2)_3$ | | O | $CH_2$-c-Pr | $OCH_2CF_3$ | 4-ethyl phenyl |
| 1228 | $(CH_2)_4$ | | O | $CH_2$-c-Pr | $OCH_2CF_3$ | 4-ethyl phenyl |
| 1229 | $(CH_2)_5$ | | O | $CH_2$-c-Pr | $OCH_2CF_3$ | 4-ethyl phenyl |
| 1230 | 5,5-spiro[2.3]hexane | | O | $CH_2$-c-Pr | $OCH_2CF_3$ | 4-ethyl phenyl |
| 1231 | Cyclopentyl | H | O | $OCH_2CF_3$ | $OCH_2CF_3$ | 4-ethyl phenyl |
| 1232 | $CH_2CH_3$ | H | O | $OCH_2CF_3$ | $OCH_2CF_3$ | 4-isopropyl phenyl |
| 1233 | $CH_2CF_3$ | H | O | $OCH_2CF_3$ | $OCH_2CF_3$ | 4-isopropyl phenyl |
| 1234 | $CH_2CH_2CH_3$ | H | O | $OCH_2CF_3$ | $OCH_2CF_3$ | 4-isopropyl phenyl |
| 1235 | $CH_2CH(CH_3)_2$ | H | O | $OCH_2CF_3$ | $OCH_2CF_3$ | 4-isopropyl phenyl |
| 1236 | cyclopropylmethyl | H | O | $OCH_2CF_3$ | $OCH_2CF_3$ | 4-isopropyl phenyl |
| 1237 | cyclobutylmethyl | H | O | $OCH_2CF_3$ | $OCH_2CF_3$ | 4-isopropyl phenyl |

-continued

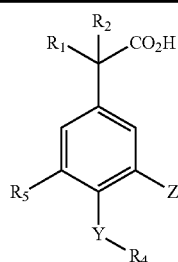

| Example | R₁ | R₂ | Y | R₄ | R₅ | Z |
|---|---|---|---|---|---|---|
| 1238 | (CH₂)₂ | | O | CH₂-c-Pr | OCH₂CF₃ | 4-isopropyl phenyl |
| 1239 | (CH₂)₃ | | O | CH₂-c-Pr | OCH₂CF₃ | 4-isopropyl phenyl |
| 1240 | (CH₂)₄ | | O | CH₂-c-Pr | OCH₂CF₃ | 4-isopropyl phenyl |
| 1241 | (CH₂)₅ | | O | CH₂-c-Pr | OCH₂CF₃ | 4-isopropyl phenyl |
| 1242 | 5,5-spiro[2.3]hexane | | O | CH₂-c-Pr | OCH₂CF₃ | 4-isopropyl phenyl |
| 1243 | Cyclopentyl | H | O | OCH₂CF₃ | OCH₂CF₃ | 4-isopropyl phenyl |
| 1244 | CH₂CH₃ | H | O | OCH₂CF₃ | OCH₂CF₃ | 4-thiomethylphenyl |
| 1245 | CH₂CF₃ | H | O | OCH₂CF₃ | OCH₂CF₃ | 4-thiomethylphenyl |
| 1246 | CH₂CH₂CH₃ | H | O | OCH₂CF₃ | OCH₂CF₃ | 4-thiomethylphenyl |
| 1247 | CH₂CH(CH₃)₂ | H | O | OCH₂CF₃ | OCH₂CF₃ | 4-thiomethylphenyl |
| 1248 | cyclopropylmethyl | H | O | OCH₂CF₃ | OCH₂CF₃ | 4-thiomethylphenyl |
| 1249 | cyclobutylmethyl | H | O | OCH₂CF₃ | OCH₂CF₃ | 4-thiomethylphenyl |
| 1250 | (CH₂)₂ | | O | CH₂-c-Pr | OCH₂CF₃ | 4-thiomethylphenyl |
| 1251 | (CH₂)₃ | | O | CH₂-c-Pr | OCH₂CF₃ | 4-thiomethylphenyl |
| 1252 | (CH₂)₄ | | O | CH₂-c-Pr | OCH₂CF₃ | 4-thiomethylphenyl |
| 1253 | (CH₂)₅ | | O | CH₂-c-Pr | OCH₂CF₃ | 4-thiomethylphenyl |
| 1254 | 5,5-spiro[2.3]hexane | | O | CH₂-c-Pr | OCH₂CF₃ | 4-thiomethylphenyl |
| 1255 | Cyclopentyl | H | O | OCH₂CF₃ | OCH₂CF₃ | 4-thiomethylphenyl |
| 1256 | CH₂CH₃ | H | O | OCH₂CF₃ | OCH₂CF₃ | 4-trifluoromethoxyphenyl |
| 1257 | CH₂CF₃ | H | O | OCH₂CF₃ | OCH₂CF₃ | 4-trifluoromethoxyphenyl |
| 1258 | CH₂CH₂CH₃ | H | O | OCH₂CF₃ | OCH₂CF₃ | 4-trifluoromethoxyphenyl |
| 1259 | CH₂CH(CH₃)₂ | H | O | OCH₂CF₃ | OCH₂CF₃ | 4-trifluoromethoxyphenyl |
| 1260 | cyclopropylmethyl | H | O | OCH₂CF₃ | OCH₂CF₃ | 4-trifluoromethoxyphenyl |
| 1261 | cyclobutylmethyl | H | O | OCH₂CF₃ | OCH₂CF₃ | 4-trifluoromethoxyphenyl |
| 1262 | (CH₂)₂ | | O | CH₂-c-Pr | OCH₂CF₃ | 4-trifluoromethoxyphenyl |
| 1263 | (CH₂)₃ | | O | CH₂-c-Pr | OCH₂CF₃ | 4-trifluoromethoxyphenyl |
| 1264 | (CH₂)₄ | | O | CH₂-c-Pr | OCH₂CF₃ | 4-trifluoromethoxyphenyl |
| 1265 | (CH₂)₅ | | O | CH₂-c-Pr | OCH₂CF₃ | 4-trifluoromethoxyphenyl |
| 1266 | 5,5-spiro[2.3]hexane | | O | CH₂-c-Pr | OCH₂CF₃ | 4-trifluoromethoxyphenyl |
| 1267 | Cyclopentyl | H | O | OCH₂CF₃ | OCH₂CF₃ | 4-trifluoromethoxyphenyl |
| 1269 | (CH₂)₃ | | O | CH₂CF₃ | Cl | 4-trifluoromethylphenyl |
| 1270 | (CH₂)₅ | | O | CH₂CF₃ | Cl | 4-trifluoromethylphenyl |
| 1271 | 5,5-spiro[2.3]hexane | | O | CH₂CF₃ | Cl | 4-trifluoromethylphenyl |
| 1273 | CH₂CH₃ | H | O | CH₂CF₃ | Cl | 4-tolyl |
| 1274 | CH₂CF₃ | H | O | CH₂CF₃ | Cl | 4-tolyl |
| 1275 | CH₂CH₂CH₃ | H | O | CH₂CF₃ | Cl | 4-tolyl |
| 1276 | CH₂CH(CH₃)₂ | H | O | CH₂CF₃ | Cl | 4-tolyl |
| 1277 | cyclopropylmethyl | H | O | CH₂CF₃ | Cl | 4-tolyl |
| 1278 | cyclobutylmethyl | H | O | CH₂CF₃ | Cl | 4-tolyl |
| 1279 | (CH₂)₂ | | O | CH₂CF₃ | Cl | 4-tolyl |
| 1280 | (CH₂)₃ | | O | CH₂CF₃ | Cl | 4-tolyl |
| 1281 | (CH₂)₄ | | O | CH₂CF₃ | Cl | 4-tolyl |
| 1282 | (CH₂)₅ | | O | CH₂CF₃ | Cl | 4-tolyl |
| 1283 | 5,5-spiro[2.3]hexane | | O | CH₂CF₃ | Cl | 4-tolyl |
| 1284 | Cyclopentyl | H | O | CH₂CF₃ | Cl | 4-tolyl |
| 1285 | CH₂CH₃ | H | O | CH₂CF₃ | Cl | 4-ethyl phenyl |
| 1286 | CH₂CF₃ | H | O | CH₂CF₃ | Cl | 4-ethyl phenyl |
| 1287 | CH₂CH₂CH₃ | H | O | CH₂CF₃ | Cl | 4-ethyl phenyl |
| 1288 | CH₂CH(CH₃)₂ | H | O | CH₂CF₃ | Cl | 4-ethyl phenyl |
| 1289 | cyclopropylmethyl | H | O | CH₂CF₃ | Cl | 4-ethyl phenyl |
| 1290 | cyclobutylmethyl | | O | CH₂CF₃ | Cl | 4-ethyl phenyl |
| 1291 | (CH₂)₂ | | O | CH₂CF₃ | Cl | 4-ethyl phenyl |
| 1292 | (CH₂)₃ | | O | CH₂CF₃ | Cl | 4-ethyl phenyl |
| 1293 | (CH₂)₄ | | O | CH₂CF₃ | Cl | 4-ethyl phenyl |
| 1294 | (CH₂)₅ | | O | CH₂CF₃ | Cl | 4-ethyl phenyl |
| 1295 | 5,5-spiro[2.3]hexane | | O | CH₂CF₃ | Cl | 4-ethyl phenyl |
| 1296 | Cyclopentyl | H | O | CH₂CF₃ | Cl | 4-ethyl phenyl |
| 1297 | CH₂CH₃ | H | O | CH₂CF₃ | Cl | 4-isopropyl phenyl |
| 1298 | CH₂CF₃ | H | O | CH₂CF₃ | Cl | 4-isopropyl phenyl |
| 1299 | CH₂CH₂CH₃ | H | O | CH₂CF₃ | Cl | 4-isopropyl phenyl |
| 1303 | (CH₂)₂ | | O | CH₂CF₃ | Cl | 4-isopropyl phenyl |
| 1304 | (CH₂)₃ | | O | CH₂CF₃ | Cl | 4-isopropyl phenyl |
| 1305 | (CH₂)₄ | | O | CH₂CF₃ | Cl | 4-isopropyl phenyl |
| 1306 | (CH₂)₅ | | O | CH₂CF₃ | Cl | 4-isopropyl phenyl |

-continued

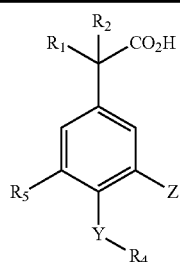

| Example | $R_1$ | $R_2$ | Y | $R_4$ | $R_5$ | Z |
|---|---|---|---|---|---|---|
| 1307 | 5,5-spiro[2.3]hexane | | O | $CH_2CF_3$ | Cl | 4-isopropyl phenyl |
| 1309 | $CH_2CH_3$ | H | O | $CH_2CF_3$ | Cl | 4-thiomethylphenyl |
| 1310 | $CH_2CF_3$ | H | O | $CH_2CF_3$ | Cl | 4-thiomethylphenyl |
| 1311 | $CH_2CH_2CH_3$ | H | O | $CH_2CF_3$ | Cl | 4-thiomethylphenyl |
| 1315 | $(CH_2)_2$ | | O | $CH_2CF_3$ | Cl | 4-thiomethylphenyl |
| 1316 | $(CH_2)_3$ | | O | $CH_2CF_3$ | Cl | 4-thiomethylphenyl |
| 1317 | $(CH_2)_4$ | | O | $CH_2CF_3$ | Cl | 4-thiomethylphenyl |
| 1318 | $(CH_2)_5$ | | O | $CH_2CF_3$ | Cl | 4-thiomethylphenyl |
| 1319 | 5,5-spiro[2.3]hexane | | O | $CH_2CF_3$ | Cl | 4-thiomethylphenyl |
| 1321 | $CH_2CH_3$ | H | O | $CH_2CF_3$ | Cl | 4-trifluoromethoxyphenyl |
| 1322 | $CH_2CF_3$ | H | O | $CH_2CF_3$ | Cl | 4-trifluoromethoxyphenyl |
| 1323 | $CH_2CH_2CH_3$ | H | O | $CH_2CF_3$ | Cl | 4-trifluoromethoxyphenyl |
| 1324 | $CH_2CH(CH_3)_2$ | H | O | $CH_2CF_3$ | Cl | 4-trifluoromethoxyphenyl |
| 1325 | cyclopropylmethyl | H | O | $CH_2CF_3$ | Cl | 4-trifluoromethoxyphenyl |
| 1326 | cyclobutylmethyl | H | O | $CH_2CF_3$ | Cl | 4-trifluoromethoxyphenyl |
| 1327 | $(CH_2)_2$ | | O | $CH_2CF_3$ | Cl | 4-trifluoromethoxyphenyl |
| 1328 | $(CH_2)_3$ | | O | $CH_2CF_3$ | Cl | 4-trifluoromethoxyphenyl |
| 1329 | $(CH_2)_4$ | | O | $CH_2CF_3$ | Cl | 4-trifluoromethoxyphenyl |
| 1330 | $(CH_2)_5$ | | O | $CH_2CF_3$ | Cl | 4-trifluoromethoxyphenyl |
| 1331 | 5,5-spiro[2.3]hexane | | O | $CH_2CF_3$ | Cl | 4-trifluoromethoxyphenyl |
| 1332 | Cyclopentyl | H | O | $CH_2CF_3$ | Cl | 4-trifluoromethoxyphenyl |
| 1333 | cyclobutylmethyl | H | O | $CH_2$-c-Pr | Cl | 4-trifluoromethylphenyl |
| 1334 | $(CH_2)_3$ | | O | $CH_2$-c-Pr | Cl | 4-trifluoromethylphenyl |
| 1335 | $(CH_2)_5$ | | O | $CH_2$-c-Pr | Cl | 4-trifluoromethylphenyl |
| 1336 | 5,5-spiro[2.3]hexane | | O | $CH_2$-c-Pr | Cl | 4-trifluoromethylphenyl |
| 1337 | Cyclopentyl | H | O | $CH_2$-c-Pr | Cl | 4-trifluoromethylphenyl |
| 1338 | $CH_2CH_3$ | H | O | $CH_2$-c-Pr | Cl | 4-tolyl |
| 1339 | $CH_2CF_3$ | H | O | $CH_2$-c-Pr | Cl | 4-tolyl |
| 1340 | $CH_2CH_2CH_3$ | H | O | $CH_2$-c-Pr | Cl | 4-tolyl |
| 1341 | $CH_2CH(CH_3)_2$ | H | O | $CH_2$-c-Pr | Cl | 4-tolyl |
| 1342 | cyclopropylmethyl | H | O | $CH_2$-c-Pr | Cl | 4-tolyl |
| 1343 | cyclobutylmethyl | H | O | $CH_2$-c-Pr | Cl | 4-tolyl |
| 1344 | $(CH_2)_2$ | | O | $CH_2$-c-Pr | Cl | 4-tolyl |
| 1345 | $(CH_2)_3$ | | O | $CH_2$-c-Pr | Cl | 4-tolyl |
| 1346 | $(CH_2)_4$ | | O | $CH_2$-c-Pr | Cl | 4-tolyl |
| 1347 | $(CH_2)_5$ | | O | $CH_2$-c-Pr | Cl | 4-tolyl |
| 1348 | 5,5-spiro[2.3]hexane | | O | $CH_2$-c-Pr | Cl | 4-tolyl |
| 1349 | Cyclopentyl | H | O | $CH_2$-c-Pr | Cl | 4-tolyl |
| 1350 | $CH_2CH_3$ | H | O | $CH_2$-c-Pr | Cl | 4-ethyl phenyl |
| 1351 | $CH_2CF_3$ | H | O | $CH_2$-c-Pr | Cl | 4-ethyl phenyl |
| 1352 | $CH_2CH_2CH_3$ | H | O | $CH_2$-c-Pr | Cl | 4-ethyl phenyl |
| 1353 | $CH_2CH(CH_3)_2$ | H | O | $CH_2$-c-Pr | Cl | 4-ethyl phenyl |
| 1354 | cyclopropylmethyl | H | O | $CH_2$-c-Pr | Cl | 4-ethyl phenyl |
| 1355 | cyclobutylmethyl | H | O | $CH_2$-c-Pr | Cl | 4-ethyl phenyl |
| 1356 | $(CH_2)_2$ | | O | $CH_2$-c-Pr | Cl | 4-ethyl phenyl |
| 1357 | $(CH_2)_3$ | | O | $CH_2$-c-Pr | Cl | 4-ethyl phenyl |
| 1358 | $(CH_2)_4$ | | O | $CH_2$-c-Pr | Cl | 4-ethyl phenyl |
| 1359 | $(CH_2)_5$ | | O | $CH_2$-c-Pr | Cl | 4-ethyl phenyl |
| 1360 | 5,5-spiro[2.3]hexane | | O | $CH_2$-c-Pr | Cl | 4-ethyl phenyl |
| 1361 | Cyclopentyl | H | O | $CH_2$-c-Pr | Cl | 4-ethyl phenyl |
| 1362 | $CH_2CH_3$ | H | O | $CH_2$-c-Pr | Cl | 4-isopropyl phenyl |
| 1363 | $CH_2CF_3$ | H | O | $CH_2$-c-Pr | Cl | 4-isopropyl phenyl |
| 1364 | $CH_2CH_2CH_3$ | H | O | $CH_2$-c-Pr | Cl | 4-isopropyl phenyl |
| 1365 | $CH_2CH(CH_3)_2$ | H | O | $CH_2$-c-Pr | Cl | 4-isopropyl phenyl |
| 1366 | cyclopropylmethyl | H | O | $CH_2$-c-Pr | Cl | 4-isopropyl phenyl |
| 1367 | cyclobutylmethyl | H | O | $CH_2$-c-Pr | Cl | 4-isopropyl phenyl |
| 1368 | $(CH_2)_2$ | | O | $CH_2$-c-Pr | Cl | 4-isopropyl phenyl |
| 1369 | $(CH_2)_3$ | | O | $CH_2$-c-Pr | Cl | 4-isopropyl phenyl |
| 1370 | $(CH_2)_4$ | | O | $CH_2$-c-Pr | Cl | 4-isopropyl phenyl |
| 1371 | $(CH_2)_5$ | | O | $CH_2$-c-Pr | Cl | 4-isopropyl phenyl |
| 1372 | 5,5-spiro[2.3]hexane | | O | $CH_2$-c-Pr | Cl | 4-isopropyl phenyl |
| 1373 | Cyclopentyl | H | O | $CH_2$-c-Pr | Cl | 4-isopropyl phenyl |
| 1374 | $CH_2CH_3$ | H | O | $CH_2$-c-Pr | Cl | 4-thiomethylphenyl |
| 1375 | $CH_2CF_3$ | H | O | $CH_2$-c-Pr | Cl | 4-thiomethylphenyl |

-continued

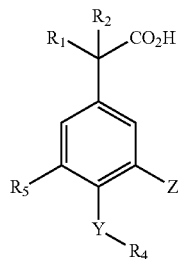

| Example | R$_1$ | R$_2$ | Y | R$_4$ | R$_5$ | Z |
|---|---|---|---|---|---|---|
| 1376 | CH$_2$CH$_2$CH$_3$ | H | O | CH$_2$-c-Pr | Cl | 4-thiomethylphenyl |
| 1377 | CH$_2$CH(CH$_3$)$_2$ | H | O | CH$_2$-c-Pr | Cl | 4-thiomethylphenyl |
| 1378 | cyclopropylmethyl | H | O | CH$_2$-c-Pr | Cl | 4-thiomethylphenyl |
| 1379 | cyclobutylmethyl | H | O | CH$_2$-c-Pr | Cl | 4-thiomethylphenyl |
| 1380 | (CH$_2$)$_2$ | | O | CH$_2$-c-Pr | Cl | 4-thiomethylphenyl |
| 1381 | (CH$_2$)$_3$ | | O | CH$_2$-c-Pr | Cl | 4-thiomethylphenyl |
| 1382 | (CH$_2$)$_4$ | | O | CH$_2$-c-Pr | Cl | 4-thiomethylphenyl |
| 1383 | (CH$_2$)$_5$ | | O | CH$_2$-c-Pr | Cl | 4-thiomethylphenyl |
| 1384 | 5,5-spiro[2.3]hexane | | O | CH$_2$-c-Pr | Cl | 4-thiomethylphenyl |
| 1385 | Cyclopentyl | H | O | CH$_2$-c-Pr | Cl | 4-thiomethylphenyl |
| 1386 | CH$_2$CH$_3$ | H | O | CH$_2$-c-Pr | Cl | 4-trifluoromethoxyphenyl |
| 1387 | CH$_2$CF$_3$ | H | O | CH$_2$-c-Pr | Cl | 4-trifluoromethoxyphenyl |
| 1388 | CH$_2$CH$_2$CH$_3$ | H | O | CH$_2$-c-Pr | Cl | 4-trifluoromethoxyphenyl |
| 1389 | CH$_2$CH(CH$_3$)$_2$ | H | O | CH$_2$-c-Pr | Cl | 4-trifluoromethoxyphenyl |
| 1390 | cyclopropylmethyl | H | O | CH$_2$-c-Pr | Cl | 4-trifluoromethoxyphenyl |
| 1391 | cyclobutylmethyl | H | O | CH$_2$-c-Pr | Cl | 4-trifluoromethoxyphenyl |
| 1392 | (CH$_2$)$_2$ | | O | CH$_2$-c-Pr | Cl | 4-trifluoromethoxyphenyl |
| 1393 | (CH$_2$)$_3$ | | O | CH$_2$-c-Pr | Cl | 4-trifluoromethoxyphenyl |
| 1394 | (CH$_2$)$_4$ | | O | CH$_2$-c-Pr | Cl | 4-trifluoromethoxyphenyl |
| 1395 | (CH$_2$)$_5$ | | O | CH$_2$-c-Pr | Cl | 4-trifluoromethoxyphenyl |
| 1396 | 5,5-spiro[2.3]hexane | | O | CH$_2$-c-Pr | Cl | 4-trifluoromethoxyphenyl |
| 1397 | Cyclopentyl | H | O | CH$_2$-c-Pr | Cl | 4-trifluoromethoxyphenyl |
| 1398 | CH$_2$CH$_3$ | H | O | CH$_2$CF$_3$ | OCH$_2$CF$_3$ | 4-trifluoromethylphenyl |
| 1399 | CH$_2$CF$_3$ | H | O | CH$_2$CF$_3$ | OCH$_2$CF$_3$ | 4-trifluoromethylphenyl |
| 1400 | CH$_2$CH$_2$CH$_3$ | H | O | CH$_2$CF$_3$ | OCH$_2$CF$_3$ | 4-trifluoromethylphenyl |
| 1401 | CH$_2$CH(CH$_3$)$_2$ | H | O | CH$_2$CF$_3$ | OCH$_2$CF$_3$ | 4-trifluoromethylphenyl |
| 1402 | cyclopropylmethyl | H | O | CH$_2$CF$_3$ | OCH$_2$CF$_3$ | 4-trifluoromethylphenyl |
| 1403 | cyclobutylmethyl | H | O | CH$_2$CF$_3$ | OCH$_2$CF$_3$ | 4-trifluoromethylphenyl |
| 1404 | (CH$_2$)$_2$ | | O | CH$_2$CF$_3$ | OCH$_2$CF$_3$ | 4-trifluoromethylphenyl |
| 1405 | (CH$_2$)$_3$ | | O | CH$_2$CF$_3$ | OCH$_2$CF$_3$ | 4-trifluoromethylphenyl |
| 1406 | (CH$_2$)$_4$ | | O | CH$_2$CF$_3$ | OCH$_2$CF$_3$ | 4-trifluoromethylphenyl |
| 1407 | (CH$_2$)$_5$ | | O | CH$_2$CF$_3$ | OCH$_2$CF$_3$ | 4-trifluoromethylphenyl |
| 1408 | 5,5-spiro[2.3]hexane | | O | CH$_2$CF$_3$ | OCH$_2$CF$_3$ | 4-trifluoromethylphenyl |
| 1409 | Cyclopentyl | H | O | CH$_2$CF$_3$ | OCH$_2$CF$_3$ | 4-trifluoromethylphenyl |
| 1410 | CH$_2$CH$_3$ | H | O | CH$_2$CF$_3$ | OCH$_2$CF$_3$ | 4-tolyl |
| 1411 | CH$_2$CF$_3$ | H | O | CH$_2$CF$_3$ | OCH$_2$CF$_3$ | 4-tolyl |
| 1412 | CH$_2$CH$_2$CH$_3$ | H | O | CH$_2$CF$_3$ | OCH$_2$CF$_3$ | 4-tolyl |
| 1413 | CH$_2$CH(CH$_3$)$_2$ | H | O | CH$_2$CF$_3$ | OCH$_2$CF$_3$ | 4-tolyl |
| 1414 | cyclopropylmethyl | H | O | CH$_2$CF$_3$ | OCH$_2$CF$_3$ | 4-tolyl |
| 1415 | cyclobutylmethyl | H | O | CH$_2$CF$_3$ | OCH$_2$CF$_3$ | 4-tolyl |
| 1416 | (CH$_2$)$_2$ | | O | CH$_2$CF$_3$ | OCH$_2$CF$_3$ | 4-tolyl |
| 1417 | (CH$_2$)$_3$ | | O | CH$_2$CF$_3$ | OCH$_2$CF$_3$ | 4-tolyl |
| 1418 | (CH$_2$)$_4$ | | O | CH$_2$CF$_3$ | OCH$_2$CF$_3$ | 4-tolyl |
| 1419 | (CH$_2$)$_5$ | | O | CH$_2$CF$_3$ | OCH$_2$CF$_3$ | 4-tolyl |
| 1420 | 5,5-spiro[2.3]hexane | | O | CH$_2$CF$_3$ | OCH$_2$CF$_3$ | 4-tolyl |
| 1421 | Cyclopentyl | H | O | CH$_2$CF$_3$ | OCH$_2$CF$_3$ | 4-tolyl |
| 1422 | CH$_2$CH$_3$ | H | O | CH$_2$CF$_3$ | OCH$_2$CF$_3$ | 4-ethyl phenyl |
| 1423 | CH$_2$CF$_3$ | H | O | CH$_2$CF$_3$ | OCH$_2$CF$_3$ | 4-ethyl phenyl |
| 1424 | CH$_2$CH$_2$CH$_3$ | H | O | CH$_2$CF$_3$ | OCH$_2$CF$_3$ | 4-ethyl phenyl |
| 1425 | CH$_2$CH(CH$_3$)$_2$ | H | O | CH$_2$CF$_3$ | OCH$_2$CF$_3$ | 4-ethyl phenyl |
| 1426 | cyclopropylmethyl | H | O | CH$_2$CF$_3$ | OCH$_2$CF$_3$ | 4-ethyl phenyl |
| 1427 | cyclobutylmethyl | H | O | CH$_2$CF$_3$ | OCH$_2$CF$_3$ | 4-ethyl phenyl |
| 1428 | (CH$_2$)$_2$ | | O | CH$_2$CF$_3$ | OCH$_2$CF$_3$ | 4-ethyl phenyl |
| 1429 | (CH$_2$)$_3$ | | O | CH$_2$CF$_3$ | OCH$_2$CF$_3$ | 4-ethyl phenyl |
| 1430 | (CH$_2$)$_4$ | | O | CH$_2$CF$_3$ | OCH$_2$CF$_3$ | 4-ethyl phenyl |
| 1431 | (CH$_2$)$_5$ | | O | CH$_2$CF$_3$ | OCH$_2$CF$_3$ | 4-ethyl phenyl |
| 1432 | 5,5-spiro[2.3]hexane | | O | CH$_2$CF$_3$ | OCH$_2$CF$_3$ | 4-ethyl phenyl |
| 1433 | Cyclopentyl | H | O | CH$_2$CF$_3$ | OCH$_2$CF$_3$ | 4-ethyl phenyl |
| 1434 | CH$_2$CH$_3$ | H | O | CH$_2$CF$_3$ | OCH$_2$CF$_3$ | 4-isopropyl phenyl |
| 1435 | CH$_2$CF$_3$ | H | O | CH$_2$CF$_3$ | OCH$_2$CF$_3$ | 4-isopropyl phenyl |
| 1436 | CH$_2$CH$_2$CH$_3$ | H | O | CH$_2$CF$_3$ | OCH$_2$CF$_3$ | 4-isopropyl phenyl |
| 1437 | CH$_2$CH(CH$_3$)$_2$ | H | O | CH$_2$CF$_3$ | OCH$_2$CF$_3$ | 4-isopropyl phenyl |
| 1438 | cyclopropylmethyl | H | O | CH$_2$CF$_3$ | OCH$_2$CF$_3$ | 4-isopropyl phenyl |
| 1439 | cyclobutylmethyl | H | O | CH$_2$CF$_3$ | OCH$_2$CF$_3$ | 4-isopropyl phenyl |

-continued

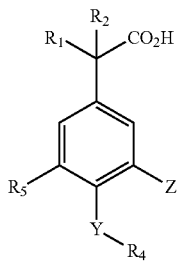

| Example | R$_1$ | R$_2$ | Y | R$_4$ | R$_5$ | Z |
|---|---|---|---|---|---|---|
| 1440 | (CH$_2$)$_2$ | | O | CH$_2$CF$_3$ | OCH$_2$CF$_3$ | 4-isopropyl phenyl |
| 1441 | (CH$_2$)$_3$ | | O | CH$_2$CF$_3$ | OCH$_2$CF$_3$ | 4-isopropyl phenyl |
| 1442 | (CH$_2$)$_4$ | | O | CH$_2$CF$_3$ | OCH$_2$CF$_3$ | 4-isopropyl phenyl |
| 1443 | (CH$_2$)$_5$ | | O | CH$_2$CF$_3$ | OCH$_2$CF$_3$ | 4-isopropyl phenyl |
| 1444 | 5,5-spiro[2.3]hexane | | O | CH$_2$CF$_3$ | OCH$_2$CF$_3$ | 4-isopropyl phenyl |
| 1445 | Cyclopentyl | H | O | CH$_2$CF$_3$ | OCH$_2$CF$_3$ | 4-isopropyl phenyl |
| 1446 | CH$_2$CH$_3$ | H | O | CH$_2$CF$_3$ | OCH$_2$CF$_3$ | 4-thiomethylphenyl |
| 1447 | CH$_2$CF$_3$ | H | O | CH$_2$CF$_3$ | OCH$_2$CF$_3$ | 4-thiomethylphenyl |
| 1448 | CH$_2$CH$_2$CH$_3$ | H | O | CH$_2$CF$_3$ | OCH$_2$CF$_3$ | 4-thiomethylphenyl |
| 1449 | CH$_2$CH(CH$_3$)$_2$ | H | O | CH$_2$CF$_3$ | OCH$_2$CF$_3$ | 4-thiomethylphenyl |
| 1450 | cyclopropylmethyl | H | O | CH$_2$CF$_3$ | OCH$_2$CF$_3$ | 4-thiomethylphenyl |
| 1451 | cyclobutylmethyl | H | O | CH$_2$CF$_3$ | OCH$_2$CF$_3$ | 4-thiomethylphenyl |
| 1452 | (CH$_2$)$_2$ | | O | CH$_2$CF$_3$ | OCH$_2$CF$_3$ | 4-thiomethylphenyl |
| 1453 | (CH$_2$)$_3$ | | O | CH$_2$CF$_3$ | OCH$_2$CF$_3$ | 4-thiomethylphenyl |
| 1454 | (CH$_2$)$_4$ | | O | CH$_2$CF$_3$ | OCH$_2$CF$_3$ | 4-thiomethylphenyl |
| 1455 | (CH$_2$)$_5$ | | O | CH$_2$CF$_3$ | OCH$_2$CF$_3$ | 4-thiomethylphenyl |
| 1456 | 5,5-spiro[2.3]hexane | | O | CH$_2$CF$_3$ | OCH$_2$CF$_3$ | 4-thiomethylphenyl |
| 1457 | Cyclopentyl | H | O | CH$_2$CF$_3$ | OCH$_2$CF$_3$ | 4-thiomethylphenyl |
| 1458 | CH$_2$CH$_3$ | H | O | CH$_2$CF$_3$ | OCH$_2$CF$_3$ | 4-trifluoromethoxyphenyl |
| 1459 | CH$_2$CF$_3$ | H | O | CH$_2$CF$_3$ | OCH$_2$CF$_3$ | 4-trifluoromethoxyphenyl |
| 1460 | CH$_2$CH$_2$CH$_3$ | H | O | CH$_2$CF$_3$ | OCH$_2$CF$_3$ | 4-trifluoromethoxyphenyl |
| 1461 | CH$_2$CH(CH$_3$)$_2$ | H | O | CH$_2$CF$_3$ | OCH$_2$CF$_3$ | 4-trifluoromethoxyphenyl |
| 1462 | cyclopropylmethyl | H | O | CH$_2$CF$_3$ | OCH$_2$CF$_3$ | 4-trifluoromethoxyphenyl |
| 1463 | cyclobutylmethyl | H | O | CH$_2$CF$_3$ | OCH$_2$CF$_3$ | 4-trifluoromethoxyphenyl |
| 1464 | (CH$_2$)$_2$ | | O | CH$_2$CF$_3$ | OCH$_2$CF$_3$ | 4-trifluoromethoxyphenyl |
| 1465 | (CH$_2$)$_3$ | | O | CH$_2$CF$_3$ | OCH$_2$CF$_3$ | 4-trifluoromethoxyphenyl |
| 1466 | (CH$_2$)$_4$ | | O | CH$_2$CF$_3$ | OCH$_2$CF$_3$ | 4-trifluoromethoxyphenyl |
| 1467 | (CH$_2$)$_5$ | | O | CH$_2$CF$_3$ | OCH$_2$CF$_3$ | 4-trifluoromethoxyphenyl |
| 1468 | 5,5-spiro[2.3]hexane | | O | CH$_2$CF$_3$ | OCH$_2$CF$_3$ | 4-trifluoromethoxyphenyl |
| 1469 | Cyclopentyl | H | O | CH$_2$CF$_3$ | OCH$_2$CF$_3$ | 4-trifluoromethoxyphenyl |
| 1470 | CH$_2$CH$_3$ | H | O | CH$_2$-c-Pr | OCH$_2$CF$_3$ | 4-trifluoromethylphenyl |
| 1471 | CH$_2$CF$_3$ | H | O | CH$_2$-c-Pr | OCH$_2$CF$_3$ | 4-trifluoromethylphenyl |
| 1472 | CH$_2$CH$_2$CH$_3$ | H | O | CH$_2$-c-Pr | OCH$_2$CF$_3$ | 4-trifluoromethylphenyl |
| 1473 | CH$_2$CH(CH$_3$)$_2$ | H | O | CH$_2$-c-Pr | OCH$_2$CF$_3$ | 4-trifluoromethylphenyl |
| 1474 | cyclopropylmethyl | H | O | CH$_2$-c-Pr | OCH$_2$CF$_3$ | 4-trifluoromethylphenyl |
| 1475 | cyclobutylmethyl | H | O | CH$_2$-c-Pr | OCH$_2$CF$_3$ | 4-trifluoromethylphenyl |
| 1476 | (CH$_2$)$_2$ | | O | CH$_2$-c-Pr | OCH$_2$CF$_3$ | 4-trifluoromethylphenyl |
| 1477 | (CH$_2$)$_3$ | | O | CH$_2$-c-Pr | OCH$_2$CF$_3$ | 4-trifluoromethylphenyl |
| 1478 | (CH$_2$)$_4$ | | O | CH$_2$-c-Pr | OCH$_2$CF$_3$ | 4-trifluoromethylphenyl |
| 1479 | (CH$_2$)$_5$ | | O | CH$_2$-c-Pr | OCH$_2$CF$_3$ | 4-trifluoromethylphenyl |
| 1480 | 5,5-spiro[2.3]hexane | | O | CH$_2$-c-Pr | OCH$_2$CF$_3$ | 4-trifluoromethylphenyl |
| 1481 | Cyclopentyl | H | O | CH$_2$-c-Pr | OCH$_2$CF$_3$ | 4-trifluoromethylphenyl |
| 1482 | CH$_2$CH$_3$ | H | O | CH$_2$-c-Pr | OCH$_2$CF$_3$ | 4-tolyl |
| 1483 | CH$_2$CF$_3$ | H | O | CH$_2$-c-Pr | OCH$_2$CF$_3$ | 4-tolyl |
| 1484 | CH$_2$CH$_2$CH$_3$ | H | O | CH$_2$-c-Pr | OCH$_2$CF$_3$ | 4-tolyl |
| 1485 | CH$_2$CH(CH$_3$)$_2$ | H | O | CH$_2$-c-Pr | OCH$_2$CF$_3$ | 4-tolyl |
| 1486 | cyclopropylmethyl | H | O | CH$_2$-c-Pr | OCH$_2$CF$_3$ | 4-tolyl |
| 1487 | cyclobutylmethyl | H | O | CH$_2$-c-Pr | OCH$_2$CF$_3$ | 4-tolyl |
| 1488 | (CH$_2$)$_2$ | | O | CH$_2$-c-Pr | OCH$_2$CF$_3$ | 4-tolyl |
| 1489 | (CH$_2$)$_3$ | | O | CH$_2$-c-Pr | OCH$_2$CF$_3$ | 4-tolyl |
| 1490 | (CH$_2$)$_4$ | | O | CH$_2$-c-Pr | OCH$_2$CF$_3$ | 4-tolyl |
| 1491 | (CH$_2$)$_5$ | | O | CH$_2$-c-Pr | OCH$_2$CF$_3$ | 4-tolyl |
| 1492 | 5,5-spiro[2.3]hexane | | O | CH$_2$-c-Pr | OCH$_2$CF$_3$ | 4-tolyl |
| 1493 | Cyclopentyl | H | O | CH$_2$-c-Pr | OCH$_2$CF$_3$ | 4-tolyl |
| 1494 | CH$_2$CH$_3$ | H | O | CH$_2$-c-Pr | OCH$_2$CF$_3$ | 4-ethyl phenyl |
| 1495 | CH$_2$CF$_3$ | H | O | CH$_2$-c-Pr | OCH$_2$CF$_3$ | 4-ethyl phenyl |
| 1496 | CH$_2$CH$_2$CH$_3$ | H | O | CH$_2$-c-Pr | OCH$_2$CF$_3$ | 4-ethyl phenyl |
| 1497 | CH$_2$CH(CH$_3$)$_2$ | H | O | CH$_2$-c-Pr | OCH$_2$CF$_3$ | 4-ethyl phenyl |
| 1498 | cyclopropylmethyl | H | O | CH$_2$-c-Pr | OCH$_2$CF$_3$ | 4-ethyl phenyl |
| 1499 | cyclobutylmethyl | H | O | CH$_2$-c-Pr | OCH$_2$CF$_3$ | 4-ethyl phenyl |
| 1500 | (CH$_2$)$_2$ | | O | CH$_2$-c-Pr | OCH$_2$CF$_3$ | 4-ethyl phenyl |
| 1501 | (CH$_2$)$_3$ | | O | CH$_2$-c-Pr | OCH$_2$CF$_3$ | 4-ethyl phenyl |
| 1502 | (CH$_2$)$_4$ | | O | CH$_2$-c-Pr | OCH$_2$CF$_3$ | 4-ethyl phenyl |
| 1503 | (CH$_2$)$_5$ | | O | CH$_2$-c-Pr | OCH$_2$CF$_3$ | 4-ethyl phenyl |

-continued

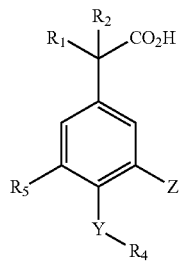

| Example | R₁ | R₂ | Y | R₄ | R₅ | Z |
|---|---|---|---|---|---|---|
| 1504 | 5,5-spiro[2.3]hexane | | O | CH₂-c-Pr | OCH₂CF₃ | 4-ethyl phenyl |
| 1505 | Cyclopentyl | H | O | CH₂-c-Pr | OCH₂CF₃ | 4-ethyl phenyl |
| 1506 | CH₂CH₃ | H | O | CH₂-c-Pr | OCH₂CF₃ | 4-isopropyl phenyl |
| 1507 | CH₂CF₃ | H | O | CH₂-c-Pr | OCH₂CF₃ | 4-isopropyl phenyl |
| 1508 | CH₂CH₂CH₃ | H | O | CH₂-c-Pr | OCH₂CF₃ | 4-isopropyl phenyl |
| 1509 | CH₂CH(CH₃)₂ | H | O | CH₂-c-Pr | OCH₂CF₃ | 4-isopropyl phenyl |
| 1510 | cyclopropylmethyl | H | O | CH₂-c-Pr | OCH₂CF₃ | 4-isopropyl phenyl |
| 1511 | cyclobutylmethyl | H | O | CH₂-c-Pr | OCH₂CF₃ | 4-isopropyl phenyl |
| 1512 | (CH₂)₂ | | O | CH₂-c-Pr | OCH₂CF₃ | 4-isopropyl phenyl |
| 1513 | (CH₂)₃ | | O | CH₂-c-Pr | OCH₂CF₃ | 4-isopropyl phenyl |
| 1514 | (CH₂)₄ | | O | CH₂-c-Pr | OCH₂CF₃ | 4-isopropyl phenyl |
| 1515 | (CH₂)₅ | | O | CH₂-c-Pr | OCH₂CF₃ | 4-isopropyl phenyl |
| 1516 | 5,5-spiro[2.3]hexane | | O | CH₂-c-Pr | OCH₂CF₃ | 4-isopropyl phenyl |
| 1517 | Cyclopentyl | H | O | CH₂-c-Pr | OCH₂CF₃ | 4-isopropyl phenyl |
| 1518 | CH₂CH₃ | H | O | CH₂-c-Pr | OCH₂CF₃ | 4-thiomethylphenyl |
| 1519 | CH₂CF₃ | H | O | CH₂-c-Pr | OCH₂CF₃ | 4-thiomethylphenyl |
| 1520 | CH₂CH₂CH₃ | H | O | CH₂-c-Pr | OCH₂CF₃ | 4-thiomethylphenyl |
| 1521 | CH₂CH(CH₃)₂ | H | O | CH₂-c-Pr | OCH₂CF₃ | 4-thiomethylphenyl |
| 1522 | cyclopropylmethyl | H | O | CH₂-c-Pr | OCH₂CF₃ | 4-thiomethylphenyl |
| 1523 | cyclobutylmethyl | H | O | CH₂-c-Pr | OCH₂CF₃ | 4-thiomethylphenyl |
| 1524 | (CH₂)₂ | | O | CH₂-c-Pr | OCH₂CF₃ | 4-thiomethylphenyl |
| 1525 | (CH₂)₃ | | O | CH₂-c-Pr | OCH₂CF₃ | 4-thiomethylphenyl |
| 1526 | (CH₂)₄ | | O | CH₂-c-Pr | OCH₂CF₃ | 4-thiomethylphenyl |
| 1527 | (CH₂)₅ | | O | CH₂-c-Pr | OCH₂CF₃ | 4-thiomethylphenyl |
| 1528 | 5,5-spiro[2.3]hexane | | O | CH₂-c-Pr | OCH₂CF₃ | 4-thiomethylphenyl |
| 1529 | Cyclopentyl | H | O | CH₂-c-Pr | OCH₂CF₃ | 4-thiomethylphenyl |
| 1529a | CH₂CH₃ | H | O | CH₂-c-Pr | OCH₂CF₃ | 4-trifluoromethoxyphenyl |
| 1530 | CH₂CF₃ | H | O | CH₂-c-Pr | OCH₂CF₃ | 4-trifluoromethoxyphenyl |
| 1531 | CH₂CH₂CH₃ | H | O | CH₂-c-Pr | OCH₂CF₃ | 4-trifluoromethoxyphenyl |
| 1532 | CH₂CH(CH₃)₂ | H | O | CH₂-c-Pr | OCH₂CF₃ | 4-trifluoromethoxyphenyl |
| 1533 | cyclopropylmethyl | H | O | CH₂-c-Pr | OCH₂CF₃ | 4-trifluoromethoxyphenyl |
| 1534 | cyclobutylmethyl | H | O | CH₂-c-Pr | OCH₂CF₃ | 4-trifluoromethoxyphenyl |
| 1535 | (CH₂)₂ | | O | CH₂-c-Pr | OCH₂CF₃ | 4-trifluoromethoxyphenyl |
| 1536 | (CH₂)₃ | | O | CH₂-c-Pr | OCH₂CF₃ | 4-trifluoromethoxyphenyl |
| 1537 | (CH₂)₄ | | O | CH₂-c-Pr | OCH₂CF₃ | 4-trifluoromethoxyphenyl |
| 1538 | (CH₂)₅ | | O | CH₂-c-Pr | OCH₂CF₃ | 4-trifluoromethoxyphenyl |
| 1539 | 5,5-spiro[2.3]hexane | | O | CH₂-c-Pr | OCH₂CF₃ | 4-trifluoromethoxyphenyl |
| 1540 | Cyclopentyl | | O | CH₂-c-Pr | OCH₂CF₃ | 4-trifluoromethoxyphenyl |
| 2704 | CH₂CH₃ | H | O | CH₂CH₂CF₃ | Cl | 4-trifluoromethylphenyl |
| 2705 | CH₂CF₃ | H | O | CH₂CH₂CF₃ | Cl | 4-trifluoromethylphenyl |
| 2706 | CH₂CH₂CH₃ | H | O | CH₂CH₂CF₃ | Cl | 4-trifluoromethylphenyl |
| 2707 | CH₂CH(CH₃)₂ | H | O | CH₂CH₂CF₃ | Cl | 4-trifluoromethylphenyl |
| 2708 | cyclopropylmethyl | H | O | CH₂CH₂CF₃ | Cl | 4-trifluoromethylphenyl |
| 2709 | cyclobutylmethyl | H | O | CH₂CH₂CF₃ | Cl | 4-trifluoromethylphenyl |
| 2710 | (CH₂)₂ | | O | CH₂CH₂CF₃ | Cl | 4-trifluoromethylphenyl |
| 2711 | (CH₂)₃ | | O | CH₂CH₂CF₃ | Cl | 4-trifluoromethylphenyl |
| 2712 | (CH₂)₄ | | O | CH₂CH₂CF₃ | Cl | 4-trifluoromethylphenyl |
| 2713 | (CH₂)₅ | | O | CH₂CH₂CF₃ | Cl | 4-trifluoromethylphenyl |
| 2714 | 5,5-spiro[2.3]hexane | | O | CH₂CH₂CF₃ | Cl | 4-trifluoromethylphenyl |
| 2715 | Cyclopentyl | H | O | CH₂CH₂CF₃ | Cl | 4-trifluoromethylphenyl |
| 2716 | CH₂CH₃ | H | O | CH₂CF₃ | CF₃ | 5-benzo[c][1,2,5]oxadiazole |
| 2717 | CH₂CF₃ | H | O | CH₂CF₃ | CF₃ | 5-benzo[c][1,2,5]oxadiazole |
| 2718 | CH₂CH₂CH₃ | H | O | CH₂CF₃ | CF₃ | 5-benzo[c][1,2,5]oxadiazole |
| 2721 | cyclobutylmethyl | H | O | CH₂CF₃ | CF₃ | 5-benzo[c][1,2,5]oxadiazole |
| 2722 | (CH₂)₂ | | O | CH₂CF₃ | CF₃ | 5-benzo[c][1,2,5]oxadiazole |
| 2723 | (CH₂)₃ | | O | CH₂CF₃ | CF₃ | 5-benzo[c][1,2,5]oxadiazole |
| 2724 | (CH₂)₄ | | O | CH₂CF₃ | CF₃ | 5-benzo[c][1,2,5]oxadiazole |
| 2725 | (CH₂)₅ | | O | CH₂CF₃ | CF₃ | 5-benzo[c][1,2,5]oxadiazole |
| 2726 | 5,5-spiro[2.3]hexane | | O | CH₂CF₃ | CF₃ | 5-benzo[c][1,2,5]oxadiazole |
| 2727 | Cyclopentyl | H | O | CH₂CF₃ | CF₃ | 5-benzo[c][1,2,5]oxadiazole |
| 2733 | cyclobutylmethyl | H | O | CH₂CF₃ | F | 5-benzo[c][1,2,5]oxadiazole |
| 2735 | (CH₂)₃ | | O | CH₂CF₃ | F | 5-benzo[c][1,2,5]oxadiazole |
| 2737 | (CH₂)₅ | | O | CH₂CF₃ | F | 5-benzo[c][1,2,5]oxadiazole |
| 2738 | 5,5-spiro[2.3]hexane | | O | CH₂CF₃ | F | 5-benzo[c][1,2,5]oxadiazole |

-continued

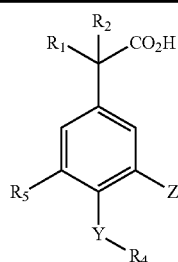

| Example | R₁ | R₂ | Y | R₄ | R₅ | Z |
|---|---|---|---|---|---|---|
| 2739 | Cyclopentyl | H | O | CH₂CF₃ | F | 5-benzo[c][1,2,5]oxadiazole |
| 2745 | cyclobutylmethyl | H | O | CH₂CF₃ | Cl | 5-benzo[c][1,2,5]oxadiazole |
| 2747 | (CH₂)₃ | | O | CH₂CF₃ | Cl | 5-benzo[c][1,2,5]oxadiazole |
| 2749 | (CH₂)₅ | | O | CH₂CF₃ | Cl | 5-benzo[c][1,2,5]oxadiazole |
| 2750 | 5,5-spiro[2.3]hexane | | O | CH₂CF₃ | Cl | 5-benzo[c][1,2,5]oxadiazole |
| 2751 | Cyclopentyl | H | O | CH₂CF₃ | Cl | 5-benzo[c][1,2,5]oxadiazole |
| 2752 | CH₂CH₃ | H | O | CH₂CF₃ | CF₃ | 5-benzo[c][1,2,5]thiadiazole |
| 2753 | CH₂CF₃ | H | O | CH₂CF₃ | CF₃ | 5-benzo[c][1,2,5]thiadiazole |
| 2754 | CH₂CH₂CH₃ | H | O | CH₂CF₃ | CF₃ | 5-benzo[c][1,2,5]thiadiazole |
| 2757 | cyclobutylmethyl | H | O | CH₂CF₃ | CF₃ | 5-benzo[c][1,2,5]thiadiazole |
| 2758 | (CH₂)₂ | | O | CH₂CF₃ | CF₃ | 5-benzo[c][1,2,5]thiadiazole |
| 2759 | (CH₂)₃ | | O | CH₂CF₃ | CF₃ | 5-benzo[c][1,2,5]thiadiazole |
| 2760 | (CH₂)₄ | | O | CH₂CF₃ | CF₃ | 5-benzo[c][1,2,5]thiadiazole |
| 2761 | (CH₂)₅ | | O | CH₂CF₃ | CF₃ | 5-benzo[c][1,2,5]thiadiazole |
| 2762 | 5,5-spiro[2.3]hexane | | O | CH₂CF₃ | CF₃ | 5-benzo[c][1,2,5]thiadiazole |
| 2763 | Cyclopentyl | H | O | CH₂CF₃ | CF₃ | 5-benzo[c][1,2,5]thiadiazole |
| 2769 | cyclobutylmethyl | H | O | CH₂CF₃ | F | 5-benzo[c][1,2,5]thiadiazole |
| 2771 | (CH₂)₃ | | O | CH₂CF₃ | F | 5-benzo[c][1,2,5]thiadiazole |
| 2773 | (CH₂)₅ | | O | CH₂CF₃ | F | 5-benzo[c][1,2,5]thiadiazole |
| 2774 | 5,5-spiro[2.3]hexane | | O | CH₂CF₃ | F | 5-benzo[c][1,2,5]thiadiazole |
| 2775 | Cyclopentyl | H | O | CH₂CF₃ | F | 5-benzo[c][1,2,5]thiadiazole |
| 2781 | cyclobutylmethyl | H | O | CH₂CF₃ | Cl | 5-benzo[c][1,2,5]thiadiazole |
| 2783 | (CH₂)₃ | | O | CH₂CF₃ | Cl | 5-benzo[c][1,2,5]thiadiazole |
| 2785 | (CH₂)₅ | | O | CH₂CF₃ | Cl | 5-benzo[c][1,2,5]thiadiazole |
| 2786 | 5,5-spiro[2.3]hexane | | O | CH₂CF₃ | Cl | 5-benzo[c][1,2,5]thiadiazole |
| 2787 | Cyclopentyl | H | O | CH₂CF₃ | Cl | 5-benzo[c][1,2,5]thiadiazole |
| 2788 | CH₂CH₃ | H | O | CH₂-c-Pr | CF₃ | 5-benzo[c][1,2,5]oxadiazole |
| 2789 | CH₂CF₃ | H | O | CH₂-c-Pr | CF₃ | 5-benzo[c][1,2,5]oxadiazole |
| 2790 | CH₂CH₂CH₃ | H | O | CH₂-c-Pr | CF₃ | 5-benzo[c][1,2,5]oxadiazole |
| 2791 | CH₂CH(CH₃)₂ | H | O | CH₂-c-Pr | CF₃ | 5-benzo[c][1,2,5]oxadiazole |
| 2792 | cyclopropylmethyl | H | O | CH₂-c-Pr | CF₃ | 5-benzo[c][1,2,5]oxadiazole |
| 2793 | cyclobutylmethyl | H | O | CH₂-c-Pr | CF₃ | 5-benzo[c][1,2,5]oxadiazole |
| 2794 | (CH₂)₂ | | O | CH₂-c-Pr | CF₃ | 5-benzo[c][1,2,5]oxadiazole |
| 2795 | (CH₂)₃ | | O | CH₂-c-Pr | CF₃ | 5-benzo[c][1,2,5]oxadiazole |
| 2796 | (CH₂)₄ | | O | CH₂-c-Pr | CF₃ | 5-benzo[c][1,2,5]oxadiazole |
| 2797 | (CH₂)₅ | | O | CH₂-c-Pr | CF₃ | 5-benzo[c][1,2,5]oxadiazole |
| 2798 | 5,5-spiro[2.3]hexane | | O | CH₂-c-Pr | CF₃ | 5-benzo[c][1,2,5]oxadiazole |
| 2799 | Cyclopentyl | H | O | CH₂-c-Pr | CF₃ | 5-benzo[c][1,2,5]oxadiazole |
| 2805 | cyclobutylmethyl | H | O | CH₂-c-Pr | F | 5-benzo[c][1,2,5]oxadiazole |
| 2807 | (CH₂)₃ | | O | CH₂-c-Pr | F | 5-benzo[c][1,2,5]oxadiazole |
| 2809 | (CH₂)₅ | | O | CH₂-c-Pr | F | 5-benzo[c][1,2,5]oxadiazole |
| 2810 | 5,5-spiro[2.3]hexane | | O | CH₂-c-Pr | F | 5-benzo[c][1,2,5]oxadiazole |
| 2811 | Cyclopentyl | H | O | CH₂-c-Pr | F | 5-benzo[c][1,2,5]oxadiazole |
| 2817 | cyclobutylmethyl | H | O | CH₂-c-Pr | Cl | 5-benzo[c][1,2,5]oxadiazole |
| 2819 | (CH₂)₃ | | O | CH₂-c-Pr | Cl | 5-benzo[c][1,2,5]oxadiazole |
| 2821 | (CH₂)₅ | | O | CH₂-c-Pr | Cl | 5-benzo[c][1,2,5]oxadiazole |
| 2822 | 5,5-spiro[2.3]hexane | | O | CH₂-c-Pr | Cl | 5-benzo[c][1,2,5]oxadiazole |
| 2823 | Cyclopentyl | H | O | CH₂-c-Pr | Cl | 5-benzo[c][1,2,5]oxadiazole |
| 2824 | CH₂CH₃ | H | O | CH₂-c-Pr | CF₃ | 5-benzo[c][1,2,5]thiadiazole |
| 2825 | CH₂CF₃ | H | O | CH₂-c-Pr | CF₃ | 5-benzo[c][1,2,5]thiadiazole |
| 2826 | CH₂CH₂CH₃ | H | O | CH₂-c-Pr | CF₃ | 5-benzo[c][1,2,5]thiadiazole |
| 2827 | CH₂CH(CH₃)₂ | H | O | CH₂-c-Pr | CF₃ | 5-benzo[c][1,2,5]thiadiazole |
| 2828 | cyclopropylmethyl | H | O | CH₂-c-Pr | CF₃ | 5-benzo[c][1,2,5]thiadiazole |
| 2829 | cyclobutylmethyl | H | O | CH₂-c-Pr | CF₃ | 5-benzo[c][1,2,5]thiadiazole |
| 2830 | (CH₂)₂ | | O | CH₂-c-Pr | CF₃ | 5-benzo[c][1,2,5]thiadiazole |
| 2831 | (CH₂)₃ | | O | CH₂-c-Pr | CF₃ | 5-benzo[c][1,2,5]thiadiazole |
| 2832 | (CH₂)₄ | | O | CH₂-c-Pr | CF₃ | 5-benzo[c][1,2,5]thiadiazole |
| 2833 | (CH₂)₅ | | O | CH₂-c-Pr | CF₃ | 5-benzo[c][1,2,5]thiadiazole |
| 2834 | 5,5-spiro[2.3]hexane | | O | CH₂-c-Pr | CF₃ | 5-benzo[c][1,2,5]thiadiazole |
| 2835 | Cyclopentyl | H | O | CH₂-c-Pr | CF₃ | 5-benzo[c][1,2,5]thiadiazole |
| 2841 | cyclobutylmethyl | H | O | CH₂-c-Pr | F | 5-benzo[c][1,2,5]thiadiazole |
| 2843 | (CH₂)₃ | | O | CH₂-c-Pr | F | 5-benzo[c][1,2,5]thiadiazole |
| 2845 | (CH₂)₅ | | O | CH₂-c-Pr | F | 5-benzo[c][1,2,5]thiadiazole |
| 2846 | 5,5-spiro[2.3]hexane | | O | CH₂-c-Pr | F | 5-benzo[c][1,2,5]thiadiazole |

-continued

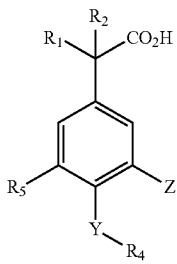

| Example | R₁ | R₂ | Y | R₄ | R₅ | Z |
|---|---|---|---|---|---|---|
| 2847 | Cyclopentyl | H | O | CH₂-c-Pr | F | 5-benzo[c][1,2,5]thiadiazole |
| 2853 | cyclobutylmethyl | H | O | CH₂-c-Pr | Cl | 5-benzo[c][1,2,5]thiadiazole |
| 2855 | (CH₂)₃ | | O | CH₂-c-Pr | Cl | 5-benzo[c][1,2,5]thiadiazole |
| 2857 | (CH₂)₅ | | O | CH₂-c-Pr | Cl | 5-benzo[c][1,2,5]thiadiazole |
| 2858 | 5,5-spiro[2.3]hexane | | O | CH₂-c-Pr | Cl | 5-benzo[c][1,2,5]thiadiazole |
| 2859 | Cyclopentyl | H | O | CH₂-c-Pr | Cl | 5-benzo[c][1,2,5]thiadiazole; | or a pharmaceutically acceptable salt thereof.

31. A pharmaceutical composition comprising the compound of any one of claims 1-30 or a pharmaceutically acceptable salt thereof and a pharmaceutically acceptable carrier or excipient.

32. A method for improving cognition comprising administering to a patient having Alzheimer's disease an effective amount of a compound of any one of claims 1-30 or a pharmaceutically acceptable salt thereof.

33. A method for the therapeutic treatment of Alzheimer's disease comprising administering to a patient in need thereof an effective amount of a compound of any one of claims 1-30 or a pharmaceutically acceptable salt thereof.

\* \* \* \* \*